US005089229A

United States Patent [19]

Heidt et al.

[11] Patent Number: 5,089,229

[45] Date of Patent: Feb. 18, 1992

[54] CHEMICAL ANALYZER

[75] Inventors: Thomas Heidt, Long Valley; Henry Will, Dover; Greydon Rhodes, Chester; Armand Placensia, Hopatoong, all of N.J.

[73] Assignee: Vettest S.A., Neuchatel, Switzerland

[21] Appl. No.: 441,451

[22] Filed: Nov. 22, 1989

[51] Int. Cl.[5] .......... G01N 21/00; G01N 35/00

[52] U.S. Cl. .......... 422/64; 422/63; 422/82.05; 436/46

[58] Field of Search .......... 422/64, 63, 82.05; 436/46, 54

[56] References Cited

U.S. PATENT DOCUMENTS

| | | | |
|---|---|---|---|
| D. 282,203 | 1/1986 | Leonard et al. | 57/66.5 |
| 2,058,516 | 10/1936 | Schaaff | 141/24 |
| 2,204,471 | 6/1940 | Campbell, Jr. et al. | 141/29 |
| 2,363,474 | 11/1944 | Schlesinger | 222/179.5 |
| 2,586,513 | 2/1952 | Butler | 210/94 |
| 2,598,869 | 6/1952 | White | 141/113 |
| 2,665,825 | 1/1954 | Poitras et al. | 222/209 |
| 2,692,820 | 10/1954 | Alway et al. | 210/659 |
| 2,721,008 | 10/1955 | Morgan, Jr. | 222/334 |
| 2,797,149 | 6/1957 | Skeggs | 436/53 |
| 2,802,605 | 8/1957 | Parker | 222/215 |
| 3,036,893 | 5/1962 | Natelson | 436/170 |
| 3,106,845 | 10/1963 | Dimmick | 73/864.11 |
| 3,164,304 | 1/1965 | Jager et al. | 222/192 |
| 3,190,731 | 6/1965 | Weiskopf | 422/102 |
| 3,300,099 | 1/1967 | Marona | 222/207 |
| 3,323,689 | 6/1967 | Elmore | 222/385 |
| 3,341,087 | 9/1967 | Rosin et al. | 222/422 |
| 3,367,746 | 2/1968 | Maurukas | 422/100 |
| 3,449,081 | 6/1969 | Hughes | 422/61 |
| 3,460,529 | 8/1969 | Leucci | 128/767 |
| 3,526,480 | 9/1970 | Findl et al. | 422/66 |
| 3,533,744 | 10/1970 | Unger | 436/63 |
| 3,572,400 | 3/1971 | Casner et al. | 141/1 |
| 3,574,064 | 4/1971 | Binnings et al. | 435/293 |
| 3,615,240 | 10/1971 | Sanz | 73/864.13 |
| 3,616,264 | 10/1971 | Ray et al. | 435/290 |
| 3,650,437 | 3/1972 | Binnings et al. | 222/136 |
| 3,659,934 | 5/1972 | Costanza et al. | 353/103 |
| 3,675,488 | 7/1972 | Victora et al. | 73/863.12 |
| 3,748,044 | 7/1973 | Liston | 356/409 |
| 3,754,866 | 8/1973 | Ritchie et al. | 422/73 |
| 3,756,920 | 9/1973 | Kelbaugh et al. | 435/291 |
| 3,758,274 | 9/1973 | Ritchie et al. | 422/50 |
| 3,788,816 | 1/1974 | Rohrbaugh et al. | 422/64 |
| 3,790,346 | 2/1974 | Ritchie | 422/64 |
| 3,810,779 | 5/1974 | Pickett et al. | 422/256 |
| 3,832,135 | 8/1974 | Drozdowski et al. | 436/47 |
| 3,856,470 | 12/1974 | Cullis et al. | 422/64 |
| 3,873,273 | 3/1975 | Moran et al. | 422/64 |
| 3,883,308 | 5/1975 | Matte | 422/64 |
| 3,904,372 | 9/1975 | Lightner | 422/63 |
| 3,915,651 | 10/1975 | Nishi | 73/864.16 |
| 3,918,913 | 11/1975 | Stevensen et al. | 73/863.72 |
| 3,926,514 | 12/1975 | Costanza et al. | 353/113 |
| 3,942,952 | 3/1976 | Atwood | 73/864.91 |
| 4,041,995 | 8/1977 | Columbus | 141/275 |
| 4,043,756 | 8/1977 | Sommervold | 436/43 |
| 4,052,161 | 10/1977 | Atwood et al. | 436/34 |
| 4,059,405 | 11/1977 | Sodickson et al. | 436/44 |
| 4,061,469 | 12/1977 | Dubose | 422/64 |

(List continued on next page.)

FOREIGN PATENT DOCUMENTS

| | | |
|---|---|---|
| 0042337 | 12/1981 | European Pat. Off. . |
| 0042340 | 12/1981 | European Pat. Off. . |

*Primary Examiner*—Robert J. Warden
*Assistant Examiner*—Theresa A. Trembley
*Attorney, Agent, or Firm*—Hoffman & Baron

[57] ABSTRACT

A chemical analyzer includes a transport mechanism having a rotatable turntable adapted to hold a plurality of reagent test slides, a sample metering device, an incubator or temperature controller, a reflectometer and associated electronics and software. The rotatable turntable preferably holds up to twelve slides about its circumference, which slides are loaded onto the turntable by an inserter mechanism. The turntable positions the reagent test slides under the metering device, which device deposits a predetermined amount of sample onto each slide. The turntable also carries the slides above a reflectometer. After testing has been completed, an ejector mechanism automatically removes the reagent slides from the turntable.

5 Claims, 70 Drawing Sheets

U.S. PATENT DOCUMENTS

| | | | |
|---|---|---|---|
| 4,067,694 | 1/1978 | Blakely et al. | 422/63 |
| 4,090,791 | 5/1978 | Siddiqi et al. | 356/414 |
| 4,119,381 | 10/1978 | Muka et al. | 356/244 |
| 4,142,656 | 3/1979 | Smith et al. | 222/325 |
| 4,152,390 | 5/1979 | Nosco et al. | 422/63 |
| 4,160,646 | 7/1979 | Furutani et al. | 436/169 |
| 4,161,508 | 7/1979 | Janchen | 422/100 |
| 4,198,483 | 4/1980 | Soqi et al. | 435/286 |
| 4,210,724 | 7/1980 | Soqi et al. | 435/292 |
| 4,219,529 | 8/1980 | Tersteeg et al. | 422/65 |
| 4,224,032 | 9/1980 | Glover et al. | 436/46 |
| 4,234,538 | 11/1980 | Ginsberg et al. | 422/64 |
| 4,234,539 | 11/1980 | Ginsberg et al. | 422/64 |
| 4,236,894 | 12/1980 | Sommervold | 436/43 |
| 4,264,560 | 4/1981 | Natelson | 422/58 |
| 4,271,123 | 6/1981 | Curry et al. | 422/64 |
| 4,272,482 | 6/1981 | Jessop et al. | 422/65 |
| 4,277,440 | 7/1981 | Jessop et al. | 422/100 |
| 4,287,155 | 9/1981 | Tersteeg et al. | 422/64 |
| 4,296,069 | 10/1981 | Smith et al. | 422/64 |
| 4,296,070 | 10/1981 | Montalto et al. | 422/65 |
| 4,298,571 | 11/1981 | DiFulvio et al. | 422/65 |
| 4,298,575 | 11/1981 | Berglund | 73/864.13 |
| 4,302,420 | 11/1981 | Jakubowicz et al. | 422/63 |
| 4,303,611 | 12/1981 | Jessop | 422/65 |
| 4,308,231 | 12/1981 | Kolber et al. | 422/64 |
| 4,321,122 | 3/1982 | Whitcomb et al. | 204/400 |
| 4,325,909 | 4/1982 | Coulter et al. | 422/63 |
| 4,335,620 | 6/1982 | Adams | 73/863.11 |
| 4,340,390 | 7/1982 | Collins et al. | 436/54 |
| 4,347,750 | 9/1982 | Tersteeg et al. | 73/864.31 |
| 4,351,799 | 9/1982 | Gross et al. | 422/63 |
| 4,359,447 | 11/1982 | Welch | 422/63 |
| 4,399,711 | 8/1983 | Klein | 73/864.16 |
| 4,420,566 | 12/1983 | Jessop et al. | 436/46 |
| 4,424,191 | 1/1984 | Jakubowicz | 552/653 |
| 4,429,373 | 1/1984 | Fletcher et al. | 364/900 |
| 4,430,299 | 2/1984 | Horne | 422/64 |
| 4,441,532 | 4/1984 | Hrubesh | 141/1 |
| 4,451,433 | 5/1984 | Yamashita et al. | 422/63 |
| 4,452,899 | 6/1984 | Alston | 436/46 |
| 4,455,280 | 6/1984 | Shinohara et al. | 422/63 |
| 4,488,810 | 12/1984 | Hatanaka et al. | 356/244 |
| 4,503,011 | 3/1985 | Hubeau | 422/73 |
| 4,512,952 | 4/1985 | Blanding et al. | 422/63 |
| 4,522,921 | 6/1985 | Ogawa | 436/47 |
| 4,539,855 | 9/1985 | Jacobs | 73/864.25 |
| 4,540,549 | 9/1985 | Manabe | 422/64 |
| 4,549,809 | 10/1985 | Minecane et al. | 356/436 |
| 4,568,519 | 2/1986 | Hamilton et al. | 422/64 |
| 4,584,275 | 4/1986 | Okano et al. | 435/290 |
| 4,599,219 | 7/1986 | Cooper et al. | 422/61 |
| 4,615,360 | 10/1986 | Jacobs | 141/18 |
| 4,629,703 | 12/1986 | Uffenheimer | 436/45 |
| 4,644,807 | 2/1987 | Mar | 73/864.62 |
| 4,647,431 | 3/1987 | Sekine et al. | 422/63 |
| 4,656,006 | 4/1987 | Assmann et al. | 422/63 |
| 4,656,007 | 4/1987 | Douchy et al. | 422/64 |
| 4,670,219 | 6/1987 | Nelson et al. | 422/63 |
| 4,671,268 | 8/1988 | Andersen et al. | 128/201.13 |
| 4,675,301 | 6/1987 | Charneski et al. | 436/180 |
| 4,678,755 | 7/1987 | Shinohara et al. | 422/43 |
| 4,680,164 | 7/1987 | Kelln | 422/72 |
| 4,681,741 | 7/1987 | Hanaway | 422/100 |
| 4,695,430 | 9/1987 | Coville et al. | 422/65 |
| 4,710,352 | 12/1987 | Slater et al. | 422/63 |
| 4,713,974 | 12/1987 | Stone | 73/864.23 |
| 4,737,344 | 4/1988 | Koizumi et al. | 422/100 |
| 4,752,449 | 6/1988 | Jackson et al. | 422/73 |
| 4,774,055 | 9/1988 | Wakatake et al. | 422/64 |
| 4,785,407 | 11/1988 | Sakagami | 364/497 |
| 4,794,085 | 12/1988 | Jessop et al. | 436/54 |
| 4,798,705 | 1/1989 | Jakubowicz et al. | 422/63 |
| 4,808,380 | 2/1989 | Minekane | 422/64 |
| 4,814,279 | 3/1989 | Sugaya | 422/63 |
| 4,826,659 | 5/1989 | Akisada | 436/46 |
| 4,837,159 | 6/1989 | Yamada | 436/45 |
| 4,855,109 | 8/1989 | Muraishi et al. | 436/46 |
| 4,863,695 | 9/1989 | Fullerman | 436/54 |
| 4,943,415 | 7/1990 | Przybylowicz et al. | 422/64 |
| 5,034,191 | 7/1991 | Porte | 422/63 |

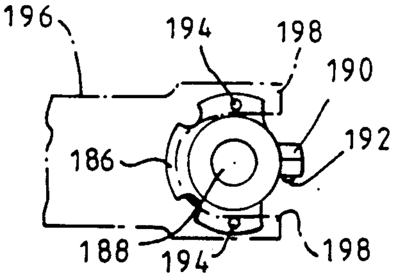
Fig.13C
Fig.13A
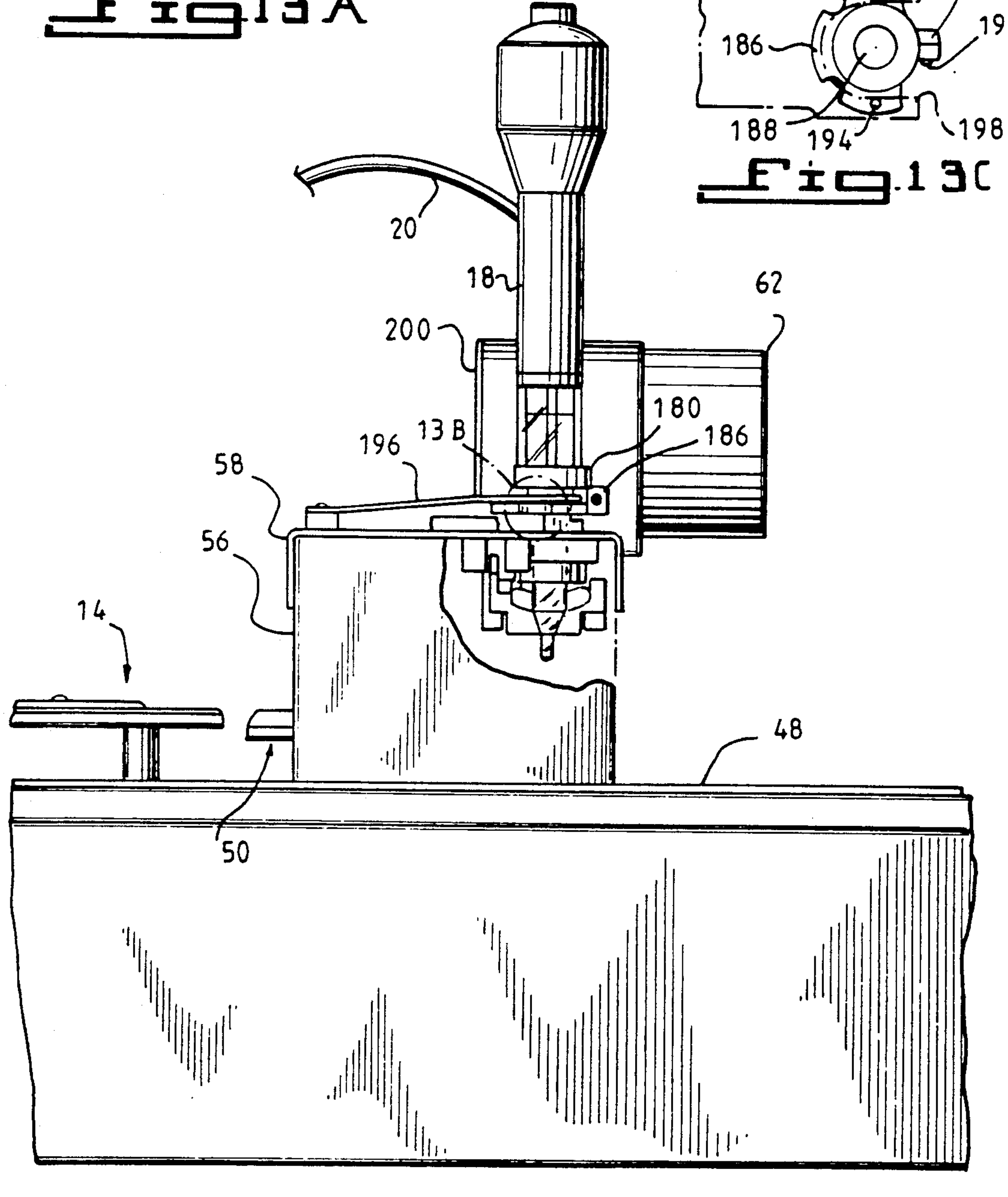
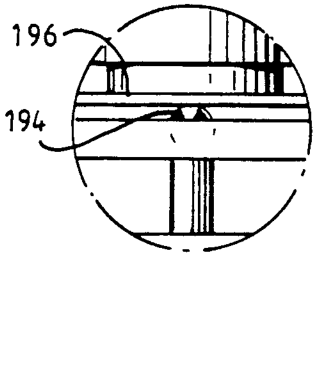
Fig.13B

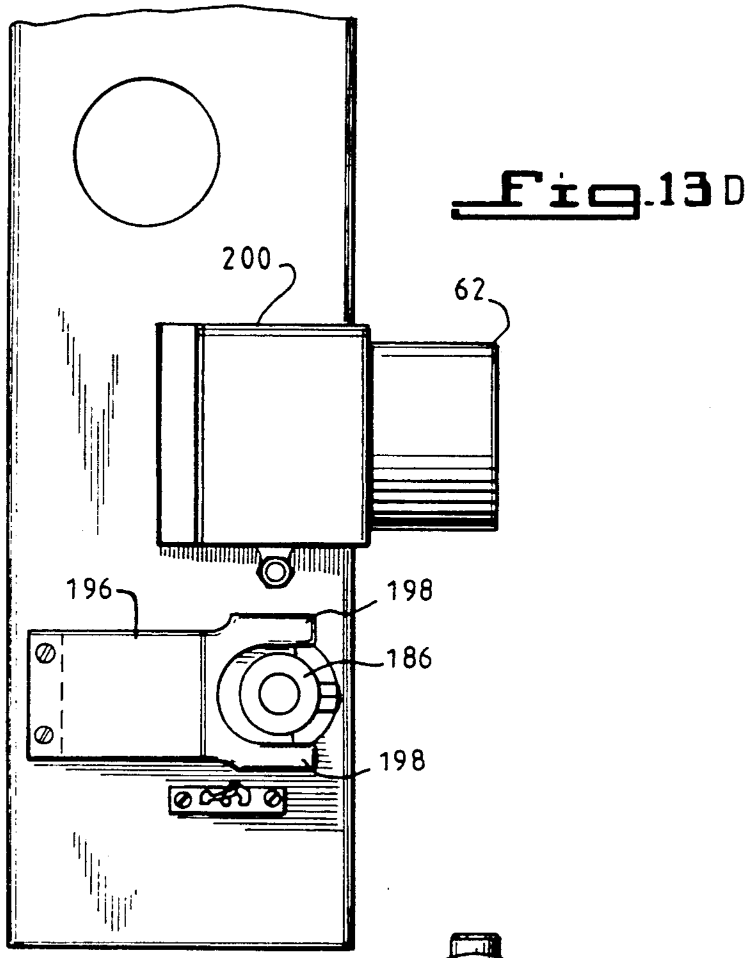
Fig.13D
Fig.13F
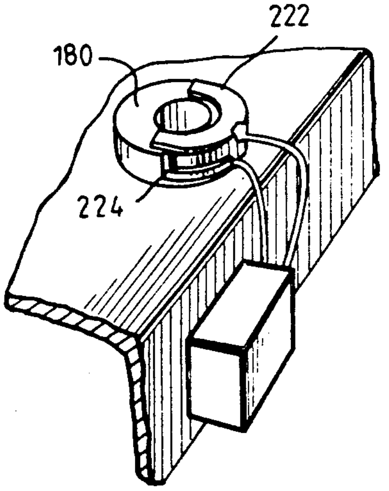
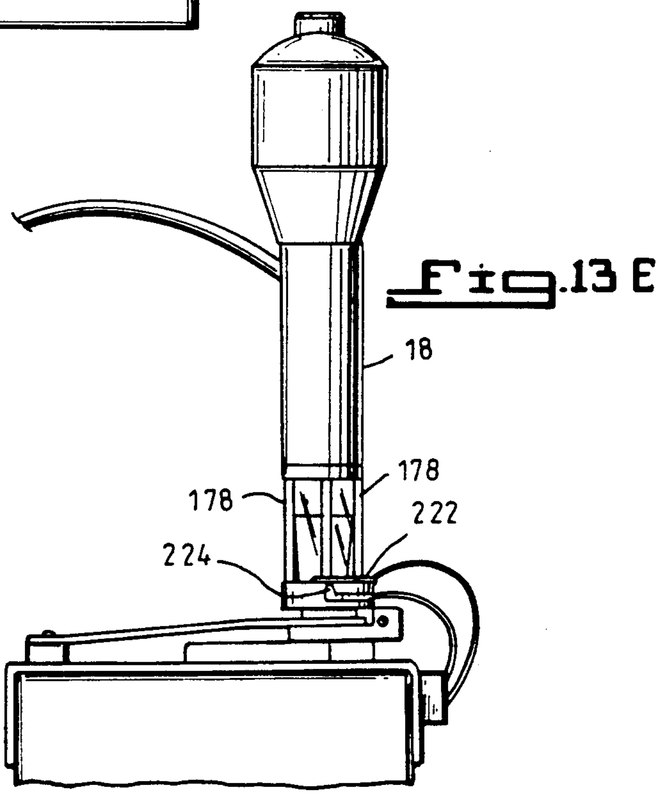
Fig.13E

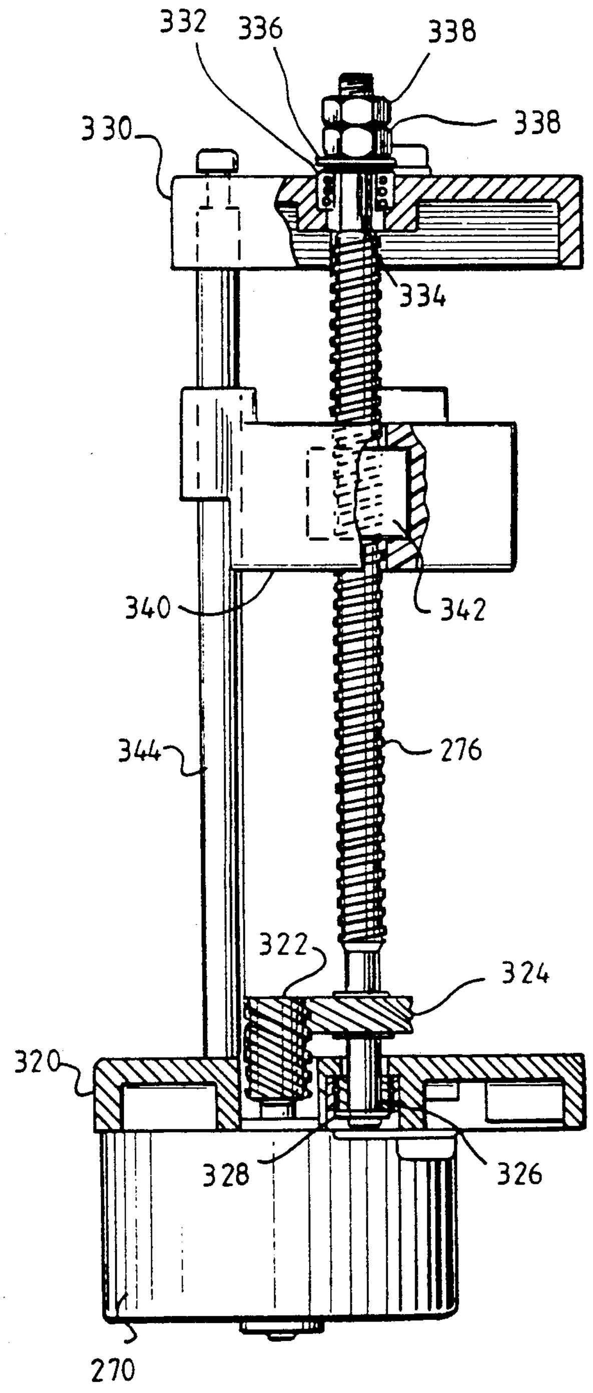
Fig.27
Fig. 28
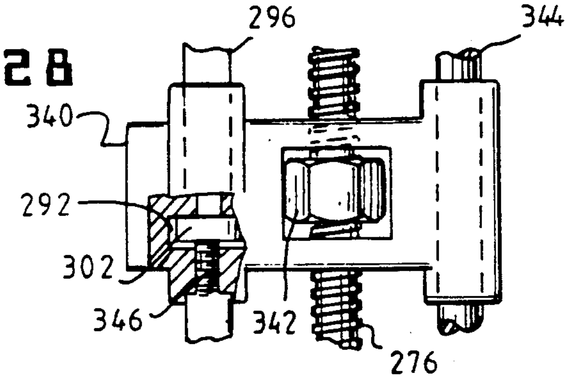

Figures 33, 34:
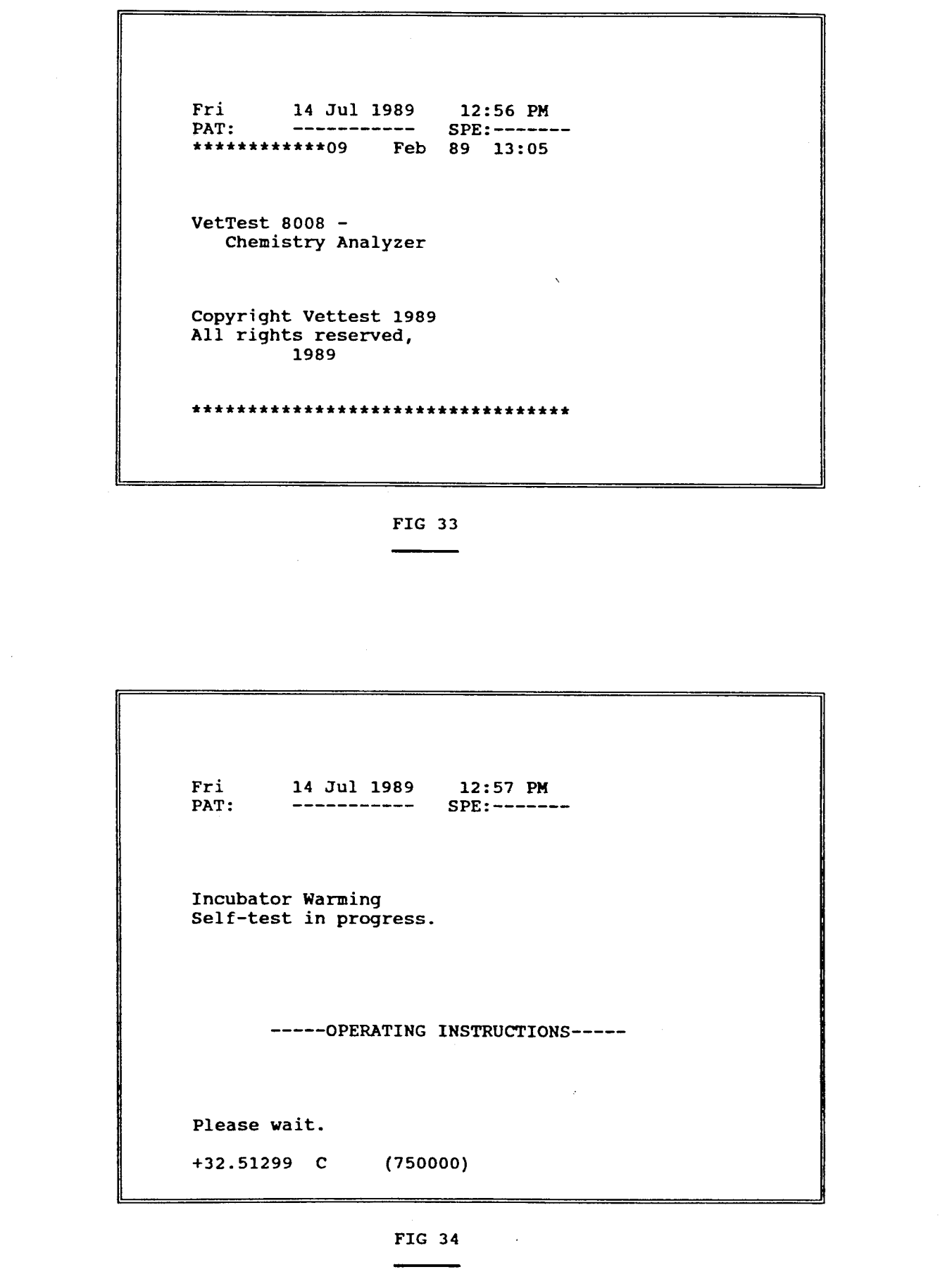

```
Fri       14 Jul 1989     12:56 PM
PAT:      -----------    SPE:-------
************09    Feb   89  13:05


VetTest 8008 -
   Chemistry Analyzer


Copyright Vettest 1989
All rights reserved,
         1989


**********************************
```

```
Fri       14 Jul 1989     12:57 PM
PAT:      -----------    SPE:-------


Incubator Warming
Self-test in progress.


       -----OPERATING INSTRUCTIONS-----


Please wait.

+32.51299  C     (750000)
```

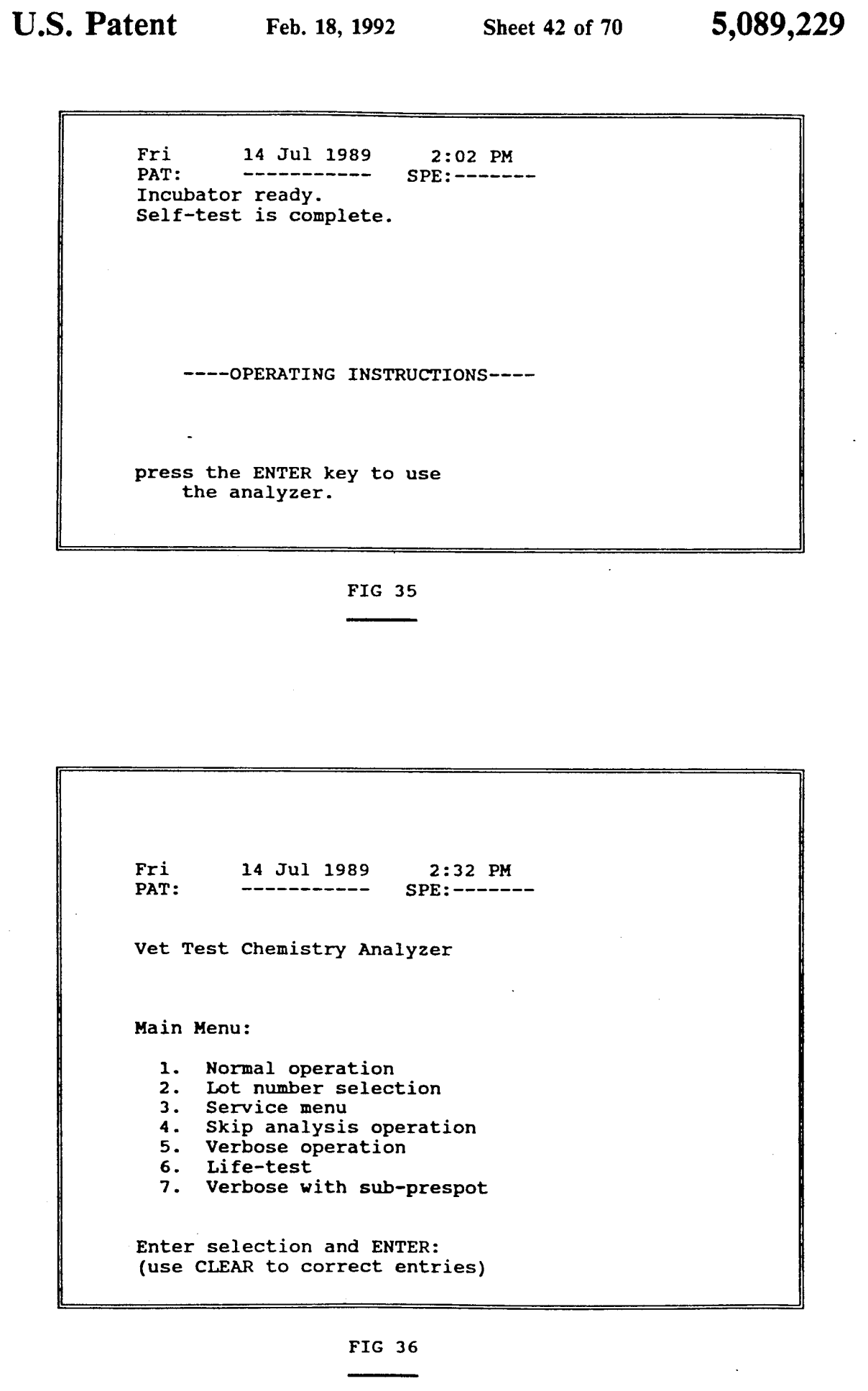

```
Fri       14 Jul 1989     2:02 PM
PAT:      -----------   SPE:-------
Incubator ready.
Self-test is complete.




    ----OPERATING INSTRUCTIONS----



press the ENTER key to use
    the analyzer.
```

FIG 35

```
Fri       14 Jul 1989     2:32 PM
PAT:      -----------   SPE:-------

Vet Test Chemistry Analyzer


Main Menu:

  1.  Normal operation
  2.  Lot number selection
  3.  Service menu
  4.  Skip analysis operation
  5.  Verbose operation
  6.  Life-test
  7.  Verbose with sub-prespot


Enter selection and ENTER:
(use CLEAR to correct entries)
```

FIG 36

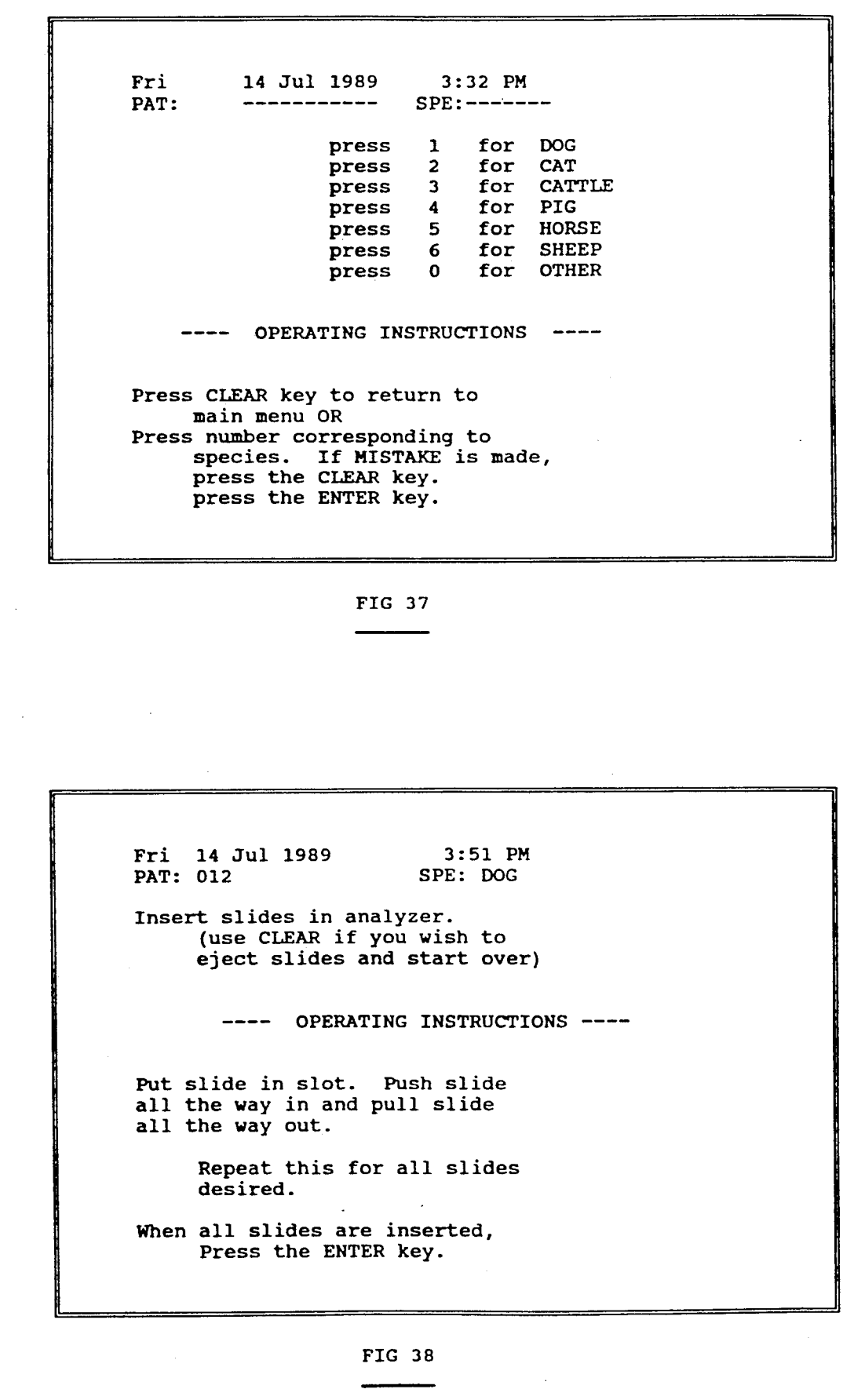

```
Fri       14 Jul 1989      3:32 PM
PAT:      -----------    SPE:-------

                 press   1   for  DOG
                 press   2   for  CAT
                 press   3   for  CATTLE
                 press   4   for  PIG
                 press   5   for  HORSE
                 press   6   for  SHEEP
                 press   0   for  OTHER


    ----  OPERATING INSTRUCTIONS  ----


Press CLEAR key to return to
     main menu OR
Press number corresponding to
     species.  If MISTAKE is made,
     press the CLEAR key.
     press the ENTER key.
```

FIG 37

```
Fri  14 Jul 1989          3:51 PM
PAT: 012                SPE: DOG

Insert slides in analyzer.
     (use CLEAR if you wish to
     eject slides and start over)


        ----  OPERATING INSTRUCTIONS ----


Put slide in slot.  Push slide
all the way in and pull slide
all the way out.

     Repeat this for all slides
     desired.

When all slides are inserted,
     Press the ENTER key.
```

FIG 38

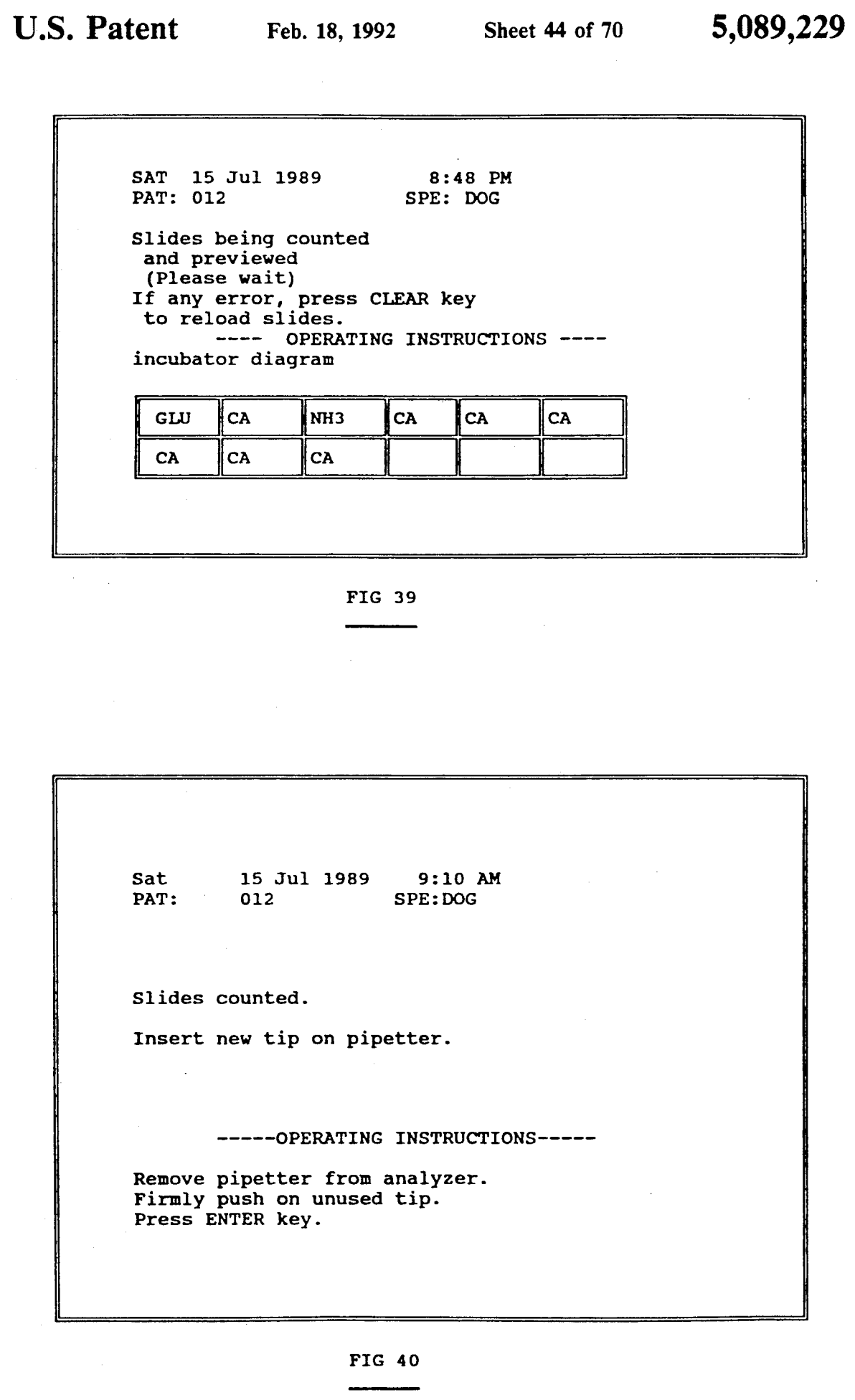

SAT 15 Jul 1989 8:48 PM
PAT: 012 SPE: DOG

Slides being counted
and previewed
(Please wait)
If any error, press CLEAR key
to reload slides.
---- OPERATING INSTRUCTIONS ----
incubator diagram

| | | | | | |
|---|---|---|---|---|---|
| GLU | CA | NH3 | CA | CA | CA |
| CA | CA | CA | | | |

FIG 39

Sat 15 Jul 1989 9:10 AM
PAT: 012 SPE:DOG

Slides counted.

Insert new tip on pipetter.

-----OPERATING INSTRUCTIONS-----

Remove pipetter from analyzer.
Firmly push on unused tip.
Press ENTER key.

FIG 40

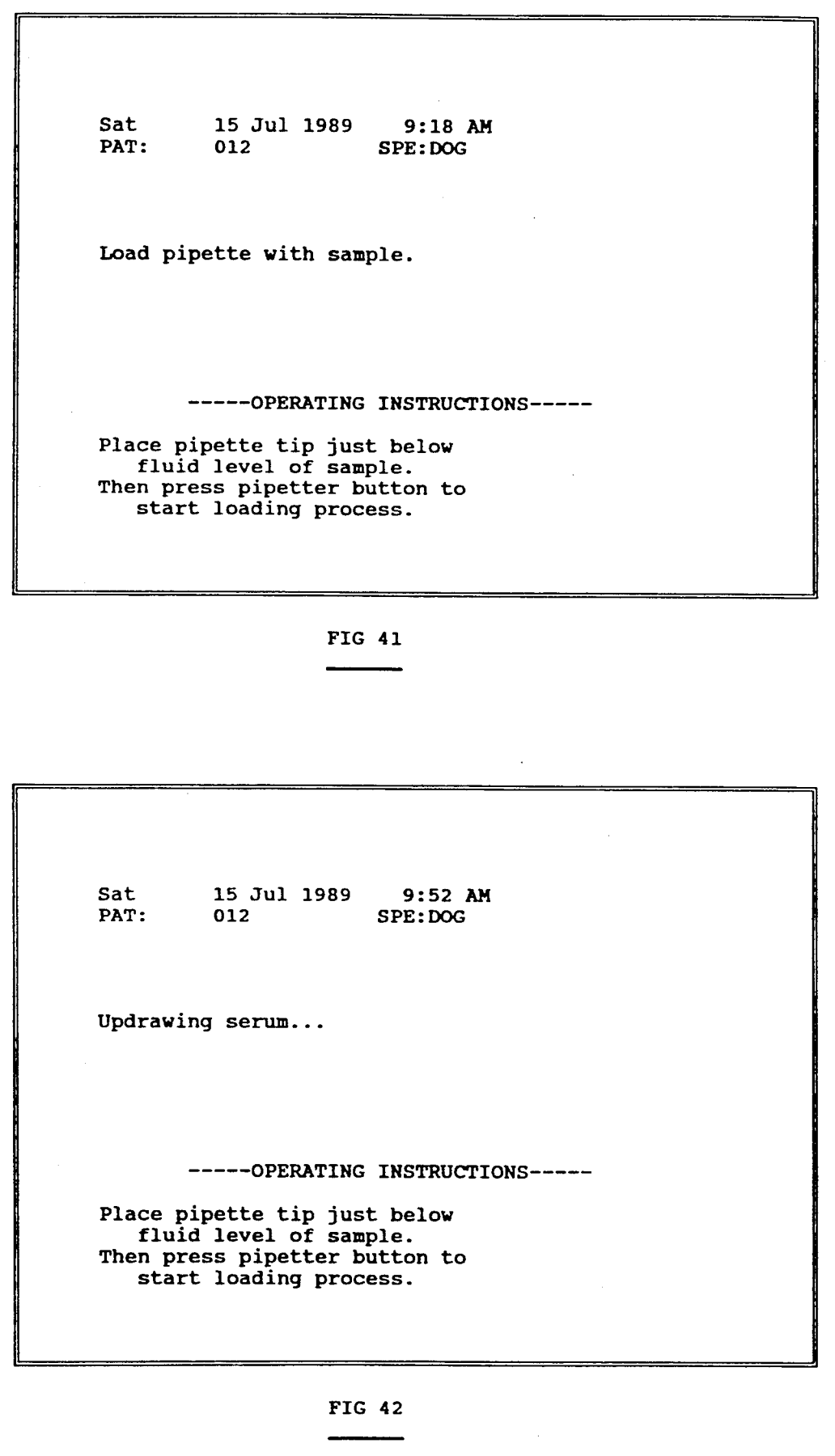

```
Sat       15 Jul 1989    9:18 AM
PAT:      012           SPE:DOG



Load pipette with sample.




       -----OPERATING INSTRUCTIONS-----

Place pipette tip just below
   fluid level of sample.
Then press pipetter button to
   start loading process.
```

FIG 41

```
Sat       15 Jul 1989    9:52 AM
PAT:      012           SPE:DOG



Updrawing serum...




       -----OPERATING INSTRUCTIONS-----

Place pipette tip just below
   fluid level of sample.
Then press pipetter button to
   start loading process.
```

FIG 42

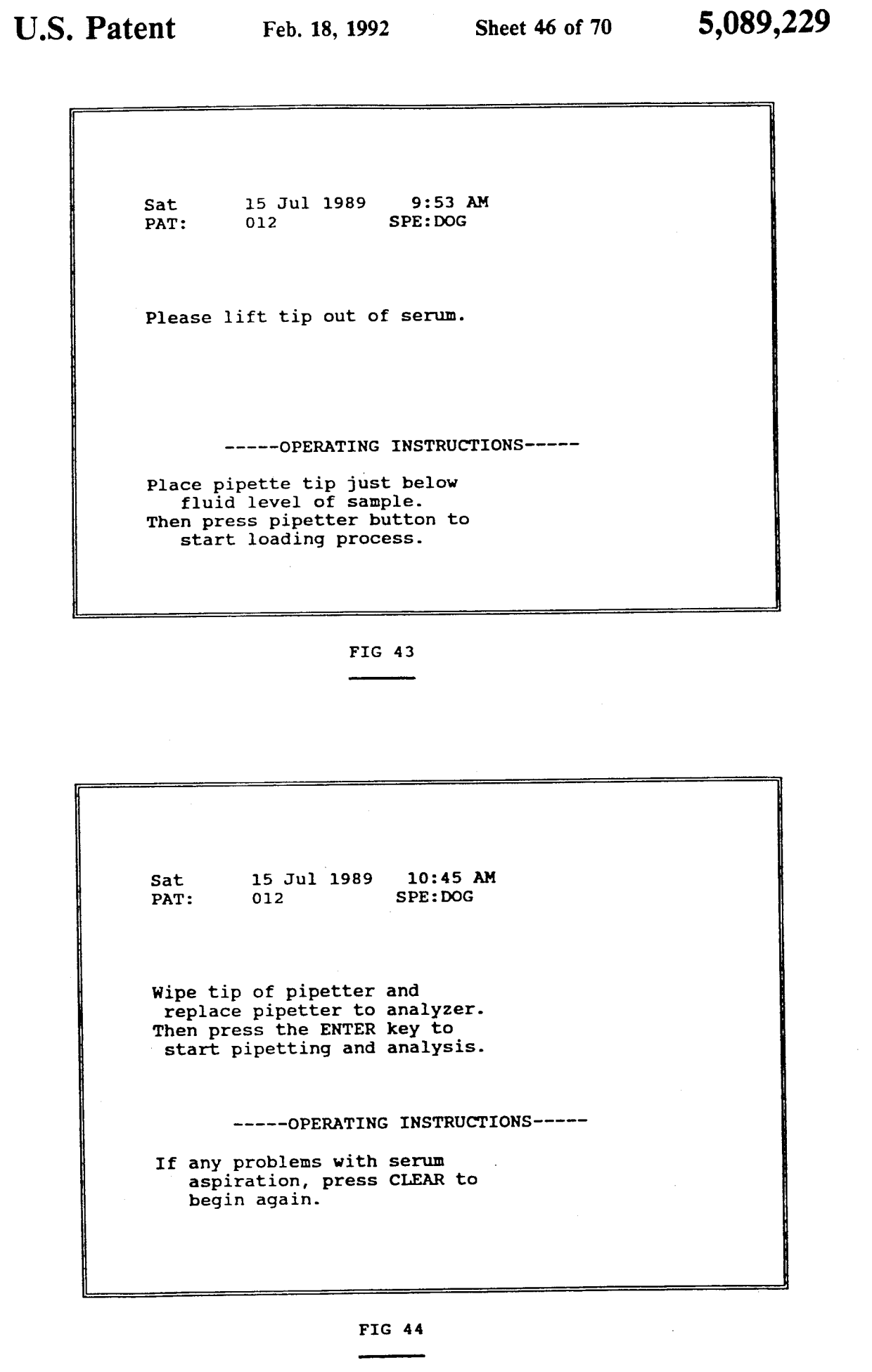

```
Sat       15 Jul 1989    9:53 AM
PAT:      012           SPE:DOG


Please lift tip out of serum.



       -----OPERATING INSTRUCTIONS-----

Place pipette tip just below
   fluid level of sample.
Then press pipetter button to
   start loading process.
```

FIG 43

```
Sat       15 Jul 1989   10:45 AM
PAT:      012           SPE:DOG


Wipe tip of pipetter and
 replace pipetter to analyzer.
Then press the ENTER key to
 start pipetting and analysis.


       -----OPERATING INSTRUCTIONS-----

If any problems with serum
   aspiration, press CLEAR to
   begin again.
```

FIG 44

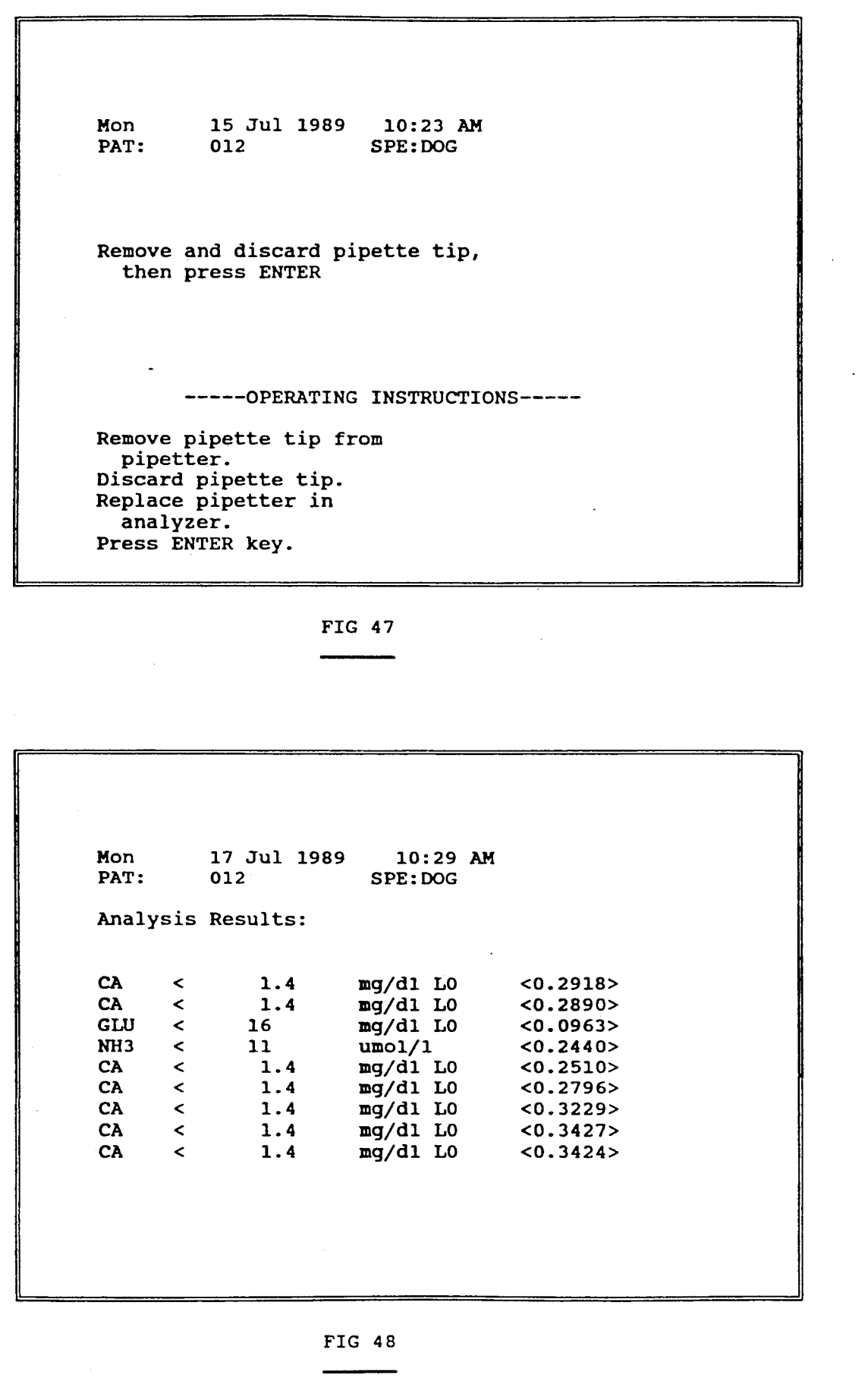

Mon 15 Jul 1989 10:23 AM
PAT: 012 SPE:DOG

Remove and discard pipette tip,
then press ENTER

-----OPERATING INSTRUCTIONS-----

Remove pipette tip from
pipetter.
Discard pipette tip.
Replace pipetter in
analyzer.
Press ENTER key.

FIG 47

Mon 17 Jul 1989 10:29 AM
PAT: 012 SPE:DOG

Analysis Results:

| | | | | |
|---|---|---|---|---|
| CA | < | 1.4 | mg/dl LO | <0.2918> |
| CA | < | 1.4 | mg/dl LO | <0.2890> |
| GLU | < | 16 | mg/dl LO | <0.0963> |
| NH3 | < | 11 | umol/l | <0.2440> |
| CA | < | 1.4 | mg/dl LO | <0.2510> |
| CA | < | 1.4 | mg/dl LO | <0.2796> |
| CA | < | 1.4 | mg/dl LO | <0.3229> |
| CA | < | 1.4 | mg/dl LO | <0.3427> |
| CA | < | 1.4 | mg/dl LO | <0.3424> |

FIG 48

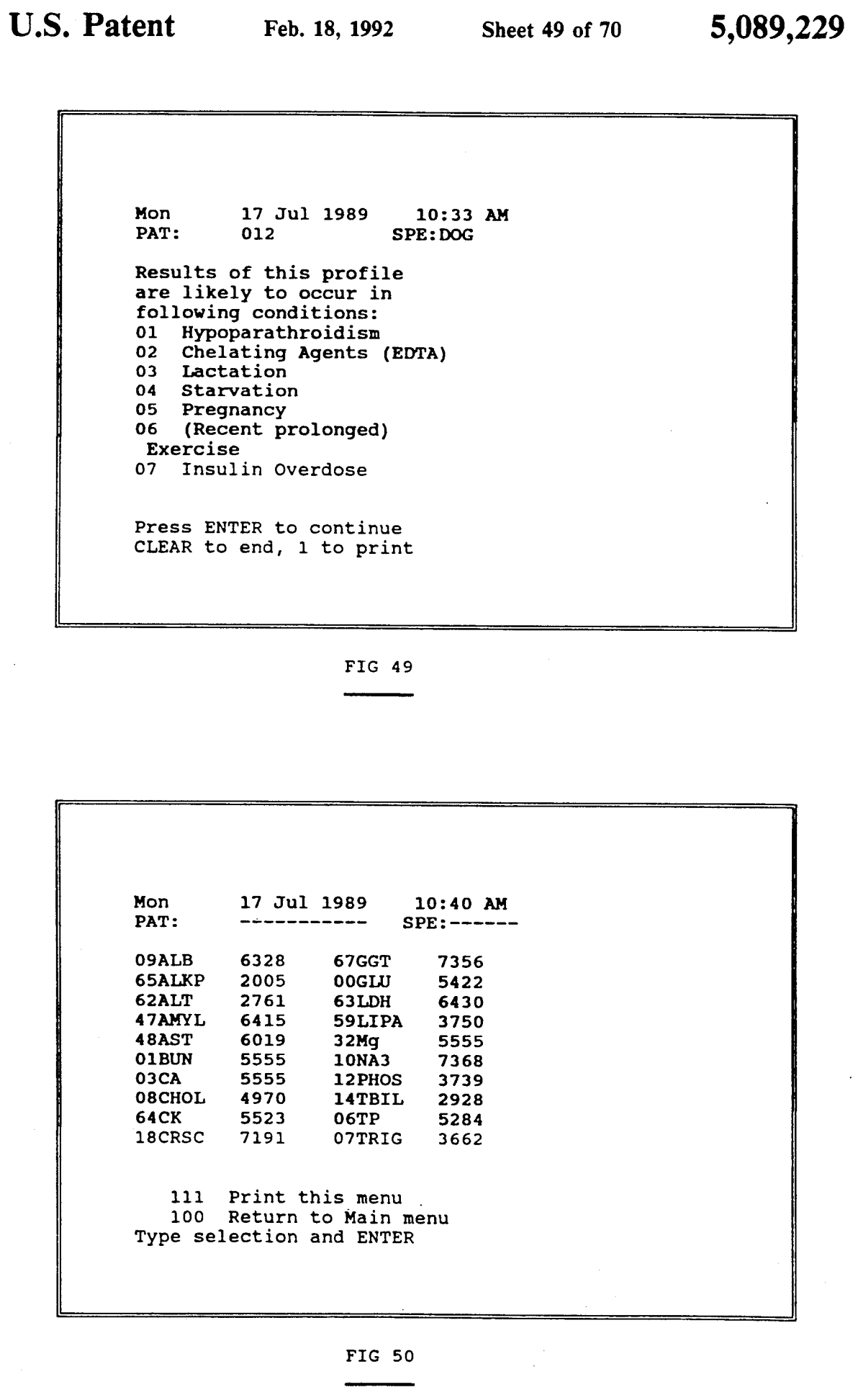

Mon 17 Jul 1989 10:33 AM
PAT: 012 SPE:DOG

Results of this profile
are likely to occur in
following conditions:
01 Hypoparathroidism
02 Chelating Agents (EDTA)
03 Lactation
04 Starvation
05 Pregnancy
06 (Recent prolonged)
Exercise
07 Insulin Overdose Press ENTER to continue
CLEAR to end, 1 to print

FIG 49

Mon 17 Jul 1989 10:40 AM
PAT: ----------- SPE:------

| | | | |
|---|---|---|---|
| 09ALB | 6328 | 67GGT | 7356 |
| 65ALKP | 2005 | 00GLU | 5422 |
| 62ALT | 2761 | 63LDH | 6430 |
| 47AMYL | 6415 | 59LIPA | 3750 |
| 48AST | 6019 | 32Mg | 5555 |
| 01BUN | 5555 | 10NA3 | 7368 |
| 03CA | 5555 | 12PHOS | 3739 |
| 08CHOL | 4970 | 14TBIL | 2928 |
| 64CK | 5523 | 06TP | 5284 |
| 18CRSC | 7191 | 07TRIG | 3662 |

111 Print this menu
100 Return to Main menu
Type selection and ENTER

FIG 50

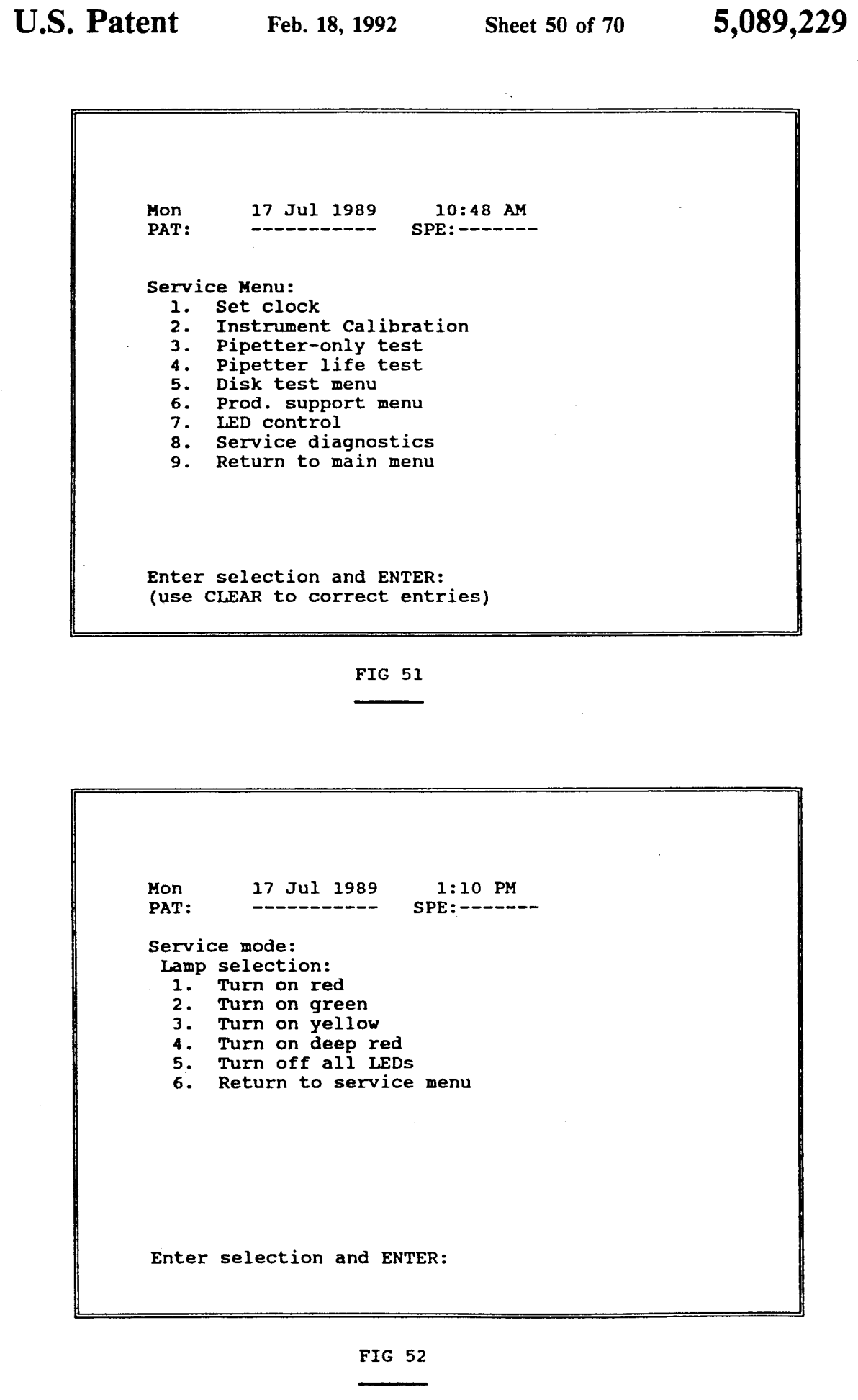

```
Mon      17 Jul 1989     10:48 AM
PAT:     -----------   SPE:-------


Service Menu:
  1.  Set clock
  2.  Instrument Calibration
  3.  Pipetter-only test
  4.  Pipetter life test
  5.  Disk test menu
  6.  Prod. support menu
  7.  LED control
  8.  Service diagnostics
  9.  Return to main menu




Enter selection and ENTER:
(use CLEAR to correct entries)
```

FIG 51

```
Mon      17 Jul 1989      1:10 PM
PAT:     -----------   SPE:-------

Service mode:
 Lamp selection:
  1.  Turn on red
  2.  Turn on green
  3.  Turn on yellow
  4.  Turn on deep red
  5.  Turn off all LEDs
  6.  Return to service menu






Enter selection and ENTER:
```

FIG 52

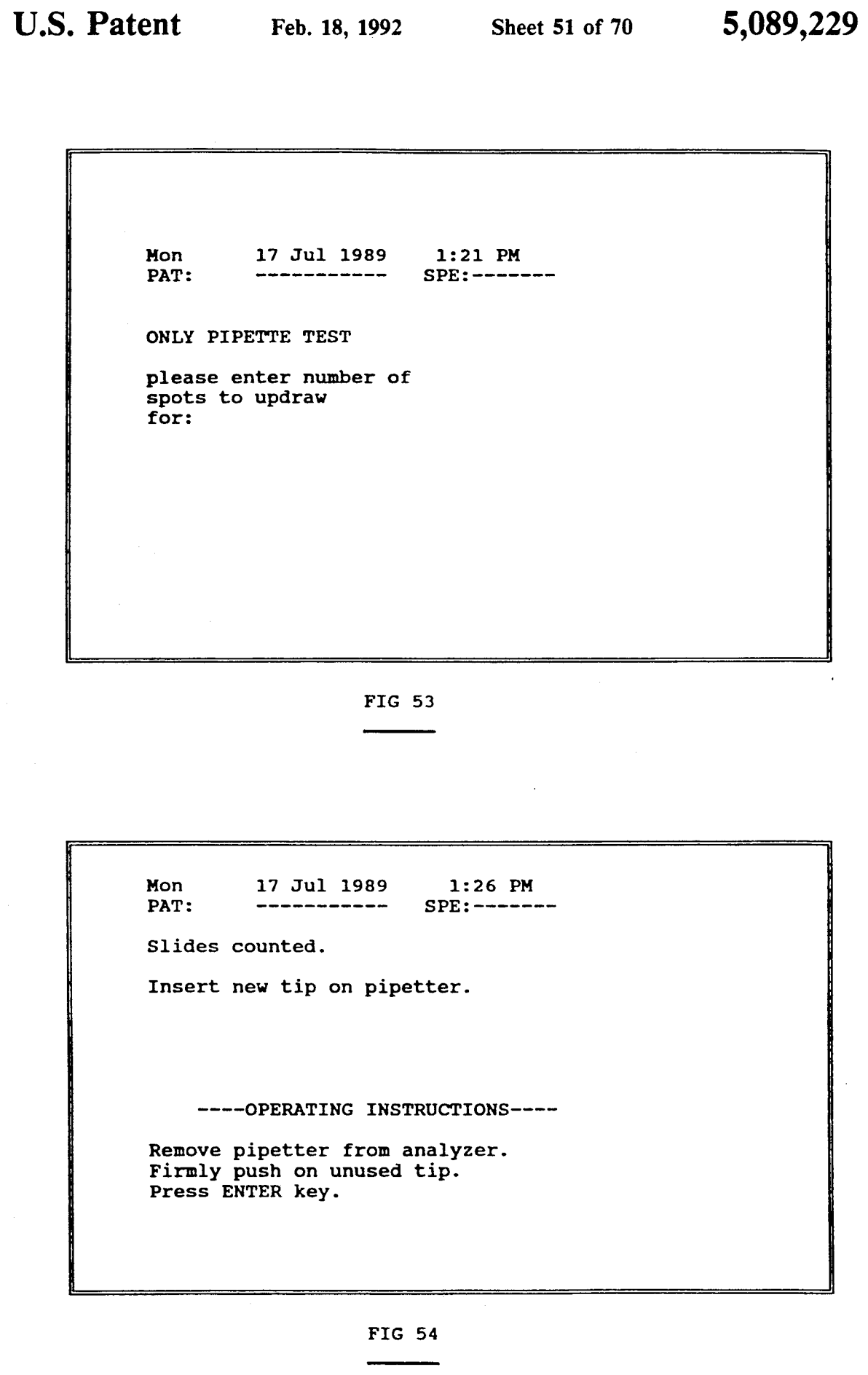

```
Mon        17 Jul 1989     1:21 PM
PAT:       -----------   SPE:-------


ONLY PIPETTE TEST

please enter number of
spots to updraw
for:
```

FIG 53

```
Mon        17 Jul 1989      1:26 PM
PAT:       -----------    SPE:-------

Slides counted.

Insert new tip on pipetter.



    ----OPERATING INSTRUCTIONS----

Remove pipetter from analyzer.
Firmly push on unused tip.
Press ENTER key.
```

FIG 54

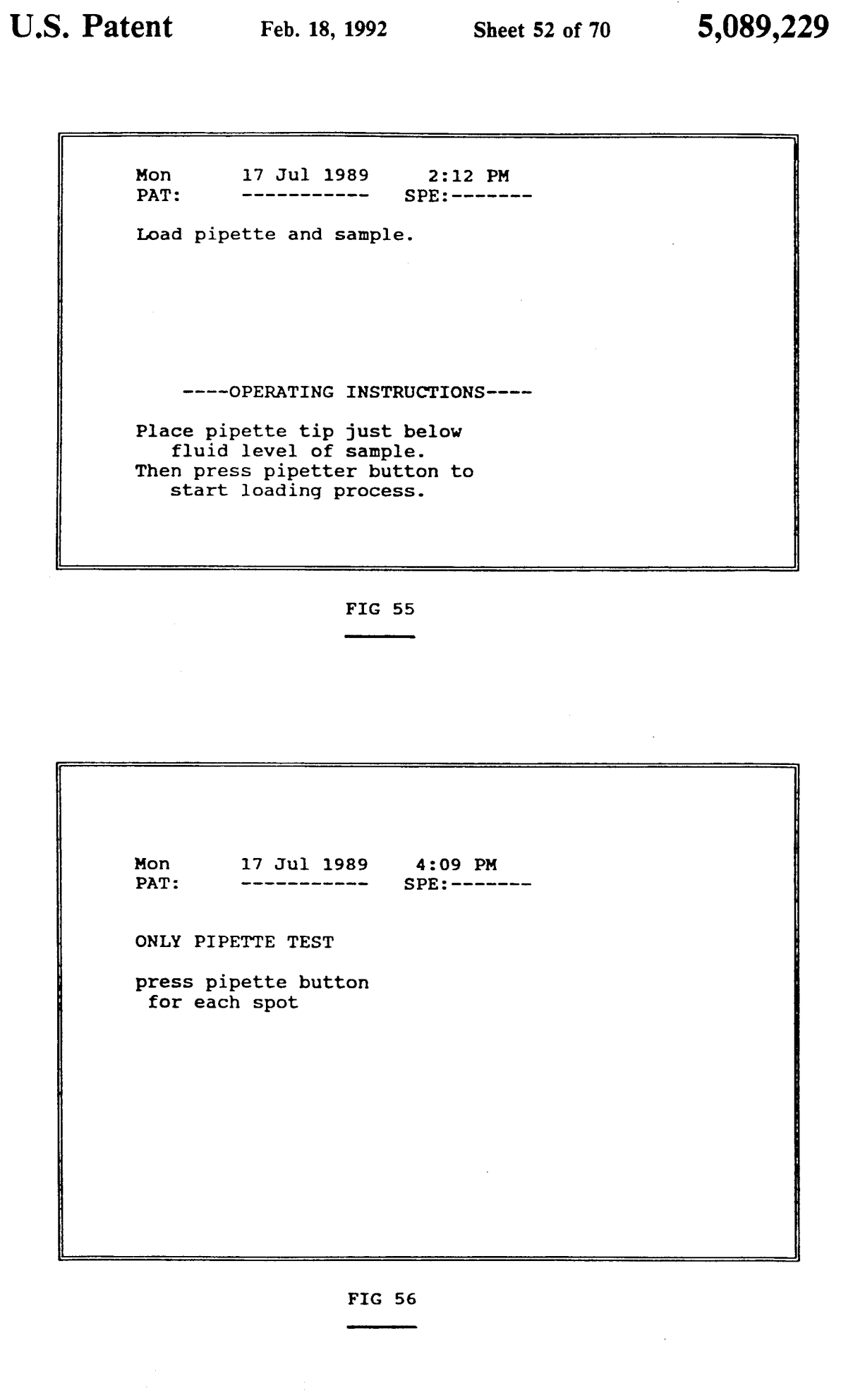

```
Mon       17 Jul 1989     2:12 PM
PAT:      -----------   SPE:-------

Load pipette and sample.




    ----OPERATING INSTRUCTIONS----

Place pipette tip just below
   fluid level of sample.
Then press pipetter button to
   start loading process.
```

FIG 55

```
Mon       17 Jul 1989    4:09 PM
PAT:      -----------   SPE:-------

ONLY PIPETTE TEST

press pipette button
 for each spot
```

FIG 56

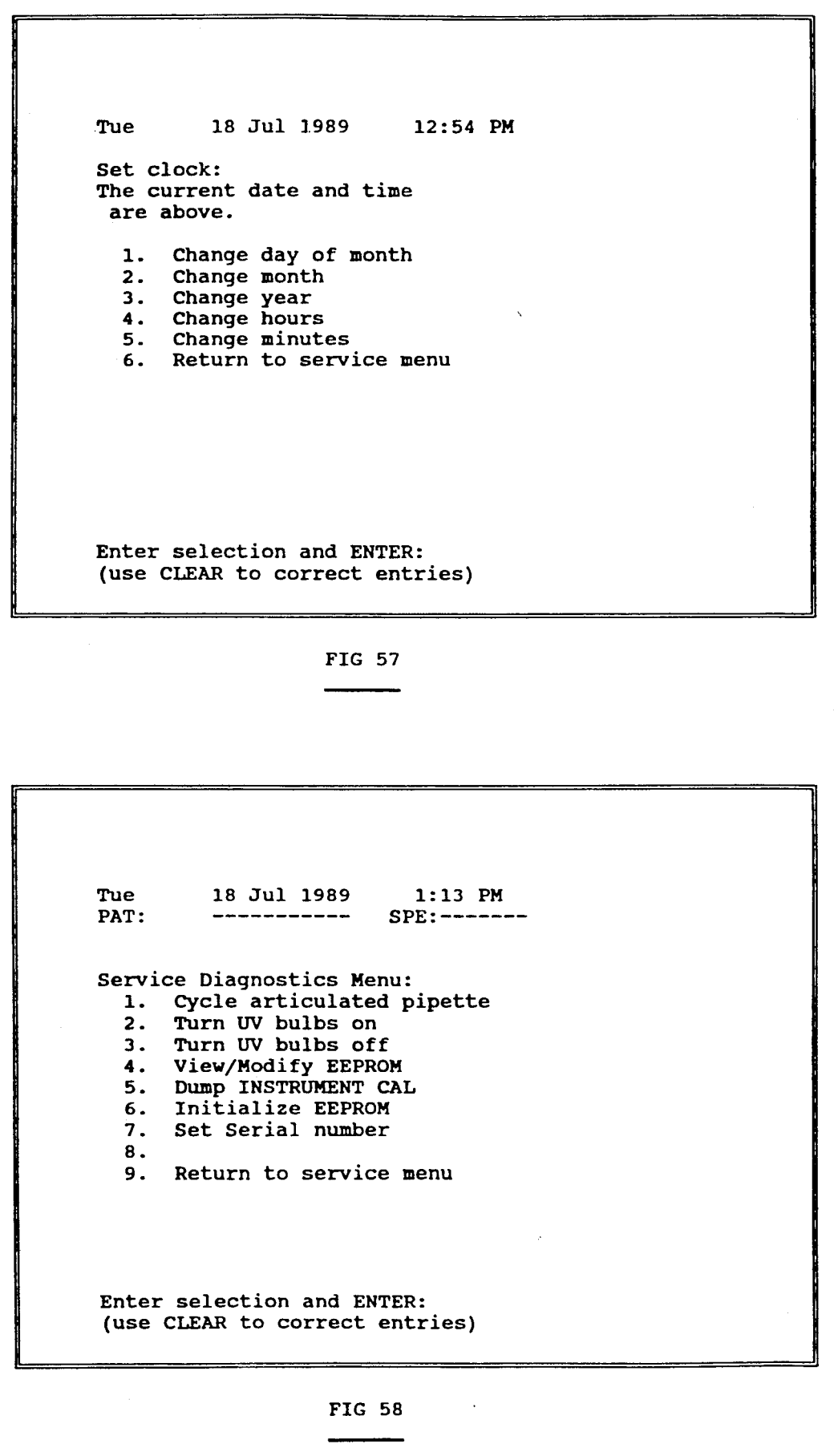

```
Tue        18 Jul 1989      12:54 PM

Set clock:
The current date and time
 are above.

  1.   Change day of month
  2.   Change month
  3.   Change year
  4.   Change hours
  5.   Change minutes
  6.   Return to service menu



Enter selection and ENTER:
(use CLEAR to correct entries)
```

FIG 57

```
Tue        18 Jul 1989      1:13 PM
PAT:       -----------    SPE:-------

Service Diagnostics Menu:
  1.   Cycle articulated pipette
  2.   Turn UV bulbs on
  3.   Turn UV bulbs off
  4.   View/Modify EEPROM
  5.   Dump INSTRUMENT CAL
  6.   Initialize EEPROM
  7.   Set Serial number
  8.
  9.   Return to service menu



Enter selection and ENTER:
(use CLEAR to correct entries)
```

FIG 58

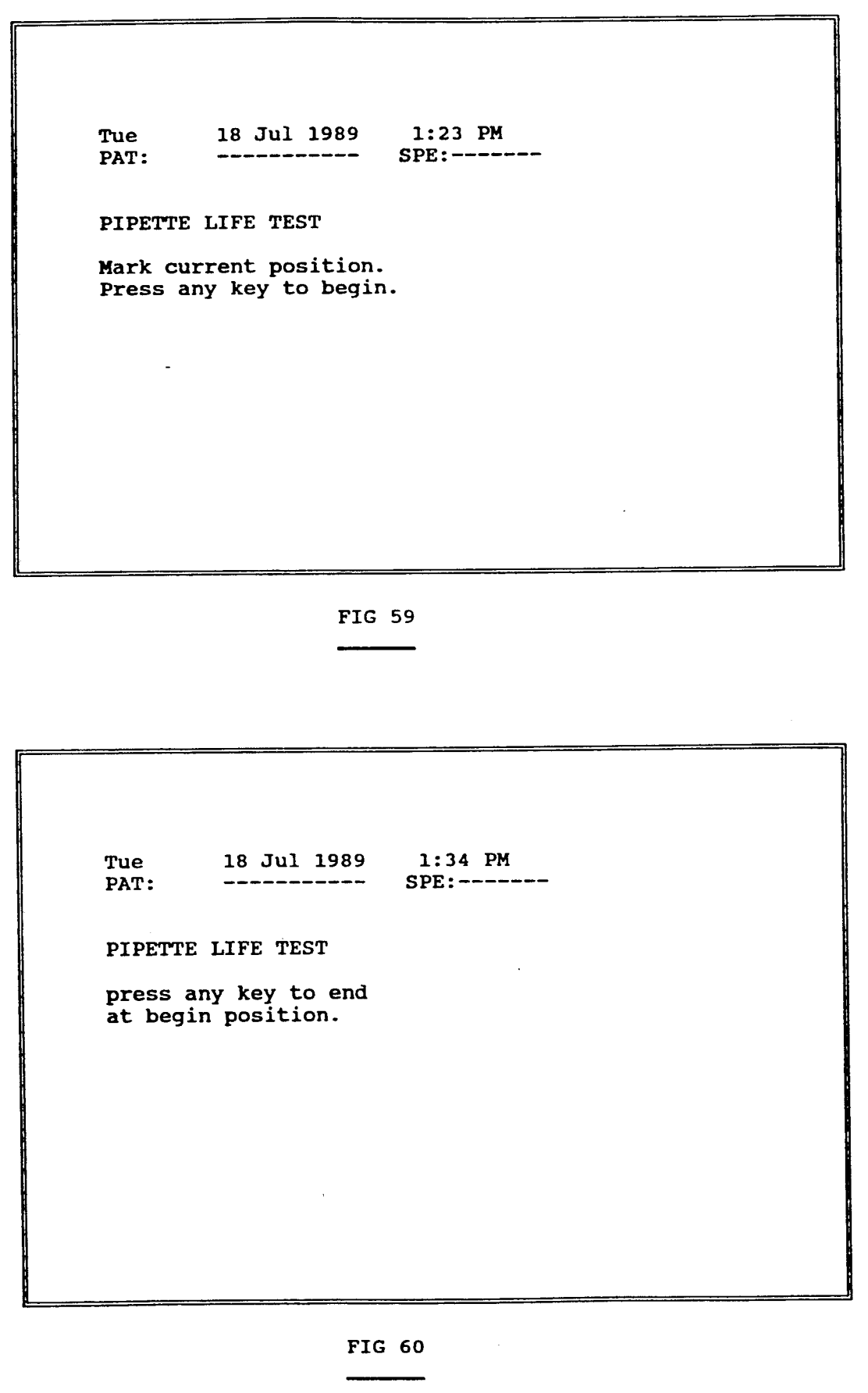

Tue 18 Jul 1989 1:23 PM
PAT: ----------- SPE:-------

PIPETTE LIFE TEST

Mark current position.
Press any key to begin.

FIG 59

Tue 18 Jul 1989 1:34 PM
PAT: ----------- SPE:-------

PIPETTE LIFE TEST press any key to end
at begin position.

FIG 60

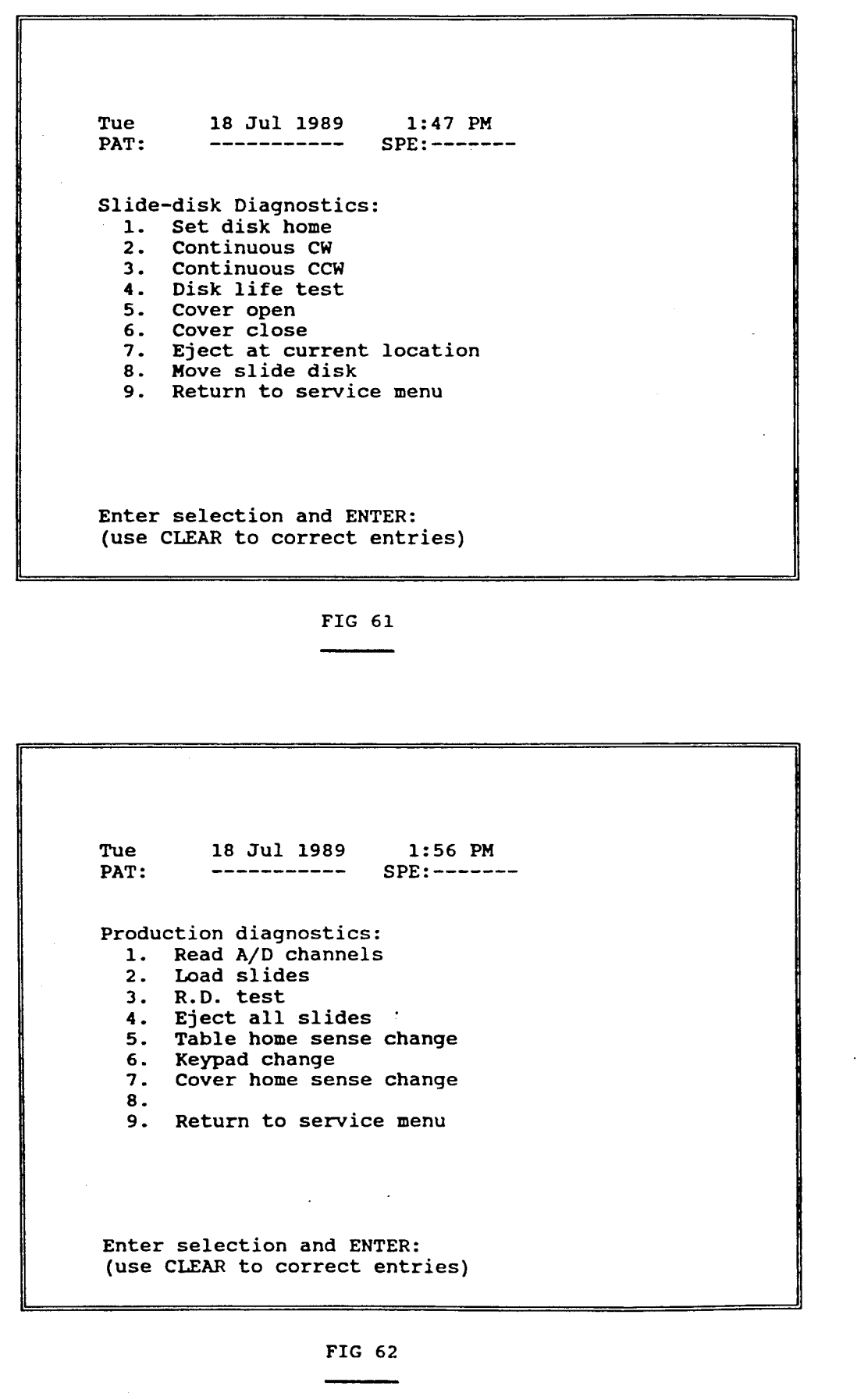

```
Tue       18 Jul 1989     1:47 PM
PAT:      -----------   SPE:-------


Slide-disk Diagnostics:
  1.  Set disk home
  2.  Continuous CW
  3.  Continuous CCW
  4.  Disk life test
  5.  Cover open
  6.  Cover close
  7.  Eject at current location
  8.  Move slide disk
  9.  Return to service menu




Enter selection and ENTER:
(use CLEAR to correct entries)
```

FIG 61

```
Tue       18 Jul 1989     1:56 PM
PAT:      -----------   SPE:-------


Production diagnostics:
  1.  Read A/D channels
  2.  Load slides
  3.  R.D. test
  4.  Eject all slides
  5.  Table home sense change
  6.  Keypad change
  7.  Cover home sense change
  8.
  9.  Return to service menu




Enter selection and ENTER:
(use CLEAR to correct entries)
```

FIG 62

Figure 63:
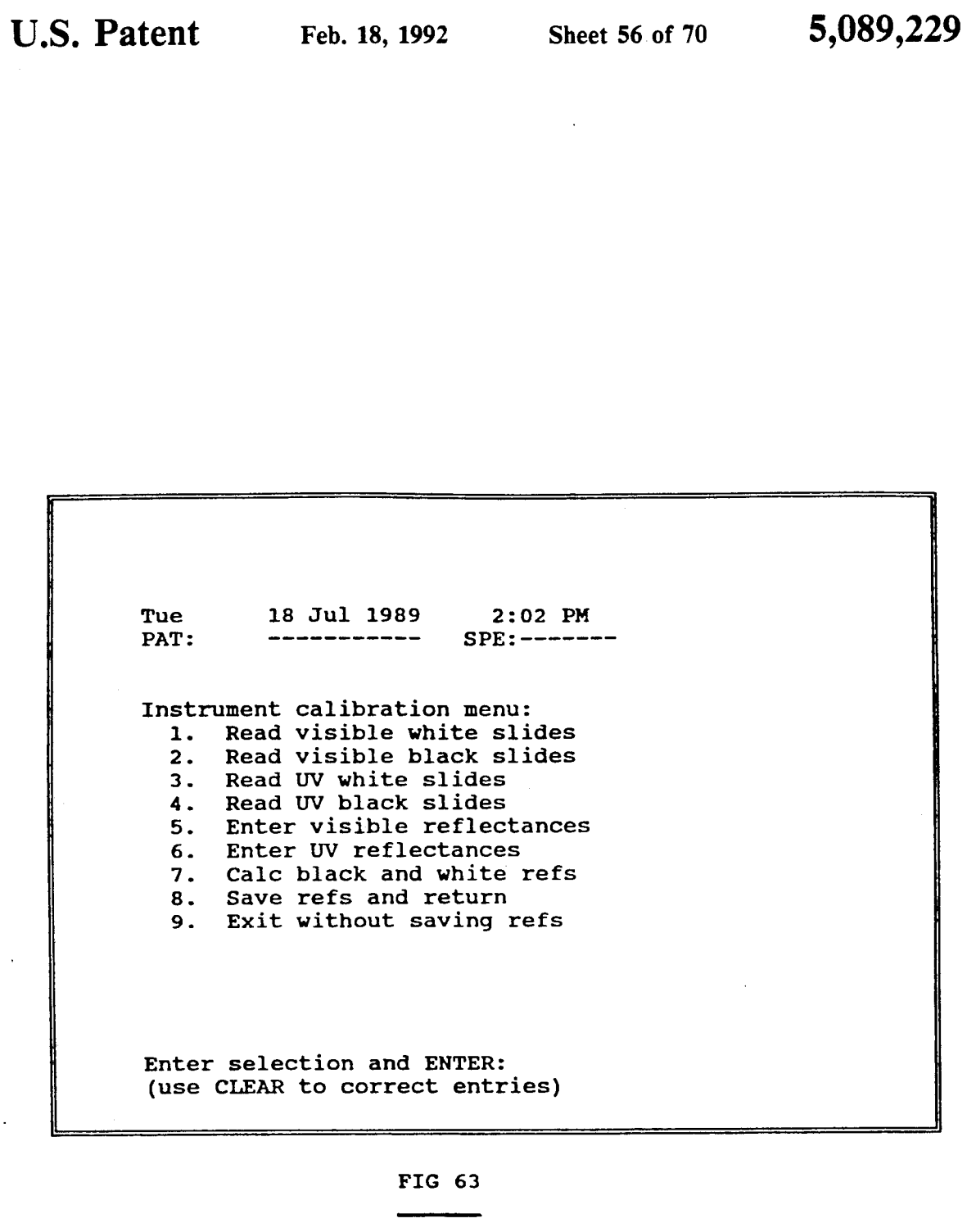

```
Tue       18 Jul 1989     2:02 PM
PAT:      -----------   SPE:-------

Instrument calibration menu:
  1.  Read visible white slides
  2.  Read visible black slides
  3.  Read UV white slides
  4.  Read UV black slides
  5.  Enter visible reflectances
  6.  Enter UV reflectances
  7.  Calc black and white refs
  8.  Save refs and return
  9.  Exit without saving refs

Enter selection and ENTER:
(use CLEAR to correct entries)
```

CHEMICAL ANALYZER

COPYRIGHT NOTICE

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

BACKGROUND OF THE INVENTION

1. Field Of The Invention

This invention relates to the chemical analysis of substances, and more particularly relates to apparatus for the automatic analysis of biological fluids. Even more specifically, this invention relates to medical testing devices particularly adapted for veterinary testing purposes wherein a change in an optical characteristic of a sample is sensed and analyzed automatically by the device.

Increasingly, the population has relied upon competent medical assistance to solve individual medical problems to a greater and greater extent. This factor, coupled with the ever growing wealth of medical knowledge, has resulted in a vast upsurge in the number of tests of various types performed as part of the diagnosis or health monitoring process. As a result, there is an increasing need for apparatus for performing such tests in an inexpensive fashion, which apparatus can be operated by relatively unskilled personnel and which will eliminate most opportunities for unreliability of results due to human error.

2. Description of The Prior Art

In recent years, a number of automated systems have been developed for carrying out quantitative chemical analysis of fluid samples. Many of the commercially available systems utilize liquid reagents and require analyzer equipment having intricate solution handling and transport capabilities. Such equipment can be referred to as "wet chemistry" analyzers. For example, U.S. Pat. No. 3,788,816, which issued to D. G. Rohrbaugh et al., discloses a liquid analysis system in which a turntable carries a plurality of receptacles containing samples to be analyzed and a plurality of tube modules which are adapted to receive preset volumes of sample and reagent. Coaxially disposed relative to the turntable is a vertically movable rotary element comprising a probe tip which serves to dispense reagents and to transfer sample to a spectrophotometer.

Wet chemistry analyzers, such as described above, are usually complex and expensive, require skilled operators and necessitate a considerable expenditure of time and effort in repetitive cleaning operations.

As an alternative to liquid analysis systems, various analyzers have been developed for automated test procedures involving essentially dry, analytical elements, which elements offer substantial storage and handling conveniences when compared to "wet chemistry" instruments.

The "dry" analytical elements are preferably in the form of test slides. The test slides are formed as a multilayer element containing the necessary reagents for reaction with components of a biological fluid, such as blood serum, deposited thereon. Certain reactions colorimetrically produce a change in optical density which is sensed by a reflectometer or other device, the amount of light reflected from the element varying in accordance with the reaction and being indicative of the amount of a particular component present in the fluid.

In a typical chemical analyzer, such as described in U.S. Pat. No. 4,296,070, which issued to Michael S. Montalto et al., the slides, which are essentially planar and contain reagents in dry form, are loaded into a cartridge and fed from the cartridge into a metering station where a predetermined amount of sample fluid is deposited on the analysis slide.

After an appropriate incubation period, the slide is moved to an analysis station where a change in the slide is sensed, the amount of change being proportional to a particular analyte in the sample fluid. The slide is used only once and is discarded after the reading is taken..

OBJECTS AND SUMMARY OF THE INVENTION

It is an object of the present invention to provide a chemical analyzer in the form of a small, desktop unit.

It is another object of the present invention to provide a chemical analyzer which can run a series of tests simultaneously in a relatively short period of time. It is still another object of the present invention to provide a chemical analyzer which is relatively inexpensive to manufacture and has a relatively low operating cost.

It is a further object of the present invention to provide a chemical analyzer which may be easily partially disassembled to facilitate cleaning.

It is yet a further object of the present invention to provide a chemical analyzer whose components are tolerant of considerable variation in slide thickness.

It is yet another object of the present invention to provide a chemical analyzer with a relatively simplified optical head for spectrophotometric analysis of slides.

It is still a further object of the present invention to provide a chemical analyzer with a simplified turntable mechanism for transporting analytical test slides as well as a turntable cover for controlling evaporation.

It is still a further object of the present invention to provide a chemical analyzer which includes an incubator having an analog heater control providing an accurate control of the temperature of the slides.

It is still a further object of the present invention to provide a chemical analyzer which includes a spectrophotometer incorporating small size, relatively low cost, high production components.

It is another object of the present invention to provide a chemical analyzer having a slide analysis portion which provides high resolution and good short-term stability.

It is a further object of the present invention to provide a chemical analyzer which provides real time information to the user as the tests are being run.

It is yet another object of the present invention to provide a chemical analyzer which includes a metering device which can dispense fluids with high accuracy and is relatively inexpensive to manufacture.

It is yet a further object of the present invention to provide a chemical analyzer having a metering device which can provide accurate drop volumes despite varying test slide thicknesses.

It is still a further object of the present invention to provide a chemical analyzer in which test results are analyzed according to species and out of normal bounds are flagged.

It is another object of the present invention to provide a chemical analyzer which automatically analyzes the results of tests conducted by the analyzer, indicates potential problems to the user and provides guidance as to the possible diseases or ailments which may have caused abnormal readings.

It is still a further object of the present invention to provide a method of analyzing an analytical test slide, of metering a predetermined volume of sample onto the test slide, of maintaining the test slide at a constant temperature, and of transporting the test slide through an analyzer apparatus.

It is yet a further object of the present invention to provide a method of metering relatively small volumes of sample onto an analytical test slide.

In accordance with one form of the present invention, the chemical analyzer comprises a transport mechanism which includes a rotating turntable adapted to hold a plurality of reagent test slides, a sample metering device, an incubator or temperature controller, a reflectometer (or spectrophotometer) and associated electronics and software.

The rotating turntable preferably holds up to twelve slides about its circumference, which slides are loaded onto the turntable by an inserter mechanism. The turntable positions the reagent test slides under the metering device, which device deposits a predetermined amount of sample onto each slide. The turntable also carries the slides above a reflectometer. After testing has been completed, an ejector mechanism automatically removes the reagent slides from the turntable.

The sample metering device includes a pipette assembly which holds a certain amount of sample in its tip. A pump provides air pressure to the pipette to force a predetermined amount of sample from the tip. The pipette assembly is adapted to move vertically downwardly to approach the slide and deposit a quantity of sample on each slide.

The incubator or heat controller of the analyzer includes a heating device, as well as a temperature sensor coupled to the rotating turntable. The turntable and the slides mounted on the turntable are maintained at a specific temperature prior to and during the analysis process. A cover is mounted on the turntable and covers the slides in order to minimize evaporation.

The reflectometer incorporates light emitting diodes (LEDs) and ultraviolet fluorescent tubes as the light sources, which sources may be individually operated, depending upon the type of test being performed. A sensor (for example, a photodiode) receives the light reflected by the reagent slide, which sensor provides a voltage to the electronic circuitry of the analyzer.

The electronic circuitry includes a computer, an analog-to-digital (A/D) converter and interface circuits. A keyboard is provided for inputting information and for controlling the operation of the analyzer. A display provides test results and operational instructions to the user.

These and other objects, features and advantages of the present invention will be apparent from the following detailed description of illustrative embodiments thereof, which is to read in connection with the accompanying drawings.

BRIEF DESCRIPTION OF THE DRAWINGS

FIG. 13A is a front view of one form of a metering device used in the chemical analyzer of the present invention.

FIG. 13B is an enlarged view of a portion of the metering device shown in circle 13B of FIG. 13A.

FIG. 13C is a top view of the metering device shown in FIG. 13A

FIG. 13D is a top view of the metering device shown in FIG. 13A.

FIG. 13E is a front view of the metering device, formed in accordance with a second embodiment of the present invention.

FIG. 13F is a perspective view of a portion of the metering device illustrated by FIG. 13E.

FIG. 27 is a bottom view, partially in section, of another alternative embodiment of the metering device of the present invention.

FIG. 28 is a detailed partial sectional view of a portion of the metering device shown in FIG. 27.

FIG. 33 is a front view of the display of the analyzer and information displayed thereon.

FIG. 34 is a front view of the display of the analyzer and information displayed thereon.

FIG. 35 is a front view of the display of the analyzer and information displayed thereon.

FIG. 36 is a front view of the display of the analyzer and information displayed thereon.

FIG. 37 is a front view of the display of the analyzer and information displayed thereon.

FIG. 38 is a front view of the display of the analyzer and information displayed thereon.

FIG. 39 is a front view of the display of the analyzer and information displayed thereon.

FIG. 40 is a front view of the display of the analyzer and information displayed thereon.

FIG. 41 is a front view of the display of the analyzer and information displayed thereon.

FIG. 42 is a front view of the display of the analyzer and information displayed thereon.

FIG. 43 is a front view of the display of the analyzer and information displayed thereon.

FIG. 44 is a front view of the display of the analyzer and information displayed thereon.

FIG. 47 is a front view of the display of the analyzer and information displayed thereon.

FIG. 48 is a front view of the display of the analyzer and information displayed thereon.

FIG. 49 is a front view of the display of the analyzer and information displayed thereon.

FIG. 50 is a front view of the display of the analyzer and information displayed thereon.

FIG. 51 is a front view of the display of the analyzer and information displayed thereon.

FIG. 52 is a front view of the display of the analyzer and information displayed thereon.

FIG. 53 is a front view of the display of the analyzer and information displayed thereon.

FIG. 54 is a front view of the display of the analyzer and information displayed thereon.

FIG. 55 is a front view of the display of the analyzer and information displayed thereon.

FIG. 56 is a front view of the display of the analyzer and information displayed thereon.

FIG. 57 is a front view of the display of the analyzer and information displayed thereon.

FIG. 58 is a front view of the display of the analyzer and information displayed thereon.

FIG. 59 is a front view of the display of the analyzer and information displayed thereon.

FIG. 60 is a front view of the display of the analyzer and information displayed thereon.

FIG. 61 is a front view of the display of the analyzer and information displayed thereon.

FIG. 62 is a front view of the display of the analyzer and information displayed thereon.

FIG. 63 is a front view of the display of the analyzer and information displayed thereon.

DETAILED DESCRIPTION OF THE PREFERRED EMBODIMENTS

Figure 1:
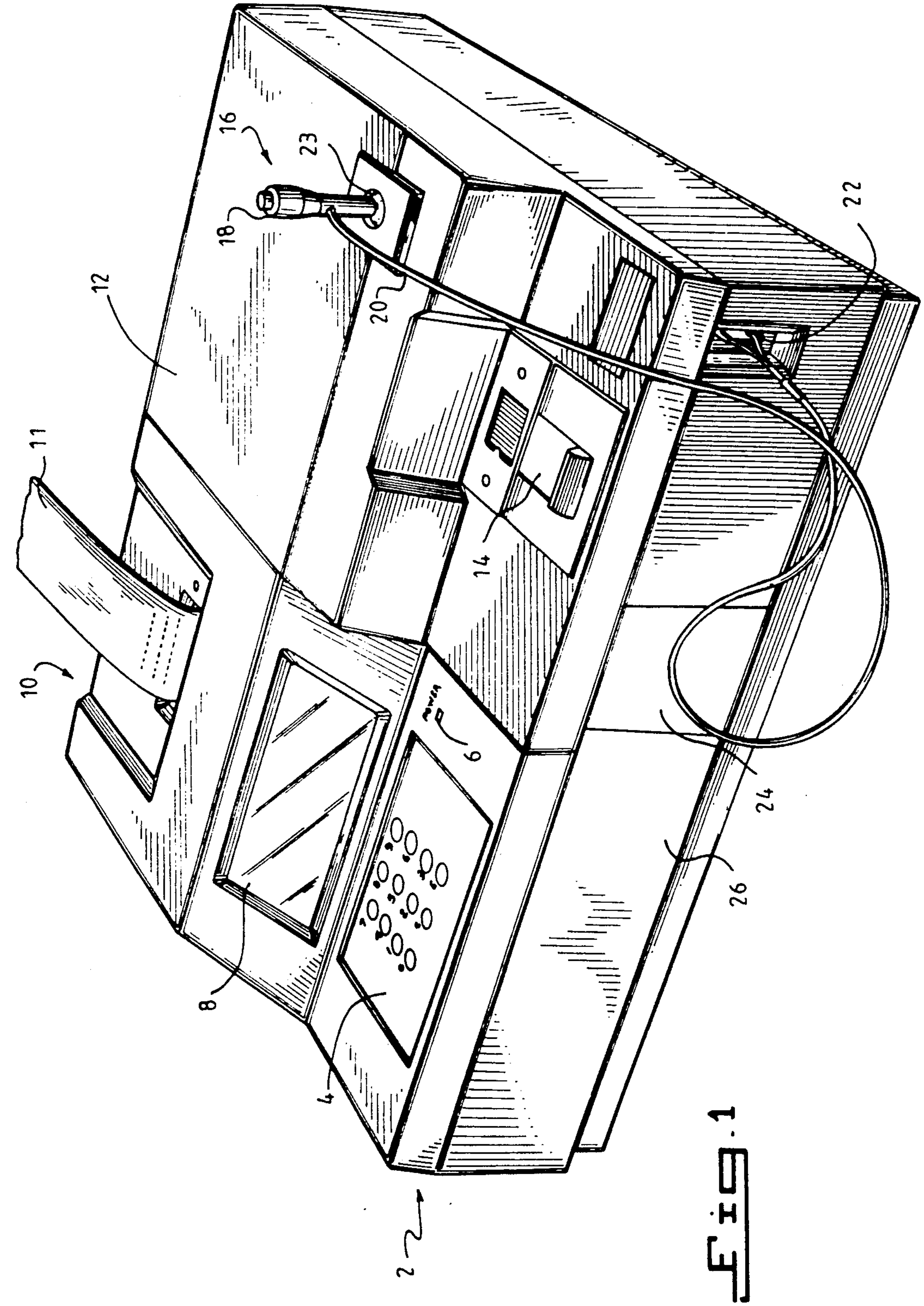
FIG. 1 is a front perspective view of a chemical analyzer formed in accordance with one form of the present invention.

Referring initially to FIG. 1 of the drawings, it will be seen that a chemical analyzer 2 formed in accordance with the present invention is a compact, desktop unit which weighs about thirty pounds. The overall dimensions of the chemical analyzer are approximately 7" in height, 19" in width, and 14" in depth. Because the unit is relatively small and lightweight, it is quite portable and may be set up conveniently on a desk or table, requiring very little space.

As can be seen from FIG. 1, the chemical analyzer 2 preferably includes a keyboard 4 for entering information and instructions to the analyzer. The keyboard 4 is preferably flush-mounted on the analyzer body, and is completely sealed and water impermeable to allow the analyzer to be easily cleaned and to prevent any malfunctions in the event that a liquid is inadvertently spilled on the keyboard.

The chemical analyzer includes a Power On indicator 6, and a display 8, which is preferably a liquid crystal display. The display 8 provides the user with diagnostic information as well as with instructions relating to the operation of the analyzer.

The chemical analyzer further includes a printer 10 so that diagnostic information and test results may be displayed in hard copy on the printer paper 11.

The chemical analyzer further includes a cover 12 which is removable to allow access to the internal mechanisms of the analyzer. As will be seen, the cover 12 protects the analyzer from dust and other contaminants which may affect the operation of the analyzer and from external light which may affect the chemical analysis.

The chemical analyzer is particularly adapted to accept test slides containing a dry analyte. Such test slides are well known in the art and are described in U.S. Pat. No. 4,647,431, which issued to Takasi, Sekine, et al.

The chemical analyzer 2 includes a slide inserter 14 which, as its name implies, is used to insert clean test slides into the analyzer. After the slides are inserted into the analyzer, a predetermined amount of serum to be analyzed will be deposited onto the test slide.

Accordingly, the chemical analyzer further includes a metering device which is shown in FIG. 1 as including a pipette assembly 16. The pipette assembly 16 includes a pipette 18 and a pipette tube 20 which interconnects the pipette to the rest of the analyzer through a connector 22. The pipette 18 is received in an opening 23 formed in the top of the cover 12 and extends partially into the analyzer.

After the chemical analyzer has completed its test of the slides, they are ejected by the analyzer into a slide tray 24. The slide tray 24 is mounted flush with the front side wall 26 of the analyzer and is slidable so that the test slides may be removed and discarded. The operation of all of the components described above in relation to FIG. 1 will again be described in greater detail.

Figure 2:
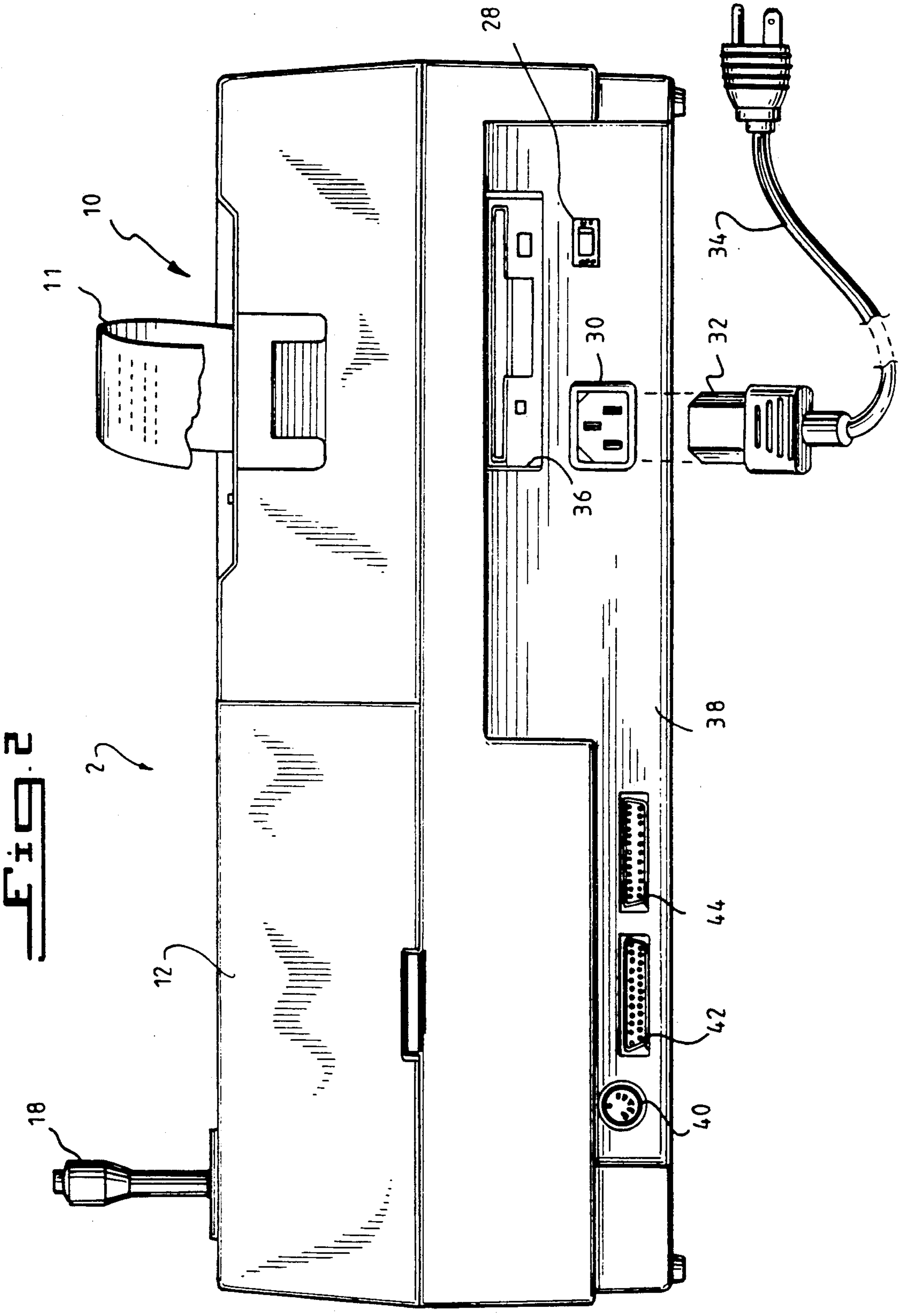
FIG. 2 is a rear perspective view of the chemical analyzer shown in FIG. 1.

FIG. 2 shows the back of the analyzer 2 in its preferred form. As can be seen from FIG. 2, the chemical analyzer includes an On/Off switch 28 which controls power to the analyzer, a standard male receptacle 30 which receives the mating female connector 32 of a grounded power line cord 34, and a disk drive assembly and reader 36 for receiving a 3½ inch computer floppy disk. The floppy disk has stored on it not only software information which controls the operation of the analyzer but also management information, such as data logging, the number of slides which have been used by the machine, leasing information (if the chemical analyzer is leased), etc.

As shown in FIG. 2, there are preferably three connectors located on the rear wall 38 of the chemical analyzer housing. The first connector 40 is a KBD type connector. It allows the chemical analyzer to interface with an external alphanumeric keyboard so that additional information in the form of alphanumeric characters may be provided to the analyzer and printed out by the printer 10 for record keeping purposes. As can be seen from FIG. 1, the keyboard 4 provided on the analyzer is rather simple and uncomplicated; however, this keyboard may be substituted with a more versatile alphanumeric keyboard, such as the one which is envisioned to be used externally and interfaced with the first connector 40.

The second connector 44 is a typical serial computer interface connector. This connector is provided for expansion purposes, for example, if the chemical analyzer is to be connected to a modem so that information may be transmitted to a central monitoring station.

The third connector 42 which is provided on the back of the chemical analyzer is adapted to plug into an external printer.

Figure 3:
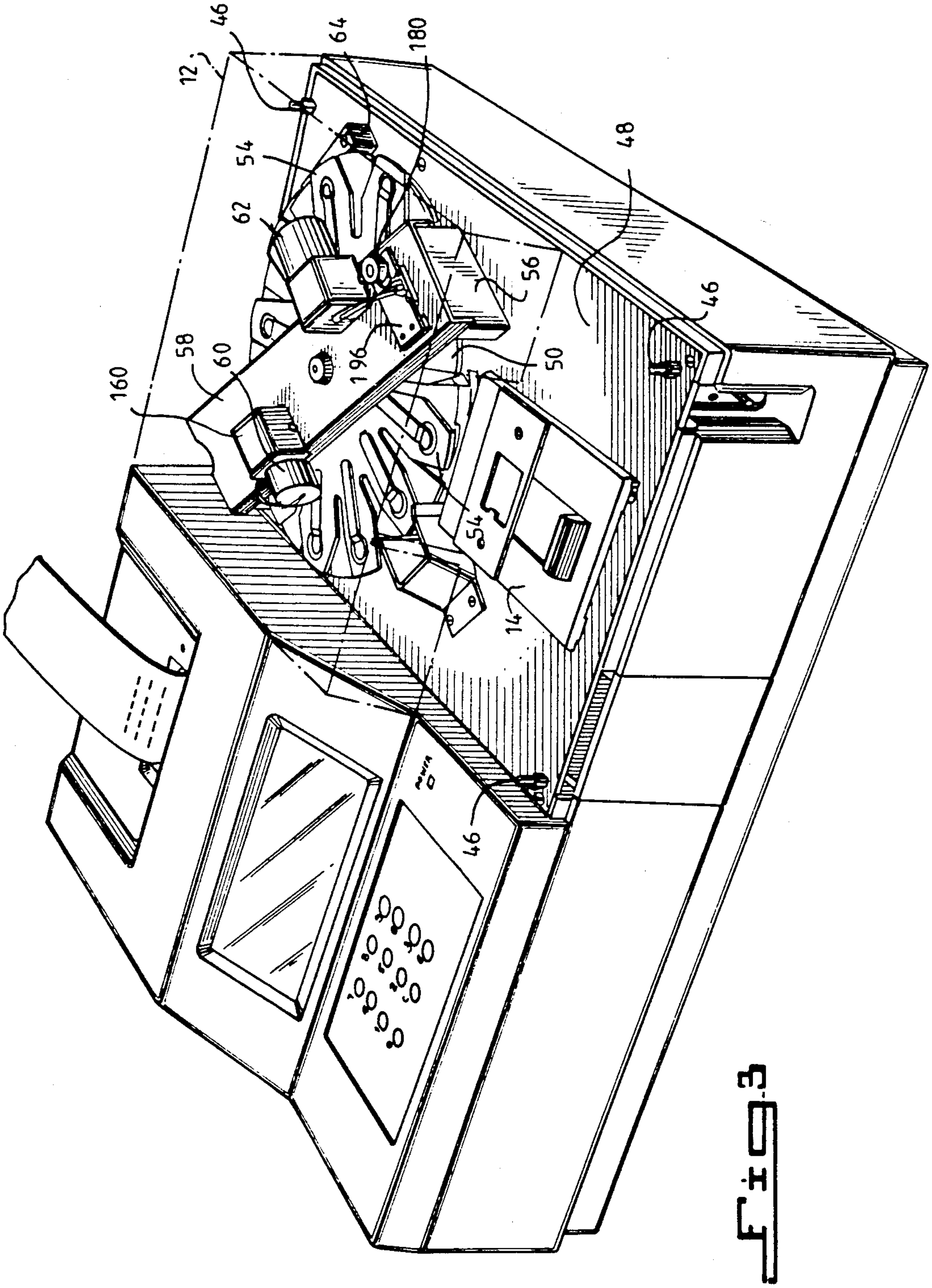
FIG. 3 is a front perspective view of the chemical analyzer shown with the cover removed.

FIG. 3 illustrates the chemical analyzer 2 with its housing cover 12 removed (but shown in phantom), which cover is normally secured to the analyzer by a plurality of posts 46 mounted on an internal base plate 48, which posts engage resilient clips (not shown) mounted on the inside surfaces of the housing cover.

As can be seen from FIG. 3, under the cover is mounted a rotatable turntable 50. The turntable 50 includes a plurality of recesses or receiving slots 52 (shown in FIG. 10A) formed in its upper surface which are adapted to receive test slides. As will be explained in greater detail, the slide inserter 14 is aligned radially with the receiving slots 52 of the rotatable turntable so that the inserter can push a test slide into a corresponding receiving slot on the rotatable turntable 50.

A cover 54 is also provided to minimize evaporation of a serum or other liquid which is deposited onto the test slide for analysis. The cover 54 is mounted on the rotatable turntable 50 and is adapted to reciprocatingly slide clockwise and counter-clockwise over the rotatable turntable to cover and uncover portions of the test slides carried by the turntable.

Two upright supports 56 are mounted on the base plate 48 on diametrically opposite sides of the rotatable turntable 50. A bridge bracket 58 is mounted on the two upright supports 56 and extends across the top of the rotatable turntable 50 and cover 54. The bridge bracket 58 supports a drive motor 60 which is provided for opening and closing the cover 54 (i.e., rotating the cover counter-clockwise and clockwise with respect to the rotatable turntable) 50, as well as another drive motor 62 which, as will be described in greater detail, provides a reciprocating vertical movement to the pipette 18 during the metering operation.

The rotatable turntable 50 transports the test slides which are spotted with a serum to be analyzed past a spectrophotometer, a portion 64 of which is shown in FIG. 3.

FIGS. 1-3 and the foregoing explanation provide a general description of the chemical analyzer of the present invention. The structure and operation of the analyzer will now be described in greater detail.

The Slide Inserter Mechanism

FIGS. 4-7 show the preferred structure of the slide inserter mechanism 14 and its relative position with respect to the rotatable turntable 50.

As mentioned previously, the test slides are manually fed to the rotatable turntable by use of the slide inserter 14. The slide inserter 14 basically includes three components: a guide plate 64, a cover plate 66 secured to the guide plate 64 and superposed on the guide plate, and a slide inserter plate 68. The slide inserter plate 68 is interposed between the cover plate 66 and the guide plate 64.

More specifically, a portion of the upper surface of the guide plate 64 is recessed to define a track 70 which extends generally longitudinally in the guide plate. The track 70 has a width which is slightly greater than that of a test slide 71 so that a test slide may be received in the track for loading into the turntable 50. In addition, the guide plate 64 includes a slot 72 which is formed through its thickness, which slot extends in a parallel direction to the track 70 formed in the surface of the guide plate.

The inserter plate 68 has a main body portion 74 which is dimensioned to be received by the track 70 formed in the guide plate 64, and an arm 76 which extends from a side of the main body portion 74. The arm 76 is L-shaped, that is, it includes a leg portion 78 which extends downwardly out of the plane in which the inserter plate primarily resides. This downward leg 78 of the arm extends through the slot 72 formed in the guide plate 64.

The inserter plate 68 further includes a grip 80 which extends upwardly from the top surface of the inserter plate and is mounted at the end of the main body 78 of inserter plate which is the most distant end from the rotatable turntable 50 when the slide inserter is properly positioned in the analyzer. The grip 80 allows a user to slide the inserter plate 68 reciprocatingly within the track 70 formed in the guide plate, in order to insert a slide in the rotatable turntable 50, as will be described.

The cover plate 66 is mounted over the guide plate 64 and secures the inserter plate 68 in place between the two and in its proper position within the track 70 formed in the guide plate. The cover plate 66 includes an elongated slot 82 formed through its thickness. The grip 80 of the inserter plate extends upwardly through this slot 82, and the slot is dimensioned to allow the grip 80 of the inserter plate to move longitudinally in the slot 82.

The cover plate 66 further includes a rectangular cutout 84 again formed through its thickness. The cutout 84 is dimensioned to be slightly larger than the peripheral dimensions of a test slide 71 so that a test slide may be inserted through the cutout and into the track 70 formed in the guide plate 64.

Figure 7:
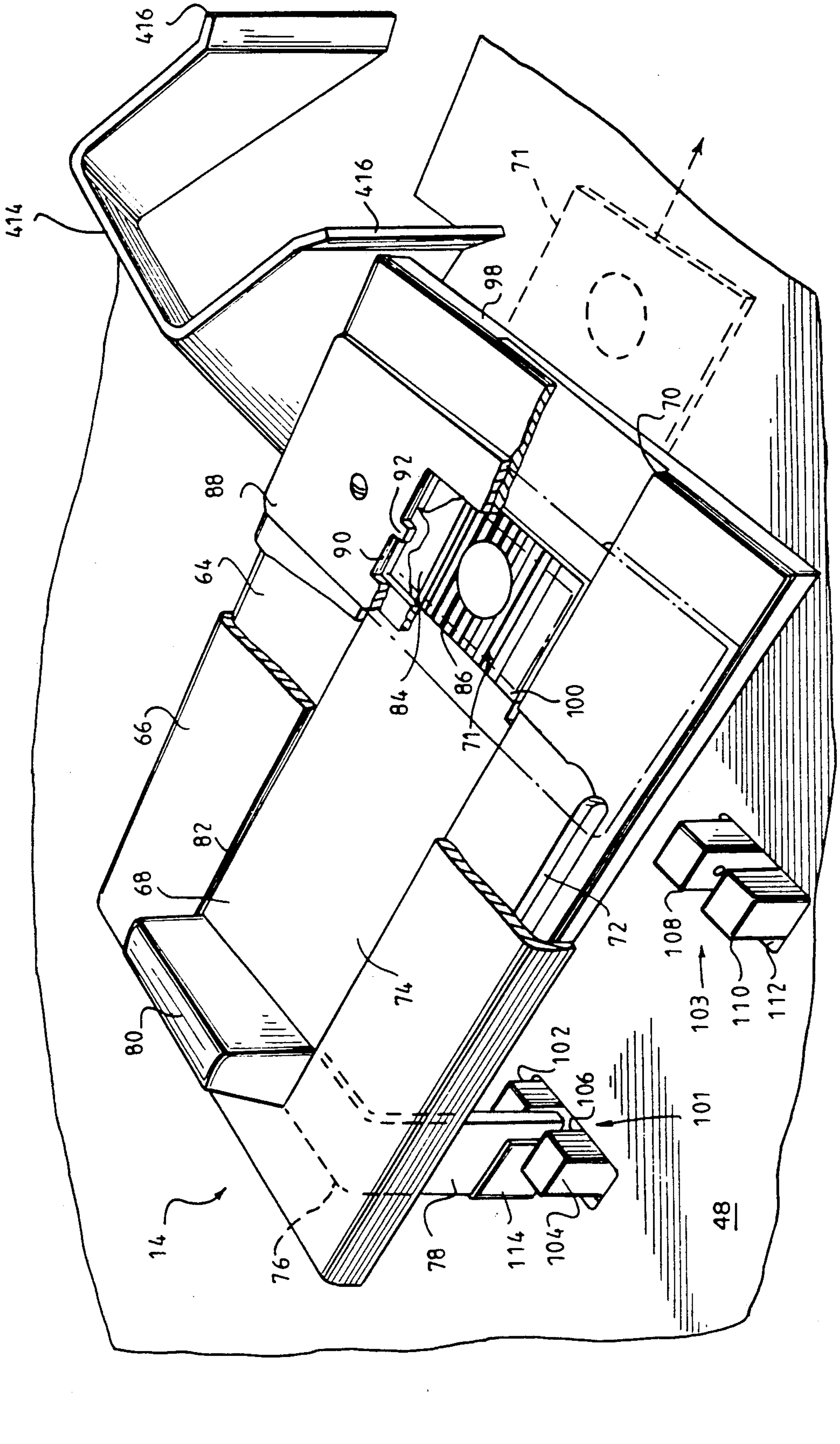
FIG. 7 is a perspective view of the inserter mechanism.

As shown in FIG. 7, the test slide 71 which is envisioned to be used with the chemical analyzer of the present invention includes a bar code 86 printed on one surface. The bar code 86 includes information concerning what type of analyte is contained on the test slide. The bar code 86 is read by the chemical analyzer, which uses this information in analyzing the test results.

The test slide 71 must be placed in a predetermined position so that the bar code 86 may be read by the analyzer and so that it may be properly received by the rotatable turntable 50. Accordingly, the slide inserter 14 may further include a slide orientation plate 88 mounted on the cover plate 66. The slide orientation plate 88 includes a slot 90 formed through its thickness having substantially the same dimensions and being aligned with the cutout 84 formed in the cover plate.

However, the slide orientation plate 88 further includes a tab 92 which extends into the slot 90 from one side. The tab 92 is adapted to align with a notch 94 (see FIG. 6) formed in a side of the conventional test slide 71. Accordingly, the user will know that the test slide 71 is properly placed in the slide inserter 14 when the notch 94 of the slide is aligned with the tab 92 on the slide orientation plate 88. Alternatively, the slot 90 and tab 92 may be formed directly in the cover plate 66 and the slide orientation plate 88 may be omitted.

Figure 5:
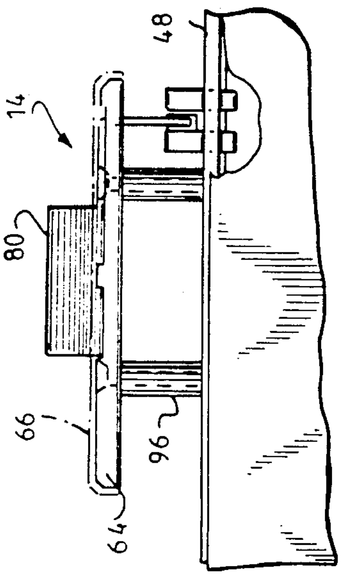
FIG. 5 is a front view of the slide inserter mechanism shown in FIG. 4.
Figure 6:
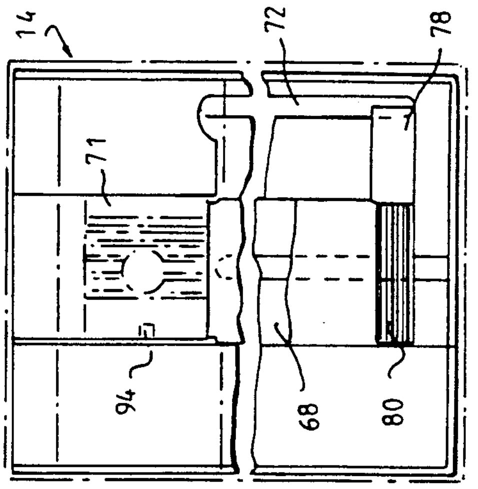
FIG. 6 is a top view of the slide inserter mechanism shown in FIG. 4, illustrating the inserter mechanism carrying a test slide.
Figure 4:
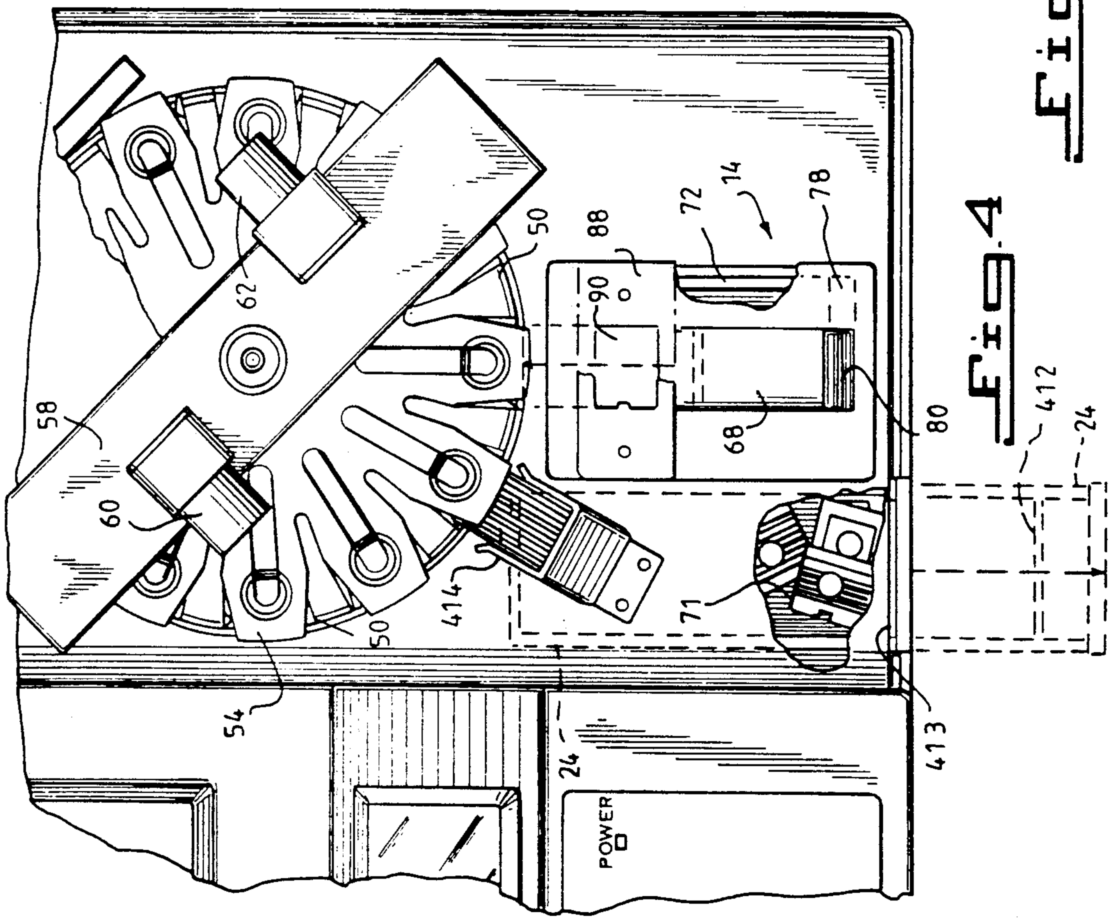
FIG. 4 is a top view of a portion of the chemical analyzer, showing a slide inserter mechanism.

As shown in FIGS. 4 and 5, the slide inserter 14 is supported above the base plate 48 of the analyzer by a plurality of stand-offs 96. The height of the slide inserter 14 is chosen to be comparable to that of the receiving slots 52 formed in the rotatable turntable 50. In this manner, slides 71 may be transferred from the slide inserter 14 to a corresponding receiving slot formed in the rotatable turntable, this action occurring in a single plane. The longitudinal axis of the slide inserter 14 is radially aligned with the rotatable turntable 50, and in particular with each corresponding receiving slot 52, of the turntable as the turntable rotates, to position a receiving slot adjacent to the end 98 of the slide inserter which is proximate to the turntable 50.

In its most fully retracted position, the inserter plate 68 allows a test slide 71 to be placed on the track 70 formed in the guide plate through the cutout 84 formed in the cover plate 66. The free end 100 of the main body of the inserter plate 68 will engage an edge of the test slide 71 when the inserter plate is moved to a forward position (i.e., towards the turntable) with respect to the guide plate 64. The inserter plate 68 will push the test slide out of the proximate end 98 of the slide inserter and into a corresponding receiving slot 52 positioned in alignment with the slide inserter 14.

Two optical sensors 101, 103 are associated with the slide inserter 14. The first optical sensor 101 includes a first pair of an LED light source 102 and a photodetector (ex., phototransistor) 104 spaced apart from each other and extending upwardly through an opening 106 formed through the thickness of the base plate 48. Similarly, the second optical sensor 103 includes a second pair of a light source 108 and photodetector 110, also spaced apart from each other, which extend upwardly through a second opening 112 formed in the base plate. The first and second pairs are separated from each other by a predetermined distance.

The first pair of light source and photodetector 102, 104 is positioned with respect to the slide inserter 14 such that the downwardly projecting leg 78 of the inserter plate is interposed between the light source 102 and the photodetector 104 of the first pair when the inserter plate 68 is in its fully retracted position (i.e., away from the turntable). The second pair of light source and photodetector 108, 110 is positioned with respect to the slide inserter 14 such that the downwardly projecting leg 78 of the inserter plate is interposed between the light source and photodetector of the second pair when the inserter plate 68 is in its fully forward position.

The light sources 102, 108 of each pair provide a light beam which extend between the light source and photodetector 104, 110 of each pair. The downwardly extending leg 78 breaks the light beam of the first pair when the inserter plate 68 is fully retracted, and breaks the light beam of the second pair when the inserter plate 68 is in its fully forward position.

The first and second pairs of light sources and photodetectors are used to signal the computer of the analyzer that the inserter plate 68 of the slide inserter 14 is in the fully retracted position, indicating that the slide inserter is ready to accept a new test slide 71 for loading, or in its fully forward position, indicating that a slide has now been fully inserted into the receiving slot 52 of the rotatable turntable by the slide inserter.

Accordingly, the procedure for loading test slides into the rotatable turntable is as follows: grasp the grip 80 of the inserter plate and pull the inserter plate backwards until it is in its fully retracted position; orient a new test slide 71 so that its notch 94 is aligned with the tab 92 formed in the slide orientation plate, and place the test slide through the slide orientation plate and the cutout 84 formed in the cover plate, so that the test slide will drop into the track 70 formed in the guide plate; and push the inserter plate 68 by using the grip to its most forward position. The main body 74 of the inserter plate will slide in the track 70 of the guide plate and push the test slide into a receiving slot 52 which is aligned with the proximate end 98 of the slide inserter 14. The computer associated with the analyzer will know that the test slide 71 has been loaded into the receiving slot 52 when the downwardly projecting leg 78 of the inserter plate breaks the light beam of the second pair of light source and photodetector 108, 110.

When the inserter plate 68 is again fully retracted, the leg 78 will break the light beam of the first pair of light source and photodetector 102, 104. The associated computer will sense the disturbance in the light beam as an indication that the slide inserter is again ready for loading, and it will signal the drive mechanism associated with the turntable 50 to rotate the turntable so that the next adjacent slide receiving slot 52 formed in the turntable is positioned in alignment with the proximate end 98 of the slide inserter 14.

Although it is shown in FIGS. 5 and 7 that separate light sources 102, 108 and photodetectors 106, 110 are used to sense the position of the inserter plate 68 with respect to the rest of the slide inserter 14, it is envisioned that the light source and photodetector of each pair may be formed as a single unit on one side of the downwardly extending leg 78 and positioned on the base plate 48 in the same position as the first and second pairs of light sources and photodetectors shown in the drawings. This is a reflective type of optical sensor, such as Part No. GP2L02 manufactured by Sharp Electric Company. The light beam produced by the light source of such a sensor is reflected from the downwardly projecting leg 78 back to the photodetector integrally formed with the light source in order to indicate the position of the inserter plate 68. If such a reflective type of sensor is used, a light reflective foil or covering 114 may be placed on the downwardly extending leg 78 to enhance the reflectivity of the leg.

Figure 7A:
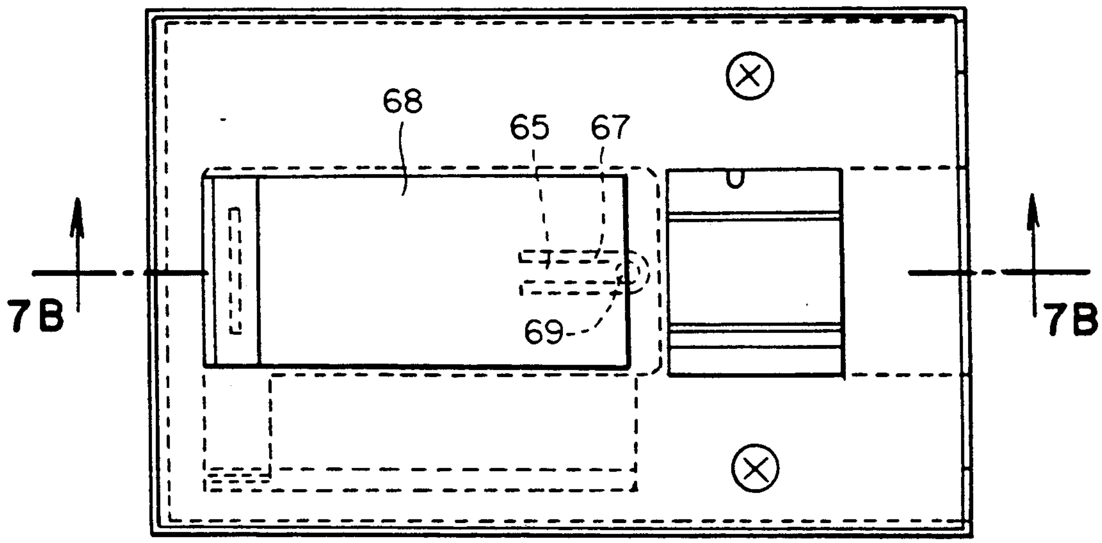
FIG. 7A is a top planar view of another embodiment of the slide inserter.
Figure 7B:
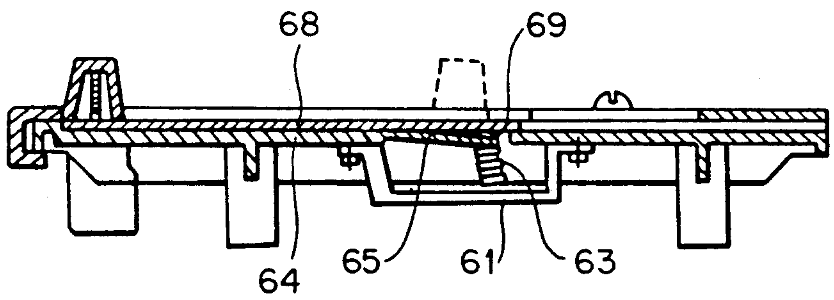
FIG. 7B is a sectional view of the slide inserter shown in FIG. 7A taken along line 7B-7B of FIG. 7A.

An alternative embodiment of the slide inserter mechanism is shown in FIGS. 7A and 7B. To prevent the inserter plate 68 from inadvertent movement due to vibration of the analyzer, the guide plate 64 may include a resilient U-shaped leaf 65 and a cutout 67 partially surrounding the leaf. The free end of the resilient leaf 65 includes a protuberance or button 69. A coil spring 63 may be positioned between the leaf and a bracket 61 suspended from and mounted to the underside cf the guide plate 64. The spring 63 is compressed between the leaf 65 and the bracket 61 and thus exerts a force on the leaf. The leaf button 69 engages the underside of the inserter plate 68. This provides sufficient friction between the guide plate 64 and the inserter plate 68 to maintain the inserter plate 64 in its desired position.

The Rotatable Turntable And Slide Cover

Figure 10:
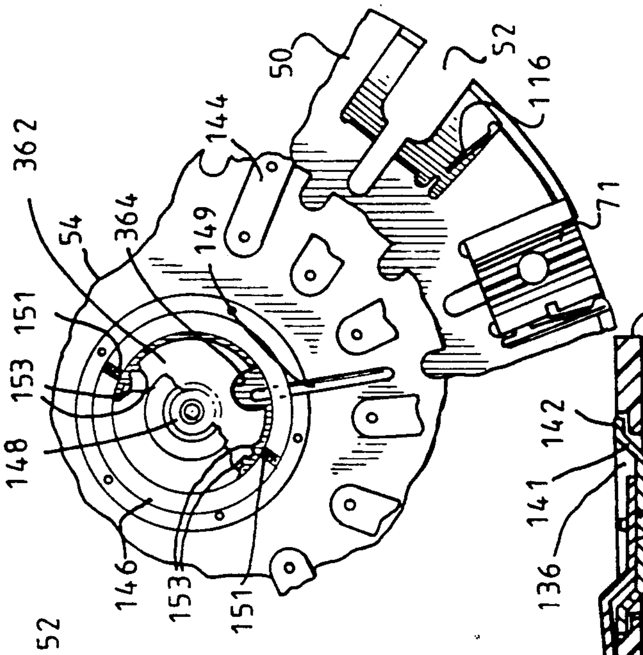
FIG. 10 is a top view partially broken away of the turntable and cover illustrating how the test slides are received by the turntable.
Figure 9:
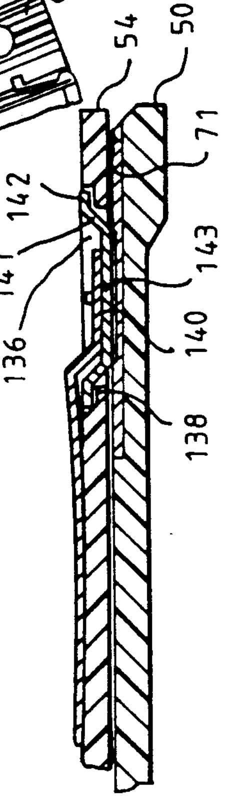
FIG. 9 is a sectional view of the turntable and cover taken along line 9—9 of FIG. 8.
Figure 8:
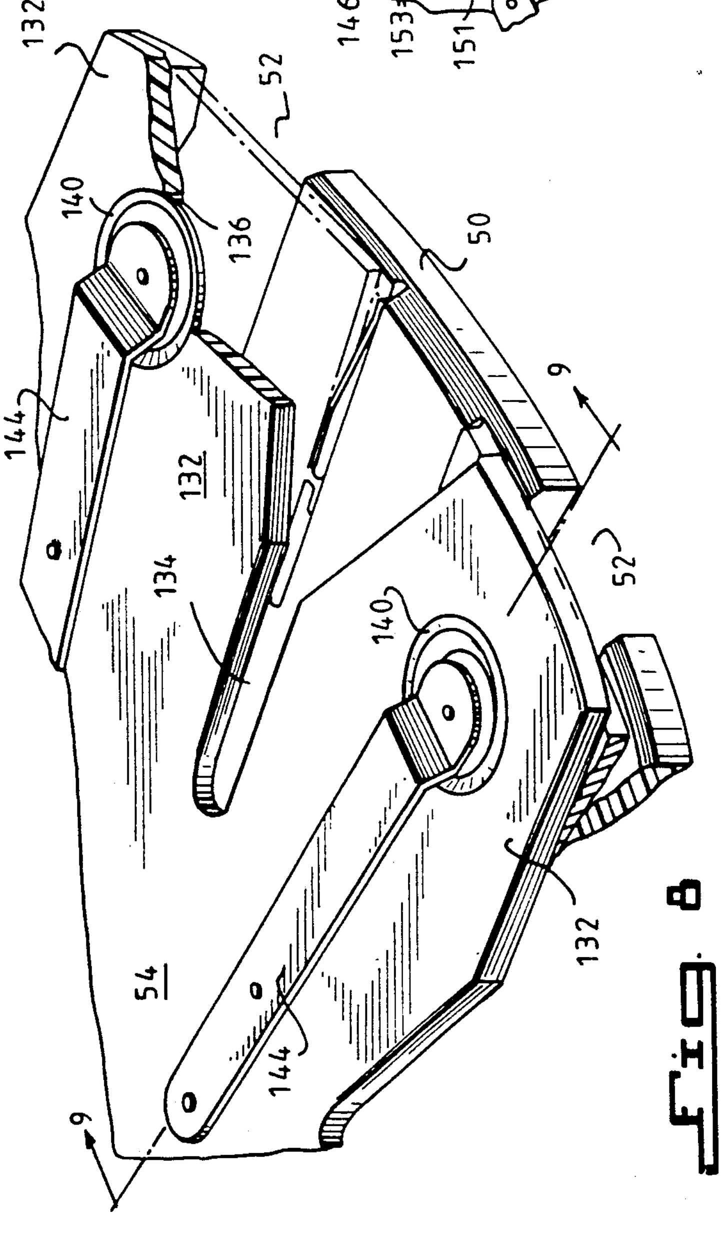
FIG. 8 is a partial perspective view of the turntable and cover of the chemical analyzer.
Figure 10A:
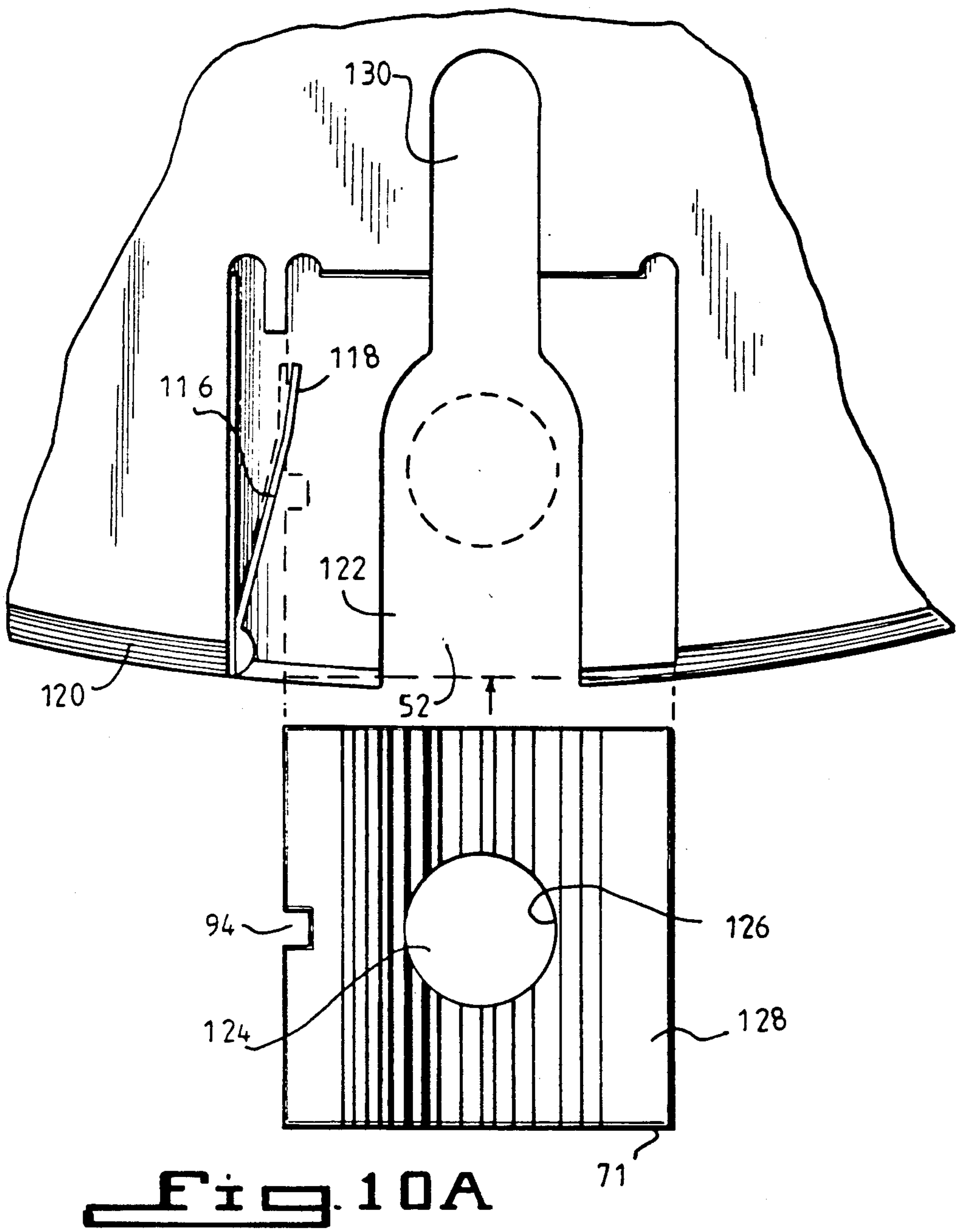
FIG. 10A is a top view partially broken away of the cover and turntable illustrating the position of the test slide before and after it is received by the turntable.
Figure 10B:
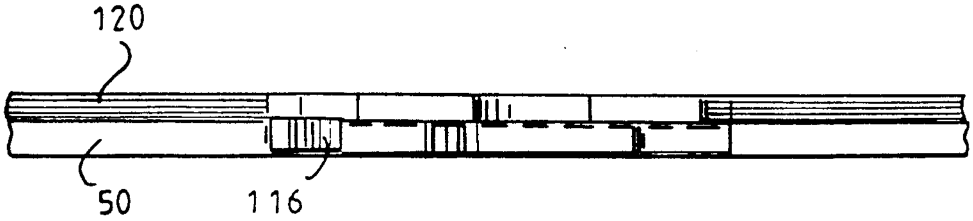
FIG. 10B is a front view of the turntable and cover and test slide shown in FIG. 10A.

FIGS. 8–10 show in greater detail the rotatable turntable 50 and slide cover 54 of the chemical analyzer in their preferred form, and illustrate how a test slide is received by the rotatable turntable and held in place.

Portions of the top surface of the rotatable turntable are recessed to define a plurality of slide receiving slots 52. Each slot 52 is dimensioned to be just slightly larger than the dimensions of a test slide 71.

A leaf spring 116 is mounted on one side of each receiving slot and, in its unbiased state, has its free end 118 extending slightly into the area of the receiving slot 52 into which the test slide is inserted. Accordingly, the leaf spring 116 exerts pressure on one edge of a test slide received by the slot 52 so that the opposite edge of the test slide abuts against the opposite side wall of the receiving slot. The action of the leaf spring 116 ensures that the test slide 71 is in its proper position in the receiving slot 52.

In its preferred form, the rotatable turntable 50 is formed with twelve receiving slots 52 spaced equidistantly around its peripheral circumference, with each receiving slot 52 having an open side 118 at the periphery of the turntable. The test slides 71 are inserted into their receiving slots 52 through the open sides 118, and are held in place by the leaf springs 116. Also, in its preferred form, the top corner of the turntable includes a bevelled edge 120 which will facilitate the slide's transfer from the inserter 14 to the turntable.

Openings 122 are formed through the thickness of the rotatable turntable 50 at the centers of the recessed portions defining the receiving slots 52. The openings 122 are provided so that light emitted by the reflectometer positioned beneath the rotatable turntable may impinge on the film portion 124 of the test slide 71 on which is deposited the dry analyte. The openings 122 are dimensioned to be slightly greater than the diameter of an opening 126 formed in the frame 128 of the test slide which exposes the analyte film.

Furthermore, a plurality of radially extending slots 130 are formed through the thickness of the turntable 50, each slot 130 being in communication with the receiving slot 52 and the opening 122 formed in each receiving slot. The radially extending slots 130 are provided for the slide ejector mechanism to push the slides out of the receiving slot 52 after the test has been completed, as will be described in greater detail.

As mentioned previously, a cover 54 is provided to minimize evaporation of the serum sample deposited on the test slides 71. As shown in FIG. 8, the cover 54 is mounted concentrically on the rotatable turntable 50 over its top surface, and generally is configured to define a plurality of radially extending fingers 132, each finger 132 being separated by its adjacent finger by an open ended slot 134 having a "V" shaped area. Each finger 132 of the cover includes an opening 136 formed through its thickness. The side walls of the cover which define the openings 136 are stepped inwardly to define a shoulder 138.

A plurality of button members 140 are mounted on the cover 54, each button member 140 being received by a corresponding opening 136. The button members 140 include peripheral lips 142 which are adapted to rest on the shoulders 138 defining the cover openings 136. The button members 140 extend slightly below the lower surface of the cover 54. Each button member further includes a tapered or sloping side wall 141 extending to an exposed circular surface 143, which surface has a diameter that is at least slightly greater than that of the test slide opening 126.

The button members 140 may be coated at least on their bottom surfaces with an essentially inert and nonabsorbing material, such as teflon TM. The coating not only reduces friction during the cover opening and closing motions, but also does not absorb gases which may be produced as the result of chemical reactions on the test slides. Such gases, if trapped in the cover material, could affect the results of the subsequent tests.

A plurality of leaf springs 144 are mounted on the upper surface of the cover 54 and extend radially. Each leaf spring 144 has a free end on which a button member 140 is mounted. The leaf springs 144 exert pressure on the button members 140 to bias the button members downwardly in the cover openings 136 so that the lips 142 of the button members engage the shoulders 138 defining the cover openings.

The cover 54 is attached to a supporting collar 146, which collar 146 has a central opening to receive a spindle 148 on which the rotatable turntable 50 and the cover 54 are mounted. Extending radially from the collar 146 is a pin 149 which, as will be described in greater detail, is used in rotating the cover 54 clockwise and counter-clockwise in order to cover and uncover the film portion 124 of each test slide 71 mounted on the rotatable turntable.

The cover is maintained in alignment with the rotatable turntable 50 by a pair of spring loaded ball bearings 151 positioned diametrically opposite one another on the collar 146 of the cover, each ball bearing 151 being partially received by one of two detents of two pairs of adjacent detents 153 formed in the hub 362 retaining the turntable to the spindle 148. The detents 153 are particularly positioned so that, when the ball bearings 151 of each pair engage one detent, of each pair of detents, the cover 54 will be in the closed position, that is, covering the receiving slot 52 and in particular the film portion 124 of a test slide located in the receiving slot, and when the ball bearings 151 of each pair are received in the other detent 153 of each pair of detents, the cover will be in the open position, that is, where the receiving slot 52 and in particular the film portion of a test slide located in the receiving slot is uncovered.

Figure 8A:
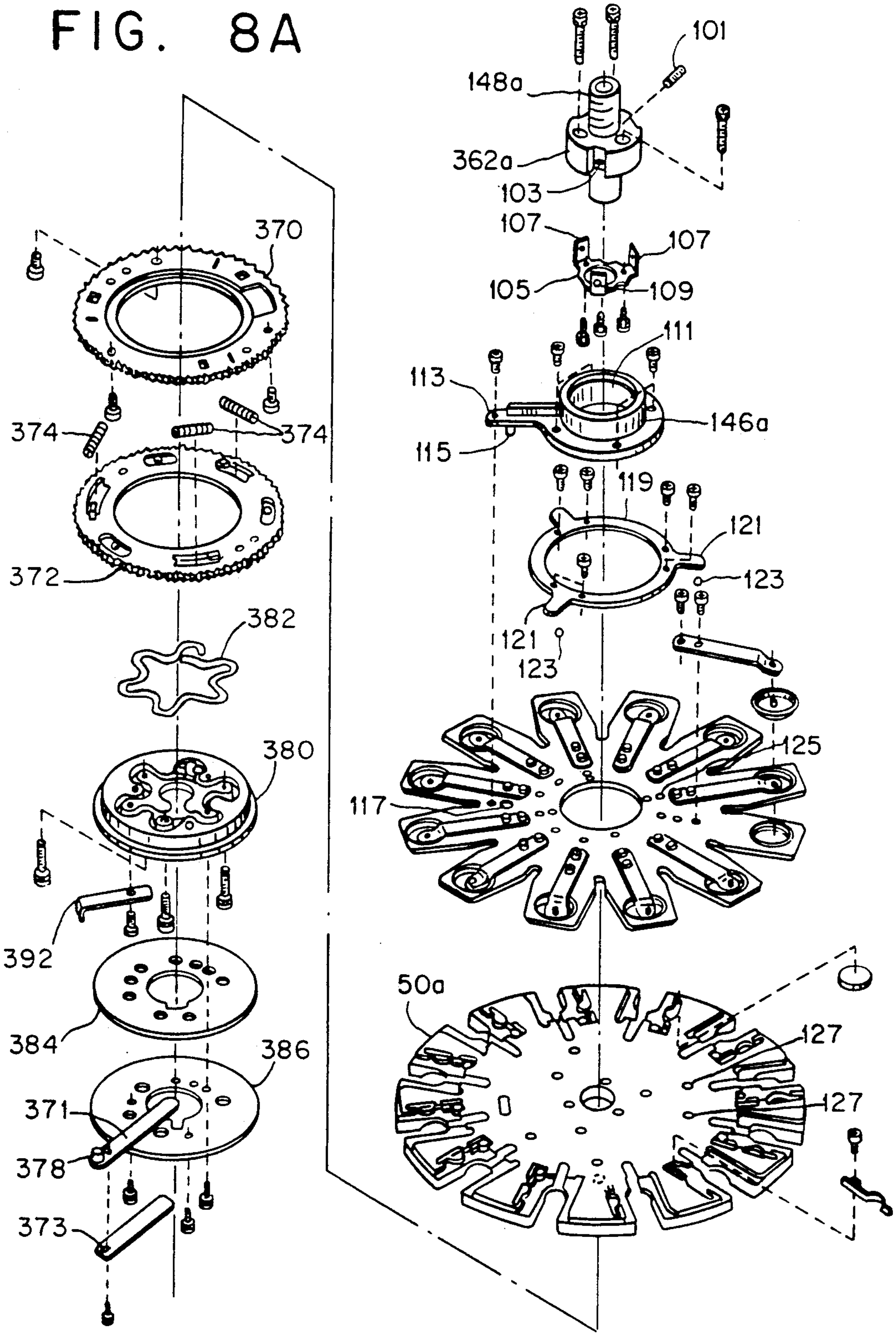
FIG. 8A is an exploded view, in perspective, of an alternative form of the turntable and cover.

An alternative form of the cover-to-turntable alignment mechanism is shown in the exploded view of FIG. 8A.

A hub member **362*a* is mounted to the vertical spindle 148*a* by a set screw 101. The hub member 362*a* includes three recesses 103 formed in its circumferential surface. An inner spring clip 105 having three upwardly extending resilient leafs 107 is mounted on the top surface of the rotatable turntable 50*a* at its center. The three leafs 107 fit into the three recesses 103 of the hub when compressed. Each leaf 107 includes an outward dimple or protrusion 109**.

A collar member **146*a* includes an axial bore 111 into which the hub 362*a* fits. The inner sidewalls of the collar defining the bore 111 include grooves (not shown), which are engaged by the protrusions 109 on the spring clip, due to the expansion of the clip inside the collar. The inner spring clip 105 takes up any play between the collar and hub and ensures proper vertical positioning of collar 146*a* on the spindle 148*a***.

The collar **146*a* has an arm 113 extending radially outwardly. The arm includes a pin 115 mounted on it and extending downwardly. The pin 115 engages an alignment hole 117 formed in the cover 54*a*, and the collar is fixedly mounted on the cover so that the collar 146*a* and the cover 54*a*** rotate together.

Interposed between the collar **146*a* and the cover 54*a* is a preferably one piece, circular leaf spring 119. The leaf spring 119 includes three radially extending resilient arms 121. Positioned beneath each arm 121 is a ball bearing 123. The ball bearings 123 are at least partially received by holes 125 formed through the thickness of the cover 54*a***.

Three pairs of detents or recesses 127 are formed in the top surface of the turntable **50*a*. The detents of each pair are separated from each other a predetermined distance (sufficient to allow the cover 54*a* to cover and uncover the receiving slots 52), and each pair is situated arcuately on the turntable and in alignment with a respective ball bearing-receiving hole 125. The force exerted on the ball bearings 123 by the arms 121 of the leaf spring causes the ball bearings 123 to engage one detent 127 of each pair. The position of the cover 54*a* relative to the turntable 50*a*** is thus maintained until a sufficient force is exerted on the cover to cause the ball bearings to move into the other detent of each pair of detents. Accordingly, the cover may be maintained in either an open or a closed position.

Figure 9A:
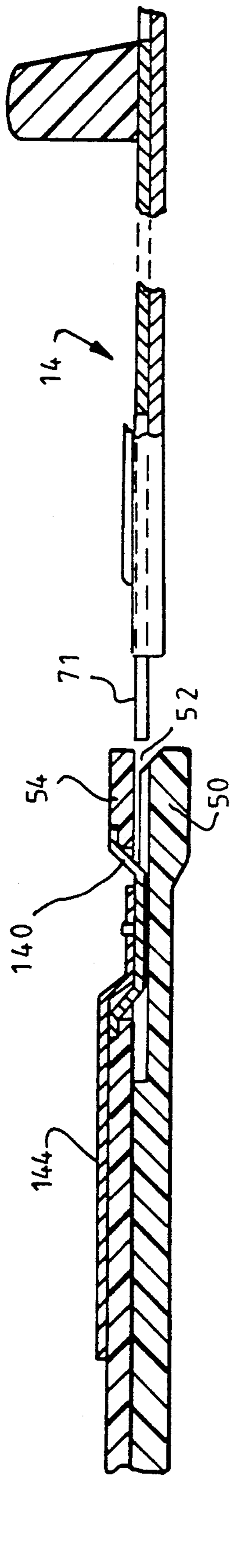
FIG. 9A is a sectional view of the turntable and cover and inserter mechanism, prior to a slide being received by the turntable.
Figure 9B:
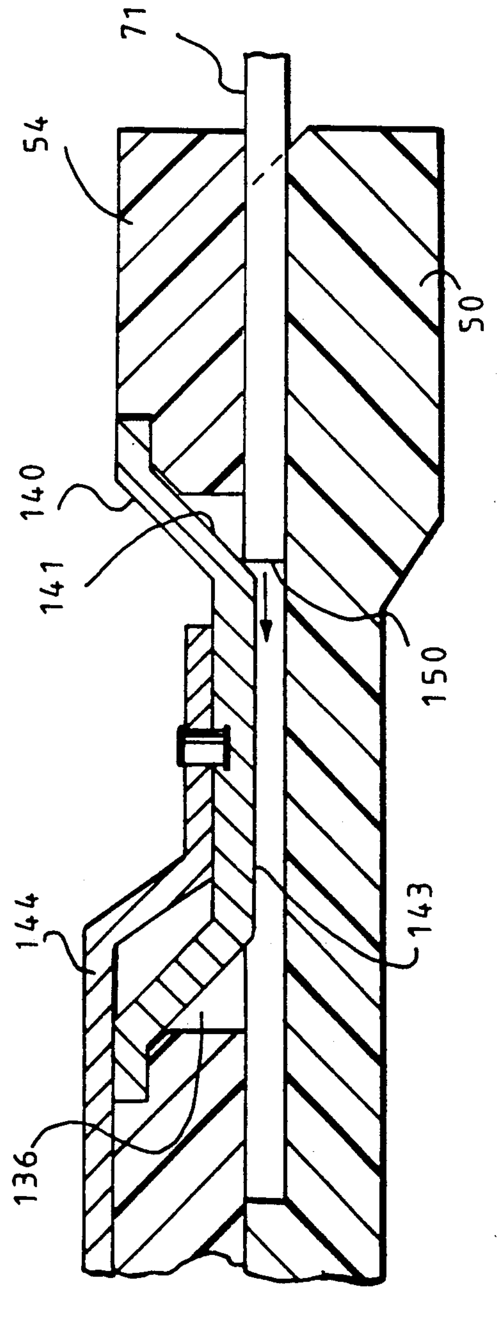
FIG. 9B is a sectional view of the turntable and cover, illustrating the test slide being received by the turntable.

FIGS. 9, 9A and 9B illustrate the sequence of loading a test slide 71 onto the rotatable turntable 50. In FIG. 9A, the slide inserter 14 is illustrated as pushing a test slide 71 into a receiving slot 52 of the turntable and between the turntable 50 and the cover 54. As stated previously, the slide inserter 14 is positioned above the base plate 48 of the analyzer at the same level as the rotatable turntable 50 so that the test slide resides in the same plane in which the receiving slots 52 the turntable are formed. This, of course, facilitates insertion of the test slides into the receiving slots.

FIG. 9B illustrates the test slide 71 being partially received by the receiving slot 52 of the rotatable turntable. The edge 150 of the test slide 71 engages the sloped side wall 141 of the button member 140, which is biased downwardly to extend below the lower surface of the cover, and the test slide will push the button member upwardly in its respective cover opening 136.

FIG. 9 illustrates the test slide 71 being fully received by the slot of the rotatable turntable 50. The button member 140 is deflected by the test slide 71 and, due to the action of the leaf spring 144, exerts a pressure on the test slide and, as shown in FIG. 9, fully covers one side of the exposed analyte film 124 of the test slide, which side of the film will receive a predetermined amount of blood serum to be analyzed.

Figure 11:
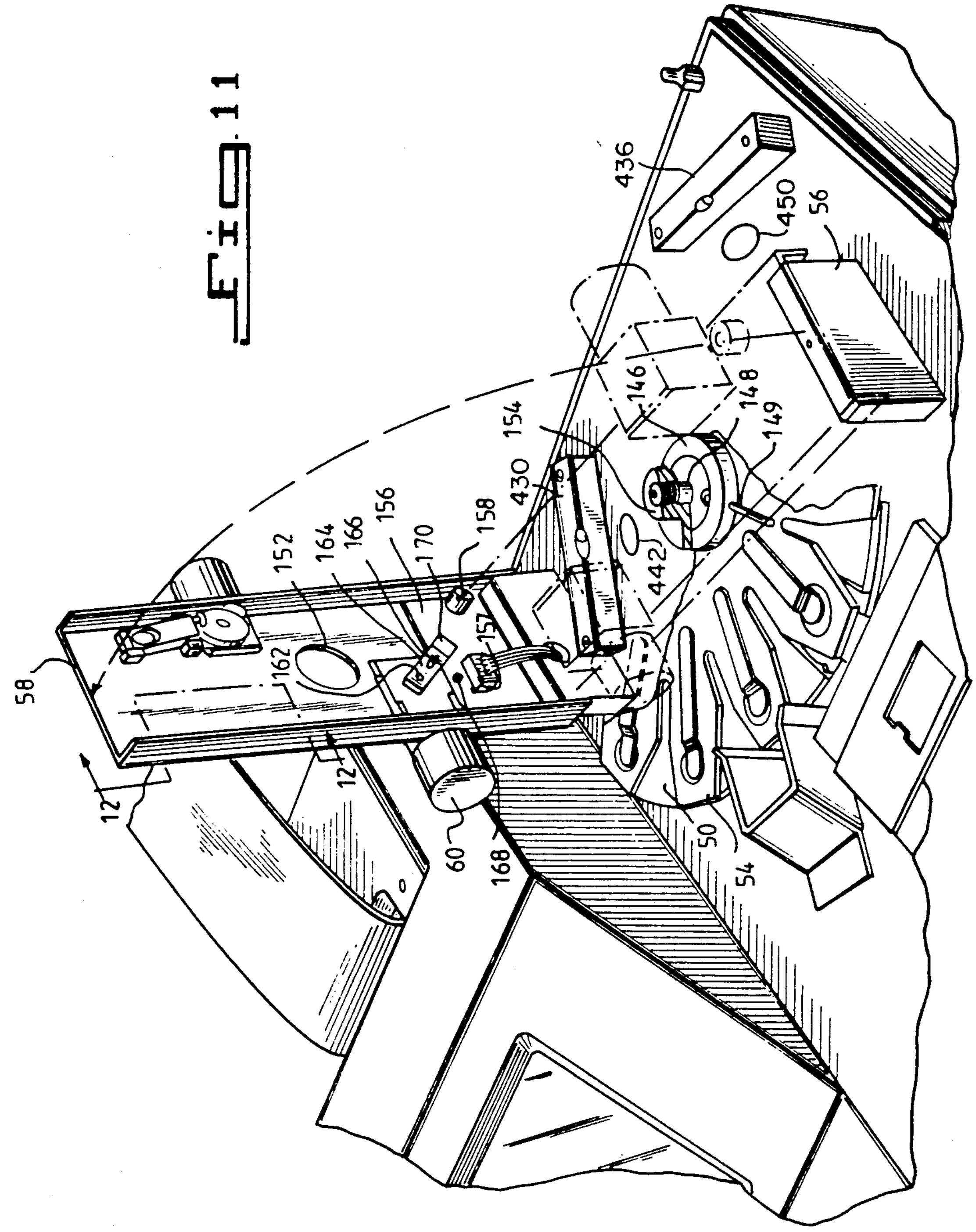
FIG. 11 is a perspective view of a portion of the analyzer in a raised and unraised position.
Figure 13:
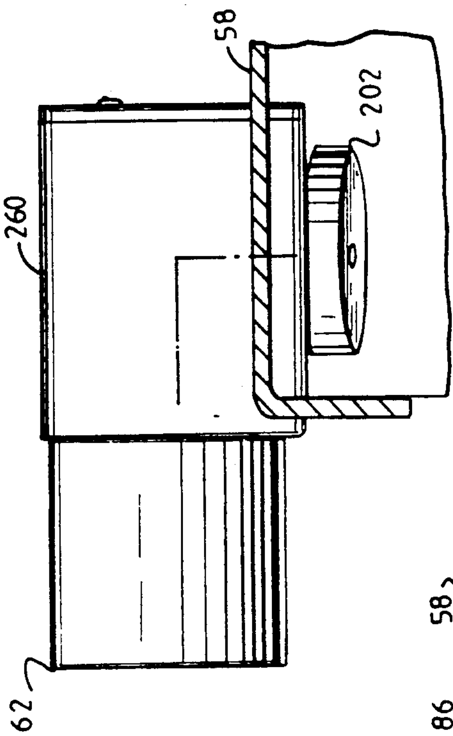
FIG. 13 is a sectional view of a portion of the analyzer shown in FIG. 12, taken along line 13—13 of FIG. 12

FIG. 11 illustrates the bridge bracket 58 shown in FIG. 3 in a raised position. As previously mentioned, the bridge bracket 58 is mounted over the cover 54 and rotatable turntable 50 and is supported at its ends by two upright supports 56. The bridge bracket 58 basically includes an elongated plate which is bent C-shape in cross-section and which is used to support a number of components of the chemical analyzer. The bridge bracket 58 is pivotally mounted on one of the supports 56 so that it may be raised to an upright position, as shown in solid lines in FIG. 11, or lowered to a second position bridging the rotatable turntable 50 and cover 54, as shown in phantom in FIG. 11.

A central opening 152 is formed in the bridge bracket 58 so that the bracket does not interfere with the spindle 148 on which the cover and rotatable turntable are mounted. The bridge bracket 58 may be conveniently raised to facilitate cleaning the cover and rotatable turntable of the analyzer and for easily accessing these components for any maintenance or repairs. It should be noted in FIG. 11 that a knurled knob 154 is screw-threaded onto the spindle 148 over the collar 146 of the cover. This knob 154 may be removed quite easily so that the cover 54 may be easily lifted from the spindle on which it is mounted.

Several additional components of the chemical analyzer of the present invention are shown in FIG. 11 On the underside of the bridge bracket 58 is mounted a printed circuit board 156. The printed circuit board 156 is coupled to the rest of the circuitry of the analyzer through a ccnnector 157. An optical code reader 158 is mounted on the printed circuit board 156. When the bridge bracket 58 is in the lowered position, the optical code reader 158 is positioned directly above the test slides 71 mounted in the receiving slots 52 of the rotatable turntable.

The optical code reader 158 senses the bar codes 86 on the top side of the test slides, and provides this information to the computer which interprets the bar code information and determines what tests are to be performed.

To enable the optical code reader 158 to read the bar codes, the cover 54 is rotated with respect to the turntable 50 so as to uncover a major portion of the test slides. In other words, the test slides 71, and in particular the bar codes 86 on the test slides, are exposed between the open "V" shaped area of the slots 134 formed in the cover. During the initial operation of the analyzer, and after the test slides have been loaded onto the turntable 50, the turntable is rotated such that each test slide 71 passes one by one under the optical code reader 158.

As mentioned previously, the cover 54 is adapted to rotate clockwise and counter-clockwise with respect to the turntable 50 in order to cover and uncover the test slides mounted on the turntable. Only a small arcuate rotation is needed to uncover the slides 71; for example, if the turntable 50 is configurated with 12 receiving slots 52, the cover 54 need only rotate 15 degrees in either direction in order to cover and uncover the test slides.

Referring for the moment to FIG. 3 of the drawings, it is seen that a reversible DC drive motor 60 is mounted on the top surface of the bridge bracket 58. The shaft of the drive motor 60 is connected to an L-drive reduction gear box 160, which gear box 160 includes a vertical shaft 162 extending through the bridge bracket 58.

Again referring to FIG. 11 of the drawings, an elongated pivot block 164 is mounted on the vertical shaft 162 of the gear box near one of its ends. A pin 166 protrudes from the underside of the pivot block 164.

When the bridge bracket 58 is in its lowered position, the pin 168 extends far enough below the pivot block 166 to engage the radially extending pin 149 of the cover collar 146.

In order to uncover the test slides, the turntable 50 (and cover 54) are rotated with the spindle 148 by the turntable drive motor until the cover pin 149 extends substantially beneath the pin block 164. The drive motor 60 is then energized to rotate in one direction such that the pin 166 on the pivot block 164 engages the cover pin 149, causing the cover to rotate with respect to the turntable. During this action, the turntable 50 is maintained in its present position so that it does not rotate with the cover 54. The pivot block 164 will sweep through a full 360 degree rotation, but the cover 54 need only rotate about 15 degrees due to the action of the pivot block 164 and pin 166 in order to uncover the test slides.

To cover the slides, the DC motor 60 is energized with a voltage of opposite polarity so that the pivot block 164 now rotates in the opposite direction. The pin 166 will again engage the cover pin 149 so that the cover will rotate with respect to the turntable about 15 degrees in the opposite direction to cover the test slides.

An optical sensor 168, which may be the reflective type, is mounted on the printed circuit board 156 directly below the end of the pivot block 164 which is opposite to the end at which the block is mounted to the gear box shaft 162. A reflective foil or tape 170 surrounds the end of the pivot block 164.

When the cover has to be rotated, the associated electronics and computer of the analyzer causes the DC motor to be energized. The pivot block 164 will rotate in one direction until the reflective foil 170 is positioned over the optical sensor 168, which will be a full 360 degree rotation. The sensor 168 will detect the presence of the end of the pivot block 164 and signal the computer of the analyzer, which will then de-energize the drive motor 60. Thus, the optical sensor will always sense when a full rotation of the pivot block 164 has occurred, either clockwise or counter-clockwise, which will indirectly indicate that the operation of covering or uncovering the test slides has been completed.

Figure 22:
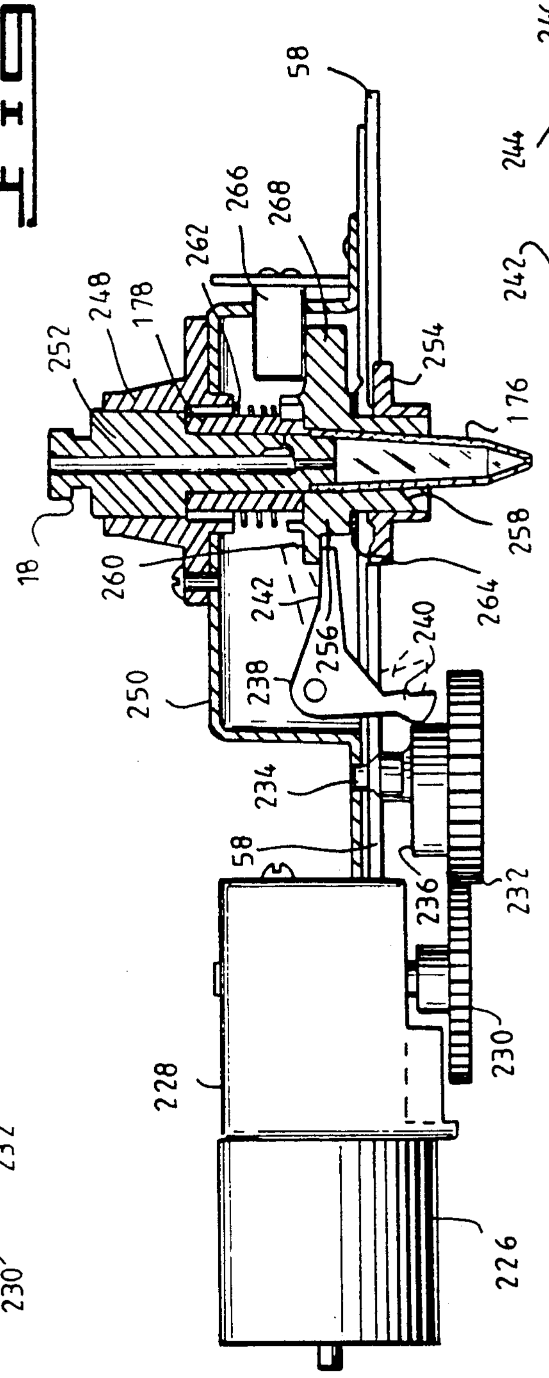
FIG. 22 is a side elevational view, partially in section, of an alternative embodiment of a metering device used in the analyzer of the present invention.
Figure 22B:
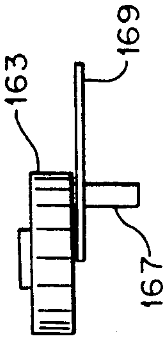
FIG. 22B is a side view of a portion of the cover opening mechanism.
Figure 22A:
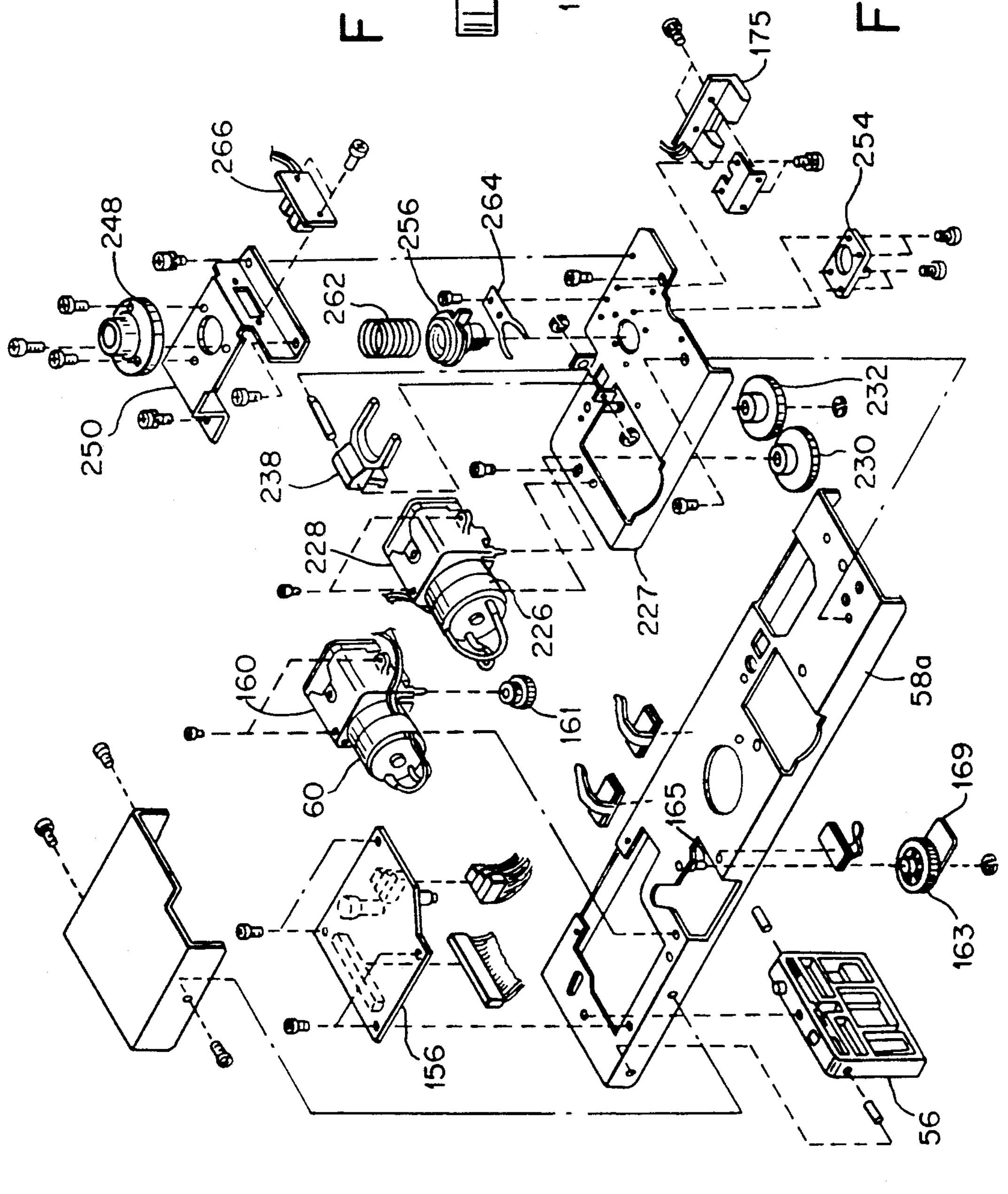
FIG. 22A is an exploded view, in perspective, of an alternative embodiment of a cover opening mechanism and of the metering device shown in FIG. 22.
Figure 26:
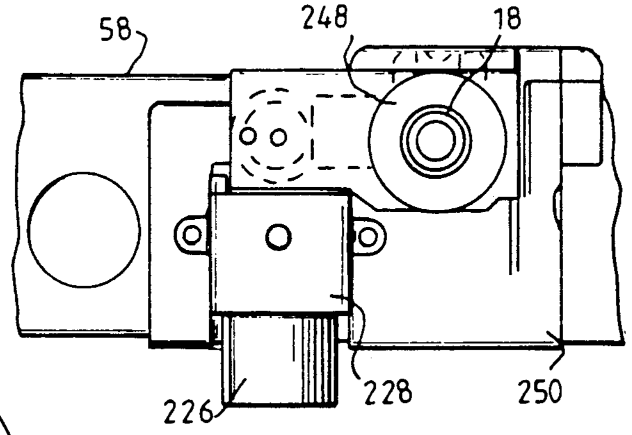
FIG. 26 is a top elevational view of the metering device shown in FIG. 25.
Figure 30:
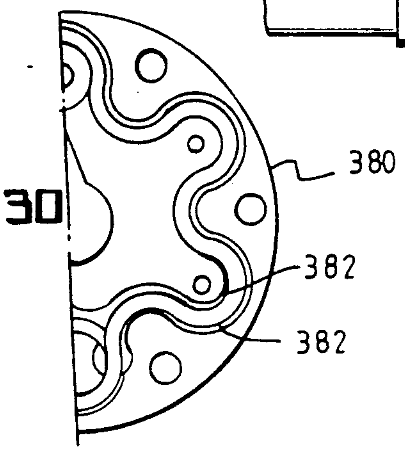
FIG. 30 is a partial bottom view of a heater mechanism for the turntable of the present invention.
Figure 25:
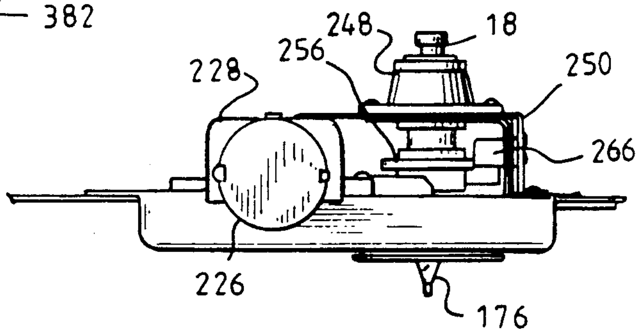
FIG. 25 is a front elevational view of the metering device of FIG. 22.
Figure 29:
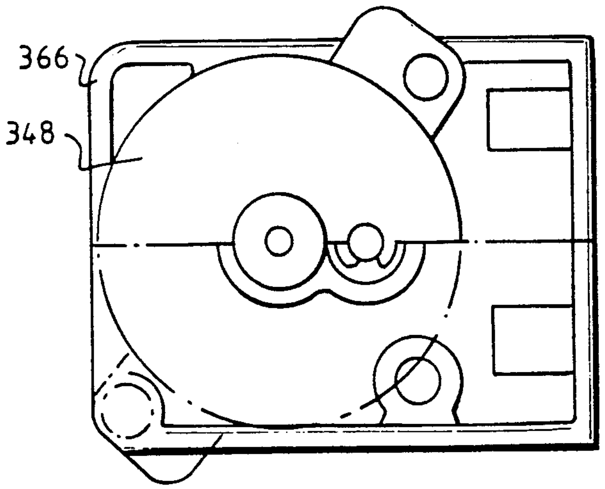
FIG. 29 is a top plan view of a portion of the drive mechanism shown in FIG. 19.

In an alternative embodiment of the cover opening mechanism, as shown in FIGS. 22A and 22B, the drive shaft of the L-drive gear box 160 has a pinion gear 161 mounted on it. The pinion gear 161 engages a secondary gear 163 with peripheral teeth, which gear 163 is rotatably mounted on a vertically extending pin 165 mounted on the underside of the bridge bracket 58*a*.

The secondary gear 163 has mounted on its underside a cover actuating pin 167, which is offset from the center of the gear. Pin 167 engages the cover pin 149 to open and close the cover in much the same way as pin 166 does in the previous embodiment.

The gear 163 further has a radially extending arm 169 mounted on it. Arm 169 cooperates with optical sensor 168 in much the same way as pivot block 164 does in the previous embodiment so that the analyzer can sense when the secondary gear 163 has made a complete revolution and has returned to its "home" position.

The Metering Assembly Of The Analyzer

One of the advantages of the present invention is that only a small amount, on the order of 10 microliters, of serum to be analyzed need be deposited on each test slide. Accordingly, the metering apparatus of the chemical analyzer need only carry approximately 120 microliters of serum if all 12 test slides are to be utilized.

FIGS. 11-17 illustrate the components of the chemical analyzer which perform the metering operation.

As discussed previously, the metering apparatus of the chemical analyzer includes a pipette assembly 16 (see FIG. 16), which assembly basically includes a pipette 18 and a tube 20 connected to the pipette 18 and to the chemical analyzer. The tube 20 carries an electrical, two wire conductor conduit 172, as well as an air conduit 174.

The pipette 18 has a tapered stainless steel end on which is fitted a removable and disposable tip 176. The tip 176 has an upper end which is formed with a series of radially extending supporting fins 178.

Figure 12:
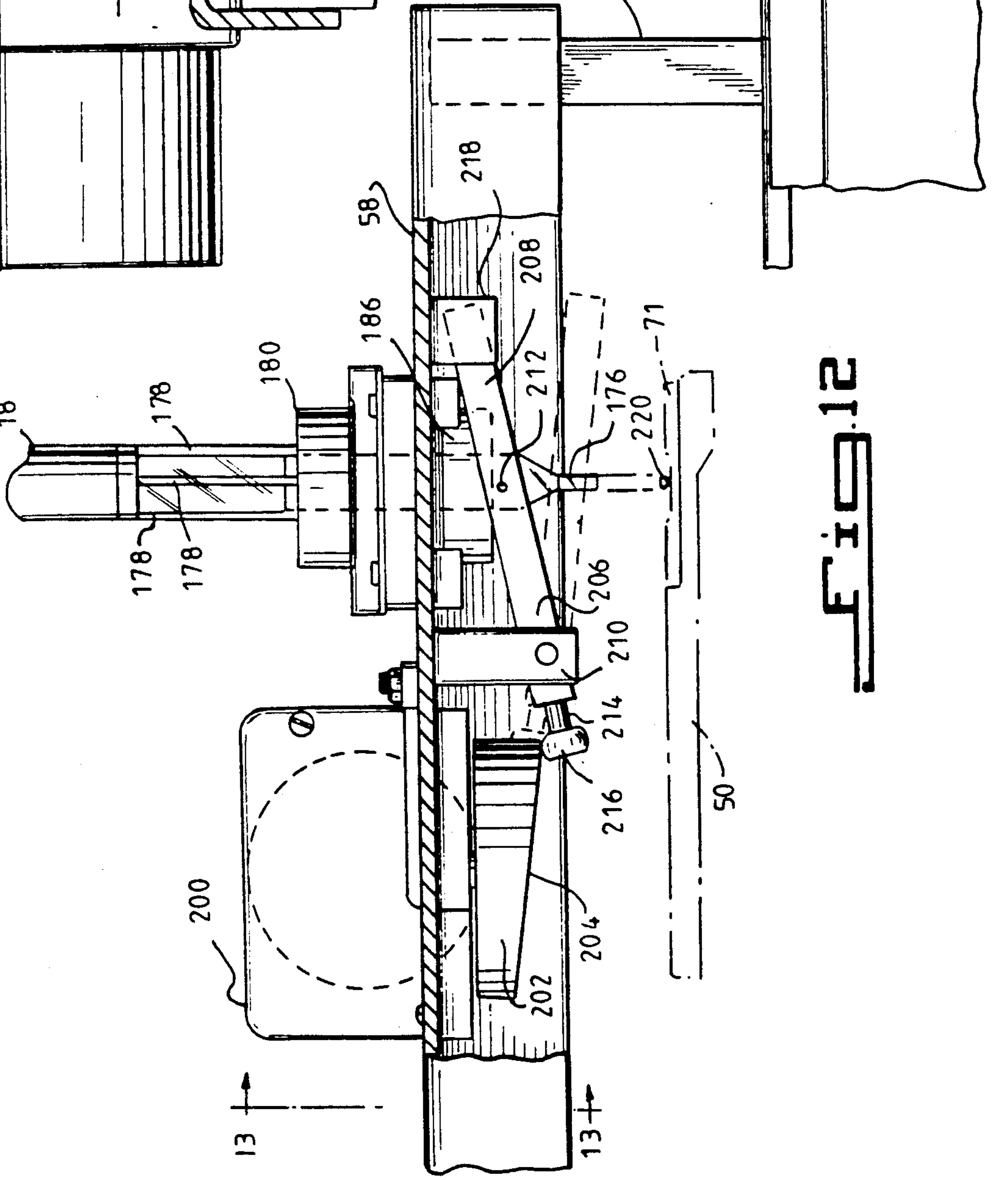
FIG. 12 is a partial sectional view of a portion of the analyzer illustrated by FIG. 11, taken along line 12—12 of FIG. 11.

After the pipette 18 has aspirated a predetermined volume of serum to be analyzed, as will be explained in greater detail, it is placed through the opening 23 in the analyzer cover 12 (see FIG. 1), and its disposable tip 176 extends through the bore of a pipette support ring 180 (see FIG. 3) situated on the bridge bracket 58, with the supporting fins 178 of the tip resting on the upper surface of the support ring 180. As shown in FIG. 12, the tip 176 of the pipette extends below the bridge bracket 58 and directly above the film portion 124 of a test slide 71 mounted on the turntable, which is rotated so that the slide is in alignment with the pipette.

A vertically upward and downward movement is provided to the pipette 18 to ensure that a drop formed on the pipette tip will be properly transferred to the analyte film portion of the slide by capillary action.

Figure 12A:
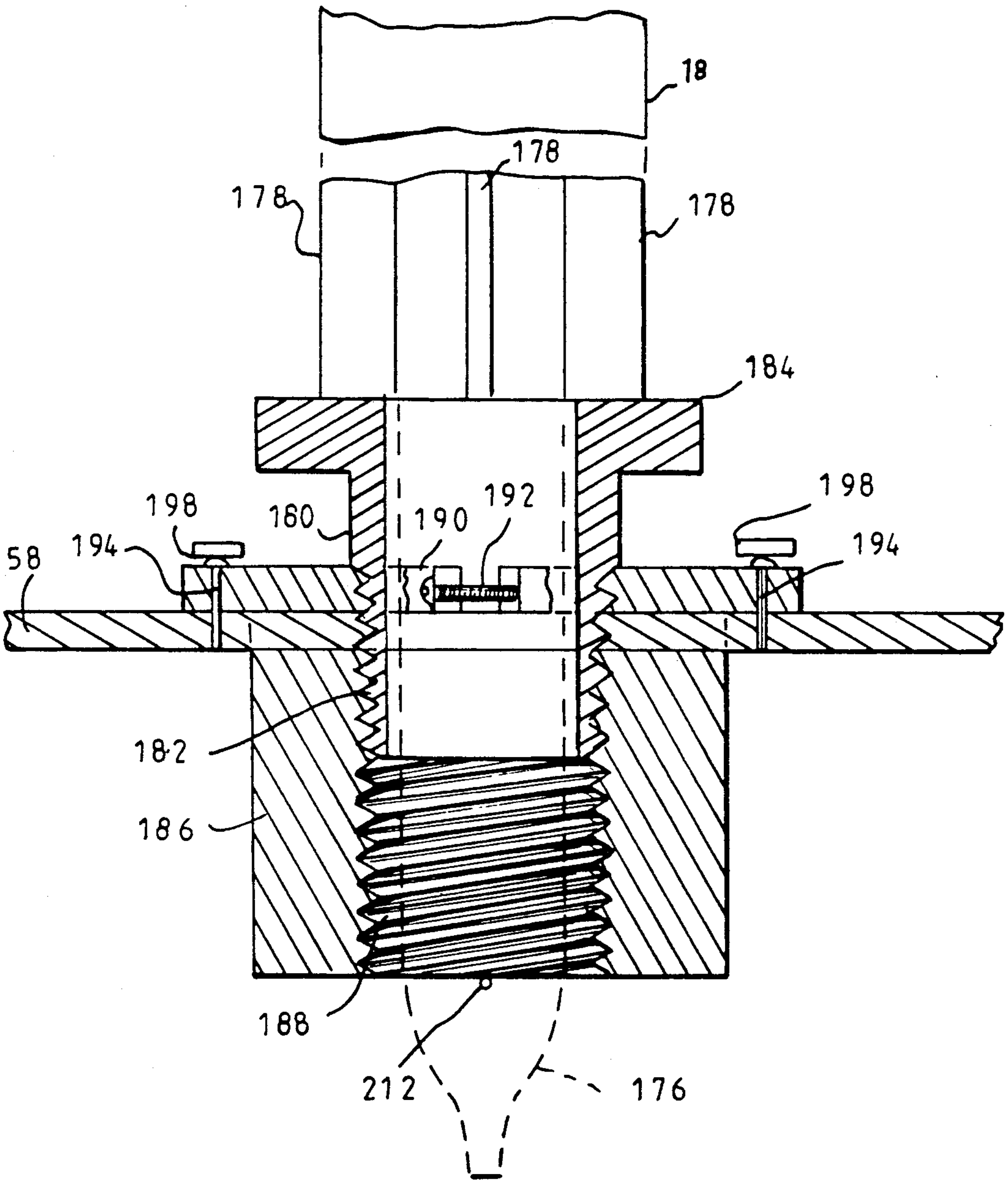
FIG. 12A is a detailed longitudinal cross-sectional view of a portion of the assembly shown in FIG. 12.

As more specifically shown in FIG. 12A, the supporting fins 178 of the pipette rest on the top surface of the support ring 180. The support ring 180 has a threaded cylindrical body 182 and an upper flange 184 extending from the cylindrical body 182, the supporting fins 178 of the disposable tip resting on the upper flange 184.

A cylindrical collar 186 which is internally threaded includes a bore 188 which receives the threaded cylindrical body 182 of the support ring. The support ring 180 may thus be threaded into the collar 186 a predetermined distance which, as will be seen, is used to adjust of the height of the pipette tip 176 in relation to the test slides mounted on the rotatable turntable. The outer collar 186 further includes a split flange 190 at its upper portion, where the flange ends are adjustably screwed together so that the outer collar 186 may be tightened about the inner support ring 180.

After the height of the pipette tip has been adjusted by threading the support ring 180 into the outer collar 186 a predetermined distance, the split flange 190 of the outer collar is tightened by adjusting the screw 192 so that the support ring will not turn within the outer collar and so that the height of the pipette will always be maintained at its proper setting.

A pair of guide pins 194 are mounted through the upper flange 190 of the outer collar and extend downwardly in the same direction as the outer collar 186. The guide pins 194, as well as the outer collar 186, pass through correspondingly dimensioned holes formed in the bridge bracket 58. The guide pins 190 prevent the support ring 180 and outer collar 186 from turning on the bridge bracket 58.

As shown in FIG. 3, a leaf spring 196 is mounted on the top surface of the bridge bracket 58. The free end of the leaf spring is split to define forked ends 198. The forked ends 198 engage the upper flange of the outer collar 186 at the heads of the guide pins 198, such that the leaf spring biases the outer collar 186 downwardly through the bridge bracket 58.

As shown in FIG. 3, and as mentioned previously, a drive motor 62 is provided to cause the pipette 18 to move vertically to deposit a serum sample on the test slides. The shaft of the drive motor 62 is coupled to an L-drive reduction gear box 200 also mounted on the upper surface of the bridge bracket 58. The vertically extending shaft of the gear box is coupled to a cam wheel 202, as shown in FIG. 12. The cam wheel 202 has a lower surface 204 which is sloped from a horizontal plane, which effectively provides the cam wheel with a non-uniform thickness.

A cam follower 206, in the form of a clevis, that is, with two ends 208 which partially surround the outer collar, 186 is pivotally mounted between a pair of extension blocks 210 from the underside of the bridge bracket. Each of the two split ends 208 includes a pin 212 which extends partially inwardly towards each other. The bottom of the outer collar 186 rests on the two pins 212. The opposite end of the cam follower 206 includes an outwardly extending pin 214 on which is rotatably mounted a cam follower wheel 216.

The leaf spring 196 biases the outer collar 186 downwardly such that it exerts a force on the pins 212 of the split ends of the cam follower 206 which, in turn, causes the cam follower wheel 216 to ride along the periphery of the sloping lower surface 204 of the cam wheel 202.

To effect a downward movement of the pipette 18 resting in the support ring 180, the drive motor 62 is energized, which causes the cam wheel 202 to rotate. Because the cam follower wheel 216 engages the lower surface of the cam wheel 202, which lower surface is sloping, the cam follower 206 will pivot downwardly, as shown in the dashed lines in FIG. 12, to its lowest position as the cam wheel 202 rotates to a point where the cam follower wheel 216 rests on the cam wheel at its narrowest portion.

The cam wheel 202 then continues to rotate until it returns to its initial position shown in FIG. 12, that is, where the thickest portion of the cam wheel 202 resides over the cam follower wheel 216 This causes the cam follower 206 to pivot on the extension blocks 210, forcing the outer collar 186 and pipette 18 upwardly against the force of the leaf spring 196.

An optical sensor 218, in the form of a pair of a light source and a photodetector spaced apart slightly from each other, is mounted on the underside of the bridge bracket 58. One of the split ends 208 of the cam follower 206 is extended such that, when the pipette 18 is in its most raised position, the end 208 will be interposed between the light source and photodetector of the sensor 218 and disturb a light beam between the two.

At the appropriate time, the associated computer and electronic circuitry of the chemical analyzer will energize the drive motor 62, causing the cam wheel 202 to rotate. The cam follower 206 will pivot downwardly, following the slope of the lower surface of the cam wheel, and the extended split end 208 of the cam follower will be pivoted away from the optical sensor 218. When the cam wheel has rotated a full 360 degrees such that the cam follower 206 and pipette 18 have returned to their initial positions, the extended split end 208 of the cam follower will again disturb the light beam between the light source and photodetector. This disturbance in the light beam is detected, thus indicating that a full reciprocatingly vertical motion of the pipette 18 has been completed. The drive motor 62 will then be de-energized by the electronic circuitry until the next test slide has been properly positioned below the tip 176 of the pipette, where upon the sequence described above is repeated.

As will be explained in greater detail, a drop of serum 220 to be analyzed is formed on the pipette tip 176 and is suspended from the tip prior to a downward motion of the pipette. After this metering of a predetermined amount of serum has taken place, the drive motor 62 is then energized to lower the pipette 18 to the test slide. Because the full drop of serum is formed on the pipette tip 176 prior to lowering the pipette to the test slide, it is not necessary to lower the pipette until its tip almost touches the film portion 124 of the test slide.

The metering operation relies on capillary action to draw the drop which has formed on the pipette tip from the pipette and onto the slide. The halfway height of a 10 microliter drop which is formed on the pipette tip has been measured to be approximately 1.2 millimeters. Accordingly, the chemical analyzer is adjusted so that the pipette tip 176 extends this distance above the film portion 124 of the test slide. However, this distance may vary in either direction by as much as 1 millimeter, as the drop will still be drawn by capillary action onto the test slide. Accordingly, stringent tolerances are not required in the present invention for proper metering to occur, as is required in many conventional chemical analyzers, so that the height tolerances in the rotatable turntable and bridge 58 may be relaxed.

FIGS. 13E and 13F show a modification to the pipette lifting mechanism. Before the pipette 18 is placed into its support ring 180 in the chemical analyzer, it is placed partially into a vial of serum so that a predetermined amount of serum may be aspirated into the disposable tip. The pipette is then placed in its support ring 180 and the user may then press a key on the keyboard 4 to indicate that serum has been drawn into the tip and that the serum is ready to be tested.

One of the problems which may occur is that there may be a time delay between when the serum is drawn into the pipette 18 and when the user signals the analyzer to begin the operation of depositing the serum onto each test slide and testing the serum. During that time delay, the temperature of the pipette may increase. This increase in temperature may cause air above the serum in the pipette tip 176 to expand. This expansion may, in turn, force some serum out of the disposable tip prior to the metering operation so that an incorrect amount of serum may possibly be deposited on the test slides.

To minimize the possibility of a time delay between the steps of drawing the serum into the pipette tip and the metering operation, so as to minimize any temperature change which in the pipette experiences, the support ring 180 may include an electrical switch to automatically sense when the pipette 18 has been properly placed in the support ring.

As shown in FIG. 13F, the switch, in one form, may include a first conductive contact 222 disposed on the top surface of the support ring 180, and a second conductive contact 224 disposed on the side wall of the support ring. When the supporting fins 178 of the disposable tip rest on the top surface of the support ring 180, as shown in FIG. 13E, the two electrical contacts will engage and provide an electrical path through the switch. This electrical path is sensed and provided to the associated computer and electronic circuitry of the analyzer which will then immediately begin the metering and testing operation. This will avoid any time delay by the user failing to immediately press the proper keyboard button after serum has been drawn into the pipette tip 176 and the pipette tip has been properly placed on the support ring 180.

Alternatively, and as shown in FIG. 22A, an optosensor 175 may be mounted on the bridge assembly. When the pipette is replaced in the pipette lifting mechanism, the tip 176 of the pipette will break a light beam of the opto-sensor 175, signalling the analyzer and its associated computer to proceed with the sample depositing operation.

An alternative form of the pipette lifter mechanism of the metering assembly is illustrated by FIGS. 22-26.

A motor 226 is mounted to a reducing L-drive gear box 228, both of which are mounted on the top side of the bridge bracket 58 (or to a supporting plate 227 mounted on bracket 58). The vertically extending output shaft of the gear box 228 has a gear 230 with peripheral teeth mounted on it. The gear box gear 230 engages an intermediary gear 232 mounted rotatably on a post 234 extending downwardly from the bridge bracket 58 (or plate 227). The intermediary gear 232 includes an eccentric boss or hub 236 which acts as a cam.

A rocker arm 238 is mounted to the bridge bracket to pivot vertically. The rocker arm 238 includes two outwardly disposed lever arms 240, 242. One lever arm 240 engages the eccentric boss 236 of the intermediary gear 232. The other lever arm 242 is split into two forked ends 244, clevis-style. Two pins 246 extend partially inwardly from each forked end 244 of the second lever arm.

The pipette 18 is mounted on the bride bracket 58 in a manner which is similar to that previously described. A guide or stabilizing collar 248 is mounted on a second bracket 250 above the bridge bracket 58 and includes an internal bore which is dimensioned to be slightly larger than a stainless steel tip portion 252 of the pipette. A second collar 254 is mounted on the underside of the bridge bracket 58 (or plate 227), and includes a central bore which is concentric with an opening formed through the thickness of the bridge bracket (or plate 227).

A pipette support ring 256 includes a lower cylindrical body 258 which is slidably received by the central bore of the second collar 254 so that the support ring 256 may reciprocatingly slide within the second collar. The support ring further includes an upper flange 260 which extends outwardly radially from the cylindrical body 25 and which rests on the inwardly disposed pins 246 of the spaced apart forked arms 244 of the rocker arm's second leg. Alternatively, pins 246 may be eliminated and flange 260 may rest directly on the forked ends 244. A compression spring 262 is mounted between the underside of the guide collar 248 and the support ring 256. The spring forces the support ring 256 downwardly into the second collar 254.

The distance from the pipette tip 176 to the test slide 71 is adjusted by adding wishbone-shaped shim washers 264 between the slidable support ring 256 and the stationary second collar 254. This distance is determined when the chemical analyzer is calibrated.

The alternative embodiment of the pipette lifter described above operates in the manner described below. The motor 216 is energized causing the gear 230 mounted on the gear box to rotate. This, in turn, causes the intermediary gear 232 to rotate on its mounting post 234. The eccentric boss 236 of the intermediary gear engages the first lever arm 240 of the rocker arm and moves with the eccentricity of the intermediary gear 232. The movement of the rocker arm 238, which pivots in a vertical plane, causes the lifter leg 242 to raise and lower the support ring 256 within the second collar 254 against the force of the compression spring 262.

A pipette 18, which is situated in the stabilizer collar 248, and with its supporting fins 178 of the disposable tip resting on the support ring 256, will follow the reciprocating movement of the support ring so that the tip 176 of the pipette will be raised and lowered with respect to a test slide situated beneath it.

The pipette lifter mechanism is initially set by the chemical analyzer to be in its "home" position. That is, the support ring 256 is raised to its highest position with respect to the second collar 254. To sense when this has occurred, an optical sensor 266 in the form of a spaced apart LED light source and a detector is positioned near the support ring 256. A portion 268 of the upper flange 260 of the support ring is extended radially so that, when the support ring is in its most upward position, the extended portion 268 of its flange is interposed between the LED light source and the detector of the sensor 266 to interfere with the light beam between the two. The optical sensor 266 is connected to the associated computer and electronic circuitry of the chemical analyzer so that the analyzer knows that the pipette mounted in the support ring is in its fully raised, "home" position.

As with the previous embodiment, the motor 226 is energized to cause the pipette 18 to lower a predetermined distance to a test slide situated beneath it and, after a drop of serum has been deposited on the test slide, to return to its raised "home" position. This reciprocating action is due to the eccentricity of the boss 236 of the intermediary gear 232, which gear will rotate a full 360 degrees. When the extended portion 268 of the upper flange of the support ring 256 rises to a position where it again interrupts the light beam between the LED source and the detector, the associated circuitry recognizes that the pipette 18 has returned to its initial position, and it will de-energize the motor 226.

Figure 14:
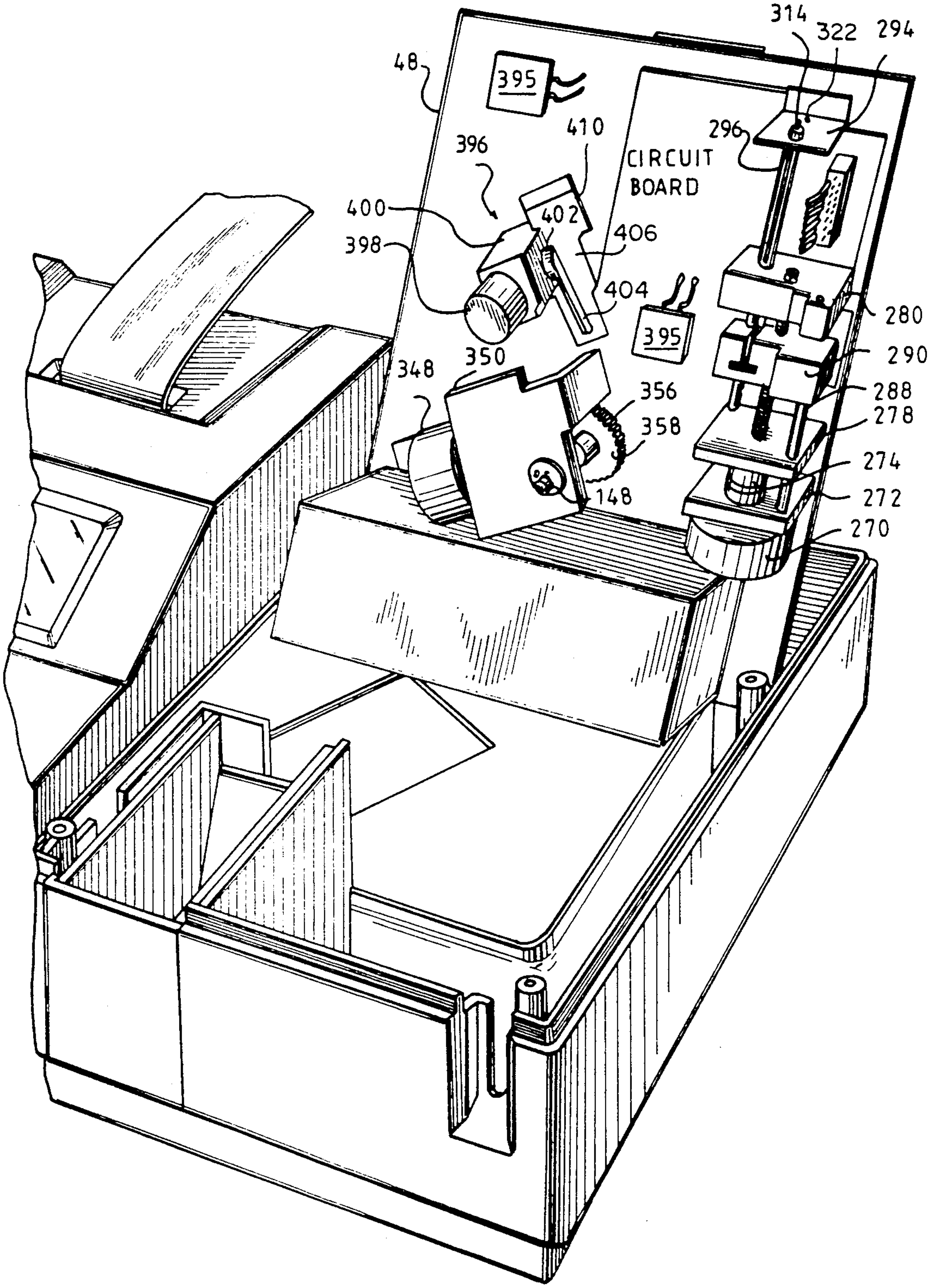
FIG. 14 is a perspective view of the chemical analyzer shown in FIG. 1 and illustrating the drive assemblies for the turntable and metering device.
Figure 15:
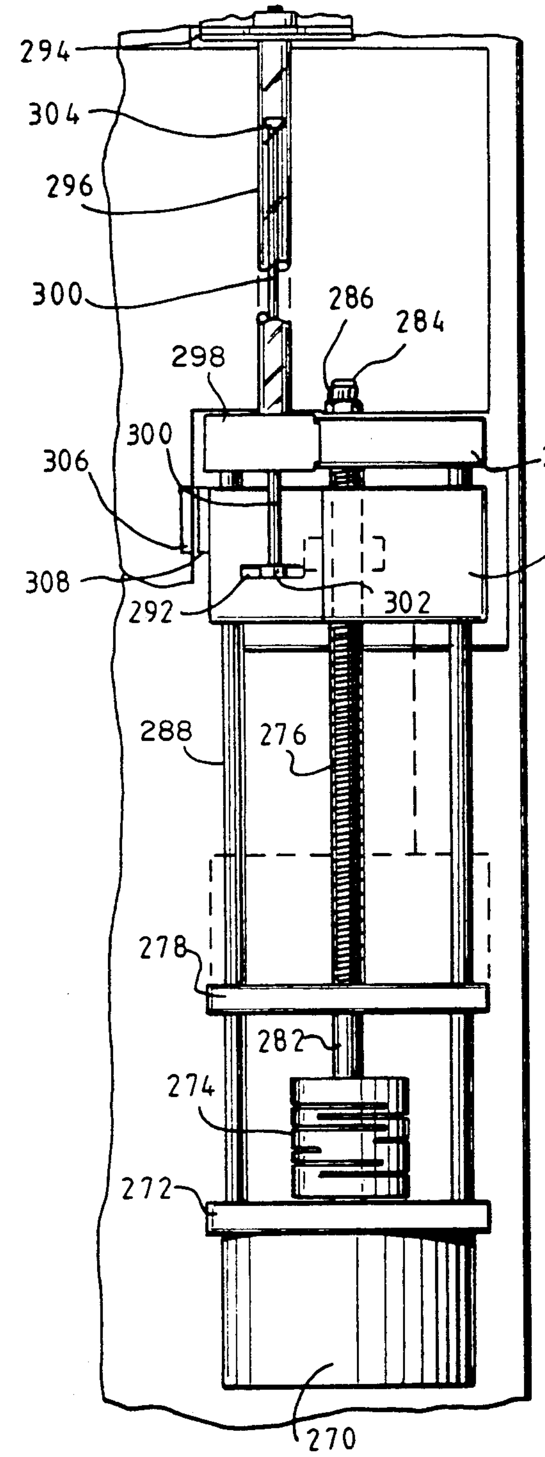
FIG. 15 is a bottom view of the metering assembly of the chemical analyzer.

FIGS. 14 and 15 show one form of the metering assembly of the present invention which is used to draw a predetermined amount of serum into the pipette tip and to deposit serum on each test slide. The metering assembly is preferably mounted on the underside of the base plate 48, which is shown in a raised position in FIG. 14.

The metering assembly includes a reversible DC stepper drive motor 270 which is mounted on a support member 272 attached to the underside of the base plate 48. The shaft of the drive motor 270 is connected to a coupler 274 which acts as a universal joint.

A lead screw 276 is mounted between a second support member 278 and a third support member 280 which are attached to the underside of the base plate. One end 282 of the lead screw is connected to the other side of the coupler 274 opposite the side to which the drive motor shaft is connected, and the other end 284 of the lead screw 276 passes through the third support member 280 and is mounted to the member 280 by appropriate hardware, such as a pair of nuts 286. The lead screw 276 is rotatable relative to the second and third support members. The metering assembly further includes a pair of guide rods 288 which extend at least between the second and third support members.

Mounted on the lead screw 276 between the second and third support members 278, 280 is a movable block 290. When the stepping motor 270 is energized, the lead screw 276 will rotate and the block 290 will move reciprocatingly up and down on lead screw between the second and third support members 278,280. The guide rods 288 also pass through the movable block 290 and prevent the movable block from twisting or rotating on the lead screw 276 as the lead screw turns.

The movable block 290 has a T-slot 292 formed in one of its surfaces. Mounted between the third support member 280 and a support bracket 294 affixed to the underside of the base plate is a syringe 296 in the form of a tubular member. More specifically, one end of the syringe 296 is placed into a U-slot formed in the third support member 280 and held in place by a cover clip 298 and the other end is secured to bracket 294.

The syringe 296 is an air-tight member which includes a plunger 300 which extends through its central bore. The plunger 300 extends out of one end of the syringe and has an enlarged head 302 which is fitted into the T-slot 292 formed in the movable block 290. A teflon ® piston 304 is mounted on the other end of the plunger 300. The piston 304 and plunger 300 are slidable within the central bore of the syringe. A syringe which is suitable for use in the chemical analyzer of the present invention is Part No. 1725 manufactured by Hamilton Co., and described in U.S. Pat. No. 3,150,801.

When the stepping motor 270 is energized with a voltage of predetermined polarity and phasing, it will turn the lead screw 276, causing the movable block 290 to advance in a direction from the second support member 278 to the third support member block 280. This, in turn, will drive the plunger 300 and piston 304 through the central bore of the syringe, causing a serum sample collected by the pipette 18 to be expelled from the pipette tip 178.

When the stepping motor 270 is energized with a voltage of opposite phasing, the lead screw 276 will rotate in an opposite direction, causing the movable block 290 to move backward on the lead screw in a direction from the third support member 280 to the second support member 278. This, in turn, will cause the plunger 300 and piston 304 to be drawn back through the syringe, causing serum to be aspirated into the pipette tip 178.

A "home" position is selected for the movable block 290 on the lead screw 276. This position is generally where the movable block is near the third support member 280. A reflective type of optical sensor 306, such as described previously, is positioned adjacent a side wall of the movable block 290 when the block is in its home position. The side wall of the block may further have mounted on it a reflective foil 308 or other material in order to optimize the effect of the optical sensor. The associated computer and electronic circuitry of the chemical analyzer will be signalled by the optical sensor 308 when the movable block 290 is in its home position, or will place the movable block in its home position, by energizing motor 270, causing the lead screw 276 to rotate until the block's home position is determined by the optical sensor, which then signals the associated electronic circuitry.

Figure 16:
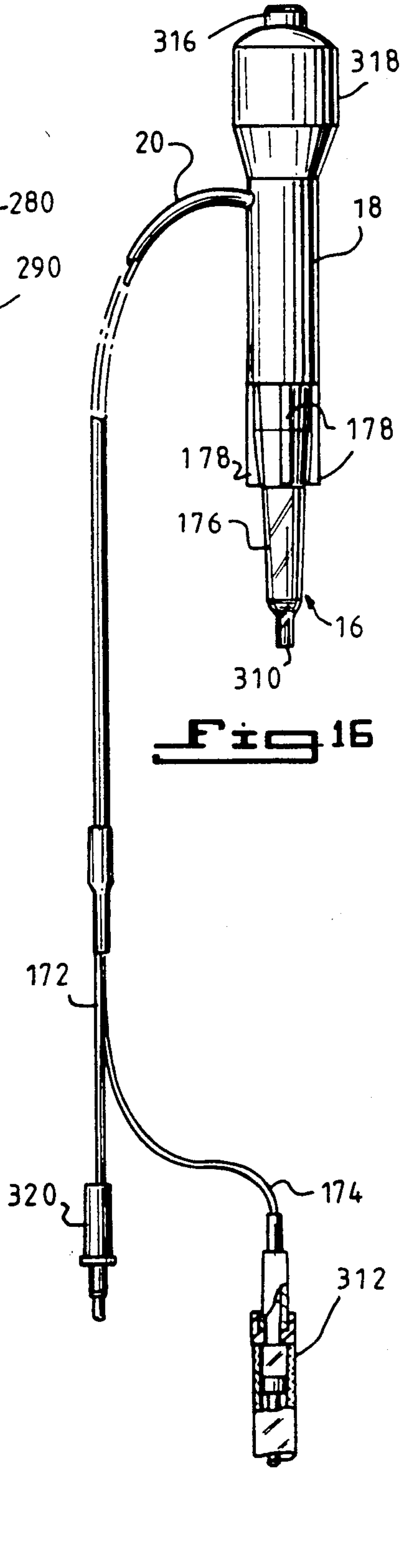
FIG. 16 is a perspective view of a portion of the metering assembly.

The pipette assembly 16 is shown in FIG. 16. As mentioned previously, the pipette assembly includes a pipette 18 having a stainless steel tip portion on which is fitted a disposable tip 176. The tip converges to form a narrow end 310 on which a drop of sample serum is formed. The opposite end of the disposable tip includes a plurality of radially extending supporting fins 178. This opposite end is fitted onto the stainless steel tip of the pipette.

The pipette assembly further includes an outer tube 20. The outer tube 20 carries an air conduit 174 and a two wire conductor electrical conduit 172. The air conduit 174 is connected at one end through the body of the pipette 18 to a central bore (not shown) formed in the body, which bore (not shown) extends to an opening formed in the stainless steel tip so that the air conduit 174 is in communication with the interior of the disposable pipette tip 176 when the disposable tip is fitted onto the stainless steel tip of the pipette 18.

The other end of the air conduit 174 includes an air-tight female connector 312 which is adapted to be inserted onto a male connector 314 mounted on the support bracket 294, which male connector is in communication with the syringe 296.

The electrical conduit 172 is connected through the pipette body to a single pole single throw (SPST) push button switch 316 mounted on an enlarged head portion 318 at the top of the pipette 18. The other end of the electrical conduit 172 is connected to a male plug connector 320 which is adapted to be received by a female connector 322 also mounted on the support bracket 294

(see FIGS. 1 and 14). The mating female connector 322 is connected to the electronic circuitry of the chemical analyzer.

At the appropriate time during operation of the chemical analyzer, the display 8 will instruct the user to insert the pipette tip 176 into a vial containing the sample serum to be analyzed. When this step has been done, the user will signal the chemical analyzer by pressing the push button switch 316 on pipette head 318 that the pipette is ready to aspirate sample serum into the tip. The chemical analyzer will then cause the stepping drive motor 270 to turn the lead screw 276 a certain number of revolutions, causing the plunger 300 to be withdrawn through the syringe a predetermined distance. The vacuum created in the disposable tip 176 will cause serum to be drawn from the sample vial into the disposable tip.

Only 10 microliters of serum is drawn into the tip for each test slide to be analyzed. Accordingly, if all twelve test slides are to be analyzed, 120 microliters of serum is drawn into the tip. An additional about 30 to about 40 microliters is preferably also drawn into the tip for proper operation.

The chemical analyzer will then signal the user to withdraw the pipette 18 from the serum vial. After this has been done, an additional 2 microliters of air is drawn into the tip 176. The purpose of drawing air into the tip 176 after the desired quantity of serum has been aspirated is so that the tip 176 may be wiped clean without drawing any serum from the tip due to capillary action caused by the wiping material touching the open end 310 of the disposable tip.

The pipette 18 is then placed in the support ring 180 through the hole 23 in the cover 12 and the user presses a key on the key pad 4 to instruct the analyzer to begin the metering operation.

The associated computer and electronic circuitry of the chemical analyzer will then energize the motor 270 so that the lead screw 276 rotates in the opposite direction from the direction which caused the sample to be aspirated, causing the plunger 300 to move through the syringe toward the support bracket 294. This will force serum out of the pipette tip 176.

Because a stepping motor 270 is used, the number of turns of the lead screw 276 may be maintained to a desired number with accuracy and, consequently, the amount of fluid discharged by the pipette 18 is accurately maintained. Accordingly, the stepping motor 270 will turn a predetermined number of revolutions to cause the syringe 296 to force the preferred 10 microliters of serum out of the pipette tip 176 for each test slide. For the first test slide to be deposited with serum, the lead screw 276 is rotated an additional amount so that the 2 microliters of air which was drawn into the tip prior to wiping the tip and 10 microliters of serum are forced out of the tip.

When the 10 microliters are forced out of the pipette tip, a drop will form and be suspended below the open end 310 of the tip. The pipette lifter assembly is then activated, which will cause the pipette tip 176 to be lowered until the drop touches the film portion 124 of the test slide, where upon, by capillary action, the sample serum will flow onto the analyte film portion of the test slide. The pipette lifter will then raise the pipette tip 176 to its normal position, and signal the associated computer and electronic circuitry of the chemical analyzer to advance the turn table 50 so that the next adjacent test slide is positioned underneath and in alignment with the pipette tip 176. The stepping motor 270 of the metering assembly is then again energized to expel an additional 10 microliters of serum out of the pipette tip to form a second drop. The pipette lifter mechanism is then again energized to deposit the drop on the next test slide. The sequence is repeated until a sample has been provided to each test slide.

It is to be noted that the metering assembly operates by first aspirating serum by having the lead screw 276 turn in one direction, and then expelling serum that it had previously aspirated by having the lead screw 276 turn in the opposite direction. This bi-directional rotation of the lead screw 276 may result in backlash between the lead screw 276 and the movable block 290, which may result in inaccuracy in the metering operation. In other words, the same number of revolutions of the lead screw in each direction may cause the movable member 290 (and, consequently, the plunger 300) to move different distances longitudinally along the lead screw 276.

One solution to this problem is to construct a lead screw/movable block assembly with little or no backlash, by fine machining techniques. However, such can be a rather expensive solution to the problem.

A more preferred and less expensive solution is to program the associated computer of the chemical analyzer with the number of turns of the lead screw which are necessary to eliminate the backlash, i.e., the difference between the number of rotational turns of the lead screw in opposite directions which will produce the same linear movement of the block 290. This number can be determined during calibration of the chemical analyzer. Thereafter, the chemical analyzer will and a certain number of rotations to the number of turns normally required to move the block 290 a predetermined distance along the lead screw, whenever the direction of the rotation of the lead screw is reversed.

Figure 27A:
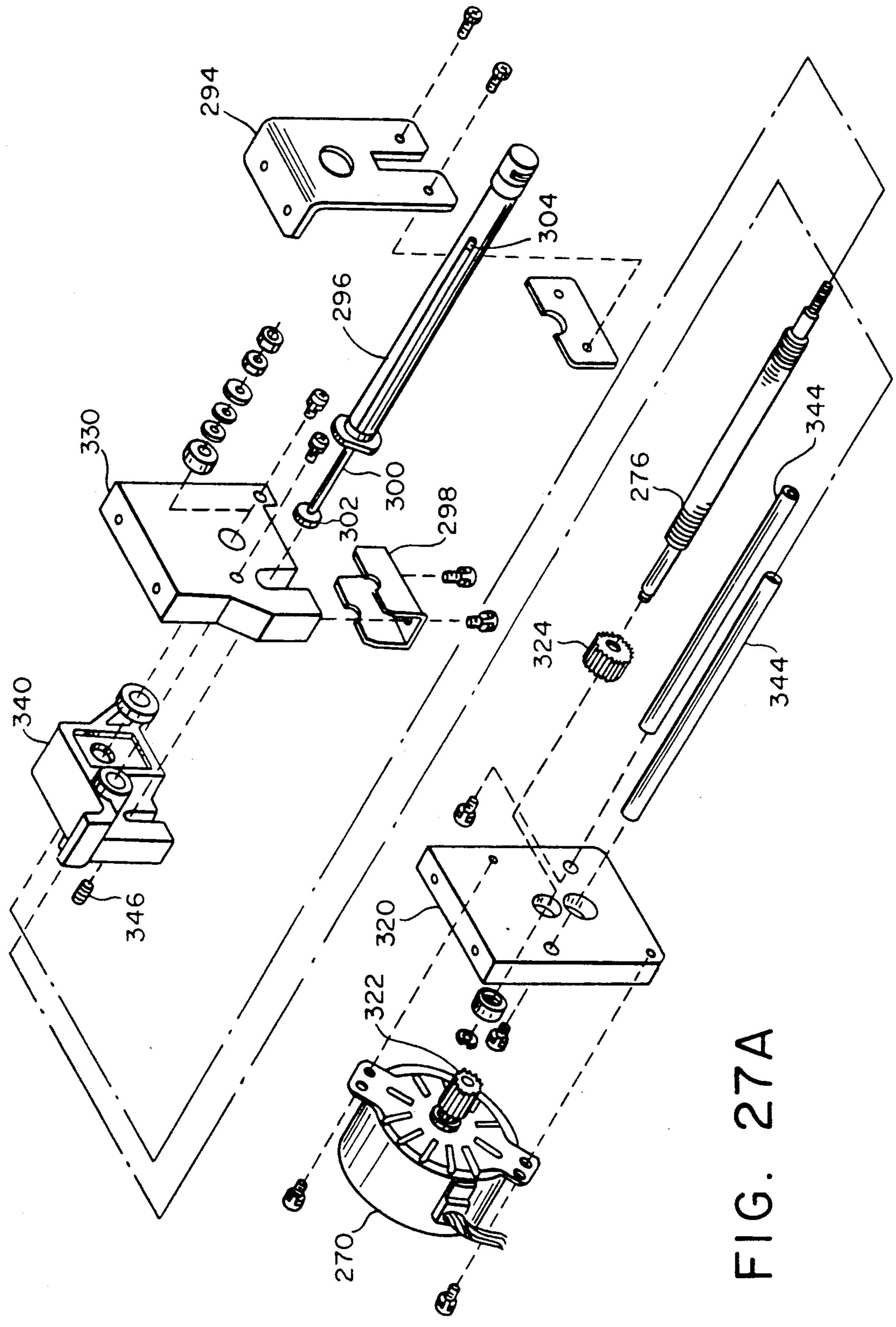
FIG. 27A is an exploded view, in perspective, of the metering device shown in FIG. 27.
Figures 31A, 31B, 31C:
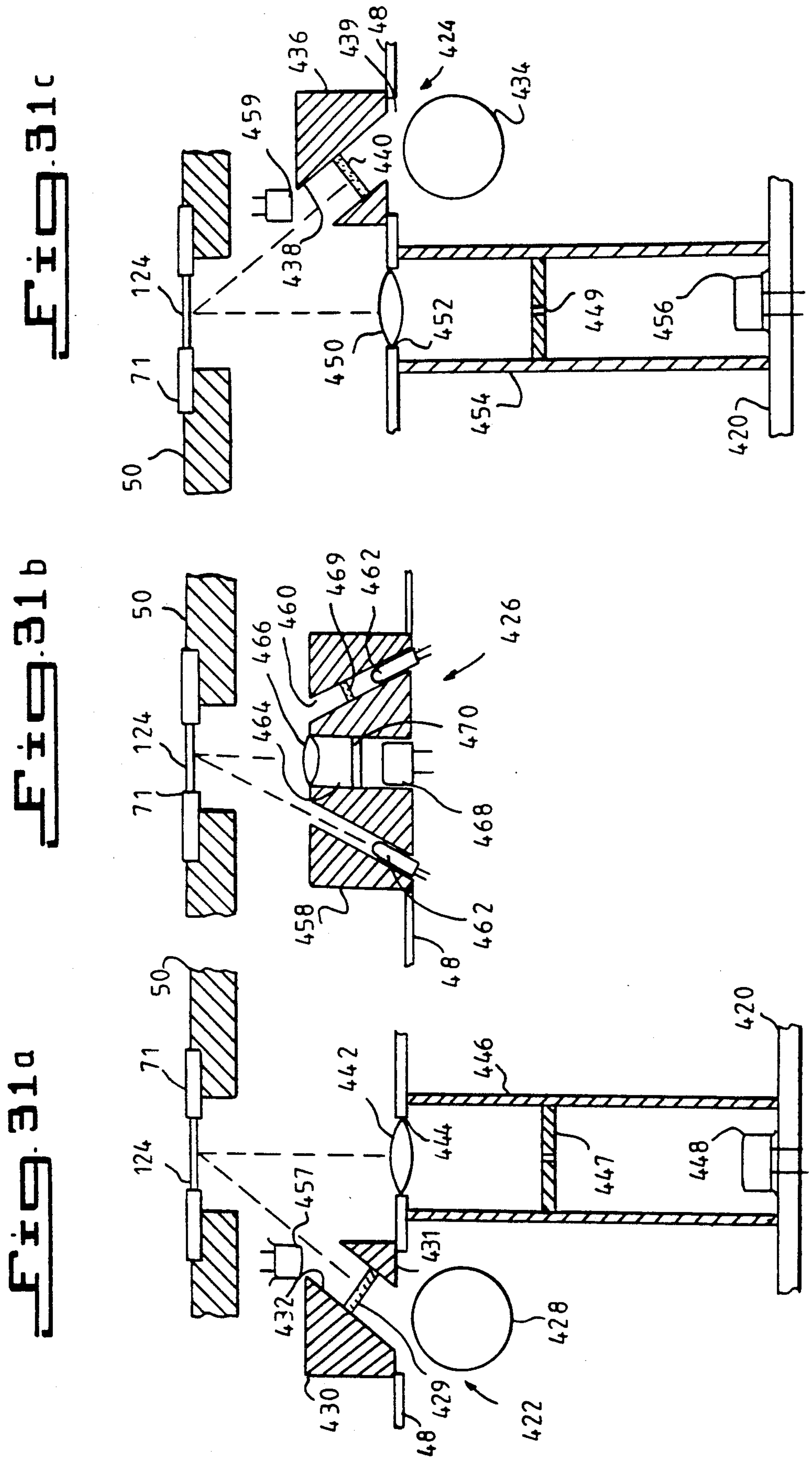
FIG. 31A is a cross-sectional view of a first portion of the reflectometer assembly of the present invention.
FIG. 31B is a cross-sectional view of a second portion of the reflectometer assembly of the present invention.
FIG. 31C is a cross-sectional view of a third portion of the reflectometer assembly of the present invention.
Figure 32A:
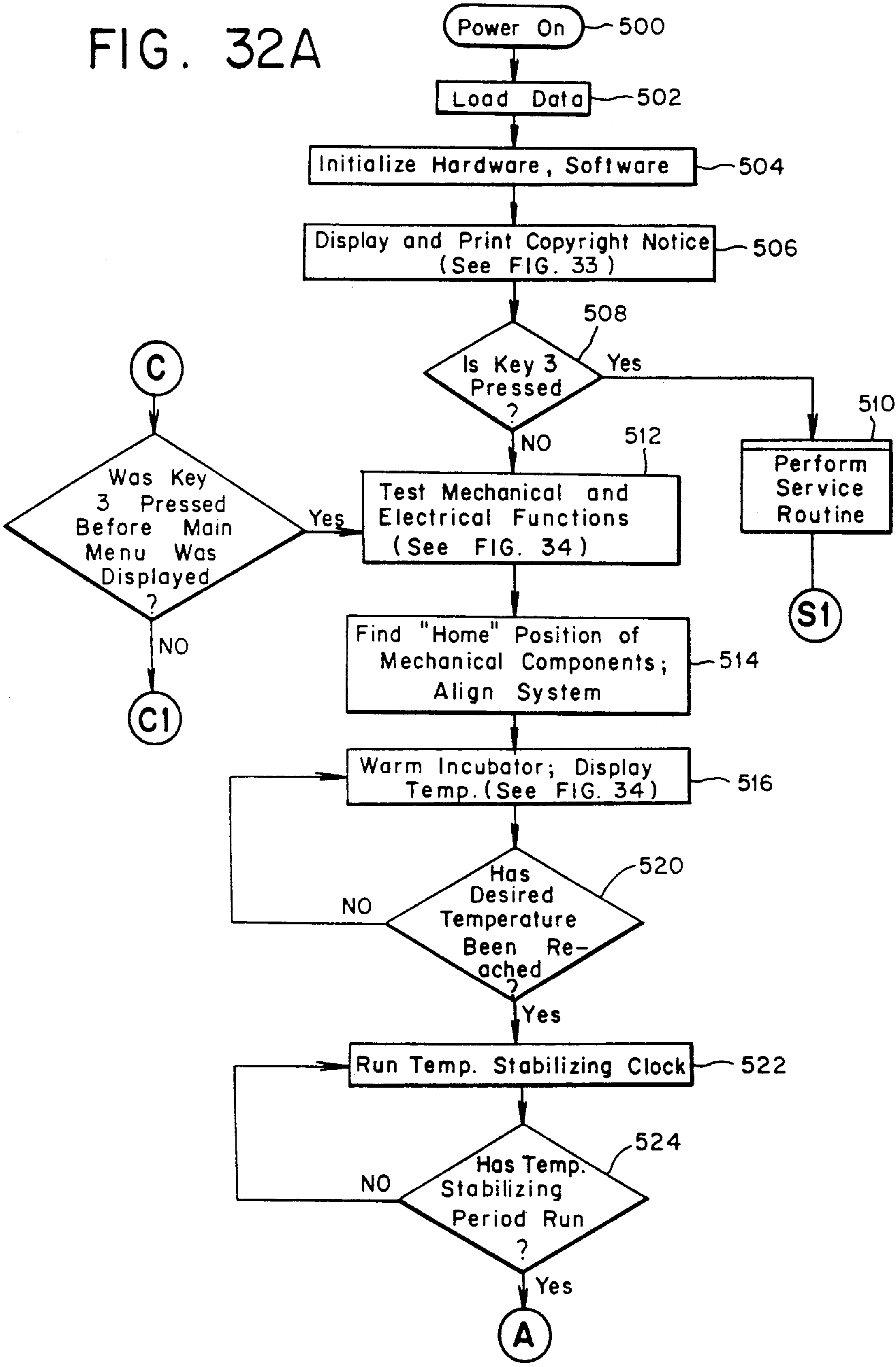
FIG. 32A–M is a flowchart of the operation of the analyzer of the present invention.
Figure 32B:
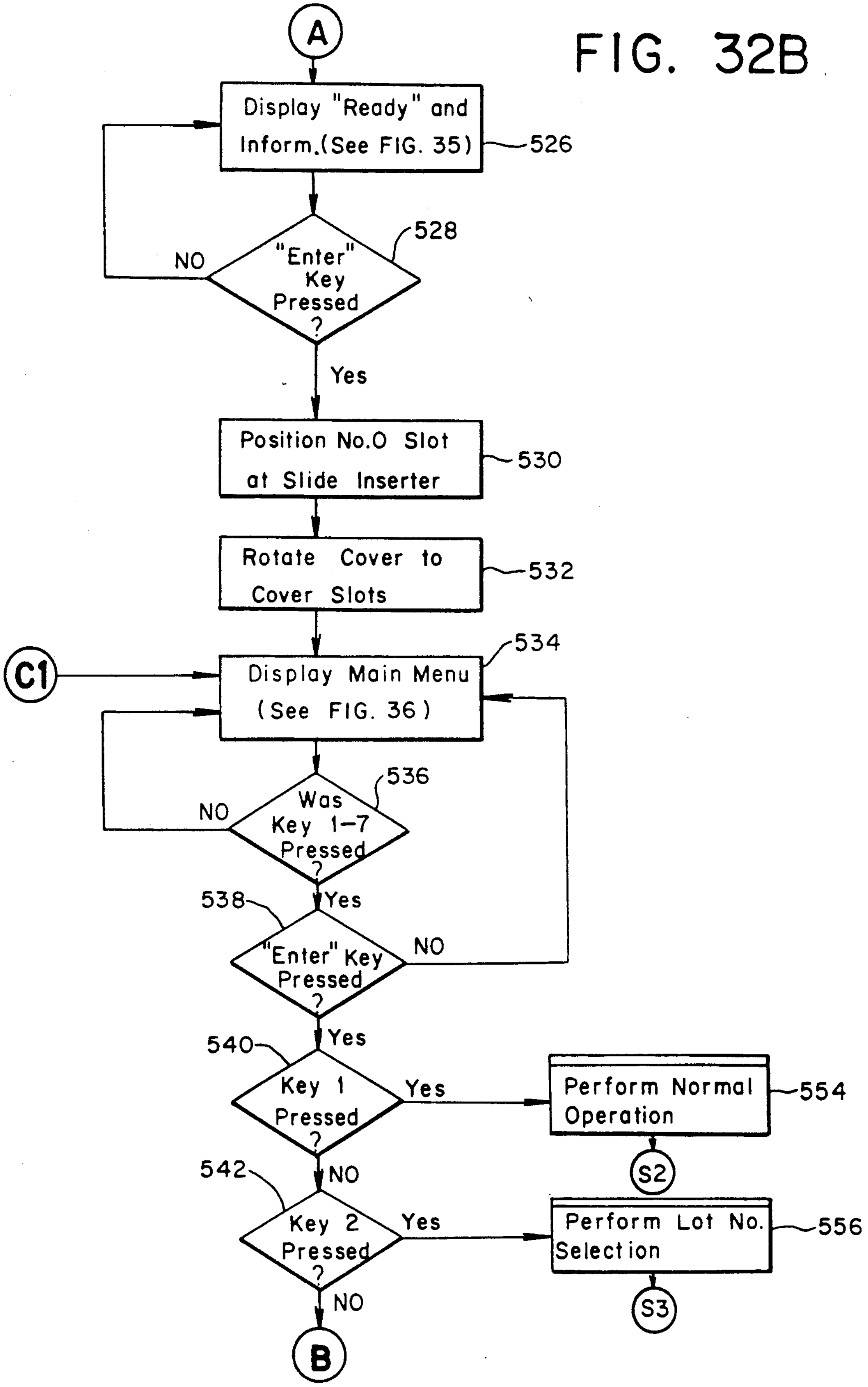
Figure 32C:
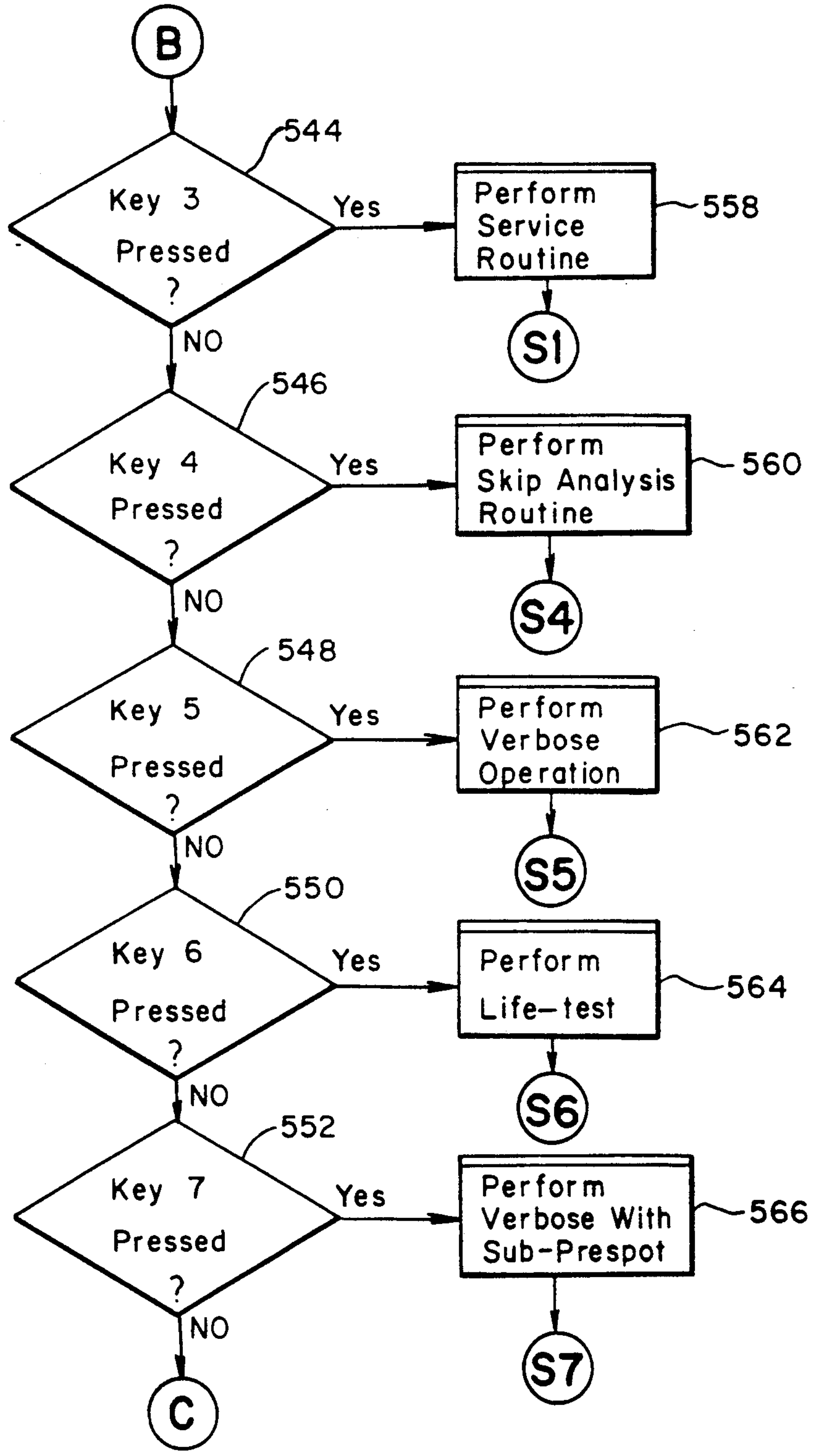
Figure 32D:
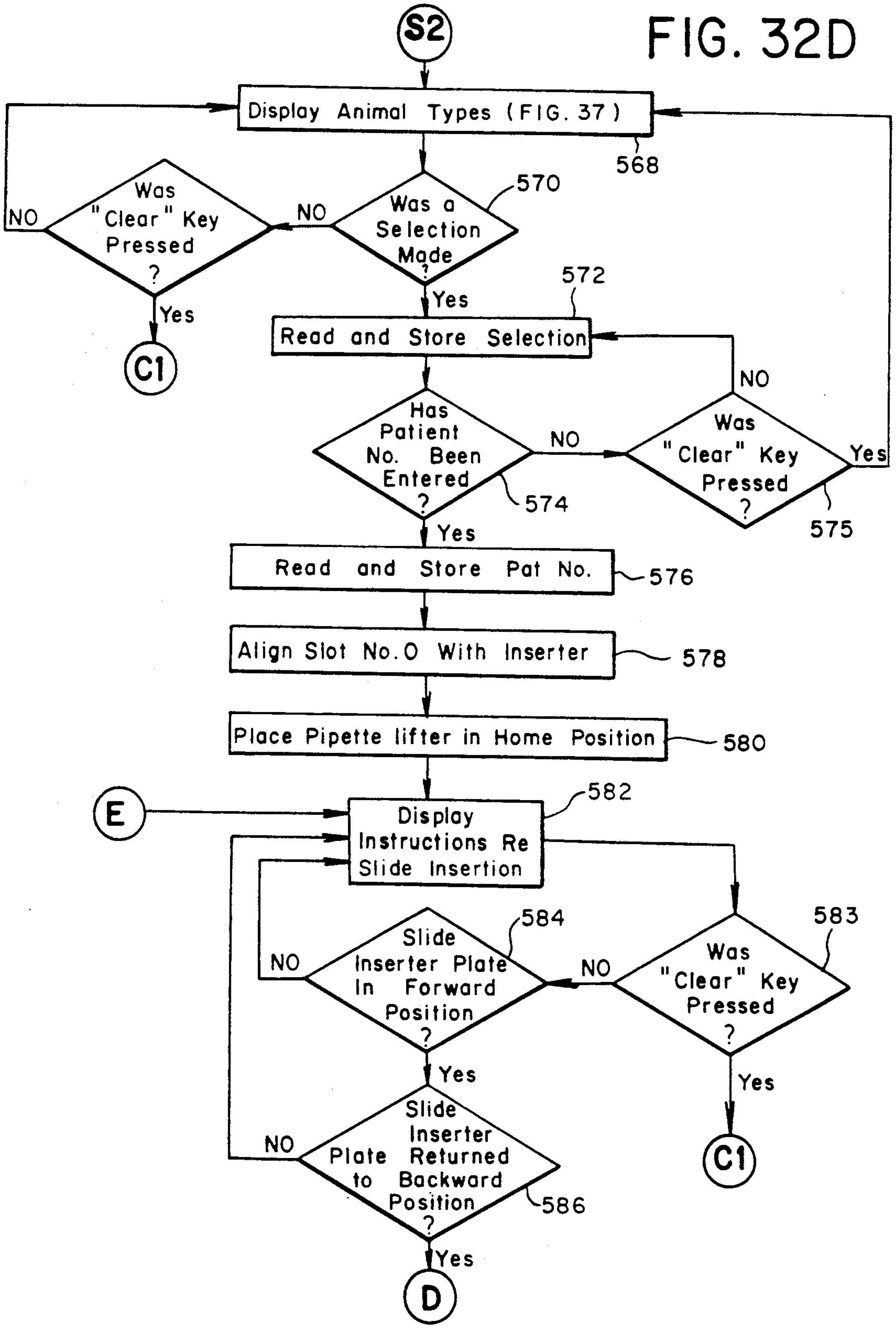
Figure 32E:
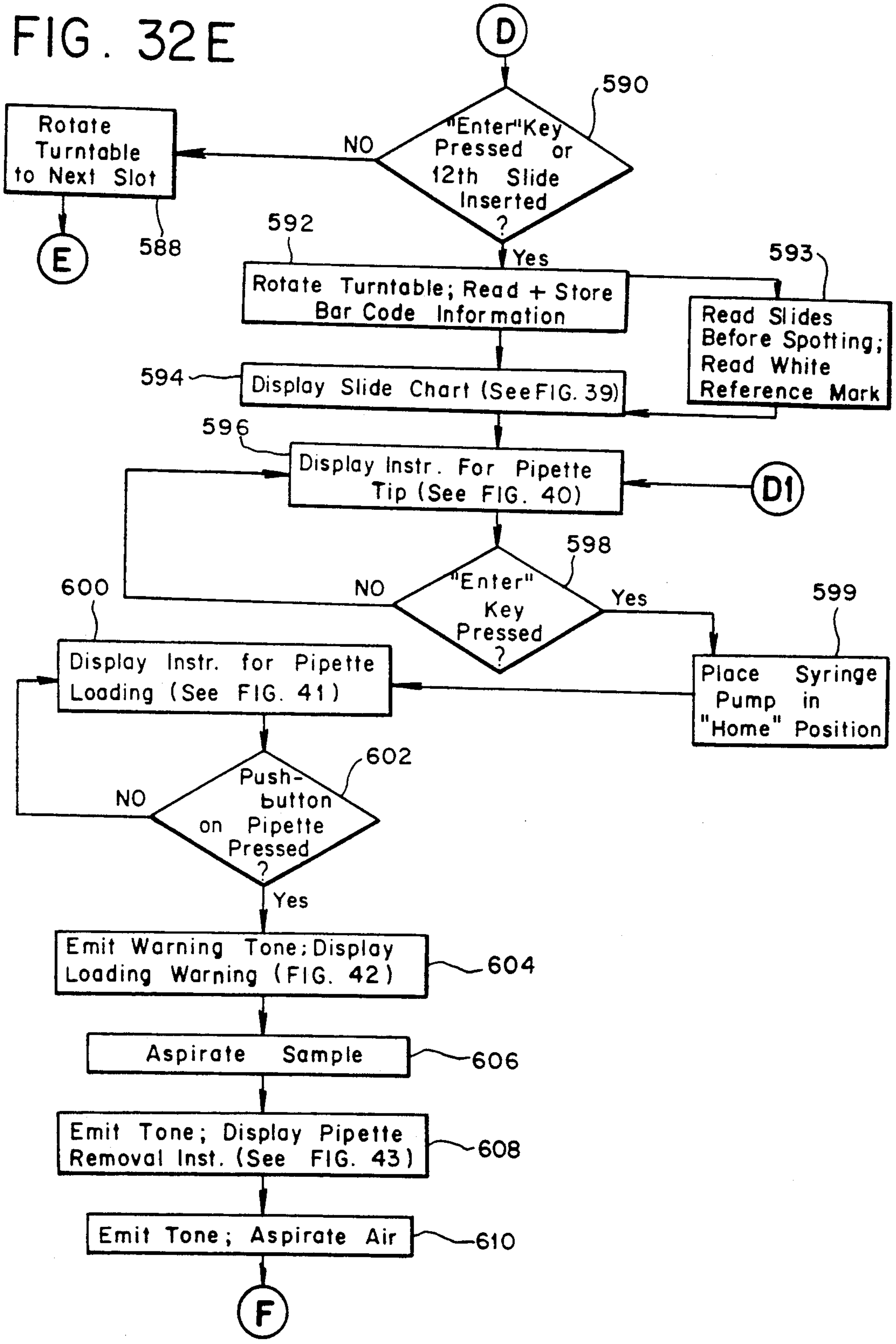
Figure 32F:
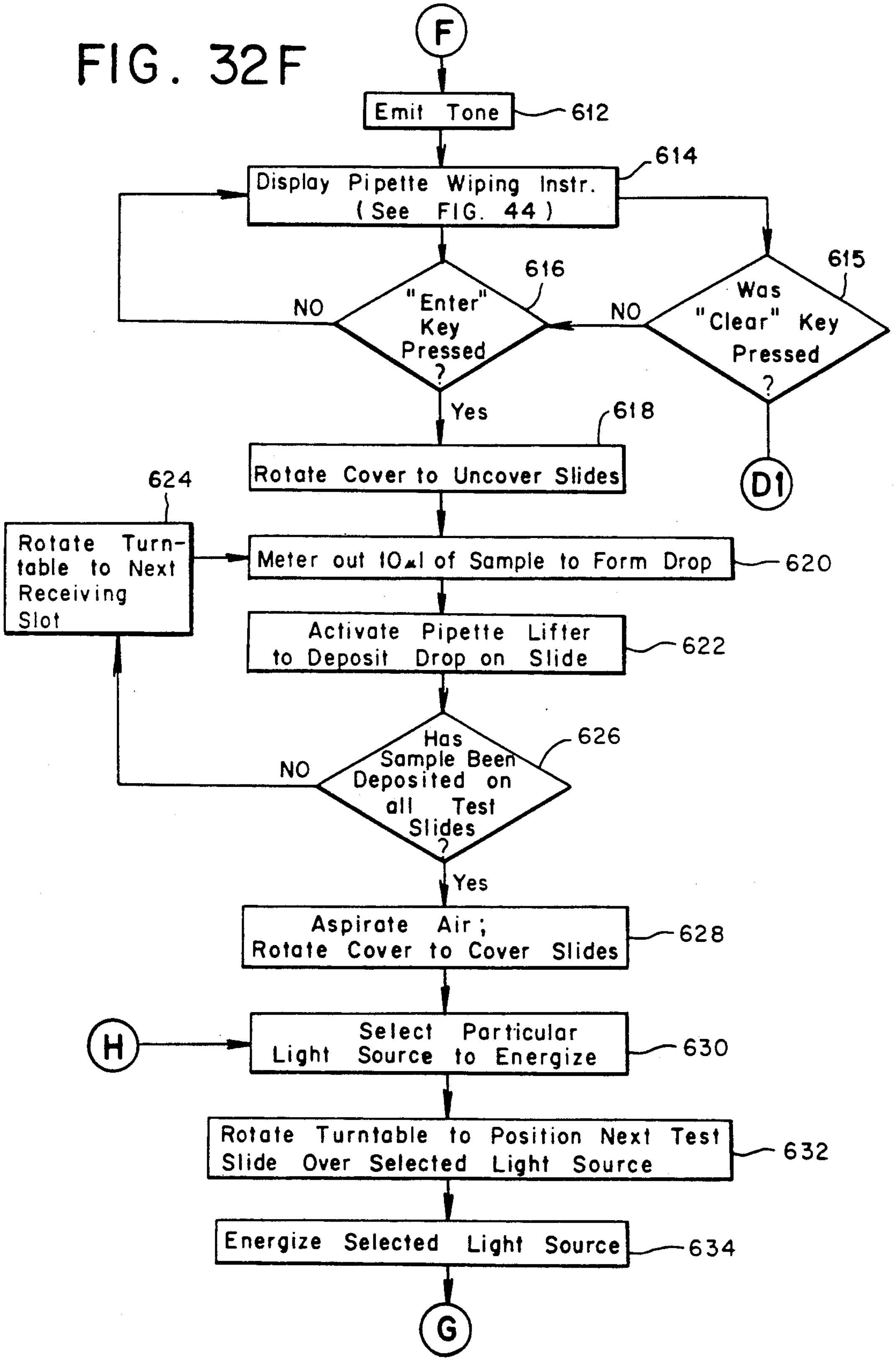
Figure 32G:
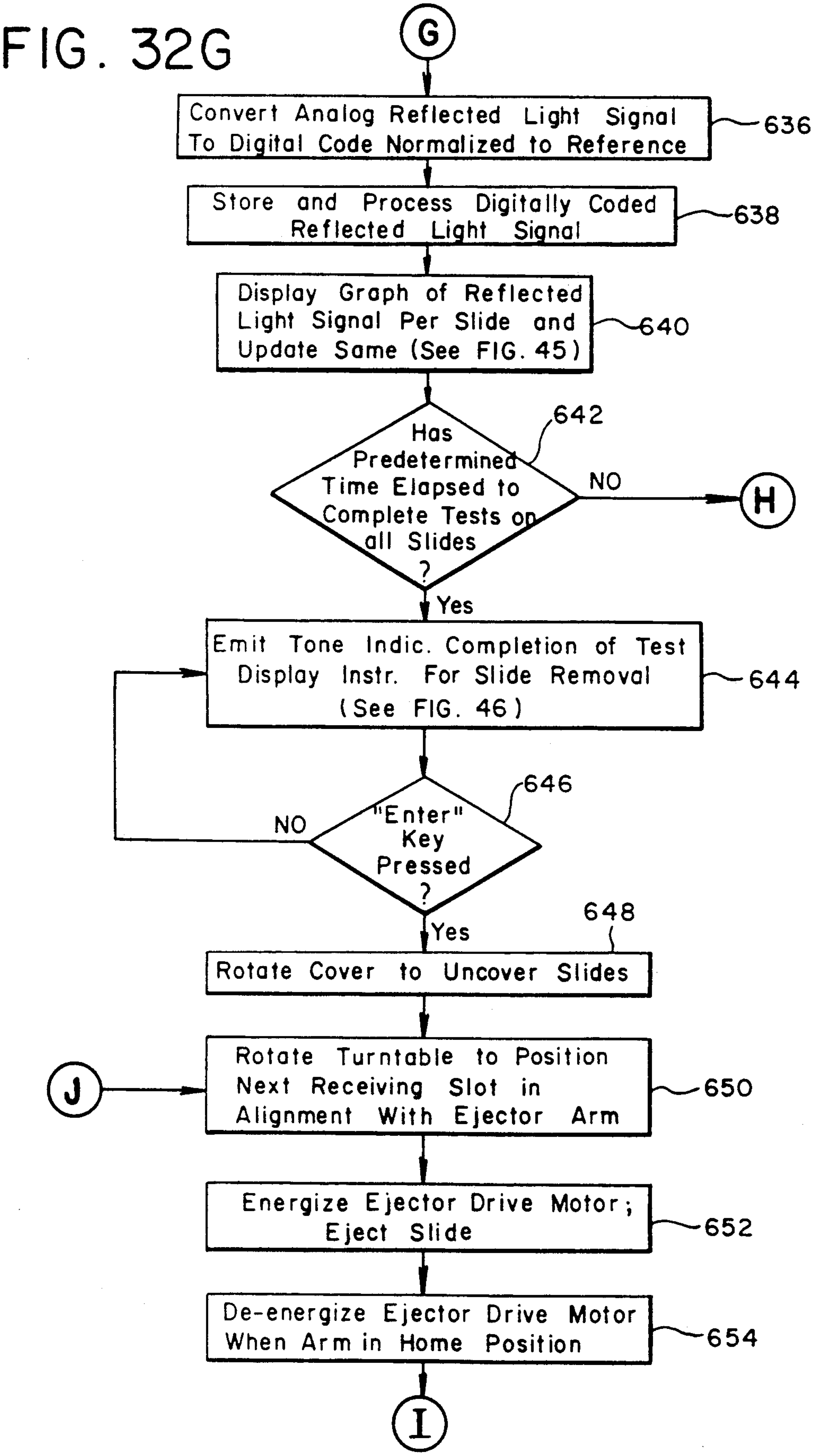
Figure 32H:
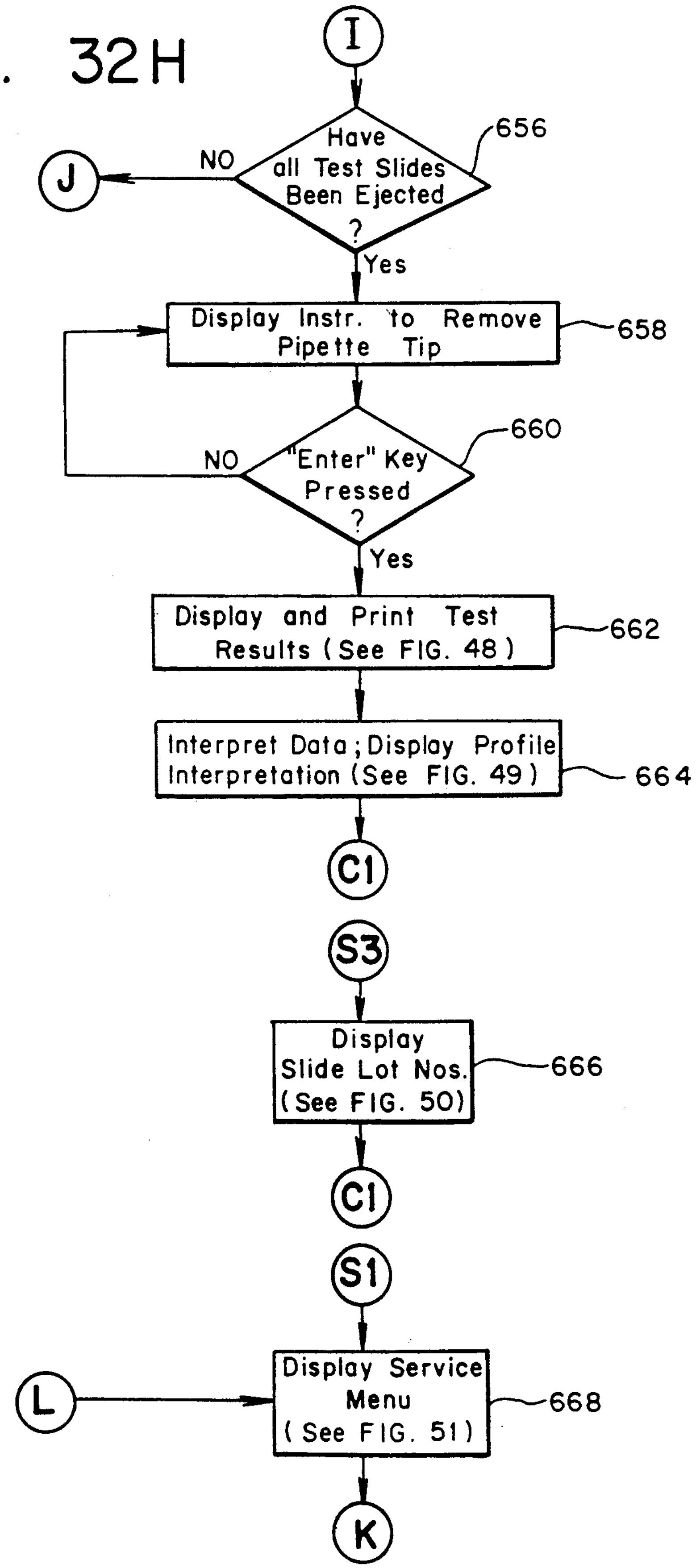
Figure 32I:
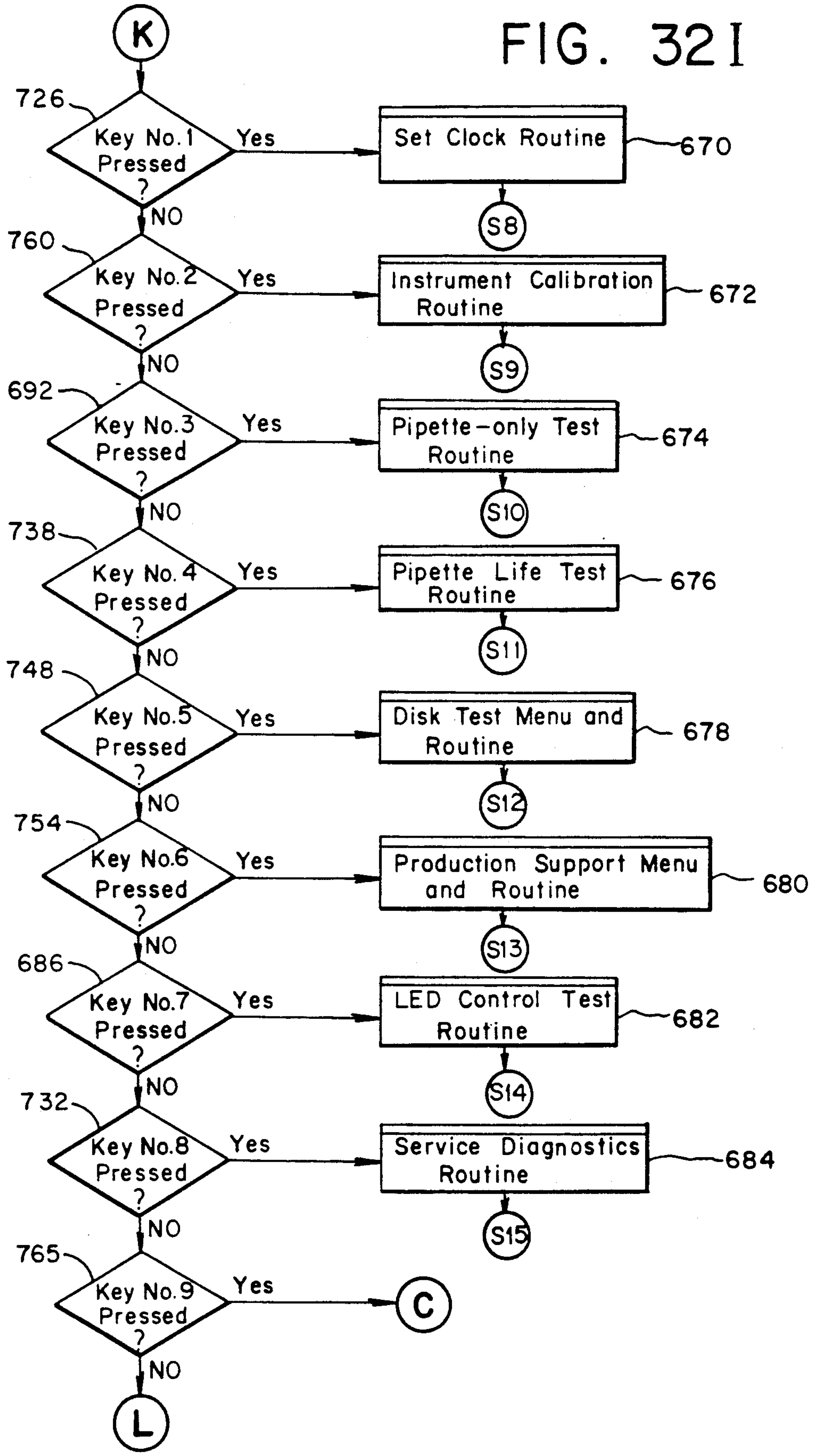
Figure 32J:
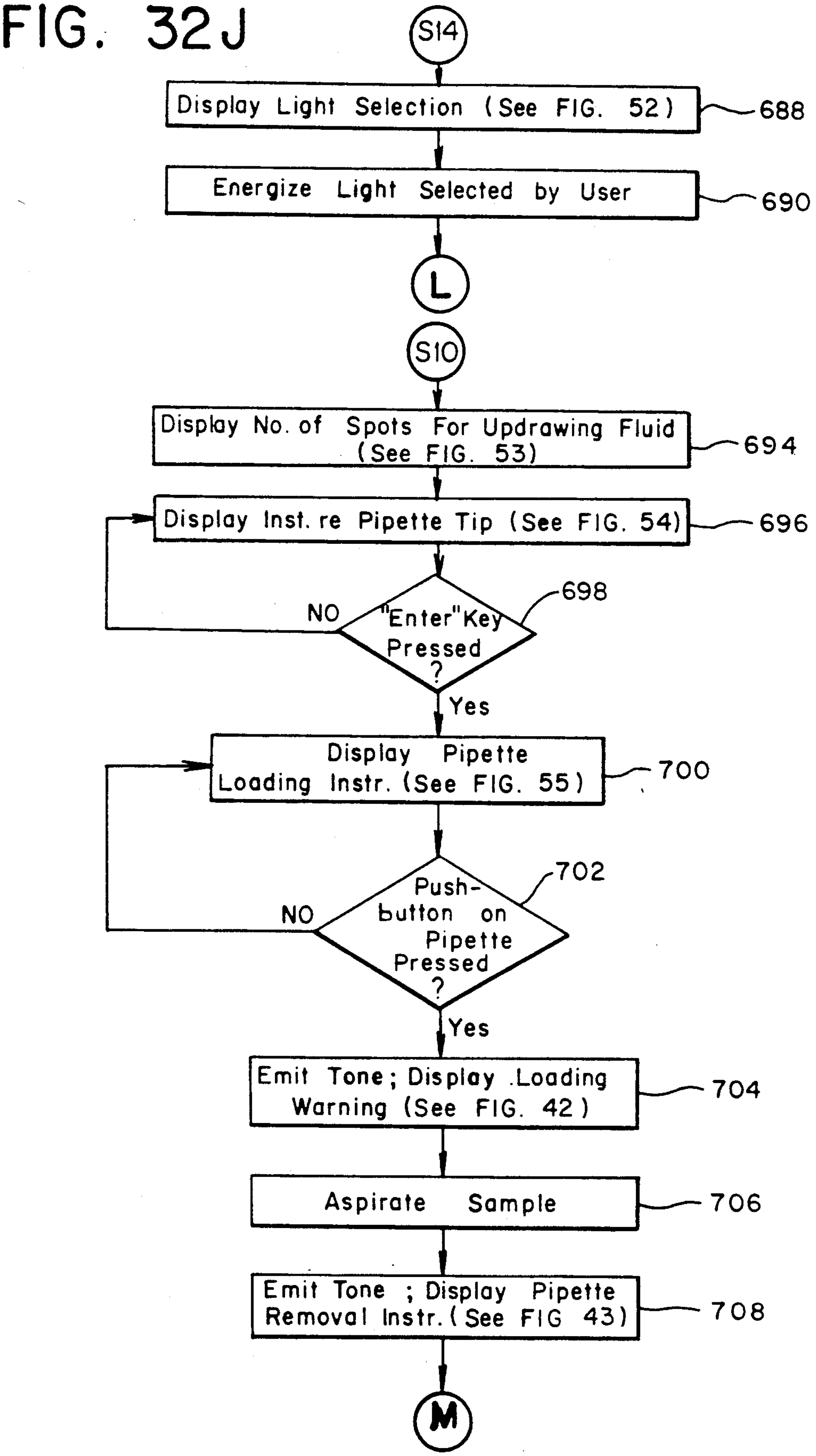
Figure 32K:
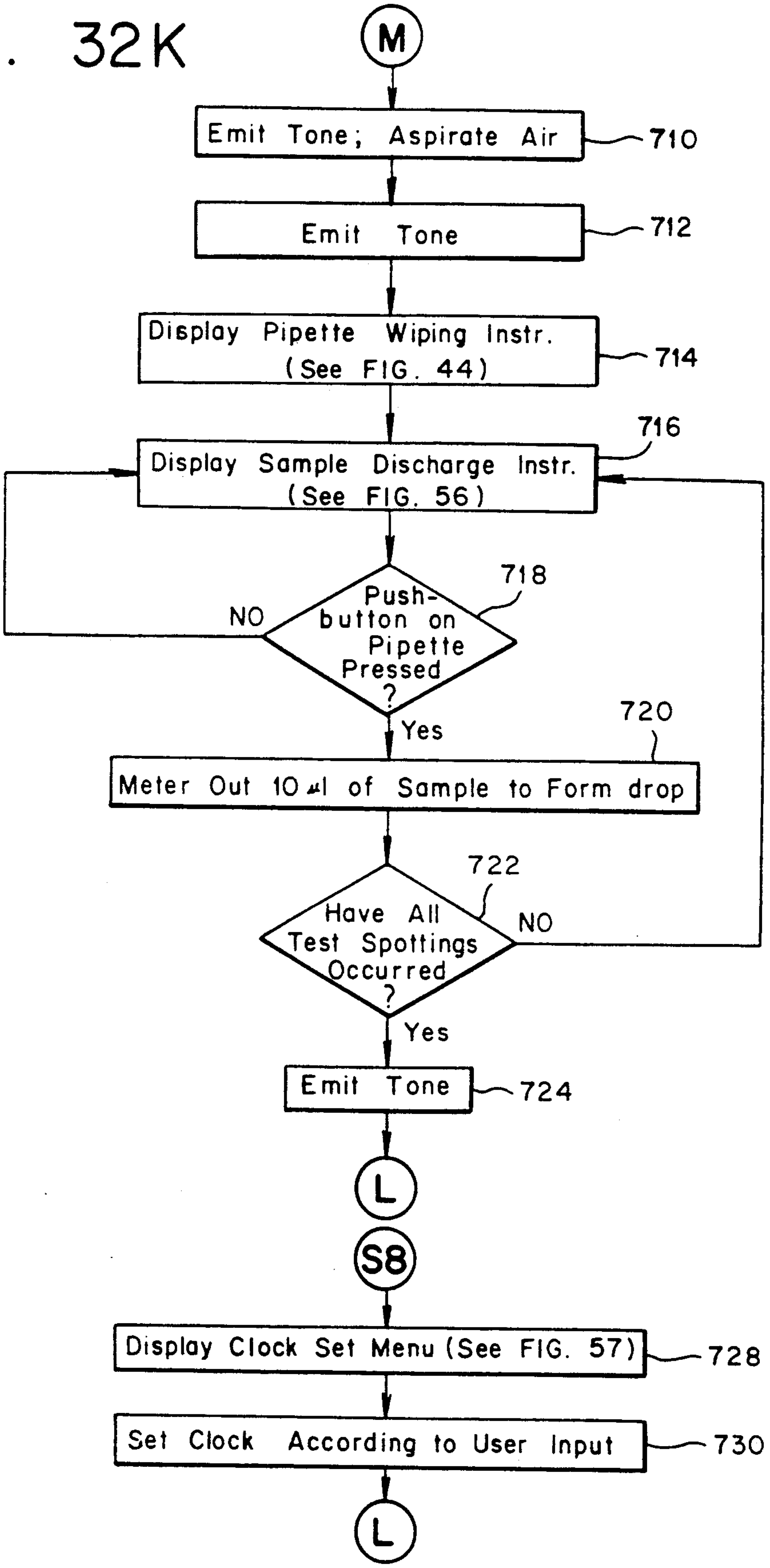
Figure 32L:
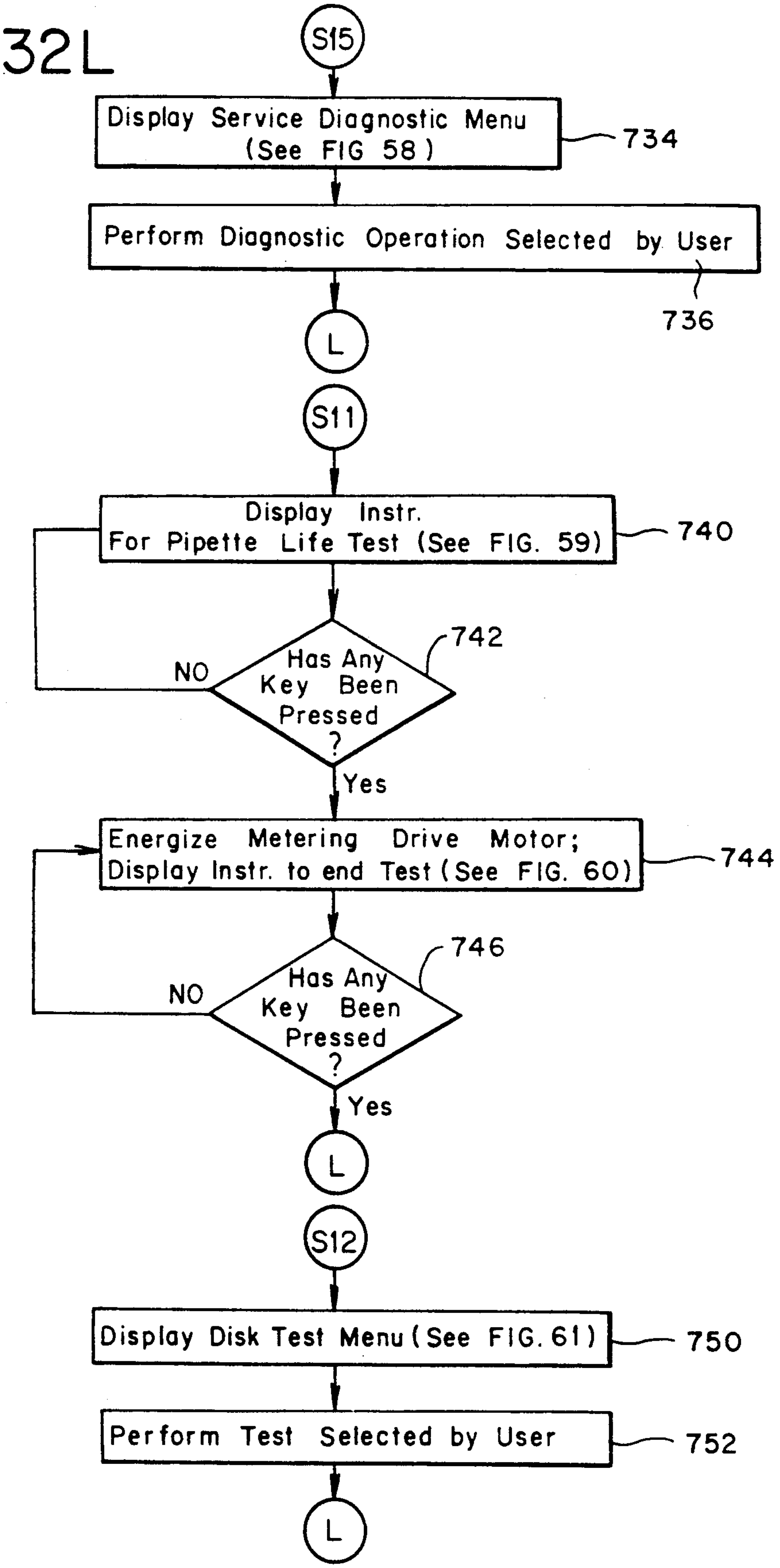
Figure 32M:
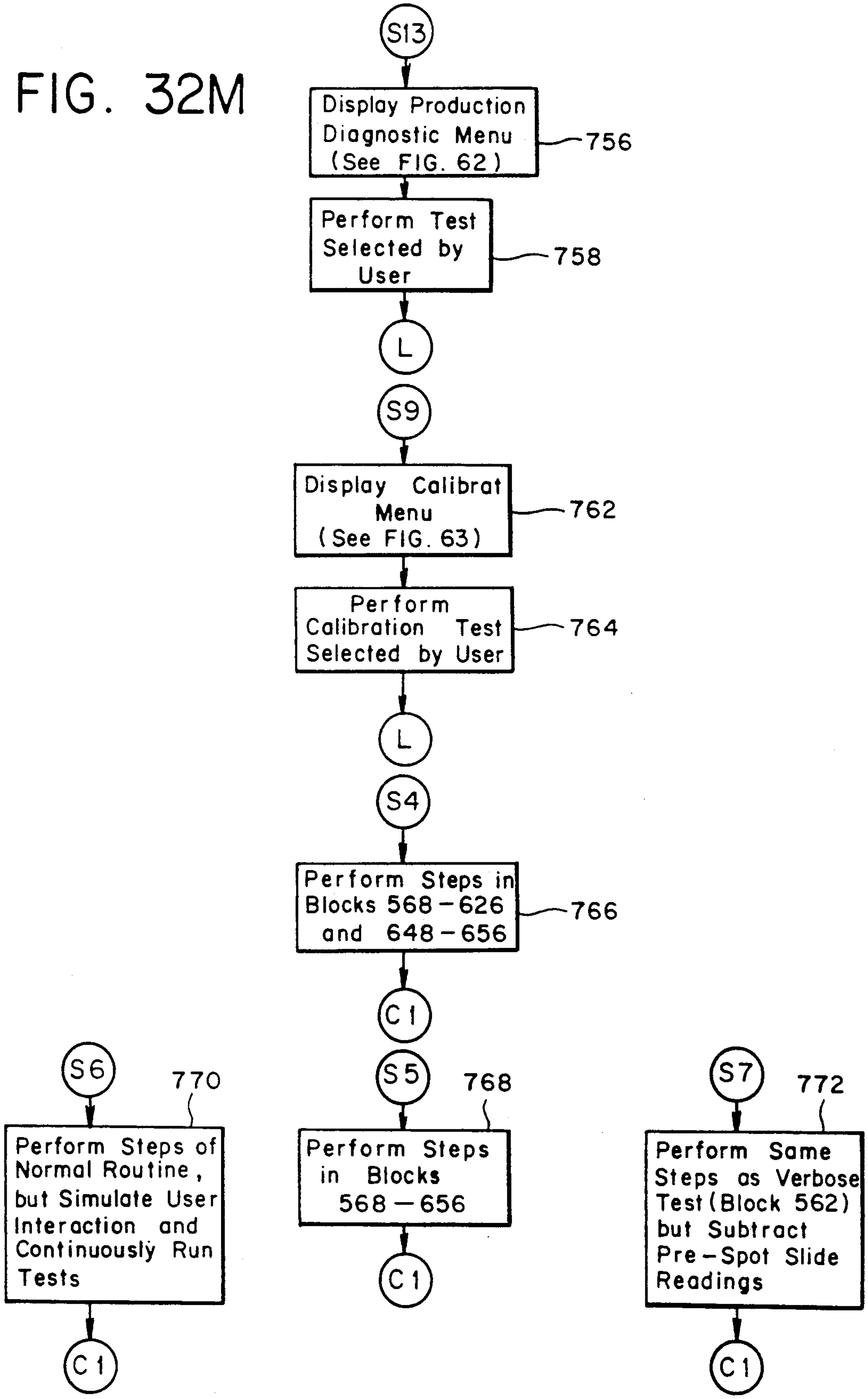

FIGS. 27, 27A and 28 illustrate an alternative form of the metering assembly of the present invention. The DC reversible stepping motor 270 is mounted on a mounting block 320 which is attached tot he underside of the base plate 48. A pinion gear 322 is mounted to the drive shaft of the motor 270. The pinion gear 322 engages another gear 324 mounted on the lead screw 276. The lead screw 276 is mounted on one end through the mounting block 320. A ball bearing bushing 326 surrounds the end of the lead screw to minimize friction. A spring clip 328 is fitted into a circumferential slot formed in the end of the lead screw 276 so that the lead screw is rotatably secured to the mounting block 320.

The other end of the lead screw 276 is mounted rotatably through an end support block 330 also attached to the underside of the base plate 48. Again, a ball bearing bushing 332 surrounds the end of the lead screw and is housed by the end support block 330. The end of the lead screw extends through the end support block 330 and is retained in place by a bellville washer 334, followed by a flat washer 336 and two nuts 338.

As in the previous embodiment, a preferably plastic guide or movable block 340 having brass threaded nut 342 internally mounted in the guide block 340 is mounted on the threaded portion of the lead screw 276. Two guide rods 344 extend between the end support block 330 and the mounting block 320 and through the plastic guide block 340 to prevent the guide block from turning relative to the lead screw 276.

The guide block 340 includes a T-slot 292 formed in one surface, as in the previous embodiment, which receives the enlarged head 302 of the plunger 300 of the syringe assembly. Once the head 302 of the plunger is properly inserted into the T-slot 292, a set screw 346 threadingly secured to the mounting block 320 may be tightened against the enlarged head 302 to secure the plunger and syringe in place. The operation of this embodiment of the metering assembly is similar in most respects to the previous embodiment described.

The Rotatable Turntable Drive Assembly

Figure 17:
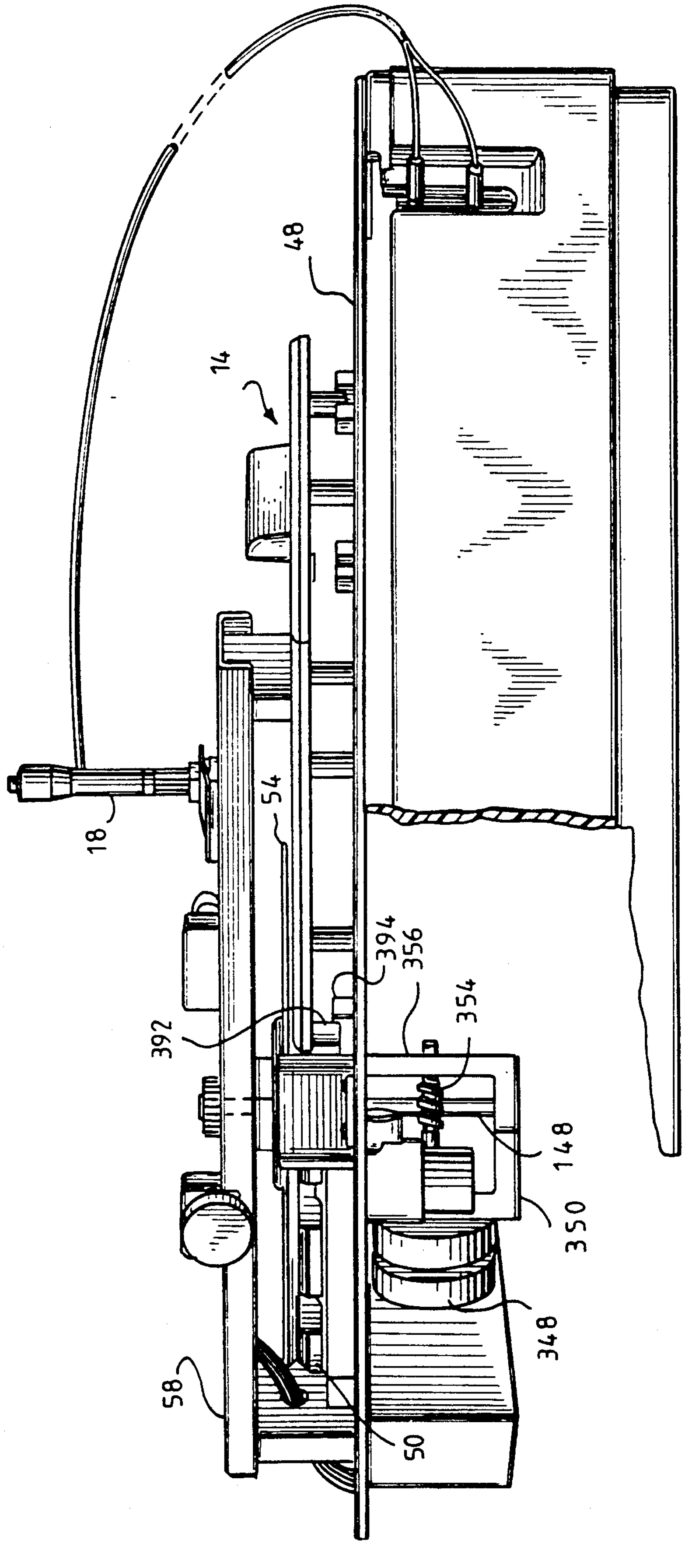
FIG. 17 is a front perspective view partially broken away illustrating the drive assembly for the turntable of the chemical analyzer.
Figure 18:
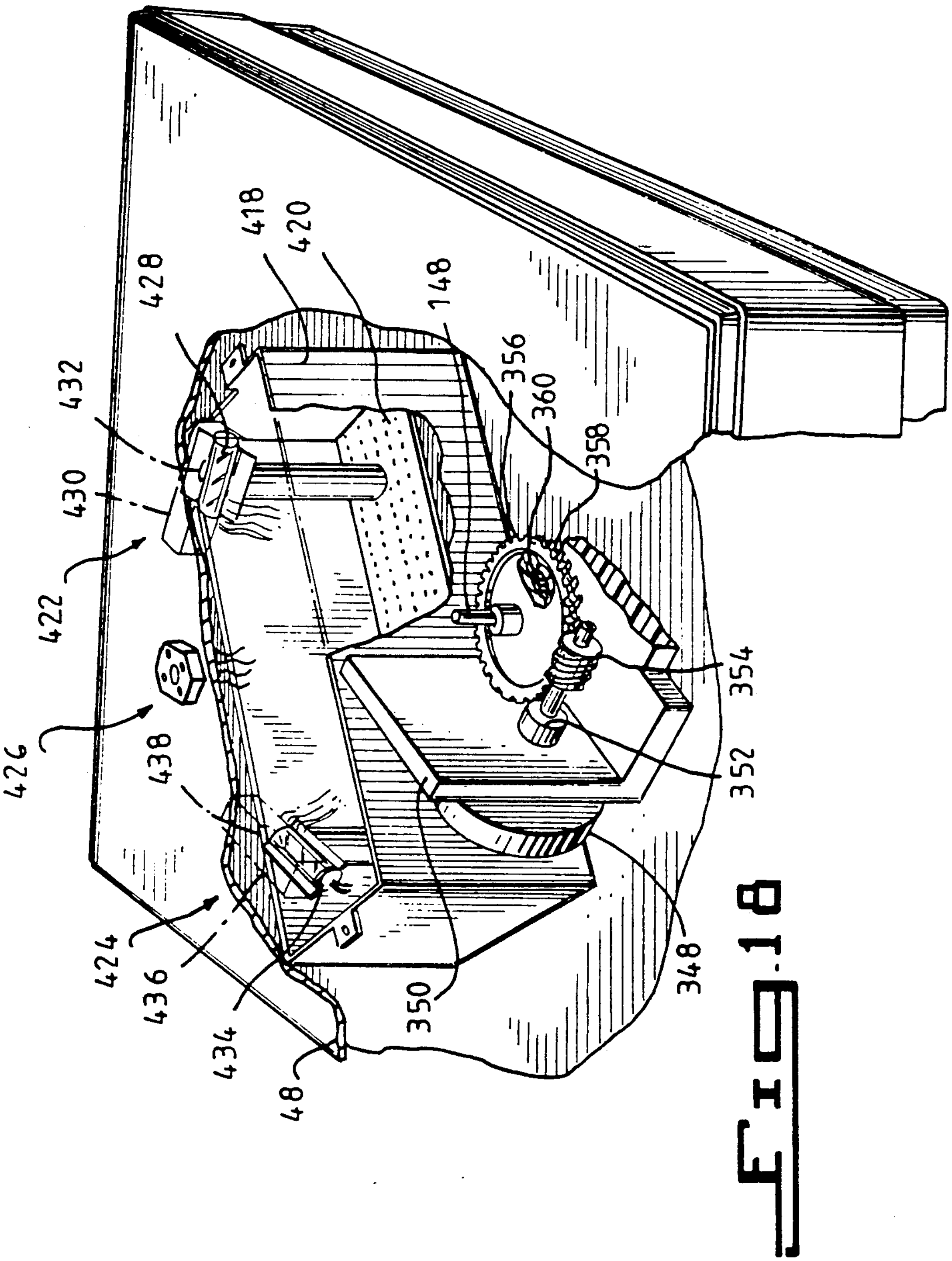
FIG. 18 is a top perspective view partially broken away, illustrating the drive mechanism of the turntable of the chemical analyzer in accordance with one form of the present invention.
Figure 19:
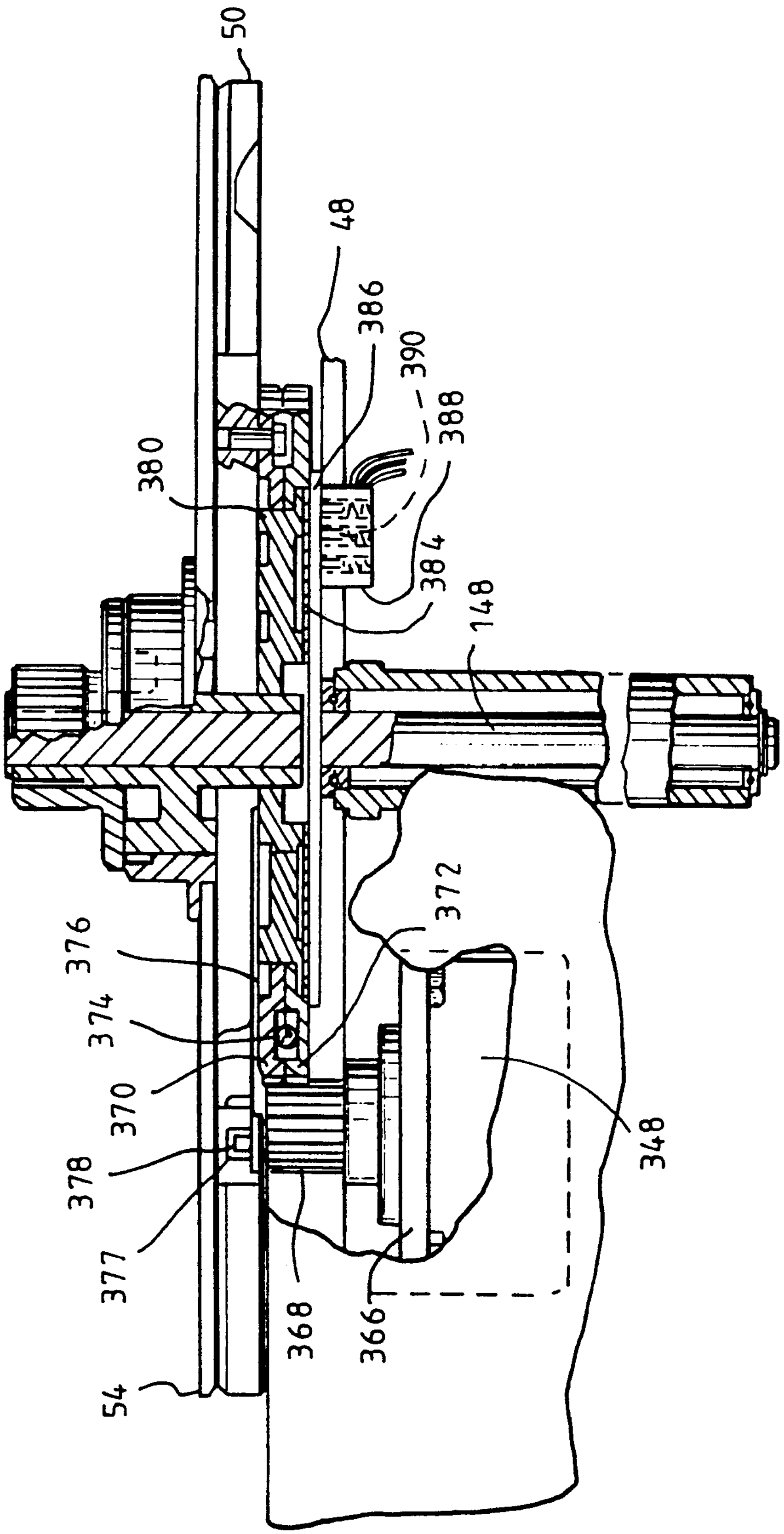
FIG. 19 is a perspective view of an alternate form of the turntable drive mechanism.

FIGS. 14, 17 and 18 illustrate one form of the drive mechanism for rotating the turntable of the chemical analyzer. The drive mechanism includes a DC reversible stepping motor 348 which is mounted to a supporting bracket 350 attached to the underside of the base plate 48. The drive shaft of the motor 348 passes through an opening formed in the supporting bracket 350 and is connected, by way of a coupler 352, to a helical gear 354 that extends between the drive shaft and an opposite wall 356 of the supporting bracket 352.

The helical gear 354 engages a pair of concentrically mounted drive gears 356, 358 having peripheral teeth, each drive gear being of the same diameter. The drive gears 356, 358 are mounted on the vertically disposed spindle 148 on which the turntable 50 is fixedly mounted. The upper gear 356 is fixedly mounted to the spindle 148. The lower gear 358 is loosely mounted on the spindle 148, but connected by a spring 360 to the upper gear 356. This arrangement minimizes the backlash between the helical gear 354 and the drive gears 356, 358 when the turntable is rotated in opposite directions.

The spindle 148 on which the rotatable turntable 50 is mounted is supported at one end by the bracket 350 and passes through the base plate 48 of the analyzer.

In one form of the present invention, as shown in FIG. 10, the rotatable turntable 50 is secured to the spindle 148 by a hub 362 mounted on the turntable. The hub 362 includes a notch 364 formed in its side wall, which notch 364 is adapted to receive part of the pin 149 used for opening and closing the cover 54.

An alternative form of the turntable drive mechanism and the turntable is illustrated by FIGS. 8A, 19, 29 and 30. The drive motor 348 is mounted vertically on the underside of the base plate from a mounting bracket 366. A pinion gear 368 mounted on the drive shaft of the motor 348 directly drives a pair of superposed gears 370, 372 mounted on the spindle 148 of the turntable. The upper gear 370 is fixedly mounted to the spindle 148 (or to the turntable 50), while the lower gear 372 is rotatably mounted on the spindle but coupled to the upper gear by way of one or more springs 374. As with the other previously described embodiment of the turntable drive mechanism, the arrangement of the two turntable gears 370, 372, is to minimize backlash.

A shallow recess 376 is formed in the underside surface of the turntable. The recess 376 houses a printed circuit board 371 (see FIG. 8A) used for sensing the temperature of the turntable. Mounted closely within another recess 377 formed in the underside surface of the turntable is a heat sensing device 378, such as a thermocouple, which is also mounted on an end of the printed circuit board 371 and which senses the temperature of the turntable 50 by heat conduction. The thermocouple 378 is connected to the associated circuitry of the analyzer as will be explained.

An insulating material 373 is provided on the bottom of the printed circuit board to prevent damage to the circuit board and its components.

A heater plate 380 (see FIGS. 8A and 30) which includes a recess formed in one of its top or bottom surfaces houses a number of conductor windings or heater elements 382, such as manufactured by Kurabe Wire and Cable Co., and is positioned on the spindle 148 adjacent to and underneath the turntable 50. Heat from the elements 382 is spread by the heater plate 380 and is conducted to the turntable in order to maintain the temperature of the test slides within a predetermined range.

A second insulator 384 is mounted below the heater plate 380, and adjacent the insulator 384 is mounted a printed circuit board 386 containing a number of slip rings (not shown).

In one form of the present invention, there are three slip rings provided on the circuit board 386: one slip ring is a common conductor; another slip ring is for providing power to the heater plate 380; and the third slip ring is for providing the signal from the sensor 378 and its associated printed circuit board to the other electronic circuitry of the analyzer.

Mounted through an opening of the base plate 48 of the analyzer is a brush assembly 388. The brush assembly 388 includes three upstanding brushes or contacts 390 which are spring loaded. The contacts 390 contact the slip rings on the printed circuit board 386. The combination of the slip rings and brush assembly provide electrical continuity to the heater plate 380 and the components of the sensor printed circuit board while the turntable 50 is rotating.

In order for the rotatable turntable 50 to be properly aligned with the slide inserter 14, ejector mechanism (which will be described) and pipette assembly 16, a "home" position of the rotatable turntable 50 is sensed optically. Mounted generally on the underside of the turntable 50 (and more specifically on the bottom surface of the heater plate 380) and rotatable with the turntable is an L-shaped bracket having a downwardly protruding leg 392 (see FIGS. 8A and 17). Extending upwardly through the base plate 48 of the analyzer is an optical sensor 394 including a pair of spaced apart LED light source and light detector. The optical sensor 394 and the downwardly extending leg 392 are situated radially with respect to each other such that, as the turntable 50 rotates, the leg 392 will pass between the light source and the detector breaking the light beam between the two.

The downwardly extending leg 392 is positioned at a particular point on the rotatable turntable 50 circumferentially. When the leg passes between the light source and detector of the optical sensor 394, the sensor will signal the associated computer and circuitry of the analyzer. The computer is programed to provide the stepping drive motor 348 with a predetermined number of pulses to drive the turntable clockwise or counterclockwise from the time the signal from the optical sensor is received in order to align a particular receiving slot 52 with any one of the slide inserter 14, the pipette assembly 16, and the ejector mechanism.

It should be noted that the base plate 48 is also maintained at a constant temperature. To accomplish this, a plurality of heaters 395 are mounted to the underside of the base plate 48 (see FIG. 14). Alternatively, a strip heater (not shown) may be mounted to the base plate 48 to maintain a constant temperature. The strip heater is basically an elongated coil inside a silicon jacket which is disposed in a circle on the underside of the base plate. Such a device is manufactured by Kurabe Wire and Cable Co., and is similar to heater element 382.

The Slide Ejector Mechanism

Figure 21:
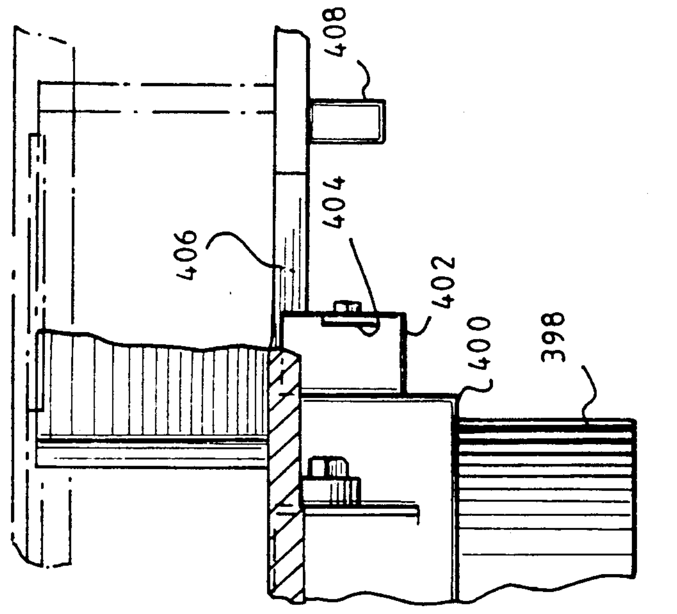
FIG. 21 is a front view of the ejector mechanism shown in FIG. 20.
Figure 20:
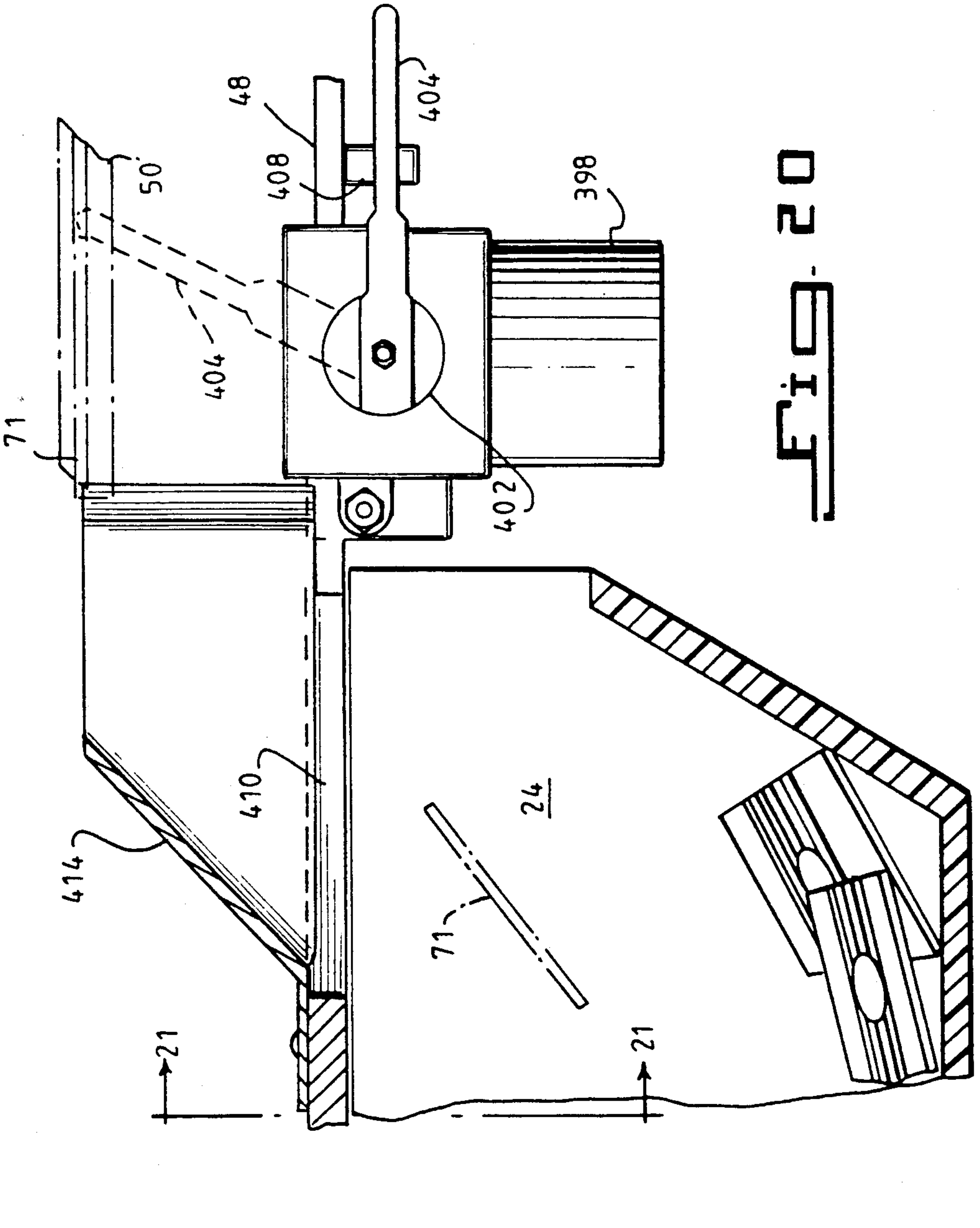
FIG. 20 is a side view of a slide ejector mechanism used in the chemical analyzer of the present invention.
Figure 24:
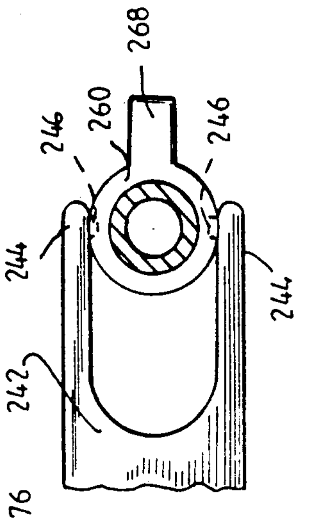
FIG. 24 is a top elevational view of a portion of the metering device of FIG. 22.
Figure 23:
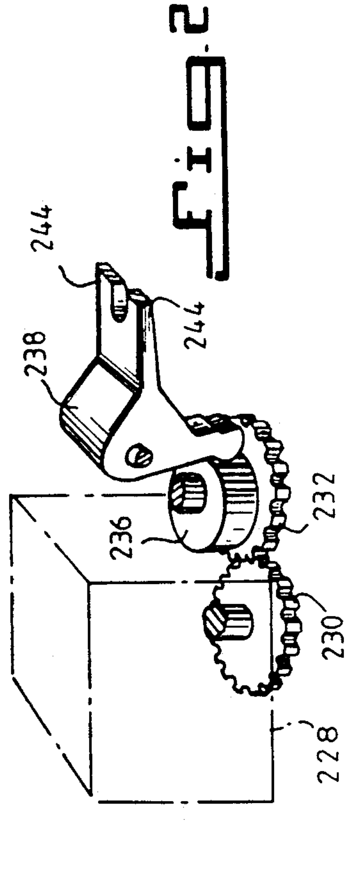
FIG. 23 is a perspective view of a portion of the metering device of FIG. 22.

FIGS. 14, 20 and 21 illustrate a preferred form of an ejector mechanism 396 which removes the slides from the rotatable turntable generally after the tests have been completed.

The slide ejector 396 basically includes a DC drive motor 398 mounted to an L-drive reduction gear box 400. The motor 398 and the L-drive reduction gear box 400 are mounted to the base plate 48 of the analyzer and positioned, for the most part, on the underside of the base plate.

The drive shaft of the motor 398 is disposed vertically. Therefore, the output shaft of the L-drive gear box 400 is disposed horizontally and positioned slightly below the underside of the base plate.

A hub 402 is mounted onto the gear box shaft, and an elongated ejector arm 404 is mounted in a key slot formed in a peripheral wall of the hub 402.

The ejector arm 404 is positioned in alignment with an opening 406 formed in the base plate 48 of the analyzer and has a length which is such that it will extend through the receiving slots 5 formed in the rotatable turntable and contact a test slide 71 in the receiving slot of the turntable when the receiving slot is positioned to be in alignment with the ejector arm 404.

When the test slides are to be unloaded from the turntable, the turntable is rotated until a receiving slot 52 is positioned in alignment with the ejector arm 404. The computer and electronic circuitry of the analyzer then energizes the drive motor 398, which causes the ejector arm 404 to rotate upwardly through the base opening 406. The ejector arm 404 contacts the edge of the slide 71 in the receiving slot 52 aligned above it and pushes the slide out of the open end of the receiving slot.

The arm 404 continues to rotate until it reaches its initial position at which time the drive motor 398 is deenergized by the computer and electronic circuitry and the movement of the arm stops. The initial or "home" position of the arm 404 is detected by using an optical sensor 408 such as the reflective type described previously or the LED/detector type, mounted on the underside of base 48 and adjacent to arm 404.

After a test slide 71 has been removed from the receiving slot 52 by the ejector, the turntable 50 is again rotated until the next adjacent receiving slot is positioned in alignment with the ejector arm 404. The computer and associated circuitry will then energize the drive motor 398 of the ejector to eject the test slide in that receiving slot. The sequence repeats itself until all of the test slides have been unloaded from the rotatable turntable 50.

As a slide 71 is removed from a receiving slot 52, it passes through a discharge opening 410 formed in the base plate 48 and is caught by the slide drawer 24 which is partially positioned under the slide discharge opening 410 formed in the base plate (see FIG. 4). The bottom of the slide drawer 24 includes a protruding lip 412 which catches on the edge 413 of the analyzer base to prevent the drawer from inadvertently sliding open.

An upstanding cowling 414 is mounted on the top surface of the base plate 48 and partially surrounds the slide discharge opening 410. The cowling 414 may include outwardly flared ends 416 which define an open side of the cowling between them. The cowling 414 is used to guide the test slide 71 into the discharge opening 410 as it is being removed from the turntable 50 (see FIG. 7).

The Reflectometer Assembly Of The Analyzer

FIGS. 18 and 31*a*, 31*b* and 31*c* illustrate the reflectometer assembly of the analyzer. The assembly is generally enclosed by a rectangular housing 418 secured to the underside of the base plate 48. The reflectometer assembly basically includes a printed circuit board 420 containing associated circuitry, and several light sources, generally designated by references numerals 422–426. The first light source 422 includes a fluorescent lamp or tube 428 emitting a light having a frequency of between about 390 and about 405 nM and is optimally about 400 nM. The fluorescent tube 428 is mounted on one side of a block 430 having a bore 432 extending through its thickness at a predetermined angle of slope with respect to the vertical. The block 430 is mounted on the top surface of the base plate 48, with the fluorescent tube 428 situated below it, and is situated over a cutout 431 formed through the thickness of the base plate 48. The block 430 is situated on the base plate 48 with respect to the turntable 50 such that light emitted by the fluorescent tube 428 through the bore of the block will impinge directly on and at a particular angle to the underside of the film portion 124 of a test slide 71. An ultra-violet bandpass filter 429 is interposed between the fluorescent lamp 428 and the test slide and is preferably mounted in the bore 432 of block 430.

A second light source 424 also includes a fluorescent lamp or tube 434 is mounted in a similar manner as that described for light source 422. This fluorescent tube 434 emits a light having a frequency in the range of about 345 to about 355 nM and is optimally about 350 nM. The second fluorescent tube light source 424 also has a block 436 having a bore 438 associated with it, which block is mounted on the base plate 48 over a second cutout 439 formed in the plate similar in structure to that previously described in relation to the first fluorescent tube light source 422. As with light source 422, light source 424 includes an ultra-violet bandpass filter 440 interposed between the fluorescent lamp 434 and the test slides and preferably is mounted in the bore 438 of block 436.

The two fluorescent tube light sources 422, 424 are particularly situated with respect to each other and to the rotatable turntable 50 such that they are adapted to form a light beam emitted by their respective fluorescent tubes on the bottom of the film portion 124 of a test slide located in a receiving slot 52.

As mentioned previously, the receiving slots 52 of the turntable 50 are preferably formed to be larger than the exposed film portion 124 of the test slide so that the receiving slot does not interfere with the light impinging on the test slide.

A first collimating lens 442 is mounted in an opening 444 formed through the thickness of the base plate 48 directly below a receiving slot 52 aligned with it. The collimating lens 442 is surrounded by a closed cylindrical tube 446 which extends upwardly from the printed circuit board 420 of the reflectometer assembly. The closed tube 446 ensures that no light enters the reflectometer assembly to interfere with the light received by the collimating lens 442. The lower end of the tube 446 surrounds a photodiode mounted 448 on the printed circuit board 420. Light from the first fluorescent lamp 428 is reflected from the test slide 71 and is received by the photodiode 448 through the lens 442. The tube may also include an optical stop 447 positioned between the lens 442 and the photodiode 448 to prevent any stray light from being received by the photodiode and affecting the measurements. Optical stop 447 includes an aperture through its thickness.

A similar arrangement as described above is provided for the second fluorescent tube light source 424. More specifically, a second collimating lens 450 is mounted in an opening 452 in the base plate 48 directly below another receiving slot of turntable 50 and a second cylindrical tube 454 is disposed between the collimating lens 450 and the printed circuit board 420. The lower end of the second tube 454 also completely surrounds and encloses a second photodiode 456 mounted on the printed circuit board. The second tube also preferably includes an optical stop 449 between the lens 450 and the photodiode 456.

An optical sensor, such as a photodiode 457, 459, is positioned partially in the light beam emitted by the fluorescent tubes 428, 434 for the purpose of determining the amount of light which is directed onto the test slides. This information is used as a reference and is compared to the light which is reflected from the test slides and detected by the photodiodes 448, 456.

Light of a particular frequency emitted by one of the fluorescent tubes 428, 434 forms a beam when passing through the bore of the corresponding mounting block 430, 436, which beam impinges on the bottom of the film portion 124 of a test slide located in a receiving slot aligned with the associated collimating lens 442, 450. A certain amount of light is reflected by the test slide into the collimating lens, which light is received by the associated photodiode 448, 456 through the enclosed tube 446, 454.

A third light source assembly 426 is also provided. The third light source assembly basically includes a mounting block 458 situated on the top surface of the base plate 48, and partially passing through an opening formed in the base plate. The third mounting block 458 includes a plurality of spaced apart bores 460 formed through its thickness. Each bore is sloped to the vertical and, preferably, is at an angle of 45 degrees to the vertical In a preferred form of the invention, four bores 460 are formed spaced equally distantly about the general periphery of the third mounting block 458.

Four light emitting diodes (LEDs) 462, each emitting a light of different frequency, are mounted in the underside of the third mounting block 458, each LED 462 being received by a corresponding bore 460. The third mounting block 458 is situated on the base plate and with respect to the rotatable turntable 50 such that light emitted by any one of the LEDs will impinge on the bottom of the film portion 124 of a test slide 71 located in a receiving slot.

A bore 464 is formed centrally through the mounting block 458. A collimating lens 466 is mounted in the bore 464 and near the top surface of the block 458. A photodiode 468 is also mounted in the bore 464 and near the lower surface of the block 458. Interposed between the lens 466 and the photodiode 468 and in bore 464 is an infrared rejection filter 470.

Light from any LED 462 impinging on the test slide 71 will be reflected directly into the photodiode 468 through the lens 466 and filter 470. The photodiode will provide a signal indicative of the amount of light reflected to the associated circuitry of the reflectometer.

As mentioned previously, four LEDs 462 are provided, each LED emitting a light of different frequency. The preferred frequencies emitted by the LEDs are in the following ranges: about 555 to about 565 nM; about 585 to about 595 nM; about 635 to about 645 nM; and about 675 to about 685 nM. The optimal frequency for each of the LEDs mentioned above is 560 nM, 590 nM, 640 nM and 680 nM, respectively. Preferably, the latter two LEDs (i.e., 640 nM and 680 nM LEDs) have filters 469 of the desired wavelength (i.e., 640 and 680 nM) positioned in their respective bores 460.

Each of the four LEDs 462 may be individually energized so that a single beam of light having a particular frequency or range of frequencies will be selected to impinge on a particular test slide. Although the fluorescent lamp light sources 422, 424 may be individually energized, they are preferably energized when the analyzer is powered up. Any test slides which have a chemistry that requires one or the other fluorescent source are positioned by the turntable over that source. During the analysis operation, the associated computer and electronic circuitry of the chemical analyzer has stored in memory what test slide is aligned with what light source.

Various tests require various test slides, each test slide carrying a different dry analyte. The various test slides must be exposed to light of selected frequencies in order to conduct a reflectometry test. The type of test slide, for example, for a calcium test, is provided by the bar code information 86 on the top surface of the slide, which information is read by the bar code optical scanner 158 and which is provided to the associated computer and circuitry of the analyzer. In its memory, the analyzer will associate a particular receiving slot 52 with a particular test slide 71 and will energize the appropriate light source 422-426 during the analysis operation when the slide is positioned over the particular light source. This will be discussed in greater detail during the explanation of the operation of the chemical analyzer.

How the Analyzer Uses Reflected Light to Determine Concentration

The slides used in the analyzer change in intensity (at certain known wavelengths) according to the concentration of the chemistry in the serum. The analyzer must read the change in intensity and derive the concentration accordingly.

The analyzer software performs this task. The software makes use of the following two equations in order to determine the concentration:

$$\text{Percent Reflectance} = \frac{\text{(ACTUAL READING)} - \text{(ABSOLUTE BLACK)}}{\text{(ABSOLUTE WHITE)} - \text{(ABSOLUTE BLACK)}} \quad 1)$$

The Percent Reflectance is a value between 0 (black) and (white).

$$\text{R.D. (Reflectance density) } \text{Log}_{10}\,(1/\text{ Percent Reflectance}) \quad (2)$$

Reflectance density usually ranges from about 0.1 (white) to about 2.0 (black).

In order for the analyzer to determine these values, it first needs to know the value of ABSOLUTE WHITE and ABSOLUTE BLACK. These are determined by putting slides in the analyzer with known Percent Reflectances when the analyzer is calibrated. These slides are called black and white references. The ACTUAL READING is then taken from these two slides and then by simple algebra the ABSOLUTE BLACK and ABSOLUTE WHITE values are determined. This procedure is referred to as INSTRUMENT CALIBRATION.

Once the absolute values are determined, the analyzer can easily determine the RD value for any slide. There are two types of slides:

1) ENDPOINT slides—The concentration of the sample is determined by taking the RD at a fixed amount of time after the sample was placed on the slide (which is usually about 8 minutes).

2) RATE slides—The concentration is determined by the rate of change in the RD. The rate is determined after the whole analysis has taken place.

First, the INITIAL RATE is determined. This is done by taking the change in RD for almost the whole analysis. During some parts of the analysis, the reaction may not be stable, so these portions are ignored. This INITIAL RATE tells if the ACTUAL RATE is a large or small one. The points to use for determining the INITIAL RATE are predetermined for each chemistry by analyzing various samples of known concentrations.

According to how large the INITIAL RATE was, points are picked to use in determining the ACTUAL RATE. If the INITIAL RATE was high, then points are picked close together (because the chemicals in the slide wear out quickly with high concentration samples). If the INITIAL RATE was low, then points are picked far apart (this provides better accuracy). These points are predetermined according to the chemistry by doing trials of the chemistry with various samples of known concentrations.

A linear regression is done over this range of points (in time) of the reaction to determine the rate.

Now, the ENDPOINT RD or RATE is used to determine the concentration of the sample. Different lot numbers for each slide chemistry have different correlations between this ENDPOINT/RATE and the concentration. These correlations are predetermined by analyzing various samples of known concentrations. A chart or table for each different correlation is made, for example:

| GLUCOSE lot 4567: concentration (mg/dl) | R.D. |
|---|---|
| 0 | 0.0500 |
| 32 | 0.1976 |
| 191 | 0.5961 |
| 396 | 0.9216 |
| 480 | 1.0200 |

This is called a CHEMISTRY CALIBRATION CURVE. By doing a linear interpolation of the sample's known RD, one can determine the concentration. For example, if the RD was 0.7854, then the concentration would be determined as follows:

$$\frac{0.7854 - 0.5961}{0.9216 - 0.5961} = \frac{? - 191}{396 - 191}$$

By simple calculation, one finds that the concentration is 310 mg/dl.

The reflectometer of the analyzer is preferably calibrated in three different ways. The first method, which was described previously, uses black and white reference test slides. The slides are inserted in the receiving slots of the rotatable turntable, and the various light sources 422-26 are energized so that their light impinges on and is reflected by the reference test slides. The reflected light is measured by the analyzer, and data corresponding to the measurements are stored in the analyzer's associated computer.

These measurements are used in the initial calibration of the analyzer envisioned to be conducted at the analyzer manufacturing facility. Because the turntable may "wobble" during rotation or have a thickness which varies slightly about its circumference, not all of the test slides mounted on the turntable may be at the same distance above the light sources of the reflectometer. This variation in distance of the turntable at the respective receiving slots with respect to the light sources may affect the amount of reflected light received by the photodiodes of the various light sources. The computer of the analyzer will associate this measurement data with each respective receiving slot location on the turntable to compensate for any disparity in the reflected light received by the photodiodes of the light sources.

The second method involves rotating the turntable to position a light reference mark situated on the underside of the turntable over each light source. This operation is performed when the analyzer is initially calibrated, but also is repeated each time the analyzer is used to test a sample. During a sample test, the light from each source is directed onto the light reference mark, and the reflected light is measured and compared with measurements taken during initial calibration. This comparison will detect any varying brightness in the light sources for drift in the intensity of the light through the optics of the reflectometer and will compensate for such changes by providing a multiplication factor which is used in the computation of the sample's concentration.

The third method is conducted during a test operation. More specifically, the analyzer will energize one of the light sources 422-426 to cause light of a particular wavelength to impinge on and be reflected by the unspotted test slides. It is possible that the wavelength of light emitted by the sources is shifted from the optimum desired wavelength (due to the variations in the light sources and associated components used in the analyzer), and this shift in wavelength may affect the accuracy of the measurements, as different amounts of light may be reflected at different frequencies. For example, about a 1% change in the wavelength of light impinging on a calcium test slide may result in about a 6% change in light reflected by the slide. This shift in wavelength will not be detected by the second method of calibration using the white reference spot, as a white color will for the most part reflect light of all frequencies. Accordingly, by "reading" the test slides prior to their being spotted to determine the wavelength shift in the analyzer's light sources (and in particular, the LED light source 426), the analyzer can appropriately adjust the density value after the test slides "develop".

There is another reason why the reflectance of the test slides are read before they are spotted. It may be possible that a previously used slide has been inadvertently reloaded into the analyzer. By looking at the reflectance of the test slides prior to spotting, the analyzer may determine if any test slides were already used and eject the slides.

The Operation Of The Analyzer

The chemical analyzer 2 of the present invention is designed to be user friendly. More specifically, the chemical analyzer will provide not only the test results of the analysis and a diagnosis of the possible ailments of the animal being tested, but also will provide instructions on its LCD display 8 for the user to follow during operation of the analyzer. The operation of the analyzer is illustrated by the flow chart shown in FIGS. 32a–f of the drawings.

The first step in the operation of the analyzer is to turn the power switch 28 on (Block 500). When this occurs, the analyzer will load data into its memory from the floppy disk (Block 502) and will initialize the hardware and software, such as by master resetting the components, etc (Block 504).

The analyzer will then not only display but also print out a copyright notice (Block 506; FIG. 33). Once the system has been initialized so that keyboard data may be read, the analyzer will look to see if a particular key (for example, key No. 3) on the keyboard 4 is pressed (Block 508). If it is, this is an indication to the analyzer that a service routine is to be performed (Block 510) as opposed to a normal analysis operation.

If key No. 3 is not pressed, the analyzer will go on to perform a self test of its electrical and mechanical functions (Block 512). For example, it will test to see if the pipette lifting mechanism is operational, whether the cover 54 can be opened and closed and whether the ejector mechanism 396 is operational.

During this time, the display will provide information to the user that the incubator is warming (Block 516) (and will display the temperature of the incubator, i.e., the turntable 50) and that a self test is in progress, and will instruct the user to wait until the test has been completed (FIG. 34).

The analyzer will then eject any slides which are left in the analyzer, and find the "home" positions of the ejector mechanism, the pipette lifter, the cover motor and the turntable by moving each mechanism until the optical sensor associated with each mechanism determines the position of the movable components (Block 514). The system then ensures that all of the components are properly aligned, for example, that a particular receiving slot (for example, slot No. 0) is in alignment with the longitudinal axis of the slide ejector, and that the cover pin is in alignment with the cover movement mechanism. All during this period, the heating plate 380 and other heating elements 39 have been energized and the temperature of the turntable 50 is being monitored (Block 516).

Since the slide inserter 14 is manually operated, the inserter plate 68 may be in the wrong position for loading. An alarm or speaker 518 incorporated into the analyzer will be activated to alert the user to grasp the grip 80 and pull the inserter plate to its most backward position on the slide inserter. The incorrect position of the inserter plate 68 is sensed by the first pair of light source 102 and photodetector 104 at this stage in the operation of the analyzer.

The incubator will continue to warm until it reaches a particular range of temperature. The incubator will then be maintained at this particular temperature, which is preferably about 37° C. ±0.2° C. All during the warming process, the temperature of the incubator may be displayed (FIG. 34).

The analyzer senses when the incubator has reached the desired temperature (Block 520). It will then start a clock (internal to the software of the associated computer) to allow the analyzer to stabilize in temperature for a predetermined period of time (Block 522).

The analyzer senses when the clock has reached the predetermined period of time (Block 524), which is preferably set for about ten minutes, and will then inform the user that the incubator is ready and that the self test is complete by displaying such information on the display (Block 526) and will also signal the user, who may not be looking at the display, by activating the alarm 518 which emits three loud tones. The user is then instructed to press the "Enter" key (E) on the keyboard 4 to use the analyzer (FIG. 3).

The analyzer will sense when the "Enter" key has been pressed (Block 528) and will then cause the turntable to rotate until the No. "0" assigned receiving slot 52 is in alignment with the slide inserter 14 (Block 530). It will further cause the cover 54 to rotate with respect to the turntable 50 such that the cover covers each receiving slot (Block 532). The cove 54 and the spring clip 116 of each receiving slot helps guide the slides 71 into a respective receiving slot at the proper time in the sequence of operations.

The analyzer will then display to the user the main menu from which the user may select the particular operation desired (Block 534; FIG. 36).

In one form of the invention, there are seven operations which are displayed to the user on the main menu. The first is a normal analyzer operation. The second is a lot number selection. The third operation is a service menu, for testing improper operation of the analyzer. The fourth operation is a skip analysis operation, the fifth is a verbose operation, the sixth is a life test and the seventh operation is a verbose operation with sub-prespotting. Each operation will be described in greater detail.

The user is instructed to enter his selection of operations by pressing one of the keys on the key pad 4 and also the "Enter" key. The analyzer will sense when a corresponding key adjacent to the displayed operation has been pressed (Block 536), as well as the "Enter" key (Block 538), will determine which key was selected (Blocks 540–552) and will perform the operation corresponding to the particular key selected (Blocks 554–566). In an alternative form, the "Enter" key need not be pressed for menu selection, the analyzer sensing when and which operation key is pressed and immediately performing the operation selected.

To facilitate an understanding of the operation of the analyzer, the following events which occur are for the normal operation of the analyzer (i.e., Block 554), as if the user pressed the key No. 1 associated with the normal operation displayed on the display.

In the "Normal Operation" routine, the analyzer will provide a display of information for the user. In its preferred form, the analyzer is particularly adapted for testing the serum of animals and for providing a diagnosis of the possible maladies of the animal being tested. The associated computer of the analyzer has stored in its memory the normal ranges for tests which are performed with respect to each category of animal. If the test results are outside of the normal ranges expected, the analyzer will alert the user to that fact and will provide the user with a possible diagnosis of the ailment. Accordingly, the analyzer will display the kind of a variety of animals (Block 568; see FIG. 37).

The user is instructed to press a particular key on the key pad for a particular animal being tested. For example, he is instructed to press the "1" key if the animal being tested is a dog, and the "2" key if the animal being tested is a cat, and so on. He is also instructed to press the "0" key for all other animals which are not displayed. The analyzer will sense when and what animal type was selected (Block 570), and the user selected information is then provided to the computer (Block 572). If the "Clear" key was pressed (Block 571) rather than making a selection, the analyzer will redisplay the main menu (Block 534).

The analyzer then provides another display (FIG. 38) in which it requests the user to enter the patient identification number. This may be a file number which is assigned to the animal by the veterinarian. In the preferred form, a patient number consisting of no more than 10 digits may be entered by the user. The analyzer will sense when the patient identification number has been entered (Block 574) and will store this information (Block 576). If the "Clear" key was pressed (Block 575) and no identification number was entered, the analyzer will redisplay the animal types (Block 568).

The analyzer, upon receiving this information, will then rotate the turntable so that receiving slot No. 0 is in alignment with the slide inserter 14 (Block 578). It should be noted that the pipette lifter was previously placed into its fully raised "home" position (Block 514).

The analyzer will then provide another display to the user (FIG. 38), instructing the user to insert the slides in the analyzer, and will inform the user how to perform this operation (Block 582). If, during the slide insertion operation, the "Clear" key is pressed (Block 583), the analyzer will eject the slides and return to displaying the main menu (Block 534).

The user inserts the slides individually into the slide inserter 14 , with the notch 94 on each slide aligned with the tab 92 formed on the slide orientation plate 88. If the slides are properly aligned, the bar code 86 on the slide will be exposed through the slot 90 formed in the orientation plate.

The user then grasps the grip 80 on the inserter plate 68 and pushes forward until the inserter plate is in the most forward position. The inserter plate will push the slide 71 into an appropriate receiving slot 52 on the rotatable turntable 50. No alarm will sound, as the operation is being performed properly. One optical sensor 108, 110 associated with the slide inserter 14 will sense when the inserter plate 68 has reached its most forward position, indicating that the slide 71 has been pushed into a receiving slot 52 on the turntable (Block 584). The user then pulls back the grip 80 on the inserter plate to its most backward position, which position is sensed by the other optical sensor 102, 104 (Block 586). When the most backward position is sensed, the analyzer will cause the turntable to rotate until the next adjacent receiving slot 52 is aligned with the slide inserter 14 (Block 588). The user will then place a second slide in the slide inserter and load that slide into the next receiving slot in the same manner as before. The turntable will then rotate so that the next adjacent receiving slot is aligned with the slot inserter, and the sequence repeats itself until the desired number of slides have been inserted by the user into the rotatable turntable.

The user then indicates to the analyzer that he has completed the loading of the test slides by pressing the "Enter" key. The analyzer will sense if the "Enter" key is pressed or if all 12 receiving slots have been filled (Block 590). The slide loading operation has been completed, and the analyzer will proceed to the next step in the operation.

After the slides have been loaded, the analyzer will rotate the turntable so that test slides loaded onto the turntable will pass beneath the optical code reader 158 so that the bar code information of each test slide will be read. This information is loaded into and stored in the computer of the analyzer (Block 592). The analyzer will then "read" the slides prior to spotting and will read the white reference mark on the underside of the rotatable turntable (Block 593), as described under the heading How the Analyzer Uses Reflected Light to Determine Concentration.

The analyzer will display (FIG. 39), for the user's information, a chart showing the type of test slide which has been loaded into each receiving slot (Block 594). If, for example, three test slides are loaded into the analyzer, one test slide being for a calcium (CA) test, another test slide being for an ammonia (NH3) test, and the third test slide being for a glucose (GLU) test, this information will be displayed in the first three boxes of the chart on the display. Since in the preferred form of the invention, there are twelve receiving slots 52, twelve boxes on the chart are displayed. The remaining boxes, which represent the unused receiving slots in this particular example, are displayed with the word "open", as no test slide had been inserted into these receiving slots.

The analyzer then informs the user that the slides have been counted, and instructs the user to insert a new disposable tip 176 on the pipette (Block 596). It also provides information to the user on its display as to how to go about putting the disposable tip on the pipette (FIG. 40). The user then signals the analyzer that this operation has been completed by pressing the Enter Key.

When the analyzer senses that the Enter key has been pressed (Block 598), it will then cause the drive motor 270 of the pipette syringe metering assembly to rotate until the syringe is in its "home" position (BLOCK 599). It is preferred to "home" the metering assembly at this stage of the operation. If the syringe homing step is performed at some other time, it is possible that any serum which the user may have accidentally left in the pipette tip may be pushed into the analyzer in an area other than on a disposable test slide. The analyzer will ten also display instructions to the user to load the pipette 18 with the sample by placing the pipette tip 176 just below the fluid level of the sample and then pressing the pipette push button switch 316 to start the sample loading process (block 600; FIG. 41). When the user presses the push button 316 on the head 318 of the pipette, this will be sensed by the analyzer (Block 602) which will then emit a tone indicating that the pipette is being loaded with serum sample. This is an indication to the user not to remove the disposable tip from below the surface of the serum sample. The analyzer will also display that the pipetting operation is underway, and that serum is being updrawn (Block 604; FIG. 42).

The analyzer will cause the drive motor 270 of the metering assembly to rotate a preselected number of turns to cause the plunger 300 of the syringe to be drawn backwardly through the syringe, which will cause serum to be aspirated into the disposable tip 176 of the pipette (Block 606).

After the proper amount of sample has been drawn into the pipette tip (which is about 10 ul per slide and about 30–40 ul to increase the pipetting accuracy), the drive motor of the metering assembly is de-energized, and the analyzer will activate the alarm 518 to emit a tone indicating that the serum sample loading operation has been completed. The analyzer will also display instructions to the user to lift the pipette tip out of the serum sample (Block 608; FIG. 43).

After a predetermined amount of time after the tone has been emitted (this time delay is provided for the user to remove the tip from the sample serum) and the user has been instructed to remove the tip from the sample serum, another tone will be emitted by the alarm 518 of the analyzer, and the analyzer will again energize the stepping motor of the metering assembly to rotate a predetermined number of steps in order to aspirate two microliters of air into the pipette tip (Block 610).

The analyzer will then provide a third tone (Block 612) and display instructions to the user to wipe the tip of the pipette and replace the pipette into the analyzer (Block 614; FIG. 44). If the user has problems with serum aspiration, he can press the "Clear" key (Block 615) and the analyzer will begin the aspiration process again at Block 596.

The user will then wipe the tip of the pipette, as instructed. The two microliters of air aspirated into the pipette tip 176 after the serum has been drawn into the pipette tip will ensure that no serum is drawn from the pipette tip by capillary action during the wiping operation. The user then places the end of the pipette through the opening 23 in the cover 12 of the analyzer and into the support ring 180 of the pipette lifter assembly. As mentioned previously, the lifter assembly has been properly positioned in its "home" position, where the pipette 18 is in its most raised position.

After the user has signaled the analyzer that he has properly placed the pipette into the pipette lifter by pressing the "Enter" key (Block 616) or automatically by sensor 175, the metering and analysis operation will now take place.

The cover 54, which had previously been placed in a position so as to cover the test slides to provide an optical background, is now rotated with respect to the turntable 50 in order to uncover the test slides so that a certain amount of sample serum may be deposited on the film portion 124 of each test slide (Block 618). Alternatively, the cover may be rotated to uncover the slides before the pipette is loaded (i.e., preferably between Block 593 and Block 594). The reason for uncovering the slides earlier in the operation is so that there is minimal delay after the filled pipette is placed in the analyzer. This allows the analyzer to start the metering operation immediately without the sample in the pipette rising in temperature appreciably. The turntable is then rotated so that each test slide 71 is sequentially positioned in alignment with the pipette tip.

More specifically, when a test slide is positioned beneath the tip 176 of the pipette, the motor 270 of the metering assembly is energized to rotate a given amount to cause the plunger 300 to move in the forward direction in the syringe 296 of the metering assembly. This forces air out of the syringe and into the disposable tip 176 of the pipette, which in turn pushes a predetermined amount of sample fluid out of the pipette tip 176. The fluid forced out of the pipette forms a drop suspended from the open end 310 of the pipette tip (Block 620). The motor 270 of the metering assembly is deenergized, and the motor 62 for the pipette lifter is then energized.

The pipette lifter lowers the pipette 18 such that the tip 176 is disposed a predetermined distance above the test slide 71, which distance is such that the drop 220 contacts the film portion 124 of the slide and is drawn by capillary action onto the film's top surface. The pipette tip is then withdrawn from the slide until the pipette reaches its home position, at which time the pipette lifter motor 62 is de-energized (Block 622). The home position of the pipette 18 is sensed by the optical sensor 218, which will signal the analyzer to rotate the turntable until the next test slide is positioned below the pipette tip (Block 624). The metering operation then repeats itself until serum has been deposited on each test slide (Block 626).

After the metering operation has been completed, about 10 ul of air is drawn up into the pipette tip (Block 628). This is done to prevent any unused serum remaining in the tip from being expelled by air in the tip above the serum sample when the air warms up, expands and exerts pressure on the sample. The cover 54 is again rotated so that it now covers each test slide (Block 628) to minimize evaporation of the deposited sample, and the analysis operation begins.

The reflectometer is energized. More specifically, depending on a particular test slide used, one or more of the LEDs will be energized depending on the test performed so that they emit and direct a light beam of a particular wavelength on the test slides (Block 630). In one form of the invention, the fluorescent lamps always remain on. Because they are separated from each other, unlike the LEDs which are grouped together, the light they emit will not interfere with that of another light source. The turntable will position the test slide over one fluorescent light source or the other, depending on the test to be performed. The reflectometry test is performed on the underside of the rotatable turntable. The cover is maintained in its covered position to prevent evaporation and to allow the reflectometry test to be performed (i.e., the reflectometer reads reflected light only, that is, color changes only on the bottom of the test slides).

The rotatable turntable is continuously rotated intermittently generally in one direction (i.e., clockwise) past the reflectometer portion of the analyzer (Block 632). The turntable positions the test slides over the particular light source 422–426 corresponding to the test to be performed and energizes a particular LED of light source 426 (Block 634). It may be necessary to rotate the turntable bi-directionally during the reflectometry test. If the "leading" slide needs to be positioned over the farther fluorescent light source 422 (in terms of normal clockwise rotation of the turntable), and the next adjacent slide (in the counterclockwise direction) needs to be positioned over the other fluorescent light source 424, which it passed, the associated computer will cause the turntable to "back up". Light reflected from each test slide is detected by the photodiodes 448, 456, 468, and this information is provided to the computer of the analyzer, where such information is converted from an analog signal to a digital code and normalized to the corresponding reference signal (Block 636) and stored in memory and processed (Block 638).

If twelve receiving slots are provided on the turntable, twelve tests will be conducted simultaneously. Accordingly, the total time required to complete all twelve tests concurrently is about six or seven minutes.

Figure 45:
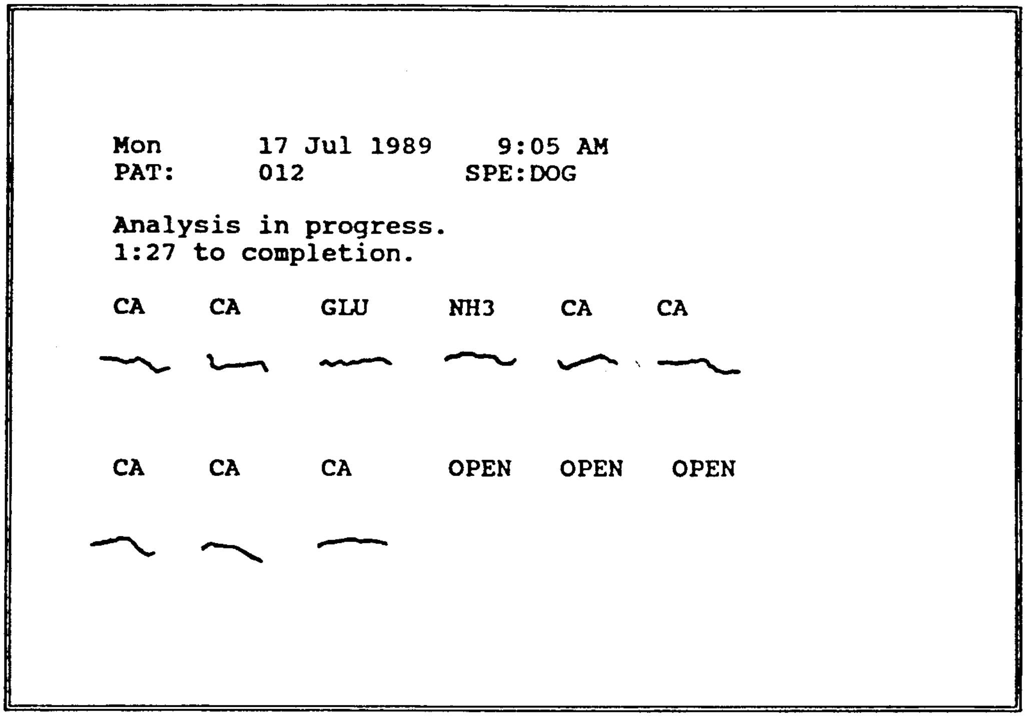
FIG. 45 is a front view of the display of the analyzer and information displayed thereon.

During the analysis operation, the analyzer will display a graph of the test results in progress (FIG. 45). If twelve test slides are being analyzed, twelve graphs will appear in two rows on the same display, so that the user may quickly and easily see the results being obtained from the test while the test is in progress. The analyzer also indicates to the user that the test is in progress, and displays the time until completion of the test (Block 640).

Figure 46:
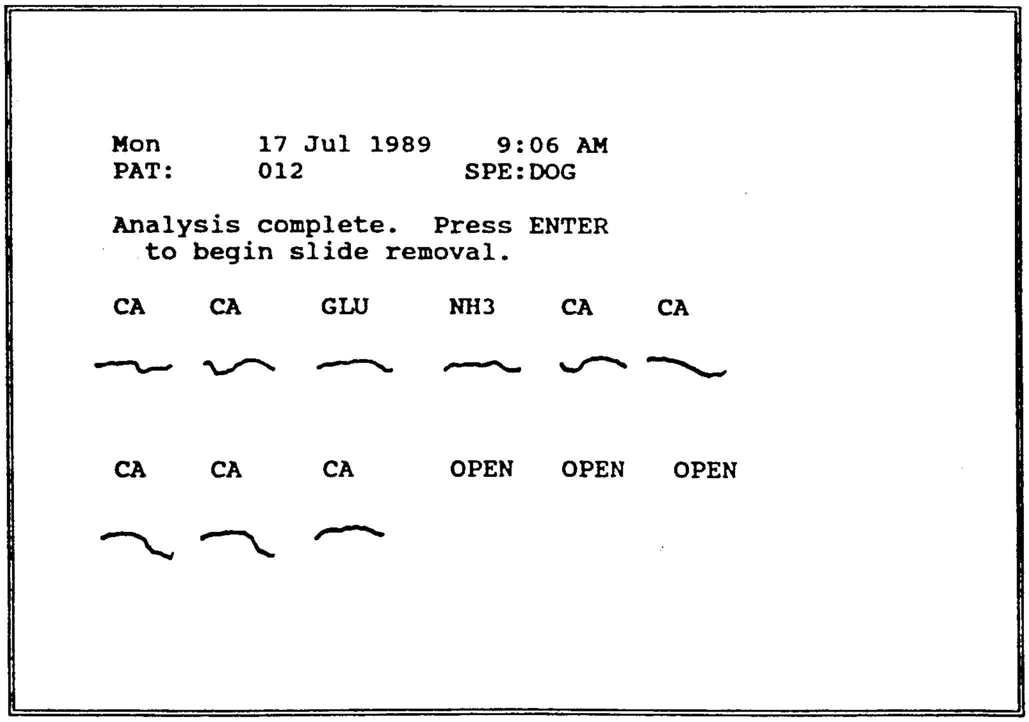
FIG. 46 is a front view of the display of the analyzer and information displayed thereon.

After a predetermined time has elapsed and the test has been completed (Block 642), the analyzer will emit a tone from the alarm 518. It will also instruct the user to press the Enter key when he wishes to begin the slide removal operation. (Block 644; FIG. 46).

After the user has instructed the analyzer to remove the slides by pressing the Enter key (Block 646), the analyzer rotates the cover 54 with respect to the turntable 50 so that the cover is now in the open position, that is, the slides are now exposed (Block 648). This will allow the ejector arm 404 to move upwardly through the receiving slots 52 to push the slides out of each receiving slot.

The turntable is then rotated intermittently so that each receiving slot is sequentially in alignment with the ejector arm 404 and with the discharge opening 410 formed in the base plate (Block 650). When a receiving slot is in proper alignment, the drive motor 398 for the ejector assembly is energized, and the ejector arm rotates upwardly through the receiving slot 52 to push the slide 71 contained in the receiving slot out of the open end of the slot and into the discharge opening 410 Block 652). The ejector arm 404 then continues to rotate to its home position, which position is sensed by the optical sensor 408 and which sensor signals the computer that the slide has been unloaded. The analyzer will then de-energize the ejector assembly drive motor 398 so that the ejector arm remains in its home position (Block 654), and will energize the drive motor 348 for the turntable so that the turntable rotates until the next adjacent receiving slot is aligned with the ejector arm 404 and discharge opening 410. The ejector assembly drive motor 398 is then energized to remove the next slide from the turntable. This sequence repeats itself until all test slides have been unloaded (Block 656).

After the slide unloading operation, the analyzer displays to the user instructions to remove and discard the pipette tip and to replace the pipette in the analyzer (Block 658; FIG. 47). The user signals the completion of this operation by pressing the Enter key (Block 660). The analyzer then displays and prints out the results cf the tests, and advises the user whether the test results are outside or within the normal range for each test (Block 662; FIG. 48). If the user desires, the analyzer will provide a printout of normal ranges for the species selected.

The analyzer will also provide a profile interpretation, if the user so desires. For example, the analyzer will interpret the test data and display to the user that the results of the profile (i.e., the test results) are likely to occur in certain conditions, for example, hypoparathyroidism, dietary deficiency, age, lactation, or others (Block 664; FIG. 49). The analysis portion of the test is then complete.

Referring back to the step where the user is requested to select the operation of the analyzer (Block 536), he may select the No. 2 listing on the main menu, "Lot Number Selection". If this is selected, the analyzer will display the lot numbers for each of the test slides (Block 666; FIG. 50).

Also displayed on the main menu is a "Service Menu" routine which the user may select by pressing key No. 3 on the keyboard (Block 544). Generally, this is only needed by the analyzer service personnel.

When key No. 3 is pressed, the analyzer will display the service menu (Block 668, FIG. 51). The service menu has listed a number of service routines, including such routines as Set Clock (Block 670), Instrument Calibration (Block 672), Pipette Only Test (Block 674), Pipette Life Test (Block 676), Disk Test Menu (Block 678), Production Support Menu (Block 680), LED Control (Block 682) and Service Diagnostics (Block 684), each of the above items being identified with a particular key on the key pad which the user may press.

For example if the key corresponding &to the LED control test routine is pressed (Block 686) , the analyzer will display a list of the various lamps and LEDs of the reflectometer portion of the analyzer (Block 688; FIG. 52), where each lamp or LED may be turned on individually to test if it is properly functioning (Block 690).

If the user presses the key corresponding to the pipette-only test routine (Block 692), the analyzer will display instructions to the user to enter the number of spots to updraw for (Block 694; FIG. 53). The analyzer will then multiply the number entered by the user by 10 microliters and will instruct the user to put a new tip on the pipette (Block 696; FIG. 54).

After this has been done, the user will inform the analyzer by pressing the Enter key (Block 696), and the analyzer will display instructions to the user to load the pipette with the sample by placing it below the fluid level of the sample vial and to then press the push button 316 on the head of the pipette 18 (Block 700; FIG. 55). When the button is pressed (Block 702), the analyzer will emit an advisory tone and display that the pipette is being loaded (Block 704; FIG. 42), aspirate a predetermined amount of sample sufficient to conduct the test (Block 706), emit a tone and display instructions to remove the pipette from the sample vial (Block 708; FIG. 43), emit another tone and aspirate a small volume of air (Block 710) and emit a fourth tone (Block 712) and display instructions for wiping the pipette tip (Block 714; FIG. 44), in much the same manner as the analyzer did during a normal operation (see Blocks 604-614).

The analyzer will then display instructions to the user to press the pushbutton 316 on the head of the pipette every time a sample is to be discharged from the pipette tip (Block 716; FIG. 56). In this way, service personnel may determine whether the proper amount of serum sample is being discharged. The analyzer will sense when the pushbutton is pressed (Block 718), and will meter out 10 $\mu$l of sample (Block 720). It will then count the number of times the push button has been pressed, and when this number equals the number entered originally in this test procedure (Block 722), an alarm will be triggered alerting the user that the test has been completed (Block 724).

For the Set Clock service routine (Block 670), the service personnel depresses the key No. 1 (Block 726). The analyzer will then display a second menu (Block 728; FIG. 57), showing the current date and time and requesting whether the user wishes to change the day of the month, the month, year, hours and minutes by an appropriate selection of a key on the key pad (Block 730).

Returning again to the service menu, if key No. 8 on the key pad is pressed (Block 732), which key corresponds to the service diagnostics operation of the analyzer (Block 684), the analyzer will display a service diagnostics menu (Block 734; FIG. 58), which includes such items as cycle articulated pipette; turn ultra-violet bulbs on; turn ultra-violet bulbs off; view/modify EE prom; dump instrument cal; initialize EE prom and set serial number. Any one of these operations may be selected by the user by his depressing the corresponding key pad number and the analyzer will perform the selected operation (Block 736).

More specifically, the "cycle articulated pipette" routine will continuously cycle the pipette lifter mechanism and display how long each cycle takes; and the "view/modify EE prom" routine will display the contents of an EE prom (which is part of the analyzer's computer memory). The EE prom contains such information as the serial no. of the analyzer, the analyzer settings and calibration data. The contents of the prom are displayable, and the service personnel may view and change the contents.

The "dump instrument cal" routine will cause the analyzer to display the calibration data. The "initialize EE prom and set serial no." routine will allow the prom to be set up or pre-programmed with initial calibration data and a serial no. This routine is envisioned to be used at the analyzer manufacturing facility.

If the pipette life test routine (Block 676) is chosen by the user pressing key No. 4 (Block 738), the analyzer will instruct the user to mark the current position of the pipette and press any key to begin (Block 740, 742; FIG. 59) and to press another key when the user wishes to end the routine (Block 744, 746, FIG. 60). This routine will test the sample metering mechanism of the analyzer, and will cause the metering drive motor 270 to be energized between key presses (Block 744).

If key No. 5 is pressed (Block 748), the analyzer will go into a disk (i.e., turntable) test routine (Block 678) in which a disk test menu will be displayed (Block 750; FIG. 61). Under this routine, the following diagnostic tests regarding the cover and turntable may be performed: set the rotatable turntable "home" position; rotate the turntable continuously in a clockwise direction; rotate the turntable continuously in a counter-clockwise rotation; a disk life test; open the cover; close the cover; operate the ejector assembly at the current location of the turntable; and move the slide turntable a predetermined number of steps. The analyzer will perform any one of these steps when the user presses a corresponding key on the key pad (Block 752).

Returning now to the service menu, the user may select the production support menu and routine (Block 680) by pressing key No. 6 (Block 754). The analyzer will display another production diagnostics menu (Block 756; FIG. 62) in which the user may select one of the following diagnostic operations: read the A/D channels; load slides; R.D. test; eject all slides; table home sense change; key pad change; and cover home sense change. Any one of these operations will be performed by the analyzer when the user presses an appropriate key (Block 758).

Again returning to the service menu when key No. 2 is pressed (Block 760), an instrument calibration routine will be performed (Block 672). The user, through this routine, may calibrate the analyzer and in particular the reflectometer portion of the analyzer. The analyzer will display an instrument calibration menu (Block 762; FIG. 63) in which the user is instructed to press a particular key to perform the following functions: read visible white slides; read visible black slides; read ultra-violet white slides; read ultra-violet black slides; enter visible reflectances; enter ultra-violet reflectances; calculate black and white references; and save references and return. In this routine, the user is instructed to insert a number of reference slides in the turntable, which reference slides are read by the ultra-violet light sources and the LED light sources in order to calibrate such light sources (Block 764).

If the user presses key No. 9 (Block 765) on the service menu, the analyzer will display the main menu. If key No. 3 was pressed before the main menu was displayed (see Block 767), the analyzer will test the mechanical and electrical functions and continue its operation starting at Block 512.

Returning again to the main menu displayed by the analyzer (Block 534; FIG. 36), the user may select the routine "skip analysis operation" (Block 560) by pressing key No. 4 on the key pad (Block 546). The analyzer will perform the steps in the normal operation routine (Blocks 568–626 and 648–656), except that it will not perform the steps associated with the actual analysis of the test slides (Blocks 628–646 and 658–664). The performance of this routine is shown in the flow chart of FIG. 32 generally by Block 766.

If, on the main menu, the user selects the verbose operation routine (Block 562) by pressing key No. 5 (Block 546), the analyzer will step through the same steps of the normal routine described previously (Blocks 568–664), except that the user is allowed to override bar codes, save the analysis data on a floppy disk, and print out the data readings of each slide. The performance of this routine is shown in the flow chart of FIG. 32 generally by Block 768.

The user may also select a "life test" (Block 564) by pressing key No. 6 (Block 550). The life test is the same as the normal routine, but it simulates all user interaction and runs tests over and over until either the analyzer is turned off or a failure occurs. The performance of the life test routine is shown in the flow chart generally by Block 770.

A "verbose with sub-prespot test" (Block 566) may be performed by the user by pressing key No. 7 (Block 552) on the main menu. This test is the same as the verbose test (Block 562), but also subtracts the pre-spot slide readings (i.e., before the serum is spotted) from all of the slide readings. The performance of this routine is shown generally by Block 772 in FIG. 32.

A computer program of the operation of the chemical analyzer in accordance with the present invention is provided herewith and is incorporated herein as part of the disclosure of the invention.

The Electronic Circuitry Of The Chemical Analyzer

FIGS. 64–68 show schematically and in block diagram form the associated electronic and computer circuitry of the blood analyzer of the present invention. The actual values and part numbers of the components used in the electronic circuitry shown in FIGS. 64–68 are for illustrative purposes only, and to facilitate an understanding of the invention. However, alternative components and values for these components may be substituted by one skilled in the art to provide the same or similar results.

Figure 64A:
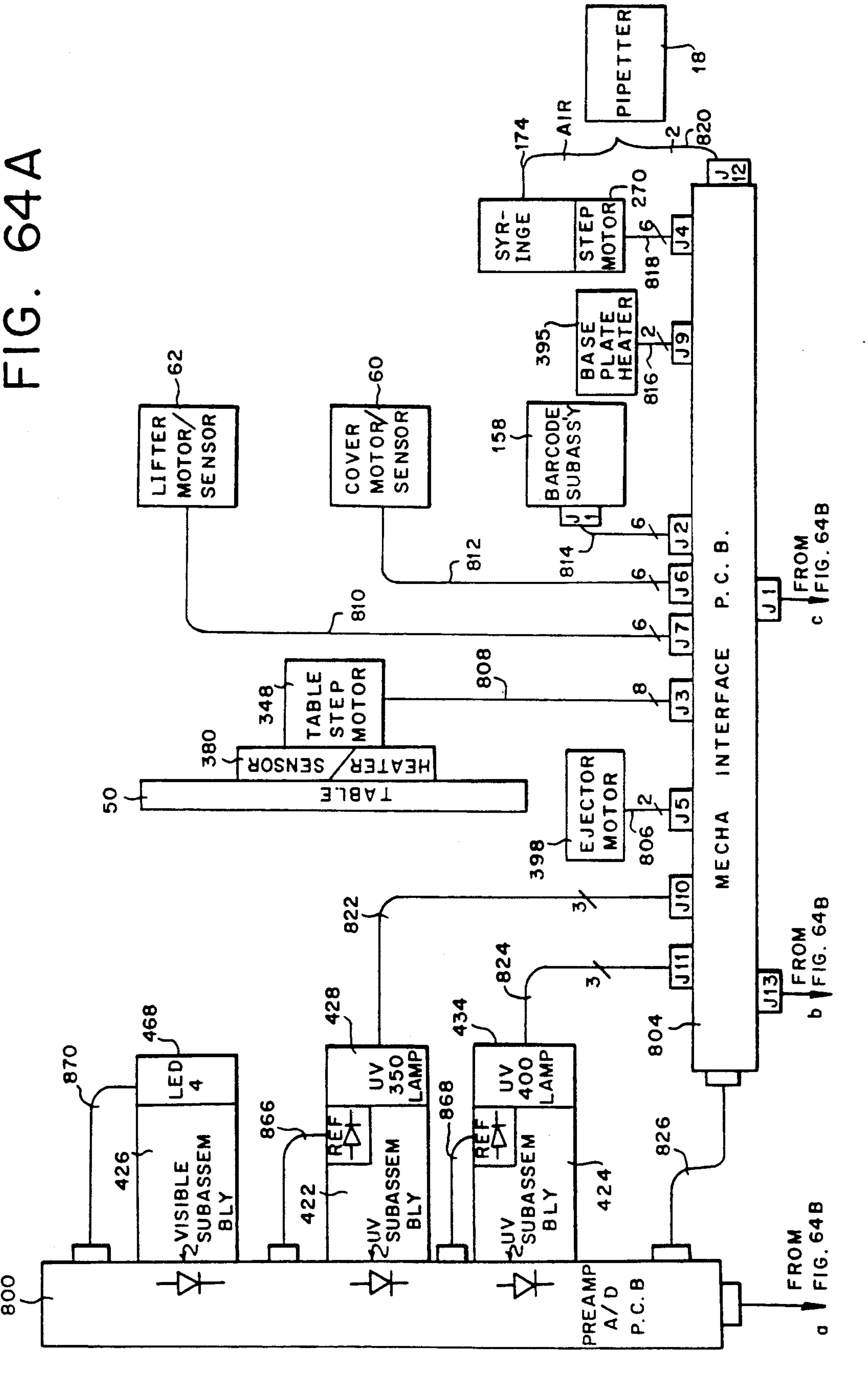
FIG. 64A–B is a block diagram of the associated electronic circuitry of the analyzer.
Figure 64B:
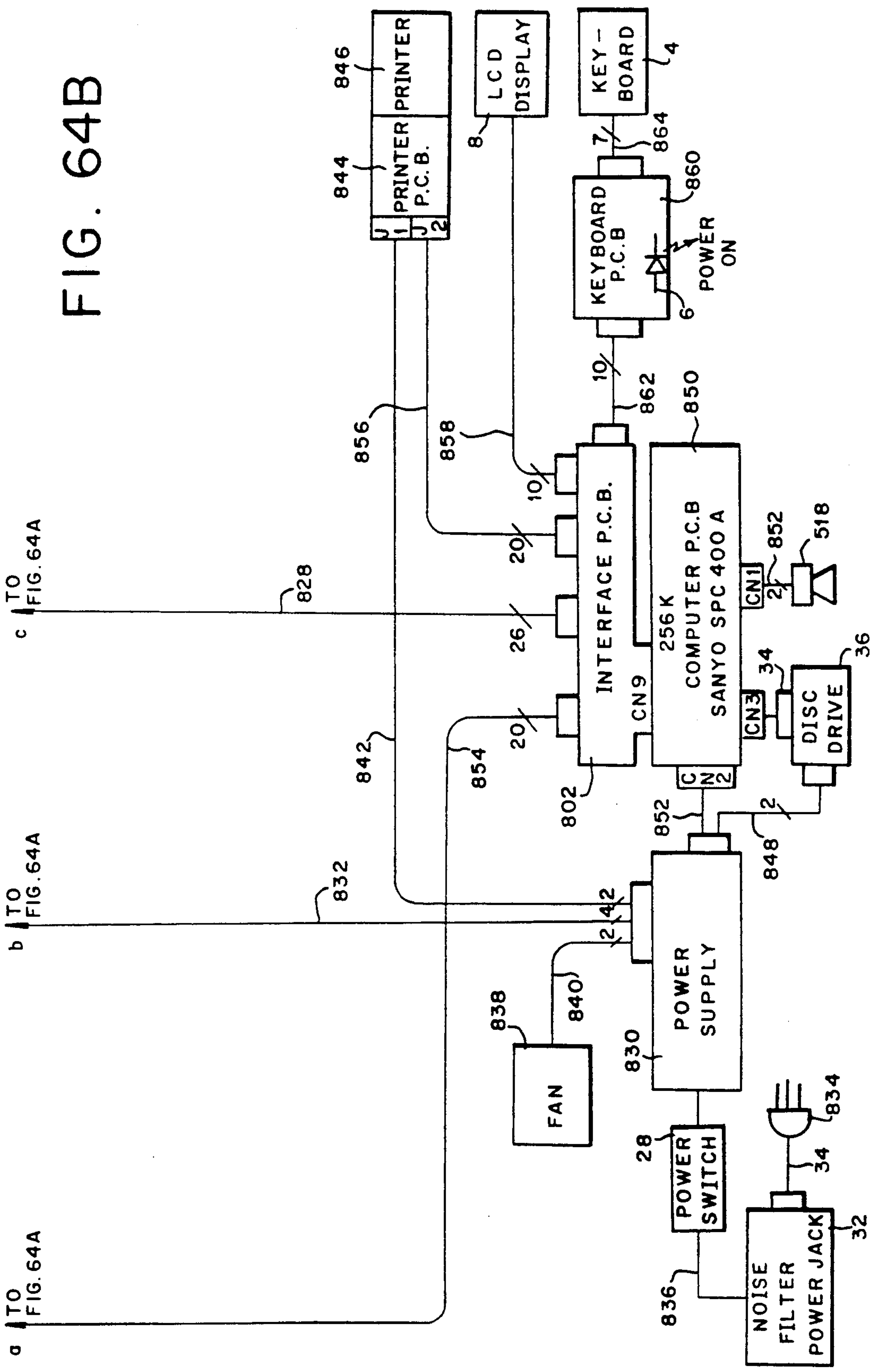

Initially referring to FIG. 64 of the drawings, a block diagram of the subassemblies and major components of the electronic circuitry of the blood analyzer is shown.

There are three major subassemblies used in the preferred form of the blood analyzer: a preamplifier and analog-to-digital subassembly 800 (shown in detail in FIG. 65); a computer interface subassembly 802 (shown in detail in FIG. 66); and a mechanical interface subassembly 804 (shown in detail in FIG. 67).

As shown in FIG. 64, the mechanical interface subassembly 804, as its name implies, serves to interface between the computer interface subassembly 802 and the various drive motors and "home" position optical sensors which are associated with the rotatable turntable 50, the cover 54 and other mechanical components of the blood analyzer.

More specifically, the mechanical interface subassembly 804 is connected by a bus line 806 to the ejector motor 398 which is used for removing slides from the turntable after the analysis operation has been completed. The interface subassembly 804 is also connected to the turntable stepping motor 348, the heater 380 for the turntable and the sensor 378 which is used in controlling the temperature of the turntable, through a bus line 808.

The interface subassembly 804 is also connected to the pipette lifter motor 62 and its associated optical sensor 218 by a bus line 810; the cover drive motor 60 and its associated position sensor 168 through a bus line 812; and the bar code subassembly 158 (shown in greater detail in FIG. 68) which optically scans the bar codes 86 on the top surface of each test slide 71 as they pass below the bridge bracket 58. This subassembly is connected by a bus line 814 to the interface subassembly 804.

Also connected to the mechanical interface subassembly by a bus line 816 is the base plate heater 395, which maintains the temperature of the base plate 48; the DC stepping drive motor 270 for the syringe metering assembly, by a bus line 818; and the pipette assembly, and in particular, the push button switch 316 located at the head of the pipette, by a two conductor bus line 820.

The mechanical interface subassembly 804 is also connected to the two ultraviolet lamps 428, 434 by appropriate bus lines 822, 824, to turn on the ultraviolet lamps under the appropriate conditions; the preamplifier and analog-to-digital subassembly 800 by an appropriate bus line 826; the computer interface subassembly 802 by appropriate bus lines 828; and to the power supply 830 by multiple lines 832.

As shown in FIG. 64, the power plug 834 is connected to the power jack 32, which plugs into the male connector 30 on the back of the analyzer (see FIG. 2). The male connector 30 is connected to the power switch 28 by appropriate lines 836, which power switch is in turn connected by lines to a conventional power supply 830, such as Part No. SR-10A manufactured by Sanyo Corporation. The power supply provides ±5 volts and ±12 volts to the associated circuitry of the blood analyzer.

More specifically, the power supply 830 provides power to a fan 838 mounted in the base portion of the analyzer by appropriate lines 840, which fan may be Part No. 6005 L manufactured by Sanwa Corporation; connected by appropriate lines 832 to the mechanical interface subassembly 804; and connected by lines 842 to a printer subassembly 844 and its associated printer 846. The printer 846 is Part No. STP201 manufactured by Seiko Company, and the printer subassembly 844, which interfaces with and drives the printer, is also manufactured by Seiko Company, and may be purchased from Seiko Company when purchasing the Seiko printer.

The power supply 830 is also connected by appropriate lines 848 to the floppy disk drive assembly 36, which may be Part No. FD235HF manufactured by Teac Company, and to the computer 850 of the blood analyzer by multiple power lines 852.

The computer 850 used in the blood analyzer preferably has a 256K memory, and may be Part No. SPC400A manufactured by Sanyo Corporation. The computer 850 is connected to the computer interface subassembly 802 (shown schematically in FIG. 66 of the drawings). The computer 850 is programmed in accordance with the flow chart described previously (see FIG. 32) and the program attached as an appendix.

The computer 850 is also connected to and drives a speaker 518 by appropriate lines 852, which speaker produces at least two tones, one to signal the user that a step has been completed, such as the aspiration of sample liquid into the pipette tip 176, and another tone to indicate that the slide inserter 14 is not in its home position.

As also shown in FIG. 64 of the drawings, the computer interface subassembly 802 is connected by appropriate bus lines 854 to the preamplifier and analog-to-digital converter subassembly 800; to the mechanical interface subassembly 804 by appropriate bus lines 856; also to the printer subassembly 844 by appropriate bus lines 828; to the display 8 of the analyzer by appropriate bus lines 858, which display is preferably a liquid crystal display (LCD) and may be Part No. LCM556 manufactured by Sanyo Corporation; and to a keyboard subassembly 860 by appropriate bus lines 862.

The keyboard subassembly 860 is basically an interconnect printed circuit board with a series of wires and which is mounted on the back of the keyboard 4, and is connected to the keyboard by a bus line 864. The keyboard subassembly 860 also includes a light emitting diode (LED) which is employed as a power on indicator 6. The keyboard 4 is basically a matrix, membrane type keyboard, and is illustrated pictorially in FIG. 1.

FIG. 64 also shows in simplified form the reflectometer portion of the blood analyzer. There are, basically, three subassemblies associated with the reflectometer. The first subassembly 426 produces a visible light spectrum. It incorporates four LEDs 462, as described previously, the light from each of which is shone on and reflected from the test slide 71 which reflected light passes through a lens 466 and onto a photodiode 468. It should be noted that a reference for the light emitted by the LEDs 462 is included in the present invention, this reference being in the form of a light colored glass (not shown) mounted on the underside of the turntable 50. Because LEDs do not drift in wavelength or intensity as much as ultraviolet lamps do, the analyzer does not need a constantly monitoring reference photodiode as is needed with the ultraviolet lamps 428, 434. During a calibration step, the analyzer will rotate the turntable 50 until the LED reference glass is aligned with the optical lens 466 of the LED optical subassembly 426 so that light from the LEDs will be reflected from the reference glass and be detected by the photodiode 468.

One ultraviolet lamp subassembly 422 includes a 350 nM lamp 428, a reference photodiode 457 which may be mounted partially in or over the bore of the block and at least positioned to receive light emitted by lamp 428, an optical lens 442, an optical stop 447 which has a single aperture through its thickness, a filter 431 interposed between the lens and the optical stop, and a sensing photodiode 448 mounted on the pre-amplifier and analog-to-digital converter printed circuit board 420.

The second ultraviolet lamp subassembly 424 similarly includes a 400 nM ultraviolet lamp 434, a lens 450, optical stop 449, filter 440, a reference photodiode 459 mounted in the block 436 in the same manner as reference diode 457 and a sensor photodiode 456, which sensor photodiode is mounted on the pre-amplifier and analog-to-digital converter subassembly board 420.

Because the reference photodiodes 457, 459 for the ultraviolet lamps are positioned near the opening in the mounting blocks 430, 436 of the ultraviolet lamps and not on the pre-amplifier printed circuit board 420, they are connected to the board by appropriate wires 866, 868. Similarly, the LEDs 468 of the visible light subassembly are connected by appropriate wires 870 to the pre-amplifier board 420.

Figure 65A:
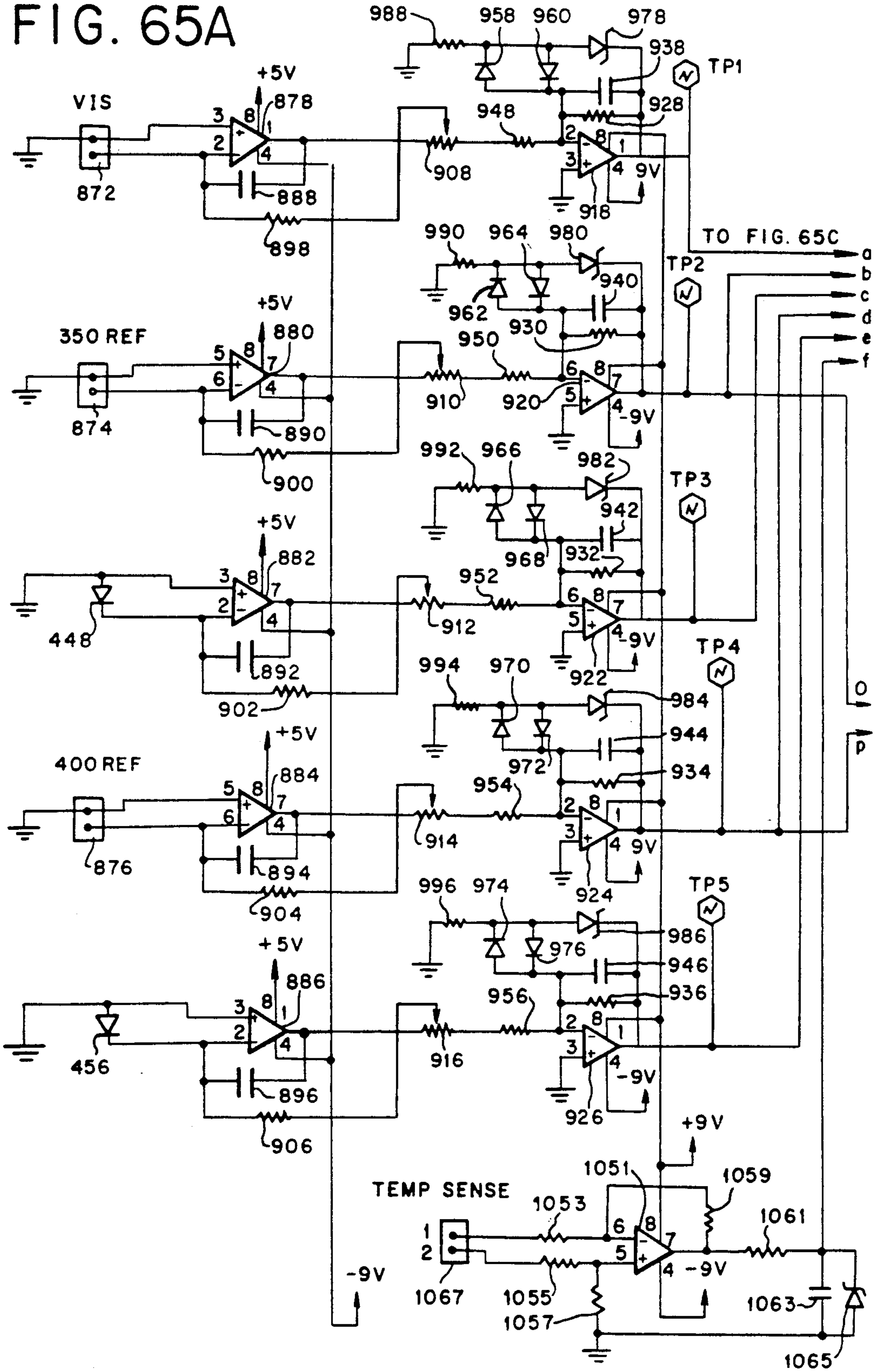
FIG. 65A–C is a schematic diagram of a first portion of the electronic circuitry of the analyzer.
Figure 65B:
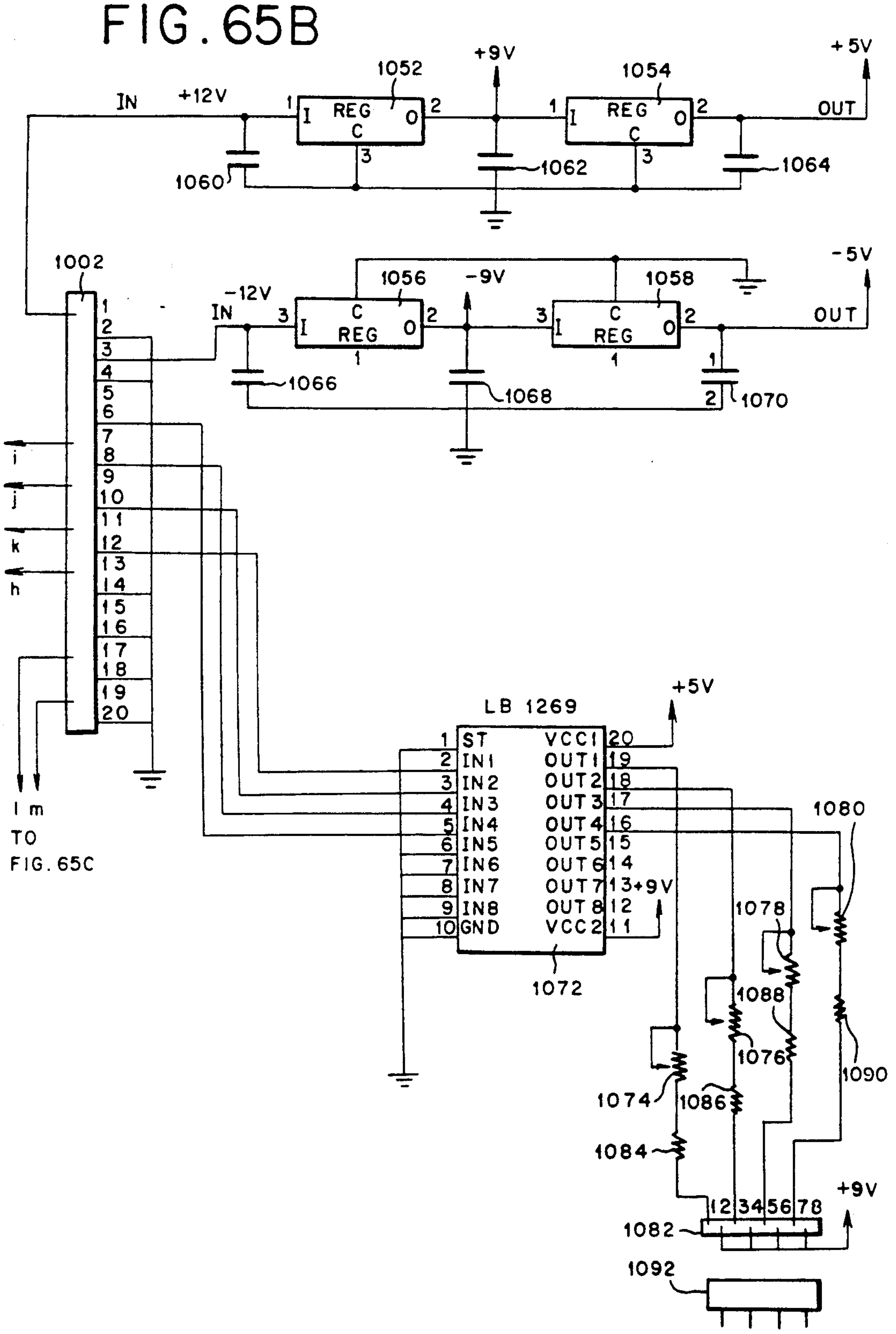
Figure 65C:
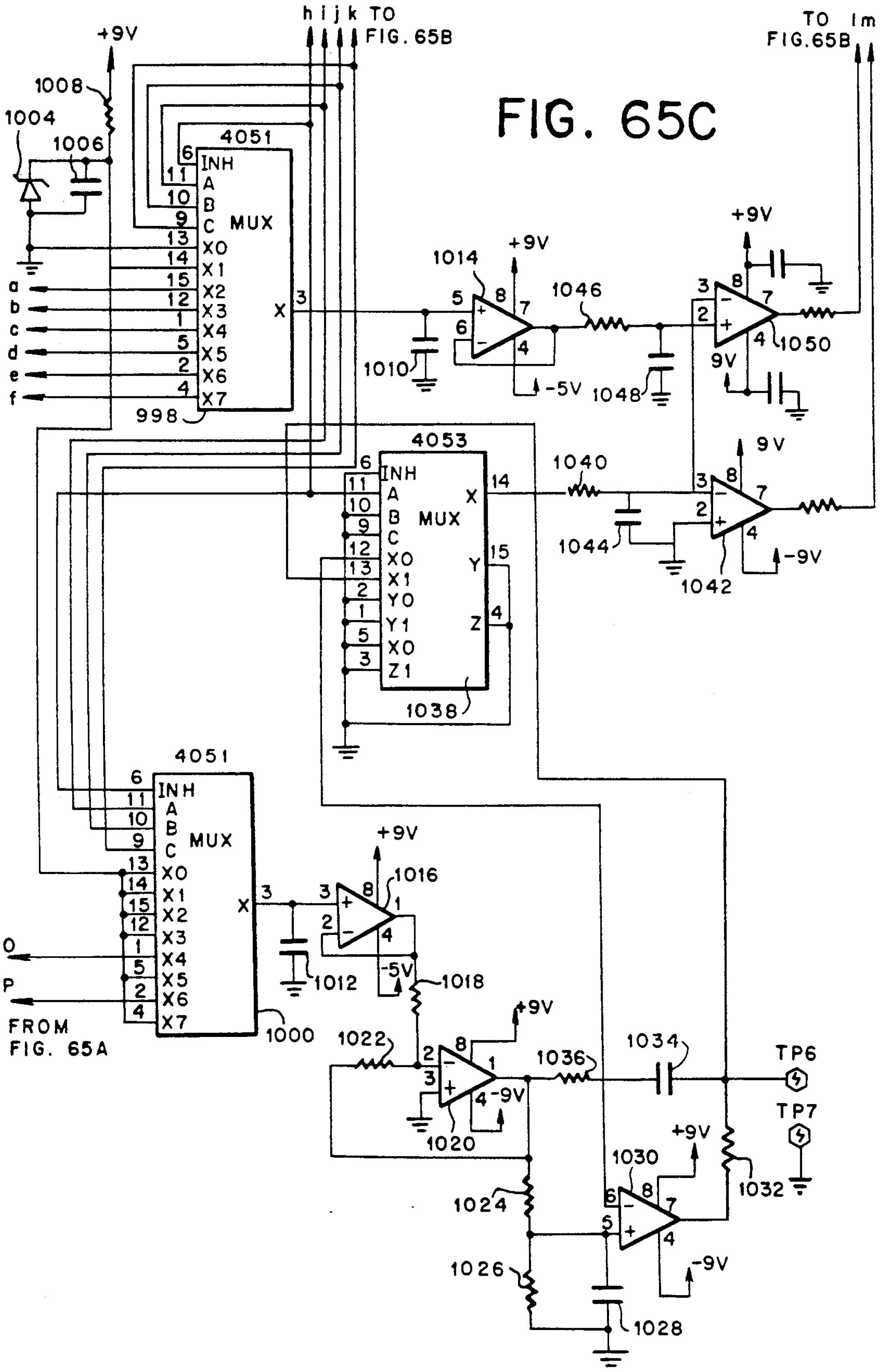
Figure 66A:
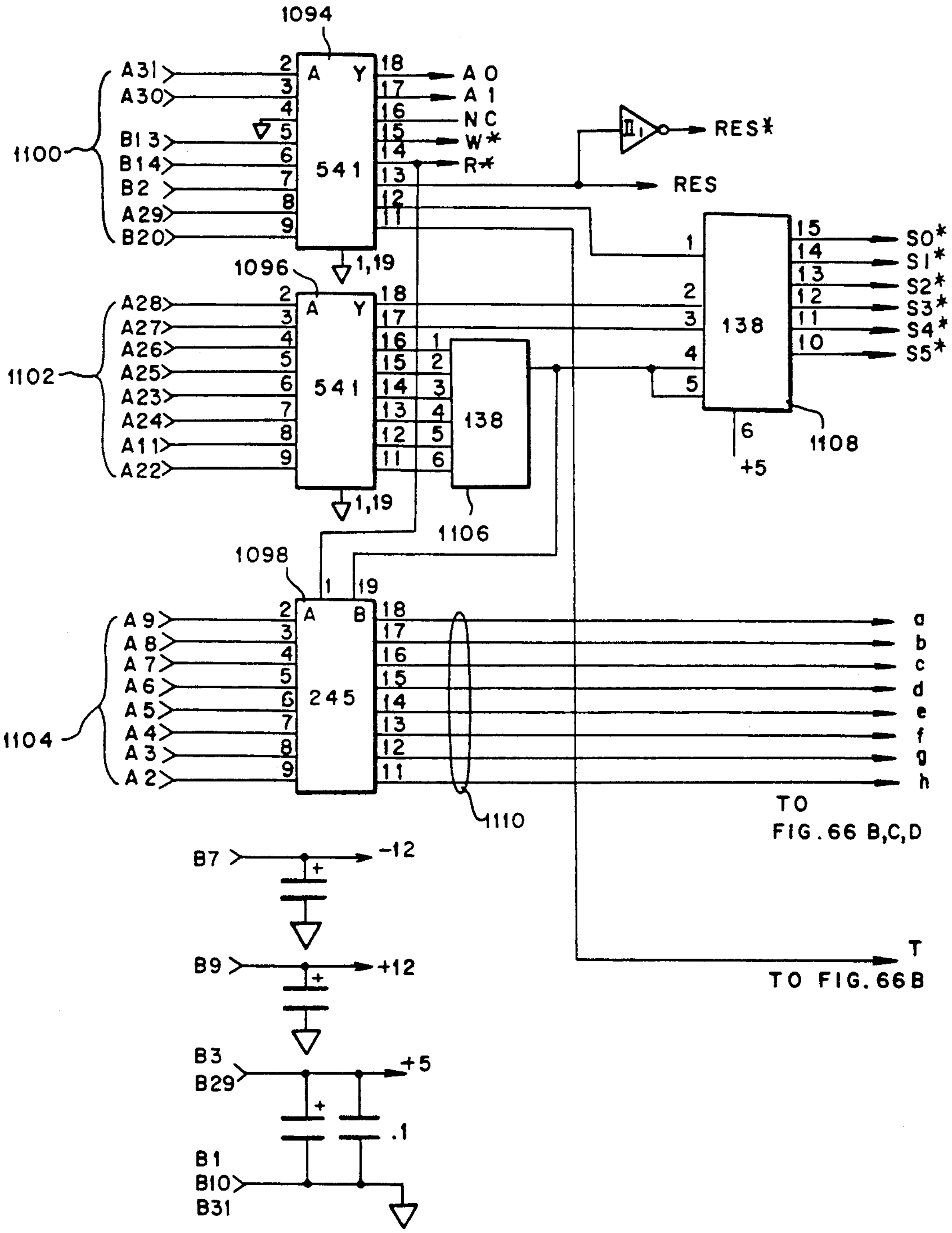
FIG. 66A–D is a schematic diagram of a second portion of the electronic circuitry of the analyzer.
Figure 66B:
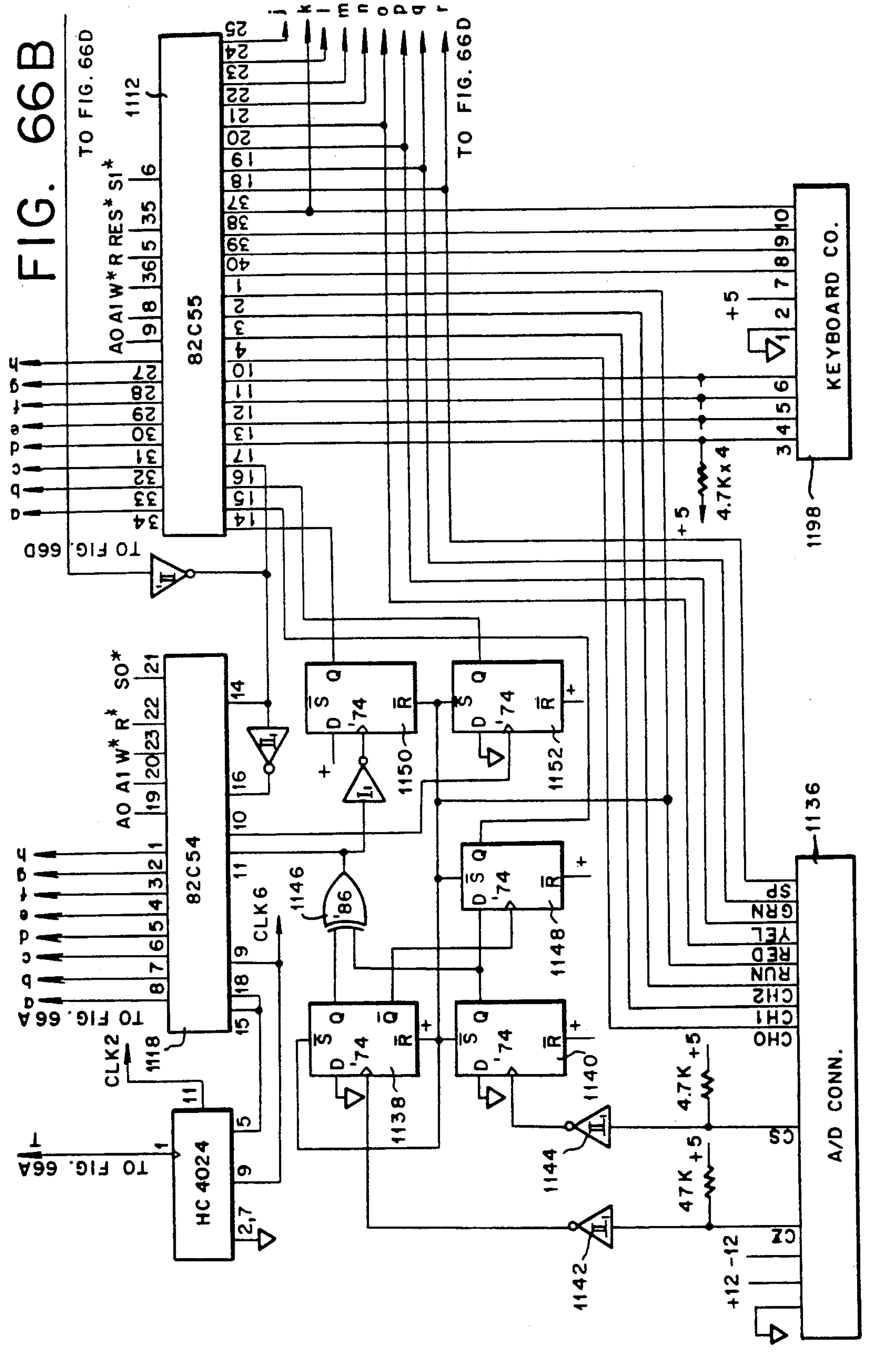
Figure 66C:
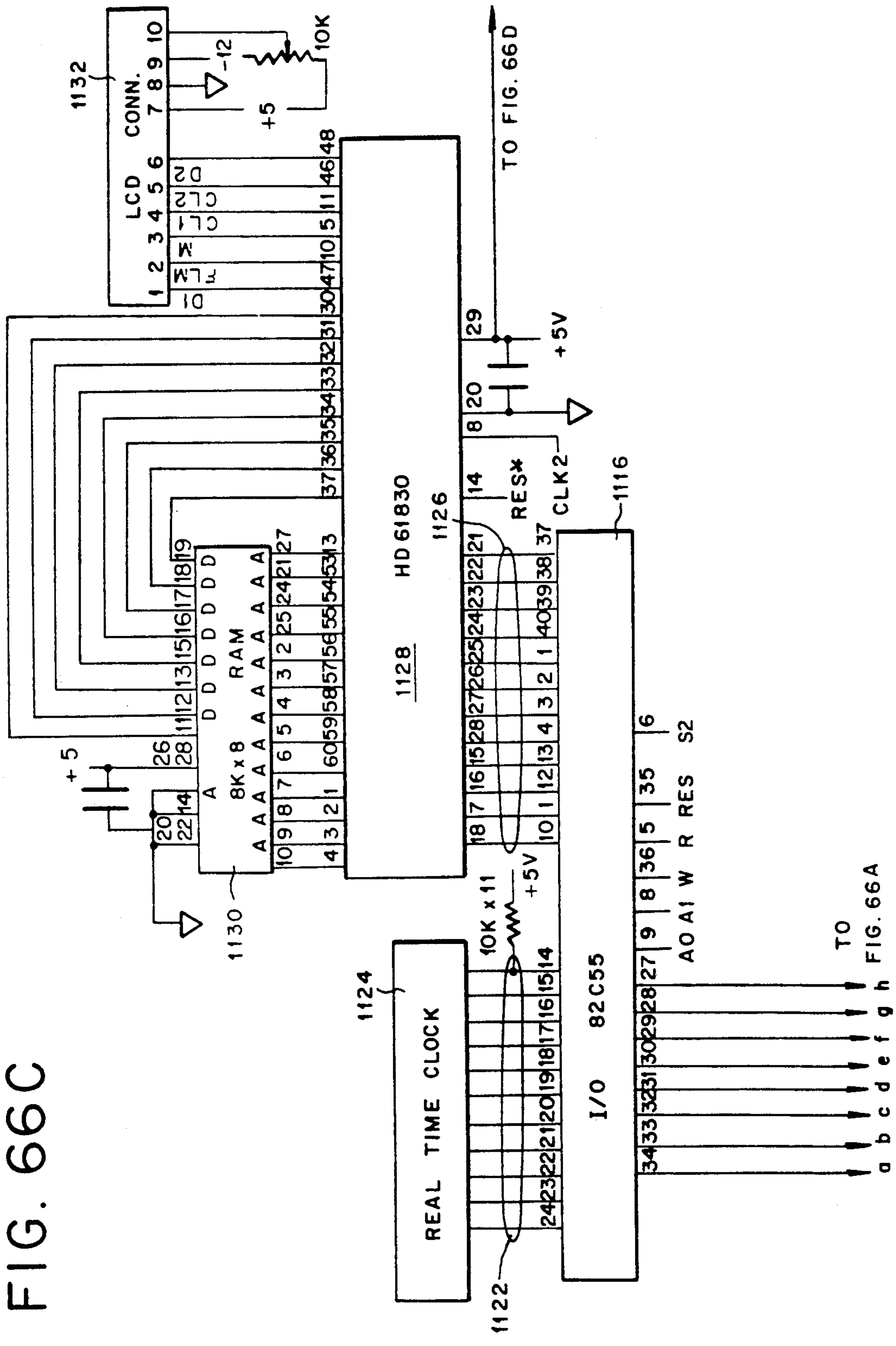
Figure 66D:
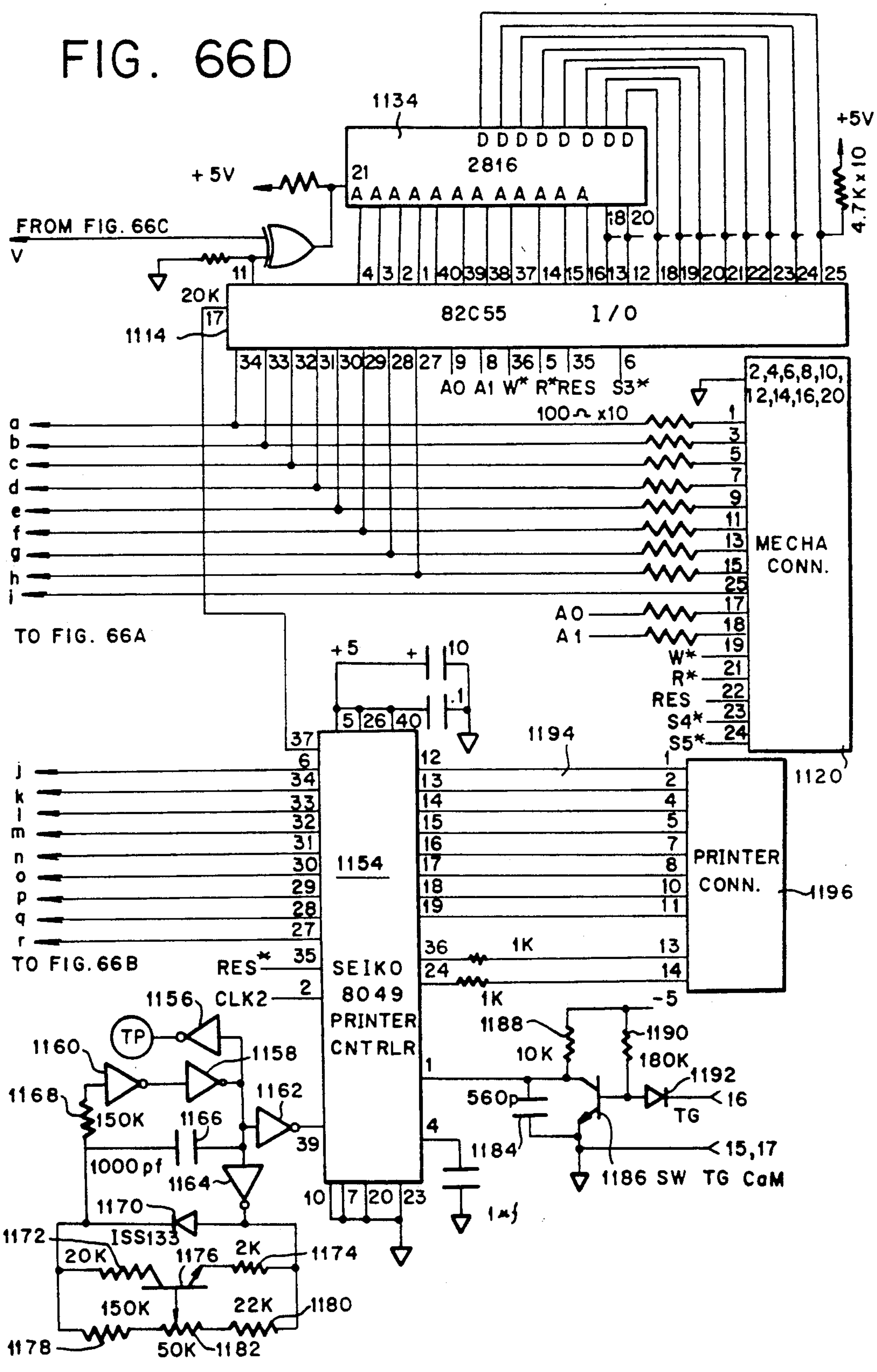
Figure 67A:
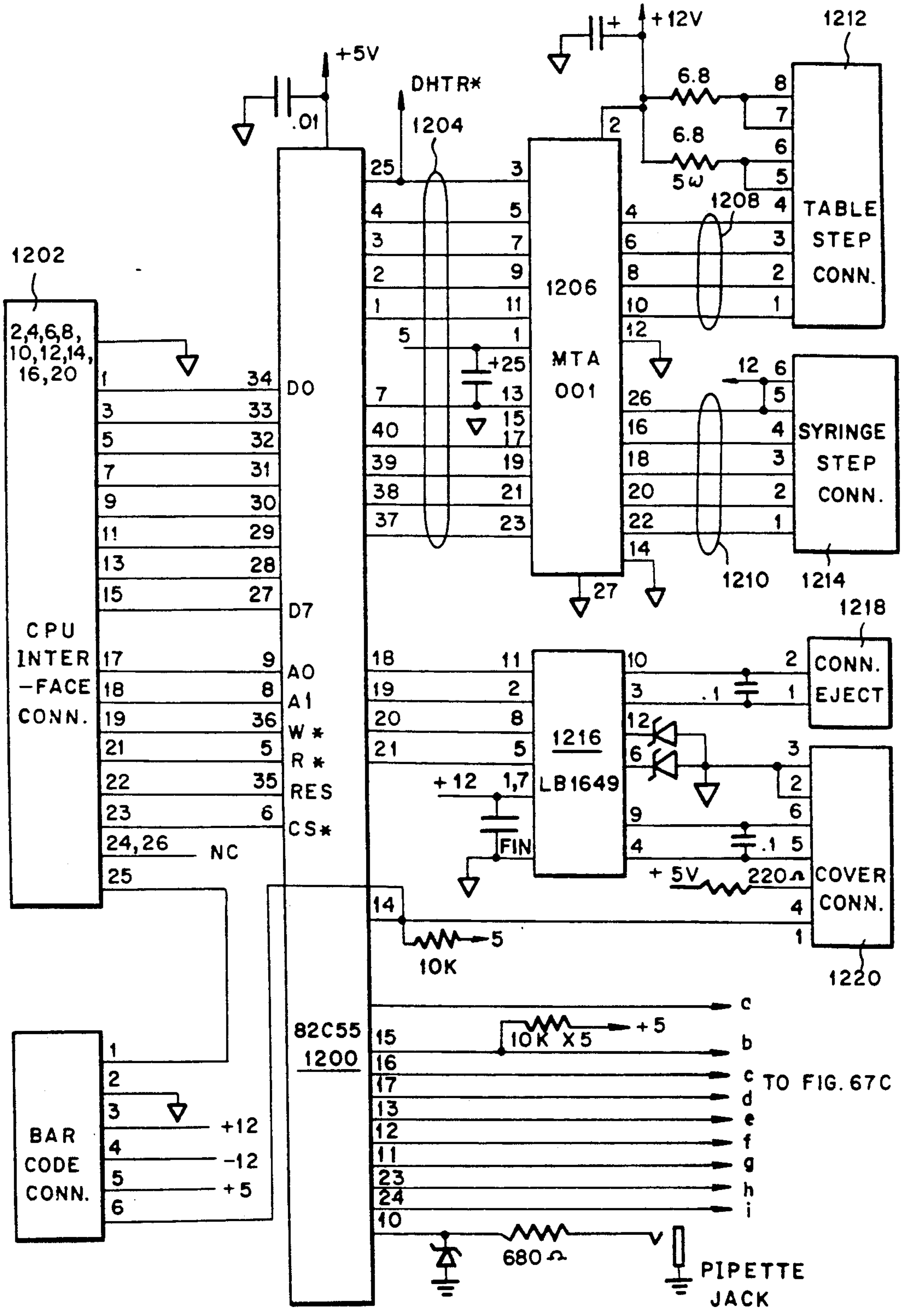
FIG. 67A–D is a schematic diagram of a third portion of the electronic circuitry of the analyzer.
Figure 67B:
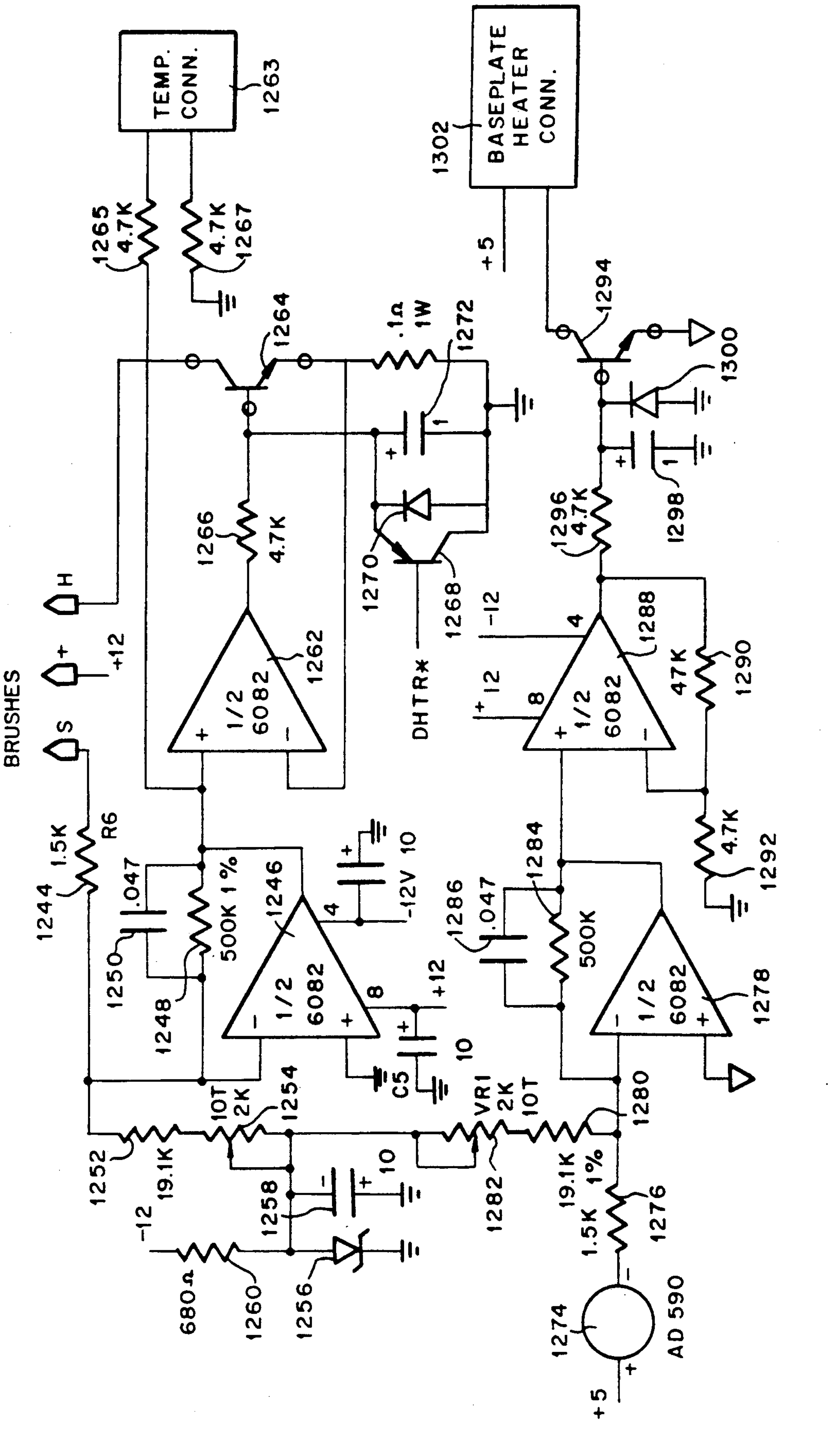
Figure 67C:
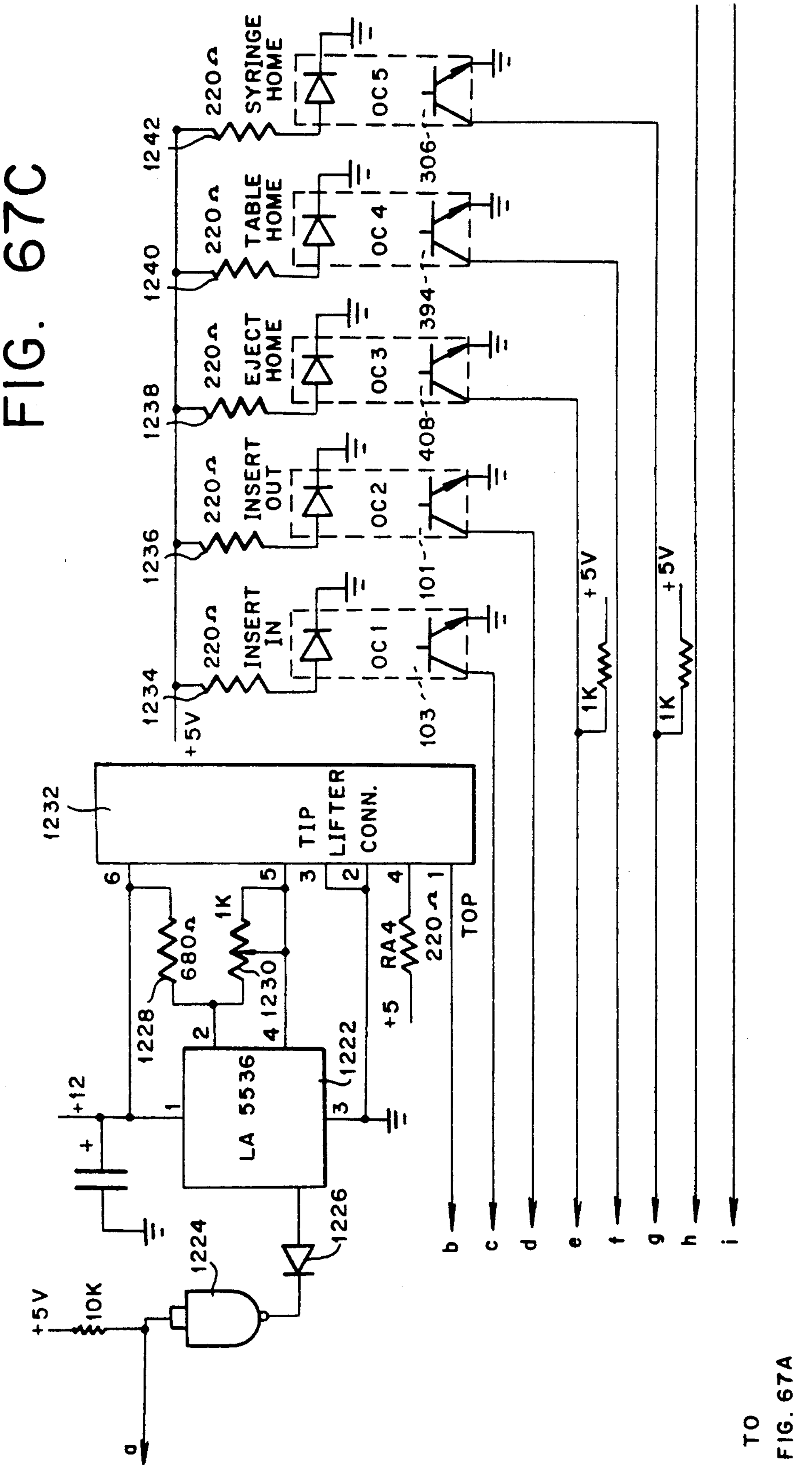
Figure 67D:
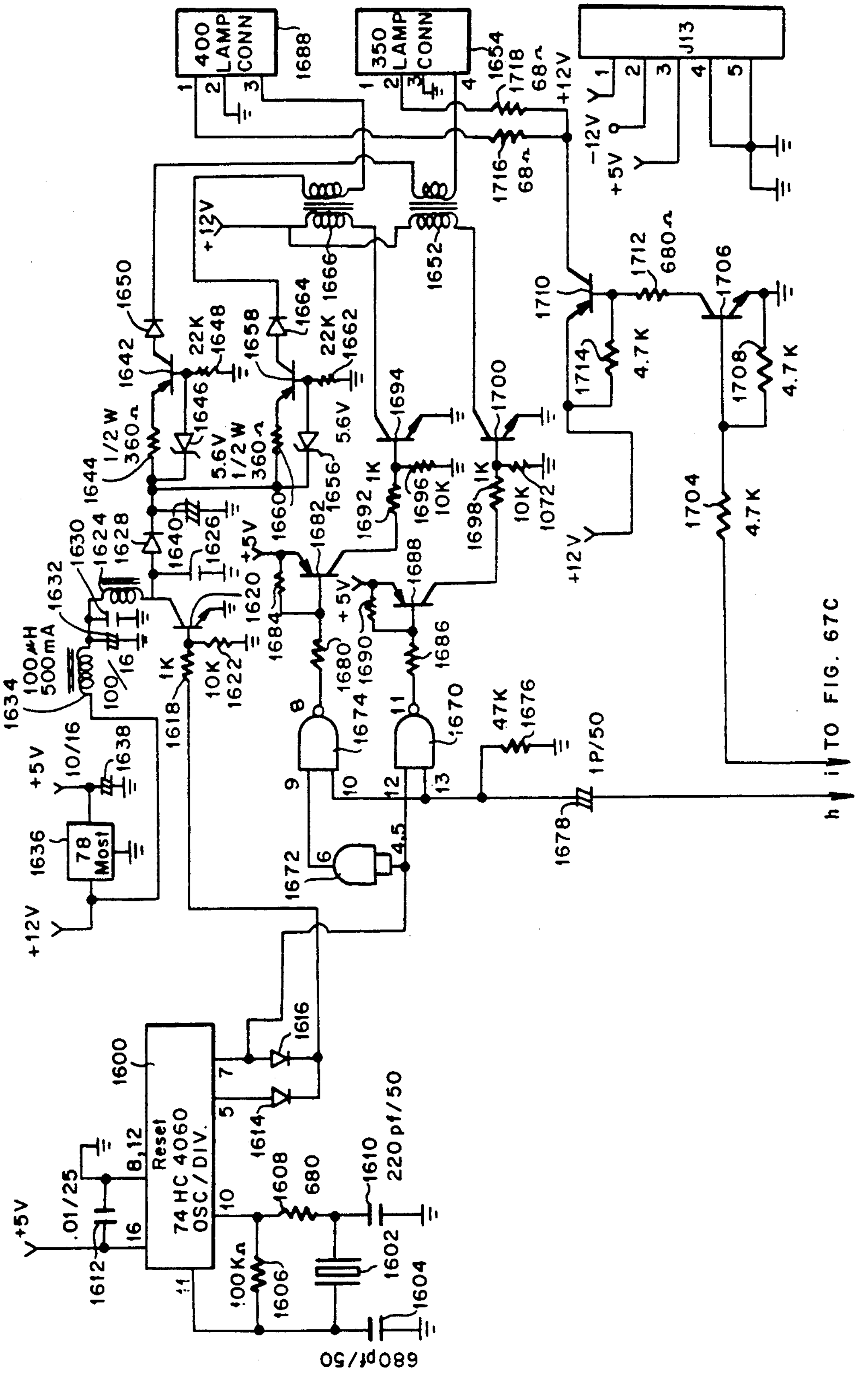

FIG. 65 illustrates the preferred form of the pre-amplifier and analog-to-digital converter subassembly 800 of the blood analyzer.

Three 2-input connectors 872-876 are used to connect the photodiodes 457, 459, 468 which are not mounted on the printed circuit board 420 of the subassembly to the rest of the circuitry on the printed circuit board. One input of each connector is grounded, and the other input is connected to one of the sensing photodiodes 468 for the visible spectrum (i.e., the LED source 426) ,the reference diode 457 for the 340 nm ultraviolet light source, and the reference diode 459 for the 400 ultraviolet light source. The other side of these photodiodes are connected to ground.

In addition, the two sensing photodiodes 448, 456 for the ultraviolet light sources are mounted on the printed circuit board 420, and have their anodes connected to ground.

Each of the photodiodes, either reference diodes or sensing diodes, are connected to trans-impedance amplifiers. Each of the trans-impedance amplifiers includes an operational amplifier 878-886, with the non-inverting (+) input connected to ground, and the inverting (−) input connected to a corresponding photodiode 468, 457, 448, 459, 456. Each amplifier includes a feedback capacitor 888-896 and a feedback resistor 898-906 connected in parallel. The trans-impedance amplifiers are basically used to convert the current which changes in the photodiodes to a variable voltage, which voltage changes in proportion to the amount of light impinging on the photodiodes.

The output of each trans-impedance amplifier is connected to one end and the wiper arm of a potentiometer 908-916. The potentiometers are used as gain controls to normalize the various photodiode "channels". The third leg of each potentiometer 908-916 is connected to a second amplifier stage consisting of an operational amplifier 918-926 and its associated feedback components, i.e., resistors 928-936 and parallelly connected capacitors 938-946.

The second stage of amplifiers is provided for several purposes. First, in conjunction with the gain adjust control potentiometers 908-916, the amplifiers normalize each of the photodiode "channels" so that the signals presented to the analog-to-digital converter circuitry, which will be explained in greater detail, are each of the same proportion.

Second, it provides a second stage of gain for each of the signals from the photodiodes, through the feedback resistors 928-936, the gain potentiometers 908-916, and input resistors 948-956 connected to the inverting inputs of each of the operational amplifiers 918-926.

Third, each of the second amplifier stages also acts as a clipper circuit through the use of a parallel arrangement of reversed polarity diodes 958-976, zener diodes 978-986 and resistors 988-996 to ground, all of which are connected in the feedback loops of the amplifiers 918-926. This will limit the output voltage of the operational amplifiers, which voltage is provided to a next stage of multiplexers to prevent damaging the multiplexers by providing them with signals that are above the absolute maximum voltages specified by the manufacturer of the multiplexers.

The output signals of the second amplifier stages are provided to the inputs of a pair of multiplexers 998, 1000. More specifically, the amplifier stages which amplified the signals from the sensor photodiodes 468, 448, 456 are provided to the first multiplexer 998, and the amplifier stages which amplify the signals from the reference photodiodes 457, 459 are connected to the inputs of the second multiplexer 1000. The channel selecting inputs A-C of the multiplexers are connected to the computer 850 of the analyzer through an output connector 1002 on the pre-amplifier subassembly. Accordingly, the computer 850 will provide the needed code to make the selection as to which of the sensor photodiode signals and reference diode signals are to pass through the multiplexers 998, 1000.

A zener diode 1004 connected in parallel with a capacitor 1006, and being further connected between ground and to a positive voltage through a resistor 1008, is also connected to the second multiplexer 1000. The zener diode circuit provides a 5 volt reference signal which will be used when the photodiode sensing signal corresponding the LED visible light assembly 426 is used.

Connected to the output of each multiplexer 998, 1000 is a capacitor 1010, 1012 to ground, and each capacitor is connected to the non-inverting input of an operational amplifier 1014, 1016, which amplifier acts essentially as a buffer with unity gain. The combination of the capacitor 1010, 1012 with its associated buffer amplifier 1014, 1016 acts as a sample-and-hold circuit so that the output of the amplifiers will correspond to outputs of the multiplexers 998, 1000, but held for the time required to do an analog-to-digital conversion of the signals.

After capacitors 1010, 1012 have charged up to the voltage level of the signals, which have passed through the multiplexers 998, 1000, the multiplexers are inhibited by a signal from the computer 850 provided to the inhibit (INH) inputs so that the output of each multiplexer will appear as an open circuit, which will prevent the sample-and-hold capacitors from discharging.

Because the reflected light multiplexer 998 and the reference multiplexer 1000 are controlled by the computer to allow the respected signals to pass through simultaneously, it is ensured that the reflected light signals and their associated reference signals are received at the same time to charge their respective sample-and-hold capacitors 1010, 1012. This particular configuration will reject noise generated by the ultraviolet lamps 428, 434 by as much as 30 dB.

It should also be noted at this point that the computer 850 will use the multiplexers 998, 1000 when conducting a self test or in order to calibrate the analyzer; in other words, it will control the multiplexers to allow the reference signals to pass through to check what the levels of these signals are and if they have changed from the last calibration.

The output of the buffer amplifier of the reference signal sample-and-hold circuit 1016 is coupled through a input resistor 1018 to the inverting input of an operational amplifier 1020, having a feedback resistor 1022. The operational amplifier 1020 is configured to provide a gain of −1, that is, it merely inverts the signal provided by the reference signal sample-and-hold circuit 1016.

The output of the inverting amplifier 1020 is provided to a resistor divider network comprising resistor 1024 in series with resistor 1026. Resistors 1024 and 1026 are chosen so that the midpoint connection of the two resistors provides a voltage which is equal to −1/5th of the reference signal. Capacitor 1028 is connected across resistor 1026 and the signal at the midpoint connection of resistors 1024 and 1026 is provided to the non-inverting input of an operational amplifier 1030. The operational amplifier 1030 has its output connected to a resistor 1032 which is connected to one side of a capacitor 1034. The other side of the capacitor 1034 is connected to a resistor 1036, whose other side is connected to the output of the inverting operational amplifier 1020, and capacitor 1034 and resistor 1036 are together connected to the inverting input of operational amplifier 1030.

Another multiplexer 1038 is provided in the pre-amplifier and analog-to-digital converter subassembly 800. The multiplexer 1038 has one of its select lines (input A) connected to the inhibit inputs (INH) of the reflected light signal multiplexer 998 and reference signal multiplexer 1000. Multiplexer 1038 is basically a quad 2-input multiplexer.

One of the inputs (XO) of one pair of inputs (X0, X1) is connected between resistor 1036 and capacitor 1034. The other input (X1) is connected to the output (X) of the multiplexer associated with that pair of inputs. The output (X) is also connected to the other side of capacitor 1034.

When the computer 850 signals to enable multiplexers 998 and 1000, it will also signal multiplexer 1038 to choose the X0-X path, which will effectively short out capacitor 1034. However, a side of capacitor 1034 connected to resistor 1032 will be at −0.2 of the reference signal voltage. Accordingly, capacitor 1034 will charge from this negative voltage level when released by multiplexer 1038.

When the computer sends an opposite signal to the inhibit inputs (INH) of multiplexers 998 and 1000, and to the "A" input of multiplexer 1038, the path between input (X1) and output (X) through the multiplexer is chosen. Capacitor 1034 will now charge positively from the −0.2 reference signal starting point at a constant slope, as current is provided through resistor 1036 to capacitor 1034.

The output (X) of multiplexer 1038 is connected through a series resistor 1040 to the inverting input of a comparator 1042. The non-inverting input of comparator 1042 is connected to ground, and a capacitor 1044 is connected between ground and resistor 1040.

Comparator 1042 is a zero-level comparator. That is, it will compare the rising voltage on charging capacitor 1034 with ground. When the voltage on capacitor 1034 rises above ground, the output of the comparator 1042 will switch states and provide a signal to the computer 850. The signal will be used to start a timer which will be used to determine the voltage of the reflected light signal, as will be explained in greater detail.

The output of the sample-and-hold circuit 1014 for the reflected light signal is connected through a low-pass filter comprising resistor 1046 connected to capacitor 1048 to the non-inverting input of a comparator 1050. The inverting input of comparator 1050 is connected to the inverting input of comparator 1042 so that both comparators 1050 and 1042 receive the same charging signal from capacitor 1034. When the charging signal rises to a level of the reflected light signal on the non-inverting input of comparator 1050, the output of the comparator will switch state and signal the computer that the capacitor 1034 has charged up to the same voltage, or substantially the same voltage, as the reflected light signal.

Because the clock, which will be described in relation to the computer interface subassembly 802 shown in FIG. 66, has started running at the zero crossing, the number of pulses generated by the clock may be counted. The clock is inhibited when the voltage on capacitor 1034 has reached the voltage level of the reflected light signal. Accordingly, because the voltage across capacitor 1034 is increasing at a constant rate, one merely has to count the number of pulses generated by the clock between the time of the zero crossing and when the level of the reflected light signal is reached to convert the reference light signal from its in analog form to a digital code.

In certain instances, the reflected light signal may be a negative voltage. Accordingly, the present invention starts the charging ramp for the analog-to-digital conversion from a negative voltage (i.e., −0.2 times the reference signal voltage), which is more negative than the reflected light signal which is expected, so that capacitor 1034 will charge up through the negative reflected light signal to the zero crossing level. In such a situation, comparators 1050 and 1042 will signal circuitry on the computer interface subassembly 802 to start the clock when the ramp voltage has reached the negative reference signal and to stop the clock when the ramp voltage has reached the zero crossing level. The number of pulses may be counted and, by knowing the slope of the charging voltage, the count signal will be indicative of the voltage level of the reflected light signal below ground. Also in such a situation, comparator 1050 will change the state of its output first, indicating that the ramp voltage has reached the negative reference voltage level, and then comparator 1042 will change state when the ramp voltage has increased to the voltage level of ground.

One of the advantages of the analog-to-digital converter of the present invention is that it is ratiometric; that is, the output digital code representing the voltage level of the reflected light signal will always be presented in relation to the reference signal associated with the particular light source used in the measurement. Also included is a circuit comprising amplifier 1051, resistors 1053, 1055, 1057, 1059, 1061, capacitor 1063 and zener diode 1065 for amplifying the temperature sense signal from connector 1067 and providing the amplified signal to multiplexer 998.

The pre-amplifier and analog-to-digital converter subassembly 800 also includes a series of voltage regulators 1052–1058 and a series of filter capacitors 1060–1070 connected to the regulators and to ground, the voltage regulators providing ±9 volts and ±5 volts.

The pre-amplifier and analog-to-digital converter subassembly 800 also includes an LED driver 1072. The inputs of the LED driver 1072 are connected to the computer through connector 1002. The computer will energize one of the inputs at a time so that a particular LED 462 for the reflectometer will be energized. Each of the outputs of the LED driver 1072 is provided to an LED brightness control potentiometer 1074–1080 and to an output connector 1082 through series connected, currently limiting resistors 1084–1090. Connector 1082 is connected to a mating connector 1092 which is connected to the LEDs 462 of the reflectometer.

The computer interface subassembly 802 will now be described with reference to FIG. 66 of the drawings. Multiple bus lines 1100–1104 carrying information to and from the computer 850 are connected to a plurality of input/output buffers 1094–1098 The bus lines 1100–1104 carry control signals, address information and data from the computer 850 to the computer interface subassembly 802 and vice versa. The address data from the computer is provided to buffers 1094 and 1096, and the outputs of buffers 1094 and 1096 are provided to address decoders 1106 and 1108. Some of the outputs of the address decoders 1106, 1108 go to various integrated circuits on the computer interface subassembly 802, as illustrated in FIG. 66. Other outputs from the address decoders are provided to the mechanical interface board 804 which is shown in detail in FIG. 67.

Buffer 1098 receives data from the computer 850 and the output of buffer 1098 is connected to an eight line data bus 1110 which is connected to various integrated circuits on the computer interface subassembly. More specifically, the data bus 1110 is connected to programmable input/output circuits 1112–1116, and a counter 1118, and is provided through an appropriate connector 1120 to the mechanical interface subassembly 804.

As mentioned previously, the data bus is connected to integrated circuits 1112 through 1116. Each of these integrated circuits is a programmable input/output device. The programmable input/output devices 1112–1116 will either take data from the data bus 1110 and hold it, or put data onto the data bus from another circuit.

Connected to the programmable input/output device 1116 by another data bus 1122 is a real time clock 1124. The real time clock 1124 is associated with the computer 850 of the analyzer, and it provides clock data to device 1116, which will output the clock data onto the data bus 1110.

Also connected by a way of a data bus 1126 is a LCD controller device 1128. LCD controller device 1128 receives data and control signals on the bus line 1126 from input/output device 1116 The LCD controller device 1128 will then address an external random access memory (RAM) 1130 which will act as a look-up table and provide data back to the LCD controller device 1128. Data which is held by the RAM is provided to controller device 1128, which then outputs this data through a connecter 1132 to the LCD display 8 of the blood analyzer.

Programmable input/output device 1114 receives address data from the data bus 1110 and provides address data to an electrically erasable programmable read only memory (EEPROM) 1134, which stores calibration parameters for the blood analyzer. Data from the EEPROM 1134 is provided back to the programmable input/output device 1114, which information may then be transmitted on the databus 1110 to the computer 850 and other associated circuitry.

Data from the computer is also provided from the data bus 1110 to input/output device Input/output device 1112 will direct data from the databus to the pre-amplifier and analog-to-digital converter subassembly 800 through a connector 1136 which is coupled to connector 1002 on the pre-amplifier subassembly 800. The data which is provided to the pre-amplifier subassembly 800 by the computer 850 and through the computer interface subassembly 802 includes data to energize one of the four LEDs 462 of the reflectometer (this data is provided to LED driver 1072 on the pre-amplifier subassembly) and to select which channel of the reflected light signals are to be processed (this data goes to the select inputs A–C of the multiplexers 998 and 1000.

The computer interface subassembly 802 also includes the remaining portion of the analog-to-digital converter not found in the pre-amplifier and analog-to-digital converter subassembly 800. More specifically, the outputs of comparators 1050 and 1042, which are provided to connector 1002 are received on connector 1136 of the computer interface subassembly 802. Each of these output signals is provided to the clock input of a D-type flip flop through a logic inverter 1142, 1144 having hysteresis. The flip flops 1138, 1140 effectively act as noise or "bounce" eliminators, as there may be a certain amount of "ringing" or uncertainty in the output state of the comparators 1050 and 1042. The "D" inputs of the flip flops 1138, 1140 are grounded, the Preset inputs are connected to a high logic level, and the Set inputs are connected together and to a signal designated in FIG. 66 by the term "RUN", which signal is provided through input/output device 1112 from the computer 850.

The Q outputs of the flip flops 1138, 1140 are provided to an exclusive or gate 1146. Gate 1146 is connected to the Enable input of counter 1118 and will be used to control the running of the counter, that is, turning the counter on and off.

A third D-type flip 1148 has its Clock input connected of the Q output of the flip flop 1138 provided with the signal from the zero crossing comparator 1042, and has its D input connected to the Q output of the flip flop 1140 which is provided with the signal from comparator 1050. Also, the Set input of flip flop 1148 is connected to the RUN signal line, and its Reset input is held to a high logic level.

Flip flop 1148 is used to determine which comparator 1042 or 1050 changed its state first, which will be reflected on the outputs of the two noise eliminator flip flops 1138, 1140 to which the comparators are indirectly connected. The Q output of flip flop 1148 will be indicative of the polarity of the reflected light signal, that is, whether it is negative or positive, and this polarity (i.e., from the Q output) signal is provided to the input/output device 1112 for transmission on the data bus 1110 to the computer 850.

The output of the exclusive or gate 1146 is also connected to the Clock input of a fourth D-type flip flop 1150, having its D inputs connected to a high logic level, its Set input also connected to a high logic level, and its Reset input connected to the "RUN" signal. The Q output of this fourth flip flop 1150 is an indication that the counter 1118 has been shut off, i.e., that analog-to-digital conversion of the reflected light signal has been completed. This signal from the Q output of flip flop 1150 is provided to the input/output device 1118 for transmission on the data bus 1110 to the computer 850.

A fifth D-type flip flop 1152 is connected to an "Overflow" output on counter 1118, and has its D input connected to ground, its Reset input connected to a high logic level and its Set input connected to the RUN signal. The Q output of the fifth flip flop 1152 provides a counter overflow or "Out of Range" signal, which signal is provided to the input/output device 1112 for transmission on the data bus 1110 to the computer 850.

Counter 1118 is used to provide a count signal which is, effectively, the digital equivalent of the analog voltage level of the unknown reflected light signal. Data from the computer 850 on the data bus 1110 is provided to the counter 1118 so that the counter may be programmed to count at a particular rate or for a particular number of counts.

Input/output device 1112 also receives data from the computer along the data bus 1110 and outputs this data to a printer controller 1154. Device 1154 controls the printer 10 of the analyzer and has associated with it circuitry comprising a number of inverters 1156-1164, a capacitor 1166, a resistor 1168, a diode 1170, resistors 1172 and 1174, a transistor 1176, resistors 1178 and 1180 and a potentiometer 1182. These components cooperate to form an oscillator for driving the printer controller 1154, and potentiometer 1182 is used as a frequency adjustment. The oscillator provides a 16 kHz signal for driving the printer controller 1154.

Printer controller 1154 is also connected to a tachometer circuit comprising a capacitor 1184, a transistor 1186, resistors 1188 and 1190 and a diode 1192. The tachometer circuit provides a signal to the printer 8 to control the position of the printer head. Printer controller 1154 also provides motor drive data on a data bus 1194 to the printer 8 through an appropriate connector 1196.

Input/output device is also connected through a connector 1198 to the keyboard 4 to receive data from the keyboard. It transmits this data along the data bus 1110 to the computer 850.

The mechanical interface subassembly 804 of the blood analyzer will now be described in detail and in relation to FIG. 67.

Input data from the data bus 1110 of the computer interface subassembly 802 is provided to a programmable input/output interface device 1200 through an appropriate connector 1202. A first set of output data from device 1200 is provided on bus line 1204 to a motor controller device 1206, which in turn provides signals on signal bus 1208, 1210 to the turntable stepping drive motor 348 and the syringe stepping drive motor 270. Through motor controller 1206 the computer can control the rotation of the drive motors 348, 270 for the turntable and the metering device to a high degree of accuracy. The data buses 1208, 1210 which carry this "stepping data" are provided to the turntable assembly and sample metering assembly through appropriate connectors, 1212 and 1214 respectively.

Also connected to the outputs of the input/output device 1200 is a second motor controller 1216. Controller 1216 is a DC motor driver for the drive motors 398, 60 of the ejector assembly and the cover assembly. The output signals to drive these motors are provided to the ejector and cover assemblies through appropriate connectors 1218 and 1220, respectively. A "HOME" signal is also received from the cover assembly optical sensor 168 and provided to the input/output device 1200 for signaling the computer when the cover 54 is in its home position.

Another motor controller 1222 is connected to input/output device 1200 through a NAND gate 1224, acting as an inverter and through a series connected diode 1226. Motor controller 1222 is actually a motor speed regulator for controlling the speed of the pipette lifter assembly. Motor controller 1222, in association with a resistor 1228 connected to a positive voltage and a potentiometer 1230, allows the speed at which the pipette 18 is raised and lowered to be accurately controlLED. Potentiometer 1230 provides an adjustment for the speed at which the pipette lifter operates. The signals from motor controller 1222 are provided to the lifter assembly by a connector 1232. The optical sensor 218 associated with the pipette lifter provides a "TOP" signal, which indicates that the pipette is in its most raised position, through connector 1232 to the input/output device 1200, which signal is provided by device 1200 to the computer 850.

Also shown in FIG. 67 are the various optical sensors used in the blood analyzer. These include sensor 103, which indicates that the inserter plate 68 is in its most forward position; sensor 101, which indicates that the inserter plate is in its most backward position; sensor 408, which indicates that the ejector arm 404 is in its home position; sensor 394, which indicates that the turntable is in its home position; and sensor 306, which indicates that the syringe of the metering assembly is in its home position. The outputs of the above sensors are provided to the input/output device 1200, which device provides these signals to the computer 850 through the computer interface subassembly 802. It is to be noted that each of the LED light sources of the sensors is connected to a positive voltage through an appropriate resistor 1234-1242.

The brushes 390 which contact the slip rings of the turntable assembly are pictorially illustrated by FIG. 67. One brush, S, receives the signal from the temperature sensor 378 of the turntable assembly. Another brush, marked with a "+" sign, provides a positive voltage to the sensor and to the heater plate 380. The third brush, H, provides a path to sink current from the coils of the heater plate 380.

The signal from the sensor 378 on brush S is provided through a series resistor 1244 to the inverting input of an operational amplifier 1246. Amplifier 1246 has a feedback resistor 1248 which is in parallel with a capacitor 1250. The non-inverting input of amplifier 1246 is connected to ground. The signal from resistor 1244 is also provided through a series resistor 1252 to one end of a potentiometer 1254, the other end and wiper of which are connected to a zener diode 1256, a capacitor 1258 to ground, and a resistor 1260 to a negative voltage.

Potentiometer 1252 is provided to adjust the current output provided to the coils of the heater plate 380. The temperature sensor 378 on the turntable provides a current output signal which is proportional to temperature and which is preferably approximately one microamp of current per degree of temperature. The potentiometer 1254 is preferably a ten turn potentiometer and is adjusted so that when the temperature of the turntable 0 is exactly at 37°, the output of amplifier 1246 will be at 0 volts.

The output of amplifier 1246 is provided to the non-inverting input of a second operational amplifier 1262.

The inverting input of amplifier 1262 is connected to the emitter of an NPN power transistor 1264, whose base is connected through a series resistor 1266 to the output of operational amplifier 1262, and to temperature connector 1263 through a resistor 1265. The collector of transistor 1264 is connected to the heater brush H. Connector 1263 is connected to resistor 1267 to ground, and to connector 1067 on preamplifier subassembly 800.

If the temperature of the turntable assembly should decrease, the voltage provided to the non-inverting input of amplifier 1262 will increase. Amplifier 1262 will then turn transistor 1264 on so that it sinks current from the coils of the heater plate of the turntable.

The heater control circuit described above also includes a PNP transistor 1268 having its base connected to the input/output device 1200, its emitter connected to the base of transistor 1264, and its collector connected to ground. Across the emitter and collector of transistor 1268 is a diode 1270 and a capacitor 1272. A signal DHTR * from the computer 850 and provided to the base of transistor 1268 will cause transistor 1268 to turn on, which in turn will bias transistor 1264 off to remove current from the heater plate coils of the turntable 50, thus shutting off the heater.

A second temperature control circuit is also part of the mechanical interface subassembly 804 of the blood analyzer and is used for controlling the temperature of the base plate 48. A positive voltage is provided to a temperature sensor 1274 which is mounted on the base plate 48. The output of sensor 1274 is connected through a series resistor 1276 to the inverting input of an operational amplifier 1278. The inverting input is also connected to a resistor 1280 which is connected to a ten turn potentiometer 1282, whose wiper and opposite side are connected to resistor 1260 and zener diode 1256. Like potentiometer 1254, potentiometer 1282 provides an adjustment to set up a zero voltage level on the output of operational amplifier 1278 when the temperature of the base plate 48 is at 37°.

Amplifier 1278 includes a feedback resistor 1284 connected in parallel with a capacitor 1286, and the non-inverting input of amplifier 1278 is connected to ground. The output of amplifier 1278 is provided to the non-inverting input of a second stage operational amplifier 1288, whose output is connected through a feedback resistor 1290 to the inverting input of the amplifier 1288 and to ground through a resistor 1292. The output of amplifier 1288 is connected to the base of an NPN transistor 1294 through a series resistor 1296, as well as to a capacitor 1298 connected to ground and a diode 1300 connected to ground. The collector of transistor 1294 is connected to the base plate heater 395 mounted on the base plate 48 of the analyzer through an appropriate connector 1302, and the emitter of transistor 1294 is connected to ground.

In the same manner as the temperature control circuit for the turntable 50, the temperature control circuit for the base plate 48 will cause transistor 1294 to turn on whenever the temperature sensed by sensor 1274 decreases. Transistor 1294 will then act as a sink for current passing through the base plate heater 395, and will turn off or go into a low conduction state when the temperature sensed by sensor 1274 increases to the desired value.

Each of the temperature control circuits for the turntable 50 and the base plate 48 described above are linear type circuits, that is, they provide a continual adjustment of approximately 0.2° C. variation over 37° C. temperature initially set up for operation. Both transistors 1264 and 1294 preferably remain active during operation of the temperature control circuits. The purpose of keeping transistors 1264 and 1294 active is to provide a greater degree of control in the temperature of the turntable 50 and base plate 48, and also to prevent transient noise on the signals of the circuitry which might result if transistors 1264 and 1294 were continually driven into saturation or cut off.

Also shown on the mechanical interface subassembly 804 is the drive circuitry for the fluorescent lamps 428, 434 of the reflectometer. The drive circuitry basically includes a DC power source, as opposed as to an AC drive circuit. It has been found that a DC drive for the ultraviolet lamps will reduce noise, will provide a more consistent current to the fluorescent lamps and will prolong the life of the fluorescent lamps.

FIG. 67 shows a schematic diagram of a preferred form of a power supply circuit for the fluorescent lamp sources 422, 424. The power supply circuit more specifically includes a start up circuit and a constant current drive circuit.

An oscillator/divider circuit 1600, which may be a 14 stage divider, has its XI terminal connected to a 455 KHZ crystal 1602 (although other frequency crystals may be used), to a capacitor 1604 to ground, and to one end of a resistor 1606. The X0 terminal of the oscillator/divider circuit 1600 is connected to the other end of resistor 1606 and to a resistor 1608. The other end of resistor 1608 is connected to the other end of crystal 1602 and to a capacitor 1610 to ground. A filter capacitor 1612 is provided between the Vcc input (Pin 16) on oscillator/divider circuit 1600 and ground, and the "Reset" input is grounded.

The "Q5" output of circuit 1600 is provided to the anode of a diode 1614. Similarly, the output signal on the "Q4" output, which has a frequency of about 30 KHZ, is provided to the anode of another diode 1616. The cathodes of the two diode 1614, 1616 are connected together and are provided to the series base resistor 1618 of an NPN transistor 1620.

By connecting diodes 1614, 1616 together, a time varying signal having a 75% duty cycle is generated and provided to transistor 1620. Transistor 1620 will thus be turned on for 75% of the time, and off for 25%.

The emitter of transistor 1620 is connected to ground, its base is further connected to a resistor 1622 to ground (which acts as a voltage divider network with resistor 1618) and the collector of transistor 1620 is provided to one side of a "flyback" inductor or choke 1624, a capacitor 1626 to ground and the anode of a diode 1628. The other end of flyback choke 1624 is connected to two capacitors 1630, 1632 to ground, and to one end of another choke 1634, whose other end is connected to +12 volts. Capacitors 1630, 1632 function as a noise filter. (The +12V source may be provided to a regulator circuit 1636 to provide a +5 volts source. The +5V output of the regulator circuit 1636 is connected to a filter capacitor 1638 to ground.)

The cathode of diode 1628 is connected to a capacitor 1640 to ground and to two identical constant current transistor circuits. One transistor circuit includes a PNP transistor 1642, having an emitter resistor 1644 connected to diode 1628, a zener diode 1646 connected between the base of transistor 1642 to diode 1628, and a base resistor 1648 connected to ground. The collector of transistor 1642 is connected to the anode of a diode 1650, whose cathode is connected to one end of the secondary winding of a step-up transformer 1652. The other end of the secondary winding of transformer 1652 is provided to a connector 1654, which is connected to the 350 nM fluorescent lamp.

The second transistor circuit includes a zener diode 1656, a PNP transistor 1658, a base resistor 1660, and an emitter resistor 1662, all connected together in the same manner as the circuit of transistor 1642. A collector diode 1664 is similarly provided, and its cathode is connected to one end of the secondary winding of a second step-up transformer 1666. The other end of the secondary winding is provided to a connector 1668, which is connected to the 400 nM fluorescent lamp.

The use of the flyback choke circuit in the constant current drives for the fluorescent lamps provides between about 100 and about 150 volts to drive the lamps. Accordingly, this voltage is generated even though only +12 volts is provided to the circuit. One of the reasons for using a constant current drive is that it has been found that the fluorescent lamps generate less noise when driven from a constant current DC source.

As mentioned previously, a start-up circuit for the fluorescent lamps is also provided. The output signal on the "Q4" output of the oscillator/divider circuit 1600 is provided to one input of a 2-input NAND gate 1670 and to the inputs of another NAND gate 1672 functioning as an inverter. The output of gate 1672 is provided to one input of a 2-input NAND gate 1674. The other inputs of gates 1670, 1674 are connected to a resistor 1676 to ground and to a capacitor 1678, whose other side is connected to the Pin 23 of the input/output circuit 1200. A "START" signal is provided by the computer on Pin 23, and is provided to capacitor 1678. Capacitor 1678, in conjunction with resistor 1676, provides a short duration "on" pulse to NAND gates 1670, 1674, enabling them and allowing the approximately 30 KHZ signal from the "Q4" output of circuit 1600 to pass through. The signals on the output of gate 1670 will be a 30 KHZ burst, of a duration proportional to the RC time constant defined by capacitor 1678 and resistor 1676. The signal on the output of gate 1674 will be the same as that of gate 1670, except opposite in state.

The outputs of the NAND gates are connected to two identical transistor drive circuits. More specifically, the output of gate 1674 is provided to a base resistor 1680 of a PNP transistor 1682. Transistor 1682 also has a resistor 1684 connected between its base and emitter, and its emitter is connected to +5 volts. The output of gate 1670 is similarly connected to a base resistor 1686 of a PNP transistor 1688, also having a base-emitter resistor 1690.

The collectors of transistors 1682, 1690 are connected to identical secondary transistor drive circuits. More specifically, transistor 1684 is connected to a series base resistor 1692 of an NPN transistor 1694, which transistor has a resistor 1696 from its base to ground, and has its emitter grounded. Transistor 1688 is connected to a base resistor 1698 of NPN transistor 1700, which also includes a base to ground resistor 1702 and has its emitter grounded.

The collector of transistor 1694 is connected to one end of the primary winding of transformer 1666, and the collector of transistor 1700 is connected to one end of the primary winding of transformer 1652. The other ends of the primary windings of transformers 1652, 1666 are connected to +12 volts.

When the START signal is generated by the computer, the circuit described above will provide a 250 volt AC signal burst to each fluorescent lamp in order to ionize the gases in the lamps. By alternating which of the two transistor drive circuits are on by using gate 1672, any noise generated when starting up the fluorescent lamps by the circuits which generate the 250 volts AC is minimized. Once the lamps have "started", there is no need for this high voltage signal. When gates 1670, 1674 have been disabled (by the short duration pulse on their inputs determined by the values of capacitor 1678 and resistor 1676), their output signals will go to a logic high state. This will turn off transistors 1684, 1688, which in turn will turn off transistors 1694, 1700. The transformers then will no longer provide 250 volts AC to the fluorescent lamps, and the lamps will draw the constant current they need to maintain the ionization of their gases from transistors 1642, 1660.

A power circuit for the filaments of the fluorescent lamps is also provided. When starting up the fluorescent lamps, the computer of the analyzer sends a "FILAMENT ON" signal through input/output circuit 1200. This signal is of short duration and is provided to the base resistor 1704 of an NPN transistor 1706, which also has a base-emitter resistor 1708 and has its emitter grounded.

The collector of transistor 1706 is connected to the base of a PNP transistor 1710 through a series base resistor 1712. Transistor 1710 also includes a base-emitter resistor 1714, and has its emitter connected to +12 volts. The collector of transistor 1710 is connected to two load resistors 1716, 1718, whose other ends are connected to the filaments of the fluorescent lamps through the respective connectors 1668, 1654.

When the fluorescent lamps are to be turned on, the computer will send the "FILAMENT ON" signal, and the signal provided by circuit 1200 to base resistor 1704 will go to a logic high state. This will turn on transistor 1706, which is turn will turn on transistor 1710, whose circuit acts as a current source for the filaments of the fluorescent lamps. The "FILAMENT ON" signal will cause the filaments to be energized for a short duration.

After about a one second delay after the "FILAMENT ON" signal was sent, the computer will send the "START" signal. The "START" signal will cause the power circuit to provide a high voltage (about 250 volts) AC signal to ionize the gases in the lamps. The high voltage is provided for only about 2 seconds. After about 3 seconds after start up, both the filament power circuit (i.e., transistors 1706, 1710) and the high voltage circuit (i.e., transistors 1684, 1690, 1694, 1700) are turned off, leaving only the constant current drive circuits (i.e., transistors 1642, 1660) to power the lamps.

Figure 68:
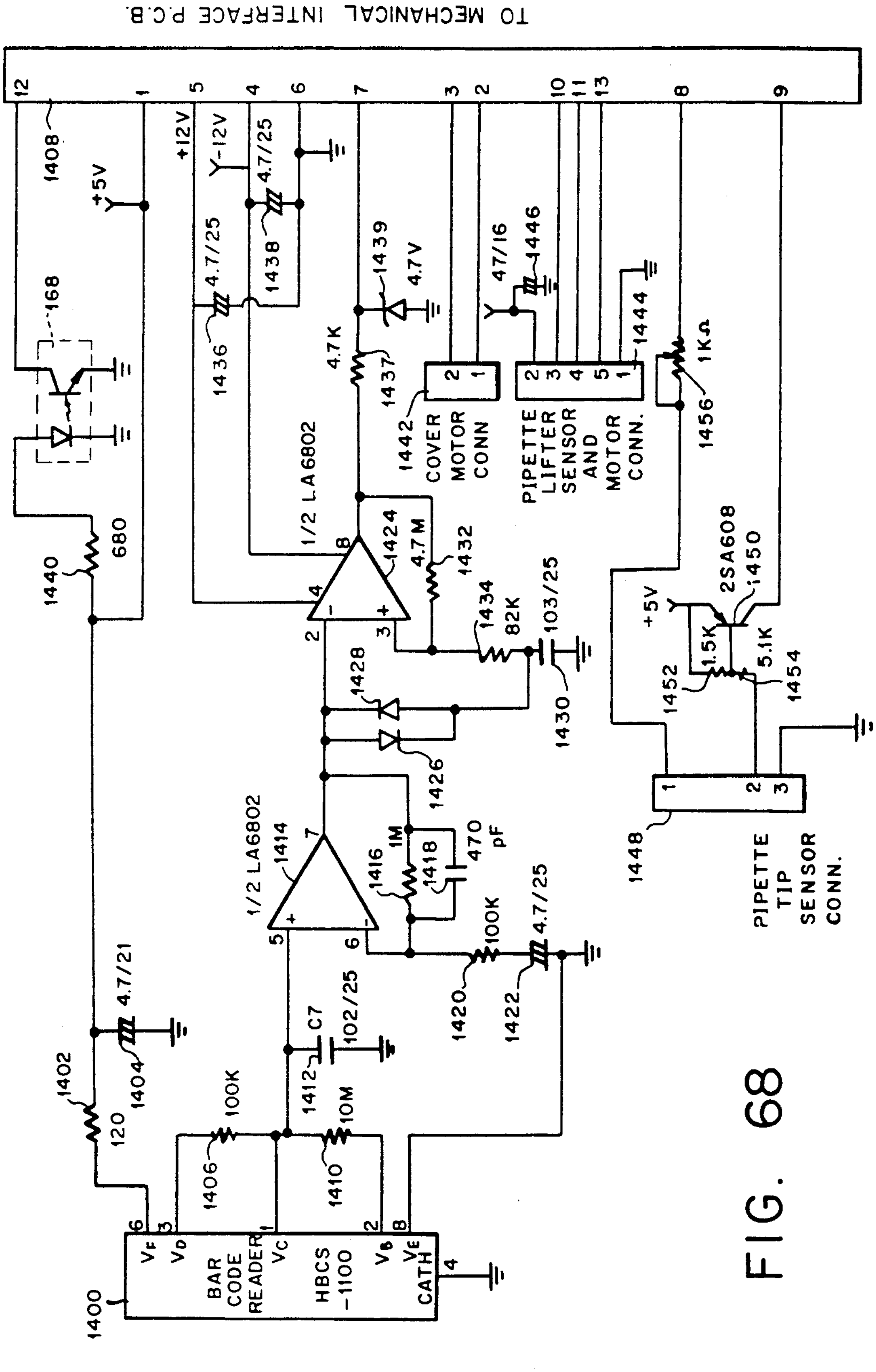
FIG. 68 is a schematic diagram of a fourth portion of the electronic circuitry of the analyzer.

FIG. 68 shows a schematic diagram of a preferred form of the circuitry of the bar code subassembly 158.

A bar code reader 1400, which is preferably Part No. HBCS-1100, manufactured by Hewlett-Packard Company, has its "$V_F$" input connected to a resistor 1402, whose other side is connected to a capacitor 1404 to ground, a resistor 1406, the "$V_D$" input of reader 1400, and to a +5V source through the subassembly's connector 1408. The "$V_C$" output of the reader 400 is connected to the other side of resistor 1406, another resistor 1410, a capacitor 1412 to ground, and the non-inverting (+) input of an operational amplifier 1414.

The "$V_B$" input of reader 1400 is connected to the other side of resistor 1410, while the "$V_E$" input and "CATH" input are connected to ground.

Resistor 1402 provides a current source for the LED in the reader 1400. Resistor 1406 is the collector load for the phototransistor of the reader 1400. Resistor 1410 provides base bias for the phototransistor.

The signal measuring the reflectance from the bar codes on the top surface of the test slides is provided on the "$V_C$" output of the reader 1400. This signal is provided to amplifier 1414, which is configured to provide a non-inverting gain of 10. More specifically, amplifier 1414 has a 1 M ohm feedback resistor 1416 (in parallel with a capacitor 1418) from its output to its inverting (−) input, and an input resistor 1420 of 100K ohms connected from its inverting input to a capacitor 1422 to ground. Operational amplifier 1414 may be ½ of Part No. LA6802, manufactured by Sanyo Corporation.

The output of amplifier 1414 is provided to a peak detector and comparator circuit. More specifically, the output of amplifier 1414 is connected to the inverting (−) input of operational amplifier 1424, which acts as a comparator and can be the other half of Part No. LA6802, the anode of diode 1426 and the cathode of diode 1428. The cathode and anode of diodes 1426 and 1428, respectively, are connected together and to a capacitor 1430 to ground. Capacitor 1430 acts as a peak detector by storing the output signal on amplifier 1414, minus the voltage drop (approximately 0.6 volts) across the diodes 1426, 1428.

The non-inverting (+) input of amplifier 1424 is connected to a feedback resistor 1432, whose other end is connected to the output of amplifier 1424, and to an input resistor 1434, whose other end is connected to the capacitor 1430. +12 volts and −12 volts are provided to amplifiers and 1424 through the connector 1408, and filter capacitors 1436 and 1438 are provided on the subassembly and connected between the voltage sources and ground.

Diodes 1426, 1428 allow capacitor 1430 to charge to the level of the signal on the output of amplifier 1414, minus 0.6 volts, the drop across the diodes. The signal on capacitor 1430 is compared with the signal on the output of amplifier 1414. The signal on the capacitor 1430 lags the output signal of amplifier 1414. If one is on a positive slope of the time varying output signal of amplifier 1414, the inverting input of comparator 1424 will always be more positive than the comparator's non-inverting input. Under such circumstances, the output of the comparator (amplifier 1424) will be −10 volts.

If the slope of the signal on the output of amplifier 1414 changes by more than 0.6 volts, the comparator will change states, because the voltage on the comparator's non-inverting input will be greater than the voltage on its inverting input. The output will then go to +10 volts. The comparator's change in state occurs in response to the optical bar code printed on the test slide scanned by the reader 1400.

The output of amplifier (comparator) 1424 is provided to a resistor 1437, whose other end is connected to a 4.7 volt zener diode 1439 to ground and to the subassembly's connector 1408. This signal, which is now 0 volts to approximately +5 volts due to the diode 1439, is provided to the computer of the analyzer for processing.

The bar code subassembly 158 further includes the optical sensor 168 for the cover motor's "home" position, and a resistor 1440 connected between sensor 168 and +5 volts to drive the LED of the sensor.

The subassembly further includes a connector 1442 providing a power signal to the cover motor 60; another connector 1444 for connection to the pipette lifter motor 226 and "home" position sensor 266, with a filter capacitor 1446 to ground on the voltage line provided to the pipette lifter assembly; and a third connector 1448 for connection to the pipette tip opto-sensor 175. Because the signal from sensor 175 is of a small magnitude, an amplifier is included on subassembly 158. More specifically, a transistor 1450 configured as a common base amplifier, with a resistor 1452 between its base and its emitter and another resistor 1454 between its base and the phototransistor of sensor 175 through connector 1448, amplifies the signal from sensor 175 and provides the amplified signal to connector 1408. Potentiometer 1456 controls the sensitivity of the sensor by adjusting the current to sensor 175.

It can be seen from the above description that the chemical analyzer of the present invention can simultaneously run twelve tests in a small, low cost, desk top unit. The total time for twelve tests is approximately seven minutes, whereas conventional analyzers may require as much as sixty minutes to complete the same tests.

The design of the cover 54 of the present invention includes individual spring-loaded portions (i.e., E button members 140) which cover the test slides and which are tolerant of considerable variation in slide thickness. Furthermore, the cover is easily removable to allow cleaning of unintentional spills.

The simplified optical head design of the reflectometer portion of the analyzer provides a single visible region E assembly which uses a single photodiode with four LEDs to select the wavelength.

The rotating cover 54 allows slides to be exposed for bar code reading and spotting with serum and covered during the test to control evaporation.

The heater control portion and associated circuitry of the incubator provides ±0.1° C. control. Thus, it accurately maintains the temperature of the test slides to within a narrow range, but yet is low cost and simple in construction. It further maintains the temperature irrespective of the voltage drop across the brushes associated with the slip rings.

In a preferred form of the analyzer, small, low cost, high production volume fluorescent lamps 424, 434 with custom phosphors are used in order to provide light in the ultraviolet wavelength region. This delivers a narrow band emission, which reduces the cost of the narrow band, ultraviolet filters 431, 440 and consumes very low power to minimize heating effects. The fluorescent lamps are relatively inexpensive, and have a long life (that is, up to 2,000 hours or more). Conventional chemical analyzers use xenon or mercury lamps, which are much more expensive and require much higher power (that is, 50 watts and more). Thus, many conventional analyzers require cooling for their lamps, which is not required in the present invention. Furthermore, such lamps produce wide band emissions, which require costly filtering, and have a shorter useful life (that is, 1,000 hours and less).

For the visible region of the spectrum, the chemical analyzer of the present invention uses low cost LEDs (producing 555–680 nM wavelength emissions) rather than high cost lamps and filters.

The chemical analyzer of the present invention also employs low cost ratiometric analog-to-digital circuitry, which provides high resolution and good short term stability.

The chemical analyzer of the present invention provides real time information to the user as the tests are run by displaying a plot of reflectance verses time so that a knowledgeable user can spot potential blood problems before the test is complete.

The metering assembly of the chemical analyzer of the present invention utilizes a low cost, off the shelf gas chromatograph syringe which provides high accuracy. Also, the articulated vertical motion pipette assembly provides highly accurate drop volumes irrespective of varying slide thicknesses.

The test results are analyzed by the chemical analyzer of the present invention according to species, and out-of-normal bounds are flagged. Additionally, a data base indicates potential problems (i.e., liver, kidney, dehydration, etc.) by examining the results of the test, and these problems are displayed by the analyzer for the user's convenience.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

CHEMICAL ANALYZER COMPUTER PROGRAM IN OBJECT CODE

PART A — ANALYZER OPERATION

©VETTEST, S.A. 1989
ALL RIGHT S RESERVED

```
C>debug
-r
AX=0000  BX=0000  CX=0000  DX=0000  SP=FFEE  BP=0000  SI=0000  DI=0000
DS=17ED  ES=17ED  SS=17ED  CS=17ED  IP=0100   NV UP EI PL NZ NA PO NC
17ED:0100 4D            DEC     BP
-n vtl.exe
-l
-r
AX=0000  BX=0001  CX=CFA3  DX=0000  SP=00E6  BP=0000  SI=0000  DI=0000
DS=1807  ES=1807  SS=35CE  CS=1817  IP=0000   NV UP EI PL NZ NA PO NC
1817:0000 BAC32E        MOV     DX,2EC3
-d cs:0 l 0
1817:0000  BA C3 2E 2E 89 16 C7 01-B4 30 CD 21 8B 2E 02 00   .........0.!....
1817:0010  8B 1E 2C 00 8E DA A3 7D-00 8C 06 7B 00 89 1E 77   ..,....}...{...w
1817:0020  00 89 2E 91 00 C7 06 81-00 FF FF E8 01 01 C4 3E   ...............>
1817:0030  75 00 8B C7 8B D8 B9 FF-7F 26 81 3D 38 37 75 19   u........&.=87u.
1817:0040  26 8B 55 02 80 FA 3D 75-10 80 E6 DF FF 06 81 00   &.U...=u........
1817:0050  80 FE 59 75 04 FF 06 81-00 F2 AE E3 3C 43 26 38   ..Yu........<C&8
1817:0060  05 75 D6 80 CD 80 F7 D9-59 0E 75 00 B9 02 00 D3   .u.........u....
1817:0070  E3 83 C3 10 E3 E3 F0 89-1E 79 00 8C D2 2B EA 8B   .........y...+..
1817:0080  3E 98 0D 81 FF 00 02 73-07 BF 00 02 89 3E 98 0D   >......s......>..
1817:0090  B1 04 D3 EF 47 3B EF 73-03 E9 13 01 8B DF 03 DA   ....G;.s........
1817:00A0  89 1E 89 00 89 1E 8D 00-A1 7B 00 2B D8 8E C0 B4   .........{.+....
1817:00B0  4A 57 CD 21 5F D3 E7 FA-8E D2 8B E7 FB 33 C0 2E   JW.!_........3..
1817:00C0  8E 06 C7 01 BF E8 42 B9-AC 70 2B CF F3 AA 0E FF   ......B..p+.....
1817:00D0  16 C2 42 9A FA 05 17 18-9A F8 06 17 18 B4 00 CD   ..B.............
1817:00E0  1A 89 16 83 00 89 0E 85-00 0E FF 16 C6 42 FF 36   .............B.6
1817:00F0  73 00 FF 36 71 00 FF 36-6F 00 FF 36 6D 00 FF 36   s..6q..6o..6m..6
1817:0100  6B 00 9A 0F 00 08 19 50-9A 0E 00 0D 2B 2E 8E 1E   k......P....+...
1817:0110  C7 01 9A 72 01 17 18 0E-FF 16 C4 42 8B EC B4 4C   ...r.......B...L
1817:0120  8A 46 04 CD 21 B9 0E 00-90 BA 2F 00 E9 87 00 1E   .F..!...../.....
1817:0130  B8 00 35 CD 21 89 1E 5B-00 8C 06 5D 00 B8 04 35   ..5.!..[...]...5
1817:0140  CD 21 89 1E 5F 00 8C 06-61 00 B8 05 35 CD 21 89   .!.._...a...5.!.
1817:0150  1E 63 00 8C 06 65 00 B8-06 35 CD 21 89 1E 67 00   .c...e...5.!..g.
1817:0160  8C 06 69 00 B8 00 25 8C-CA 8E DA BA 25 01 CD 21   ..i...%.....%..!
1817:0170  1F C3 1E B8 00 25 C5 16-5B 00 CD 21 1F 1E B8 04   .....%..[..!....
1817:0180  25 C5 16 5F 00 CD 21 1F-1E B8 05 25 C5 16 63 00   %.._..!....%..c.
1817:0190  CD 21 1F 1E B8 06 25 C5-16 67 00 CD 21 1F CB C7   .!....%..g..!...
1817:01A0  06 81 00 00 00 C3 C3 B4-40 BB 02 00 CD 21 C3 B9   ........@....!..
1817:01B0  1E 00 90 BA 3D 00 2E 8E-1E C7 01 E8 E9 FF B8 03   ....=...........
1817:01C0  00 50 9A 0D 01 17 18 00-00 55 8B EC 83 EC 02 54   .P.......U.....T
1817:01D0  58 3B C4 75 33 CD 11 25-02 00 74 64 33 C0 E6 F0   X;.u3..%..td3...
1817:01E0  D9 E3 9B D9 E8 9B D9 EE-9B DE F9 9B D9 C0 9B D9   ................
```

```
1817:01F0  E0 9B DE D9 9B DD 7E FE-8B 46 FE 9E 75 05 B9 02   ......~..F..u...
1817:0200  00 E8 3D 98 03 00 E8 38-33 C0 E6 F0 DB E3 C7 46   ..=....83......F
1817:0210  FE 00 00 D9 7E FE B9 14-00 E2 FE 8B 46 FE 25 3F   ....~.......F.%?
1817:0220  0F 3D 3F 03 B8 00 00 75-17 C7 46 FE FF FF DD 7E   .=?....u..F....~
1817:0230  FE B9 14 00 E2 FE F7 46-FE BF B8 75 03 B8 01 00   .......F...u....
1817:0240  8B E5 5D C3 00 00 00 00-00 00 00 00 00 00 00 00   ..].............
1817:0250  00 00 00 00 00 00 00 00-00 00 00 00 00 00 00 00   ................
1817:0260  00 00 00 00 00 00 00 00-00 00 00 00 00 00 00 00   ................
1817:0270  00 00 00 00 50 32 C0 E6-F0 B0 20 E6 A0 E6 20 58   ....P2.... ... X
1817:0280  CD 02 CF 57 06 9A 9F 05-17 18 B8 34 35 B9 0B 00   ...W........45...
1817:0290  BF 44 02 CD 21 2E 89 1D-2E 8C 45 02 83 C7 04 40   .D..!.....E....@
1817:02A0  E2 F1 B8 75 35 CD 21 2E-89 1D 2E 8C 45 02 07 5F   ...u5.!.....E.._
1817:02B0  83 3E 81 00 FF 75 06 E8-0F FF A3 81 00 1E 55 8B   .>...u........U.
1817:02C0  EC 83 EC 08 B8 C3 2E 8E-D8 8B D8 83 3E 81 00 00   .............>...
1817:02D0  C7 46 FC EB 02 C7 46 FE-1B 2A C7 46 F8 6B 03 C7   .F....F..*.F.k..
1817:02E0  46 FA 1B 2A 75 14 C7 46-FC A7 20 C7 46 FE 8B 27   F..*u..F.. .F..'
1817:02F0  C7 46 F8 77 1D C7 46 FA-3B 27 B3 34 25 B9 0A 00   .F.w..F..'.4%...
1817:0300  C5 56 FC CD 21 40 E2 FB-B9 3E 25 C5 56 F8 CD 21   .V..!@...>%.V..!
1817:0310  8E DB 83 3E 81 00 00 74-19 A1 7D 00 86 E0 3D 10   ...>...t..}...=.
1817:0320  03 7C 0F 3D 00 0A 7D 0A-B8 75 25 0E 1F BA 74 02   .|.=..}..u%...t.
1817:0330  CD 21 CD 37 E3 C7 46 FE-30 13 CD 35 6E FE 8B E5   .!.7..F.0..5n...
1817:0340  5D 1F CB 9A BA 05 17 18-1E B8 34 25 3B 44 02 B9   ].........4%.D..
1817:0350  0B 00 2E C5 17 CD 21 83-C3 04 40 E2 F5 B8 75 25   ......!...@...u%
1817:0360  2E C5 17 CD 21 1F CB E8-A9 01 FB 51 06 53 8B 84   ....!......Q.S..
1817:0370  3B 8B 4C 0A 89 4F 06 8B-4C 0C 89 4F 08 8B 4C 06   ;.L..O..L..O..L.
1817:0380  89 4F 0A 8B 4C 08 89 4F-0C 81 67 0C 00 F0 80 E5   .O..L..O..g.....
1817:0390  07 80 CD D8 89 4F 04 C7-47 02 01 00 8B 4C 08 80   .....O..G....L..
1817:03A0  E5 07 8B D9 80 E3 C0 80-FB C0 74 03 80 E1 38 83   ..........t...8.
1817:03B0  3E 81 00 00 74 1D A8 05-74 05 E8 70 01 EB 14 A8   >...t...t..p....
1817:03C0  02 74 05 E8 40 00 EB 32-A8 18 74 07 50 E8 85 01   .t..@..2..t.P...
1817:03D0  58 EB 00 25 3D 00 74 22-52 33 D2 8B D8 42 D1 EB   X..%=.t"R3...B..
1817:03E0  73 FB 89 16 84 3B C7 06-86 3B 01 00 1E BE 84 3B   s....;...;.....;
1817:03F0  56 9A 06 00 5D 2A 83 C4-04 5A 5B 07 59 5E 58 1F   V...]*...Z[.Y^X.
1817:0400  0E E8 01 00 90 CF 83 3E-81 00 03 7D 72 E8 EC 00   .......>...}r...
1817:0410  8B C1 24 F8 81 F9 00 01-74 65 81 F9 00 05 74 5F   ..$.....te....t_
1817:0420  81 F9 28 03 74 59 3D C0-01 74 54 3D E4 01 74 4F   ..(.tY=..tT=..tO
1817:0430  3D 10 00 74 4A 3D 18 00-74 45 3D 10 04 74 40 3D   =..tJ=..tE=..t@=
1817:0440  18 04 74 3B 3D D0 00 74-36 3D D8 00 74 31 3D D9   ..t;=..t6=..t1=.
1817:0450  06 74 2C 3D 10 06 74 27-3D 18 06 74 22 3D 10 02   .t,=..t'=..t"=..
1817:0460  74 1D 3D 18 02 74 18 C4-5C 0A 3D 30 00 75 11 E8   t.=..t..\.=0.u..
1817:0470  F5 00 CD 3C D9 07 E8 26-00 CD 3A F9 E8 FD 00 C3   ...<...&..:.....
1817:0480  3D 30 04 75 13 E8 DF 00-50 CD 3C DD 07 E8 0F 00   =0.u....P.<.....
1817:0490  CD 3A F9 58 E8 E5 00 C3-E8 92 00 E8 5E 00 C3 CD   .:.X........^...
1817:04A0  35 E5 CD 39 3E 78 3B CD-3D A1 78 3B 25 00 47 A9   5..9>x;.=.x;%.G.
1817:04B0  00 40 74 06 A9 00 01 74-01 C3 A9 00 45 74 0D A9   .@t....t....Et..
1817:04C0  00 40 75 01 C3 CD 39 D8-CD 35 EE C3 CD 37 3E 7A   .@u...9..5...7>z
1817:04D0  3B 52 CD 3B 2E 7A 3B A1-82 3B 8B D0 81 E2 00 80   ;R.;.z;..;......
1817:04E0  CD 37 3E 7A 3B 33 C2 CD-3D 03 06 82 3B 2D 3E 40   .7>z;3..=...;->@
1817:04F0  33 C2 A3 82 3B CD 37 2E-7A 3B 5A C3 51 50 B9 08   3...;.7.z;Z.QP..
1817:0500  00 E8 9B FF 83 3E 81 00-00 74 05 CD 35 F7 E2 F1   .....>...t..5...
1817:0510  58 59 C3 CD 37 E2 50 8A-04 8A 64 02 0C 40 22 E0   XY..7.P...d..@".
1817:0520  80 E4 7F 63 64 02 CD 35-24 58 CD 3D C3 80 FB C0   ....d..5$X.=....
1817:0530  74 03 80 C9 07 80 CD D8-96 E9 89 0E E4 3B E8 BB   t.............;..
1817:0540  FF E8 23 00 1E C5 5C 0A-9A E3 3B C3 2E 1F EB 2B   ..#...\...:.....+
1817:0550  00 E3 A8 FF C3 8B C1 25-F8 FF 25 D0 01 3D 10 01   .......%..%..=..
1817:0560  74 01 C3 E8 C7 FF C3 CD-35 3E 78 3B CD 3D A1 78   t.......5>x;.=.x
1817:0570  3B 93 0E 78 3B 3F CD 35-2E 78 3B C3 51 CD 35 34   ;..x;?.5.x;.Q.54
1817:0580  CD 37 E2 89 04 8A 64 02-9B C8 F6 D1 22 E9 80 E5   .7....d....."...
1817:0590  3F 2A E5 8B 64 02 CD 35-24 8A C5 2A E4 59 C3 B8   ?*..d..5$..*.Y..
1817:05A0  02 35 CD 21 8C 06 68 3B-89 1E 66 3B 8C 0E D4 3B   .5.!..h;..f;...;
1817:05B0  BA 92 3B B8 02 25 CD 21-F8 CB 1E C5 16 66 3B B8   ..;..%.!.....f;.
1817:05C0  02 25 CD 21 F8 1F CB 55-8B EC 83 EC 0C CD 35 7E   .%.!...U......5~
1817:05D0  F4 CD 3D 8B 46 F4 0D 00-0C 89 46 F6 CD 35 6E F6   ..=.F.....F..5n.
1817:05E0  CD 3B 7E F8 CD 35 6E F4-8B 56 FA 8B 46 F8 8B E5   .;~..5n..V..F...
1817:05F0  5D CB 00 00 00 00 00 00-00 00 2E 8F 06 F2 05 2E   ]...............
1817:0600  8F 06 F4 05 2E 8C 1E F6-05 FC 8E 06 7B 00 BE 80   .............{...
1817:0610  00 32 E4 26 AC 40 8C C5-87 D6 93 8B 36 75 00 83   .2.&.@......6u..
1817:0620  C6 02 B9 01 00 80 3E 7D-00 03 72 11 8E 06 77 00   ......>}..r...w.
1817:0630  8B FE 91 7F 32 C0 F2 AE-E3 76 80 F1 7F 83 EC 02   ....2...v.......
1817:0640  B8 01 00 03 C3 03 C1 25-FE FF 8B FC 2B F8 72 60   .......%....+.r`
1817:0650  8B E7 8C C0 8E D8 8C D0-8E C0 51 49 F3 A4 32 C0   ..........QI..2.
```

```
1817:0660  AA 8E DD 87 F2 87 D9 8B-C3 8B D0 43 E8 19 00 77   ...........C...w
1817:0670  07 72 42 E8 12 00 77 F9-3C 20 74 08 3C 0D 74 04   .rB...w.< t.<.t.
1817:0680  3C 09 75 E8 32 C0 EB E4-0B C0 74 07 42 AA 0A C0   <.u.2.....t.B...
1817:0690  75 01 43 86 E0 32 C0 F9-E3 15 AC 49 2C 22 74 0F   u.C..2.....I,"t.
1817:06A0  04 22 3C 5C 75 07 80 3C-22 75 02 AC 49 0B F6 C3   ."<\u..<"u..I...
1817:06B0  EA AF 01 17 18 59 03 CA-2E 8E 1E F6 05 89 1E 6B   .....Y.........k
1817:06C0  00 43 03 DB 03 DB 8B F4-8B EC 2B EB 72 E2 8B E5   .C........+.r...
1817:06D0  89 2E 6D 00 8C 16 6F 00-E3 11 89 76 00 8C 56 02   ..m...o....v..V.
1817:06E0  83 C5 04 36 AC 0A C0 E0-FA 74 ED 33 C0 89 46 00   ...6.....t.3..F.
1817:06F0  89 46 02 2E FF 2E F2 05-8E 06 77 00 33 FF 06 FF   .F........w.3...
1817:0700  36 79 00 9A 00 00 14 2B-93 C4 02 8B D8 07 A3 71   6y.....+.......q
1817:0710  00 89 16 73 00 1E 8E DA-0B C2 75 05 EA AF 01 17   ...s......u.....
1817:0720  18 33 C0 B9 FF FF 89 3F-8C 47 02 83 C3 04 F2 AE   .3.....?.G......
1817:0730  26 38 05 75 F1 89 07 89-47 02 1F CB 0B C9 7D 0D   &8.u....G.....}.
1817:0740  F7 D3 F7 D1 83 C3 01 83-D1 00 EB 2D 90 03 C3 73   ...........-...s
1817:0750  04 81 C2 00 10 8A E9 B1-04 D2 E5 02 F5 8A E8 D3   ................
1817:0760  E8 03 D0 8A C5 25 0F 00-C8 0B C9 7D 0C F7 D3 F7   .....%.....}....
1817:0770  D1 83 C3 01 83 D1 00 EB-D4 2B C3 73 04 81 EA 00   ..........+.s....
1817:0780  10 8A F9 B1 04 D2 E7 32-DB 2B D3 8A E8 D3 E8 03   .......2.+......
1817:0790  D0 8A C5 25 0F 00 CB 51-8A E8 B1 04 D3 E8 03 D0   ...%...Q........
1817:07A0  8A C5 8A E3 D3 EB 59 03-CB 8A DC 25 0F 00 83 E3   ......Y....%....
1817:07B0  0F 3B D1 75 02 3B C3 CB-56 96 92 85 C0 74 02 F7   .;.u.;..V....t..
1817:07C0  E3 91 85 C0 74 04 F7 E6-03 C8 96 F7 E3 03 D1 5E   ....t..........^
1817:07D0  CB BA E8 40 EB 03 BA ED-40 B9 05 00 90 B4 40 5B   ...@....@.....@.
1817:07E0  02 00 CD 21 B9 27 00 90-BA F2 40 B4 40 CD 21 EA   ...!.'....@.@.!.
1817:07F0  AF 01 17 18 FF 2E C8 42-55 8B EC EB 18 C4 5E 04   ........BU.....^.
1817:0800  FF 46 04 26 8A 07 C4 5E-08 FF 46 08 26 3A 07 74   .F.&...^..F.&:.t
1817:0810  04 33 C0 EB 0E C4 5E 04-26 80 3F 00 75 DF B8 01   .3....^.&.?.u...
1317:0820  00 EB 00 5D C2 08 00 B8-30 11 B7 00 B2 FF 9A 3C   ...]....0......<
1817:0830  08 17 18 8A C2 FE C0 B4-00 EB 00 C3 56 57 89 2E   .............VW..
1917:0840  6E 70 CD 10 8B 2E 6E 70-5F 5E CB B4 0F 0E E8 EB   np....np_^......
1817:0850  FF 50 9A 6C 08 17 18 59-B4 08 B7 00 0E E8 DC FF   .P.l...Y........
1817:0860  80 E4 7F 88 26 99 41 E8-26 98 41 C8 55 8B EC 8A   ....&.A.&.A.U...
1817:0870  46 06 3C 03 76 06 3C 07-74 02 B0 03 A2 9A 41 B4   F.<.v.<.t.....A.
1817:0980  0F 0E E8 B7 FF 3A 06 9A-41 74 12 A0 9A 41 B4 00   ......:..At...A..
1817:0890  0E E8 A8 FF B4 0F 0E E8-A2 FF A2 9A 41 88 26 9C   .............A.&.
1817:08A0  41 80 3E 9A 41 03 76 0C-80 3E 9A 41 07 74 05 B8   A.>.A.v..>.A.t..
1817:08B0  01 00 EB 02 33 C0 A2 9D-41 C6 06 9B 41 19 80 3E   ....3...A...A..>
1817:08C0  9A 41 07 74 20 BA 00 F0-B8 EA FF 52 50 1E B8 A5   .A.t ......RP...
1817:08D0  41 50 E8 23 FF 0B C0 75-0C E8 4B FF 0B C0 75 05   AP.#...u..K...u.
1817:08E0  B6 01 00 EB 02 33 C0 A2-9E 41 80 3E 9A 41 07 75   .....3...A.>.A.u
1817:08F0  05 B8 00 B0 EB 03 B8 00-58 A3 A1 41 C7 06 9F 41   ............A...A
1817:0900  00 00 B0 00 A2 95 41 A2-94 41 A0 9C 41 04 FF A2   .......A..A..A...
1817:0910  96 41 C6 06 97 41 13 5D-CB C8 33 C9 E8 0D B9 01   .A...A.]..3.....
1817:0920  00 EB 08 B9 02 00 E8 03-B9 03 00 55 56 57 8B EC   ............UVW..
1817:0930  8B F9 8B 46 0A 8B 56 0C-9B 5E 0E 8B 4E 10 0B C9   ...F..V..^..N...
1817:0940  75 08 0B D2 74 69 0B DB-74 65 F7 C7 01 00 75 1C   u...ti..te....u.
1817:0950  0B D2 79 0A F7 DA F7 D8-83 DA 00 93 CF 0C 0B C9   ..y.............
1817:0960  79 0A F7 D9 F7 DB 83 D9-00 83 F7 04 8B E9 B9 20   y.............
1817:0970  00 57 33 FF 33 F6 D1 E0-D1 D2 D1 D6 D1 D7 3B FD   .W3.3.........;.
1817:0980  72 0B 77 04 3B F3 72 05-2B F3 1B FD 40 E2 E7 5B   r.w.;.r.+...@..[
1817:0990  F7 C3 02 00 74 06 8B C6-8B D7 D1 EB F7 C3 04 00   ....t...........
1817:09A0  74 07 F7 DA F7 D8 83 DA-00 5F 5E 5D CA 08 00 F7   t........_^]....
1817:09B0  F3 F7 C7 02 00 74 02 8B-C2 33 D2 EB EC 53 74 61   .....t...3...Sta
1817:09C0  63 6B 20 6F 76 65 72 66-6C 6F 77 21 0D 0A 24 8C   ck overflow!..$.
1817:09D0  C8 8E D8 3A BD 09 B4 09-CD 21 EA 0D 01 17 18 57   ..........!.....W
1817:09E0  8B F9 8A EE B1 04 D3 E2-D2 ED 03 D0 80 D5 00 8B   ................
1817:09F0  C7 D3 E7 D2 EC 03 DF 80-D4 00 2B D3 1A EC 8A C5   ...........+.....
1817:0A00  98 92 5F CB 55 8B EC 56-57 1E C5 76 06 C4 7E 0A   .._.U..VW..v..~.
1817:0A10  FC D1 E9 F3 A5 13 C9 F3-A4 1F 5F 5E 5D CA 08 00   ..........._^]...
1817:0A20  55 8B EC 83 EC 0E 56 57-39 26 98 0D 77 05 9A CF   U.....VW9&..w...
1817:0A30  09 17 18 8C 5E F4 C7 46-F2 5C 0D 1E B8 69 0D 50   ....^..F.\...i.P
1817:0A40  FF 76 F4 FF 76 F2 9A 1A-02 5C 2B 83 C4 08 89 56   .v..v....\+....V
1817:0A50  F8 89 46 F6 0B D0 75 33-33 FF EB 0B 8B DF D1 E3   ..F...u33.......
1817:0A60  C7 87 48 55 00 00 47 83-FF 64 7C F0 C7 06 10 56   ..HU..G..d!....V
1817:0A70  00 00 1E B8 14 56 50 1E-B8 12 56 50 1E B8 13 56   .....VP...VP...V
1817:0A80  50 9A A4 03 A2 1A 83 C4-0C EB 4A FF 76 F8 FF 76   P.........J.v..v
1817:0A90  F6 B8 01 00 50 B8 D0 00-50 1E B8 48 55 50 9A 12   ....P...P..HUP..
1817:0AA0  01 13 2C 83 C4 0C 3D 01-00 73 1D FF 76 F8 FF 76   ......=..s..v..v
1817:0AB0  F6 9A 28 15 A2 1A 59 59-B8 20 00 50 9A E8 03 B9   ..(...YY. .P....
1817:0AC0  13 59 B8 20 00 E9 3A 03-FF 76 F8 FF 76 F6 9A 28   .Y. ..:..v..v..(
```

```
1817:0AD0  15 A2 1A 59 59 33 F6 EB-21 8B DE D1 E3 8B 9F 0D   ...YY3..!.......
1817:0AE0  6E D1 E3 81 BF 48 55 00-FA 73 0E 8B DE D1 E3 8B   n....HU..s......
1817:0AF0  9F 0D 6E D1 E3 FF 87 48-55 46 3B 36 3D 6E 7C D9   ..n....HUF;6=n|.
1817:0B00  81 3E 10 56 00 FA 73 04-FF 06 10 56 1E B8 17 56   .>.V..s....V...V
1817:0B10  50 1E B8 15 56 50 1E B8-16 56 50 9A A4 03 A2 1A   P...VP...VP.....
1817:0B20  83 C4 0C 1E B8 6C 0D 50-FF 76 F4 FF 76 F2 9A 1A   .....l.P.v..v...
1817:0B30  02 5C 2B 83 C4 08 89 56-F8 89 46 F6 0B D0 75 1D   .\+....V..F...u.
1817:0B40  FF 76 F8 FF 76 F6 9A 28-15 A2 1A 59 59 B8 20 00   .v..v..(...YY. .
1817:0B50  50 9A E8 03 59 18 59 B8-20 00 E9 A5 02 FF 76 F8   P.....Y. .....v.
1817:0B60  FF 76 F6 B8 01 00 50 B8-D0 00 50 1E B8 48 55 50   .v....P...P..HUP
1817:0B70  9A 0B 00 3A 2C 83 C4 0C-3D 01 00 73 1D FF 76 F8   ...:,...=..s..v.
1817:0B80  FF 76 F6 9A 28 15 A2 1A-59 59 B8 20 00 50 9A E8   .v..(...YY. .P..
1817:0B90  03 B9 18 59 B8 20 00 E9-68 02 FF 76 F8 FF 76 F6   ...Y. ..h..v..v.
1817:0BA0  9A 28 15 A2 1A 59 59 8C-5E F4 C7 46 F2 6F 0D 1E   .(...YY.^..F.o..
1817:0BB0  B8 7B 0D 50 FF 76 F4 FF-76 F2 9A 1A 02 5C 2B 83   .{.P.v..v....\+.
1817:0BC0  C4 08 89 56 F8 89 46 F6-0B D0 75 10 B8 1E 00 50   ...V..F...u....P
1817:0BD0  9A E8 03 B9 18 59 B8 1E-00 E9 26 02 16 8D 46 FD   .....Y....&...F.
1817:0BE0  50 16 8D 46 FB 50 16 8D-46 FC 50 9A A4 03 A2 1A   P..F.P..F.P.....
1817:0BF0  83 C4 0C FF 76 F8 FF 76-F6 B8 01 00 50 B8 01 00   ....v..v....P...
1817:0C00  50 16 8D 46 FC 50 9A 0B-00 3A 2C 83 C4 0C 3D 01   P..F.P...:,....=.
1817:0C10  00 73 1D FF 76 F8 FF 76-F6 9A 28 15 A2 1A 59 59   .s..v..v..(...YY
1817:0C20  B8 1E 00 50 9A E8 03 B9-18 59 B8 1E 00 E9 D2 01   ...P.....Y......
1817:0C30  FF 76 F8 FF 76 F6 B8 01-00 50 B8 01 00 50 16 8D   .v..v....P...P..
1817:0C40  46 FB 50 9A 0B 00 3A 2C-83 C4 0C 3D 01 00 73 1D   F.P...:,...=..s.
1817:0C50  FF 76 F8 FF 76 F6 9A 28-15 A2 1A 59 59 B8 1E 00   .v..v..(...YY...
1817:0C60  50 9A E8 03 B9 18 59 B8-1E 00 E9 95 01 FF 76 F8   P.....Y.......v.
1817:0C70  FF 76 F6 B8 01 00 50 B8-01 00 50 16 8D 46 FD 50   .v....P...P..F.P
1817:0C80  9A 0B 00 3A 2C 83 C4 0C-3D 01 00 73 1D FF 76 F8   ...:,...=..s..v.
1817:0C90  FF 76 F6 9A 28 15 A2 1A-59 59 B8 1E 00 50 9A E8   .v..(...YY...P..
1817:0CA0  03 B9 18 59 B8 1E 00 E9-58 01 FF 76 F8 FF 76 F6   ...Y....X..v..v.
1817:0CB0  B8 01 00 50 B8 02 00 50-1E B8 FB 00 50 9A 0B 00   ...P...P....P...
1817:0CC0  3A 2C 83 C4 0C 3D 01 00-73 1D FF 76 F8 FF 76 F6   :,...=..s..v..v.
1817:0CD0  9A 28 15 A2 1A 59 59 B8-1E 00 50 9A E8 03 B9 18   .(...YY...P.....
1817:0CE0  59 B8 1E 00 E9 1B 01 FF-76 F8 FF 76 F6 B8 01 00   Y.......v..v....
1817:0CF0  50 B8 02 00 50 1E B8 FF-00 50 9A 0B 00 3A 2C 83   P...P....P...:,.
1817:0D00  C4 0C 3D 01 00 73 1D FF-76 F8 FF 76 F6 9A 28 15   ..=..s..v..v..(.
1817:0D10  A2 1A 59 59 B8 1E 00 50-9A E8 03 B9 18 59 B8 1E   ..YY...P.....Y..
1817:0D20  00 E9 DE 00 FF 76 F8 FF-76 F6 B8 01 00 50 B8 02   .....v..v....P..
1817:0D30  00 50 1E B8 01 01 50 9A-0B 00 3A 2C 83 C4 0C 3D   .P....P...:,...=
1817:0D40  01 00 73 1D FF 76 F8 FF-76 F6 9A 28 15 A2 1A 59   ..s..v..v..(...Y
1817:0D50  59 B8 1E 00 50 9A E8 03-59 18 59 B8 1E 00 E9 A1   Y...P.....Y.....
1817:0D60  00 FF 76 F8 FF 76 F6 B8-01 00 50 B8 02 00 50 1E   ..v..v....P...P.
1817:0D70  B8 3D 6E 50 9A 0B 00 3A-2C 83 C4 0C 3D 01 00 73   .=nP...:,...=..s
1817:0D80  1C FF 76 F8 FF 76 F6 9A-28 15 A2 1A 59 59 B8 1E   ..v..v..(...YY..
1817:0D90  00 50 9A E8 03 B9 18 59-B8 1E 00 EB 65 C7 46 FE   .P.....Y....e.F.
1817:0DA0  00 00 EB 44 FF 76 F8 FF-76 F6 B8 01 00 50 B8 02   ...D.v..v....P..
1817:0DB0  00 50 1E 8B 46 FE D1 E0-05 0D 6E 50 9A 0B 00 3A   .P..F.....nP...:
1817:0DC0  2C 83 C4 0C 3D 01 00 73-1C FF 76 F8 FF 76 F6 9A   ,...=..s..v..v..
1817:0DD0  28 15 A2 1A 59 59 B8 1E-00 50 9A E8 03 B9 18 59   (...YY...P.....Y
1817:0DE0  B8 1E 00 EB 1D FF 46 FE-8B 46 FE 3B 06 3D 6E 7C   ......F..F.;.=n|
1817:0DF0  B3 FF 76 F8 FF 76 F6 9A-28 15 A2 1A 59 59 33 C0   ..v..v..(...YY3.
1817:0E00  EB 00 5F 5E 8B E5 5D CB-55 8B EC 83 EC 08 56 57   .._^..].U.....VW
1817:0E10  39 26 98 0D 77 05 9A CF-09 17 18 8B 7E 06 8C 5E   9&..w.......~..^
1817:0E20  FA C7 46 F8 7E 0D 1E B8-8B 0D 50 FF 76 FA FF 76   ..F.~.....P.v..v
1817:0E30  F8 9A 1A 02 5C 2B 83 C4-08 89 56 FE 89 46 FC 0B   ....\+....V..F..
1817:0E40  D0 75 2E 33 F6 EB 0B 8B-DE D1 E3 C7 87 42 48 00   .u.3.........BH.
1817:0E50  00 46 81 FE 96 00 7C EF-1E B8 70 49 50 1E B8 6E   .F....|...pIP..n
1817:0E60  49 50 1E B8 6F 49 50 9A-A4 03 A2 1A 83 C4 0C EB   IP..oIP.........
1817:0E70  3D FF 76 FE FF 76 FC B8-01 00 50 B8 32 01 50 1E   =.v..v....P.2.P.
1817:0E80  B8 42 48 50 9A 12 01 13-2C 83 C4 0C 3D 01 00 73   .BHP....,...=..s
1817:0E90  10 FF 76 FE FF 76 FC 9A-28 15 A2 1A 59 59 E9 A8   ..v..v..(...YY..
1817:0EA0  00 FF 76 FE FF 76 FC 9A-28 15 A2 1A 59 59 81 FF   ..v..v..(...YY..
1817:0EB0  96 00 7C 02 EB 14 8B DF-D1 E3 81 BF 42 48 00 FA   ..|.........BH..
1817:0EC0  73 08 8B DF D1 E3 FF 87-42 48 1E B8 73 49 50 1E   s.......BH..sIP.
1817:0ED0  B8 71 49 50 1E B8 72 49-50 9A A4 03 A2 1A 83 C4   .qIP..rIP.......
1817:0EE0  0C 1E B8 8E 0D 50 FF 76-FA FF 76 F8 9A 1A 02 5C   .....P.v..v....\
1817:0EF0  2B 83 C4 08 89 56 FE 89-46 FC 0B D0 75 0F FF 76   +....V..F...u..v
1817:0F00  FE FF 76 FC 9A 28 15 A2-1A 59 59 EB 3C FF 76 FE   ..v..(...YY.<.v.
1817:0F10  FF 76 FC B8 01 00 50 B8-32 01 50 1E B8 42 48 50   .v....P.2.P..BHP
1817:0F20  9A 0B 00 3A 2C 83 C4 0C-3D 01 00 73 0F FF 76 FE   ...:,...=..s..v.
1817:0F30  FF 76 FC 9A 28 15 A2 1A-59 59 EB 0D FF 76 FE FF   .v..(...YY...v..
```

```
1817:0F40  76 FC 9A 28 15 A2 1A 59-59 5F 5E 8B E5 5D CB 55   v..(...YY_^..].U
1817:0F50  8B EC 83 EC 04 56 57 39-26 98 0D 77 05 9A CF 09   .....VW9&..w....
1817:0F60  17 18 9A 0A 00 40 19 1E-B8 F6 47 50 9A 02 00 30   .....@....GP...0
1817:0F70  2E 59 59 0B C0 74 4B 9A-8A 02 6B 1C 8B F0 8B C6   .YY..tK...k.....
1817:0F80  0B C0 74 07 56 9A 07 00-72 1D 59 9A 98 00 A4 20   ..t.V...r.Y....
1817:0F90  8B F0 8B C6 0B C0 74 07-56 9A 07 00 72 1D 59 B8   ......t.V...r.Y.
1817:0FA0  01 00 50 B8 01 00 50 9A-0C 00 CF 20 59 59 8B F0   ..P...P.... YY..
1817:0FB0  8B C6 0B C0 74 07 56 9A-07 00 72 1D 59 C6 06 94   ....t.V...r.Y...
1817:0FC0  00 00 1E B8 9A 0D 50 1E-B8 40 55 50 9A 08 00 87   ......P..@UP....
1817:0FD0  2C 83 C4 08 1E B8 A1 0D-50 1E B8 18 56 50 9A 08   ,.......P...VP..
1817:0FE0  00 87 2C 83 C4 08 C7 06-FB 00 FF FF C7 06 FF 00   ..,.............
1817:0FF0  00 00 C7 06 01 01 00 00-1E B8 AC 0D 50 9A 0A 00   ............P...
1817:1000  D7 19 59 59 9A FE 00 A4-20 8B F0 8B C6 0B C0 74   ..YY.... ......t
1817:1010  07 56 9A 07 00 72 1D 59-C7 06 03 01 00 00 B8 01   .V...r.Y........
1817:1020  00 50 9A 21 00 6B 1C 59-C7 06 58 0D 01 00 C7 06   .P.!.k.Y..X.....
1817:1030  CF 00 00 00 C7 06 D1 00-60 00 C7 06 5A 0D 01 00   .............Z...
1817:1040  C7 06 F7 00 1F 00 C7 06-4E 0C 00 00 1E B8 B5 0D   .........N.......
1817:1050  50 9A 0A 00 D7 19 59 59-83 3E 4C 0C 01 75 03 E9   P.....YY.>L..u..
1817:1060  F4 01 C7 46 FE 00 00 33-FF EB 43 33 C0 50 9A 39   ...F...3..C3.P.9
1817:1070  04 A2 1A 59 9A 70 06 A2-1A 3D 01 00 75 30 9A 40   ...Y.p...=..u0.@
1817:1080  08 A2 1A 98 3D 0D 00 74-0C 3D 30 00 74 0A 3D 39   ....=..t.=0.t.=9
1817:1090  00 74 0C EB 12 E9 8E 01-FF 46 FE 33 FF EB 0F C7   .t.......F.3....
1817:10A0  46 FE 00 00 47 EB 07 C7-46 FE 00 00 33 FF 83 7E   F...G...F...3..~
1817:10B0  FE 02 7D 0C 83 FF 02 7D-07 80 3E 94 00 00 74 AB   ..}....}..>...t.
1817:10C0  80 3E 94 00 00 74 6D 1E-B8 BE 0D 50 9A 0A 00 D7   .>...tm....P....
1817:10D0  19 59 59 EB 09 33 C0 50-9A 39 04 A2 1A 59 EA 12   .YY..3.P.9...Y..
1817:10E0  03 EC A8 08 74 EF 9A 8A-02 6B 1C 8B F0 8B C6 0B   ....t....k......
1817:10F0  C0 74 07 56 9A 07 00 72-1D 59 9A 98 00 A4 20 8B   .t.V...r.Y.... .
1817:1100  F0 8B C6 0B C0 74 07 56-9A 07 00 72 1D 59 B8 01   .....t.V...r.Y..
1817:1110  00 50 B8 01 00 50 9A 0C-00 CF 20 59 59 8B F0 8B   .P...P.... YY...
1817:1120  C6 0B C0 74 07 56 9A 07-00 72 1D 59 C6 06 94 00   ...t.V...r.Y....
1817:1130  00 E9 33 FE 83 FF 02 7D-03 E9 83 00 1E B8 C7 0D   ..3....}........
1817:1140  50 9A 0A 00 D7 19 59 59-9A 40 08 A2 1A 88 46 FD   P.....YY.@....F.
1817:1150  3C 31 7C 06 80 7E FD 39-7E 07 9A A1 06 A2 1A EB   <1|..~.9~.......
1817:1160  E7 FF 06 32 3F 7D 13 8A-46 FD FF 06 3E 3F C4 1E   ...2?}..F...>?..
1817:1170  3E 3F 4B 26 88 07 B4 00-EB 10 1E B8 32 3F 50 FF   >?K&........2?P.
1817:1180  76 FD 9A 09 00 AA 2C 83-C4 06 8A 46 FD 98 2D 31   v.....,....F..-1
1817:1190  00 3D 06 00 77 4F 8B D8-D1 E3 2E FF A7 5F 02 6D   .=..wO......._.m
1817:11A0  02 6F 02 77 02 7F 02 87-02 8F 02 97 02 EB 3E 9A   .o.w..........>.
1817:11B0  0C 00 0B 21 E9 85 FF 9A-01 00 D1 21 E9 A8 FD C7   ...!.......!....
1817:11C0  06 CF 00 01 00 EB 26 C7-06 D1 00 01 00 EB 1E C7   ......&.........
1817:11D0  06 4C 0C 01 00 EB 16 C7-06 D1 00 01 00 C7 06 4E   .L.............N
1817:11E0  0C 01 00 EB 08 9A A1 06-A2 1A E9 4F FF EB 67 1E   ...........O..g.
1817:11F0  B8 D0 0D 50 9A 0A 00 D7-19 59 59 9A 40 08 A2 1A   ...P.....YY.@...
1817:1200  98 8B 06 00 5B D6 02 2E-3B 07 74 06 43 43 E2 F7   .........;.t.CC..
1817:1210  EB 3D 2E FF 67 0C 08 00-0D 00 31 00 32 00 33 00   .=..g.....1.2.3.
1817:1220  34 00 0C 03 0A 03 EE 02-F5 02 FC 02 03 03 9A 07   4...............
1817:1230  00 ED 22 EB 8A 9A 07 00-ED 22 EB 83 9A A1 06 A2   .."......"......
1817:1240  1A EB 88 9A A1 06 A2 1A-EB 81 EB 0A E9 D9 FD 9A   ................
1817:1250  A1 06 A2 1A EB A5 9A 03-00 70 1A 3D 2B 00 75 03   .........p.=+.u.
1817:1260  E9 04 FD B8 01 00 50 9A-0B 00 F7 1B 59 3D 02 00   ......P.....Y=..
1817:1270  75 03 E9 F2 FC 9A 0A 00-CA 1D 8B F0 8B C6 0B C0   u...............
1817:1280  74 0F 83 FE 2B 75 03 E9-DD FC 56 9A 07 00 72 1D   t...+u....V...r.
1817:1290  59 E9 D3 FC 5F 5E 8B E5-5D CB 55 8B EC 83 EC 02   Y..._^..].U.....
1817:12A0  56 57 39 26 98 0D 77 05-9A CF 09 17 18 1E B8 F6   VW9&..w.........
1817:12B0  47 50 9A 02 00 30 2E 59-59 9A A9 03 ED 22 9A 89   GP...0.YY....."..
1817:12C0  05 D7 19 B0 89 BA 07 03-EE C7 06 78 49 67 00 A0   .............xIg..
1817:12D0  78 49 BA 04 03 EE C7 06-7C 49 80 00 A0 7C 49 BA   xI......|I...|I.
1817:12E0  05 03 EE B0 81 BA 0B 03-EE B0 80 BA 0F 03 EE B0   ................
1817:12F0  00 BA CC 03 EE B0 00 BA-0E 03 EE B0 8B BA 0F 03   ................
1817:1300  EE B0 89 BA 13 03 EE C7-06 7A 49 FF 00 A0 7A 49   ..........zI...zI
1817:1310  BA 10 03 EE C7 06 7E 49-90 00 A0 7E 49 BA 11 03   ......~I...~I...
1817:1320  EE B8 08 00 50 9A 0B 00-C9 2D 59 89 16 76 6E A3   ....P....-Y..vn.
1817:1330  74 6E B8 88 19 50 B8 07-00 50 B8 08 00 50 9A 1D   tn...P...P...P..
1817:1340  00 C9 2D 83 C4 06 1E B8-F6 47 50 9A 02 00 30 2E   ..-......GP...0.
1817:1350  59 59 B8 88 19 50 B8 A6-04 50 9A 2C 00 B8 2D 59   YY...P...P.,..-Y
1817:1360  59 9A E5 01 A2 1A 1E B8-E0 0D 50 1E B8 40 55 50   Y.........P..@UP
1817:1370  9A 08 00 87 2C 83 C4 08-1E B8 E7 0D 50 1E B8 18   ..............P...
1817:1380  56 50 9A 08 00 87 2C 83-C4 08 9A 41 03 17 22 8B   VP......,....A..".
1817:1390  F0 1E B8 F6 47 50 9A 02-00 30 2E 59 59 0B C0 74   ....GP...0.YY..t
1817:13A0  02 EB E7 0B F6 74 07 56-9A 07 00 72 1D 59 1E B8   .....t.V...r.Y..
```

```
1817:13B0  F6 47 50 9A 02 00 30 2E-59 59 9A 81 0D 3B 24 8B   .GP...0.YY...;$.
1817:13C0  F8 8B C7 0B C0 74 07 57-9A 07 00 72 1D 59 1E B9   .....t.W...r.Y..
1817:13D0  F6 47 50 9A 02 00 30 2E-59 59 1E B8 F2 0D 50 9A   .GP...0.YY....P.
1817:13E0  0A 00 D7 19 59 59 B8 01-00 50 9A 36 03 A2 1A 59   ....YY...P.6...Y
1817:13F0  1E 59 F8 0D 50 9A 05 00-A8 2C 59 59 1E B8 07 0E   ....P....,YY....
1817:1400  50 9A 05 00 A8 2C 59 59-1E B8 09 0E 50 9A 05 00   P....,YY....P...
1817:1410  A8 2C 59 59 B8 18 00 50-9A 30 0E A2 1A 59 1E B8   .,YY...P.0...Y..
1817:1420  12 0E 50 9A 0A 00 D7 19-59 59 83 3E DA 0D 00 75   ..P.....YY.>...u
1817:1430  0B 9A 07 00 4B 21 C7 06-DA 0D 01 00 9A 9C 10 A2   ....K!..........
1817:1440  1A 8B F0 8B C6 0B C0 74-07 56 9A 07 00 72 1D 59   .......t.V...r.Y
1817:1450  9A 0E 00 A4 20 8B F0 8B-C6 0B C0 74 21 9A 0E 00   .... ......t!...
1817:1460  A4 20 8B F0 8B C6 0B C0-74 14 9A 0E 00 A4 20 8B   . ......t..... .
1817:1470  F0 8B C6 0B C0 74 07 56-9A 07 00 72 1D 59 9A 09   .....t.V...r.Y..
1817:1480  03 10 1D 8B F0 8B C6 0B-C0 74 21 9A 09 03 10 1D   ..........t!....
1817:1490  8B F0 8B C6 0B C0 74 14-9A 09 03 10 1D 8B F0 8B   ......t.........
1817:14A0  C6 0B C0 74 07 56 9A 07-00 72 1D 59 9A C2 02 CF   ...t.V...r.Y....
1817:14B0  20 8B F0 8B C6 0B C0 74-07 56 9A 07 00 72 1D 59    ......t.V...r.Y
1817:14C0  9A 8A 02 6B 1C 0B C0 74-49 C7 06 C9 00 01 00 B8   ...k...tI.......
1817:14D0  07 00 50 9A 71 01 6B 1C-59 EB 09 33 C0 50 9A 39   ..P.q.k.Y..3.P.9
1817:14E0  04 A2 1A 59 83 3E 9D 00-00 75 F0 9A A5 02 CF 20   ...Y.>...u......
1817:14F0  8B F0 8B C6 0B C0 74 07-56 9A 07 00 72 1D 59 9A   ......t.V...r.Y.
1817:1500  8A 02 6B 1C 0B C0 74 0A-B8 05 00 50 9A 07 00 72   ..k...t....P...r
1817:1510  1D 59 C7 06 03 01 00 00-B8 01 00 50 9A 21 00 6B   .Y.........P.!.k
1817:1520  1C 59 9A 03 00 10 1D 8B-F0 8B C6 0B C0 74 07 56   .Y...........t.V
1817:1530  9A 07 00 72 1D 59 9A 98-00 A4 20 8B F0 8B C6 0B   ...r.Y.... .....
1817:1540  C0 74 07 56 9A 07 00 72-1D 59 9A FE 00 A4 20 8B   .t.V...r.Y.... .
1817:1550  F0 8B C6 0B C0 74 07 56-9A 07 00 72 1D 59 B8 01   .....t.V...r.Y..
1817:1560  00 50 33 C0 50 9A 0C 00-CF 20 59 59 8B F0 8B C6   .P3.P.... YY....
1817:1570  0B C0 74 07 56 9A 07 00-72 1D 59 9A 99 03 10 1D   ..t.V...r.Y.....
1817:1580  8B F0 8B C6 0B C0 74 21-9A 89 03 10 1D 8B F0 8B   ......t!........
1817:1590  C6 0B C0 74 14 9A 89 03-10 1D 8B F0 8B C6 0B C0   ...t............
1817:15A0  74 07 56 9A 07 00 72 1D-59 83 3E DC 0D 00 75 1A   t.V...r.Y.>...u.
1817:15B0  9A 02 00 98 25 8B F0 8B-C6 0B C0 74 07 56 9A EB   ....%......t.V..
1817:15C0  03 B9 18 59 C7 06 DC 0D-01 00 C6 46 FF 61 1E B8   ...Y.......F.a..
1817:15D0  1A 0E 50 9A 8D 00 D7 19-59 59 83 3E DE 0D 00 75   ..P.....YY.>...u
1817:15E0  08 BA 0B 00 B8 B0 71 EB-05 33 D2 B8 02 00 89 16   ......q..3......
1817:15F0  97 00 A3 95 00 C7 06 32-0D F4 01 E9 86 00 CD 39   .......2.......9
1817:1600  06 35 0E 83 EC 0A CD 37-7E F0 CD 3D 33 C0 50 9A   .5.....7~..=3.P.
1817:1610  6D 11 A2 1A 44 44 CD 37-6E F0 CD 3D 83 C4 0A CD   m...DD.7n..=....
1817:1620  3A D9 CD 39 3E DC 6F CD-3D 8A 26 DD 6F 9E 76 0C   :..9>.o.=.&.o.v.
1817:1630  C7 06 97 00 0B 00 C7 06-95 00 B0 71 9A 70 06 A2   ............q.p..
1817:1640  1A 0B C0 74 08 9A CE 05-A2 1A 88 46 FF 83 3E 32   ...t.......F..>2
1817:1650  CD 00 75 30 80 7E FF 61-75 07 B8 23 0E 8C DA EB   ..u0.~.au..#....
1817:1660  05 B8 2C 0E 8C DA 52 50-9A 8D 00 D7 19 59 59 80   ......RP.....YY.
1817:1670  7E FF 61 74 04 B0 61 EB-02 B0 62 88 46 FF C7 06   ~.at..a...b.F...
1817:1680  32 0D F4 01 80 7E FF 35-74 0C A1 95 00 0B 06 97   2....~.5t.......
1817:1690  00 74 03 E9 68 FF 80 7E-FF 35 74 06 C7 06 DE 0D   .t..h..~.5t.....
1817:16A0  01 00 C7 06 03 01 00 00-B8 01 00 50 9A 21 00 6B   ...........P.!.k
1817:16B0  1C 59 33 C0 50 9A B9 07-A2 1A 59 5F 5E 5B E5 5D   .Y3.P.....Y_^..]
1817:16C0  CB 55 8B EC 83 EC 04 39-26 98 0D 77 05 9A CF 09   .U.....9&..w....
1817:16D0  17 18 1E B8 44 0E 50 1E-B8 3D 0E 50 9A 1A 02 5C   ....D.P..=.P...\
1817:16E0  2B 83 C4 08 89 56 FE 89-46 FC FF 76 0A FF 76 08   +....V..F..v..v.
1817:16F0  FF 76 06 1E B8 46 0E 50-FF 76 FE FF 76 FC 9A 0A   .v...F.P.v..v...
1817:1700  00 65 2D 83 C4 0E FF 76-FE FF 76 FC 9A 0F 00 F9   .e-....v..v.....
1817:1710  2B 59 59 8B E5 5D CB 50-53 51 52 06 1E 56 57 55   +YY..].PSQR..VWU
1817:1720  BD C3 2E 8E DD 8B EC 83-EC 0A 39 26 98 0D 77 05   ..........9%..w.
1817:1730  9A CF 09 17 18 B0 36 E6-43 B0 FF E6 40 B0 03 E6   ......6.C...@...
1817:1740  40 A1 95 00 0B 06 97 00-74 0A 83 2E 95 00 01 83   @.......t.......
1817:1750  1E 97 00 00 83 3E 32 0D-00 74 04 FF 0E 32 0D 83   .....>2..t...2..
1817:1760  3E F9 00 01 75 1A BA 12-03 EC A8 08 75 12 C7 06   >...u.......u...
1817:1770  4E 0D 04 00 C7 06 4C 0D-14 00 C7 06 50 0D 01 00   N.....L.....P...
1817:1780  83 3E F9 00 01 75 0D BA-12 03 EC A8 04 74 05 C6   .>...u.......t..
1817:1790  06 94 00 01 83 3E F9 00-00 75 05 C6 06 94 00 00   .....>...u......
1817:17A0  83 3E 9D 00 00 75 03 E9-1B 01 FF 0E B3 00 7E 03   .>...u........~.
1817:17B0  E9 0F 01 83 3E AF 00 02-74 09 FF 0E B1 00 74 03   ....>...t.....t.
1817:17C0  E9 8E 00 83 3E 48 0D 00-75 04 FF 0E 9D 00 83 3E   ....>H..u......>
1817:17D0  B3 58 09 75 06 C7 06 B5-58 00 00 83 3E 9D 00 09   .X.u....X...>...
1817:17E0  7F 0D 83 3E B5 58 00 75-06 C7 06 B5 58 FF FF 83   ...>.X.u....X...
1817:17F0  3E 9D 00 09 7F 0D 83 3E-B5 58 01 75 06 C7 06 B5   >......>.X.u....
1817:1800  58 00 00 A1 B5 58 01 06-B3 58 83 3E B3 58 00 7D   X....X...X.>.X.}
1817:1810  06 C7 06 B3 58 00 00 83-3E 9D 00 01 75 05 B8 01   ....X...>...u...
```

```
1817:1820  00 EB 03 B8 02 00 A3 B1-00 83 3E 9D 00 00 74 21   ..........>...t!
1817:1830  A1 C9 00 01 06 CB 00 83-3E CB 00 00 7D 06 81 06   ........>...}...
1817:1840  CB 00 90 06 A1 CB 00 8B-90 06 99 F7 FB 89 16 CB   ................
1817:1850  00 8B 1E B3 58 D1 E3 8B-87 B5 00 50 B8 02 00 99   ....X......P....
1817:1860  F7 3E AF 00 8B D8 58 99-F7 FB A3 B3 00 83 3E 9D   .>....X.......>.
1817:1870  00 00 74 41 A1 C9 00 F7-26 AF 00 01 06 9B 00 83   ..tA....&.......
1817:1880  3E 9B 00 00 7D 05 83 06-9B 00 08 A1 9B 00 8B 08   >...}...........
1817:1890  00 99 F7 FB 89 16 9B 00-81 26 7A 49 F0 00 8B 1E   .........&zI....
1817:18A0  9B 00 D1 E3 8B 87 9F 00-09 06 7A 49 A0 7A 49 BA   ..........zI.zI.
1817:18B0  10 03 EE EB 0D 81 0E 7E-49 80 00 A0 7E 49 BA 11   .......~I...~I..
1817:18C0  03 EE E9 BE 00 83 3E D3-00 00 75 03 E9 B4 00 FF   ......>...u.....
1817:18D0  0E D9 00 7E 03 E9 AB 00-83 3E DB 00 00 74 04 FF   ...~.....>...t..
1817:18E0  0E DB 00 83 3E DB 00 00-75 08 C7 06 D9 00 05 00   ....>...u.......
1817:18F0  EB 06 C7 06 D9 00 0A 00-83 3E D3 00 05 7F 06 C7   .........>......
1817:1900  06 D9 00 0A 00 83 3E ED-00 02 74 06 FF 0E EF 00   ......>...t.....
1817:1910  75 16 FF 0E D3 00 83 3E-D3 00 01 75 05 B8 01 00   u.......>...u...
1817:1920  EB 03 B8 02 00 A3 EF 00-83 3E D3 00 00 74 41 A1   ..........>...tA.
1817:1930  D5 00 F7 26 ED 00 01 06-D7 00 83 3E D7 00 00 7D   ...&.......>...}
1817:1940  05 83 06 D7 00 08 A1 D7-00 8B 08 00 99 F7 FB 89   ................
1817:1950  16 D7 00 81 26 7A 49 0F-00 8B 1E D7 00 D1 E3 8B   ....&zI.........
1817:1960  87 DD 00 09 06 7A 49 A0-7A 49 BA 10 03 EE EB 13   .....zI.zI......
1817:1970  81 26 7A 49 0F 00 81 0E-7A 49 F0 00 A0 7A 49 BA   .&zI....zI...zI.
1817:1980  10 03 EE FF 06 99 00 A1-99 00 3D 40 00 7C 1A C7   ..........=@.|..
1817:1990  06 99 00 00 00 83 3E 46-0D 01 75 07 9C FF 1E 74   ......>F..u....t
1817:19A0  6E EB 04 B0 20 E6 20 EB-04 B0 20 E6 20 FF 06 50   n... . .... . ..P
1817:19B0  0E A1 50 0E 3D 04 00 7D-03 E9 EE 01 C7 06 50 0E   ..P.=..}......P.
1817:19C0  00 00 C7 46 F6 00 00 EB-25 8B 5E F6 D1 E3 D1 E3   ...F....%.^.....
1817:19D0  8B 87 3F 6E 0B 87 41 6E-74 11 8B 5E F6 D1 E3 D1   ..?n..Ant..^....
1817:19E0  E3 83 AF 3F 6E 01 83 9F-41 6E 00 FF 46 F6 83 7E   ...?n...An..F..~
1817:19F0  F6 0C 7C D5 83 3E 4C 0D-00 74 15 FF 0E 4C 0D 75   ..|..>L..t...L.u
1817:1A00  0F E4 61 B4 00 25 FC 00-89 46 FE 8A 46 FE E6 61   ..a..%...F..F..a
1817:1A10  83 3E 52 0E 00 74 03 E9-CC 00 FF 06 F5 00 A1 F5   .>R..t..........
1817:1A20  00 3D 19 00 7F 03 E9 BA-00 C7 06 F5 00 00 00 F7   .=..............
1817:1A30  06 78 49 10 00 75 09 33-F6 C7 46 F8 50 00 EB 1A   .xI..u.3..F.P...
1817:1A40  F7 06 78 49 20 00 75 0A-BE 04 00 C7 46 F8 30 00   ..xI .u.....F.0.
1817:1A50  EB 08 BE 08 00 C7 46 F8-60 00 BA 06 03 EC B4 00   ......F.`.......
1817:1A60  25 F0 00 89 46 FA 3D F0-00 74 64 F7 46 FA 10 00   %...F.=..td.F...
1817:1A70  75 02 EB 18 F7 46 FA 20-00 75 03 46 EB 0E F7 46   u....F. .u.F...F
1817:1A80  FA 40 00 75 04 46 46 EB-03 83 C6 03 C7 06 4E 0D   .@.u.FF.......N.
1817:1A90  06 00 A1 F1 00 40 25 0F-00 89 46 FC 3B 06 F3 00   .....@%...F.;...
1817:1AA0  74 1B 8A 84 34 0D 98 8B-1E F1 00 D1 E3 89 87 22   t...4.........."
1817:1AB0  48 8B 46 FC A3 F1 00 C7-06 4E 0D 0A 00 C7 06 52   H.F......N.....R
1817:1AC0  0E 01 00 C7 06 4C 0D 14-00 C7 06 50 0D 01 00 81   .....L.....P....
1817:1AD0  26 78 49 8F 00 8B 46 F8-09 06 78 49 A0 78 49 BA   &xI...F...xI.xI.
1817:1AE0  04 03 EE E9 9B 00 83 3E-52 0E 01 74 02 EB 64 81   .......>R..t..d.
1817:1AF0  26 78 49 8F 00 81 0E 78-49 60 00 A0 78 49 BA 04   &xI....xI`..xI..
1817:1B00  03 EE 33 FF EB 01 47 83-FF 14 7C FA BA 06 03 EC   ..3...G...|.....
1817:1B10  B4 00 25 F0 00 3D B0 00-74 02 EB 37 81 26 78 49   ..%..=..t..7.&xI
1817:1B20  8F 00 81 0E 78 49 30 00-A0 78 49 BA 04 03 EE 33   ....xI0..xI....3
1817:1B30  FF EB 01 47 83 FF 14 7C-FA BA 06 03 EC B4 00 25   ...G...|.......%
1817:1B40  F0 00 3D E0 00 75 0C C7-06 4A 0D 01 00 C7 06 52   ..=..u...J.....R
1817:1B50  0E 02 00 81 26 78 49 8F-00 A0 78 49 BA 04 03 EE   ....&xI...xI....
1817:1B60  81 0E 78 49 60 00 BA 06-03 EC B4 00 25 F0 00 3D   ..xI`.......%..=
1817:1B70  F0 00 75 0D C7 06 52 0E-00 00 A0 78 49 BA 04 03   ..u...R....xI...
1817:1B80  EE 83 3E 50 0D 00 74 22-C7 06 50 0D 00 00 B0 B6   ..>P..t"..P.....
1817:1B90  E6 43 B0 00 E6 42 A0 4E-0D E6 42 E4 61 B4 00 0D   .C...B.N..B.a...
1817:1BA0  03 00 89 46 FE 8A 46 FE-E6 61 8B E5 5D 5F 5E 1F   ...F..F..a..]_^.
1817:1BB0  07 5A 59 5B 58 CF 55 8B-EC 83 EC 10 39 26 98 0D   .ZY[X.U.....9&..
1817:1BC0  77 05 9A CF 09 17 18 C6-46 F1 01 C6 46 F5 06 C6   w.......F...F...
1817:1BD0  46 F4 07 16 8D 46 F0 50-16 8D 46 F0 50 B8 10 00   F....F.P..F.P...
1817:1BE0  50 9A 03 00 D5 2D 83 C4-0A FF 36 76 6E FF 36 74   P....-.....6vn.6t
1817:1BF0  6E 58 08 00 50 9A 1D 00-C9 2D 83 C4 06 9A 18 02   n...P....-......
1817:1C00  A2 1A 33 C0 EB 00 8B E5-5D CB 55 8B EC 39 26 98   ..3.....].U...9&.
1817:1C10  0D 77 05 9A CF 09 17 18-9A 63 02 A2 1A 58 01 00   .w.......c......
1817:1C20  50 9A 39 04 A2 1A 59 9A-3B 00 D7 19 FF 76 08 FF   P.9...Y.;....v..
1817:1C30  76 06 9A 8D 00 D7 19 8B-E5 5D CB 39 26 98 0D 77   v........].9&..w
1817:1C40  05 9A CF 09 17 18 83 3E-FB 00 FF 74 25 58 01 00   .......>...t%...
1817:1C50  50 33 C0 50 9A F7 02 A2-1A 59 59 1E B8 18 56 50   P3.P.....YY...VP
1817:1C60  1E B8 40 55 50 1E B8 73-0E 50 9A 05 00 A8 3C 83   ..@UP..s.P....,.
1817:1C70  C4 0C B8 02 00 50 33 C0-50 9A F7 02 A2 1A 59 59   .....P3.P.....YY
```

```
1817:1C80  1E B8 7C 0E 50 9A 05 00-A8 2C 59 59 CB 55 8B EC   ..|.P....,YY.U..
1817:1C90  39 26 98 0D 77 05 9A CF-09 17 18 33 C0 50 33 C0   9&..w......3.P3.
1817:1CA0  50 9A F7 02 A2 1A 8B E5-FF 76 08 FF 76 06 9A B7   P........v..v...
1817:1CB0  00 D7 19 8B E5 5D CB 55-8B EC 39 26 98 0D 77 05   .....].U..9&..w.
1817:1CC0  9A CF 09 17 18 FF 76 08-FF 76 06 1E B8 32 3F 50   ......v..v...2?P
1817:1CD0  9A D9 00 D7 19 8B E5 5D-CB 55 8B EC 83 EC 16 56   .......].U.....V
1817:1CE0  57 39 26 98 0D 77 05 9A-CF 09 17 18 16 8D 46 F6   W9&..w........F.
1817:1CF0  50 1E B8 54 0E 50 B9 09-00 9A 04 0A 17 18 B8 01   P..T.P..........
1817:1D00  00 50 9A 39 04 A2 1A 59-33 F6 EB 08 C4 5E 0A 26   .P.9...Y3....^.&
1817:1D10  8A 00 36 88 42 F6 46 83-FE 08 7D 12 C4 5E 0A 26   ..6.B.F...}..^.&
1817:1D20  80 38 2E 74 09 C4 5E 0A-26 80 38 00 75 DE EB 06   .8.t..^.&.8.u...
1817:1D30  36 C6 42 F6 20 46 83 FE-08 7C F5 C7 46 F0 00 00   6.B. F...|..F...
1817:1D40  8B 3E 7C 6E 4F BE 01 00-C7 46 F4 00 00 EB 68 8B   .>|nO....F....h.
1817:1D50  C7 03 46 F0 8B 02 00 99-F7 FB 89 46 F2 3B 7E F0   ..F........F.;~.
1817:1D60  75 05 C7 46 F4 01 00 B8-08 00 50 1E 8B 46 F2 BA   u..F......P..F..
1817:1D70  0C 00 F7 E2 05 B9 58 50-16 8D 46 F6 50 9A 03 00   ......XP..F.P...
1817:1D80  4C 2E 83 C4 0A 8B F0 8B-C6 0B C0 7D 16 8B C7 2B   L..........}...+
1817:1D90  46 F0 3D 01 00 7E 05 8B-46 F2 EB 03 8B 46 F0 8B   F.=..~..F....F..
1817:1DA0  F8 EB 14 8B C7 2B 46 F0-3D 01 00 7E 05 8B 46 F2   .....+F.=..~..F.
1817:1DB0  EB 02 8B C7 89 46 F0 0B-F6 74 09 83 7E F4 00 75   .....F...t..~..u
1817:1DC0  03 E9 8B FF 0B F6 74 33-9A 18 02 A2 1A B8 04 00   ......t3........
1817:1DD0  50 33 C0 50 9A F7 02 A2-1A 59 59 FF 76 0C FF 76   P3.P.....YY.v..v
1817:1DE0  0A 1E B8 9D 0E 50 9A 05-00 A8 2C 83 C4 08 B8 23   .....P.........#
1817:1DF0  00 50 9A E8 03 59 18 59-E9 ED 01 B8 D0 07 50 FF   .P.....Y......P.
1817:1E00  36 78 6E A1 7A 6E 50 8B-46 F2 BA 0C 00 F7 E2 8B   6xn.znP.F.......
1817:1E10  D8 81 C3 B9 58 1E 07 26-FF 77 08 8B 46 F2 BA 0C   ....X..&.w..F...
1817:1E20  00 F7 E2 8B D8 81 C3 B9-58 1E 07 26 8B 47 0A 50   ........X..&.G.P
1817:1E30  9A 0A 00 E2 2D 83 C4 0A-C4 1E 78 6E 8C 06 80 6E   ....-.....xn...n
1817:1E40  89 1E 7E 6E E9 6C 01 83-7E EA 1B 74 03 E9 C6 00   ..~n.l..~..t....
1817:1E50  C4 1E 7E 6E FF 06 7E 6E-26 8A 07 98 89 46 EA 3D   ..~n..~n&....F.=
1817:1E60  01 00 75 03 E9 81 01 83-7E EA 5B 74 03 E9 A3 00   ..u.....~.[t....
1817:1E70  C7 46 EE 00 00 EB 26 83-7E EA 01 75 03 E9 68 01   .F....&.~..u..h.
1817:1E80  83 7E EA 30 7C 17 83 7E-EA 39 7F 11 8B 46 EE BA   .~.0|..~.9...F..
1817:1E90  0A 00 F7 E2 03 46 EA 05-D0 FF 89 46 EE C4 1E 7E   .....F.....F...~
1817:1EA0  6E FF 06 7E 6E 26 8A 07-98 89 46 EA 3D 3B 00 75   n..~n&....F.=;.u
1817:1EB0  C6 FF 4E EE 7D 05 C7 46-EE 00 00 C7 46 EC 00 00   ..N.}..F....F...
1817:1EC0  EB 26 83 7E EA 01 75 03-E9 1D 01 83 7E EA 30 7C   .&.~..u.....~.0|
1817:1ED0  17 83 7E EA 39 7F 11 8B-46 EC BA 0A 00 F7 E2 03   ..~.9...F.......
1817:1EE0  46 EA 05 D0 FF 89 46 EC-C4 1E 7E 6E FF 06 7E 6E   F.....F...~n..~n
1817:1EF0  26 8A 07 98 89 46 EA 3D-48 00 75 C6 FF 4E EC 7D   &....F.=H.u..N.}
1817:1F00  05 C7 46 EC 00 00 FF 76-EE FF 76 EC 9A F7 02 A2   ..F....v..v.....
1817:1F10  1A 59 59 E9 9D 00 83 7E-EA 02 7C 34 83 7E EA 05   .YY....~..|4.~..
1817:1F20  7F 2E 16 8D 46 EE 50 16-8D 46 EC 50 9A AE 02 A2   ....F.P..F.P....
1817:1F30  1A 83 C4 08 8B 46 EC 8B-5E EA 4B D1 E3 89 87 21   .....F..^.K....!
1817:1F40  0C 8B 46 EE 8B 5E EA 4B-D1 E3 89 87 2B 0C EB 63   ..F..^.K....+..c
1817:1F50  C4 5E 06 26 FF 07 7D 16-8A 46 EA C4 5E 06 26 FF   .^.&..}..F..^.&.
1817:1F60  47 0C 26 C4 5F 0C 4B 26-88 07 B4 00 EB 11 FF 76   G.&._.K&.......v
1817:1F70  08 FF 76 06 FF 76 EA 9A-09 00 AA 2C 83 C4 06 83   ..v..v.....,....
1817:1F80  7E EA 0A 75 2E C4 5E 06-26 FF 07 7D 15 80 0D C4   ~..u..^.&..}....
1817:1F90  5E 06 26 FF 47 0C 26 C4-5F 0C 4B 26 88 07 B4 00   ^.&.G.&._.K&....
1817:1FA0  EB 11 FF 76 08 FF 76 06-80 0D 50 9A 09 00 AA 2C   ...v..v...P....,
1817:1FB0  83 C4 06 C4 1E 7E 6E FF-06 7E 6E 26 8A 07 98 89   .....~n..~n&....
1817:1FC0  46 EA 3D 01 00 74 03 E9-7D FE 16 8D 46 EE 50 16   F.=..t..}...F.P.
1817:1FD0  8D 46 EC 50 9A AE 02 A2-1A 83 C4 08 8B 46 EC A3   .F.P.........F..
1817:1FE0  21 0C 8B 46 EE A3 2B 0C-5F 5E 8B E5 5D CB 55 8B   !..F..+._^..].U.
1817:1FF0  EC 83 EC 12 56 57 39 26-98 0D 77 05 9A CF 09 17   ....VW9&..w.....
1817:2000  18 16 8D 46 F6 50 1E B8-5D 0E 50 B9 09 00 9A 04   ...F.P..].P.....
1817:2010  0A 17 18 33 FF EB 08 C4-5E 0A 26 8A 01 36 88 43   ...3....^.&..6.C
1817:2020  F6 47 83 FF 08 7D 12 C4-5E 0A 26 80 39 2E 74 09   .G...}..^.&.9.t.
1817:2030  C4 5E 0A 26 80 39 00 75-DE EB 06 36 C6 43 F6 20   .^.&.9.u...6.C.
1817:2040  47 83 FF 08 7C F5 C7 46-EE 00 00 8B 36 7C 6E 4E   G...|..F....6|nN
1817:2050  BF 01 00 C7 46 F0 00 00-EB 68 8B C6 03 46 EE 8B   ....F....h...F..
1817:2060  02 00 99 F7 F5 89 46 F2-3B 76 EE 75 05 C7 46 F0   ......F.;v.u..F.
1817:2070  01 00 B8 08 00 50 1E 8B-46 F2 BA 0C 00 F7 E2 05   .....P..F.......
1817:2080  B9 58 50 16 8D 46 F6 50-9A 03 00 4C 2E 83 C4 0A   .XP..F.P...L....
1817:2090  8B F8 8B C7 0B C0 7D 16-8B C6 2B 46 EE 3D 01 00   ......}...+F.=..
1817:20A0  7E 05 8B 46 F2 EB 03 8B-46 EE 8B F0 EB 14 8B C6   ~..F....F.......
1817:20B0  2B 46 EE 3D 01 00 7E 05-8B 46 F2 EB 02 8B C6 89   +F.=..~..F......
1817:20C0  46 EE 0B FF 74 09 83 7E-F0 00 75 03 E9 8B FF 0B   F...t..~..u.....
1817:20D0  FF 74 33 9A 18 02 A2 1A-B8 04 00 50 33 C0 50 9A   .t3........P3.P.
1817:20E0  F7 02 A2 1A 59 59 FF 76-0C FF 76 0A 1E B8 BD 0E   ....YY.v..v.....
1817:20F0  50 9A 05 00 A8 2C 83 C4-08 B8 23 00 50 9A E8 03   P.........#.P...
```

```
1817:2100  B9 18 59 E9 7D 00 B8 D0-07 50 FF 36 78 6E A1 7A  ..Y.}....P.6xn.z
1817:2110  6E 50 8B 46 F2 BA 0C 00-F7 E2 8B D8 81 C3 B9 58  nP.F...........X
1817:2120  1E 07 26 FF 77 08 8B 46-F2 BA 0C 00 F7 E2 85 D8  ..&.w..F........
1817:2130  81 C3 B9 58 1E 07 26 8B-47 0A 50 9A 0A 00 E2 2D  ...X..&.G.P....-
1817:2140  83 C4 0A C4 1E 78 6E 8C-06 80 6E E9 1E 7E 6E 33  .....xn...n..~n3
1817:2150  F6 EB 0A 8A 46 F5 C4 5E-06 26 88 00 46 C4 1E 7E  ....F..^.&..F..~
1817:2160  6E FF 06 7E 6E 26 8A 07-88 46 F5 3C 01 74 05 3B  n..~n&...F.<.t.;
1817:2170  76 0E 7C DF EB 08 C4 5E-06 26 C6 00 20 46 3B 76  v.|....^.&.. F;v
1817:2180  0E 7C F3 5F 5E 8B E5 5D-CB 55 8B EC 83 EC 16 56  .|._^..].U.....V
1817:2190  57 39 26 98 0D 77 05 9A-CF 09 17 18 16 8D 46 EE  W9&..w........F.
1817:21A0  50 1E E8 66 0E 50 B9 0D-00 9A 04 0A 17 18 33 C0  P..f.P........3.
1817:21B0  50 9A 39 04 A2 1A 59 C7-46 FC 00 00 1E 38 DD 0E  P.9...Y.F.......
1817:21C0  50 16 8D 46 EE 50 9A 1A-02 5C 2B 83 C4 08 89 56  P..F.P...\+....V
1817:21D0  EC 89 46 EA 0B D0 75 4F-FF 46 FC 8B 46 FC 3D 03  ..F...uO.F..F.=.
1817:21E0  00 7D 02 EB D7 B8 23 00-50 9A E8 03 B9 18 59 9A  .}....#.P.....Y.
1817:21F0  18 02 A2 1A 1E 88 DF 0E-50 9A 05 00 A8 2C 59 59  .........P....YY
1817:2200  1E B8 F5 0E 50 9A 05 00-A8 2C 59 59 1E B8 1A 0F  ....P....,YY....
1817:2210  50 9A 05 00 A8 2C 59 59-B8 18 00 50 9A 30 0E A2  P....,YY...P.0..
1817:2220  1A 59 EB FE E9 66 03 B8-D0 07 50 9A 00 00 14 2B  .Y...f....P....+
1817:2230  59 89 16 7A 6E A3 78 6E-0B D0 75 3F B8 23 00 50  Y..zn.xn..u?.#.P
1817:2240  9A E8 03 B9 18 59 9A 18-02 A2 1A 1E B8 2C 0F 50  .....Y........,.P
1817:2250  9A 05 00 A8 2C 59 59 1E-B8 43 0F 50 9A 05 00 A8  ....,YY..C.P....
1817:2260  2C 59 59 1E B8 66 0F 50-9A 05 00 A8 2C 59 59 B8  ,YY..f.P....,YY.
1817:2270  18 00 50 9A 30 0E A2 1A-59 EB FE C7 06 7C 6E 00  ..P.0...Y....|n.
1817:2280  00 C6 46 FF 61 E9 EF 02-33 F6 C4 1E 78 6E 8C 06  ..F.a...3...xn..
1817:2290  80 6E 99 1E 7E 6E 33 FF-1E 58 78 0F 50 1E A1 7C  .n..~n3...x.P..|
1817:22A0  6E BA 0C 00 F7 E2 05 B9-58 50 9A 08 00 87 2C 83  n.......XP.....,.
1817:22B0  C4 08 EB 1E 83 FF 08 7D-19 8A 46 FF 50 A1 7C 6E  .......}..F.P.|n
1817:22C0  BA 0C 00 F7 E2 8B D8 81-C3 B9 58 1E 07 58 26 83  ..........X..X&.
1817:22D0  01 47 C4 5E EA 26 FF 0F-7C 11 C4 5E EA 26 FF 47  .G.^.&..|..^.&.G
1817:22E0  0C 26 C4 5F 0C 4B 26 8A-07 EB 0D FF 76 EC FF 76  .&._.K&.....v..v
1817:22F0  EA 9A D9 00 8C 2B 59 59-E8 46 FF 3C FF 74 06 80  .....+YY.F.<.t..
1817:2300  7E FF 0A 75 AF 80 7E FF-FF 75 03 E9 69 02 E9 84  ~..u..~..u..i...
1817:2310  00 8A 46 FF C4 1E 7E 6E-26 88 07 46 FF 06 7E 6E  ..F...~n&..F..~n
1817:2320  81 FE D0 07 75 3F B8 23-00 50 9A E8 03 B9 18 59  ....u?.#.P.....Y
1817:2330  9A 18 02 A2 1A 1E 58 81-0F 50 9A 05 00 A8 2C 59  .........P....,Y
1817:2340  59 1E B8 98 0F 50 9A 05-00 A8 2C 59 59 1E 38 B1  Y....P....,YY...
1817:2350  0F 50 9A 05 00 A8 2C 59-59 B8 18 00 50 9A 30 0E  .P....,YY...P.0.
1817:2360  A2 1A 59 EB FE 80 7E FF-01 75 2A C4 5E EA 26 FF  ..Y...~..u*.^.&.
1817:2370  0F 7C 13 C4 5E EA 26 FF-47 0C 26 C4 5F 0C 4B 26  .|..^.&.G.&._.K&
1817:2380  8A 07 B4 00 EB 0D FF 76-EC FF 76 EA 9A D9 00 8C  .......v..v.....
1817:2390  2B 59 59 EB 30 C4 5E EA-26 FF 0F 7C 11 C4 5E EA  +YY.0.^.&..|..^.
1817:23A0  26 FF 47 0C 26 C4 5F 0C-4B 26 8A 07 EB 0D FF 76  &.G.&._.K&.....v
1817:23B0  EC FF 76 EA 9A D9 00 8C-2B 59 59 88 46 FF 3C FF  ..v.....+YY.F.<.
1817:23C0  74 03 E9 4C FF 80 7E FF-FF 75 03 E9 A9 01 8B C6  t..L..~..u......
1817:23D0  33 D2 52 50 9A 01 02 14-2B 59 59 52 50 A1 7C 6E  3.RP....+YYRP.|n
1817:23E0  BA 0C 00 F7 E2 8B D8 81-C3 B9 58 1E 07 58 5A 26  ..........X..XZ&
1817:23F0  89 57 0A 26 89 47 08 0B-D0 75 3F B8 23 00 50 9A  .W.&.G...u?.#.P.
1817:2400  E8 03 B9 18 59 9A 18 02-A2 1A 1E B8 C4 0F 50 9A  ....Y.........P.
1817:2410  05 00 A8 2C 59 59 1E B8-DB 0F 50 9A 05 00 A8 2C  ...,YY....P....,
1817:2420  59 59 1E B8 EB 0F 50 9A-05 00 A8 2C 59 59 B8 18  YY....P....,YY..
1817:2430  00 50 9A 30 0E A2 1A 59-EB FE 56 A1 7C 6E BA 0C  .P.0...Y..V.|n..
1817:2440  00 F7 E2 8B D8 81 C3 B9-58 1E 07 26 FF 77 08 A1  .........X..&.w..
1817:2450  7C 6E BA 0C 00 F7 E2 8B-D8 81 C3 B9 58 1E 07 26  |n..........X..&
1817:2460  8B 47 0A 50 FF 36 78 6E-A1 7A 6E 50 9A 0A 00 E2  .G.P.6xn.znP....
1817:2470  2D 83 C4 0A FF 06 7C 6E-A1 7C 6E 3D 01 00 7F 03  -.....|n.|n=....
1817:2480  E9 98 00 58 08 00 50 1E-A1 7C 6E 05 FE FF BA 0C  ......P..|n.....
1817:2490  00 F7 E2 05 B9 58 50 1E-A1 7C 6E 48 BA 0C 00 F7  .....XP..|nH....
1817:24A0  E2 05 B9 58 50 9A 03 00-4C 2E 83 C4 0A 0B C0 7D  ...XP...L......}
1817:24B0  6A B8 23 00 50 9A E8 03-B9 18 59 9A 18 02 A2 1A  j.#.P.....Y.....
1817:24C0  1E B8 FE 0F 50 9A 05 00-A8 2C 59 59 1E B8 15 10  ....P....,YY....
1817:24D0  50 9A 05 00 A8 2C 59 59-1E A1 7C 6E 05 FE FF BA  P....,YY..|n....
1817:24E0  0C 00 F7 E2 05 B9 58 50-1E A1 7C 6E 48 BA 0C 00  .......XP..|nH...
1817:24F0  F7 E2 05 B9 58 50 1E B8-39 10 50 9A 05 00 A8 2C  ....XP..9.P....,
1817:2500  83 C4 0C 1E B8 5C 10 50-9A 05 00 A8 2C 59 59 B8  .....\.P....,YY.
1817:2510  18 00 50 9A 30 0E A2 1A-59 EB FE 81 3E 7C 6E 2C  ..P.0...Y...>|n,
1817:2520  01 7E 54 B8 23 00 50 9A-E8 03 B9 18 59 9A 18 02  .~T.#.P.....Y...
1817:2530  A2 1A 1E B8 6F 10 50 9A-05 00 A8 2C 59 59 1E B8  ....o.P....,YY..
1817:2540  86 10 50 9A 05 00 A8 2C-59 59 B8 2C 01 50 FF 36  ..P....,YY.,.P.6
1817:2550  7C 6E 1E B8 AE 10 50 9A-05 00 A8 2C 83 C4 08 1E  |n....P....,....
1817:2560  B8 B5 10 50 9A 05 00 A8-2C 59 59 B8 18 00 50 9A  ...P....,YY...P.
```

```
1817:2570  30 0E A2 1A 59 EB FE 80-7E FF FF 74 03 E9 08 FD   O...Y...~..t....
1817:2580  FF 76 EC FF 76 EA 9A 28-15 A2 1A 59 59 5F 5E 8B   .v..v..(...YY_^.
1817:2590  E5 5D CB 55 8B EC 83 EC-04 56 57 39 26 98 0D 77   .].U.....VW9%..w
1817:25A0  05 9A CF 09 17 18 C7 06-FB 00 FF FF 1E B8 CE 10   ................
1817:25B0  50 1E B8 40 55 50 9A 08-00 87 2C 83 C4 08 1E B8   P..@UP....,.....
1817:25C0  D5 10 50 1E B8 18 56 50-9A 08 00 87 2C 83 C4 08   ..P...VP....,...
1817:25D0  1E B8 E0 10 50 9A 0A 00-D7 19 59 59 C7 06 C9 66   ....P.....YY...f
1817:25E0  02 00 E9 18 01 83 3E 4C-0C 00 74 07 C6 46 FD 30   ......>L..t..F.0
1817:25F0  E9 98 00 E9 80 00 33 C0-50 9A 39 04 A2 1A 59 80   ......3.P.9...Y.
1817:2600  3E 94 00 00 74 70 1E B8-E9 10 50 9A 0A 00 D7 19   >...tp....P.....
1817:2610  59 59 EB 09 33 C0 50 9A-39 04 A2 1A 59 BA 12 03   YY..3.P.9...Y...
1817:2620  EC A8 08 74 EF 9A 6A 02-6B 1C 8B F0 8B C6 0B C0   ...t....k.......
1817:2630  74 07 56 9A 07 00 72 1D-59 9A 98 00 A4 20 8B F0   t.V...r.Y.... ..
1817:2640  8B C6 0B C0 74 07 56 9A-07 00 72 1D 59 B8 01 00   ....t.V...r.Y...
1817:2650  50 B8 01 00 50 9A 0C 00-CF 20 59 59 8B F0 8B C6   P...P.... YY....
1817:2660  0B C0 74 07 56 9A 07 00-72 1D 59 C6 06 94 00 00   ..t.V...r.Y.....
1817:2670  B8 2B 00 E9 43 02 9A 70-06 A2 1A 3D 01 00 74 03   .+..C..p...=..t.
1817:2680  E9 73 FF 9A 40 08 A2 1A-88 46 FD 8A 46 FD 98 B9   .s..@....F..F...
1817:2690  0B 00 BB 14 01 2E 3B 07-74 06 43 43 E2 F7 EB 56   ......;.t.CC...V
1817:26A0  2E FF 67 16 08 00 30 00-31 00 32 00 33 00 34 00   ..g...0.1.2.3.4.
1817:26B0  35 00 36 00 37 00 38 00-39 00 40 01 46 01 46 01   5.6.7.8.9.@.F.F.
1817:26C0  46 01 46 01 46 01 46 01-46 01 46 01 46 01 46 01   F.F.F.F.F.F.F.F.
1817:26D0  B8 2B 00 E9 E3 01 8A 46-FD 98 05 D0 FF 3B 06 C9   .+.....F.....;..
1817:26E0  66 7E 07 9A A1 06 A2 1A-EB 13 8A 46 FD 98 05 D0   f~.........F....
1817:26F0  FF A3 FB 00 EB 07 9A A1-06 A2 1A EB 00 83 3E FB   ..............>.
1817:2700  00 FF 75 03 E9 DE FE A1-FB 00 0B C0 74 3C 3D 01   ..u.........t<=.
1817:2710  00 74 07 3D 02 00 74 1A-EB 30 B8 06 00 50 1E B8   .t.=..t..0...P..
1817:2720  F2 10 50 1E B8 40 55 50-9A EE 03 D7 19 83 C4 0A   ..P..@UP........
1817:2730  EB 30 B8 06 00 50 1E B8-F6 10 50 1E B8 40 55 50   .0...P....P..@UP
1817:2740  9A EE 03 D7 19 83 C4 0A-EB 18 B8 06 00 50 1E B8   .............P..
1817:2750  FA 10 50 1E B8 40 55 50-9A EE 03 D7 19 83 C4 0A   ..P..@UP........
1817:2760  EB 00 1E B8 00 11 50 1E-B8 18 56 50 9A 08 00 87   ......P...VP....
1817:2770  2C 83 C4 08 1E B8 02 11-50 9A 0A 00 D7 19 59 59   ,.......P.....YY
1817:2780  9A 6C 03 A2 1A 33 FF C6-46 FD 32 E9 01 01 9A 3B   .l...3..F.2....;
1817:2790  00 D7 19 83 3E 4C 0C 00-74 11 0B FF 75 06 C6 46   ....>L..t...u..F
1817:27A0  FD 31 EB 04 C6 46 FD 0D-E9 92 00 E9 7B 00 33 C0   .1...F......(.3.
1817:27B0  50 9A 39 04 A2 1A 59 80-3E 94 00 00 74 6B 1E B8   P.9...Y.>...tk..
1817:27C0  12 11 50 9A 0A 00 D7 19-59 59 EB 09 33 C0 50 9A   ..P.....YY..3.P.
1817:27D0  39 04 A2 1A 59 BA 12 03-EC A8 08 74 EF 9A 8A 02   9...Y......t....
1817:27E0  6B 1C 8B F0 8B C6 0B C0-74 07 56 9A 07 00 72 1D   k.......t.V...r.
1817:27F0  59 9A 98 00 A4 20 8B F0-8B C6 0B C0 74 07 56 9A   Y.... ......t.V.
1817:2800  07 00 72 1D 59 B8 01 00-50 B8 01 00 50 9A 0C 00   ..r.Y...P...P...
1817:2810  CF 20 59 59 8B F0 8B C6-0B C0 74 07 56 9A 07 00   . YY......t.V...
1817:2820  72 1D 59 B8 2B 00 E9 90-00 9A 70 06 A2 1A 0B C0   r.Y.+.....p.....
1817:2830  75 03 E9 79 FF 9A 40 08-A2 1A 88 46 FD 80 7E FD   u..y..@....F..~.
1817:2840  08 75 1F 0B FF 75 05 E9-5C FD EB 14 1E B8 1B 11   .u...u..\.......
1817:2850  50 1E B8 18 56 50 9A 08-00 87 2C 83 C4 08 33 FF   P...VP....,...3.
1817:2860  EB 2D 80 7E FD 20 7C 1C-80 7E FD 7E 7F 16 83 FF   .-.~. |..~.~....
1817:2870  0A 7D 0A 8A 46 FD 88 85-18 56 47 EB 05 9A A1 06   .}..F....VG.....
1817:2880  A2 1A EB 0B 80 7E FD 0D-74 05 9A A1 06 A2 1A 80   .....~..t.......
1817:2890  7E FD 0D 74 03 E9 F6 FE-0B FF 75 03 E9 EF FE 89   ~..t......u.....
1817:28A0  7E FE EB 0B 8B 5E FE C6-87 18 56 20 FF 46 FE 83   ~....^....V .F..
1817:28B0  7E FE 0A 7C EF 33 C0 EB-00 5F 5E 8B E5 5D CB 55   ~..|.3..._^..].U
1817:28C0  8B EC 83 EC 02 56 57 39-26 98 0D 77 05 9A CF 09   .....VW9%..w....
1817:28D0  17 18 8B 7E 06 8B 46 0C-99 52 50 CD 37 46 F6 CD   ...~..F..RP.7F..
1817:28E0  3D 83 C4 04 CD 38 36 63-11 9A C7 05 17 18 89 46   =....86c.......F
1817:28F0  FE 33 F6 E9 8F 00 FF 76-08 8B C7 03 C6 50 9A 59   .3.....v.....P.Y
1817:2900  10 A2 1A 59 59 8B 46 08-03 46 0C 50 8B C7 03 C6   ...YY.F..F.P....
1817:2910  50 9A 59 10 A2 1A 59 59-83 FE 04 7D 29 8B 46 08   P.Y...YY...}).F.
1817:2920  03 46 FE 50 8B C7 03 C6-50 9A 59 10 A2 1A 59 59   .F.P....P.Y...YY
1817:2930  8B 46 08 03 46 FE 05 05-00 50 8B C7 03 C6 50 9A   .F..F....P....P.
1817:2940  59 10 A2 1A 59 59 3B 76-0C 7F 39 8B 46 08 03 C6   Y...YY;v..9.F...
1817:2950  50 8B C7 03 46 0A 50 9A-59 10 A2 1A 59 59 8B 46   P...F.P.Y...YY.F
1817:2960  08 03 C6 50 3B 76 FE 7C-0A 8B 46 FE 05 05 00 3B   ...P;v.|..F....;
1817:2970  C6 7D 04 8B C7 EB 05 8B-C7 05 04 00 50 9A 59 10   .}..........P.Y.
1817:2980  A2 1A 59 59 46 3B 76 0A-7D 03 E9 69 FF 5F 5E 8B   ..YYF;v.}..i._^.
1817:2990  E5 5D CB 55 8B EC 83 EC-02 56 39 26 98 0D 77 05   .].U.....V9%..w.
1817:29A0  9A CF 09 17 18 8B 76 06-9A 6C 03 A2 1A C7 06 09   ......v..l......
1817:29B0  01 00 00 C7 06 03 01 00-00 E9 A8 00 83 FE 01 74   ...............t
1817:29C0  1B B8 01 00 50 9A 36 03-A2 1A 59 FF 36 09 01 1E   ....P.6...Y.6...
1817:29D0  B8 6B 11 50 9A 05 00 A8-2C 83 C4 06 B8 01 00 50   .k.P....,......P
```

```
1817:29E0  9A 21 00 6B 1C 59 C7 06-F9 00 00 00 E8 28 9A 70   .!.k.Y.......(.p
1817:29F0  06 A2 1A 0B C0 74 1F 9A-CE 05 A2 1A 58 46 FF C7   .....t.......F..
1817:2A00  06 F9 00 01 00 80 7E FF-08 75 08 A1 09 01 F7 D8   ......~..u......
1817:2A10  A3 09 01 E9 70 00 BA 12-03 EC A8 04 75 07 83 3E   ....p.......u..>
1817:2A20  4C 0C 00 74 C9 EB 00 BA-12 03 EC A8 08 75 07 83   L..t.........u..
1817:2A30  3E 4C 0C 00 74 F1 C7 06-F9 00 01 00 FF 06 09 01   >L..t...........
1817:2A40  83 FE 01 74 1B B8 01 00-50 9A 36 03 A2 1A 59 FF   ...t....P.6...Y.
1817:2A50  36 09 01 1E B8 71 11 50-9A 05 00 A8 2C 83 C4 06   6....q.P...,....
1817:2A60  FF 06 03 01 A1 03 01 3B-C6 7D 0A 83 3E 4C 0C 00   .......;.}..>L..
1817:2A70  75 03 E9 47 FF 83 3E 4C-0C 01 75 0A 83 3E 03 01   u..G..>L..u..>..
1817:2A80  08 7D 03 E9 36 FF 9A A1-06 A2 1A A1 09 01 EB 00   .}..6...........
1817:2A90  5E 8B E5 5D CB 55 8B EC-83 EC 10 39 26 98 0D 77   ^..].U.....9&..w
1817:2AA0  05 9A CF 09 17 18 C6 46-F1 01 C6 46 F5 FF 16 8D   .......F...F....
1817:2AB0  46 F0 50 16 8D 46 F0 50-B8 10 00 50 9A 03 00 D5   F.P..F.P...P....
1817:2AC0  2D 83 C4 0A 8B E5 5D CB-55 8B EC 83 EC 10 39 26   -.....].U.....9&
1817:2AD0  98 0D 77 05 9A CF 09 17-18 C7 46 F0 00 06 C6 46   ..w.......F....F
1817:2AE0  F3 00 C7 46 F4 00 00 C7-46 F6 4F 18 16 8D 46 F0   ...F....F.O...F.
1817:2AF0  50 16 8D 46 F0 50 B8 10-00 50 9A 03 00 D5 2D 83   P..F.P...P....-.
1817:2B00  C4 0A 33 C0 50 33 C0 50-9A F7 02 A2 1A 59 59 8B   ..3.P3.P.....YY.
1817:2B10  E5 5D CB 55 8B EC 83 EC-10 39 26 98 0D 77 05 9A   .].U.....9&..w..
1817:2B20  CF 09 17 18 C7 46 F0 00-06 C6 46 F3 00 C7 46 F4   .....F....F...F.
1817:2B30  00 02 C7 46 F6 4F 18 16-8D 46 F0 50 16 8D 46 F0   ...F.O...F.P..F.
1817:2B40  50 B8 10 00 50 9A 03 00-D5 2D 83 C4 0A 33 C0 50   P...P....-...3.P
1817:2B50  33 C0 50 9A F7 02 A2 1A-59 59 8B E5 5D CB 55 8B   3.P.....YY..].U.
1817:2B60  EC 83 EC 10 39 26 98 0D-77 05 9A CF 09 17 18 C6   ....9&..w.......
1817:2B70  46 F1 03 C6 46 F3 00 16-8D 46 F0 50 16 8D 46 F0   F...F....F.P..F.
1817:2B80  50 B8 10 00 50 9A 03 00-D5 2D 83 C4 0A 8A 46 F7   P...P....-....F.
1817:2B90  B4 00 C4 5E 0A 26 89 07-8A 46 F6 B4 00 C4 5E 06   ...^.&...F....^.
1817:2BA0  26 89 07 8B E5 5D CB 55-8B EC 83 EC 10 39 26 98   &....].U.....9&.
1817:2BB0  0D 77 05 9A CF 09 17 18-C6 46 F1 02 C6 46 F3 00   .w.......F...F..
1817:2BC0  8A 46 06 88 46 F6 8A 46-08 88 46 F7 16 8D 46 F0   .F..F..F..F...F.
1817:2BD0  50 16 8D 46 F0 50 B8 10-00 50 9A 03 00 D5 2D 83   P..F.P...P....-.
1817:2BE0  C4 0A 8B E5 5D CB 55 8B-EC 56 39 26 98 0D 77 05   ....].U..V9&..w.
1817:2BF0  9A CF 09 17 18 8B 76 06-0B F6 7C 05 83 FE 04 7E   ......v...|....^
1817:2C00  02 33 F6 8B DE D1 E3 FF-B7 2B 0C 8B DE D1 E3 FF   .3.......+......
1817:2C10  B7 21 0C 0E E8 90 FF 59-59 5E 5D CB 39 26 98 0D   .!.....YY^].9&..
1817:2C20  77 05 9A CF 09 17 18 EB-05 9A CE 05 A2 1A 9A 70   w..............P
1817:2C30  06 A2 1A 0B C0 75 F2 CB-39 26 98 0D 77 05 9A CF   .....u..9&..w...
1817:2C40  09 17 18 33 C0 50 9A 39-04 A2 1A 59 9A FE 03 A2   ...3.P.9...Y....
1817:2C50  1A EB 00 CB 55 8B EC 83-EC 08 39 26 98 0D 77 05   ....U.....9&..w.
1817:2C60  9A CF 09 17 18 16 8D 46-F8 50 9A 46 00 3F 2E 59   .......F.P.F.?.Y
1817:2C70  59 16 8D 46 F8 50 9A 35-02 8C 2D 59 59 89 56 FE   Y..F.P.5..-YY.V.
1817:2C80  89 46 FC C4 5E FC 26 8A-47 06 C4 5E 06 26 88 07   .F..^.&.G..^.&..
1817:2C90  C4 5E FC 26 8A 47 08 C4-5E 0A 26 88 07 C4 5E FC   .^.&.G..^.&...^.
1817:2CA0  26 8A 47 0A C4 5E 0E 26-88 07 8B E5 5D CB 55 8B   &.G..^.&....].U.
1817:2CB0  EC 83 EC 08 39 26 98 0D-77 05 9A CF 09 17 18 16   ....9&..w.......
1817:2CC0  8D 46 F8 50 9A 46 00 3F-2E 59 59 16 8D 46 F8 50   .F.P.F.?.YY..F.P
1817:2CD0  9A 35 02 8C 2D 59 59 89-56 FE 89 46 FC C4 5E FC   .5..-YY.V..F..^.
1817:2CE0  26 8B 07 EB 00 8B E5 5D-CB 55 8B EC 83 EC 4C 56   &......].U....LV
1817:2CF0  57 39 26 98 0D 77 05 9A-CF 09 17 18 16 8D 46 BC   W9&..w.........F.
1817:2D00  50 1E B8 26 11 50 B9 15-00 9A 04 0A 17 18 16 8D   P..&.P..........
1817:2D10  46 D2 50 1E B8 3B 11 50-B9 24 00 9A 04 0A 17 18   F.P..;.P.$......
1817:2D20  16 8D 46 B4 50 9A 46 00-3F 2E 59 59 16 8D 46 B4   ..F.P.F.?.YY..F.
1817:2D30  50 9A 35 02 8C 2D 59 59-89 56 BA 89 46 B8 C4 5E   P.5..-YY.V..F..^
1817:2D40  B8 26 8B 07 89 46 FA A1-B7 58 3B 46 FA 75 09 83   .&...F...X;F.u..
1817:2D50  7E 06 01 74 03 E9 20 01-16 8D 46 FE 50 16 8D 46   ~..t.. ...F.P..F
1817:2D60  FC 50 0E E8 F8 FD 83 C4-08 33 FF A1 B7 58 3B 46   .P.......3...X;F
1817:2D70  FA 74 16 8B 7E FA 3B 3E-B7 58 7D 03 83 C7 3C 2B   .t..~.;>.X}...<+
1817:2D80  3E B7 58 8B 46 FA A3 B7-58 C4 5E B8 26 83 7F 04   >.X.F...X.^.&...
1817:2D90  0C 7D 0A 8C 5E F8 C7 46-F6 77 11 EB 08 8C 5E F8   .}..^..F.w....^.
1817:2DA0  C7 46 F6 7A 11 C4 5E B8-26 8B 77 04 83 FE 0C 7E   .F.z..^.&.w....~
1817:2DB0  07 BB C6 05 F4 FF EB F0-0B F6 75 03 BE 0C 00 33   ............u...3
1817:2DC0  C0 50 33 C0 50 0E E8 DE-FD 59 59 FF 76 F8 FF 76   .P3.P....YY.v..v
1817:2DD0  F6 C4 5E B8 26 FF 77 02-56 C4 5E B8 26 8B 47 0A   ..^.&.w.V.^.&.G.
1817:2DE0  05 6C 07 50 16 C4 5E B8-26 8B 47 08 BA 03 00 F7   .l.P..^.&.G.....
1817:2DF0  E2 8D 56 D2 03 C2 50 C4-5E B8 26 FF 77 06 16 C4   ..V...P.^.&.w...
1817:2E00  5E B8 26 8B 47 0C BA 03-00 F7 E2 8D 56 BC 03 C2   ^.&.G.......V...
1817:2E10  50 1E B8 7D 11 50 9A 05-00 A8 2C 83 C4 18 A1 05   P..}.P...,......
1817:2E20  01 0B 06 07 01 74 45 29-3E 07 01 83 3E 07 01 00   .....tE)>...>...
1817:2E30  7D 09 83 06 07 01 3C FF-0E 05 01 83 3E 05 01 00   }.....<.....>...
1817:2E40  7D 08 33 C0 A3 07 01 A3-05 01 B8 03 00 50 33 C0   }.3..........P3.
```

```
1817:2E50  50 0E E8 52 FD 59 59 FF-36 07 01 FF 36 05 01 1E   P..R.YY.6...6...
1817:2E60  B8 9E 11 50 9A 05 00 A8-2C 83 C4 08 FF 76 FE FF   ...P....,....v..
1817:2E70  76 FC 0E E8 31 FD 59 59-5F 5E 8B E5 5D CB 56 57   v...1.YY_^..].VW
1817:2E80  39 26 98 0D 77 05 9A CF-09 17 18 EB 0D 9A FC 0D   9%..w...........
1817:2E90  A2 1A 33 C0 50 0E E8 50-FE 59 9A 70 06 A2 1A 0B   ..3.P..P.Y.p....
1817:2EA0  C0 74 EA A1 F1 00 3B 06-F3 00 75 07 9A 06 00 7E   .t....;...u....~
1817:2EB0  2D E8 18 8B 1E F3 00 D1-E3 8B 5F 22 48 8B 36 F3   -..........."H.6.
1817:2EC0  00 46 81 E6 0F 00 89 36-F3 00 8B C7 EB 00 5F 5E   .F.....6......_^
1817:2ED0  CB 55 8B EC 83 EC 02 39-26 98 0D 77 05 9A CF 09   .U.....9%..w....
1817:2EE0  17 18 0E E8 98 FF 89 46-FE 3D FF FF 74 29 FF 06   .......F.=..t)..
1817:2EF0  32 3F 7D 13 8A 46 FE FF-06 3E 3F C4 1E 3E 3F 4B   2?}..F...>?..>?K
1817:2F00  26 88 07 B4 00 E8 10 1E-B8 32 3F 50 FF 76 FE 9A   &........2?P.v..
1817:2F10  09 00 AA 2C 83 C4 06 8B-46 FE EB 00 8B E5 5D CB   ...,....F.....].
1817:2F20  39 26 98 0D 77 05 9A CF-09 17 18 9A FC 0D A2 1A   9%..w...........
1817:2F30  A1 F1 00 3B 06 F3 00 74-05 B8 01 00 EB 12 9A 04   ...;...t........
1817:2F40  00 E2 2D 0B C0 75 04 33-C0 E8 03 B8 01 00 EB 00   ..-..u.3........
1817:2F50  CB 39 26 98 0D 77 05 9A-CF 09 17 18 C7 06 4C 0D   .9%..w........L.
1817:2F60  96 00 C7 06 4E 0D 05 00-C7 06 50 0D 01 00 EB 08   ....N.....P.....
1817:2F70  33 C0 50 0E E8 72 FD 59-83 3E 4C 0D 00 75 F1 C7   3.P..r.Y.>L..u..
1817:2F80  06 32 0D 32 00 E8 00 83-3E 32 0D 00 75 F9 CB 56   .2.2....>2..u..V
1817:2F90  39 26 98 0D 77 05 9A CF-09 17 18 33 F6 EB 3F C7   9%..w......3..?.
1817:2FA0  06 4C 0D 96 00 C7 06 4E-0D 30 00 C7 06 50 0D 01   .L.....N.0...P..
1817:2FB0  00 EB 14 A1 4C 0D 8B 04-00 99 F7 FB 05 08 00 A3   ....L...........
1817:2FC0  4E 0D A0 4E 0D E6 42 83-3E 4C 0D 00 75 E5 C7 06   N..N..B.>L..u...
1817:2FD0  32 0D 1E 00 EB 00 83 3E-32 0D 00 75 F9 46 83 FE   2......>2..u.F..
1817:2FE0  03 7C 8C 5E CB 55 8B EC-56 57 39 26 98 0D 77 05   .!.^.U..VW9%..w.
1817:2FF0  9A CF 09 17 18 8B 7E 06-33 F6 EB 53 C7 06 4C 0D   ......~.3..S..L.
1817:3000  50 00 C7 06 4E 0D 04 00-C7 06 50 0D 01 00 EB 14   P...N.....P.....
1817:3010  83 FF 01 75 0F 0E E8 07-FF 3D 01 00 75 06 0E E8   ...u.....=..u...
1817:3020  5C FE EB 41 83 3E 4C 0D-00 75 E5 C7 06 32 0D 50   \..A.>L..u...2.P
1817:3030  00 EB 14 83 FF 01 75 0F-0E E8 E4 FE 3D 01 00 75   ......u.....=..u
1817:3040  06 0E E8 39 FE EB 1E 83-3E 32 0D 00 75 E5 46 83   ...9....>2..u.F.
1817:3050  FE 0A 7C A8 83 FF 01 75-0C 83 3E 4C 0C 01 74 05   ..!....u..>L..t.
1817:3060  9A 40 08 A2 1A 5F 5E 5D-CB 55 8B EC 56 39 26 98   .@..._^].U..V9%.
1817:3070  0D 77 05 9A CF 09 17 18-0E E8 A0 FB 33 F6 EB 1A   .w..........3...
1817:3080  0E E8 CD FE 83 7E 06 01-75 0F 0E E8 92 FE 3D 01   .....~..u.....=.
1817:3090  00 75 06 0E E8 E7 FD EB-18 46 83 FE 03 7C E1 83   .u.......F...!..
1817:30A0  7E 06 01 75 0C 83 3E 4C-0C 01 74 05 9A 40 08 A2   ~..u..>L..t..@..
1817:30B0  1A 5E 5D CB 39 26 98 0D-77 05 9A CF 09 17 18 0E   .^].9%..w.......
1817:30C0  E8 8E FE CB 39 26 98 0D-77 05 9A CF 09 17 18 0E   ....9%..w.......
1817:30D0  E8 7E FE 0E E8 7A FE CB-39 26 98 0D 77 05 9A CF   .~...z..9%..w...
1817:30E0  09 17 18 0E E8 6A FE 0E-E8 66 FE 0E E8 62 FE CB   .....j...f...b..
1817:30F0  39 26 98 0D 77 05 9A CF-09 17 18 E8 08 33 C0 50   9%..w........3.P
1817:3100  0E E8 E5 FB 59 0E E8 17-FE 0B C0 74 F0 0E E8 6D   ....Y......t...m
1817:3110  FD E8 00 CB 39 26 98 0D-77 05 9A CF 09 17 18 0E   ....9%..w.......
1817:3120  E8 F9 FA E8 00 0E E8 C7-FF 3C 0D 75 F8 CB 55 8B   .........<.u..U.
1817:3130  EC 39 26 98 0D 77 05 9A-CF 09 17 18 EB 5E 06 D1   .9%..w.......^..
1817:3140  E3 8B 87 0D 6E 8A 1C 00-F7 E2 05 0D 01 8C DA 05   ....n...........
1817:3150  0A 00 EB 00 5D CB 55 8B-EC 83 EC 04 56 57 39 26   ....].U.....VW9%
1817:3160  98 0D 77 05 9A CF 09 17-18 33 FF BE 01 00 C6 46   ..w......3.....F
1817:3170  FF 61 C7 46 FC 00 00 E9-92 00 0E E8 00 FD 8B 46   .a.F...........F
1817:3180  FF 3C 0D 74 1D 80 7E FF-30 7C 06 80 7E FF 39 7E   .<.t..~.0!..~.9~
1817:3190  11 33 F6 80 7E FF 08 75-07 0B FF 75 03 BE 02 00   .3..~..u...u....
1817:31A0  EB 5A 80 7E FF 0D 74 4D-FF 06 32 3F 7D 13 8A 46   .Z.~..tM..2?}..F
1817:31B0  FF FF 06 3E 3F C4 1E 3E-3F 4B 26 88 07 B4 00 E8   ...>?..>?K&.....
1817:31C0  10 1E B8 32 3F 50 FF 76-FF 9A 09 00 AA 2C 83 C4   ...2?P.v.....,..
1817:31D0  06 47 8B C7 3D 05 00 7E-04 33 F6 EB 16 8B 46 FC   .G..=..~.3....F.
1817:31E0  BA 0A 00 F7 E2 50 8A 46-FF 98 5A 03 D0 83 C2 D0   .....P.F..Z.....
1817:31F0  89 56 FC EB 07 0B FF 75-03 BE 03 00 80 7E FF 0D   .V.....u.....~..
1817:3200  74 03 83 FE 01 75 03 E9-70 FF 83 FE 01 75 09 8B   t....u..p....u..
1817:3210  46 FC C4 5E 06 26 89 07-8B C6 EB 00 5F 5E 8B E5   F..^.&......_^..
1817:3220  5D CB 55 8B EC 83 EC 1A-56 57 39 26 98 0D 77 05   ].U.....VW9%..w.
1817:3230  9A CF 09 17 18 33 FF BE-01 00 C6 46 EF 61 C7 46   .....3.....F.a.F
1817:3240  F6 00 00 C7 46 F4 00 00-C7 46 F2 00 00 C7 46 F0   ....F....F....F.
1817:3250  00 00 C7 46 FE F0 3F C7-46 FC 00 00 C7 46 FA 00   ...F..?.F....F..
1817:3260  00 C7 46 F8 00 00 83 7E-06 02 74 03 E9 12 01 E9   ..F....~..t.....
1817:3270  F9 00 0E E8 08 FC 88 46-EF 3C 0D 74 34 80 7E EF   .......F.<.t4.~.
1817:3280  30 7C 06 80 7E EF 39 7E-28 80 7E EF 2E 74 22 08   0!..~.9~(.~..t".
1817:3290  FF 75 0C 80 7E EF 2B 74-12 80 7E EF 2D 74 12 33   .u..~.+t..~.-t.3
1817:32A0  F6 80 7E EF 08 75 07 0B-FF 75 03 BE 02 00 E9 8A   ..~..u...u......
1817:32B0  00 80 7E EF 30 7C 62 80-7E EF 39 7F 5C FF 06 32   ..~.0!b.~.9.\..2
```

```
1817:32C0  3F 7D 13 8A 46 EF FF 06-3E 3F C4 1E 3E 3F 4B 26   ?}..F...>?..>?K&
1817:32D0  88 07 B4 00 EB 10 1E B8-32 3F 50 FF 76 EF 9A 09   ........2?P.v...
1817:32E0  00 AA 2C 83 C4 06 47 8B-C7 3D 07 00 7E 04 33 F6   ......G..=..~.3.
1817:32F0  EB 25 CD 39 46 F0 CD 38-0E A7 11 8A 46 EF 98 05   .%.9F..8....F...
1817:3300  D0 FF 99 52 50 CD 37 46-DE CD 3D 83 C4 04 CD 3A   ...RP.7F..=....:
1817:3310  C1 CD 39 5E F0 CD 3D EB-52 80 7E EF 0D 75 09 0B   ..9^..=.R.~..u..
1817:3320  FF 75 03 BE 03 00 EB 43-FF 06 32 3F 7D 13 8A 46   .u.....C..2?}..F
1817:3330  EF FF 06 3E 3F C4 1E 3E-3F 4B 26 88 07 B4 00 EB   ...>?..>?K&.....
1817:3340  10 1E B8 32 3F 50 FF 76-EF 9A 09 00 AA 2C 83 C4   ...2?P.v.....,..
1817:3350  06 80 7E EF 2D 75 14 C7-46 FE F0 BF C7 46 FC 00   ..~.-u..F....F..
1817:3360  00 C7 46 FA 00 00 C7 46-F8 00 00 80 7E EF 0D 74   ..F....F....~..t
1817:3370  0E 83 FE 01 75 09 80 7E-EF 2E 74 03 E9 F3 FE EB   ....u..~..t.....
1817:3380  2D C6 46 EF 2E FF 06 32-3F 7D 13 8A 46 EF FF 06   -.F....2?}..F...
1817:3390  3E 3F C4 1E 3E 3F 4B 26-88 07 B4 00 EB 10 1E B8   >?..>?K&........
1817:33A0  32 3F 50 FF 76 EF 9A 09-00 AA 2C 83 C4 06 80 7E   2?P.v.....,....~
1817:33B0  EF 2E 74 03 E9 52 00 C7-46 EC 99 3F C7 46 EA 99   ..t.....F..?.F..
1817:33C0  99 C7 46 E8 99 99 C7 46-E6 9A 99 E9 8D 00 0E E8   ..F....F........
1817:33D0  AC FA 88 46 EF 3C 0D 74-11 80 7E EF 30 7C 06 80   ...F.<.t..~.0|..
1817:33E0  7E EF 39 7E 05 33 F6 E9-71 00 80 7E EF 30 7C 6B   ~.9~.3..q..~.0|k
1817:33F0  80 7E EF 39 7F 65 FF 06-32 3F 7D 13 8A 46 EF FF   .~.9.e..2?}..F..
1817:3400  06 3E 3F C4 1E 3E 3F 4B-26 88 07 B4 00 EB 10 1E   .>?..>?K&.......
1817:3410  B8 32 3F 50 FF 76 EF 9A-09 00 AA 2C 83 C4 06 47   .2?P.v.....,...G
1817:3420  8B C7 3D 07 00 7E 04 33-F6 EB 30 8A 46 EF 98 05   ..=..~.3..0.F...
1817:3430  D0 FF 99 52 50 CD 37 46-DE CD 3D 83 C4 04 CD 38   ...RP.7F..=....8
1817:3440  4E E6 CD 38 46 F0 CD 39-5E F0 CD 3D CD 39 46 E6   N..8F..9^..=.9F.
1817:3450  CD 38 36 A7 11 CD 39 5E-E6 CD 3D 80 7E EF 0D 74   .86...9^..=.~..t
1817:3460  08 83 FE 01 75 03 E9 65-FF 0B FF 75 07 83 FE 01   ....u..e...u....
1817:3470  75 02 33 F6 83 FE 01 75-11 CD 39 46 F8 CD 38 4E   u.3....u..9F..8N
1817:3480  F0 C4 5E 08 CD 3C DD 1F-CD 3D 8B C6 EB 00 5F 5E   ..^..<...=...._^
1817:3490  8B E5 5D CB 39 26 98 0D-77 05 9A CF 09 17 18 81   ..].9&..w.......
1817:34A0  26 7C 49 F0 00 A0 7C 49-BA 05 03 EE CB 55 8B EC   &|I...|I.....U..
1817:34B0  56 39 26 98 0D 77 05 9A-CF 09 17 18 8B 46 06 3D   V9&..w.......F.=
1817:34C0  05 00 77 28 8B D8 D1 E3-2E FF A7 1D 0C 29 0C 33   ..w(.........).3
1817:34D0  0C 2E 0C 38 0C 38 0C 3C-0C BE 08 00 EB 13 BE 02   ...8.8.<........
1817:34E0  00 EB 0E BE 04 00 EB 09-33 F6 EB 05 BE 01 00 EB   ........3.......
1817:34F0  00 81 26 7C 49 F0 00 09-36 7C 49 A0 7C 49 BA 05   ..&|I...6|I.|I..
1817:3500  03 EE 5E 5D CB 55 8B EC-56 39 26 98 0D 77 05 9A   ..^].U..V9&..w..
1817:3510  CF 09 17 18 8B 46 06 3D-05 00 77 1F 8B D8 D1 E3   .....F.=..w.....
1817:3520  2E FF A7 75 0C 81 0C 81-0C 81 0C 86 0C 89 0C 81   ...u............
1817:3530  0C BE 02 00 EB 0A BE 04-00 EB 05 BE 06 00 EB 00   ................
1817:3540  56 9A D7 0D A2 1A 59 5E-5D CB 55 8B EC 56 39 26   V.....Y^].U..V9&
1817:3550  98 0D 77 05 9A CF 09 17-18 8B 46 06 3D 05 00 77   ..w.......F.=..w
1817:3560  2E 8B D8 D1 E3 2E FF A7-BA 0C C6 0C D0 0C CB 0C   ................
1817:3570  D5 0C DA 0C DF 0C BE 06-00 EB 19 BE 06 00 EB 14   ................
1817:3580  BE 06 00 EB 0F BE 04 00-EB 0A BE 05 00 EB 05 BE   ................
1817:3590  06 00 EB 00 56 9A 21 00-6B 1C 59 5E 5D CB 55 8B   ....V.!.k.Y^].U.
1817:35A0  EC 83 EC 02 56 57 39 26-98 0D 77 05 9A CF 09 17   ....VW9&..w.....
1817:35B0  18 C7 46 FE FF FF B0 34-BA 03 03 EE B0 FF BA 00   ..F....4........
1817:35C0  03 EE B0 FF BA 00 03 EE-FA 81 0E 78 49 08 00 A0   ...........xI...
1817:35D0  78 49 BA 04 03 EE FB 33-F6 C4 5E 06 26 C7 47 02   xI.....3..^.&.G.
1817:35E0  00 00 26 C7 07 00 00 EB-20 BA 06 03 EC A8 01 74   ..&..... ......t
1817:35F0  02 EB 33 BA 06 03 EC A8-04 75 02 EB 24 C4 5E 06   ..3......u..$.^.
1817:3600  26 83 07 01 26 83 57 02-00 C4 5E 06 26 83 7F 02   &...&.W...^.&...
1817:3610  00 7C 06 75 07 26 81 3F-30 75 72 CD 8E 0F 00 EB   .|.u.&.?0ur.....
1817:3620  4D BE 10 00 EB 48 BA 00-03 EC B4 00 8B F8 BA 00   M....H..........
1817:3630  03 EC 84 00 B1 08 D3 E0-03 F8 8B 46 FE 33 C7 33   ...........F.3.3
1817:3640  D2 C4 5E 06 26 89 57 02-26 89 07 8A 06 03 EC A8   ..^.&.W.&.......
1817:3650  02 75 1B C4 5E 06 26 8B-57 02 26 8B 07 F7 DA F7   .u..^.&.W.&.....
1817:3660  D8 83 DA 00 C4 5E 06 26-89 57 02 26 89 07 FA 81   ......^.&.W.&...
1817:3670  26 78 49 F7 00 A0 78 49-BA 04 03 EE FB 8B C6 EB   &xI...xI........
1817:3680  00 5F 5E 8B E5 5D CB 55-8B EC 39 26 98 0D 77 05   ._^..].U..9&..w.
1817:3690  9A CF 09 17 18 FA A1 78-49 25 F8 00 0B 46 06 A3   .......xI%...F..
1817:36A0  78 49 A0 78 49 BA 04 03-EE FB 5D CB 56 39 26 98   xI.xI.....].V9&.
1817:36B0  0D 77 05 9A CF 09 17 18-83 3E 4A 0D 00 74 1F B8   .w.......>J..t..
1817:36C0  30 00 50 9A 30 0E A2 1A-59 8B F0 8B C6 0B C0 74   0.P.0...Y......t
1817:36D0  07 56 9A 07 00 72 1D 59-C7 06 4A 0D 00 00 5E CB   .V...r.Y..J...^.
1817:36E0  55 8B EC 83 EC 06 56 57-39 26 98 0D 77 05 9A CF   U.....VW9&..w...
1817:36F0  09 17 18 16 8D 46 FC 50-1E B8 5F 11 50 B9 04 00   .....F.P.._.P...
1817:3700  9A 04 0A 17 18 B0 0D 50-9A 73 0F A2 1A 59 8B F0   .......P.s...Y..
1817:3710  8B C6 0B C0 74 05 8B C6-E9 02 01 33 FF EB 18 36   ....t......3...6
1817:3720  FF 73 FC 9A 73 0F A2 1A-59 8B F0 8B C6 0B C0 74   .s..s...Y......t
```

```
1817:3730  05 8B C6 E9 E7 00 47 83-FF 04 7C E3 33 FF EB 18   ......G...|.3...
1817:3740  FF 55 47 0C 9A 73 0F A2-1A 59 8B F0 8B C6 0B C0   ..G..s...Y......
1817:3750  74 05 8B C6 E9 C6 00 47-83 FF 05 7C E3 B0 0D 50   t......G...|...P
1817:3760  9A 73 0F A2 1A 59 8B F0-8B C6 0B C0 74 05 8B C6   .s...Y......t...
1817:3770  E9 AA 00 B0 0A 50 9A 73-0F A2 1A 59 8B F0 8B C6   .....P.s...Y....
1817:3780  0B C0 74 05 8B C6 E9 94-00 C7 46 FA 00 00 EB 5E   ..t.......F....^
1817:3790  33 FF EB 13 57 FF 76 FA-9A F5 0F A2 1A 59 59 3D   3...W.v.......YY=
1817:37A0  20 00 74 02 EB 08 47 3B-7E 06 7C E8 EB 3D 33 FF    .t...G;~.|..=3.
1817:37B0  EB 1F 57 FF 76 FA 9A F5-0F A2 1A 59 59 50 9A 73   ..W.v......YYP.s
1817:37C0  0F A2 1A 59 8B F0 8B C6-0B C0 74 04 8B C6 EB 4D   ...Y......t....M
1817:37D0  47 3B 7E 06 7C DC B0 0A-50 9A 73 0F A2 1A 59 8B   G;~.|...P.s...Y.
1817:37E0  F0 8B C6 0B C0 74 04 8B-C6 EB 32 FF 46 FA 83 7E   .....t....2.F..~
1817:37F0  FA 10 7C 9C C7 46 FA 01-00 EB 18 B0 0D 50 9A 73   ..|..F.......P.s
1817:3800  0F A2 1A 59 8B F0 8B C6-0B C0 74 04 8B C6 EB 0D   ...Y......t.....
1817:3810  FF 46 FA 83 7E FA 01 7E-E2 33 C0 E5 00 5F 5E 8B   .F..~..~.3..._^.
1817:3820  E5 5D CB 55 8B EC 83 EC-10 56 39 26 98 0D 77 05   .].U.....V9%..w.
1817:3830  9A CF 09 17 18 33 F6 EB-28 C6 46 F1 02 C7 46 F6   .....3..(.F...F.
1817:3840  00 00 16 8D 46 F0 50 16-8D 46 F0 50 B8 17 00 50   ....F.P..F.P...P
1817:3850  9A 03 00 D5 2D 83 C4 0A-F6 46 F1 80 74 02 EB 0C   ....-....F..t...
1817:3860  46 81 FE 30 75 7C D2 B8-09 00 EB 34 C6 46 F1 00   F..Ou|.....4.F..
1817:3870  8A 46 06 88 46 F0 C7 46-F6 00 00 16 8D 46 F0 50   .F..F..F.....F.P
1817:3880  16 8D 46 F0 50 B8 17 00-50 9A 03 00 D5 2D 83 C4   ..F.P...P....-..
1817:3890  0A F6 46 F1 01 74 05 B8-09 00 EB 02 33 C0 EB 00   ..F..t......3...
1817:38A0  5E 8B E5 5D CB 55 8B EC-83 EC 10 39 26 98 0D 77   ^..].U.....9%..w
1817:38B0  05 9A CF 09 17 18 C6 46-F1 02 C6 46 F3 00 8A 46   .......F...F...F
1817:38C0  06 88 46 F7 8A 46 08 88-46 F6 16 8D 46 F0 50 16   ..F..F..F...F.P.
1817:38D0  8D 46 F0 50 B8 10 00 50-9A 03 00 D5 2D 83 C4 0A   .F.P...P....-...
1817:38E0  C6 46 F1 08 C6 46 F3 00-16 8D 46 F0 50 16 8D 46   .F...F....F.P..F
1817:38F0  F0 50 B8 10 00 50 9A 03-00 D5 2D 83 C4 0A 8A 46   .P...P....-....F
1817:3900  F0 B4 00 EB 00 EB E5 5D-CB 55 8B EC 83 EC 10 39   .......].U.....9
1817:3910  26 98 0D 77 05 9A CF 09-17 18 C6 46 F1 0C C6 46   &..w.......F...F
1817:3920  F0 03 C6 46 F3 00 8B 46-06 89 46 F4 8B 46 08 89   ...F...F..F..F..
1817:3930  46 F6 16 8D 46 F0 50 16-8D 46 F0 50 B8 10 00 50   F...F.P..F.P...P
1817:3940  9A 03 00 D5 2D 83 C4 0A-8B E5 5D CB 56 57 39 26   ....-.....].VW9%
1817:3950  98 0D 77 05 9A CF 09 17-18 33 FF BE 1D 00 E9 85   ..w......3......
1817:3960  00 FA 81 26 7E 49 DF 00-81 26 7E 49 BF 00 A0 7E   ...&~I...&~I...~
1817:3970  49 BA 11 03 EE FB C7 06-97 00 00 00 C7 06 95 00   I...............
1817:3980  6A 18 EB 00 A1 95 00 0B-06 97 00 75 F7 FA 81 0E   j..........u....
1817:3990  7E 49 40 00 A0 7E 49 BA-11 03 EE FB C7 06 97 00   ~I@..~I.........
1817:39A0  00 00 C7 06 95 00 C4 09-EB 00 A1 95 00 0B 06 97   ................
1817:39B0  00 75 F7 FA 81 0E 7E 49-20 00 81 26 7E 49 BF 00   .u....~I ..&~I..
1817:39C0  A0 7E 49 BA 11 03 EE FB-C7 06 97 00 00 00 C7 06   .~I.............
1817:39D0  95 00 C4 09 EB 00 A1 95-00 0B 06 97 00 75 F7 9A   .............u..
1817:39E0  7F 13 A2 1A 8B F0 47 8B-C7 3D 02 00 7F 07 0B F6   ......G..=......
1817:39F0  74 03 E9 6C FF 8B C6 EB-00 5F 5E CB 39 26 98 0D   t..l....._^.9&..
1817:3A00  77 05 9A CF 09 17 18 FA-81 26 7E 49 DF 00 81 26   w........&~I...&
1817:3A10  7E 49 BF 00 A0 7E 49 BA-11 03 EE FB C3 55 8B EC   ~I...~I......U..
1817:3A20  83 EC 14 56 39 26 98 0D-77 05 9A CF 09 17 18 EB   ...V9%..w.......
1817:3A30  76 06 C7 46 FE 00 00 C7-46 FC 00 00 C7 46 FA 00   v..F....F....F..
1817:3A40  00 C7 46 F8 00 00 08 F6-74 0F 83 FE 64 74 0A 56   ..F.....t...dt.V
1817:3A50  33 C0 50 0E E8 50 F1 59-59 B8 07 00 50 0E E8 26   3.P..P.YY...P..&
1817:3A60  FC 59 16 8D 46 EC 50 0E-E8 33 FB 59 59 0B C0 74   .Y..F.P..3.YY..t
1817:3A70  28 0B F6 74 11 83 FE 64-74 0C 1E B8 AF 11 50 9A   (..t...dt.....P.
1817:3A80  05 00 A8 2C 59 59 C7 46-F2 FF FF C7 46 F0 78 EC   ...,YY.F....F.x.
1817:3A90  0E E8 FB F4 E9 49 01 EB-28 0B F6 74 18 83 FE 64   .....I..(..t...d
1817:3AA0  74 13 FF 76 EE FF 76 EC-1E B8 8B 11 50 9A 05 00   t..v..v.....P...
1817:3AB0  A8 2C 83 C4 08 8B 56 EE-8B 46 EC 89 56 F2 89 46   .,....V..F..V..F
1817:3AC0  F0 0B F6 74 10 83 FE 64-74 0B 56 B8 0B 00 50 0E   ...t...dt.V...P.
1817:3AD0  E8 D4 F0 59 59 B8 01 00-50 0E E8 AA FB 59 16 8D   ...YY...P....Y..
1817:3AE0  46 EC 50 0E E8 B7 FA 59-59 0B C0 74 28 0B F6 74   F.P....YY..t(..t
1817:3AF0  11 83 FE 64 74 0C 1E B8-C8 11 50 9A 05 00 A8 2C   ...dt.....P....,
1817:3B00  59 59 C7 46 F6 00 00 C7-46 F4 50 C3 0E E8 7F F4   YY.F....F.P.....
1817:3B10  E9 CD 00 EB 4E 8B 46 EC-0B 46 EE 74 2A 0B F6 74   ....N.F..F.t*..t
1817:3B20  18 83 FE 64 74 13 FF 76-EE FF 76 EC 1E B8 D4 11   ...dt..v..v.....
1817:3B30  50 9A 05 00 A8 2C 83 C4-08 8B 56 EE 8B 46 EC 89   P.........V..F..
1817:3B40  56 F6 89 46 F4 EB 1C 0B-F6 74 11 83 FE 64 74 0C   V..F.....t...dt.
1817:3B50  1E B8 E1 11 50 9A 05 00-A8 2C 59 59 0E E8 2F F4   ....P....,YY../.
1817:3B60  E9 7D 00 8B 56 F2 8B 46-F0 52 50 CD 37 46 E6 CD   .}..V..F.RP.7F..
1817:3B70  3D 83 C4 04 8B 56 F6 8B-46 F4 52 50 CD 37 46 E6   =....V..F.RP.7F.
1817:3B80  CD 3D 83 C4 04 CD 38 36-F9 11 CD 3A E9 CD 39 5E   .=....86...:..9^
1817:3B90  F8 CD 3D 8B 46 F4 0B 46-F6 74 1D 8B 56 F6 8B 46   ..=.F..F.t..V..F
```

```
1817:3BA0  F4 52 50 CD 37 46 E6 CD-3D 83 C4 04 CD 38 7E F8   .RP.7F..=....8~.
1817:3BB0  CD 39 5E F8 CD 3D EB 14-C7 46 FE 00 40 C7 46 FC   .9^..=...F..@.F.
1817:3BC0  00 00 C7 46 FA 00 00 C7-46 F8 00 00 CD 39 46 F8   ...F....F....9F.
1817:3BD0  CD 38 0E A7 11 CD 38 2E-01 12 CD 39 5E F8 CD 3D   .8....8....9^..=
1817:3BE0  0B F6 74 11 83 FE 64 74-0C 1E B8 EC 11 50 9A 05   ..t...dt.....P..
1817:3BF0  00 A8 2C 59 59 83 FE 64-75 0D 58 0F 00 50 33 C0   ..,YY..du....P3.
1817:3C00  50 0E E8 A2 EF 59 59 0B-F6 74 19 FF 76 FE FF 76   P....YY..t..v..v
1817:3C10  FC FF 76 FA FF 76 F8 1E-B8 EE 11 50 9A 05 00 A8   ..v..v.....P....
1817:3C20  2C 83 C4 0C CD 39 46 F8-EB 00 5E 8B E5 5D CB 55   ,....9F...^..].U
1817:3C30  8B EC 83 EC 04 56 57 39-26 98 0D 77 05 9A CF 09   .....VW9%..w....
1817:3C40  17 18 B8 03 00 50 0E E8-3D FA 59 C7 06 97 00 00   .....P..=.Y.....
1817:3C50  00 C7 06 95 00 7D 00 E8-00 A1 95 00 0B 06 97 00   .....}..........
1817:3C60  75 F7 33 FF EB 00 16 8D-46 FC 50 0E E8 2F F9 59   u.3.....F.P../.Y
1817:3C70  59 8B F0 8B C6 0B C0 74-09 47 8B C7 3D 04 00 7C   Y......t.G..=..|
1817:3C80  E5 0B F6 74 05 8B C6 E9-73 00 83 7E FE 00 7F 0E   ...t....s..~....
1817:3C90  7C 07 81 7E FC A0 0F 73-05 B8 1D 00 EB 5F E8 05   |..~...s....._..
1817:3CA0  00 50 0E E8 E1 F9 59 C7-06 97 00 00 00 C7 06 95   .P....Y.........
1817:3CB0  00 7D 00 E8 00 A1 95 00-0B 06 97 00 75 F7 33 FF   .}..........u.3.
1817:3CC0  EB 00 16 8D 46 FC 50 0E-E8 D3 F8 59 59 8B F0 8B   ....F.P....YY...
1817:3CD0  C6 0B C0 74 08 47 8B C7-3D 04 00 7C E5 0B F6 74   ...t.G..=..|...t
1817:3CE0  04 8B C6 EB 19 83 7E FE-00 7F 0E 7C 07 81 7E FC   ......~....|..~.
1817:3CF0  A0 0F 73 05 B8 22 00 EB-04 33 C0 EB 00 5F 5E 8B   ..s.."...3..._^.
1817:3D00  E5 5D CB 55 8B EC 39 26-98 0D 77 05 9A CF 09 17   .].U..9%..w.....
1817:3D10  18 0E E8 63 ED 1E B8 09-12 50 9A 05 00 A8 2C 8B   .........P....,.
1817:3D20  E5 1E B8 18 12 50 9A 05-00 A8 2C 83 E5 C4 5E 06   .....P....,...^.
1817:3D30  26 8B 07 48 3D 04 00 77-4F 8B D8 D1 E3 2E FF A7   &..H=..wO.......
1817:3D40  92 14 9C 14 A8 14 B4 14-C0 14 CC 14 1E B8 36 12   ..............6.
1817:3D50  50 9A 05 00 A8 2C 8B E5-1E B8 44 12 50 9A 05 00   P.........D.P...
1817:3D60  A8 2C 8B E5 1E B8 57 12-50 9A 05 00 A8 2C 8B E5   .,....W.P....,..
1817:3D70  1E B8 67 12 50 9A 05 00-A8 2C 8B E5 1E B8 78 12   ..g.P....,....x.
1817:3D80  50 9A 05 00 A8 2C 8B E5-C4 5E 06 26 FF 37 1E B8   P....,...^.&.7..
1817:3D90  99 12 50 9A 05 00 A8 2C-8B E5 1E B8 A3 12 50 9A   ..P....,......P.
1817:3DA0  05 00 A8 2C 8B E5 C4 5E-06 CD 3C DD 47 0E 83 EC   .......^..<.G...
1817:3DB0  08 CD 39 5E F8 CD 3D C4-5E 06 CD 3C DD 47 06 83   ..9^..=.^..<.G..
1817:3DC0  EC 08 CD 39 5E F0 CD 3D-1E B8 B4 12 50 9A 05 00   ...9^..=....P...
1817:3DD0  A8 2C 8B E5 EB FE 5D CB-55 8B EC 56 39 26 98 0D   .,....].U..V9%..
1817:3DE0  77 05 9A CF 09 17 18 FF-76 08 FF 76 06 9A 0F 00   w.......v..v....
1817:3DF0  F9 2B 59 59 8B F0 A0 78-49 9A 04 03 EE A0 7C 49   .+YY...xI.....|I
1817:3E00  BA 05 03 EE 3B C6 EB 00-5E 5D CB 55 8B EC 83 EC   ........^].U....
1817:3E10  08 56 57 39 26 98 0D 77-05 9A CF 09 17 18 9A 8A   .VW9%..w........
1817:3E20  02 6B 1C 8B F0 8B C6 0B-C0 74 07 56 9A 07 00 72   .k.......t.V...r
1817:3E30  1D 59 9A FE 00 A4 20 8B-F0 8B C6 0B C0 74 07 56   .Y.... ......t.V
1817:3E40  9A 07 00 72 1D 59 C7 06-03 01 00 00 B8 01 00 50   ...r.Y.........P
1817:3E50  9A 21 00 6B 1C 59 80 3E-94 00 00 74 21 1E B8 D0   .!.k.Y.>...t!...
1817:3E60  12 50 9A 0A 00 D7 19 59-59 EB 09 33 C0 50 9A 39   .P.....YY..3.P.9
1817:3E70  04 A2 1A 59 BA 12 03 EC-A8 08 74 EF EB 33 1E B8   ...Y......t..3..
1817:3E80  D9 12 50 9A 0A 00 D7 19-59 59 B8 1C 00 50 B8 22   ..P.....YY...P."
1817:3E90  00 50 B8 32 00 50 B8 0C-00 50 9A 0F 00 A2 1A 83   .P.2.P...P......
1817:3EA0  C4 08 B9 0C 00 50 9A E3-00 A2 1A 59 3D 01 00 7D   .....P.....Y=..}
1817:3EB0  51 9A 8A 02 6B 1C 8B F0-8B C6 0B C0 74 07 56 9A   Q...k.......t.V.
1817:3EC0  07 00 72 1D 59 9A 98 00-A4 20 8B F0 8B C6 0B C0   ..r.Y.... ......
1817:3ED0  74 07 56 9A 07 00 72 1D-59 B8 01 00 50 B8 01 00   t.V...r.Y...P...
1817:3EE0  50 9A 0C 00 CF 20 59 59-8B F0 8B C6 0B C0 74 07   P.... YY......t.
1817:3EF0  56 9A 07 00 72 1D 59 C6-06 94 00 00 B8 02 00 E9   V...r.Y.........
1817:3F00  C1 04 1E B8 E2 12 50 9A-0A 00 D7 19 59 59 C7 46   ......P.....YY.F
1817:3F10  FE 00 00 E8 36 5B 1C 00-50 B8 22 00 50 83 7E FE   ....6...P.".P.~.
1817:3F20  06 7D 05 B8 32 00 EB 03-B8 5A 00 50 8B 46 FE B8   .}..2....Z.P.F..
1817:3F30  06 00 99 F7 FB 8B C2 BA-28 00 F7 E2 05 06 00 50   ........(......P
1817:3F40  9A 0F 00 A2 1A 83 C4 08-FF 46 FE 83 46 FE 3B 06   .........F..F.;.
1817:3F50  09 01 7C C1 9A 8A 02 6B-1C 0B C0 74 1D 9A 8A 02   ..|....k...t....
1817:3F60  6B 1C 0B C0 74 14 9A 8A-02 6B 1C 8B F0 8B C6 0B   k...t....k......
1817:3F70  C0 74 07 56 9A 07 00 72-1D 59 9A 98 00 A4 20 8B   .t.V...r.Y.... .
1817:3F80  F0 8B C6 0B C0 74 07 56-9A 07 00 72 1D 59 9A FE   .....t.V...r.Y..
1817:3F90  00 A4 20 8B F0 8B C6 0B-C0 74 07 56 9A 07 00 72   .. ......t.V...r
1817:3FA0  1D 59 9A 98 00 A4 20 8B-F0 8B C6 0B C0 74 07 56   .Y.... ......t.V
1817:3FB0  9A 07 00 72 1D 59 C7 46-FE 00 00 EB 0E 8B 5E FE   ...r.Y.F......^.
1817:3FC0  D1 E3 C7 87 0D 6E 64 00-FF 46 FE 83 7E FE 0C 7C   .....nd..F..~..|
1817:3FD0  EC C7 06 3D 6E 00 00 C7-06 03 01 00 00 59 AC 03   ...=n...........
1817:3FE0  9A 70 06 A2 1A 0B C0 74-2E 9A CE 05 A2 1A 3D 05   .p.....t......=.
1817:3FF0  00 75 24 B8 01 00 50 B8-01 00 50 9A 0C 00 CF 20   .u$...P...P....
1817:4000  59 59 8B F0 8B C6 0B C0-74 07 56 9A 07 00 72 1D   YY......t.V...r.
```

```
1817:4010  59 B8 02 00 E9 AC 03 C7-46 F8 01 00 C7 46 FA 01   Y.......F....F..
1817:4020  00 BF 03 00 E9 55 03 9A-01 00 9F 1C 2B FB 83 3E   .....U.........>
1817:4030  4C 0C 00 75 03 E9 81 00-BF 04 00 A1 03 01 3D 07   L..u..........=.
1817:4040  00 76 03 E9 7B 00 8B D8-D1 E3 2E FF A7 4F 02 5F   .v..{........O._
1817:4050  02 6D 02 7B 02 89 02 97-02 A5 02 B3 02 C1 02 8B   .m.{............
1817:4060  1E 03 01 D1 E3 C7 87 0D-6E 06 00 EB 62 8B 1E 03   ........n...b...
1817:4070  01 D1 E3 C7 87 0D 6E 01-00 EB 54 8B 1E 03 01 D1   ......n...T.....
1817:4080  E3 C7 87 0D 6E 07 00 EB-46 8B 1E 03 01 D1 E3 C7   ....n...F.......
1817:4090  87 0D 6E 03 00 EB 38 8B-1E 03 01 D1 E3 C7 87 0D   ..n...8.........
1817:40A0  6E 30 00 EB 2A 8B 1E 03-01 D1 E3 C7 87 0D 6E 41   n0..*.........nA
1817:40B0  00 EB 1C 8B 1E 03 01 D1-E3 C7 87 0D 6E 08 00 EB   ............n...
1817:40C0  0E 8B 1E 03 01 D1 E3 C7-87 0D 6E 40 00 EB 00 8B   ..........n@....
1817:40D0  1E 03 01 D1 E3 8B 9F 0D-6E D1 E3 8B 87 FF 56 8B   ........n.....V.
1817:40E0  1E 03 01 D1 E3 89 87 0A-48 9A C9 05 F7 1B 8B C7   ........H.......
1817:40F0  3D 04 00 76 03 E9 39 02-8B D8 D1 E3 2E FF A7 01   =..v..9.........
1817:4100  03 31 05 C8 03 C8 03 EE-04 0B 03 83 3E D1 00 01   .1.........>...
1817:4110  75 03 E9 80 00 16 8D 46-FC 50 8B 1E 03 01 D1 E3   u......F.P......
1817:4120  FF B7 0A 48 8B 1E 03 01-D1 E3 FF 87 0D 6E 9A 1F   ...H.........n..
1817:4130  05 4B 21 E3 C4 08 8B F0-8B 1E 03 01 D1 E3 8B 87   .K!.............
1817:4140  0D 6E BA 1C 00 F7 E2 8B-D8 81 C3 0D 01 1E 07 26   .n.............&
1817:4150  83 7F 02 01 75 23 16 8D-46 FC 50 8B 1E 03 01 D1   ....u#..F.P.....
1817:4160  E3 FF B7 0A 48 8B 1E 03-01 D1 E3 FF 87 0D 6E 9A   ....H.........n.
1817:4170  00 0E 3B 24 83 C4 08 23-F0 0B F6 75 48 83 7E 06   ..;$...#...uH.~.
1817:4180  01 75 42 1E 8B EA 12 50-16 8D 46 FA 50 16 8D 46   .uB....P..F.P..F
1817:4190  F8 50 9A 2E 06 F7 1B 83-C4 0C 0B C0 75 24 B8 01   .P..........u$..
1817:41A0  00 50 B8 01 00 50 9A 0C-00 CF 20 59 59 8B F0 8B   .P...P.... YY...
1817:41B0  C6 0B C0 74 07 56 9A 07-00 72 1D 59 B8 02 00 E9   ...t.V...r.Y....
1817:41C0  01 02 8F 02 00 E9 B4 01-1E B8 F2 12 50 9A ED 00   ............P...
1817:41D0  D7 19 59 59 9A CE 05 A2-1A B9 05 00 BB EF 03 2E   ..YY............
1817:41E0  3B 07 74 07 43 43 E2 F7-E9 DE 00 2E FF 67 0A 08   ;.t.CC.......g..
1817:41F0  00 31 00 32 00 33 00 34-00 03 04 06 04 32 04 5D   .1.2.3.4.....2.]
1817:4200  04 88 04 E9 05 01 8B 1E-03 01 D1 E3 C7 87 0D 6E   ...............n
1817:4210  09 00 BF 04 00 8B 1E 03-01 D1 E3 8B 9F 0D 6E D1   ..............n.
1817:4220  E3 8B 87 FF 56 8B 1E 03-01 D1 E3 89 87 0A 48 E9   ....V.........H.
1817:4230  9F 00 8B 1E 03 01 D1 E3-C7 87 0D 6E 3B 00 BF 04   ............n;..
1817:4240  00 8B 1E 03 01 D1 E3 8B-9F 0D 6E D1 E3 8B 87 FF   ............n...
1817:4250  56 8B 1E 03 01 D1 E3 89-87 0A 48 EB 74 8B 1E 03   V.........H.t...
1817:4260  01 D1 E3 C7 87 0D 6E 0E-00 BF 04 00 8B 1E 03 01   ......n.........
1817:4270  D1 E3 8B 9F 0D 6E D1 E3-8B 87 FF 56 8B 1E 03 01   .....n.....V....
1817:4280  D1 E3 89 87 0A 48 EB 49-1E B8 F8 12 50 16 8D 46   .....H.I....P..F
1817:4290  FA 50 16 8D 46 F8 50 9A-2E 06 F7 1B 83 C4 0C 0B   .P..F.P.........
1817:42A0  C0 75 24 B8 01 00 50 B8-01 00 50 9A 0C 00 CF 20   .u$...P...P....
1817:42B0  59 59 8B F0 8B C6 0B C0-74 07 56 9A 07 00 72 1D   YY......t.V...r.
1817:42C0  59 B8 02 00 E9 FC 00 EB-08 9A A1 06 A2 1A E9 03   Y...............
1817:42D0  FF 1E B8 03 13 50 9A 8D-00 D7 19 59 59 9A C9 05   .....P.....YY...
1817:42E0  F7 1B E9 97 00 FF 46 FA-8B 46 FA 3D 02 00 7E 3F   ......F..F.=..~?
1817:42F0  1E B8 0B 13 50 16 8D 46-FA 50 16 8D 46 F8 50 9A   ....P..F.P..F.P.
1817:4300  2E 06 F7 1B 83 C4 0C 0B-C0 75 24 B8 01 00 50 B8   .........u$...P.
1817:4310  01 00 50 9A 0C 00 CF 20-59 59 8B F0 8B C6 0B C0   ..P.... YY......
1817:4320  74 07 56 9A 07 00 72 1D-59 B8 02 00 E9 94 00 EB   t.V...r.Y.......
1817:4330  4B FF 46 F8 8B 46 F8 3D-03 00 7E 3E 1E B8 14 13   K.F..F.=..~>....
1817:4340  50 16 8D 46 FA 50 16 8D-46 F8 50 9A 2E 06 F7 1B   P..F.P..F.P.....
1817:4350  83 C4 0C 0B C0 75 23 B8-01 00 50 B8 01 00 50 9A   .....u#...P...P.
1817:4360  0C 00 CF 20 59 59 8B F0-8B C6 0B C0 74 07 56 9A   ... YY......t.V.
1817:4370  07 00 72 1D 59 B8 02 00-EB 49 EB 00 83 FF 04 74   ..r.Y....I.....t
1817:4380  03 E9 A3 FC FF 06 3D 6E-FF 06 03 01 A1 03 01 3B   ......=n.......;
1817:4390  06 09 01 7D 03 E9 48 FC-9A 3A 02 6B 1C 0B C0 74   ...}..H....k...t
1817:43A0  1D 9A 3A 02 6B 1C 0B C0-74 14 9A 3A 02 6B 1C 8B   ....k...t....k..
1817:43B0  F0 8B C6 0B C0 74 07 56-9A 07 00 72 1D 59 B8 01   .....t.V...r.Y..
1817:43C0  00 EB 00 5F 5E 8B E5 5D-C3 55 8B EC 83 EC 02 56   ..._^..].U.....V
1817:43D0  57 39 26 98 0D 77 05 9A-CF 09 17 18 33 F6 EB 42   W9&..w......3..B
1817:43E0  83 FE 06 7D 05 BF 07 00-EB 03 BF 0C 00 8B C6 BB   ...}............
1817:43F0  06 00 99 F7 FB 8B C2 BA-05 00 F7 E2 40 89 46 FE   ............@.F.
1817:4400  57 FF 76 FE 9A F7 02 A2-1A 59 59 56 9A 7E 08 A2   W.v......YYV.~..
1817:4410  1A 59 52 50 1E B8 1C 13-50 9A 05 00 A8 2C 83 C4   .YRP....P....,..
1817:4420  08 46 3B 36 03 01 7E B8-5F 5E 8B E5 5D CB 55 8B   .F;6..~._^..].U.
1817:4430  EC 56 57 39 26 98 0D 77-05 9A CF 09 17 18 B8 07   .VW9&..w........
1817:4440  00 50 9A 21 00 6B 1C 59-9A E4 00 CF 20 33 F0 8B   .P.!.k.Y.... ...
1817:4450  C6 0B C0 74 07 56 9A 07-00 72 1D 59 9A FE 00 A4   ...t.V...r.Y....
1817:4460  20 8B F0 8B C6 0B C0 74-07 56 9A 07 00 72 1D 59    .......t.V...r.Y
1817:4470  B8 01 00 50 9A 21 00 6B-1C 59 1E B8 22 13 50 9A   ...P.!.k.Y..".P.
```

```
1817:4480  0A 00 D7 19 59 59 33 FF-E8 32 B8 1C 00 50 B8 22   ....YY3..2...P."
1817:4490  00 50 83 FF 06 7D 05 E8-32 00 E8 03 89 5A 00 50   .P...}..2....Z.P
1817:44A0  8B C7 8B 06 00 99 F7 FB-8B C2 BA 28 00 F7 E2 05   ...........(....
1817:44B0  06 00 50 9A 0F 00 A2 1A-83 C4 06 47 3B 3E 09 01   ..P........G;>..
1817:44C0  7C C3 0E E8 03 FF FF 76-10 FF 76 0E 9A 9D 00 D7   |......v..v.....
1817:44D0  19 59 59 C4 5E 06 26 C7-07 01 00 C4 5E 0A 26 C7   .YY.^.&.....^.&.
1817:44E0  07 01 00 C7 06 F9 00 00-00 E8 18 9A 70 06 A2 1A   ............p...
1817:44F0  3D 01 00 75 0E 9A CE 05-A2 1A 3D 08 00 75 04 33   =..u......=..u.3
1817:4500  C0 EB 3D BA 12 03 EC A8-04 74 E0 E8 00 BA 12 03   ..=......t......
1817:4510  EC A8 08 74 FB C7 06 F9-00 01 00 1E E8 2A 13 50   ...t.........*.P
1817:4520  9A 3D 00 D7 19 59 59 9A-98 00 A4 20 8B F0 9B C6   .....YY.... ....
1817:4530  08 C0 74 07 56 9A 07 00-72 1D 59 E8 01 00 E8 00   ..t.V...r.Y.....
1817:4540  5F 5E 5D CB 39 26 98 0D-77 05 9A CF 09 17 18 FF   _^].9%..w.......
1817:4550  06 03 01 83 3E 03 01 0C-7C 06 C7 06 03 01 00 00   ....>...|.......
1817:4560  C8 55 8B EC 83 EC 02 56-57 39 26 98 0D 77 05 9A   .U....VW9%..w..
1817:4570  CF 09 17 18 8B 46 06 48-3D 05 00 77 69 8B D8 D1   .....F.H=..wi...
1817:4580  E3 2E FF A7 46 00 5E 00-62 00 67 00 6C 00 71 00   ....F.^.b.g.l.q.
1817:4590  76 00 7B 00 80 00 86 00-8C 00 92 00 9C 00 33 F6   v.{...........3.
1817:45A0  EB 44 BE D3 01 EB 3F BE-78 05 EB 3A BE D4 03 EB   .D...?.x..:.....
1817:45B0  35 BE BC 02 EB 30 BE 48-03 EB 29 BE 8C 00 EB 26   5....0.H..+....&
1817:45C0  8B 36 92 0D EB 20 8B 36-94 0D EB 1A 8B 36 96 0D   .6... .6.....6..
1817:45D0  EB 14 8B 36 96 0D 81 C6-8C 00 EB 0A 8B 36 96 0D   ...6.........6..
1817:45E0  81 C6 74 FF EB 00 A1 03-01 BA 8C 00 F7 E2 03 C6   ..t.............
1817:45F0  03 06 19 0C 8B 90 06 99-F7 FB 89 56 FE 8B 7E FE   ..........V..~.
1817:4600  2B 3E C8 00 0B FF 75 02-EB 41 0B FF 7D 04 81 C7   +>....u..A..}...
1817:4610  90 06 81 FF 48 03 7D 0F-C7 06 C9 00 01 00 57 9A   ....H.}.......W.
1817:4620  71 01 6B 1C 59 E8 12 C7-06 C9 00 FF FF 8B 90 06   q.k.Y...........
1817:4630  2B C7 50 9A 71 01 6B 1C-59 33 C0 50 9A 39 04 A2   +.P.q.k.Y3.P.9..
1817:4640  1A 59 EB 00 83 3E 9D 00-00 75 F9 5F 5E 8B E5 5D   .Y...>...u._^..]
1817:4650  CB 55 8B EC 56 39 26 98-0D 77 05 9A CF 09 17 18   .U..V9%..w......
1817:4660  8B 76 06 2B 36 C8 00 0B-F6 75 02 EB 41 0B F6 7D   .v.+6....u..A..}
1817:4670  04 81 C6 90 06 81 FE 48-03 7D 0F C7 06 C9 00 01   .......H.}......
1817:4680  00 56 9A 71 01 6B 1C 59-EB 12 C7 06 C9 00 FF FF   .V.q.k.Y........
1817:4690  8B 90 06 2B C6 50 9A 71-01 6B 1C 59 33 C0 50 9A   ...+.P.q.k.Y3.P.
1817:46A0  39 04 A2 1A 59 EB 00 83-3E 9D 00 00 75 F9 5E 5D   9...Y...>...u.^]
1817:46B0  CB 55 8B EC 39 26 98 0D-77 05 9A CF 09 17 18 83   .U..9%..w.......
1817:46C0  3E 44 0D 00 75 08 C7 06-AF 00 02 00 EB 0C C7 06   >D..u...........
1817:46D0  AF 00 01 00 C7 06 B1 00-02 00 FF 76 06 9A CA 01   ...........v....
1817:46E0  6B 1C 59 5D CB 55 8B EC-39 26 98 0D 77 05 9A CF   k.Y].U..9%..w...
1817:46F0  09 17 18 C7 06 AF 00 01-00 C7 06 B1 00 02 00 FF   ................
1817:4700  76 06 9A CA 01 6B 1C 59-5D CB 55 8B EC 39 26 98   v....k.Y].U..9%.
1817:4710  0D 77 05 9A CF 09 17 18-FA 81 26 7A 49 F0 00 8B   .w........&zI...
1817:4720  1E 98 00 D1 E3 8B 87 9F-00 09 06 7A 49 81 26 7E   ...........zI.&~
1817:4730  49 7F 00 A0 7A 49 BA 10-03 EE A0 7E 49 BA 11 03   I...zI.....~I...
1817:4740  EE FB C7 06 B3 58 00 00-C7 06 B5 58 01 00 A1 B5   .....X.....X....
1817:4750  00 50 B8 02 00 99 F7 3E-AF 00 8B D8 58 99 F7 FB   .P.....>....X...
1817:4760  A3 B3 00 8B 46 06 40 A3-9D 00 5D CB 39 26 98 0D   ....F.@...].9%..
1817:4770  77 05 9A CF 09 17 18 FA-81 26 7A 49 F0 00 8B 1E   w........&zI....
1817:4780  98 00 D1 E3 8B 87 9F 00-09 06 7A 49 81 26 7E 49   ..........zI.&~I
1817:4790  7F 00 A0 7A 49 BA 10 03-EE A0 7E 49 BA 11 03 EE   ...zI.....~I....
1817:47A0  FB CB 39 26 98 0D 77 05-9A CF 09 17 18 FA 81 26   ..9%..w........&
1817:47B0  7A 49 F0 00 A0 7A 49 BA-10 03 EE 81 0E 7E 49 80   zI...zI......~I.
1817:47C0  00 A0 7E 49 BA 11 03 EE-FB CB 55 8B EC 83 EC 02   ..~I......U.....
1817:47D0  56 57 39 26 98 0D 77 05-9A CF 09 17 18 33 F6 C7   VW9%..w......3..
1817:47E0  06 52 0D 00 00 C7 06 C9-00 FF FF B8 1C 07 50 0E   .R............P.
1817:47F0  E8 EE FE 59 BF 01 00 33-F6 C7 46 FE 00 00 EB 22   ...Y...3..F...."
1817:4800  3B 36 9D 00 74 1C 8B 36-9D 00 BA 12 03 EC 24 20   ;6..t..6......$
1817:4810  32 06 F5 47 0A C0 75 05-FF 46 FE EB 05 C7 46 FE   2..G..u..F....F.
1817:4820  00 00 83 3E 9D 00 00 74-06 83 7E FE 03 7C D1 33   ...>...t..~..|.3
1817:4830  F6 EB 26 3B 36 9D 00 74-20 8B 36 9D 00 BA 12 03   ..%;6..t .6.....
1817:4840  EC 24 20 32 06 F5 47 0A-C0 74 0E C7 06 C8 00 00   .$ 2..G..t......
1817:4850  00 33 FF C7 06 52 0D 01-00 83 3E 9D 00 00 74 05   .3...R....>...t.
1817:4860  83 FF 01 74 CE EB 09 33-C0 50 9A 39 04 A2 1A 59   ...t...3.P.9...Y
1817:4870  83 3E 9D 00 00 75 F0 8B-C7 EB 00 5F 5E 8B E5 5D   .>...u....._^..]
1817:4880  CB 55 8B EC 81 EC 82 00-56 57 39 26 98 0D 77 05   .U......VW9%..w.
1817:4890  9A CF 09 17 18 C7 46 BE-FF FF 16 8D 46 C0 50 1E   ......F.....F.P.
1817:48A0  B8 32 13 50 B9 40 00 9A-04 0A 17 18 83 3E D1 00   .2.P.@.......>..
1817:48B0  01 75 1A E8 05 00 50 33-C0 50 9A F7 02 A2 1A 59   .u....P3.P.....Y
1817:48C0  59 1E B8 72 13 50 9A 05-00 A8 2C 59 59 B8 02 00   Y..r.P....,YY...
1817:48D0  50 9A 21 00 6B 1C 59 C7-06 C9 00 01 00 C7 06 46   P.!.k.Y........F
1817:48E0  0D 00 00 B8 18 01 50 9A-71 01 6B 1C 59 33 C0 89   ......P.q.k.Y3..
```

```
1817:48F0  46 B0 89 46 AE C7 86 4E-FF 00 00 EB 00 83 3E 9D   F..F...N......>.
1817:4900  00 58 7F F9 C7 86 54 FF-00 00 EB 14 54 06 03 EC   .X....T.........
1817:4910  A8 08 74 08 C7 86 54 FF-00 00 EB 04 FF 86 54 FF   ..t...T.......T.
1817:4920  83 BE 54 FF 19 7D 07 83-3E 9D 00 00 75 DE 83 3E   ..T..}.....u..>
1817:4930  9D 00 00 75 03 E9 45 01-B0 70 BA 03 03 EE B0 FF   ...u..E..p......
1817:4940  BA 01 03 EE B0 FF BA 01-03 EE C7 86 54 FF 00 00   ............T...
1817:4950  EB 14 BA 06 03 EC A8 08-74 06 FF 86 54 FF EB 06   ........t...T...
1817:4960  C7 86 54 FF 00 00 83 BE-54 FF 19 7D 07 83 3E 9D   ..T.....T..}..>.
1817:4970  00 00 75 DE 83 3E 9D 00-00 75 03 E9 FF 00 B0 B0   ..u..>...u......
1817:4980  BA 03 03 EE B0 FF BA 02-03 EE B0 FF BA 02 03 EE   ................
1817:4990  C7 86 54 FF 00 00 EB 14-BA 06 03 EC A8 08 74 08   ..T...........t.
1817:49A0  C7 86 54 FF 00 00 EB 04-FF 86 54 FF 83 BE 54 FF   ..T.......T...T.
1817:49B0  19 7D 07 83 3E 9D 00 00-75 DE 83 3E 9D 00 00 75   .}..>...u..>...u
1817:49C0  03 E9 99 00 BA 01 03 EC-B4 00 89 86 58 FF BA 01   ............X...
1817:49D0  03 EC B4 00 B1 08 D3 E0-01 86 58 FF B0 70 BA 03   ..........X..p..
1817:49E0  03 EE B0 FF BA 01 03 EE-B0 FF BA 01 03 EE 8B 86   ................
1817:49F0  58 FF 33 46 BE 8B 5E AE-D1 E3 8D 96 5E FF 03 DA   X.3F..^.....^...
1817:4A00  36 89 07 FF 46 AE C7 86-54 FF 00 00 EB 14 BA 06   6...F...T.......
1817:4A10  03 EC A8 08 74 06 FF 86-54 FF EB 06 C7 86 54 FF   ....t...T.....T.
1817:4A20  00 00 83 BE 54 FF 19 7D-07 83 3E 9D 00 00 75 DE   ....T..}..>...u.
1817:4A30  83 3E 9D 00 00 75 02 EB-44 BA 02 03 EC B4 00 89   .>...u..D.......
1817:4A40  86 58 FF BA 02 03 EC B4-00 B1 08 D3 E0 01 86 58   .X.............X
1817:4A50  FF B0 30 BA 03 03 EE B0-FF BA 02 03 EE B0 FF BA   ................
1817:4A60  02 03 EE 8B 86 58 FF 33-46 BE 8B 5E B0 D1 E3 8D   .....X.3F..^....
1817:4A70  56 86 03 DA 36 89 07 FF-46 B0 E9 13 FF C7 06 46   V...6...F......F
1817:4A80  0D 01 00 33 C0 89 46 B8-89 46 B6 33 C0 89 46 BC   ...3..F..F.3..F.
1817:4A90  89 46 BA 83 7E AE 0E 7D-06 BE 32 00 E9 3C 02 C7   .F..~..}..2..<..
1817:4AA0  86 52 FF 00 00 33 FF EB-75 8B DF D1 E3 8D 96 5A   .R...3..u......Z
1817:4AB0  FF 03 D8 36 C7 07 00 00-8B 96 52 FF 89 86 50 FF   ...6.......R...P.
1817:4AC0  EB 2D 8B C7 BA 28 00 F7-E2 8B D8 8D 86 5E FF 03   .-...(.......^..
1817:4AD0  D8 16 07 8B 86 50 FF D1-E0 03 D8 26 89 07 8B DF   .....P.....&....
1817:4AE0  D1 E3 8D 96 5A FF 03 DA-36 01 07 FF 86 50 FF 8B   ....Z...6....P..
1817:4AF0  86 52 FF 05 0C 00 3B 86-50 FF 7F C6 8B DF D1 E3   .R....;.P.......
1817:4B00  8D 86 5A FF 03 D8 36 8B-07 3B 0A 00 33 D2 F7 F3   ..Z...6.....3...
1817:4B10  8B DF D1 E3 8D 96 5A FF-03 DA 36 89 07 47 83 FF   ......Z...6..G..
1817:4B20  02 7C 96 83 86 52 FF 02-33 FF E9 96 00 83 86 52   .|...R..3......R
1817:4B30  FF 89 86 50 FF EB 76 8B-DF D1 E3 8D 46 BA 03 D8   ...P..v.....F...
1817:4B40  36 8B 07 BA 0C 00 2B D7-3B C2 7D 5D 8B DF D1 E3   6.....+.;.}]....
1817:4B50  8D 46 B6 03 D8 36 8B 07-D1 E0 8B DF D1 E3 8D 56   .F...6.........V
1817:4B60  B6 03 DA 36 89 07 8B C7-BA 28 00 F7 E2 8B D8 8D   ...6.....(......
1817:4B70  86 5E FF 03 D8 16 07 8B-86 50 FF D1 E0 03 D8 26   .^.......P.....&
1817:4B80  8B 07 8B DF D1 E3 8D 96-5A FF 03 DA 36 3B 07 76   ........Z...6;.v
1817:4B90  0C 8B DF D1 E3 8D 46 B6-03 D8 36 FF 07 8B DF D1   ......F...6.....
1817:4BA0  E3 8D 46 BA 03 D8 36 FF-07 FF 86 50 FF 8B DF D1   ..F...6....P....
1817:4BB0  E3 8D 46 AE 03 D8 36 8B-07 3B 86 50 FF 7E 03 E9   ..F...6..;.P.~..
1817:4BC0  75 FF 47 83 FF 01 7F 03-E9 62 FF EB 64 00 83 7E   u.G......b..d..~
1817:4BD0  BA 0C 7D 03 E9 04 01 5E-65 00 83 7E BC 0B 7D 03   ..}.....e..~..}.
1817:4BE0  E9 F3 00 5E F4 01 8B 46-B6 25 03 00 3D 02 00 75   .......F.%..=..u
1817:4BF0  07 F7 46 B8 01 00 74 03-E9 E0 00 C7 86 4E FF 00   ..F...t......N..
1817:4C00  00 BE 58 02 8B 5E B8 B1-06 D3 E3 81 E3 1F 00 D1   ..X..^..........
1817:4C10  E3 8D 46 C0 03 D8 36 8B-07 89 86 4E FF 3D 09 00   ..F...6....N.=..
1817:4C20  7E 03 E9 96 00 BE BC 02-8B 5E B6 B1 07 D3 EB 81   ~........^......
1817:4C30  E3 1F 00 D1 E3 8D 46 C0-03 D8 36 8B 07 BA 0A 00   ......F...6.....
1817:4C40  F7 E2 01 86 4E FF 8B 86-4E FF 3D 63 00 7E 03 E9   ....N...N.=c.~..
1817:4C50  89 00 C7 86 56 FF 00 00-BE BE 02 8B 5E B8 D1 EB   ....V.......^...
1817:4C60  81 E3 1F 00 D1 E3 8D 46-C0 03 D8 36 8B 07 89 86   .......F...6....
1817:4C70  56 FF 3D 09 00 7E 02 EB-62 BE C1 02 8B 5E B6 D1   V.=..~..b....^..
1817:4C80  EB D1 EB 81 E3 1F 00 D1-E3 8D 46 C0 03 D8 36 8B   ..........F...6.
1817:4C90  07 BA 0A 00 F7 E2 01 86-56 FF 8B 86 56 FF 3D 63   ........V...V.=c
1817:4CA0  00 7E 02 EB 36 BE 04 00-83 BE 56 FF 31 7E 02 EB   .~..6.....V.1~..
1817:4CB0  2A 83 BE 56 FF 00 74 23-8B 1E 03 01 D1 E3 8B 87   *..V..t#........
1817:4CC0  0A 48 3B 86 56 FF 74 13-8B 86 56 FF 8B 1E 03 01   .H;.V.t...V.....
1817:4CD0  D1 E3 89 87 0A 48 9A 18-03 17 22 83 3E D1 00 01   .....H...."..>...
1817:4CE0  74 03 E9 13 02 83 FE 04-75 2E 8B 86 4E FF BA 1C   t.......u...N...
1817:4CF0  00 F7 E2 8B D8 81 C3 0D-01 1E 07 26 83 7F 18 00   ...........&....
1817:4D00  75 16 8B 86 4E FF 8B 1E-03 01 D1 E3 89 87 0D 6E   u...N..........n
1817:4D10  9A C9 05 F7 1B E9 AF 00-9A 6C 03 A2 1A 9A A1 06   ..........l.....
1817:4D20  A2 1A 83 3E 03 01 00 7E-0D 8B 1E 03 01 4B D1 E3   ...>...~.....K..
1817:4D30  8B 87 0D 6E EB 02 33 C0-8B 1E 03 01 D1 E3 89 87   ...n..3.........
```

```
1817:4D40  0D 6E 9A C9 05 F7 1B B8-05 00 50 B8 1A 00 50 9A   .n........P...P.
1817:4D50  F7 02 A2 1A 59 59 1E B8-93 13 50 9A 05 00 A8 2C   ....YY....P.....,
1817:4D60  59 59 B8 C5 00 50 33 C0-50 9A F7 02 A2 1A 59 59   YY...P3.P.....YY
1817:4D70  8B 1E 03 01 D1 E3 FF B7-0D 6E A1 03 01 40 50 1E   ..........n...@P.
1817:4D80  B8 9A 13 50 9A 05 00 A8-2C 83 C4 08 1E A1 03 01   ...P............
1817:4D90  D1 E0 05 0D 6E 50 9A A6-08 A2 1A 59 59 89 46 B4   ....nP.....YY.F.
1817:4DA0  0B C0 74 06 83 7E B4 02-75 03 E9 6B FF 8B 1E 03   ..t..~..u..k....
1817:4DB0  01 D1 E3 83 BF 0D 6E 64-7C 08 9A A1 06 A2 1A E9   ......nd!.......
1817:4DC0  56 FF 9A C9 05 F7 1B 9A-6C 03 A2 1A 8B 1E 03 01   V.......l.......
1817:4DD0  D1 E3 8B 9F 0D 6E D1 E3-8B 87 FF 56 8B 1E 03 01   .....n.....V....
1817:4DE0  D1 E3 89 87 0A 48 83 3E-03 01 00 74 3B C7 46 B2   .....H.>...t;.F.
1817:4DF0  00 00 E9 2B 8B 1E 03 01-D1 E3 8B 87 0D 6E 8B 5E   ...+.........n.^
1817:4E00  B2 D1 E3 3B 87 0D 6E 75-13 8B 5E B2 D1 E3 8B 87   ...;..nu..^.....
1817:4E10  0A 48 8B 1E 03 01 D1 E3-89 87 0A 48 FF 46 B2 EB   .H.........H.F..
1817:4E20  46 B2 3B 06 03 01 7C CC-B8 05 00 50 B8 1B 00 50   F.;...!....P...P
1817:4E30  9A F7 02 A2 1A 59 59 1E-B8 B7 13 50 9A 05 00 A8   .....YY....P....
1817:4E40  2C 59 59 B8 05 00 50 33-C0 50 9A F7 02 A2 1A 59   .YY...P3.P.....Y
1817:4E50  59 8B 1E 03 01 D1 E3 FF-B7 0A 48 A1 03 01 40 50   Y.........H...@P
1817:4E60  1E B8 BD 13 50 9A 05 00-A8 2C 83 C4 08 1E A1 03   ....P...,.......
1817:4E70  01 D1 E0 05 0A 48 50 9A-A6 08 A2 1A 59 59 89 46   .....HP.....YY.F
1817:4E80  B4 0B C0 74 06 83 7E B4-02 75 03 E9 39 FF B8 05   ...t..~..u..9...
1817:4E90  00 50 33 C0 50 9A F7 02-A2 1A 59 59 1E B8 D9 13   .P3.P.....YY....
1817:4EA0  50 9A 05 00 A8 2C 59 59-8E 03 00 8B 1E 03 01 D1   P.....YY........
1817:4EB0  E3 83 BF 0D 6E 64 75 03-E8 02 00 8B 1E 03 01 D1   ....ndu.........
1817:4EC0  E3 8B 87 0D 6E BA 1C 00-F7 E2 83 D8 81 C3 0D 01   ....n...........
1817:4ED0  1E 07 26 83 7F 18 00 75-06 B8 04 00 E9 AE 00 83   ..&....u........
1817:4EE0  FE 02 75 0C 8E 1E 03 01-D1 E3 C7 87 0D 6E 64 00   ..u..........nd.
1817:4EF0  8B C6 E9 98 00 E9 95 00-83 FE 04 75 3F 8B 86 4E   ...........u?..N
1817:4F00  FF BA 1C 00 F7 E2 8B D8-81 C3 0D 01 1E 07 26 83   ..............&.
1817:4F10  7F 18 00 75 27 8B 86 4E-FF 8B 1E 03 01 D1 E3 89   ...u'..N........
1817:4F20  87 0D 6E 8B 9E 4E FF D1-E3 8B 87 FF 56 8B 1E 03   ..n..N......V...
1817:4F30  01 D1 E3 89 87 0A 48 E8-04 00 EB 51 83 FE 04 75   ......H....Q...u
1817:4F40  2B 8B 86 4E FF BA 1C 00-F7 E2 8B D8 81 C3 0D 01   +..N............
1817:4F50  1E 07 26 83 7F 18 01 75-13 8B 86 4E FF 8B 1E 03   ..&....u...N....
1817:4F60  01 D1 E3 89 87 0D 6E E8-03 00 EB 21 8B 1E 03 01   ......n....!....
1817:4F70  D1 E3 C7 87 0D 6E 64 00-83 FE 32 74 05 83 FE 02   .....nd...2t....
1817:4F80  75 05 B8 02 00 EB 06 33-F6 8B C6 EB 00 5F 5E 8B   u......3....._^.
1817:4F90  E5 5D CB 56 57 39 26 98-0D 77 05 9A CF 09 17 18   .].VW9%..w......
1817:4FA0  9A 61 00 10 1D 8B F8 8B-C7 0B C0 74 04 8B C7 EB   .a.........t....
1817:4FB0  3D A1 3F 0C 8A 06 00 F7-E2 8B F0 C7 06 D5 00 01   =.?.............
1817:4FC0  00 56 9A 08 02 10 1D 59-EB 09 33 C0 50 9A 39 04   .V.....Y..3.P.9.
1817:4FD0  A2 1A 59 83 3E D3 00 00-75 F0 8A 12 03 EC A8 40   ..Y.>...u......@
1817:4FE0  75 05 B8 11 00 EB 07 9A-61 00 10 1D EB 00 5F 5E   u.......a....._^
1817:4FF0  CB 56 57 39 26 98 0D 77-05 9A CF 09 17 18 33 FF   .VW9%..w......3.
1817:5000  EB 2E 8A 12 03 EC A8 40-75 02 EB 29 8B 36 3F 0C   .......@u..).6?.
1817:5010  C7 06 D5 00 FF FF 56 9A-08 02 10 1D 59 EB 09 33   ......V.....Y..3
1817:5020  C0 50 9A 39 04 A2 1A 59-83 3E D3 00 00 75 F0 47   .P.9...Y.>...u.G
1817:5030  83 FF 19 7C C3 0B FF 74-24 A1 3F 0C 8B 02 00 99   ...!...t$.?.....
1817:5040  F7 FB 8B F0 56 9A 08 02-10 1D 59 EB 09 33 C0 50   ....V.....Y..3.P
1817:5050  9A 39 04 A2 1A 59 83 3E-D3 00 00 75 F0 BA 12 03   .9...Y.>...u....
1817:5060  EC A8 40 74 05 B8 03 00-EB 04 33 C0 EB 00 5F 5E   ..@t......3..._^
1817:5070  CB 55 8B EC 56 57 39 26-98 0D 77 05 9A CF 09 17   .U..VW9%..w.....
1817:5080  18 A1 3F 0C F7 66 06 8B-F0 03 36 3D 0C C7 06 D5   ..?..f....6=....
1817:5090  00 01 00 56 9A 08 02 10-1D 59 EB 09 33 C0 50 9A   ...V.....Y..3.P.
1817:50A0  39 04 A2 1A 59 83 3E D3-00 00 75 F0 9A 14 03 A2   9...Y.>...u.....
1817:50B0  1A 9A 8B 03 A2 1A C5 03-00 EB 3C 00 99 F7 FB 8B   ..........<.....
1817:50C0  FA EB 00 9A 3B 03 A2 1A-3B C7 75 F7 8B 36 41 0C   ........;.u..6A.
1817:50D0  C7 06 D5 00 01 00 56 9A-08 02 10 1D 59 C7 06 FA   ......V.....Y...
1817:50E0  13 01 00 EB 09 33 C0 50-9A 39 04 A2 1A 59 83 3E   .....3.P.9...Y.>
1817:50F0  D3 00 00 75 F0 9A 29 08-A2 1A 5F 5E 5D CB 56 39   ...u..(..._^].V9
1817:5100  26 98 0D 77 05 9A CF 09-17 18 8B 36 3F 0C 83 3E   %..w.......6?..>
1817:5110  FA 13 01 75 09 A1 41 0C-03 06 45 0C 03 F0 C7 06   ...u..A...E.....
1817:5120  FA 13 00 00 C7 06 D5 00-FF FF 56 9A 08 02 10 1D   ..........V.....
1817:5130  59 EB 00 83 3E D3 00 00-75 F9 5E CB 56 39 26 98   Y...>...u.^.V9%.
1817:5140  0D 77 05 9A CF 09 17 18-8B 36 41 0C C7 06 D5 00   .w.......6A.....
1817:5150  01 00 56 9A 08 02 10 1D-59 C7 06 FA 13 01 00 EB   ..V.....Y.......
1817:5160  00 83 3E D3 00 00 75 F9-5E CB 56 39 26 98 0D 77   ..>...u.^.V9%..w
1817:5170  05 9A CF 09 17 18 8B 36-3F 0C C7 06 D5 00 01 00   .......6?.......
1817:5180  56 9A 08 02 10 1D 59 C7-06 FA 13 01 00 EB 00 83   V.....Y.........
1817:5190  3E D3 00 00 75 F9 5E CB-55 8B EC 39 26 98 0D 77   >...u.^.U..9%..w
1817:51A0  05 9A CF 09 17 18 FA 8B-1E D7 00 D1 E3 8B 87 DD   ................
```

```
1817:51B0  00 E8 16 7A 49 81 E2 0F-00 0B C2 A3 7A 49 F8 A0   ...zI.......zI..
1817:51C0  7A 49 8A 10 03 EE C7 06-ED 00 02 00 C7 06 EF 00   zI..............
1817:51D0  02 00 C7 06 D9 00 05 00-C7 06 DB 00 04 00 8B 46   ...............F
1817:51E0  06 40 A3 D3 00 5D CB 56-39 26 98 0D 77 05 9A CF   .@...].V9%..w...
1817:51F0  09 17 18 9A 18 02 A2 1A-0E E8 97 FD 89 36 3F 0C   .............6?.
1817:5200  C7 06 D5 00 01 00 56 0E-E8 8D FF 59 EB 09 33 C0   ......V....Y..3.
1817:5210  50 9A 39 04 A2 1A 59 83-3E D3 00 00 75 F0 1E B8   P.9...Y.>...u...
1817:5220  FC 13 50 9A 0A 00 D7 19-59 59 9A CE 05 A2 1A 1E   ..P.....YY......
1817:5230  B8 05 14 50 9A 0A 00 D7-19 59 59 EB 50 A1 3F 0C   ...P.....YY.P.?.
1817:5240  8A 0A 00 F7 E2 8B F0 C7-06 D5 00 01 00 56 0E E8   .............V..
1817:5250  46 FF 59 EB 09 33 C0 50-9A 39 04 A2 1A 59 83 3E   F.Y..3.P.9...Y.>
1817:5260  D3 00 00 75 F0 A1 3F 0C-8A 0A 00 F7 E2 8B F0 C7   ...u..?.........
1817:5270  06 D5 00 FF FF 56 0E E8-1E FF 59 EB 09 33 C0 50   .....V....Y..3.P
1817:5280  9A 39 04 A2 1A 59 83 3E-D3 00 00 75 F0 9A 70 06   .9...Y.>...u..p.
1817:5290  A2 1A 3D 01 00 75 A6 5E-CB 56 39 26 98 0D 77 05   ..=..u.^.V9%..w.
1817:52A0  9A CF 09 17 18 33 F6 FA-81 0E 7E 49 10 00 A0 7E   .....3....~I...~
1817:52B0  49 8A 11 03 EE F8 8A 12-03 EC A8 02 75 55 FA 81   I...........uU..
1817:52C0  26 7E 49 EF 00 A0 7E 49-8A 11 03 EE F8 C7 06 97   &~I...~I........
1817:52D0  00 00 00 C7 06 95 00 E2-04 EB 0D 8A 12 03 EC A8   ................
1817:52E0  02 74 03 46 EB 02 33 F6-83 FE 03 7D 09 A1 95 00   .t.F..3....}....
1817:52F0  0B 06 97 00 75 E5 FA 81-0E 7E 49 10 00 A0 7E 49   ....u....~I...~I
1817:5300  8A 11 03 EE F8 A1 95 00-0B 06 97 00 75 05 B8 19   ............u...
1817:5310  00 EB 04 33 C0 EB 00 5E-CB 56 39 26 98 0D 77 05   ...3...^.V9%..w.
1817:5320  9A CF 09 17 18 C7 06 03-01 00 00 B8 03 00 50 9A   ..............P.
1817:5330  21 00 6B 1C 59 9A F7 03-10 1D E8 F0 8B C6 0B C0   !.k.Y...........
1817:5340  74 04 8B C6 EB 3F C7 06-97 00 00 00 C7 06 95 00   t....?..........
1817:5350  0D 00 EB 00 A1 95 00 0B-06 97 00 75 F7 C7 06 97   ...........u....
1817:5360  00 00 00 C7 06 95 00 40-06 EB 0D 8A 12 03 EC A8   .......@........
1817:5370  02 75 05 B8 18 00 EB 0D-A1 95 00 0B 06 97 00 75   .u.............u
1817:5380  EA 33 C0 EB 00 5E C8 56-39 26 98 0D 77 05 9A CF   .3...^.V9%..w...
1817:5390  09 17 18 FA 81 26 7E 49-EF 00 A0 7E 49 8A 11 03   .....&~I...~I...
1817:53A0  EE F8 33 F6 C7 06 97 00-00 00 C7 06 95 00 E2 04   ..3.............
1817:53B0  EB 0D 8A 12 03 EC A8 02-75 03 46 EB 02 33 F6 83   ........u.F..3..
1817:53C0  FE 03 7D 09 A1 95 00 0B-06 97 00 75 E5 A1 95 00   ..}........u....
1817:53D0  0B 06 97 00 75 14 FA 81-0E 7E 49 10 00 A0 7E 49   ....u....~I...~I
1817:53E0  8A 11 03 EE F8 B8 16 00-EB 63 C7 06 97 00 00 00   .........c......
1817:53F0  C7 06 95 00 3F 00 EB 00-A1 95 00 0B 06 97 00 75   ....?..........u
1817:5400  F7 33 F6 C7 06 97 00 00-00 C7 06 95 00 E2 04 EB   .3..............
1817:5410  0D 8A 12 03 EC A8 02 74-03 46 EB 02 33 F6 83 FE   .......t.F..3...
1817:5420  03 7D 09 A1 95 00 0B 06-97 00 75 E5 FA 81 0E 7E   .}........u....~
1817:5430  49 10 00 A0 7E 49 8A 11-03 EE F8 A1 95 00 0B 06   I...~I..........
1817:5440  97 00 75 05 B8 17 00 EB-04 33 C0 EB 00 5E CB 56   ..u......3...^.V
1817:5450  57 39 26 98 0D 77 05 9A-CF 09 17 18 1E B8 0E 14   W9%..w..........
1817:5460  50 9A 0A 00 D7 19 59 59-0E E8 8E F8 8B F8 8B C7   P.....YY........
1817:5470  0B C0 74 07 57 9A 07 00-72 1D 59 A1 3F 0C 8A 06   ..t.W...r.Y.?...
1817:5480  00 F7 E2 8B F0 C7 06 D5-00 01 00 56 0E E8 08 FD   ...........V....
1817:5490  59 EB 09 33 C0 50 9A 39-04 A2 1A 59 83 3E D3 00   Y..3.P.9...Y.>..
1817:54A0  00 75 F0 1E B8 17 14 50-9A 0A 00 D7 19 59 59 C7   .u.....P.....YY.
1817:54B0  06 45 0C 00 00 9A CE 05-A2 1A 3D 0D 00 74 3E 3D   .E........=..t.=
1817:54C0  31 00 74 02 EB 36 FF 06-45 0C C7 06 D5 00 FF FF   1.t..6..E.......
1817:54D0  B8 01 00 50 0E E8 C0 FC-59 EB 09 33 C0 50 9A 39   ...P....Y..3.P.9
1817:54E0  04 A2 1A 59 83 3E D3 00-00 75 F0 EB C8 FF 0E 45   ...Y.>...u.....E
1817:54F0  0C 7D 07 9A A1 06 A2 1A-EB B5 EB 07 9A A1 06 A2   .}..............
1817:5500  1A EB 82 9A 9D 05 17 22-5F 5E CB 55 8B EC 83 EC   ......."_^.U....
1817:5510  04 56 57 39 26 98 0D 77-05 9A CF 09 17 18 1E B8   .VW9%..w........
1817:5520  20 14 50 9A 0A 00 D7 19-59 59 0E E8 C3 FA 1E B8    .P.....YY......
1817:5530  29 14 50 9A 0A 00 D7 19-59 59 16 8D 46 FE 50 9A   ).P.....YY..F.P.
1817:5540  A6 08 A2 1A 59 59 8B F8-8B C7 0B C0 74 05 83 FF   ....YY......t...
1817:5550  03 75 02 EB D9 83 FF 02-75 02 EB 55 A1 3F 0C F7   .u......u..U.?..
1817:5560  66 FE 89 46 FC C7 06 D5-00 01 00 FF 76 FC 0E E8   f..F........v...
1817:5570  26 FC 59 EB 09 33 C0 50-9A 39 04 A2 1A 59 83 3E   &.Y..3.P.9...Y.>
1817:5580  D3 00 00 75 F0 1E B8 32-14 50 9A 0A 00 D7 19 59   ...u...2.P.....Y
1817:5590  59 33 F6 EB 17 9A CE 05-A2 1A 3D 08 00 75 02 EB   Y3........=..u..
1817:55A0  10 C7 06 FA 13 00 00 0E-E8 53 F9 46 3B 76 FE 7C   .........S.F;v.|
1817:55B0  E4 5F 5E 8B E5 5D CB 55-8B EC 56 39 26 98 0D 77   ._^..].U..V9%..w
1817:55C0  05 9A CF 09 17 18 83 76-06 56 9A EB 03 B9 18 59   .......v.V.....Y
1817:55D0  9A DF 06 A2 1A 8B 56 48-3D 33 00 76 03 E9 74 03   .......H=3.v..t.
1817:55E0  8B D8 D1 E3 2E FF A7 39-00 A1 00 B0 00 BF 00 CE   .......9........
1817:55F0  00 DD 00 EC 00 FB 00 0A-01 19 01 28 01 37 01 46   ...........(.7.F
1817:5600  01 55 01 64 01 73 01 82-01 91 01 A0 01 AF 01 BE   .U.d.s..........
1817:5610  01 CD 01 DC 01 EB 01 FA-01 09 02 18 02 27 02 36   .............'.6
```

```
1817:5620  02 45 02 54 02 63 02 72-02 81 02 90 02 A4 03 9F   .E.T.c.r........
1817:5630  02 AE 02 BD 02 CC 02 DB-02 EA 02 F9 02 A4 03 08   ................
1817:5640  03 17 03 26 03 35 03 43-03 51 03 5F 03 6D 03 7B   ...&.5.C.Q._.m.{
1817:5650  03 1E B8 3C 14 50 9A 0A-00 D7 19 59 59 E9 02 03   ...<.P.....YY...
1817:5660  1E B8 45 14 50 9A 0A 00-D7 19 59 59 E9 F3 02 1E   ..E.P.....YY....
1817:5670  B8 4E 14 50 9A 0A 00 D7-19 59 59 E9 E4 02 1E B8   .N.P.....YY.....
1817:5680  57 14 50 9A 0A 00 D7 19-59 59 E9 D5 02 1E B8 60   W.P.....YY.....`
1817:5690  14 50 9A 0A 00 D7 19 59-59 E9 C6 02 1E B8 69 14   .P.....YY.....i.
1817:56A0  50 9A 0A 00 D7 19 59 59-E9 B7 02 1E B8 72 14 50   P.....YY.....r.P
1817:56B0  9A 0A 00 D7 19 59 59 E9-A8 02 1E B8 7B 14 50 9A   .....YY.....{.P.
1817:56C0  0A 00 D7 19 59 59 E9 99-02 1E B8 84 14 50 9A 0A   ....YY.......P..
1817:56D0  00 D7 19 59 59 E9 8A 02-1E B8 8D 14 50 9A 0A 00   ...YY.......P...
1817:56E0  D7 19 59 59 E9 7B 02 1E-B8 96 14 50 9A 0A 00 D7   ..YY.{.....P....
1817:56F0  19 59 59 E9 6C 02 1E B8-9F 14 50 9A 0A 00 D7 19   .YY.l.....P.....
1817:5700  59 59 E9 5D 02 1E B8 A8-14 50 9A 0A 00 D7 19 59   YY.].....P.....Y
1817:5710  59 E9 4E 02 1E B8 AF 14-50 9A 0A 00 D7 19 59 59   Y.N.....P.....YY
1817:5720  E9 3F 02 1E B8 B7 14 50-9A 0A 00 D7 19 59 59 E9   .?.....P.....YY.
1817:5730  30 02 1E B8 C0 14 50 9A-0A 00 D7 19 59 59 E9 21   0.....P.....YY.!
1817:5740  02 1E B8 C3 14 50 9A 0A-00 D7 19 59 59 E9 12 02   .....P.....YY...
1817:5750  1E B8 D1 14 50 9A 0A 00-D7 19 59 59 E9 03 02 1E   ....P.....YY....
1817:5760  B8 DA 14 50 9A 0A 00 D7-19 59 59 E9 F4 01 1E B8   ...P.....YY.....
1817:5770  E3 14 50 9A 0A 00 D7 19-59 59 E9 E5 01 1E B8 EC   ..P.....YY......
1817:5780  14 50 9A 0A 00 D7 19 59-59 E9 D6 01 1E B8 F5 14   .P.....YY.......
1817:5790  50 9A 0A 00 D7 19 59 59-E9 C7 01 1E B8 FE 14 50   P.....YY.......P
1817:57A0  9A 0A 00 D7 19 59 59 E9-B8 01 1E B8 07 15 50 9A   .....YY.......P.
1817:57B0  0A 00 D7 19 59 59 E9 A9-01 1E B8 0F 15 50 9A 0A   ....YY.......P..
1817:57C0  00 D7 19 59 59 E9 9A 01-1E B8 17 15 50 9A 0A 00   ...YY.......P...
1817:57D0  D7 19 59 59 E9 8B 01 1E-B8 20 15 50 9A 0A 00 D7   ..YY...... .P....
1817:57E0  19 59 59 E9 7C 01 1E B8-29 15 50 9A 0A 00 D7 19   .YY.|...).P.....
1817:57F0  59 59 E9 6D 01 1E B8 31-15 50 9A 0A 00 D7 19 59   YY.m...1.P.....Y
1817:5800  59 E9 5E 01 1E B8 38 15-50 9A 0A 00 D7 19 59 59   Y.^...8.P.....YY
1817:5810  E9 4F 01 1E B8 3E 15 50-9A 0A 00 D7 19 59 59 E9   .O...>.P.....YY.
1817:5820  40 01 1E B8 43 15 50 9A-0A 00 D7 19 59 59 E9 31   @...C.P.....YY.1
1817:5830  01 1E B8 49 15 50 9A 0A-00 D7 19 59 59 E9 22 01   ...I.P.....YY.".
1817:5840  1E B8 51 15 50 9A 0A 00-D7 19 59 59 E9 13 01 1E   ..Q.P.....YY....
1817:5850  B8 58 15 50 9A 0A 00 D7-19 59 59 E9 04 01 1E B8   .X.P.....YY.....
1817:5860  61 15 50 9A 0A 00 D7 19-59 59 E9 F5 00 1E B8 69   a.P.....YY.....i
1817:5870  15 50 9A 0A 00 D7 19 59-59 E9 E6 00 1E B8 71 15   .P.....YY.....q.
1817:5880  50 9A 0A 00 D7 19 59 59-E9 D7 00 1E B8 79 15 50   P.....YY.....y.P
1817:5890  9A 0A 00 D7 19 59 59 E9-C8 00 1E B8 81 15 50 9A   .....YY.......P.
1817:58A0  0A 00 D7 19 59 59 E9 B9-00 1E B8 89 15 50 9A 0A   ....YY.......P..
1817:58B0  00 D7 19 59 59 E9 AA 00-1E B8 91 15 50 9A 0A 00   ...YY.......P...
1817:58C0  D7 19 59 59 E9 9B 00 1E-B8 99 15 50 9A 0A 00 D7   ..YY.......P....
1817:58D0  19 59 59 E9 8C 00 1E B8-A1 15 50 9A 0A 00 D7 19   .YY.......P.....
1817:58E0  59 59 E9 7D 00 1E B8 AA-15 50 9A 0A 00 D7 19 59   YY.}.....P.....Y
1817:58F0  59 EB 6F 1E B8 B3 15 50-9A 0A 00 D7 19 59 59 EB   Y.o....P.....YY.
1817:5900  61 1E B8 BC 15 50 9A 0A-00 D7 19 59 59 EB 53 1E   a....P.....YY.S.
1817:5910  B8 C5 15 50 9A 0A 00 D7-19 59 59 EB 45 1E B8 CE   ...P.....YY.E...
1817:5920  15 50 9A 0A 00 D7 19 59-59 EB 37 1E B8 D7 15 50   .P.....YY.7....P
1817:5930  9A 0A 00 D7 19 59 59 B8-02 00 50 9A 36 03 A2 1A   .....YY...P.6...
1817:5940  59 FF 36 1F 0C 1E B8 E0-15 50 9A 05 00 A8 2C 83   Y.6......P....,.
1817:5950  C4 06 EB 0E 1E B8 E3 15-50 9A 0A 00 D7 19 59 59   .........P.....YY
1817:5960  EB 00 B3 01 00 50 9A 36-03 A2 1A 59 56 1E B8 EA   .....P.6...YV...
1817:5970  15 50 9A 05 00 A8 2C 83-C4 06 B8 18 00 50 9A 30   .P...........P.0
1817:5980  0E A2 1A 59 9A FC 0D A2-1A 9A 70 06 A2 1A 3D 01   ...Y......p...=.
1817:5990  00 75 22 9A CE 05 A2 1A-1E B8 ED 15 50 9A 0A 00   .u".........P...
1817:59A0  D7 19 59 59 B8 01 00 50-1E 53 F6 47 50 9A 3B 00   ..YY...P...GP.;.
1817:59B0  30 2E 83 C4 06 EB CD 5E-5D CB 55 8B EC 83 EC 02   0......^].U.....
1817:59C0  56 39 26 98 0D 77 05 9A-CF 09 17 18 1E B8 F6 15   V9&..w..........
1817:59D0  50 9A 0A 00 D7 19 59 59-83 3E 4C 0C 00 75 24 EB   P.....YY.>L..u$.
1817:59E0  05 9A A1 06 A2 1A 9A 40-06 A2 1A 88 46 FF 3C 0D   .......@....F.<.
1817:59F0  74 06 80 7E FF 08 75 E9-80 7E FF 08 75 05 33 C0   t..~..u..~..u.3.
1817:5A00  E9 32 01 1E B8 FD 15 50-9A 0A 00 D7 19 59 59 9A   .2.....P.....YY.
1817:5A10  61 00 10 1D 1E B8 06 16-50 9A 0A 00 D7 19 59 59   a.......P.....YY
1817:5A20  EB 22 9A 70 06 A2 1A 3D-01 00 75 0F 9A CE 05 A2   .".p...=..u.....
1817:5A30  1A 3D 08 00 75 05 33 C0-E9 FA 00 33 C0 50 9A 39   .=..u.3....3.P.9
1817:5A40  04 A2 1A 59 8A 12 03 EC-A8 80 74 07 83 3E 4C 0C   ...Y......t..>L.
1817:5A50  00 74 CF 9A 04 08 A2 1A-FF 36 3D 6E 9A E1 00 10   .t.......6=n....
1817:5A60  1D 59 C7 06 32 0D A3 61-83 3E 4C 0C 00 74 03 E9   .Y..2..a.>L..t..
1817:5A70  9E 00 C6 46 FF 61 C7 06-97 00 00 00 C7 06 95 00   ...F.a..........
1817:5A80  02 00 33 F6 EB 4A 9A 70-06 A2 1A 08 C0 74 08 9A   ..3..J.p.....t..
```

```
1817:5A90  CE 05 A2 1A 8B 46 FF A1-95 00 0B 06 97 00 75 30   .....F........u0
1817:5AA0  C7 06 97 00 00 00 C7 06-95 00 02 00 F7 06 43 0C   ..............C.
1817:5AB0  01 00 75 0F 8A 0E 03 EC-A8 05 75 03 46 EB 02 33   ..u.......u.F..3
1817:5AC0  F6 EB 0D 8A 0E 03 EC A8-08 74 03 46 EB 02 33 F6   .........t.F..3.
1817:5AD0  83 FE 08 7D 0D 80 7E FF-08 74 07 83 3E 32 0D 00   ...}..~..t..>2..
1817:5AE0  75 A4 80 7E FF 08 75 03-E9 E1 FE 83 3E 32 0D 00   u..~..u.....>2..
1817:5AF0  75 19 1E B8 0F 16 50 9A-0A 00 D7 19 59 59 B8 01   u.....P.....YY..
1817:5B00  00 50 9A 35 07 A2 1A 59-E9 C1 FE 9A A1 06 A2 1A   .P.5...Y........
1817:5B10  F7 06 43 0C 04 00 74 19-C7 06 32 0D C4 09 EB 09   ..C...t...2.....
1817:5B20  33 C0 50 9A 39 04 A2 1A-59 83 3E 32 0D 00 75 F0   3.P.9...Y.>2..u.
1817:5B30  B8 01 00 E8 00 5E 8B E5-5D CB 55 8B EC 81 EC 38   .....^..].U.....
1817:5B40  00 56 57 3B EC 72 06 39-26 98 0D 77 05 9A CF 09   .VW:.r.9%..w....
1817:5B50  17 18 95 16 DE 47 A1 DC-47 52 50 CD 37 86 20 FF   .....G..GRP.7. .
1817:5B60  CD 3D 83 C4 04 CD 39 9E-70 FF CD 3D EB 16 E6 47   .=....9.p..=...G
1817:5B70  A1 E4 47 52 50 CD 37 86-20 FF CD 3D 83 C4 04 CD   ..GRP.7. ..=....
1817:5B80  39 9E 78 FF CD 3D 8B 16-EA 47 A1 E8 47 52 50 CD   9.x..=...G..GRP.
1817:5B90  37 86 20 FF CD 3D 83 C4-04 CD 39 5E 80 CD 3D 8B   7. ..=....9^..=.
1817:5BA0  16 E2 47 A1 E0 47 52 50-CD 37 86 20 FF CD 3D 83   ..G..GRP.7. ..=.
1817:5BB0  C4 04 CD 39 5E 99 CD 3D-8B 16 EE 47 A1 EC 47 52   ...9^..=...G..GR
1817:5BC0  50 CD 37 86 20 FF CD 3D-83 C4 04 CD 39 5E 90 CD   P.7. ..=....9^..
1817:5BD0  3D 8B 16 F2 47 A1 F0 47-52 50 CD 37 86 20 FF CD   =...G..GRP.7. ..
1817:5BE0  3D 83 C4 04 CD 39 5E 99-CD 3D 9A A9 03 ED 22 9A   =....9^..=....".
1817:5BF0  FE 00 A4 20 8B F0 8B C6-0B C0 74 07 56 9A 07 00   ... ......t.V...
1817:5C00  72 1D 59 C7 86 2A FF 00-00 8B 16 56 43 A1 54 43   r.Y..*.....VC.TC
1817:5C10  52 50 CD 37 86 20 FF CD-3D 83 C4 04 CD 39 9E 60   RP.7. ..=....9.`
1817:5C20  FF CD 3D 8B 16 5A 43 A1-58 43 52 50 CD 37 86 20   ..=..ZC.XCRP.7.
1817:5C30  FF CD 3D 83 C4 04 CD 39-9E 58 FF CD 3D C7 06 03   ..=....9.X..=...
1817:5C40  01 00 00 E9 D9 00 33 FF-EB 31 A1 03 01 BA E0 00   ......3..1......
1817:5C50  F7 E2 8B D8 81 C3 8C 4A-1E 07 8B C7 D1 E0 D1 E0   .......J........
1817:5C60  03 D8 26 C7 47 1A 00 00-26 C7 47 18 00 00 8B 1E   ..&.G...&.G.....
1817:5C70  03 01 D1 E3 C7 87 25 6E-01 00 47 3B 3E F7 00 7C   ......%n..G;>..|
1817:5C80  C9 C7 86 30 FF 00 00 EB-04 FF 86 30 FF 83 BE 30   ...0.......0...0
1817:5C90  FF 15 7D 16 8B 9E 30 FF-D1 E3 8B 87 50 0C 8B 1E   ..}...0.....P...
1817:5CA0  03 01 D1 E3 3B 87 0D 6E-75 DF 83 BE 30 FF 15 75   ....;..nu...0..u
1817:5CB0  2A 8B 1E 03 01 D1 E3 D1-E3 C7 87 B4 6E 00 00 C7   *...........n...
1817:5CC0  87 B2 6E 00 00 8B 1E 03-01 D1 E3 D1 E3 C7 87 B4   ..n.............
1817:5CD0  6E 00 00 C7 87 B2 6E 00-FA EB 40 8B 9E 30 FF D1   n.....n...@..0..
1817:5CE0  E3 D1 E3 8B 97 D0 0C 89-97 CE 0C 8B 1E 03 01 D1   ................
1817:5CF0  E3 D1 E3 89 97 B4 6E 89-97 B2 6E 8B 9E 30 FF D1   ......n...n..0..
1817:5D00  E3 D1 E3 8B 97 7C 0C 89-97 7A 0C 8B 1E 03 01 D1   .....|...z......
1817:5D10  E3 D1 E3 89 97 B4 6E 89-97 B2 6E FF 06 03 01 83   ......n...n.....
1817:5D20  3E 03 01 0C 7D 03 E9 1D-FF 9A 75 00 A4 27 3D 2B   >...}......u..'=+
1817:5D30  00 75 06 E8 2B 00 E9 2B-1F C7 06 03 01 00 00 B8   .u..+..+........
1817:5D40  07 00 50 9A D7 0D A2 1A-59 C7 86 2C FF 00 00 B8   ..P.....Y.......
1817:5D50  03 00 50 33 C0 50 9A F7-02 A2 1A 59 59 8B 1E 03   ..P3.P.....YY...
1817:5D60  01 D1 E3 D1 E3 C7 87 41-6E 02 00 C7 87 3F 6E 48   .......An....?nH
1817:5D70  65 EB 09 33 C0 50 9A 39-04 A2 1A 59 8B 1E 03 01   e..3.P.9...Y....
1817:5D80  D1 E3 D1 E3 8B 97 41 6E-8B 87 3F 6E 3B 16 56 0D   ......An..?n;.V.
1817:5D90  7F E1 75 06 3B 06 54 0D-77 D9 16 8D 86 34 FF 50   ..u.;.T.w....4.P
1817:5DA0  9A EE 0C A2 1A 59 59 89-96 28 FF 0B C0 74 36 83   .....YY..(...t6.
1817:5DB0  3E D1 00 01 75 0C 1E B8-19 16 50 9A 05 00 A8 2C   >...u.....P....,
1817:5DC0  59 59 9A A1 06 A2 1A C7-06 1A 4A 00 00 C7 06 18   YY........J.....
1817:5DD0  4A 00 00 FF 86 2C FF 8B-86 2C FF 3D 04 00 7D 03   J.....,..,.=..}.
1817:5DE0  E9 6C FF E8 0F 8B 96 36-FF 8B 86 34 FF 89 16 1A   .l.....6...4....
1817:5DF0  4A A3 18 4A 33 C0 50 9A-D7 0D A2 1A 59 C7 86 2C   J..J3.P.....Y..,
1817:5E00  FF 00 00 B8 01 00 50 B8-0E 00 50 9A F7 02 A2 1A   ......P...P.....
1817:5E10  59 59 8B 1E 03 01 D1 E3-D1 E3 C7 87 41 6E 02 00   YY..........An..
1817:5E20  C7 87 3F 6E 48 65 EB 09-33 C0 50 9A 39 04 A2 1A   ..?nHe..3.P.9...
1817:5E30  59 8B 1E 03 01 D1 E3 D1-E3 8B 97 41 6E 8B 87 3F   Y...........An..?
1817:5E40  6E 3B 16 56 0D 7F E1 75-06 3B 06 54 0D 77 D9 16   n;.V...u.;.T.w..
1817:5E50  8D 86 34 FF 50 9A EE 0C-A2 1A 59 59 89 86 28 FF   ..4.P.....YY..(.
1817:5E60  0B C0 74 31 83 3E D1 00-01 75 0C 1E B8 2B 16 50   ..t1.>...u...+.P
1817:5E70  9A 05 00 A8 2C 59 59 C7-06 2A 4A 00 00 C7 06 28   ....,YY..*J....(
1817:5E80  4A 00 00 FF 86 2C FF 8B-86 2C FF 3D 04 00 7D 03   J.....,....=..}.
1817:5E90  E9 70 FF E8 0F 8B 96 36-FF 8B 86 34 FF 89 16 2A   .p.....6...4...*
1817:5EA0  4A A3 28 4A 8B 16 2A 4A-A1 28 4A 89 16 3E 55 A3   J.(J..*J.(J..>U.
1817:5EB0  3C 55 B8 01 00 50 9A D7-0D A2 1A 59 C7 86 2C FF   <U...P.....Y..,.
1817:5EC0  00 00 B8 03 00 50 B8 09-00 50 9A F7 02 A2 1A 59   .....P...P.....Y
1817:5ED0  59 8B 1E 03 01 D1 E3 D1-E3 C7 87 41 6E 02 00 C7   Y...........An...
1817:5EE0  87 3F 6E 48 65 EB 09 33-C0 50 9A 39 04 A2 1A 59   .?nHe..3.P.9...Y
1817:5EF0  8B 1E 03 01 D1 E3 D1 E3-8B 97 41 6E 8B 87 3F 6E   ..........An..?n
```

```
1817:5F00  3B 16 56 0D 7F E1 75 06-3B 06 54 0D 77 D9 16 8D   ;.V...u.;.T.w...
1817:5F10  86 48 FF 50 9A EE 0C A2-1A 59 59 89 86 28 FF 0B   .H.P.....YY..(..
1817:5F20  C0 74 3D 83 3E D1 00 01-75 0C 1E 83 3D 16 50 9A   .t=.>...u...=.P.
1817:5F30  05 00 A8 2C 59 59 9A A1-06 A2 1A C7 06 22 4A 00   ...,YY......."J.
1817:5F40  00 C7 06 20 4A 50 C3 FF-86 2C FF 9B 86 2C FF 3D   ... JP..,......=
1817:5F50  04 00 7D 03 E9 6B FF 56-9A 07 00 72 1D 59 EB 0F   ..}..k.V...r.Y..
1817:5F60  8B 96 4A FF 8B 86 48 FF-89 16 22 4A A3 20 4A 8B   ..J...H..."J. J.
1817:5F70  16 3E 55 A1 3C 55 29 86-48 FF 19 96 4A FF 8B 96   .>U.<U).H...J...
1817:5F80  4A FF 8B 86 48 FF 52 50-CD 37 86 20 FF CD 3D 83   J...H.RP.7. ..*.
1817:5F90  C4 04 CD 39 9E 68 FF CD-3D 9A 7F 13 A2 1A 8B F0   ...9.h..=.......
1817:5FA0  8B C6 0B C0 74 07 56 9A-07 00 72 1D 59 9A 75 00   ....t.V...r.Y.u.
1817:5FB0  A4 27 3D 2B 00 75 06 8B-2B 00 E9 A7 1C C7 06 03   .'=+.u..+.......
1817:5FC0  01 06 00 B8 04 00 50 9A-21 00 6B 1C 59 33 C0 50   ......P.!.k.Y3.P
1817:5FD0  9A 55 0C A2 1A 59 33 C0-50 9A FD 0B A2 1A 59 8B   .U...Y3.P.....Y.
1817:5FE0  1E 03 01 D1 E3 D1 E3 C7-87 41 6E 02 00 C7 87 3F   ..........An....?
1817:5FF0  6E 48 65 EB 00 8B 1E 03-01 D1 E3 D1 E3 8B 97 41   nHe............A
1817:6000  6E 8B 87 3F 6E 3B 16 56-0D 7F EA 75 06 3B 06 54   n..?n;.V...u.;.T
1817:6010  0D 77 E2 16 8D 86 4C FF-50 9A EE 0C A2 1A 59 59   .w....L.P.....YY
1817:6020  8B F0 8B C6 0B C0 74 11-C7 06 05 01 00 00 C7 06   ......t.........
1817:6030  07 01 00 00 8B C6 E9 2B-1C 9A E4 0B A2 1A 8B 16   .......+........
1817:6040  3E 55 A1 3C 55 29 86 4C-FF 19 96 4E FF 8B 96 4E   >U.<U).L...N...N
1817:6050  FF 8B 86 4C FF 52 50 CD-37 86 20 FF CD 3D 83 C4   ...L.RP.7. ..=..
1817:6060  04 CD 39 5E A0 CD 3D B8-01 00 50 9A 55 0C A2 1A   ..9^..=...P.U...
1817:6070  59 B8 01 00 50 9A FD 0B-A2 1A 59 8B 1E 03 01 D1   Y...P.....Y.....
1817:6080  E3 D1 E3 C7 87 41 6E 02-00 C7 87 3F 6E 48 65 EB   .....An....?nHe.
1817:6090  00 8B 1E 03 01 D1 E3 D1-E3 8B 97 41 6E 8B 87 3F   ............An..?
1817:60A0  6E 3B 16 56 0D 7F EA 75-06 3B 06 54 0D 77 E2 16   n;.V...u.;.T.w..
1817:60B0  8D 86 4C FF 50 9A EE 0C-A2 1A 59 59 8B F0 8B C6   ..L.P.....YY....
1817:60C0  0B C0 74 11 C7 06 05 01-00 00 C7 06 07 01 00 00   ..t.............
1817:60D0  8B C6 E9 8F 1B 9A E4 0B-A2 1A 8B 16 3E 55 A1 3C   ............>U.<
1817:60E0  55 29 86 4C FF 19 96 4E-FF 8B 96 4E FF 8B 86 4C   U).L...N...N...L
1817:60F0  FF 52 50 CD 37 86 20 FF-CD 3D 83 C4 04 CD 39 5E   .RP.7. ..=....9^
1817:6100  B0 CD 3D B8 02 00 50 9A-55 0C A2 1A 59 B8 02 00   ..=...P.U...Y...
1817:6110  50 9A FD 0B A2 1A 59 8B-1E 03 01 D1 E3 D1 E3 C7   P.....Y.........
1817:6120  87 41 6E 02 00 C7 87 3F-6E 48 65 EB 00 8B 1E 03   .An....?nHe.....
1817:6130  01 D1 E3 D1 E3 8B 97 41-6E 8B 87 3F 6E 3B 16 56   .......An..?n;.V
1817:6140  0D 7F EA 75 06 3B 06 54-0D 77 E2 16 8D 86 4C FF   ...u.;.T.w....L.
1817:6150  50 9A EE 0C A2 1A 59 59-8B F0 8B C6 0B C0 74 03   P.....YY......t.
1817:6160  E9 61 FF 9A E4 0B A2 1A-8B 16 3E 55 A1 3C 55 29   .a........>U.<U)
1817:6170  86 4C FF 19 96 4E FF 8B-96 4E FF 8B 86 4C FF 52   .L...N...N...L.R
1817:6180  50 CD 37 86 20 FF CD 3D-83 C4 04 CD 39 5E A8 CD   P.7. ..=....9^..
1817:6190  3D B8 03 00 50 9A 55 0C-A2 1A 59 B8 03 00 50 9A   =...P.U...Y...P.
1817:61A0  FD 0B A2 1A 59 8B 1E 03-01 D1 E3 D1 E3 C7 87 41   ....Y..........A
1817:61B0  6E 02 00 C7 87 3F 6E 48-65 EB 00 8B 1E 03 01 D1   n....?nHe.......
1817:61C0  E3 D1 E3 8B 97 41 6E 8B-87 3F 6E 3B 16 56 0D 7F   .....An..?n;.V..
1817:61D0  EA 75 06 3B 06 54 0D 77-E2 16 8D 86 4C FF 50 9A   .u.;.T.w....L.P.
1817:61E0  EE 0C A2 1A 59 59 8B F0-8B C6 0B C0 74 03 E9 D3   ....YY......t...
1817:61F0  FE 9A E4 0B A2 1A 8B 16-3E 55 A1 3C 55 29 86 4C   ........>U.<U).L
1817:6200  FF 19 96 4E FF 8B 96 4E-FF 8B 86 4C FF 52 50 CD   ...N...N...L.RP.
1817:6210  37 86 20 FF CD 3D 83 C4-04 CD 39 5E B8 CD 3D B8   7. ..=....9^..=.
1817:6220  0B 00 50 9A 21 00 6B 1C-59 B8 03 00 50 9A 55 0C   ..P.!.k.Y...P.U.
1817:6230  A2 1A 59 8B 1E 03 01 D1-E3 D1 E3 C7 87 41 6E 02   ..Y..........An.
1817:6240  00 C7 87 3F 6E 48 65 EB-00 8B 1E 03 01 D1 E3 D1   ...?nHe.........
1817:6250  E3 8B 97 41 6E 8B 87 3F-6E 3B 16 56 0D 7F EA 75   ...An..?n;.V...u
1817:6260  06 3B 06 54 0D 77 E2 16-8D 86 4C FF 50 9A EE 0C   .;.T.w....L.P...
1817:6270  A2 1A 59 59 8B F0 8B C6-0B C0 74 03 E9 45 FE 8B   ..YY......t..E..
1817:6280  16 3E 55 A1 3C 55 29 86-4C FF 19 96 4E FF 8B 96   .>U.<U).L...N...
1817:6290  4E FF 8B 86 4C FF 52 50-CD 37 86 20 FF CD 3D 83   N...L.RP.7. ..*.
1817:62A0  C4 04 CD 39 5E C0 CD 3D-B8 0C 00 50 9A 21 00 6B   ...9^..=...P.!.k
1817:62B0  1C 59 B8 04 00 50 9A 55-0C A2 1A 59 8B 1E 03 01   .Y...P.U...Y....
1817:62C0  D1 E3 D1 E3 C7 87 41 6E-02 00 C7 87 3F 6E 48 65   ......An....?nHe
1817:62D0  EB 00 8B 1E 03 01 D1 E3-D1 E3 8B 97 41 6E 8B 87   ............An..
1817:62E0  3F 6E 3B 16 56 0D 7F EA-75 06 3B 06 54 0D 77 E2   ?n;.V...u.;.T.w.
1817:62F0  16 8D 86 4C FF 50 9A EE-0C A2 1A 59 59 8B F0 8B   ...L.P.....YY...
1817:6300  C6 0B C0 74 03 E9 8C FD-8B 16 3E 55 A1 3C 55 29   ...t......>U.<U)
1817:6310  86 4C FF 19 96 4E FF 8B-96 4E FF 8B 86 4C FF 52   .L...N...N...L.R
1817:6320  50 CD 37 86 20 FF CD 3D-83 C4 04 CD 39 5E C8 CD   P.7. ..=....9^..
1817:6330  3D C7 86 28 FF 00 00 C7-06 03 01 00 00 E9 C6 01   =..(............
1817:6340  9A 75 00 A4 27 3D 2B 00-75 06 8B 2B 00 E9 14 19   .u..'=+.u..+....
1817:6350  8B 1E 03 01 D1 E3 C7 87-F5 6D 00 00 8B 1E 03 01   .........m......
1817:6360  D1 E3 83 BF 0D 6E 64 75-03 E9 96 01 8B 1E 03 01   .....ndu........
```

```
1817:6370  D1 E3 8B 87 0D 6E 8A 1C-00 F7 E2 8B D8 81 C3 0D   .....n..........
1817:6380  01 1E 07 26 FF 37 9A 9A-0C A2 1A 59 8B 1E 03 01   ...&.7.....Y....
1817:6390  D1 E3 8B 87 0D 6E 8A 1C-00 F7 E2 8B D8 81 C3 0D   .....n..........
1817:63A0  01 1E 07 26 FF 37 9A 55-0C A2 1A 59 8B 1E 03 01   ...&.7.U...Y....
1817:63B0  D1 E3 8B 87 0D 6E 8A 1C-00 F7 E2 8B D8 81 C3 0D   .....n..........
1817:63C0  01 1E 07 26 FF 37 9A FD-0B A2 1A 59 8B 1E 03 01   ...&.7.....Y....
1817:63D0  D1 E3 D1 E3 C7 87 41 6E-02 00 C7 87 3F 6E 48 65   ......An....?nHe
1817:63E0  E8 09 33 C0 50 9A 39 04-A2 1A 59 8B 1E 03 01 D1   ..3.P.9...Y.....
1817:63F0  E3 D1 E3 8B 97 41 6E 8B-87 3F 6E 3B 16 56 0D 7F   .....An..?n;.V..
1817:6400  E1 75 06 3B 06 54 0D 77-D9 C7 86 2C FF 00 00 16   .u.;.T.w...,....
1817:6410  8D 86 34 FF 50 9A EE 0C-A2 1A 59 59 89 86 28 FF   ..4.P.....YY..(.
1817:6420  0B C0 74 33 A1 03 01 8A-E0 00 F7 E2 8B D8 81 C3   ..t3............
1817:6430  8C 4A 1E 07 26 C7 47 16-00 00 26 C7 47 14 8C 7F   .J..&.G...&.G...
1817:6440  FF 86 2C FF 83 96 2C FF-3D 04 00 7D 02 EB C0 9A   .......,.=..}....
1817:6450  A1 06 A2 1A E9 A6 00 8B-16 3E 55 A1 3C 55 29 86   ..........>U.<U).
1817:6460  34 FF 19 96 36 FF 8B 96-36 FF 3B 86 34 FF 52 50   4...6...6...4.RP
1817:6470  CD 37 86 20 FF CD 3D 83-C4 04 CD 39 9E 50 FF CD   .7. ..=....9.P..
1817:6480  3D 8B 1E 03 01 D1 E3 8B-87 0D 6E 8A 1C 00 F7 E2   =.........n.....
1817:6490  8B D8 81 C3 0D 01 1E 07-26 83 3F 03 7D 07 CD 39   ........&.?.}..9
1817:64A0  86 60 FF EB 05 CD 39 86-58 FF CD 38 86 68 FF CD   .`....9.X..8.h..
1817:64B0  38 8E 50 FF CD 39 9E 50-FF CD 3D CD 39 86 50 FF   8.P..9.P..=.9.P.
1817:64C0  9A C7 05 17 18 89 96 36-FF 89 86 34 FF 8B 96 36   .......6...4...6
1817:64D0  FF 8B 86 34 FF 52 50 A1-03 01 8A E0 00 F7 E2 8B   ...4.RP.........
1817:64E0  D8 81 C3 8C 4A 1E 07 58-5A 26 89 57 16 26 89 47   ....J..XZ&.W.&.G
1817:64F0  14 8B 1E 03 01 D1 E3 C7-87 F5 6D 01 00 9A E4 0B   ..........m.....
1817:6500  A2 1A FF 06 03 01 83 3E-03 01 0C 7D 03 E9 30 FE   ........>...}..0.
1817:6510  9A 98 00 A4 20 8B F0 8B-C6 0B C0 74 07 56 9A 07   .... ......t.V..
1817:6520  00 72 1D 59 9A 7F 13 A2-1A 8B F0 8B C6 0B C0 74   .r.Y...........t
1817:6530  07 56 9A 07 00 72 1D 59-C7 06 03 01 00 00 8B 03   .V...r.Y........
1817:6540  00 50 9A 21 00 6B 1C 59-9A 0A 00 B2 1D 0B C0 75   .P.!.k.Y.......u
1817:6550  2F 1E B8 4F 16 50 9A 0A-00 D7 19 59 59 33 C0 50   /..O.P.....YY3.P
1817:6560  B8 01 00 50 9A 0C 00 CF-20 59 59 8B F0 8B C6 0B   ...P.... YY.....
1817:6570  C0 74 07 56 9A 07 00 72-1D 59 B8 2B 00 E9 E4 16   .t.V...r.Y.+....
1817:6580  1E B8 58 16 50 9A 0A 00-D7 19 59 59 C7 06 07 01   ..X.P.....YY....
1817:6590  14 00 C7 06 05 01 09 00-9A 0B 00 A4 27 C7 86 42   ...........'..B
1817:65A0  FF 02 00 C7 86 40 FF 7D-62 C7 86 46 FF 02 00 C7   .....@.}b..F....
1817:65B0  86 44 FF 01 63 C7 06 03-01 00 00 E9 57 01 B8 03   .D..c.......W...
1817:65C0  00 50 9A 21 00 6B 1C 59-83 3E 03 01 00 74 48 8B   .P.!.k.Y.>...tH.
1817:65D0  1E 03 01 4B D1 E3 D1 E3-8B 97 41 6E 8B 87 3F 6E   ...K......An..?n
1817:65E0  3B 96 42 FF 7F 12 7C 06-3B 86 40 FF 73 0A B8 14   ;.B...|.;.@.s...
1817:65F0  00 50 9A 07 00 72 1D 59-EB 00 8B 1E 03 01 4B D1   .P...r.Y......K.
1817:6600  E3 D1 E3 8B 97 41 6E 8B-87 3F 6E 3B 96 42 FF 75   .....An..?n;.B.u
1817:6610  E9 3B 86 40 FF 75 E3 8B-1E 03 01 D1 E3 D1 E3 C7   .;.@.u..........
1817:6620  87 41 6E 02 00 C7 87 3F-6E 48 65 8B 1E 03 01 D1   .An....?nHe.....
1817:6630  E3 83 BF 0D 6E 64 75 03-E9 7E 00 F7 06 43 0C 02   ....ndu..~...C..
1817:6640  00 74 6C F7 06 43 0C 01-00 75 08 8A 0E 03 EC A8   .tl..C...u......
1817:6650  08 75 10 F7 06 43 0C 01-00 74 54 8A 0E 03 EC A8   .u...C...tT.....
1817:6660  08 75 4C 1E B8 61 16 50-9A 0A 00 D7 19 59 59 C7   .uL..a.P.....YY.
1817:6670  06 05 01 00 00 C7 06 07-01 00 00 9A 40 03 A2 1A   ............@...
1817:6680  1E B8 6A 16 50 9A 0A 00-D7 19 59 59 33 C0 50 B8   ..j.P.....YY3.P.
1817:6690  01 00 50 9A 0C 00 CF 20-59 59 8B F0 8B C6 0B C0   ..P.... YY......
1817:66A0  74 07 56 9A 07 00 72 1D-59 B8 2B 00 E9 B5 15 9A   t.V...r.Y.+.....
1817:66B0  6E 01 10 1D 9A F7 03 10-1D 9A 75 00 A4 27 3D 2B   n.........u..'=+
1817:66C0  00 75 06 B8 2B 00 E9 9B-15 8B 1E 03 01 D1 E3 D1   .u..+...........
1817:66D0  E3 8B 97 41 6E 8B 87 3F-6E 3B 96 46 FF 7F 12 75   ...An..?n;.F...u
1817:66E0  06 3B 86 44 FF 77 0A B8-15 00 50 9A 07 00 72 1D   .;.D.w....P...r.
1817:66F0  59 EB 00 8B 1E 03 01 D1-E3 D1 E3 8B 97 41 6E 8B   Y............An.
1817:6700  87 3F 6E 3B 96 46 FF 7F-EA 75 06 3B 86 44 FF 77   .?n;.F...u.;.D.w
1817:6710  E2 FF 06 03 01 83 3E 03-01 0C 7D 03 E9 9F FE 9A   ......>...}.....
1817:6720  F8 00 A4 20 8B F0 8B C6-0B C0 74 07 56 9A 07 00   ... ......t.V...
1817:6730  72 1D 59 9A DA 01 10 1D-83 3E CF 00 01 75 30 C7   r.Y......>...u0.
1817:6740  06 05 01 00 00 C7 06 07-01 08 00 33 C0 50 B8 01   ...........3.P..
1817:6750  00 50 9A 0C 00 CF 20 59-59 8B F0 8B C6 0B C0 74   .P.... YY......t
1817:6760  07 56 9A 07 00 72 1D 59-8B 86 2A FF E9 F5 14 83   .V...r.Y..*.....
1817:6770  3E 5A 0D 01 75 03 E9 8E-02 C7 06 03 01 00 00 C7   >Z..u...........
1817:6780  86 28 FF 00 00 33 FF E9-4E 02 8B 1E 03 01 D1 E3   .(...3..N.......
1817:6790  83 BF 0D 6E 64 75 03 E9-F3 01 8B 1E 03 01 D1 E3   ...ndu..........
1817:67A0  83 BF F5 6D 01 74 03 E9-E3 01 8B 1E 03 01 D1 E3   ...m.t..........
1817:67B0  8B 87 0D 6E 8A 1C 00 F7-E2 8B D8 81 C3 0D 01 1E   ...n............
1817:67C0  07 26 FF 37 9A 9A 0C A2-1A 59 E8 00 33 D2 B8 6C   .&.7.....Y..3..l
1817:67D0  21 52 50 8B 1E 03 01 D1-E3 D1 E3 FF B7 41 6E FF   !RP..........An.
```

```
1817:67E0  B7 3F 6E 9A 23 09 17 18-0B D2 7F E0 75 05 3D 64   .?n.#.......u.=d
1817:67F0  00 77 D9 EB 00 33 D2 B8-6C 21 52 50 8B 1E 03 01   .w...3..l!RP....
1817:6800  D1 E3 D1 E3 FF B7 41 6E-FF B7 3F 6E 9A 23 09 17   ......An..?n.#..
1817:6810  18 0B D0 75 E0 8B 1E 03-01 D1 E3 8B 87 0D 6E BA   ...u..........n.
1817:6820  1C 00 F7 E2 8B D8 81 C3-0D 01 1E 07 26 FF 37 9A   ............&.7.
1817:6830  55 0C A2 1A 59 8B 1E 03-01 D1 E3 8B 87 0D 6E BA   U...Y.........n.
1817:6840  1C 00 F7 E2 8B D8 81 C3-0D 01 1E 07 26 FF 37 9A   ............&.7.
1817:6850  FD 0B A2 1A 59 C7 86 42-FF 00 00 C7 86 40 FF 36   ....Y..B.....@.6
1817:6860  21 EB 00 33 D2 B8 6C 21-52 50 8B 1E 03 01 D1 E3   !..3..l!RP......
1817:6870  D1 E3 FF B7 41 6E FF B7-3F 6E 9A 23 09 17 18 3B   ....An..?n.#...;
1817:6880  96 42 FF 75 DE 3B 86 40-FF 75 D8 16 8D 86 34 FF   .B.u.;.@.u....4.
1817:6890  50 9A EE 0C A2 1A 59 59-89 86 28 FF 0B C0 74 33   P.....YY..(...t3
1817:68A0  A1 03 01 BA E0 00 F7 E2-8B D8 81 C3 BC 4A 1E 07   .............J..
1817:68B0  8B C7 D1 E0 D1 E0 03 D8-26 C7 47 1A 00 00 26 C7   ........&.G...&.
1817:68C0  47 18 01 00 8B 1E 03 01-D1 E3 C7 87 F5 6D 00 00   G............m..
1817:68D0  E9 B3 00 8B 16 3E 55 A1-3C 55 29 86 34 FF 19 96   .....>U.<U).4...
1817:68E0  36 FF 8B 96 36 FF 8B 86-34 FF 52 50 CD 37 86 20   6...6...4.RP.7.
1817:68F0  FF CD 3D 83 C4 04 CD 39-9E 50 FF CD 3D 8B 1E 03   ..=....9.P..=...
1817:6900  01 D1 E3 8B 87 0D 6E BA-1C 00 F7 E2 8B D8 81 C3   ......n.........
1817:6910  0D 01 1E 07 26 83 3F 03-7D 07 CD 39 86 60 FF EB   ....&.?.}..9.`..
1817:6920  05 CD 39 86 58 FF CD 38-86 68 FF CD 38 8E 50 FF   ..9.X..8.h..8.P.
1817:6930  CD 39 9E 50 FF CD 3D CD-39 86 50 FF 9A C7 05 17   .9.P..=.9.P.....
1817:6940  18 89 96 36 FF 89 86 34-FF FF B6 36 FF FF B6 34   ...6...4...6...4
1817:6950  FF 57 9A 3A 21 CA 1D 83-C4 06 8B 96 36 FF 8B 86   .W.:!.......6...
1817:6960  34 FF 52 50 A1 03 01 BA-E0 00 F7 E2 8B D8 81 C3   4.RP............
1817:6970  BC 4A 1E 07 8B C7 D1 E0-D1 E0 03 D8 58 5A 26 89   .J..........XZ&.
1817:6980  57 1A 26 89 47 18 9A E4-0B A2 1A EB 32 33 C0 50   W.&.G.......23.P
1817:6990  9A 9A 0C A2 1A 59 EB 00-33 D2 B8 6C 21 52 50 8B   .....Y..3..l!RP.
1817:69A0  1E 03 01 D1 E3 D1 E3 FF-B7 41 6E FF B7 3F 6E 9A   .........An..?n.
1817:69B0  23 09 17 18 0B D2 7F E0-75 05 3D 64 00 77 D9 FF   #.......u.=d.w..
1817:69C0  06 03 01 A1 03 01 B3 0C-00 99 F7 FB 89 16 03 01   ................
1817:69D0  83 3E 03 01 00 75 01 47-3B 3E F7 00 7D 26 83 BE   .>...u.G;>..}&..
1817:69E0  28 FF 00 75 1F 8B 1E 03-01 D1 E3 D1 E3 83 BF 41   (..u...........A
1817:69F0  6E 00 7E 03 E9 93 FD 75-0B 81 BF 3F 6E 35 24 76   n.~....u...?n5$v
1817:6A00  03 E9 86 FD E9 A2 04 C7-06 03 01 00 00 C7 86 28   ...............(
1817:6A10  FF 00 00 33 FF E9 26 02-8B 1E 03 01 D1 E3 83 BF   ...3..&.........
1817:6A20  0D 6E 64 75 03 E9 CA 01-8B 1E 03 01 D1 E3 83 BF   .ndu............
1817:6A30  F5 6D 01 74 03 E9 2A 01-8B 1E 03 01 D1 E3 8B 87   .m.t............
1817:6A40  0D 6E BA 1C 00 F7 E2 8B-D8 81 C3 0D 01 1E 07 26   .n.............&
1817:6A50  FF 37 9A 9A 0C A2 1A 59-9A 75 00 A4 27 3D 2B 00   .7.....Y.u..'=+.
1817:6A60  75 06 B3 2B 00 E9 FC 11-EB 00 33 D2 B8 6C 01 52   u..+......3..l.R
1817:6A70  50 FF 36 41 6E FF 36 3F-6E 9A 23 09 17 18 0B D0   P.6An.6?n.#.....
1817:6A80  75 E8 8B 1E 03 01 D1 E3-8B 87 0D 6E BA 1C 00 F7   u..........n....
1817:6A90  E2 8B D8 81 C3 0D 01 1E-07 26 FF 37 9A 55 0C A2   .........&.7.U..
1817:6AA0  1A 59 8B 1E 03 01 D1 E3-8B 87 0D 6E BA 1C 00 F7   .Y.........n....
1817:6AB0  E2 8B D8 81 C3 0D 01 1E-07 26 FF 37 9A FD 0B A2   .........&.7....
1817:6AC0  1A 59 C7 86 42 FF 00 00-C7 86 40 FF 36 01 E8 00   .Y..B.....@.6...
1817:6AD0  33 D2 B8 6C 01 52 50 FF-36 41 6E FF 36 3F 6E 9A   3..l.RP.6An.6?n.
1817:6AE0  23 09 17 18 3B 96 42 FF-75 E6 3B 86 40 FF 75 E0   #...;.B.u.;.@.u.
1817:6AF0  16 8D 86 34 FF 50 9A EE-0C A2 1A 59 59 89 86 28   ...4.P.....YY..(
1817:6B00  FF 0B C0 74 33 A1 03 01-BA E0 00 F7 E2 8B D8 81   ...t3...........
1817:6B10  C3 BC 4A 1E 07 8B C7 D1-E0 D1 E0 03 D8 26 C7 47   ..J..........&.G
1817:6B20  1A 00 00 26 C7 47 18 01-00 8B 1E 03 01 D1 E3 C7   ...&.G..........
1817:6B30  87 F5 6D 00 00 E9 B3 00-8B 16 3E 55 A1 3C 55 29   ..m.......>U.<U)
1817:6B40  86 34 FF 19 96 36 FF 8B-96 36 FF 8B 86 34 FF 52   .4...6...6...4.R
1817:6B50  50 CD 37 86 20 FF CD 3D-83 C4 04 CD 39 9E 50 FF   P.7. ..=....9.P.
1817:6B60  CD 3D 8B 1E 03 01 D1 E3-8B 87 0D 6E BA 1C 00 F7   .=.........n....
1817:6B70  E2 8B D8 81 C3 0D 01 1E-07 26 83 3F 03 7D 07 CD   .........&.?.}..
1817:6B80  39 86 60 FF EB 05 CD 39-86 58 FF CD 38 B6 68 FF   9.`....9.X..8.h.
1817:6B90  CD 38 8E 50 FF CD 39 9E-50 FF CD 3D CD 39 86 50   .8.P..9.P..=.9.P
1817:6BA0  FF 9A C7 05 17 18 89 96-36 FF 89 86 34 FF FF B6   ........6...4...
1817:6BB0  36 FF FF B6 34 FF 57 9A-3A 21 CA 1D 83 C4 06 8B   6...4.W.:!......
1817:6BC0  96 36 FF 8B 86 34 FF 52-50 A1 03 01 BA E0 00 F7   .6...4.RP.......
1817:6BD0  E2 8B D8 81 C3 BC 4A 1E-07 8B C7 D1 E0 D1 E0 03   ......J.........
1817:6BE0  D8 58 5A 26 89 57 1A 26-89 47 18 9A E4 0B A2 1A   .XZ&.W.&.G......
1817:6BF0  EB 33 33 C0 50 9A 9A 0C-A2 1A 59 9A 75 00 A4 27   .33.P.....Y.u..'
1817:6C00  3D 2B 00 75 06 B8 28 00-E9 59 10 EB 00 33 D2 B8   =+.u..+..Y...3..
1817:6C10  6C 01 52 50 FF 36 41 6E-FF 36 3F 6E 9A 23 09 17   l.RP.6An.6?n.#..
1817:6C20  18 0B D0 75 E8 FF 06 03-01 A1 03 01 BB 0C 00 99   ...u............
1817:6C30  F7 FB 89 16 03 01 83 3E-03 01 00 75 01 47 A1 F7   .......>...u.G..
1817:6C40  00 48 3B C7 7E 26 83 BE-28 FF 00 75 1F 8B 1E 03   .H;.~&..(..u....
```

```
1817:6C50  01 D1 E3 D1 E3 83 BF 41-6E 00 7E 03 E9 B9 FD 75   ........An.~....u
1817:6C60  0B 81 BF 3F 6E 35 24 76-03 E9 AC FD C7 06 03 01   ...?n5$v........
1817:6C70  00 00 E9 29 02 8B 1E 03-01 D1 E3 83 BF 0D 6E 64   ...)..........nd
1817:6C80  75 03 E9 DA 01 8B 1E 03-01 D1 E3 83 BF F5 6D 01   u.............m.
1817:6C90  74 03 E9 CA 01 8B 1E 03-01 D1 E3 8B 87 0D 6E BA   t.............n.
1817:6CA0  1C 00 F7 E2 8B D8 81 C3-0D 01 1E 07 26 FF 37 9A   ............&.7.
1817:6CB0  9A 0C A2 1A 59 9A 75 00-A4 27 3D 2B 00 75 06 B8   ....Y.u..'=+.u..
1817:6CC0  2B 00 E9 9F 0F EB 00 33-D2 B9 6C 21 52 50 8B 1E   +......3..l!RP..
1817:6CD0  03 01 D1 E3 D1 E3 FF B7-41 6E FF B7 3F 6E 9A 23   ........An..?n.#
1817:6CE0  09 17 18 0B D0 75 E0 8B-1E 03 01 D1 E3 8B 87 0D   .....u..........
1817:6CF0  6E BA 1C 00 F7 E2 8B D8-81 C3 0D 01 1E 07 26 FF   n.............&.
1817:6D00  37 9A 55 0C A2 1A 59 8B-1E 03 01 D1 E3 8B 87 0D   7.U...Y.........
1817:6D10  6E BA 1C 00 F7 E2 8B D8-81 C3 0D 01 1E 07 26 FF   n.............&.
1817:6D20  37 9A FD 0B A2 1A 59 C7-86 42 FF 00 00 C7 86 40   7.....Y..B.....@
1817:6D30  FF 36 21 EB 00 33 D2 B9-6C 21 52 50 8B 1E 03 01   .6!..3..l!RP....
1817:6D40  D1 E3 D1 E3 FF B7 41 6E-FF B7 3F 6E 9A 23 09 17   ......An..?n.#..
1817:6D50  18 3B 96 42 FF 75 DE 3B-86 40 FF 75 D8 16 8D 86   .;.B.u;.@.u.....
1817:6D60  34 FF 50 9A EE 0C A2 1A-59 59 89 86 28 FF 0B C0   4.P.....YY..(...
1817:6D70  74 33 A1 03 01 BA E0 00-F7 E2 8B D8 81 C3 8C 4A   t3.............J
1817:6D80  1E 07 8B C7 D1 E0 D1 E0-03 D8 26 C7 47 1A 00 00   ..........&.G...
1817:6D90  26 C7 47 18 01 00 EB 1E-03 01 D1 E3 C7 87 F5 6D   &.G............m
1817:6DA0  00 00 E9 B3 C0 8B 16 3E-55 A1 3C 55 29 86 34 FF   .......>U.<U).4.
1817:6DB0  19 96 36 FF 8B 96 36 FF-8B 86 34 FF 52 50 CD 37   ..6...6...4.RP.7
1817:6DC0  86 20 FF CD 3D 83 C4 04-CD 39 9E 50 FF CD 3D 8B   . ..=....9.P..=.
1817:6DD0  1E 03 01 D1 E3 8B 87 0D-6E BA 1C 00 F7 E2 8B D8   ........n.......
1817:6DE0  81 C3 0D 01 1E 07 26 83-3F 03 7D 07 CD 39 86 60   ......&.?.}..9.`
1817:6DF0  FF EB 05 CD 39 86 58 FF-CD 38 86 68 FF CD 38 8E   ....9.X..8.h..8.
1817:6E00  50 FF CD 39 9E 50 FF CD-3D CD 39 86 50 FF 9A C7   P..9.P..=.9.P...
1817:6E10  05 17 18 89 96 36 FF 89-86 34 FF FF B6 36 FF FF   .....6...4...6..
1817:6E20  B6 34 FF 57 9A 3A 21 CA-1D 83 C4 06 8B 96 36 FF   .4.W.:!.......6.
1817:6E30  8B 86 34 FF 52 50 A1 03-01 BA E0 00 F7 E2 8B D8   ..4.RP..........
1817:6E40  81 C3 8C 4A 1E 07 8B C7-D1 E0 D1 E0 03 D8 58 5A   ...J..........XZ
1817:6E50  26 89 57 1A 26 89 47 18-9A E4 0B A2 1A EB 3B 33   &.W.&.G.......;3
1817:6E60  C0 50 9A 9A 0C A2 1A 59-9A 75 00 A4 27 3D 2B 00   .P.....Y.u..'=+.
1817:6E70  75 06 B8 2B 00 E9 EC 0D-EB 00 33 D2 B8 6C 21 52   u..+......3..l!R
1817:6E80  50 8B 1E 03 01 D1 E3 D1-E3 FF B7 41 6E FF B7 3F   P.........An..?
1817:6E90  6E 9A 23 09 17 18 0B D0-75 E0 FF 06 03 01 83 3E   n.#.....u......>
1817:6EA0  03 01 0C 7D 03 E9 CD FD-47 9A 7F 13 A2 1A 8B F0   ...}....G.......
1817:6EB0  8B C6 0B C0 74 07 56 9A-07 00 72 1D 59 33 C0 50   ....t.V...r.Y3.P
1817:6EC0  9A 39 04 A2 1A 59 C7 06-03 01 06 00 8B 0A 00 50   .9...Y.........P
1817:6ED0  9A 21 00 6B 1C 59 9A 75-00 A4 27 3D 2B 00 75 06   .!.k.Y.u..'=+.u.
1817:6EE0  B8 2B 00 E9 7E 0D 33 C0-50 9A 55 0C A2 1A 59 33   .+..~.3.P.U...Y3
1817:6EF0  C0 50 9A FD 0B A2 1A 59-8B 1E 03 01 D1 E3 D1 E3   .P.....Y........
1817:6F00  C7 87 41 6E 02 00 C7 87-3F 6E 48 65 EB 00 8B 1E   ..An....?nHe....
1817:6F10  03 01 D1 E3 D1 E3 8B 97-41 6E 8B 87 3F 6E 3B 16   ........An..?n;.
1817:6F20  56 0D 7F EA 75 06 3B 06-54 0D 77 E2 16 8D 86 4C   V...u.;.T.w....L
1817:6F30  FF 50 9A EE 0C A2 1A 59-59 8B F0 8B C6 0B C0 74   .P.....YY......t
1817:6F40  03 E9 80 F1 9A E4 0B A2-1A 8B 16 3E 55 A1 3C 55   ...........>U.<U
1817:6F50  29 86 4C FF 19 96 4E FF-8B 96 4E FF 8B 86 4C FF   ).L...N...N...L.
1817:6F60  52 50 CD 37 86 20 FF CD-3D 83 C4 04 CD 39 5E D0   RP.7. ..=....9^.
1817:6F70  CD 3D 33 C0 50 9A 39 04-A2 1A 59 B8 01 00 50 9A   .=3.P.9...Y...P.
1817:6F80  55 0C A2 1A 59 B8 01 00-50 9A FD 0B A2 1A 59 8B   U...Y...P.....Y.
1817:6F90  1E 03 01 D1 E3 D1 E3 C7-87 41 6E 02 00 C7 87 3F   ..........An....?
1817:6FA0  6E 48 65 EB 00 8B 1E 03-01 D1 E3 D1 E3 8B 97 41   nHe............A
1817:6FB0  6E 8B 87 3F 6E 3B 16 56-0D 7F EA 75 06 3B 06 54   n..?n;.V...u.;.T
1817:6FC0  0D 77 E2 16 8D 86 4C FF-50 9A EE 0C A2 1A 59 59   .w....L.P.....YY
1817:6FD0  8B F0 8B C6 0B C0 74 03-E9 E9 F0 9A E4 0B A2 1A   ......t.........
1817:6FE0  8B 16 3E 55 A1 3C 55 29-86 4C FF 19 96 4E FF 8B   ..>U.<U).L...N..
1817:6FF0  96 4E FF 8B 86 4C FF 52-50 CD 37 86 20 FF CD 3D   .N...L.RP.7. ..=
1817:7000  83 C4 04 CD 39 5E E0 CD-3D 9A 75 00 A4 27 3D 2B   ....9^..=.u..'=+
1817:7010  00 75 06 B8 2B 00 E9 4B-0C B8 02 00 50 9A 55 0C   .u..+..K....P.U.
1817:7020  A2 1A 59 B8 02 00 50 9A-FD 0B A2 1A 59 8B 1E 03   ..Y...P.....Y...
1817:7030  01 D1 E3 D1 E3 C7 87 41-6E 02 00 C7 87 3F 6E 48   .......An....?nH
1817:7040  65 EB 00 8B 1E 03 01 D1-E3 D1 E3 8B 97 41 6E 8B   e.............An.
1817:7050  87 3F 6E 3B 16 56 0D 7F-EA 75 06 3B 06 54 0D 77   .?n;.V...u.;.T.w
1817:7060  E2 16 8D 86 4C FF 50 9A-EE 0C A2 1A 59 59 8B F0   ....L.P.....YY..
1817:7070  8B C6 0B C0 74 03 E9 4B-F0 9A E4 0B A2 1A 8B 16   ....t..K........
1817:7080  3E 55 A1 3C 55 29 86 4C-FF 19 96 4E FF 8B 96 4E   >U.<U).L...N...N
1817:7090  FF 8B 86 4C FF 52 50 CD-37 86 20 FF CD 3D 83 C4   ...L.RP.7. ..=..
1817:70A0  04 CD 39 5E D3 CD 3D B8-05 00 50 9A 55 0C A2 1A   ..9^..=...P.U...
1817:70B0  59 B8 05 00 50 9A FD 0B-A2 1A 59 8B 1E 03 01 D1   Y...P.....Y.....
```

```
1817:70C0  E3 D1 E3 C7 87 41 6E 02-00 C7 87 3F 6E 48 65 EB   .....An....?nHe.
1817:70D0  00 8B 1E 03 01 D1 E3 D1-E3 8B 97 41 6E 8B 87 3F   ...........An..?
1817:70E0  6E 3B 16 56 0D 7F EA 75-06 3B 06 54 0D 77 E2 16   n;.V...u.:.T.w..
1817:70F0  8D 86 4C FF 50 9A EE 0C-A2 1A 59 59 8B F0 8B C6   ..L.P.....YY....
1817:7100  0B C0 74 03 E9 BD EF 9A-E4 0B A2 1A 8B 16 3E 55   ..t...........>U
1817:7110  A1 3C 55 29 36 4C FF 19-96 4E FF 8B 96 4E FF 8B   .<U).L...N...N..
1817:7120  86 4C FF 52 50 CD 37 86-20 FF CD 3D 83 C4 04 CD   .L.RP.7. ..=....
1817:7130  39 5E 8B CD 3D B8 0B 00-50 9A 21 00 6B 1C 59 9A   9^..=...P.!.k.Y.
1817:7140  75 00 A4 27 3D 2B 00 75-06 B8 2B 00 E9 15 0B 33   u..'=+.u..+....3
1817:7150  C0 50 9A 39 04 A2 1A 59-5B 03 00 50 9A 55 0C A2   .P.9...Y...P.U..
1817:7160  1A 59 8B 1E 03 01 D1 E3-D1 E3 C7 87 41 6E 02 00   .Y..........An..
1817:7170  C7 87 3F 6E 48 65 EB 00-8B 1E 03 01 D1 E3 D1 E3   ..?nHe..........
1817:7180  8B 97 41 6E 8B 87 3F 6E-3B 16 56 0D 7F EA 75 06   ..An..?n;.V...u.
1817:7190  3B 06 54 0D 77 E2 16 8D-86 4C FF 50 9A EE 0C A2   ;.T.w....L.P....
1817:71A0  1A 59 59 8B F0 8B C6 0B-C0 74 03 E9 16 EF 8B 16   .YY......t......
1817:71B0  3E 55 A1 3C 55 29 86 4C-FF 19 96 4E FF 8B 96 4E   >U.<U).L...N...N
1817:71C0  FF 8B 86 4C FF 52 50 CD-37 86 20 FF CD 3D 83 C4   ...L.RP.7. ..=..
1817:71D0  04 CD 39 5E F0 CD 3D 9A-75 00 A4 27 3D 2B 00 75   ..9^..=.u:.'=+.u
1817:71E0  06 B8 2B 00 E9 7D 0A B8-0C 00 50 9A 21 00 6B 1C   ..+..}....P.!.k.
1817:71F0  59 5B 04 00 50 9A 55 0C-A2 1A 59 8B 1E 03 01 D1   Y...P.U...Y.....
1817:7200  E3 D1 E3 C7 87 41 6E 02-00 C7 87 3F 6E 48 65 EB   .....An....?nHe.
1817:7210  00 8B 1E 03 01 D1 E3 D1-E3 8B 97 41 6E 8B 87 3F   ...........An..?
1817:7220  6E 3B 16 56 0D 7F EA 75-06 3B 06 54 0D 77 E2 16   n;.V...u.:.T.w..
1817:7230  8D 86 4C FF 50 9A EE 0C-A2 1A 59 59 8B F0 8B C6   ..L.P.....YY....
1817:7240  0B C0 74 03 E9 7D EE 8B-16 3E 55 A1 3C 55 29 96   ..t..}...>U.<U).
1817:7250  4C FF 19 96 4E FF 8B 96-4E FF 8B 86 4C FF 52 50   L...N...N...L.RP
1817:7260  CD 37 86 20 FF CD 3D 83-C4 04 CD 39 5E F8 CD 3D   .7. ..=....9^..=
1817:7270  9A 75 00 A4 27 3D 2B 00-75 06 B8 2B 00 E9 E4 09   .u..'=+.u..+....
1817:7280  83 3E 58 0D 01 74 03 E9-D6 01 C7 06 03 01 00 00   .>X..t..........
1817:7290  E9 C3 01 33 C0 50 9A 39-04 A2 1A 59 C7 86 2E FF   ...3.P.9...Y....
1817:72A0  FF FF E9 A2 01 83 BE 2E-FF FF 75 2D A1 03 01 BA   ..........u-....
1817:72B0  E0 00 F7 E2 8B D8 81 C3-BC 4A 1E 07 26 8B 57 16   .........J..&.W.
1817:72C0  26 8B 47 14 52 50 CD 37-86 20 FF CD 3D 83 C4 04   &.G.RP.7. ..=...
1817:72D0  CD 39 9E 50 FF CD 3D EB-35 A1 03 01 BA E0 00 F7   .9.P..=.5.......
1817:72E0  E2 8B D8 81 C3 BC 4A 1E-07 8B 86 2E FF D1 E0 D1   ......J.........
1817:72F0  E0 03 D8 26 8B 57 1A 26-8B 47 18 52 50 CD 37 86   ...&.W.&.G.RP.7.
1817:7300  20 FF CD 3D 83 C4 04 CD-39 9E 50 FF CD 3D 8B 1E    ..=....9.P..=..
1817:7310  03 01 D1 E3 8B 87 0D 6E-8A 1C 00 F7 E2 8B D8 81   .......n........
1817:7320  C3 0D 01 1E 07 26 83 07-3D 05 00 76 03 E9 9C 00   .....&..=..v....
1817:7330  8B D8 D1 E3 2E FF A7 09-18 15 18 44 18 2D 18 70   ...........D.-.p
1817:7340  18 86 18 5A 18 CD 39 86-70 FF CD 3B 76 D0 CD 3B   ...Z..9.p..8v..8
1817:7350  8E 50 FF CD 39 9E 50 FF-CD 3D E9 87 00 CD 39 86   .P..9.P..=....9.
1817:7360  78 FF CD 3B 76 D8 CD 3B-8E 50 FF CD 39 9E 50 FF   x..8v..8.P..9.P.
1817:7370  CD 3D EB 70 CD 39 46 80-CD 3B 76 E0 CD 3B 8E 50   .=.p.9F..8v..8.P
1817:7380  FF CD 39 9E 50 FF CD 3D-EB 5A CD 39 46 88 CD 3B   ..9.P..=.Z.9F..8
1817:7390  76 E8 CD 3B 8E 50 FF CD-39 9E 50 FF CD 3D EB 44   v..8.P..9.P..=.D
1817:73A0  CD 39 46 90 CD 3B 76 F0-CD 3B 8E 50 FF CD 39 9E   .9F..8v..8.P..9.
1817:73B0  50 FF CD 3D EB 2E CD 39-46 98 CD 3B 76 F8 CD 3B   P..=...9F..8v..8
1817:73C0  8E 50 FF CD 39 9E 50 FF-CD 3D EB 18 9A 18 02 A2   .P..9.P..=......
1817:73D0  1A 1E 89 73 16 50 9A 05-00 A8 2C 59 59 9A CE 05   ...s.P....,YY...
1817:73E0  A2 1A EB 00 83 BE 2E FF-FF 75 28 CD 39 86 50 FF   .........u(.9.P.
1817:73F0  9A C7 05 17 18 52 50 A1-03 01 BA E0 00 F7 E2 8B   .....RP.........
1817:7400  D8 81 C3 BC 4A 1E 07 58-5A 26 89 57 16 26 89 47   ....J..XZ&.W.&.G
1817:7410  14 EB 30 CD 39 86 50 FF-9A C7 05 17 18 52 50 A1   ..0.9.P......RP.
1817:7420  03 01 BA E0 00 F7 E2 8B-D8 81 C3 BC 4A 1E 07 8B   ............J...
1817:7430  86 2E FF D1 E0 D1 E0 03-D8 58 5A 26 89 57 1A 26   .........XZ&.W.&
1817:7440  89 47 18 FF 86 2E FF 83-BE 2E FF 3B C7 7D 03 E9   .G.........;.}..
1817:7450  53 FE FF 06 03 01 83 3E-03 01 0C 7D 03 E9 33 FE   S......>...}..3.
1817:7460  C7 06 03 01 00 00 C7 06-03 01 00 00 E8 18 8B 1E   ................
1817:7470  03 01 D1 E3 8B 87 0A 42-8B 1E 03 01 D1 E3 89 87   ........H.......
1817:7480  F8 49 FF 06 03 01 83 3E-03 01 0C 7C E1 A1 58 0D   .I......>...|..X.
1817:7490  A3 78 4A CD 39 86 70 FF-9A C7 05 17 18 89 16 32   .xJ.9.p........2
1817:74A0  4A A3 30 4A CD 39 86 78-FF 9A C7 05 17 18 89 16   J.0J.9.x........
1817:74B0  36 4A A3 34 4A CD 39 46-80 9A C7 05 17 18 89 16   6J.4J.9F........
1817:74C0  3A 4A A3 38 4A CD 39 46-88 9A C7 05 17 18 89 16   :J.8J.9F........
1817:74D0  3E 4A A3 3C 4A CD 39 46-90 9A C7 05 17 18 89 16   >J.<J.9F........
1817:74E0  42 4A A3 40 4A CD 39 46-98 9A C7 05 17 18 89 16   BJ.@J.9F........
1817:74F0  46 4A A3 44 4A CD 39 46-A0 9A C7 05 17 18 89 16   FJ.DJ.9F........
1817:7500  4A 4A A3 48 4A CD 39 46-A8 9A C7 05 17 18 89 16   JJ.HJ.9F........
1817:7510  4E 4A A3 4C 4A CD 39 46-B0 9A C7 05 17 18 89 16   NJ.LJ.9F........
1817:7520  52 4A A3 50 4A CD 39 46-B8 9A C7 05 17 18 89 16   RJ.PJ.9F........
```

```
1817:7530  56 4A A3 54 4A CD 39 46-C0 9A C7 05 17 18 89 16   VJ.TJ.9F........
1817:7540  5A 4A A3 58 4A CD 39 46-C8 9A C7 05 17 18 89 16   ZJ.XJ.9F........
1817:7550  5E 4A A3 5C 4A CD 39 46-D0 9A C7 05 17 18 89 16   ^J.\J.9F........
1817:7560  62 4A A3 60 4A CD 39 46-D8 9A C7 05 17 18 89 16   bJ.`J.9F........
1817:7570  66 4A A3 64 4A CD 39 46-E0 9A C7 05 17 18 89 16   fJ.dJ.9F........
1817:7580  6A 4A A3 68 4A CD 39 46-E8 9A C7 05 17 18 89 16   jJ.hJ.9F........
1817:7590  6E 4A A3 6C 4A CD 39 46-F0 9A C7 05 17 18 89 16   nJ.lJ.9F........
1817:75A0  72 4A A3 70 4A CD 39 46-F8 9A C7 05 17 18 89 16   rJ.pJ.9F........
1817:75B0  76 4A A3 74 4A 89 3E 7A-4A 9A 75 00 A4 27 3D 2B   vJ.tJ.>zJ.u..'=+
1817:75C0  00 75 06 E8 2B 00 E9 9E-06 33 C0 50 9A 39 04 A2   .u..+....3.P.9..
1817:75D0  1A 59 B8 07 00 50 9A D7-0D A2 1A 59 C7 86 2C FF   .Y...P.....Y..,.
1817:75E0  00 00 C7 06 03 01 00 00-9E 04 00 50 33 C0 50 9A   ...........P3.P.
1817:75F0  F7 02 A2 1A 59 59 E8 1E-03 01 D1 E3 D1 E3 C7 87   ....YY..........
1817:7600  41 6E 02 00 C7 87 3F 6E-48 65 EB 09 33 C0 50 9A   An....?nHe..3.P.
1817:7610  39 04 A2 1A 59 E8 1E 03-01 D1 E3 D1 E3 8B 97 41   9...Y..........A
1817:7620  6E 8B 87 3F 6E 3B 16 56-0D 7F E1 75 06 3B 06 54   n..?n;.V...u.;.T
1817:7630  0D 77 D9 16 8D 86 34 FF-50 9A EE 0C A2 1A 59 59   .w....4.P.....YY
1817:7640  89 86 28 FF 0B C0 74 36-83 3E D1 00 01 75 0C 1E   ..(...t6.>...u..
1817:7650  B8 94 16 50 9A 05 00 A8-2C 59 59 9A A1 06 A2 1A   ...P....,YY.....
1817:7660  C7 06 1E 4A 00 00 C7 06-1C 4A 00 00 FF 86 2C FF   ...J.....J....,.
1817:7670  8B 86 2C FF 3D 04 00 7D-03 E9 6C FF EB 0F 8B 96   ..,.=..}..l.....
1817:7680  36 FF 8B 86 34 FF 89 16-1E 4A A3 1C 4A B8 01 00   6...4....J..J...
1817:7690  50 9A D7 0D A2 1A 59 C7-86 2C FF 00 00 B8 04 00   P.....Y..,......
1817:76A0  50 B8 09 00 50 9A F7 02-A2 1A 59 59 E8 1E 03 01   P...P.....YY....
1817:76B0  D1 E3 D1 E3 C7 87 41 6E-02 00 C7 87 3F 6E 48 65   ......An....?nHe
1817:76C0  EB 09 33 C0 50 9A 39 04-A2 1A 59 E8 1E 03 01 D1   ..3.P.9...Y.....
1817:76D0  E3 D1 E3 8B 97 41 6E 8B-87 3F 6E 3B 16 56 0D 7F   .....An..?n;.V..
1817:76E0  E1 75 06 3B 06 54 0D 77-D9 16 8D 86 34 FF 50 9A   .u.;.T.w....4.P.
1817:76F0  EE 0C A2 1A 59 59 89 86-28 FF 0B C0 74 36 83 3E   ....YY..(...t6.>
1817:7700  D1 00 01 75 0C 1E B8 A7-16 50 9A 05 00 A8 2C 59   ...u.....P....,Y
1817:7710  59 9A A1 06 A2 1A C7 06-26 4A 00 00 C7 06 24 4A   Y.......&J....$J
1817:7720  00 00 FF 86 2C FF 8B 86-2C FF 3D 04 00 7D 03 E9   ....,...,.=..}..
1817:7730  6B FF EB 0F 8B 96 36 FF-8B 86 34 FF 89 16 26 4A   k.....6...4...&J
1817:7740  A3 24 4A 33 C0 50 9A D7-0D A2 1A 59 C7 86 2C FF   .$J3.P.....Y..,.
1817:7750  00 00 B8 05 00 50 33 C0-50 9A F7 02 A2 1A 59 59   .....P3.P.....YY
1817:7760  E8 1E 03 01 D1 E3 D1 E3-C7 87 41 6E 02 00 C7 87   ..........An....
1817:7770  3F 6E 48 65 EB 09 33 C0-50 9A 39 04 A2 1A 59 E8   ?nHe..3.P.9...Y.
1817:7780  1E 03 01 D1 E3 D1 E3 8B-97 41 6E 8B 87 3F 6E 3B   .........An..?n;
1817:7790  16 56 0D 7F E1 75 06 3B-06 54 0D 77 D9 16 8D 86   .V...u.;.T.w....
1817:77A0  34 FF 50 9A EE 0C A2 1A-59 59 89 86 28 FF 0B C0   4.P.....YY..(...
1817:77B0  74 36 83 3E D1 00 01 75-0C 1E B8 B9 16 50 9A 05   t6.>...u.....P..
1817:77C0  00 A8 2C 59 59 9A A1 06-A2 1A C7 06 2E 4A 00 00   ...YY........J..
1817:77D0  C7 06 2C 4A 00 00 FF 86-2C FF 8B 86 2C FF 3D 04   ..,J....,...,.=.
1817:77E0  00 7D 03 E9 6C FF EB 0F-8B 96 36 FF 8B 86 34 FF   .}..l.....6...4.
1817:77F0  89 16 2E 4A A3 2C 4A 9A-75 00 A4 27 3D 2B 00 75   ...J.,J.u..'=+.u
1817:7800  06 E8 2B 00 E9 5D 04 33-C0 50 9A 39 04 A2 1A 59   ..+..].3.P.9...Y
1817:7810  9A 00 00 B9 18 33 C0 50-9A 39 04 A2 1A 59 9A 75   .....3.P.9...Y.u
1817:7820  00 A4 27 3D 2B 00 75 06-E8 2B 00 E9 36 04 C7 06   ..'=+.u..+..6...
1817:7830  03 01 00 00 E9 83 03 33-C0 50 9A 39 04 A2 1A 59   .......3.P.9...Y
1817:7840  8B 1E 03 01 D1 E3 83 BF-F5 6D 00 74 06 A1 03 01   .........m.t....
1817:7850  40 EB 02 33 C0 50 A1 03-01 BA E0 00 F7 E2 8B D8   @..3.P..........
1817:7860  81 C3 BC 4A 1E 07 58 26-89 07 8B 1E 03 01 D1 E3   ...J..X&........
1817:7870  83 BF F5 6D 00 75 03 E9-BA 02 8B 1E 03 01 D1 E3   ...m.u..........
1817:7880  8B 87 0D 6E 50 A1 03 01-BA E0 00 F7 E2 8B D8 81   ...nP...........
1817:7890  C3 BC 4A 1E 07 58 26 89-47 02 8B 1E 03 01 D1 E3   ..J..X&.G.......
1817:78A0  8B 87 0D 6E BA 1C 00 F7-E2 8B D8 81 C3 0D 01 1E   ...n............
1817:78B0  07 26 8B 07 BA 60 00 F7-E2 8B D8 81 C3 5C 43 1E   .&...`.......\C.
1817:78C0  07 A1 03 01 D1 E0 D1 E0-D1 E0 03 D8 CD 3C DD 07   .............<..
1817:78D0  A1 03 01 BA E0 00 F7 E2-8B D8 81 C3 BC 4A 1E 07   .............J..
1817:78E0  CD 3C DD 5F 04 CD 3D 8B-1E 03 01 D1 E3 8B 87 0D   .<._..=.........
1817:78F0  6E BA 1C 00 F7 E2 8B D8-81 C3 0D 01 1E 07 26 8B   n.............&.
1817:7900  07 BA 60 00 F7 E2 8B D8-81 C3 9C 45 1E 07 A1 03   ..`........E....
1817:7910  01 D1 E0 D1 E0 D1 E0 03-D8 CD 3C DD 07 A1 03 01   ..........<.....
1817:7920  BA E0 00 F7 E2 8B D8 81-C3 BC 4A 1E 07 CD 3C DD   .........J...<.
1817:7930  5F 0C CD 3D 8B 1E 03 01-D1 E3 8B 87 0D 6E BA 1C   _..=.........n..
1817:7940  00 F7 E2 8B D8 81 C3 0D-01 1E 07 26 8B 07 BA 60   ...........&...`
1817:7950  00 F7 E2 8B D8 81 C3 5C-43 1E 07 A1 03 01 D1 E0   .......\C.......
1817:7960  D1 E0 D1 E0 03 D8 CD 3C-DD 07 9A C7 05 17 18 89   .......<........
1817:7970  96 3A FF 89 86 38 FF 8B-1E 03 01 D1 E3 8B 87 0D   .:...8..........
1817:7980  6E BA 1C 00 F7 E2 8B D8-81 C3 0D 01 1E 07 26 8B   n.............&.
1817:7990  07 BA 60 00 F7 E2 8B D8-81 C3 9C 45 1E 07 A1 03   ..`........E....
```

```
1817:79A0  01 D1 E0 D1 E0 D1 E0 03-D3 CD 3C DD 07 9A C7 05   ..........<.....
1817:79B0  17 18 89 96 3E FF 89 86-3C FF 8B 96 3A FF 8B 96   ....>...<...:...
1817:79C0  3B FF 3B 96 3E FF 7F 1E-75 06 3B 86 3C FF 77 16   ;.;.>...u.;.<.w.
1817:79D0  8B 96 3E FF 8B 86 3C FF-05 01 00 83 D2 00 89 96   ..>...<.........
1817:79E0  3A FF 89 86 38 FF 1E 8B-6E 3F 50 33 C0 50 1E A1   :...8...n?P3.P..
1817:79F0  03 01 D1 E0 D1 E0 D1 E0-05 F8 49 50 8B 1E 03 01   ..........IP....
1817:7A00  D1 E3 8B 87 0D 6E BA 1C-00 F7 E2 8B D8 81 C3 0D   .....n..........
1817:7A10  01 1E 07 26 FF 77 06 8B-1E 03 01 D1 E3 8B 87 0D   ...&.w..........
1817:7A20  6E BA 1C 00 F7 E2 8B D8-81 C3 0D 01 1E 07 26 FF   n.............&.
1817:7A30  77 04 8B 1E 03 01 D1 E3-8B 87 0D 6E BA 1C 00 F7   w..........n....
1817:7A40  E2 8B D8 81 C3 0D 01 1E-07 26 FF 77 02 8B 96 3A   .........&.w...:
1817:7A50  FF 8B 96 38 FF 52 50 CD-37 26 10 FF CD 3D 83 C4   ...8.RP.7....=..
1817:7A60  04 83 EC 08 CD 39 9E 0C-FF CD 3D 8B 96 3E FF 8B   .....9....=..>..
1817:7A70  86 3C FF 52 50 CD 37 86-08 FF CD 3D 83 C4 04 83   .<.RP.7....=....
1817:7A80  EC 08 CD 39 9E 04 FF CD-3D FF 36 03 01 9A 08 00   ...9....=.6.....
1817:7A90  3B 24 83 C4 22 EB 1E 03-01 D1 E3 89 B7 F5 6D 1E   ;$.."........m.
1817:7AA0  A1 03 01 D1 E0 D1 E0 D1-E0 05 E8 42 50 E8 1E 03   ...........BP...
1817:7AB0  01 D1 E3 FF B7 0A 48 8B-1E 03 01 D1 E3 FF B7 0D   ......H.........
1817:7AC0  6E 8B 1E 03 01 D1 E3 D1-E3 D1 E3 CD 39 87 99 49   n...........9..I
1817:7AD0  83 EC 08 CD 39 9E 14 FF-CD 3D 8B 1E 03 01 D1 E3   ....9....=......
1817:7AE0  FF B7 F5 6D 94 0F 01 4B-21 83 C4 12 8B 1E 03 01   ...m...K!.......
1817:7AF0  8B 87 48 43 3C 21 75 0C-8B 1E 03 01 D1 E3 C7 87   ..HC<!u.........
1817:7B00  F5 6D 00 00 8B 1E 03 01-D1 E3 83 BF F5 6D 01 75   .m...........m.u
1817:7B10  0E 8B 1E 03 01 80 BF 48-43 3E 74 03 E9 87 00 83   .......HC>t.....
1817:7B20  1E 03 01 D1 E3 83 BF 0D-6E 64 75 03 E9 77 00 A1   ........ndu..w..
1817:7B30  03 01 BB 06 00 99 F7 FB-BA 30 00 F7 E2 05 2C 00   .........0....,.
1817:7B40  89 86 32 FF E8 49 A1 03-01 BB 06 00 99 F7 FB 8B   ..2..I..........
1817:7B50  C2 BA 28 00 F7 E2 05 0C-00 89 96 30 FF E8 13 FF   ..(.......0.....
1817:7B60  B6 32 FF FF B6 30 FF 9A-59 10 A2 1A 59 59 FF B6   .2...0..Y...YY..
1817:7B70  30 FF A1 03 01 BB 06 00-99 F7 FB 8B C2 BA 28 00   0.............(.
1817:7B80  F7 E2 05 28 00 3B 86 30-FF 7F D4 FF B6 32 FF A1   ...(.;.0.....2..
1817:7B90  03 01 BB 06 00 99 F7 FB-BA 30 00 F7 E2 05 48 00   .........0....H.
1817:7BA0  3B 86 32 FF 7F A0 9A 75-00 A4 27 3D 2B 00 75 06   ;.2....u..'=+.u.
1817:7BB0  B8 2B 00 E9 AE 00 FF 06-03 01 83 3E 03 01 0C 7D   .+.........>...}
1817:7BC0  03 E9 73 FC C7 06 05 01-00 00 C7 06 07 01 00 00   ..s.............
1817:7BD0  9A A9 03 ED 22 1E 89 CE-16 50 9A 8D 00 D7 19 59   ...."....P.....Y
1817:7BE0  59 8B 01 00 50 9A 89 07-A2 1A 59 1E 8B D4 16 50   Y...P.....Y....P
1817:7BF0  9A 0A 00 D7 19 59 59 33-C0 50 B8 01 00 50 9A 0C   .....YY3.P...P..
1817:7C00  00 CF 20 59 59 23 F0 8B-C6 0B C0 74 0B 83 BE 2A   .. YY......t...*
1817:7C10  FF 00 75 04 89 B6 2A FF-1E B8 DD 16 50 9A 0A 00   ..u...*.....P...
1817:7C20  D7 19 59 59 83 3E 4C 0C-00 75 05 9A 64 08 A2 1A   ..YY.>L..u..d...
1817:7C30  83 3E D1 00 01 75 11 1E-B8 18 56 50 9A 01 00 3A   .>...u....VP...:
1817:7C40  23 59 59 9A 05 00 58 23-9A 0D 00 E8 1F 83 3E 2A   #YY...X#.......*
1817:7C50  FF 00 74 0A FF B6 2A FF-9A 07 00 72 1D 59 8B B6   ..t...*....r.Y..
1817:7C60  2A FF EB 00 5F 5E 8B E5-5D CB 55 8B EC 56 57 39   *..._^..].U..VW9
1817:7C70  26 98 0D 77 05 9A CF 09-17 18 8B 1E 03 01 D1 E3   &..w............
1817:7C80  D1 E3 8B 97 84 6E 8B 87-82 6E 29 46 08 19 56 0A   .....n...n)F..V.
1817:7C90  83 7E 0A 00 7F 12 7C 06-83 7E 08 00 73 0A C7 46   .~....|..~..s..F
1817:7CA0  0A 00 00 C7 46 08 00 00-A1 03 01 BB 06 00 99 F7   ....F...........
1817:7CB0  FB 8B C2 BA 28 00 F7 E2-8B F8 03 7E 06 83 C7 08   ....(......~....
1817:7CC0  8B 1E 03 01 D1 E3 D1 E3-8B 97 84 6E 8B 87 82 6E   ...........n...n
1817:7CD0  3B 56 0A 7F 1D 7C 05 3B-46 08 73 16 8B 1E 03 01   ;V...|.;F.s.....
1817:7CE0  D1 E3 D1 E3 8B 97 84 6E-8B 87 82 6E 89 56 0A 89   .......n...n.V..
1817:7CF0  46 08 89 1E 03 01 D1 E3-D1 E3 8B 97 84 6E 8B 87   F............n..
1817:7D00  82 6E 52 50 CD 37 46 F8-CD 3D 83 C4 04 CD 3B 3E   .nRP.7F..=....;>
1817:7D10  E6 16 8B 56 0A 8B 46 08-52 50 CD 37 46 F8 CD 3D   ...V..F.RP.7F..=
1817:7D20  83 C4 04 CD 3A C9 9A C7-05 17 18 8B F0 A1 03 01   ....:...........
1817:7D30  BB 06 00 99 F7 FB BA 30-00 F7 E2 05 2C 00 03 F0   .......0........
1817:7D40  56 57 9A 59 10 A2 1A 59-59 5F 5E 5D CB 55 8B EC   VW.Y...YY_^].U..
1817:7D50  83 EC 28 56 57 39 26 98-0D 77 05 9A CF 09 17 18   ..(VW9&..w......
1817:7D60  1E B8 EE 16 50 9A 0A 00-D7 19 59 59 1E B8 F6 16   ....P.....YY....
1817:7D70  50 1E 98 6E 3F 50 9A 0A-00 65 2D 83 C4 08 1E B8   P..n?P...e-.....
1817:7D80  47 0C 50 B8 05 00 50 B8-05 00 50 1E B8 F8 16 50   G.P...P...P....P
1817:7D90  1E B8 6E 3F 50 9A 0A 00-65 2D 83 C4 10 C7 46 E6   ..n?P...e-....F.
1817:7DA0  00 00 EB 27 FF 76 E6 33-C0 50 9A F5 0F A2 1A 59   ...'.v.3.P.....Y
1817:7DB0  59 50 9A 73 0F A2 1A 59-89 46 E4 0B C0 74 09 FF   YP.s...Y.F...t..
1817:7DC0  76 E4 9A 07 00 72 1D 59-FF 46 E6 83 7E E6 17 7C   v....r.Y.F..~..|
1817:7DD0  D3 1E B8 18 56 50 1E B8-40 55 50 1E E8 04 17 50   ....VP..@UP....P
1817:7DE0  1E B8 6E 3F 50 9A 0A 00-65 2D 83 C4 10 83 3E D1   ..n?P...e-....>.
1817:7DF0  00 01 74 45 33 F6 EB 01-46 3B 36 09 01 7D 0B 8B   ..tE3...F;6..}..
```

```
1817:7E00  DE D1 E3 83 BF 25 6E 01-74 EE 3B 36 09 01 7D 29  .....%n.t.;6..})
1817:7E10  1E B8 11 17 50 9A 0A 00-D7 19 59 59 B8 18 00 50  ....P.....YY...P
1817:7E20  9A 30 0E A2 1A 59 89 46-E4 0B C0 74 09 FF 76 E4  .0...Y.F...t..v.
1817:7E30  9A 07 00 72 1D 59 E9 9F-0A 33 C0 50 9A 36 03 A2  ...r.Y...3.P.6..
1817:7E40  1A 59 33 F6 E9 53 05 8B-DE D1 E3 C7 87 80 49 00  .Y3..S........I.
1817:7E50  00 EB DE D1 E3 83 BF 0D-6E 64 75 03 E9 3A 05 56  ........ndu..:.V
1817:7E60  9A 7E 08 A2 1A 59 52 50-1E B8 1A 17 50 9A 05 00  .~...YRP....P...
1817:7E70  A8 2C 83 C4 08 56 9A 7E-08 A2 1A 59 52 50 1E B8  .....V.~...YRP..
1817:7E80  21 17 50 1E B8 6E 3F 50-9A 0A 00 65 2D 83 C4 0C  !.P..n?P...e-...
1817:7E90  8B DE D1 E3 83 BF 25 6E-01 74 1E 1E B8 28 17 50  ......%n.t...(.P
1817:7EA0  9A B7 00 D7 19 59 59 1E-B8 2F 17 50 1E B8 6E 3F  .....YY../.P..n?
1817:7EB0  50 9A D9 00 D7 19 83 C4-08 80 BC 48 43 21 75 02  P..........HC!u.
1817:7EC0  EB 2F 8B DE D1 E3 83 BF-F5 6D 00 75 03 E9 03 04  ./.......m.u....
1817:7ED0  16 8D 46 E2 50 8B DE D1-E3 FF B7 0A 48 8B DE D1  ..F.P.......H...
1817:7EE0  E3 FF B7 0D 6E 9A 1F 05-4B 21 83 C4 08 05 C0 75  ....n...K!.....u
1817:7EF0  6C 1E B8 36 17 50 9A B7-00 D7 19 59 59 1E B8 3D  l..6.P.....YY..=
1817:7F00  17 50 1E B8 6E 3F 50 9A-D9 00 D7 19 83 C4 08 8B  .P..n?P.........
1817:7F10  DE D1 E3 D1 E3 D1 E3 CD-39 87 98 49 83 EC 08 CD  ........9..I....
1817:7F20  39 5E CC CD 3D 1E B8 44-17 50 9A 05 00 A8 2C 83  9^..=..D.P.....,.
1817:7F30  C4 0C 8B DE D1 E3 D1 E3-D1 E3 CD 39 87 98 49 83  ...........9..I.
1817:7F40  EC 08 CD 39 5E CC CD 3D-1E B8 4E 17 50 1E B8 6E  ...9^..=..N.P..n
1817:7F50  3F 50 9A 0A 00 65 2D 83-C4 10 E9 3C 04 8A 84 48  ?P...e-....<...H
1817:7F60  43 98 50 1E B8 59 17 50-9A 05 00 A8 2C 83 C4 06  C.P..Y.P........
1817:7F70  8A 84 48 43 98 50 1E B8-5C 17 50 1E B8 6E 3F 50  ..HC.P..\.P..n?P
1817:7F80  9A 0A 00 65 2D 83 C4 0A-8B DE D1 E3 8B 87 0D 6E  ...e-..........n
1817:7F90  BA 1C 00 F7 E2 8B D8 81-C3 0D 01 1E 07 26 83 7F  .............&..
1817:7FA0  10 00 75 03 E9 E0 00 8B-DE D1 E3 8B 87 0D 6E BA  ..u............n.
1817:7FB0  1C 00 F7 E2 05 0D 01 8C-DA 05 12 00 52 50 8B DE  ..............RP..
1817:7FC0  D1 E3 D1 E3 D1 E3 CD 39-87 E8 42 83 EC 08 CD 39  ........9..B....9
1817:7FD0  5E C8 CD 3D 8B DE D1 E3-8B 87 0D 6E BA 1C 00 F7  ^..=........n....
1817:7FE0  E2 8B D8 81 C3 0D 01 1E-07 26 FF 77 10 8B DE D1  .........&.w....
1817:7FF0  E3 8B 87 0D 6E BA 1C 00-F7 E2 8B D8 81 C3 0D 01  ....n...........
1817:8000  1E 07 26 FF 77 0E 1E B8-5F 17 50 9A 05 00 A8 2C  ..&.w..._.P....,
1817:8010  83 C4 14 8B DE D1 E3 8B-87 0D 6E BA 1C 00 F7 E2  ..........n.....
1817:8020  05 0D 01 8C DA 05 12 00-52 50 8B DE D1 E3 D1 E3  ........RP......
1817:8030  D1 E3 CD 39 87 E8 42 83-EC 08 CD 39 5E C8 CD 3D  ...9..B....9^..=
1817:8040  8B DE D1 E3 8B 87 0D 6E-BA 1C 00 F7 E2 8B D8 81  .......n........
1817:8050  C3 0D 01 1E 07 26 FF 77-10 8B DE D1 E3 8B 87 0D  .....&.w........
1817:8060  6E BA 1C 00 F7 E2 8B D8-81 C3 0D 01 1E 07 26 FF  n..............&.
1817:8070  77 0E 1E B8 6D 17 50 1E-B8 6E 3F 50 9A 0A 00 65  w...m.P..n?P...e
1817:8080  2D 83 C4 18 E9 A3 00 8B-DE D1 E3 D1 E3 D1 E3 CD  -...............
1817:8090  39 87 E8 42 9A C7 05 17-18 89 56 E0 89 46 DE 8B  9..B......V..F..
1817:80A0  DE D1 E3 8B 87 0D 6E BA-1C 00 F7 E2 05 0D 01 8C  .......n........
1817:80B0  DA 05 12 00 52 50 FF 76-E0 FF 76 DE 8B DE D1 E3  ....RP.v..v.....
1817:80C0  8B 87 0D 6E BA 1C 00 F7-E2 8B D8 81 C3 0D 01 1E  ...n............
1817:80D0  07 26 FF 77 0E 1E B8 78-17 50 9A 05 00 A8 2C 83  .&.w...(.P....,.
1817:80E0  C4 0E 8B DE D1 E3 8B 87-0D 6E BA 1C 00 F7 E2 05  .........n......
1817:80F0  0D 01 8C DA 05 12 00 52-50 FF 76 E0 FF 76 DE 8B  .......RP.v..v..
1817:8100  DE D1 E3 8B 87 0D 6E BA-1C 00 F7 E2 8B D8 81 C3  .......n........
1817:8110  0D 01 1E 07 26 FF 77 0E-1E B8 87 17 50 1E B8 6E  ....&.w.....P..n
1817:8120  3F 50 9A 0A 00 65 2D 83-C4 12 8B 1E F8 00 D1 E3  ?P...e-.........
1817:8130  83 BF 23 56 02 7C 03 E9-07 01 8B 1E F8 00 D1 E3  ..#V.!..........
1817:8140  8B 87 23 56 BA 20 03 F7-E2 8B D8 81 C3 B5 67 1E  ..#V. .........g.
1817:8150  07 06 53 8B DE D1 E3 8B-87 0D 6E D1 E0 D1 E0 5B  ..S.......n....[
1817:8160  07 03 D8 C3 3C D9 87 90-01 8B DE D1 E3 D1 E3 D1  ....<...........
1817:8170  E3 CD 38 9F E8 42 CD 39-3E DC 6F CD 3D 8A 26 DD  ..8..B.9>.o.=.&.
1817:8180  6F 9E 76 2B 1E B8 93 17-50 9A B7 00 D7 19 59 59  o.v+....P.....YY
1817:8190  1E B8 97 17 50 1E B8 6E-3F 50 9A D9 00 D7 19 83  ....P..n?P......
1817:81A0  C4 08 8B DE D1 E3 C7 87-80 49 02 00 E9 90 00 8B  ..........I......
1817:81B0  1E FB 00 D1 E3 8B 87 23-56 BA 20 03 F7 E2 8B D8  .......#V. .....
1817:81C0  81 C3 B5 67 1E 07 06 53-8B DE D1 E3 8B 87 0D 6E  ...g...S.......n
1817:81D0  D1 E0 D1 E0 5B 07 03 D8-CD 3C D9 07 8B DE D1 E3  ....[....<......
1817:81E0  D1 E3 D1 E3 CD 38 9F E8-42 CD 39 3E DC 6F CD 3D  .....8..B.9>.o.=
1817:81F0  8A 26 DD 6F 9E 73 2A 1E-B8 9B 17 50 9A B7 00 D7  .&.o.s*....P....
1817:8200  19 59 59 1E B8 A0 17 50-1E B8 6E 3F 50 9A D9 00  .YY....P..n?P...
1817:8210  D7 19 83 C4 08 8B DE D1-E3 C7 87 80 49 01 00 EB  .............I...
1817:8220  1E 1E B8 A5 17 50 9A B7-00 D7 19 59 59 1E B8 AC  .....P.....YY...
1817:8230  17 50 1E B8 6E 3F 50 9A-D9 00 D7 19 83 C4 08 EB  .P..n?P.........
1817:8240  1E 1E B8 B3 17 50 9A B7-00 D7 19 59 59 1E B8 BA  .....P.....YY...
1817:8250  17 50 1E B8 6E 3F 50 9A-D9 00 D7 19 83 C4 08 1E  .P..n?P.........
```

```
1817:8260  58 C1 17 50 1E B8 6E 3F-50 9A 0A 00 65 2D 83 C4   ...P..n?P...e-..
1817:8270  08 83 3E D1 00 01 75 4D-8B DE D1 E3 D1 E3 D1 E3   ..>...uM........
1817:8280  CD 39 87 98 49 83 EC 08-CD 39 5E CC CD 3D 1E B8   .9..I....9^..=..
1817:8290  C4 17 50 9A 05 00 A8 2C-83 C4 0C 8B DE D1 E3 D1   ..P.....,.......
1817:82A0  E3 D1 E3 CD 39 87 98 49-83 EC 08 CD 39 5E CC CD   ....9..I....9^..
1817:82B0  3D 1E B8 CE 17 50 1E B8-6E 3F 50 9A 0A 00 65 2D   =....P..n?P...e-
1817:82C0  83 C4 10 EB 0C 1E B8 E2-17 50 9A 05 00 A8 2C 59   .........P.....,Y
1817:82D0  59 EB 3C 1E B8 E4 17 50-9A B7 00 D7 19 59 59 1E   Y.<....P.....YY.
1817:82E0  B8 ED 17 50 1E B8 6E 3F-50 9A D9 00 D7 19 83 C4   ...P..n?P.......
1817:82F0  08 1E B8 F6 17 50 9A 05-00 A8 2C 59 59 1E B8 F8   .....P....,YY...
1817:8300  17 50 1E B8 6E 3F 50 9A-0A 00 65 2D 83 C4 08 83   .P..n?P...e-....
1817:8310  3E D1 00 01 75 03 E9 80-00 8B 1E FB 00 D1 E3 8B   >...u...........
1817:8320  87 23 56 8A 20 03 F7 E2-8B D8 81 C3 B5 67 1E 07   .#V. ........g..
1817:8330  06 53 8B DE D1 E3 8B 87-0D 6E D1 E0 D1 E0 5B 07   .S.......n....[.
1817:8340  03 D8 CD 3C D9 07 83 EC-08 CD 39 5E CC CD 3D 9B   ...<......9^..=.
1817:8350  1E FB 00 D1 E3 8B 87 23-56 8A 20 03 F7 E2 8B D8   .......#V. .....
1817:8360  81 C3 B5 67 1E 07 06 53-8B DE D1 E3 8B 87 0D 6E   ...g...S.......n
1817:8370  D1 E0 D1 E0 5B 07 03 D8-CD 3C D9 27 90 01 83 EC   ....[....<......
1817:8380  08 CD 39 5E C4 CD 3D 1E-B8 FB 17 50 1E B8 6E 3F   ..9^..=....P..n?
1817:8390  50 9A 0A 00 65 2D 83 C4-18 46 83 FE 0C 7D 03 E9   P...e-...F...}..
1817:83A0  A5 FA 8B 16 1A 4A A1 18-4A 52 50 CD 37 46 D0 CD   .....J..JRP.7F..
1817:83B0  3D 83 C4 04 8B 16 22 4A-A1 20 4A 52 50 CD 37 46   =....."J. JRP.7F
1817:83C0  D0 CD 3D 83 C4 04 CD 38-36 09 19 CD 3A E9 CD 39   ..=....86...:..9
1817:83D0  5E F8 CD 3D A1 20 4A 08-06 22 4A 74 1E 8B 16 22   ^..=. J.."Jt..."
1817:83E0  4A A1 20 4A 52 50 CD 37-46 D0 CD 3D 83 C4 04 CD   J. JRP.7F..=....
1817:83F0  38 7E F8 CD 39 5E F8 CD-3D EB 14 C7 46 FE 00 40   8~..9^..=...F..@
1817:8400  C7 46 FC 00 00 C7 46 FA-00 00 C7 46 F8 00 00 CD   .F....F....F....
1817:8410  39 46 F8 CD 38 0E 11 19-CD 38 2E 19 19 CD 39 5E   9F..8....8....9^
1817:8420  F8 CD 3D CD 39 06 21 19-CD 39 46 F8 CD 3A D9 CD   ..=.9.!..9F..:..
1817:8430  39 3E DC 6F CD 3D 8A 26-DD 6F 9E 72 1A CD 39 06   9>.o.=.&.o.r..9.
1817:8440  29 19 CD 39 46 F8 CD 3A-D9 CD 39 3E DC 6F CD 3D   )..9F..:..9>.o.=
1817:8450  8A 26 DD 6F 9E 76 30 1E-B8 13 18 50 1E B8 6E 3F   .&.o.v0....P..n?
1817:8460  50 9A D9 00 D7 19 83 C4-08 FF 76 FE FF 76 FC FF   P.........v..v..
1817:8470  76 FA FF 76 F8 1E B8 1C-18 50 1E B8 6E 3F 50 9A   v..v.....P..n?P.
1817:8480  0A 00 65 2D 83 C4 10 8B-16 1E 4A A1 1C 4A 52 50   ..e-......J..JRP
1817:8490  CD 37 46 D0 CD 3D 83 C4-04 8B 16 26 4A A1 24 4A   .7F..=.....&J.$J
1817:84A0  52 50 CD 37 46 D0 CD 3D-83 C4 04 CD 38 36 09 19   RP.7F..=....86..
1817:84B0  CD 3A E9 CD 39 5E F8 CD-3D A1 24 4A 08 06 26 4A   .:..9^..=.$J..&J
1817:84C0  74 1E 8B 16 26 4A A1 24-4A 52 50 CD 37 46 D0 CD   t...&J.$JRP.7F..
1817:84D0  3D 83 C4 04 CD 38 7E F8-CD 39 5E F8 CD 3D EB 14   =....8~..9^..=..
1817:84E0  C7 46 FE 00 40 C7 46 FC-00 00 C7 46 FA 00 00 C7   .F..@.F....F....
1817:84F0  46 F8 00 00 CD 39 46 F8-CD 38 0E 11 19 CD 38 2E   F....9F..8....8.
1817:8500  19 19 CD 39 5E F8 CD 3D-CD 39 06 21 19 CD 39 46   ...9^..=.9.!..9F
1817:8510  F8 CD 3A D9 CD 39 3E DC-6F CD 3D 8A 26 DD 6F 9E   ..:..9>.o.=.&.o.
1817:8520  72 1A CD 39 06 29 19 CD-39 46 F8 CD 3A D9 CD 39   r..9.)..9F..:..9
1817:8530  3E DC 6F CD 3D 8A 26 DD-6F 9E 76 30 1E B8 25 18   >.o.=.&.o.v0..%.
1817:8540  50 1E B8 6E 3F 50 9A D9-00 D7 19 83 C4 08 FF 76   P..n?P.........v
1817:8550  FE FF 76 FC FF 76 FA FF-76 F8 1E B8 2E 18 50 1E   ..v..v..v.....P.
1817:8560  B8 6E 3F 50 9A 0A 00 65-2D 83 C4 10 1E B8 37 18   .n?P...e-.....7.
1817:8570  50 1E B8 6E 3F 50 9A 0A-00 65 2D 83 C4 08 1E B8   P..n?P...e-.....
1817:8580  3A 18 50 9A 8D 00 D7 19-59 59 C6 46 E9 31 E9 2D   :.P.....YY.F.1.-
1817:8590  03 83 3E 4C 0C 00 75 0A-9A CE 05 A2 1A 88 46 E9   ..>L..u.......F.
1817:85A0  EB 04 C6 46 E9 08 80 7E-E9 32 74 03 E9 0F 03 1E   ...F...~.2t.....
1817:85B0  B8 43 18 50 9A 0A 00 D7-19 59 59 9A 6C 03 A2 1A   .C.P.....YY.l...
1817:85C0  33 FF EB 10 80 7E D3 08-75 02 EB E3 8A 46 D3 36   3....~..u....F.6
1817:85D0  88 43 EA 47 9A 21 06 A2-1A 88 46 D8 3C 0D 74 05   .C.G.!....F.<.t.
1817:85E0  83 FF 0D 7C DF 83 FF 0D-7C 07 9A A1 06 A2 1A EB   ...|....|.......
1817:85F0  BE 36 C6 43 EA 00 9A 18-02 A2 1A 16 8D 46 EA 50   .6.C.........F.P
1817:8600  1E B8 4C 18 50 9A 05 00-A8 2C 83 C4 08 1E B8 5E   ..L.P....,.....^
1817:8610  18 50 9A 04 00 D7 2C 59-59 9A 21 06 A2 1A 88 46   .P....,YY.!....F
1817:8620  D9 80 7E D9 0D 75 04 C6-46 D9 79 80 7E D9 08 75   ..~..u..F.y.~..u
1817:8630  04 C6 46 D9 6E 80 7E D9-4E 74 06 80 7E D9 6E 75   ..F.n.~.Nt..~.nu
1817:8640  03 E9 6B FF 80 7E D9 59-74 08 80 7E D9 79 74 02   ..k..~.Yt..~.yt.
1817:8650  EB A4 1E B8 76 18 50 16-8D 46 EA 50 9A 1A 02 5C   ....v.P..F.P...\
1817:8660  2B 83 C4 08 89 56 DC 89-46 DA 0B D0 75 15 16 8D   +....V..F...u...
1817:8670  46 EA 50 1E B8 79 18 50-9A 05 00 A8 2C 83 C4 08   F.P..y.P....,...
1817:8680  E9 2C FF 33 F6 E9 FE 01-8B DE D1 E3 83 BF 0D 6E   .,.3...........n
1817:8690  64 75 03 E9 EF 01 56 9A-7E 08 A2 1A 59 52 50 1E   du....V.~...YRP.
1817:86A0  B8 90 18 50 FF 76 DC FF-76 DA 9A 0A 00 65 2D 83   ...P.v..v....e-.
1817:86B0  C4 0C 8B DE D1 E3 83 BF-25 6E 01 74 13 1E B8 97   ........%n.t....
1817:86C0  18 50 FF 76 DC FF 76 DA-9A 0A 00 65 2D 83 C4 08   .P.v..v....e-...
```

```
1817:86D0  8B DE D1 E3 83 BF F5 6D-00 75 03 E9 82 01 16 8D   .......m.u......
1817:86E0  46 E2 50 E8 DE D1 E3 FF-87 0A 48 8B DE D1 E3 FF   F.P.......H.....
1817:86F0  87 0D 6E 9A 1F 05 4B 21-83 C4 06 0B C0 75 2C 8B   ..n...K!.....u,.
1817:8700  DE D1 E3 D1 E3 D1 E3 CD-39 87 98 49 83 EC 08 CD   .........9..I...
1817:8710  39 5E CC CD 3D 1E B8 9F-18 50 FF 76 DC FF 76 DA   9^..=....P.v..v.
1817:8720  9A 0A 00 65 2D 83 C4 10-E9 5A 01 8A 84 48 43 98   ...e-....Z...HC.
1817:8730  50 1E B8 55 18 50 FF 76-DC FF 76 DA 9A 0A 00 65   P....P.v..v....e
1817:8740  2D 83 C4 0A 8B DE D1 E3-8B 87 0D 6E 8A 1C 00 F7   -..........n....
1817:8750  E2 8B D8 81 C3 0D 01 1E-07 26 83 7F 10 00 74 74   .........&....tt
1817:8760  8B DE D1 E3 8B 87 0D 6E-8A 1C 00 F7 E2 05 0D 01   .......n........
1817:8770  8C DA 05 12 00 52 50 8B-DE D1 E3 D1 E3 D1 E3 CD   .....RP.........
1817:8780  39 87 E8 42 83 EC 08 CD-39 5E C8 CD 3D 8B DE D1   9..B....9^..=...
1817:8790  E3 8B 87 0D 6E 8A 1C 00-F7 E2 8B D8 81 C3 0D 01   ....n...........
1817:87A0  1E 07 26 FF 77 10 8B DE-D1 E3 8B 87 0D 6E 8A 1C   ..&.w........n..
1817:87B0  00 F7 E2 8B D8 81 C3 0D-01 1E 07 26 FF 77 0E 1E   ...........&.w..
1817:87C0  B8 88 18 50 FF 76 DC FF-76 DA 9A 0A 00 65 2D 83   ...P.v..v....e-.
1817:87D0  C4 18 E8 61 8B DE D1 E3-D1 E3 D1 E3 CD 39 87 E8   ...a.........9..
1817:87E0  42 9A C7 05 17 18 89 56-E0 89 46 DE 8B DE D1 E3   B......V..F.....
1817:87F0  8B 87 0D 6E 8A 1C 00 F7-E2 05 0D 01 8C DA 05 12   ...n............
1817:8800  00 52 50 FF 76 E0 FF 76-DE 8B DE D1 E3 8B 87 0D   .RP.v..v........
1817:8810  6E 8A 1C 00 F7 E2 8B D8-81 C3 0D 01 1E 07 26 FF   n.............&.
1817:8820  77 0E 1E B8 C8 18 50 FF-76 DC FF 76 DA 9A 0A 00   w.....P.v..v....
1817:8830  65 2D 83 C4 12 8B DE D1-E3 D1 E3 D1 E3 CD 39 87   e-............9.
1817:8840  98 49 83 EC 08 CD 39 5E-CC CD 3D 1E B8 D6 18 50   .I....9^..=....P
1817:8850  FF 76 DC FF 76 DA 9A 0A-00 65 2D 83 C4 10 EB 25   .v..v....e-....%
1817:8860  1E B8 E1 18 50 FF 76 DC-FF 76 DA 9A D9 00 D7 19   ....P.v..v......
1817:8870  83 C4 08 1E B8 EA 18 50-1E B8 6E 3F 50 9A 0A 00   .......P..n?P...
1817:8880  65 2D 83 C4 08 46 83 FE-0C 7D 03 E9 FA FD FF 76   e-...F...}.....v
1817:8890  DC FF 76 DA 9A 28 15 A2-1A 59 59 16 8D 46 EA 50   ..v..(...YY..F.P
1817:88A0  1E B8 EC 18 50 1E B8 6E-3F 50 9A 0A 00 65 2D 83   ....P..n?P...e-.
1817:88B0  C4 0C 1E B8 00 19 50 9A-8D 00 D7 19 59 59 80 7E   ......P.....YY.~
1817:88C0  E9 0D 74 09 80 7E E9 08-74 03 E9 C4 FC 80 7E E9   ..t..~..t.....~.
1817:88D0  0D 75 05 9A 06 00 A2 25-5F 5E 8B E5 5D CB 56 39   .u.....%_^..].V9
1817:88E0  26 98 0D 77 05 9A CF 09-17 18 9A 7A 02 A4 20 B8   &..w.......z.. .
1817:88F0  04 00 50 9A 64 01 A4 20-59 8B F0 E8 C6 0B C0 74   ..P.d.. Y......t
1817:8900  1E 9A 98 02 A4 20 B8 08-00 50 9A 64 01 A4 20 59   ..... ...P.d.. Y
1817:8910  8B F0 E8 C6 0B C0 74 07-56 9A 07 00 72 1D 59 C7   ......t.V...r.Y.
1817:8920  06 97 00 00 00 C7 06 95-00 7D 00 E8 00 A1 95 00   .........}......
1817:8930  0B 06 97 00 75 F7 C7 06-97 00 00 00 C7 06 95 00   ....u...........
1817:8940  E2 04 E8 10 BA 12 03 EC-24 01 32 06 F4 47 0A C0   ........$.2..G..
1817:8950  75 02 EB 0D A1 95 00 0B-06 97 00 75 E7 33 C0 EB   u..........u.3..
1817:8960  05 B8 06 00 EB 00 5E CB-55 8B EC 83 EC 02 56 57   ......^.U.....VW
1817:8970  39 26 98 0D 77 05 9A CF-09 17 18 A1 03 01 89 46   9&..w..........F
1817:8980  FE C7 06 03 01 00 00 B8-08 00 50 9A 21 00 6B 1C   ..........P.!.k.
1817:8990  59 8B 46 FE A3 03 01 33-FF EB 24 9A 2C 02 6B 1C   Y.F....3..$.,.k.
1817:89A0  9A 7A 02 A4 20 B8 04 00-50 9A 64 01 A4 20 59 8B   .z.. ...P.d.. Y.
1817:89B0  F0 9A 62 02 6B 1C 0B F6-75 04 8B C6 EB 0A 47 83   ..b.k...u.....G.
1817:89C0  FF 03 7C D7 8B C6 E8 00-5F 5E 8B E5 5D CB 55 8B   ..|....._^..].U.
1817:89D0  EC 83 EC 02 56 57 39 26-98 0D 77 05 9A CF 09 17   ....VW9&..w.....
1817:89E0  18 A1 03 01 89 46 FE C7-06 03 01 00 00 B8 09 00   .....F..........
1817:89F0  50 9A 21 00 6B 1C 59 8B-46 FE A3 03 01 33 FF EB   P.!.k.Y.F....3..
1817:8A00  24 9A 2C 02 6B 1C 9A 8B-02 A4 20 B8 08 00 50 9A   $.,.k..... ...P.
1817:8A10  64 01 A4 20 59 8B F0 9A-62 02 6B 1C 0B F6 75 04   d.. Y...b.k...u.
1817:8A20  8B C6 EB 0A 47 83 FF 03-7C D7 8B C6 E8 00 5F 5E   ....G...|....._^
1817:8A30  8B E5 5D CB 55 8B EC 56-39 26 98 0D 77 05 9A CF   ..].U..V9&..w...
1817:8A40  09 17 18 C7 06 97 00 00-00 C7 06 95 00 E2 04 33   ...............3
1817:8A50  F6 EB 2E C7 06 32 0D 02-00 EB 00 83 3E 32 0D 00   .....2......>2..
1817:8A60  75 F9 BA 12 03 EC 24 01-32 06 F4 47 0A C0 75 03   u.....$.2..G..u.
1817:8A70  46 EB 02 33 F6 A1 95 00-0B 06 97 00 75 03 E9 52   F..3........u...
1817:8A80  00 83 FE 3C 72 CD C7 06-97 00 00 00 C7 06 95 00   ...<r...........
1817:8A90  E2 04 33 F6 EB 2D C7 06-32 0D 02 00 EB 00 83 3E   ..3..-..2......>
1817:8AA0  32 0D 00 75 F9 BA 12 03-EC 24 01 32 06 F4 47 0A   2..u.....$.2..G.
1817:8AB0  C0 74 03 46 EB 02 33 F6-A1 95 00 0B 06 97 00 75   .t.F..3........u
1817:8AC0  03 EB 18 83 FE 06 72 CE-FA 81 26 7E 49 F3 00 A0   ......r...&~I...
1817:8AD0  7E 49 BA 11 03 EE FB 33-C0 E8 6C FA 81 26 7E 49   ~I.....3..l..&~I
1817:8AE0  F3 00 8B 46 06 09 06 7E-49 A0 7E 49 BA 11 03 EE   ...F...~I.~I....
1817:8AF0  FB C7 06 97 00 00 00 C7-06 95 00 E2 04 33 F6 EB   .............3..
1817:8B00  2D C7 06 32 0D 02 00 EB-00 83 3E 32 0D 00 75 F9   -..2......>2..u.
1817:8B10  BA 12 03 EC 24 01 32 06-F4 47 0A C0 74 03 46 EB   ....$.2..G..t.F.
1817:8B20  02 33 F6 A1 95 00 0B 06-97 00 75 02 EB 05 83 FE   .3........u.....
1817:8B30  06 72 CE FA 81 26 7E 49-F3 00 A0 7E 49 BA 11 03   .r...&~I...~I...
```

```
1817:8B40  EE FB B3 07 00 EB 00 5E-5D C3 39 26 98 0D 77 05   .......^].9%..w.
1817:8B50  9A CF 09 17 18 FA 81 26-7E 49 FC 00 81 0E 7E 49   .......&~I....~I
1817:8B60  08 00 A0 7E 49 BA 11 03-EE FB C3 39 26 98 0D 77   ...~I......9%..w
1817:8B70  05 9A CF 09 17 18 FA 81-26 7E 49 FC 00 81 0E 7E   ........&~I....~
1817:8B80  49 04 00 A0 7E 49 BA 11-03 EE FB C3 55 8B EC 56   I...~I......U..V
1817:8B90  57 39 26 98 0D 77 05 9A-CF 09 17 18 8F 0C 00 83   W9%..w..........
1817:8BA0  7E 08 01 74 21 83 3E 09-01 00 74 1A 83 3E 09 01   ~..t!.>...t..>..
1817:8BB0  0C 7D 13 83 3E 09 01 00-7D 08 83 3E 09 01 F7 DF   .}..>...}..>....
1817:8BC0  E8 04 83 3E 09 01 A1 09-01 01 06 0B 01 9A 98 00   ...>............
1817:8BD0  A4 20 8B F0 8B C6 0B C0-74 05 8B C6 E9 81 00 C7   . ......t.......
1817:8BE0  06 03 01 00 00 E8 1F 58-07 00 50 9A 21 00 6B 1C   ..........P.!.k.
1817:8BF0  59 9A E4 00 CF 20 8B F0-8B C6 0B C0 74 04 8B C6   Y.... ......t...
1817:8C00  E8 5E FF 06 03 01 A1 03-01 3B C7 7C DA 83 7E 06   .^.......;.|..~.
1817:8C10  01 75 23 83 3E 0B 01 32-7E 1C C7 06 0B 01 00 00   .u#.>..2~.......
1817:8C20  1E B8 32 19 50 9A 0A 00-D7 19 59 59 E8 01 00 50   ..2.P.....YY...P
1817:8C30  9A 59 07 A2 1A 59 9A 8A-02 6B 1C 0B C0 74 1D 9A   .....Y...k...t..
1817:8C40  8A 02 6B 1C 0B C0 74 14-9A 8A 02 6B 1C 8B F0 8B   ..k...t....k....
1817:8C50  C6 0B C0 74 07 56 9A 07-00 72 1D 59 8B C6 EB 00   ...t.V...r.Y....
1817:8C60  5F 5E 5D CB 55 8B EC 83-EC 08 56 57 39 26 98 0D   _^].U.....VW9%..
1817:8C70  77 05 9A CF 09 17 18 9A-3C 02 6B 1C C7 46 FC 00   w.........k..F..
1817:8C80  00 E9 59 01 C7 06 46 0D-00 00 C7 06 97 00 00 00   ......F.........
1817:8C90  C7 06 95 00 A9 03 FA 81-26 7E 49 FC 00 81 0E 7E   ........&~I....~
1817:8CA0  49 01 00 A0 7E 49 BA 11-03 EE FB 33 FF EB 0D BA   I...~I.....3....
1817:8CB0  12 03 EC A8 10 74 03 47-EB 02 33 FF 81 FF 2C 01   .....t.G..3...,.
1817:8CC0  7D 09 A1 95 00 0B 06 97-00 75 E4 A1 95 00 0B 06   }.........u.....
1817:8CD0  97 00 75 18 FA 81 26 7E-49 FC 00 A0 7E 49 BA 11   ..u...&~I...~I..
1817:8CE0  03 EE FB C7 06 46 0D 01-00 BE 0C 00 E9 9F 00 C7   .....F..........
1817:8CF0  06 97 00 00 00 C7 06 95-00 53 07 EB 00 BA 12 03   .........S......
1817:8D00  EC A8 10 74 09 A1 95 00-0B 06 97 00 75 EF 8B 16   ...t........u...
1817:8D10  97 00 A1 95 00 89 56 FA-89 46 F8 FA 81 26 7E 49   ......V..F...&~I
1817:8D20  FC 00 A0 7E 49 BA 11 03-EE FB 8B 46 F8 0B 46 FA   ...~I......F..F.
1817:8D30  75 22 9A C2 02 CF 20 8B-F0 8B C6 0B C0 75 0D C7   u".... ......u..
1817:8D40  06 46 0D 01 00 BE 1C 00-EB 44 EB 08 C7 06 46 0D   .F.......D....F.
1817:8D50  01 00 EB 3A C7 06 97 00-00 00 C7 06 95 00 1E 00   ...:............
1817:8D60  EB 13 BA 12 03 EC A8 10-74 08 C7 06 46 0D 01 00   ........t...F...
1817:8D70  BE 0E 00 EB 19 A1 95 00-0B 06 97 00 75 E4 C7 06   ............u...
1817:8D80  46 0D 01 00 9A 62 02 6B-1C 33 C0 E9 91 00 9A 62   F....b.k.3.....b
1817:8D90  02 6B 1C 1E B8 32 19 50-9A 0A 00 D7 19 59 59 9A   .k....2.P.....YY.
1817:8DA0  A1 06 A2 1A 83 3E 4C 0C-00 75 05 9A 40 0C A2 1A   .....>L..u..@...
1817:8DB0  1E B8 44 19 50 9A 0A 00-D7 19 59 59 A1 C8 00 59   ..D.P.....YY....
1817:8DC0  46 FE 9A 8A 02 6B 1C 0B-C0 74 1D 9A 8A 02 6B 1C   F....k...t....k.
1817:8DD0  0B C0 74 14 9A 8A 02 6B-1C 8B F0 8B C6 0B C0 74   ..t....k.......t
1817:8DE0  07 56 9A 07 00 72 1D 59-9A 98 00 A4 20 8B F0 8B   .V...r.Y.... ...
1817:8DF0  C6 0B C0 74 07 56 9A 07-00 72 1D 59 FF 76 FE 9A   ...t.V...r.Y.v..
1817:8E00  11 01 6B 1C 59 9A 3C 02-6B 1C FF 46 FC 83 7E FC   ..k.Y...k..F..~.
1817:8E10  06 7D 03 E9 6E FE 9A 62-02 6B 1C 8B C6 EB 00 5F   .}..n..b.k....._
1817:8E20  5E 8B E5 5D CB 39 26 98-0D 77 05 9A CF 09 17 18   ^..].9%..w......
1817:8E30  0E E8 30 FE 0B C0 74 05-B8 08 00 EB 04 33 C0 EB   ..0...t......3..
1817:8E40  00 CB 55 8B EC 83 EC 04-39 26 98 0D 77 05 9A CF   ..U.....9%..w...
1817:8E50  09 17 18 C7 06 46 0D 00-00 FA 81 26 7E 49 FC 00   .....F.....&~I..
1817:8E60  81 0E 7E 49 02 00 A0 7E-49 BA 11 03 EE FB C7 06   ..~I...~I.......
1817:8E70  97 00 00 00 C7 06 95 00-53 07 EB 00 BA 12 03 EC   ........S.......
1817:8E80  A8 10 74 09 A1 95 00 0B-06 97 00 75 EF 8B 16 97   ..t........u....
1817:8E90  00 A1 95 00 89 56 FE 89-46 FC FA 81 26 7E 49 FC   .....V..F...&~I.
1817:8EA0  00 A0 7E 49 BA 11 03 EE-FB 8B 46 FC 0B 46 FE 75   ..~I......F..F.u
1817:8EB0  63 FA 81 26 7E 49 FC 00-81 0E 7E 49 01 00 A0 7E   c..&~I....~I...~
1817:8EC0  49 BA 11 03 EE FB C7 06-97 00 00 00 C7 06 95 00   I...............
1817:8ED0  53 07 EB 00 BA 12 03 EC-A8 10 74 09 A1 95 00 0B   S.........t.....
1817:8EE0  06 97 00 75 EF 8B 16 97-00 A1 95 00 89 56 FE 89   ...u.........V..
1817:8EF0  46 FC FA 81 26 7E 49 FC-00 A0 7E 49 BA 11 03 EE   F...&~I...~I....
1817:8F00  FB 8B 46 FC 0B 46 FE 75-08 C7 06 46 0D 01 00 B8   ..F..F.u...F....
1817:8F10  0D 00 EB 34 C7 06 97 00-00 00 C7 06 95 00 1E 00   ...4............
1817:8F20  EB 13 BA 12 03 EC A8 10-74 08 C7 06 46 0D 01 00   ........t...F...
1817:8F30  B8 0E 00 EB 13 A1 95 00-0B 06 97 00 75 E4 C7 06   ............u...
1817:8F40  46 0D 01 00 33 C0 EB 00-8B E5 5D CB 55 8B EC 83   F...3.....].U...
1817:8F50  EC 18 56 57 39 26 98 0D-77 05 9A CF 09 17 18 8C   ..VW9%..w.......
1817:8F60  5E F8 C7 46 F6 4E 19 1E-B8 5D 19 50 9A 0A 00 D7   ^..F.N...].P....
1817:8F70  19 59 59 33 FF EB 64 83-FF 0B 7D 04 33 C0 EB 03   .YY3..d...}.3...
1817:8F80  8B 0D 00 89 46 EA 83 C7-23 03 00 99 F7 FB 42 42   ....F.........BB
1817:8F90  89 56 EC FF 76 EC FF 76-EA 9A F7 02 A2 1A 59 59   .V..v..v......YY
1817:8FA0  E8 DF D1 E3 8B 9F 50 0C-D1 E3 FF B7 FF 56 8B DF   ......P......V..
```

```
1817:8FB0  D1 E3 8B 87 50 0C BA 1C-00 F7 E2 05 0D 01 8C DA   ....P...........
1817:8FC0  05 0A 00 52 50 8B DF D1-E3 FF B7 50 0C 1E B8 66   ...RP......P...f
1817:8FD0  19 50 9A 05 00 A8 2C 83-C4 0C 47 83 FF 15 7C 97   .P.....,...G...|.
1817:8FE0  33 C0 50 9A 36 03 A2 1A-59 16 8D 46 E8 50 9A A6   3.P.6...Y..F.P..
1817:8FF0  08 A2 1A 59 59 89 46 F2-3D 01 00 74 34 83 7E F2   ...YY.F.=..t4.~.
1817:9000  02 75 03 E9 3B 03 83 7E-F2 03 75 1D B8 18 00 50   .u..;..~..u....P
1817:9010  9A 30 0E A2 1A 59 89 46-F2 0B C0 74 09 FF 76 F2   .0...Y.F...t..v.
1817:9020  9A 07 00 72 1D 59 E9 4A-FF 9A A1 06 A2 1A E9 36   ...r.Y.J.......6
1817:9030  FF 83 7E E8 64 7D 1F 8B-46 E8 BA 1C 00 F7 E2 8B   ..~.d}..F.......
1817:9040  D8 81 C3 0D 01 1E 07 26-83 7F 18 01 75 08 9A A1   ........&....u..
1817:9050  06 A2 1A E9 11 FF 81 7E-E8 DE 00 75 03 E9 36 01   .......~...u..6.
1817:9060  81 7E E8 4D 01 75 03 E9-04 02 83 7E E8 64 7D 03   .~.M.u.....~.d}.
1817:9070  83 7E E8 00 7C 02 EB 08-9A A1 06 A2 1A E9 E7 FE   .~..|...........
1817:9080  1E B8 77 19 50 9A 0A 00-D7 19 59 59 B8 01 00 50   ..w.P.....YY...P
1817:9090  9A 36 03 A2 1A 59 8B 46-E8 BA 1C 00 F7 E2 05 0D   .6...Y.F........
1817:90A0  01 8C DA 05 0A 00 52 50-1E B8 80 19 50 9A 05 00   ......RP....P...
1817:90B0  A8 2C 83 C4 06 B8 02 00-50 9A 36 03 A2 1A 59 8B   .,......P.6...Y.
1817:90C0  5E E8 D1 E3 FF B7 FF 56-1E B8 86 19 50 9A 05 00   ^......V....P...
1817:90D0  A8 2C 83 C4 06 B8 03 00-50 9A 36 03 A2 1A 59 16   .,......P.6...Y.
1817:90E0  8D 46 EE 50 9A A6 08 A2-1A 59 59 3D 01 00 74 03   .F.P.....YY=..t.
1817:90F0  E9 9B 00 83 7E EE 00 7D-03 E9 92 00 81 7E EE 10   ....~..}.....~..
1817:9100  27 7C 03 E9 88 00 1E B8-8C 19 50 9A 0A 00 D7 19   '|........P.....
1817:9110  59 59 8B 46 EE 8B 5E E8-D1 E3 89 87 FF 56 16 8D   YY.F..^......V..
1817:9120  46 F0 50 E8 5E E8 D1 E3-FF B7 FF 56 FF 76 E8 9A   F.P.^......V.v..
1817:9130  1F 05 4B 21 83 C4 08 89-46 F4 8B 46 E8 BA 1C 00   ..K!....F..F....
1817:9140  F7 E2 8B D8 81 C3 0D 01-1E 07 26 83 7F 02 01 75   ..........&....u
1817:9150  1C 16 8D 46 F0 50 8B 5E-E8 D1 E3 FF B7 FF 56 FF   ...F.P.^.......V.
1817:9160  76 E8 9A 00 0E 3B 24 83-C4 08 21 46 F4 9A 18 08   v....;$...!F....
1817:9170  17 22 83 7E F4 00 75 11-1E B8 95 19 50 9A 0A 00   .".~..u.....P...
1817:9180  D7 19 59 59 9A DE 05 A2-1A E9 DB FD EB 08 9A A1   ..YY............
1817:9190  06 A2 1A E9 CA FE 1E B8-9E 19 50 9A 0A 00 D7 19   ..........P.....
1817:91A0  59 59 33 F6 EB 12 80 7E-FB 08 75 02 EB E8 8A 46   YY3....~..u....F
1817:91B0  FB C4 5E F6 26 88 00 46-9A 21 06 A2 1A 88 46 FB   ..^.&..F.!....F.
1817:91C0  3C 0D 74 05 83 FE 0D 7C-DD 83 FE 0D 7C 07 9A A1   <.t....|....|...
1817:91D0  06 A2 1A EB C1 C4 5E F6-26 C6 00 2E 46 C4 5E F6   ......^.&...F.^.
1817:91E0  26 C6 00 6C 46 C4 5E F6-26 C6 00 6F 46 C4 5E F6   &..lF.^.&..oF.^.
1817:91F0  26 C6 00 74 46 C4 5E F6-26 C6 00 00 1E B8 A7 19   &..tF.^.&.......
1817:9200  50 FF 76 F8 FF 76 F6 9A-1A 02 5C 2B 83 C4 08 89   P.v..v....\+....
1817:9210  56 FE 89 46 FC 0B D0 75-08 9A A1 06 A2 1A E9 75   V..F...u.......u
1817:9220  FF FF 76 FE FF 76 FC B8-01 00 50 B8 C8 00 50 1E   ..v..v....P...P.
1817:9230  B8 FF 56 50 9A 12 01 13-2C 83 C4 0C 89 46 F2 3D   ..VP.........F.=
1817:9240  01 00 7D 15 9A A1 06 A2-1A FF 76 FE FF 76 FC 9A   ..}.......v..v..
1817:9250  28 15 A2 1A 59 59 E9 3D-FF FF 76 FE FF 76 FC 9A   (...YY.=..v..v..
1817:9260  28 15 A2 1A 59 59 9A 18-08 17 22 E9 F9 FC 1E B8   (...YY....".....
1817:9270  AA 19 50 9A 0A 00 D7 19-59 59 33 F6 EB 12 80 7E   ..P.....YY3....~
1817:9280  FB 08 75 02 EB E8 8A 46-FB C4 5E F6 26 88 00 46   ..u....F..^.&..F
1817:9290  9A 21 06 A2 1A 88 46 FB-3C 0D 74 05 83 FE 0D 7C   .!....F.<.t....|
1817:92A0  DD 83 FE 0D 7C 07 9A A1-06 A2 1A EB C1 C4 5E F6   ....|.........^.
1817:92B0  26 C6 00 2E 46 C4 5E F6-26 C6 00 6C 46 C4 5E F6   &...F.^.&..lF.^.
1817:92C0  26 C6 00 6F 46 C4 5E F6-26 C6 00 74 46 C4 5E F6   &..oF.^.&..tF.^.
1817:92D0  26 C6 00 00 1E B8 B3 19-50 FF 76 F8 FF 76 F6 9A   &.......P.v..v..
1817:92E0  1A 02 5C 2B 83 C4 08 89-56 FE 89 46 FC 0B D0 75   ..\+....V..F...u
1817:92F0  08 9A A1 06 A2 1A E9 75-FF FF 76 FE FF 76 FC B8   .......u..v..v..
1817:9300  01 00 50 B8 C8 00 50 1E-B8 FF 56 50 9A CB 00 3A   ..P...P...VP...:
1817:9310  2C 83 C4 0C 89 46 F2 3D-01 00 7D 15 9A A1 06 A2   ,....F.=..}.....
1817:9320  1A FF 76 FE FF 76 FC 9A-28 15 A2 1A 59 59 E9 3D   ..v..v..(...YY.=
1817:9330  FF FF 76 FE FF 76 FC 9A-28 15 A2 1A 59 59 E9 26   ..v..v..(...YY.&
1817:9340  FC 5F 5E 8B E5 5D CB 55-8B EC 83 EC 06 56 57 39   ._^..].U.....VW9
1817:9350  26 98 0D 77 05 9A CF 09-17 18 33 D2 8B 26 15 52   &..w......3..&.R
1817:9360  50 9A 01 02 14 2B 59 59-89 16 76 49 A3 74 49 0B   P....+YY..vI.tI.
1817:9370  D0 74 03 E9 90 00 9A 18-02 A2 1A 1E B8 B6 19 50   .t.............P
1817:9380  9A 05 00 A8 2C 59 59 1E-B8 D2 19 50 9A 05 00 A8   .....YY....P....
1817:9390  2C 59 59 1E B8 F3 19 50-9A 05 00 A8 2C 59 59 9A   ,YY....P....,YY.
1817:93A0  01 00 31 2D 89 56 FE 89-46 FC FF 76 FE FF 76 FC   ..1-.V..F..v..v.
1817:93B0  1E B8 15 1A 50 9A 05 00-A8 2C 83 C4 08 9A 09 00   ....P....,......
1817:93C0  31 2D 89 56 FE 89 46 FC-FF 76 FE FF 76 FC 1E B8   1-.V..F..v..v...
1817:93D0  2D 1A 50 9A 05 00 A8 2C-83 C4 08 1E B8 45 1A 50   -.P...........E.P
1817:93E0  9A 05 00 A8 2C 59 59 C7-46 FE 00 00 C7 46 FC 26   ....,YY.F....F.&
1817:93F0  1E FF 76 FE FF 76 FC 1E-B8 62 1A 50 9A 05 00 A8   ..v..v...b.P....
1817:9400  2C 83 C4 08 EB FE 33 FF-C4 1E 74 49 26 C7 07 00   ,.....3...tI&...
1817:9410  00 33 F6 E8 2B 16 8D 46-FA 50 E8 DE D1 E3 8B 9F   .3..+..F.P......
1817:9420  50 0C D1 E3 FF B7 FF 56-E8 DE D1 E3 FF B7 50 0C   P......V......P.
```

```
1817:9430  9A 1F 05 4B 21 83 C4 08-0B C0 75 03 E9 13 00 46   ...K!.....u....F
1817:9440  83 FE 15 7C D0 8B C7 EB-00 5F 5E 8B E5 5D CB 55   ...|...._^..].U
1817:9450  8B EC 83 EC 14 56 57 39-26 98 0D 77 05 9A CF 09   .....VW9&..w....
1817:9460  17 18 16 8D 46 EC 50 FF-76 12 FF 76 10 9A 1F 05   ....F.P.v..v....
1817:9470  4B 21 83 C4 08 0B C0 75-13 CD 39 06 79 1A C4 5E   K!.....u..9.y..^
1817:9480  14 CD 3C DD 1F CD 3D B0-21 E9 FF 02 C7 46 EE 00   ..<...=.!....F..
1817:9490  00 8B 46 EC BA F6 00 F7-E2 C4 1E 74 49 03 D8 26   ..F........tI..&
1817:94A0  8B 77 06 CD 3F 06 81 1A-8B 46 EC BA F6 00 F7 E2   .w..?....F......
1817:94B0  C4 1E 74 49 03 D8 CD 3C-DD 47 10 CD 3A D9 CD 39   ..tI...<.G..:..9
1817:94C0  3E DC 6F CD 3D 8A 26 DD-6F 9E 73 04 4E FF 46 EE   >.o.=.&.o.s.N.F.
1817:94D0  33 FF EB 5B 8B 46 EC BA-F6 00 F7 E2 C4 1E 74 49   3..[.F........tI
1817:94E0  03 D8 8B C7 03 46 EE B1-04 D3 E0 03 D8 CD 3C DD   .....F........<.
1817:94F0  47 05 8B DF D1 E3 D1 E3-D1 E3 CD 39 9F E2 6E CD   G..........9..n.
1817:9500  3D 8B 46 EE BA F6 00 F7-E2 C4 1E 74 49 03 D8 8B   =.F........tI...
1817:9510  C7 03 46 EE B1 04 D3 E0-03 D8 CD 3C DD 47 10 9B   ..F........<.G..
1817:9520  DF D1 E3 D1 E3 D1 E3 CD-39 9F 5A 6F CD 3D 47 3B   ........9.Zo.=G;
1817:9530  FE 7C A1 A1 60 6F 89 46-F6 A1 5E 6F 89 46 F4 A1   .|..`o.F..^o.F..
1817:9540  5C 6F 89 46 F2 A1 5A 6F-89 46 F0 8B DE 4B D1 E3   \o.F..Zo.F...K..
1817:9550  D1 E3 D1 E3 CD 39 87 5A-6F CD 39 5E F8 CD 3D CD   .....9.Zo.9^..=.
1817:9560  39 46 F0 CD 38 5E F8 CD-39 3E DC 6F CD 3D 8A 26   9F..8^..9>.o.=.&
1817:9570  DD 6F 9E 76 0C A1 60 6F-89 46 FE A1 5E 6F 89 46   .o.v..`o.F..^o.F
1817:9580  FC A1 5C 6F 89 46 FA A1-5A 6F 89 46 F8 8B DE 4B   ..\o.F..Zo.F...K
1817:9590  D1 E3 D1 E3 D1 E3 CD 39-87 5A 6F CD 39 5E F0 CD   .......9.Zo.9^..
1817:95A0  3D 83 7E 06 02 75 12 CD-39 46 F8 C4 5E 14 CD 3C   =.~..u..9F..^..<
1817:95B0  DD 1F CD 3D B0 3E E9 D2-01 CD 39 46 08 CD 38 1E   ...=.>....9F..8.
1817:95C0  E2 6E CD 39 3E DC 6F CD-3D 8A 26 DD 6F 9E 73 5C   .n.9>.o.=.&.o.s\
1817:95D0  CD 39 06 5A 6F C4 5E 14-CD 3C DD 1F CD 3D 8B DE   .9.Zo.^..<...=..
1817:95E0  4B D1 E3 D1 E3 D1 E3 CD-39 87 5A 6F CD 38 1E 5A   K.......9.Zo.8.Z
1817:95F0  6F CD 39 3E DC 6F CD 3D-8A 26 DD 6F 9E 76 28 CD   o.9>.o.=.&.o.v(.
1817:9600  39 06 81 1A C4 5E 14 CD-3C DD 07 CD 3A D9 CD 39   9....^..<...:..9
1817:9610  3E DC 6F CD 3D 8A 26 DD-6F 9E 74 04 B0 3C EB 02   >.o.=.&.o.t..<..
1817:9620  B0 3D E9 66 01 EB 05 B0-3E E9 5F 01 8B DE 4B D1   .=.f....>._...K.
1817:9630  E3 D1 E3 D1 E3 CD 39 87-E2 6E CD 38 5E 08 CD 39   ......9..n.8^..9
1817:9640  3E DC 6F CD 3D 8A 26 DD-6F 9E 73 65 8B DE 4B D1   >.o.=.&.o.se..K.
1817:9650  E3 D1 E3 D1 E3 CD 39 87-5A 6F C4 5E 14 CD 3C DD   ......9.Zo.^..<.
1817:9660  1F CD 3D 8B DE 4B D1 E3-D1 E3 D1 E3 CD 39 87 5A   ..=..K.......9.Z
1817:9670  6F CD 38 1E 5A 6F CD 39-3E DC 6F CD 3D 8A 26 DD   o.8.Zo.9>.o.=.&.
1817:9680  6F 9E 76 07 B0 3E E9 02-01 EB 26 CD 39 06 81 1A   o.v..>....&.9...
1817:9690  C4 5E 14 CD 3C DD 07 CD-3A D9 CD 39 3E DC 6F CD   .^..<...:..9>.o.
1817:96A0  3D 8A 26 DD 6F 9E 74 04-B0 3C EB 02 B0 3D E9 DA   =.&.o.t..<...=..
1817:96B0  00 56 FF 76 0E FF 76 0C-FF 76 0A FF 76 08 9A 51   .V.v..v..v..v..Q
1817:96C0  04 4B 21 83 C4 0A C4 5E-14 CD 3C DD 1F CD 3D 83   .K!....^..<...=.
1817:96D0  7E 10 03 75 15 C4 5E 14-CD 3C DD 07 CD 38 06 3E   ~..u..^..<...8.5
1817:96E0  0C C4 5E 14 CD 3C DD 1F-CD 3D 83 7E 10 0A 75 22   ..^..<...=.~..u"
1817:96F0  C4 5E 14 CD 3C DD 07 A1-1B 0C 99 52 50 CD 37 46   .^..<......RP.7F
1817:9700  E4 CD 3D 83 C4 04 CD 3A-C1 C4 5E 14 CD 3C DD 1F   ..=....:..^..<..
1817:9710  CD 3D C4 5E 14 CD 3C DD-07 CD 38 5E F0 CD 39 3E   .=.^..<...8^..9>
1817:9720  DC 6F CD 3D 8A 26 DD 6F-9E 73 32 CD 39 46 F0 C4   .o.=.&.o.s2.9F..
1817:9730  5E 14 CD 3C DD 1F CD 3D-CD 39 06 81 1A C4 5E 14   ^..<...=.9....^.
1817:9740  CD 3C DD 07 CD 3A D9 CD-39 3E DC 6F CD 3D 8A 26   .<...:..9>.o.=.&
1817:9750  DD 6F 9E 74 04 B0 3C EB-02 B0 3D EB 2E C4 5E 14   .o.t..<...=...^.
1817:9760  CD 3C DD 07 CD 38 5E F8-CD 39 3E DC 6F CD 3D 8A   .<...8^..9>.o.=.
1817:9770  26 DD 6F 9E 76 11 CD 39-46 F8 C4 5E 14 CD 3C DD   &.o.v..9F..^..<.
1817:9780  1F CD 3D B0 3E EB 04 B0-3D EB 00 5F 5E 8B E5 5D   ..=.>...=.._^..]
1817:9790  CB 55 8B EC 83 EC 02 56-57 39 26 98 0D 77 05 9A   .U....VW9&..w..
1817:97A0  CF 09 17 18 33 F6 8B 7E-0E 4F EB 4A 8B C7 03 C6   ....3..~.O.J....
1817:97B0  99 52 50 CD 37 46 F6 CD-3D 83 C4 04 CD 38 36 89   .RP.7F..=....86.
1817:97C0  1A CD 38 06 91 1A 9A C7-05 17 18 89 46 FE 8B 5E   ..8.........F..^
1817:97D0  FE D1 E3 D1 E3 D1 E3 CD-39 87 E2 6E CD 38 5E 06   ........9..n.8^.
1817:97E0  CD 39 3E DC 6F CD 3D 8A-26 DD 6F 9E 76 05 8B 7E   .9>.o.=.&.o.v..~
1817:97F0  FE EB 03 8B 76 FE 8B C7-2B C6 3D 01 00 7F AD 8B   ....v...+.=.....
1817:9800  DF D1 E3 D1 E3 D1 E3 CD-39 87 5A 6F 8B DE D1 E3   ........9.Zo....
1817:9810  D1 E3 D1 E3 CD 38 A7 5A-6F 8B DE D1 E3 D1 E3 D1   .....8.Zo.......
1817:9820  E3 CD 39 97 E2 6E CD 38-6E 06 CD 3A C9 8B DF D1   ..9..n.8n..:....
1817:9830  E3 D1 E3 D1 E3 CD 39 87-E2 6E 8B DE D1 E3 D1 E3   ......9..n......
1817:9840  D1 E3 CD 38 A7 E2 6E CD-3A F9 8B DE D1 E3 D1 E3   ...8..n.:.......
1817:9850  D1 E3 CD 38 87 5A 6F EB-00 5F 5E 8B E5 5D CB 55   ...8.Zo.._^..].U
1817:9860  8B EC 81 EC 04 01 56 57-3B EC 72 06 39 26 98 0D   ......VW;.r.9&..
1817:9870  77 05 9A CF 09 17 18 BF-01 00 C4 1E 74 49 26 83   w...........tI&.
1817:9880  3F 00 74 5C C4 5E 0A 26-C7 07 00 00 E9 43 C4 5E   ?.t\.^.&.....C.^
1817:9890  0A 26 8B 07 BA F6 00 F7-E2 C4 1E 74 49 03 D8 26   .&.........tI..&
1817:98A0  8B 47 02 3B 46 06 75 23-C4 5E 0A 26 8B 07 BA F6   .G.;F.u#.^.&....
1817:98B0  00 F7 E2 C4 1E 74 49 03-D8 26 8B 47 04 3B 46 08   .....tI..&.G.;F.
```

```
1817:98C0  75 07 8B C7 E9 D4 02 8B-02 EB 15 C4 5E 0A 26 FF   u...........^.&.
1817:98D0  07 C4 5E 0A 26 8B 07 C4-1E 74 49 26 3B 07 7C AE   ..^.&....tI&;.|.
1817:98E0  8C 9E 02 FF C7 86 00 FF-99 1A 83 46 06 EB 0A 00   ...........F....
1817:98F0  99 F7 FB EB 0A 00 99 F7-FB 80 C2 30 C4 9E 00 FF   ...........0....
1817:9900  26 88 57 04 8B 46 06 EB-0A 00 99 F7 FB 80 C2 30   &.W..F.........0
1817:9910  C4 9E 00 FF 26 88 57 05-1E B8 A4 1A 50 FF B6 02   ....&.W.....P...
1817:9920  FF FF B6 00 FF 9A 1A 02-5C 2B 83 C4 08 89 96 FE   .........\+.....
1817:9930  FE 89 86 FC FE 0B D0 75-03 E9 59 02 FF B6 FE FE   .......u..Y.....
1817:9940  FF B6 FC FE B8 01 00 50-B8 02 00 50 16 8D 86 0C   .......P...P....
1817:9950  FF 50 9A 12 01 13 2C 83-C4 0C 3D 01 00 74 03 E9   .P....,...=..t..
1817:9960  24 02 83 BE 0C FF 00 75-03 E9 1A 02 C7 86 0E FF   $......u........
1817:9970  00 00 E9 04 02 FF B6 FE-FE FF B6 FC FE B8 01 00   ................
1817:9980  50 B8 02 00 50 16 8D 86-06 FF 50 9A 12 01 13 2C   P...P.....P....,
1817:9990  83 C4 0C 3D 01 00 74 03-E9 EB 01 8B 86 06 FF 3B   ...=..t........;
1817:99A0  46 08 74 03 E9 79 01 C4-5E 0A 26 C7 07 00 00 EB   F.t..y..^.&.....
1817:99B0  22 C4 5E 0A 26 8B 07 BA-F6 00 F7 E2 C4 1E 74 49   ".^.&.........tI
1817:99C0  03 D8 26 8B 47 02 3B 46-06 75 02 EB 15 C4 5E 0A   ..&.G.;F.u....^.
1817:99D0  26 FF 07 C4 5E 0A 26 8B-07 C4 1E 74 49 26 3B 07   &...^.&....tI&;.
1817:99E0  7C CF FF B6 FE FE FF B6-FC FE B8 01 00 50 B8 02   |............P..
1817:99F0  00 50 16 8D 86 04 FF 50-9A 12 01 13 2C 83 C4 0C   .P.....P........
1817:9A00  3D 01 00 74 03 E9 7E 01-33 F6 EB 41 83 FE 0F 7D   =..t..~.3..A...}
1817:9A10  04 8B C6 EB 03 B8 0E 00-99 86 08 FF FF B6 FE FE   ................
1817:9A20  FF B6 FC FE B8 01 00 50-B8 10 00 50 16 8D 86 08   .......P...P....
1817:9A30  FF B1 04 D3 E0 8D 96 10-FF 03 C2 50 9A 12 01 13   ...........P....
1817:9A40  2C 83 C4 0C 3D 01 00 74-03 E9 3A 01 46 3B B6 04   ,...=..t..:.F;..
1817:9A50  FF 7C 89 8B 46 06 C4 5E-0A 50 26 8B 07 BA F6 00   .|..F..^.P&.....
1817:9A60  F7 E2 C4 1E 74 49 03 D8-58 26 89 47 02 8B 46 08   ....tI..X&.G..F.
1817:9A70  C4 5E 0A 50 26 8B 07 BA-F6 00 F7 E2 C4 1E 74 49   .^.P&.........tI
1817:9A80  03 D8 58 26 89 47 04 FF-86 08 FF 8B 86 08 FF C4   ..X&.G..........
1817:9A90  5E 0A 50 26 8B 07 BA F6-00 F7 E2 C4 1E 74 49 03   ^.P&.........tI.
1817:9AA0  D8 58 26 89 47 06 C7 86-0A FF 00 00 EB 3C C4 5E   .X&.G........<.^
1817:9AB0  0A 26 8B 07 BA F6 00 F7-E2 C4 1E 74 49 03 D8 8B   .&.........tI...
1817:9AC0  86 0A FF B1 04 D3 E0 03-D8 83 C3 08 06 53 8B 9E   .............S..
1817:9AD0  0A FF B1 04 D3 E3 8D 86-10 FF 03 D8 16 53 E8 10   .............S..
1817:9AE0  00 9A 04 0A 17 18 FF 86-0A FF 8B 86 0A FF 3B 86   ..............;.
1817:9AF0  08 FF 7C BA C4 5E 0A 26-8B 07 C4 1E 74 49 26 3B   ..|..^.&....tI&;
1817:9B00  07 75 07 C4 1E 74 49 26-FF 07 FF 86 FE FE FF B6   .u...tI&........
1817:9B10  FC FE 9A 28 15 A2 1A 59-59 8B C7 E9 7D 00 E5 55   ...(...YY...}..U
1817:9B20  FF B6 FE FE FF B6 FC FE-B8 01 00 50 B8 02 00 50   ...........P...P
1817:9B30  16 8D 86 04 FF 50 9A 12-01 13 2C 83 C4 0C 3D 01   .....P....,...=.
1817:9B40  00 74 03 E9 41 33 F6 EB-26 FF B6 FE FE FF B6 FC   .t..A3..&.......
1817:9B50  FE B8 01 00 50 B8 10 00-50 16 8D 86 10 FF 50 9A   ....P...P.....P.
1817:9B60  12 01 13 2C 83 C4 0C 3D-01 00 74 03 EB 13 46 3B   ...,...=..t...F;
1817:9B70  B6 04 FF 7C D4 FF 86 0E-FF 8B 86 0E FF 3B 86 0C   ...|.........;..
1817:9B80  FF 7D 03 E9 5F FD FF B6-FE FE FF B6 FC FE 9A 28   .}.............(
1817:9B90  15 A2 1A 59 59 33 FF 8B-C7 EB 00 5F 5E 8B E5 5D   ...YY3`...._^..]
1817:9BA0  CB 55 8B EC 83 EC 02 56-39 26 98 0D 77 05 9A CF   .U.....V9&..w...
1817:9BB0  09 17 18 1E B8 A6 1A 50-9A 0A 00 D7 19 59 59 9A   .......P.....YY.
1817:9BC0  CE 05 A2 1A 8B 46 FF 3C-31 7C 06 80 7E FF 39 7E   .....F.<1|..~.9~
1817:9BD0  10 80 7E FF 38 75 03 E9-37 00 9A A1 06 A2 1A EB   ..~..u..........
1817:9BE0  DE FF 06 32 3F 7D 13 8A-46 FF FF 06 3E 3F C4 1E   ...2?}..F...>?..
1817:9BF0  3E 3F 4B 26 88 07 B4 00-EB 10 1E B8 32 3F 50 FF   >?K&........2?P.
1817:9C00  76 FF 9A 09 00 AA 2C 83-C4 06 8A 46 FF 98 2D 31   v.....,....F..-1
1817:9C10  00 3D 08 00 77 73 8B D8-D1 E3 2E FF A7 7F 00 91   .=..ws..........
1817:9C20  00 99 00 A9 00 C1 00 C9-00 D1 00 D9 00 E1 00 E9   ................
1817:9C30  00 9A 07 00 ED 22 E9 7A-FF 1E B8 B0 1A 50 9A 0A   .....".z.....P..
1817:9C40  00 D7 19 59 59 9A 40 08-A2 1A E9 66 FF 1E B8 B7   ...YY.@....f....
1817:9C50  1A 50 9A 0A 00 D7 19 59-59 9A 40 08 A2 1A E9 52   .P.....YY.@....R
1817:9C60  FF 9A 57 02 10 1D E9 4A-FF 9A 09 00 56 25 E9 42   ..W....J....V%.B
1817:9C70  FF 9A 05 00 DE 25 E9 3A-FF 9A 6F 01 D1 21 E9 32   .....%.:..o..!.2
1817:9C80  FF 9A 08 00 3C 25 E9 2A-FF 9A A1 06 A2 1A E9 22   ....<%.*......."
1817:9C90  FF 1E B8 BE 1A 50 9A 0A-00 D7 19 59 59 9A 8A 02   .....P.....YY...
1817:9CA0  6B 1C 83 F0 8B C6 0B C0-75 2F 9A 52 06 17 22 0B   k.......u/.R..".
1817:9CB0  C0 74 14 9A 52 06 17 22-3B F0 8B C6 0B C0 74 07   .t..R.."......t.
1817:9CC0  56 9A 07 00 72 1D 59 C7-06 03 01 00 00 E9 01 00   V...r.Y.........
1817:9CD0  50 9A 21 00 65 1C 59 EB-07 56 9A 07 00 72 1D 59   P.!.e.Y..V...r.Y
1817:9CE0  5E 8B E5 5D CB 55 8B EC-39 26 98 0D 77 05 9A CF   ^..].U..9&..w...
1817:9CF0  09 17 18 B8 01 00 EB 00-5D CB 55 8B EC 39 26 98   ........].U..9&.
1817:9D00  0D 77 05 9A CF 09 17 18-B8 02 00 EB 00 5D CB 55   .w...........].U
1817:9D10  8B EC 83 EC 06 56 39 26-98 0D 77 05 9A CF 09 17   .....V9&..w.....
1817:9D20  18 9A E4 0B A2 1A 1E B8-C7 1A 50 9A 0A 00 D7 19   ..........P.....
1817:9D30  59 59 E9 B5 00 C6 46 FB-32 C7 06 03 01 00 00 8A   YY....F.2.......
1817:9D40  46 FB 98 05 D0 FF 50 9A-D7 0D A2 1A 59 8B 1E 03   F.....P.....Y...
```

```
1817:9D50  01 D1 E3 D1 E3 C7 87 41-6E 02 00 C7 87 3F 6E 48   .......An....?nH
1817:9D60  65 E8 00 8B 1E 03 01 D1-E3 D1 E3 8B 97 41 6E 8B   e............An.
1817:9D70  97 3F 6E 3B 16 56 0D 7F-EA 75 06 3B 06 54 0D 77   .?n;.V...u.;.T.w
1817:9D80  E2 B8 01 00 50 9A 36 03-A2 1A 59 16 8D 46 FC 50   ....P.6...Y..F.P
1817:9D90  9A EE 0C A2 1A 59 59 8B-F0 8B C6 0B C0 74 33 8A   .....YY......t3.
1817:9DA0  46 F8 98 50 1E B8 D0 1A-50 9A 05 00 A8 2C 83 C4   F..P....P......,..
1817:9DB0  06 1E B8 D5 1A 50 9A B7-00 D7 19 59 59 56 1E B8   .....P.....YYV..
1817:9DC0  D5 1A 50 9A 05 00 A8 2C-83 C4 06 9A A1 06 A2 1A   ..P...,.........
1817:9DD0  EB 18 FF 76 FE FF 76 FC-8A 46 F8 98 50 1E B8 E5   ...v..v..F..P...
1817:9DE0  1A 50 9A 05 00 A8 2C 83-C4 0A 9A 70 06 A2 1A 3D   .P....,....p...=
1817:9DF0  01 00 74 03 E9 3E FF 33-C0 50 9A 36 03 A2 1A 59   ..t..>.3.P.6...Y
1817:9E00  9A CE 05 A2 1A 8B 46 FA-3C 31 7C 06 80 7E FA 35   ......F.<1|..~.5
1817:9E10  7E 11 80 7E FA 08 75 03-E9 93 00 9A A1 06 A2 1A   ~..~..u.........
1817:9E20  E9 0F FF FF 06 32 3F 7D-13 8A 46 FA FF 06 3E 3F   .....2?}..F...>?
1817:9E30  C4 1E 3E 3F 4B 26 88 07-B4 00 EB 10 1E B8 32 3F   ..>?K&........2?
1817:9E40  50 FF 76 FA 9A 09 00 AA-2C 83 C4 06 9A E4 0B A2   P.v.............
1817:9E50  1A 8A 46 FA 98 2D 31 00-3D 04 00 77 49 8B D8 D1   ..F..-1.=..wI...
1817:9E60  E3 2E FF A7 C6 02 D0 02-DC 02 E9 02 F6 02 03 03   ................
1817:9E70  33 C0 50 9A FD 0B A2 1A-59 E9 86 FE B8 02 00 50   3.P.....Y......P
1817:9E80  9A FD 0B A2 1A 59 E9 A9-FE B8 01 00 50 9A FD 0B   .....Y......P...
1817:9E90  A2 1A 59 E9 9C FE B8 05-00 50 9A FD 0B A2 1A 59   ..Y......P.....Y
1817:9EA0  E9 8F FE E9 8C FE 9A A1-06 A2 1A E9 84 FE 9A E4   ................
1817:9EB0  0B A2 1A 5E 8B E5 5D CB-56 39 26 98 0D 77 05 9A   ...^..].V9%..w..
1817:9EC0  CF 09 17 18 1E 89 F3 1A-50 9A 05 00 A8 2C 59 59   ........P....,YY
1817:9ED0  FF 36 5A 43 FF 36 58 43-FF 36 56 43 FF 36 54 43   .6ZC.6XC.6VC.6TC
1817:9EE0  1E B8 0F 1E 50 9A 05 00-A8 2C 83 C4 0C 33 F6 E9   ....P....,...3..
1817:9EF0  A0 00 C7 06 03 01 00 00-E9 8C 00 8B C6 8A 60 00   ..............`.
1817:9F00  F7 E2 8B D8 81 C3 5C 43-1E 07 A1 03 01 D1 E0 D1   ......\C........
1817:9F10  E0 D1 E0 03 D8 8D 3C DD-07 83 EC 08 55 8B EC CD   ......<.....U...
1817:9F20  39 5E 02 5D CD 3D 8B C6-8A 60 00 F7 E2 8B D8 81   9^.].=...`......
1817:9F30  C3 9C 45 1E 07 A1 03 01-D1 E0 D1 E0 D1 E0 03 D8   ..E.............
1817:9F40  CD 3C DD 07 83 EC 08 55-8B EC CD 39 5E 02 5D CD   .<.....U...9^.].
1817:9F50  3D 56 A1 03 01 40 50 1E-B8 26 1B 50 9A 05 00 A8   =V...@P..%.P....
1817:9F60  2C 83 C4 18 9A 70 06 A2-1A 0B C0 74 16 9A CE 05   ,....p.....t....
1817:9F70  A2 1A 3D 06 00 75 02 EB-21 9A 6C 03 A2 1A 9A CE   ..=..u..!.l.....
1817:9F80  05 A2 1A FF 06 03 01 83-3E 03 01 0C 7D 03 E9 6A   ........>...}..j
1817:9F90  FF 46 83 FE 06 7D 03 E9-58 FF 1E B8 61 1B 50 9A   .F...}..X...a.P.
1817:9FA0  05 00 A8 2C 59 59 FF 36-F2 47 FF 36 F0 47 FF 36   ...,YY.6.G.6.G.6
1817:9FB0  EE 47 FF 36 EC 47 1E B8-85 1B 50 9A 05 00 A8 2C   .G.6.G....P....,
1817:9FC0  83 C4 0C FF 36 EA 47 FF-36 E8 47 FF 36 DE 47 FF   ....6.G.6.G.6.G.
1817:9FD0  36 DC 47 1E B8 97 1B 50-9A 05 00 A8 2C 83 C4 0C   6.G....P....,...
1817:9FE0  FF 36 E2 47 FF 36 E0 47-FF 36 E6 47 FF 36 E4 47   .6.G.6.G.6.G.6.G
1817:9FF0  1E B8 A9 1B 50 9A 05 00-A8 2C 83 C4 0C 1E B8 BB   ....P....,......
1817:A000  1B 50 9A 05 00 A8 2C 59-59 5E CB 55 8B EC 83 EC   .P....,YY^.U....
1817:A010  02 56 57 39 26 98 0D 77-05 9A CF 09 17 18 1E B8   .VW9%..w........
1817:A020  C2 1B 50 9A 0A 00 D7 19-59 59 9A 6C 03 A2 1A 9A   ..P.....YY.l....
1817:A030  CE 05 A2 1A 8B 46 FF 3C-31 7C 06 80 7E FF 32 7E   .....F.<1|..~.2~
1817:A040  07 9A A1 06 A2 1A EB D6-FF 06 32 3F 7D 13 8A 46   ..........2?}..F
1817:A050  FF FF 06 3E 3F C4 1E 3E-3F 4B 26 88 07 B4 00 EB   ...>?..>?K&.....
1817:A060  10 1E B8 32 3F 50 FF 76-FF 9A 09 00 AA 2C 83 C4   ...2?P.v.....,..
1817:A070  06 9A CE 05 A2 1A 3D 0D-00 74 02 EB A1 80 7E FF   ......=..t....~.
1817:A080  32 74 03 E9 85 02 33 FF-E8 1B 33 C0 50 57 9A 90   2t....3...3.PW..
1817:A090  0B 17 22 59 59 8B F0 8B-C6 0B C0 74 07 56 9A 07   .."YY......t.V..
1817:A0A0  00 72 1D 59 47 81 FF 00-08 7C DF B8 24 00 50 B8   .r.YG....|..$.P.
1817:A0B0  FC 07 50 9A 90 0B 17 22-59 59 8B F0 8B C6 0B C0   ..P...."YY......
1817:A0C0  74 07 56 9A 07 00 72 1D-59 B8 49 00 50 B8 FC 07   t.V...r.Y.I.P...
1817:A0D0  50 9A 90 0B 17 22 59 59-8B F0 8B C6 0B C0 74 07   P...."YY......t.
1817:A0E0  56 9A 07 00 72 1D 59 B8-92 00 50 B8 FE 07 50 9A   V...r.Y...P...P.
1817:A0F0  90 0B 17 22 59 59 8B F0-8B C6 0B C0 74 07 56 9A   ..."YY......t.V.
1817:A100  07 00 72 1D 59 B8 01 00-50 B8 FB 07 50 9A 90 0B   ..r.Y...P...P...
1817:A110  17 22 59 59 8B F0 8B C6-0B C0 74 07 56 9A 07 00   ."YY......t.V...
1817:A120  72 1D 59 B8 01 00 50 B8-FA 07 50 9A 90 0B 17 22   r.Y...P...P...."
1817:A130  59 59 8B F0 8B C6 0B C0-74 07 56 9A 07 00 72 1D   YY......t.V...r.
1817:A140  59 33 FF EB 0B 8B DF D1-E3 C7 87 FF 56 00 00 47   Y3..........V..G
1817:A150  83 FF 64 7C F0 9A 18 08-17 22 C6 06 47 0C 30 C6   ..d|....."..G.0.
1817:A160  06 48 0C 30 C6 06 49 0C-30 C6 06 4A 0C 30 C6 06   .H.0..I.0..J.0..
1817:A170  4B 0C 30 9A 23 06 17 22-C7 06 19 0C 00 00 9A D7   K.0.#.."........
1817:A180  06 17 22 C6 06 F5 47 00-A0 F5 47 98 50 B8 C3 05   .."...G...G.P...
1817:A190  50 9A 90 0B 17 22 59 59-0B C0 74 0A B8 25 00 50   P...."YY..t..%.P
1817:A1A0  9A 07 00 72 1D 59 9A 46-0C 17 22 C6 06 F4 47 01   ...r.Y.F.."...G.
1817:A1B0  A0 F4 47 98 50 B8 D9 05-50 9A 90 0B 17 22 59 59   ..G.P...P...."YY
1817:A1C0  0B C0 74 0A B8 29 00 50-9A 07 00 72 1D 59 C7 06   ..t..).P...r.Y..
1817:A1D0  45 0C 00 00 9A 9D 05 17-22 C7 06 92 0D 30 02 EB   E......."....0..
```

```
1817:A1E0  02 00 50 B8 40 06 50 1E-B8 92 0D 50 9A D5 0A 17   ..P.@.P....P....
1817:A1F0  22 83 C4 08 8B F0 8B C6-0B C0 74 07 56 9A 07 00   "..........t.V...
1817:A200  72 1D 59 C7 06 94 0D 76-02 B8 02 00 50 B8 42 06   r.Y....v....P.B.
1817:A210  50 1E B8 94 0D 50 9A D5-0A 17 22 83 C4 08 8B F0   P....P....".....
1817:A220  8B C6 0B C0 74 07 56 9A-07 00 72 1D 59 C7 06 96   ....t.V...r.Y...
1817:A230  0D 1A 04 B8 02 00 50 B8-44 06 50 1E B8 96 0D 50   ......P.D.P....P
1817:A240  9A D5 0A 17 22 83 C4 08-8B F0 8B C6 0B C0 74 07   ....".........t.
1817:A250  56 9A 07 00 72 1D 59 C7-06 43 0C 04 00 B8 02 00   V...r.Y..C......
1817:A260  50 B8 46 06 50 1E B8 43-0C 50 9A D5 0A 17 22 83   P.F.P..C.P....".
1817:A270  C4 08 8B F0 8B C6 0B C0-74 07 56 9A 07 00 72 1D   ........t.V...r.
1817:A280  59 C7 06 3D 0C 06 02 C7-06 3F 0C AD 00 C7 06 41   Y..=.....?.....A
1817:A290  0C 34 00 B8 02 00 50 B8-48 06 50 1E B8 3D 0C 50   .4....P.H.P..=.P
1817:A2A0  9A D5 0A 17 22 83 C4 08-8B F0 8B C6 0B C0 74 07   ....".........t.
1817:A2B0  56 9A 07 00 72 1D 59 B8-02 00 50 B8 4A 06 50 1E   V...r.Y...P.J.P.
1817:A2C0  B8 3F 0C 50 9A D5 0A 17-22 83 C4 08 8B F0 8B C6   .?.P....".......
1817:A2D0  0B C0 74 07 56 9A 07 00-72 1D 59 B8 02 00 50 B8   ..t.V...r.Y...P.
1817:A2E0  4C 06 50 1E B8 41 0C 50-9A D5 0A 17 22 83 C4 08   L.P..A.P...."...
1817:A2F0  8B F0 8B C6 0B C0 74 07-56 9A 07 00 72 1D 59 C7   ......t.V...r.Y.
1817:A300  06 3B 0C 00 00 C7 06 39-0C 00 00 C7 06 37 0C 00   .;.....9.....7..
1817:A310  00 C7 06 35 0C 00 00 9A-64 08 17 22 C7 06 1B 0C   ...5....d.."....
1817:A320  00 00 9A E4 08 17 22 C6-06 1D 0C 00 C6 06 1E 0C   ......".........
1817:A330  00 9A 0A 09 17 22 9A 6C-01 3C 25 5F 5E 8B E5 5D   .....".l.<%_^..]
1817:A340  CB 56 39 26 98 0D 77 05-9A CF 09 17 18 B8 FC 07   .V9%..w.........
1817:A350  50 9A 2F 0B 17 22 59 3D-24 00 75 1E B8 FD 07 50   P./.."Y=$.u....P
1817:A360  9A 2F 0B 17 22 59 3D 49-00 75 0F B8 FE 07 50 9A   ./.."Y=I.u....P.
1817:A370  2F 0B 17 22 59 3D 92 00-74 06 B8 21 00 E9 C4 01   /.."Y=..t..!....
1817:A380  B8 02 00 50 B8 40 06 50-1E B8 92 0D 50 9A 96 0A   ...P.@.P....P...
1817:A390  17 22 83 C4 08 81 3E 92-0D 90 06 7F 07 83 3E 92   ."....>.......>.
1817:A3A0  0D 00 7D 06 C7 06 92 0D-42 01 B8 02 00 50 B8 42   ..}.....B....P.B
1817:A3B0  06 50 1E B8 94 0D 50 9A-96 0A 17 22 83 C4 08 81   .P....P....."....
1817:A3C0  3E 94 0D 90 06 7F 07 83-3E 94 0D 00 7D 06 C7 06   >.......>...}...
1817:A3D0  94 0D 68 01 B8 02 00 50-B8 44 06 50 1E B8 96 0D   ..h....P.D.P....
1817:A3E0  50 9A 96 0A 17 22 83 C4-08 81 3E 96 0D 90 06 7F   P...."....>.....
1817:A3F0  07 83 3E 96 0D 00 7D 06-C7 06 96 0D B8 01 B8 02   ..>...}.........
1817:A400  00 50 B8 46 06 50 1E B8-43 0C 50 9A 96 0A 17 22   .P.F.P..C.P...."
1817:A410  83 C4 08 B8 02 00 50 B8-48 06 50 1E B8 3D 0C 50   ......P.H.P..=.P
1817:A420  9A 96 0A 17 22 83 C4 08-B8 02 00 50 B8 4A 06 50   ....".....P.J.P
1817:A430  1E B8 3F 0C 50 9A 96 0A-17 22 83 C4 08 B8 02 00   ..?.P...."......
1817:A440  50 B8 4C 06 50 1E B8 41-0C 50 9A 96 0A 17 22 83   P.L.P..A.P....".
1817:A450  C4 08 9A 93 08 17 22 9A-E9 08 17 22 9A 58 09 17   ......"....".X..
1817:A460  22 9A CC 05 17 22 8B F0-8B C6 0B C0 74 05 8B C6   "....".......t...
1817:A470  E9 D1 00 9A 46 05 17 22-8B F0 8B C6 0B C0 74 05   ....F.."......t.
1817:A480  8B C6 E9 BF 00 B8 C8 05-50 9A 2F 0B 17 22 59 A2   ........P./.."Y.
1817:A490  F5 47 80 3E F5 47 00 74-05 C6 06 F5 47 20 B8 D9   .G.>.G.t....G ..
1817:A4A0  05 50 9A 2F 0B 17 22 59-A2 F4 47 80 3E F4 47 00   .P./.."Y..G.>.G.
1817:A4B0  74 05 C6 06 F4 47 01 9A-73 0C 17 22 8B F0 8B C6   t....G..s.."....
1817:A4C0  0B C0 74 05 8B C6 E9 7B-00 B8 02 00 50 33 C0 50   ..t....{....P3.P
1817:A4D0  9A F7 02 A2 1A 59 59 9A-06 07 17 22 0B C0 74 1A   .....YY...."..t.
1817:A4E0  9A 06 07 17 22 0B C0 74-11 9A 06 07 17 22 8B F0   ...."..t....."..
1817:A4F0  8B C6 0B C0 74 04 8B C6-EB 4A 9A B2 07 17 22 0B   ....t....J....".
1817:A500  C0 74 1A 9A B2 07 17 22-0B C0 74 11 9A B2 07 17   .t....."..t.....
1817:A510  22 8B F0 8B C6 0B C0 74-04 8B C6 EB 27 9A 52 06   "......t....'.R.
1817:A520  17 22 0B C0 74 1A 9A 52-06 17 22 0B C0 74 11 9A   ."..t..R.."..t..
1817:A530  52 06 17 22 8B F0 8B C6-0B C0 74 04 8B C6 EB 04   R.."......t.....
1817:A540  33 C0 EB 00 5E CB 39 26-98 0D 77 05 9A CF 09 17   3...^.9%..w.....
1817:A550  18 B8 FC 07 50 9A 2F 0B-17 22 59 3D 24 00 75 1E   ....P./.."Y=$.u.
1817:A560  B8 FD 07 50 9A 2F 0B 17-22 59 3D 49 00 75 0F B8   ...P./.."Y=I.u..
1817:A570  FE 07 50 9A 2F 0B 17 22-59 3D 92 00 74 05 B8 2F   ..P./.."Y=..t../
1817:A580  00 EB 19 B8 02 00 50 B8-3F 05 50 1E B8 45 0C 50   ......P...P..E.P
1817:A590  9A 96 0A 17 22 83 C4 08-33 C0 EB 00 CB 39 26 98   ...."...3....9%.
1817:A5A0  0D 77 05 9A CF 09 17 18-B8 02 00 50 B8 DF 05 50   .w.........P...P
1817:A5B0  1E B8 45 0C 50 9A D5 0A-17 22 83 C4 08 0B C0 74   ..E.P...."......t
1817:A5C0  0A B8 2E 00 50 9A 07 00-72 1D 59 CB 39 26 98 0D   ....P...r.Y.9%..
1817:A5D0  77 05 9A CF 09 17 18 B8-FC 07 50 9A 2F 0B 17 22   w.........P./.."
1817:A5E0  59 3D 24 00 75 1E B8 FD-07 50 9A 2F 0B 17 22 59   Y=$.u....P./.."Y
1817:A5F0  3D 49 00 75 0F B8 FE 07-50 9A 2F 0B 17 22 59 3D   =I.u....P./.."Y=
1817:A600  92 00 74 05 B8 2D 00 EB-19 B8 05 00 50 B8 DA 05   ..t..-......P...
1817:A610  50 1E B8 47 0C 50 9A 96-0A 17 22 83 C4 08 33 C0   P..G.P...."...3.
1817:A620  EB 00 CB 39 26 98 0D 77-05 9A CF 09 17 18 B8 05   ...9%..w........
1817:A630  00 50 B8 DA 05 50 1E B8-47 0C 50 9A D5 0A 17 22   .P...P..G.P...."
1817:A640  83 C4 08 0B C0 74 0A B8-2C 00 50 9A 07 00 72 1D   .....t....P...r.
1817:A650  59 CB 39 26 98 0D 77 05-9A CF 09 17 18 B8 FC 07   Y.9%..w.........
1817:A660  50 9A 2F 0B 17 22 59 3D-24 00 75 1E B8 FD 07 50   P./.."Y=$.u....P
```

```
1817:A670  9A 2F 0B 17 22 59 3D 49-00 75 0F B8 FE 07 50 9A   ./.."Y=I.u....P.
1817:A680  2F 0B 17 22 59 3D 92 00-74 05 E8 03 00 EB 47 B8   /.."Y=..t.....G.
1817:A690  02 00 50 E8 01 00 50 1E-E8 19 0C 50 9A 96 0A 17   ..P...P....P....
1817:A6A0  22 83 C4 08 81 3E 19 0C-90 06 7F 07 83 3E 19 0C   "....>.......>..
1817:A6B0  00 7D 1F A1 19 0C 8B 90-06 99 F7 FB 89 16 19 0C   .}..............
1817:A6C0  83 3E 19 0C 00 7C 06 81-06 19 0C 90 06 9A 27 06   .>...|..........
1817:A6D0  17 22 33 C0 E8 00 C3 39-26 98 0D 77 05 9A CF 09   ."3....9%..w....
1817:A6E0  17 18 B8 02 00 50 B8 01-00 50 1E E8 19 0C 50 9A   .....P...P....P.
1817:A6F0  D5 0A 17 22 83 C4 08 0B-C0 74 0A B8 04 00 50 9A   ..."......t....P.
1817:A700  07 00 72 1D 59 C3 39 26-98 0D 77 05 9A CF 09 17   ..r.Y.9%..w.....
1817:A710  18 B8 FC 07 50 9A 2F 0B-17 22 59 3D 24 00 75 2D   ....P./.."Y=$.u-
1817:A720  B8 FD 07 50 9A 2F 0B 17-22 59 3D 49 00 75 1E B8   ...P./.."Y=I.u..
1817:A730  FE 07 50 9A 2F 0B 17 22-59 3D 92 00 75 0F B8 FB   ..P./.."Y=..u...
1817:A740  07 50 9A 2F 0B 17 22 59-3D 01 00 74 05 B8 0A 00   .P./.."Y=..t....
1817:A750  EB 19 B8 A0 04 50 B8 05-00 50 1E E8 54 43 50 9A   .....P...P..TCP.
1817:A760  96 0A 17 22 83 C4 08 33-C0 EB 00 C3 39 26 98 0D   ..."...3....9%..
1817:A770  77 05 9A CF 09 17 18 B8-A0 04 50 B8 05 00 50 1E   w.........P...P.
1817:A780  E8 54 43 50 9A D5 0A 17-22 83 C4 08 0B C0 74 05   .TCP...."......t.
1817:A790  B8 0B 00 EB 1C B8 01 00-50 B8 FB 07 50 9A 90 0B   ........P...P...
1817:A7A0  17 22 59 59 0B C0 74 05-B8 0B 00 EB 04 33 C0 EB   ."YY..t......3..
1817:A7B0  00 C3 39 26 98 0D 77 05-9A CF 09 17 18 B8 FC 07   ..9%..w.........
1817:A7C0  50 9A 2F 0B 17 22 59 3D-24 00 75 2D B8 FD 07 50   P./.."Y=$.u-...P
1817:A7D0  9A 2F 0B 17 22 59 3D 49-00 75 1E B8 FE 07 50 9A   ./.."Y=I.u....P.
1817:A7E0  2F 0B 17 22 59 3D 92 00-75 0F B8 F4 07 50 9A 2F   /.."Y=..u....P./
1817:A7F0  0B 17 22 59 3D 01 00 74-05 B8 18 00 EB 19 B8 C8   .."Y=..t........
1817:A800  00 50 B8 00 0E 50 1E B8-FF 56 50 9A 96 0A 17 22   .P...P...VP...."
1817:A810  83 C4 08 33 C0 EB 00 C3-39 26 98 0D 77 05 9A CF   ...3....9&..w...
1817:A820  09 17 18 B8 C8 00 50 B8-00 0E 50 1E B8 FF 56 50   ......P...P...VP
1817:A830  9A D5 0A 17 22 83 C4 08-0B C0 74 0A B8 1A 00 50   ...."......t....P
1817:A840  9A 07 00 72 1D 59 B8 01-00 50 B8 FA 07 50 9A 90   ...r.Y...P...P..
1817:A850  0B 17 22 59 59 0B C0 74-0A B8 1A 00 50 9A 07 00   .."YY..t....P...
1817:A860  72 1D 59 C3 39 26 98 0D-77 05 9A CF 09 17 18 B8   r.Y.9%..w.......
1817:A870  08 00 50 B8 E1 05 50 1E-B8 35 0C 50 9A D5 0A 17   ..P...P..5.P....
1817:A880  22 83 C4 08 0B C0 74 0A-B8 32 00 50 9A 07 00 72   "......t..2.P...r
1817:A890  1D 59 C3 39 26 98 0D 77-05 9A CF 09 17 18 B8 08   .Y.9%..w........
1817:A8A0  00 50 B8 E1 05 50 1E B8-35 0C 50 9A 96 0A 17 22   .P...P..5.P...."
1817:A8B0  83 C4 08 C3 39 26 98 0D-77 05 9A CF 09 17 18 B8   ....9%..w.......
1817:A8C0  02 00 50 B8 E7 05 50 1E-B8 18 0C 50 9A D5 0A 17   ..P...P....P....
1817:A8D0  22 83 C4 08 0B C0 74 10-C7 06 1F 0C E9 05 B8 34   "......t.......4
1817:A8E0  00 50 9A 07 00 72 1D 59-C3 39 26 98 0D 77 05 9A   .P...r.Y.9%..w..
1817:A8F0  CF 09 17 18 B8 02 00 50-B8 E9 05 50 1E B8 18 0C   .......P...P....
1817:A900  50 9A 96 0A 17 22 83 C4-08 C3 55 8B EC 83 EC 02   P...."....U.....
1817:A910  39 26 98 0D 77 05 9A CF-09 17 18 A0 1E 0C 21 07   9%..w...........
1817:A920  D2 E0 24 80 02 06 1D 0C-8B 46 FF B8 01 00 50 B8   ..$......F....P.
1817:A930  EB 05 50 16 8D 46 FF 50-9A D5 0A 17 22 83 C4 08   ..P..F.P...."...
1817:A940  0B C0 74 10 C7 06 1F 0C-E8 05 B8 34 00 50 9A 07   ..t........4.P..
1817:A950  00 72 1D 59 8B E5 5D CB-55 8B EC 83 EC 02 39 26   .r.Y..].U.....9%
1817:A960  98 0D 77 05 9A CF 09 17-18 B8 01 00 50 B8 EB 05   ..w.........P...
1817:A970  50 16 8D 46 FF 50 9A 96-0A 17 22 83 C4 08 8A 46   P..F.P...."....F
1817:A980  FF 24 7F A2 1D 0C 8A 46-FF 24 01 A2 1E 0C 8B E5   .$.....F.$......
1817:A990  5D CB 55 8B EC 83 EC 04-56 39 26 98 0D 77 05 9A   ].U.....V9%..w..
1817:A9A0  CF 09 17 18 1E B8 C5 1E-50 9A 0A 00 D7 19 59 59   ........P.....YY
1817:A9B0  16 8D 46 FC 50 9A A6 08-A2 1A 59 59 8B F0 8B C6   ..F.P.....YY....
1817:A9C0  0B C0 75 02 EB DE 83 FE-01 74 03 E9 33 00 83 7E   ..u.......t.....~
1817:A9D0  FC 00 74 07 81 7E FC FF-07 7E 02 EB C7 1E B8 D3   ..t..~...~......
1817:A9E0  1B 50 9A 0A 00 D7 19 59-59 B8 04 00 50 B8 05 00   .P.....YY...P...
1817:A9F0  50 9A F7 02 A2 1A 59 59-FF 76 FC 9A 2F 0B 17 22   P.....YY.v../.."
1817:AA00  59 89 46 FE FF 76 FE FF-76 FC 1E B8 D3 1B 50 9A   Y.F..v..v.....P.
1817:AA10  05 00 A8 2C 83 C4 08 B8-04 00 50 B8 0E 00 50 9A   ..........P...P.
1817:AA20  F7 02 A2 1A 59 59 16 8D-46 FE 50 9A A6 08 A2 1A   ....YY..F.P.....
1817:AA30  59 59 3D 03 00 77 5A 8B-D8 D1 E3 2E FF A7 40 0A   YY=..wZ.......@.
1817:AA40  48 0A 4A 0A 7C 0A 7F 0A-EB 9F 83 7E FE 00 7C 07   H.J.|......~..|.
1817:AA50  81 7E FE FF 00 7E 07 9A-A1 06 A2 1A EB 9B FF 76   .~...~.........v
1817:AA60  FE FF 76 FC 9A 90 0B 17-22 59 59 8B F0 8B C6 0B   ..v....."YY.....
1817:AA70  C0 74 07 56 9A 07 00 72-1D 59 EB 03 E9 25 FF FF   .t.V...r.Y...%..
1817:AA80  46 FC 8B 46 FC 89 00 03-99 F7 FB 29 56 FC E9 58   F..F........V..X
1817:AA90  FF 5E 8B E5 5D CB 55 8B-EC 83 EC 04 56 39 26 98   .^..].U.....V9%.
1817:AAA0  0D 77 05 9A CF 09 17 18-C4 5E 06 8C 46 FE 89 5E   .w.......^..F..^
1817:AAB0  FC 33 F6 EB 16 8B 46 0A-03 C6 50 9A 2F 0B 17 22   .3....F...P./.."
1817:AAC0  59 C4 5E FC 26 88 07 FF-46 FC 46 3B 76 0C 7C E5   Y.^.&...F.F;v.|.
1817:AAD0  5E 8B E5 5D CB 55 8B EC-83 EC 06 56 57 39 26 98   ^..].U.....VW9%.
1817:AAE0  0D 77 05 9A CF 09 17 18-C4 5E 06 8C 46 FE 89 5E   .w.......^..F..^
1817:AAF0  FC 33 F6 EB 2B C4 5E FC-26 8A 07 B4 00 89 46 FA   .3..+.^.&.....F.
```

```
1817:AB00  FF 46 FC FF 76 FA 8B 46-0A 03 C6 50 9A 90 0B 17   .F..v..F...P....
1817:AB10  22 59 59 EB F8 8B C7 0B-C0 74 04 2B C7 EB 0A 46   "YY......t.....F
1817:AB20  3B 76 0C 7C D0 33 C0 EB-00 5F 5E 8B E5 5D CB 55   ;v.|.3..._^..].U
1817:AB30  8B EC 56 57 39 26 98 0D-77 05 9A CF 09 17 18 8B   ..VW9&..w.......
1817:AB40  76 06 B0 92 BA 0F 03 EE-8B C6 24 FF BA 0C 03 EE   v.........$.....
1817:AB50  8B C6 25 00 0F B1 08 D3-F8 0C 30 BA 0E 03 EE 8B   ..%.............
1817:AB60  C6 25 00 0F B1 08 D3 F8-0C 30 BA 0E 03 EE BA 0D   .%..............
1817:AB70  03 EC B4 00 8B F8 B0 00-BA 0C 03 EE B0 B0 BA 0E   ................
1817:AB80  03 EE B0 8B BA 0F 03 EE-8B C7 EB 00 5F 5E 5D CB   ............_^].
1817:AB90  55 8B EC 56 57 39 26 98-0D 77 05 9A CF 09 17 18   U..VW9&..w......
1817:ABA0  8B 76 06 B0 30 BA 0F 03-EE 8B C6 24 FF BA 0C 03   .v........$.....
1817:ABB0  EE 8B C6 25 00 0F B1 08-D3 F8 0C B0 BA 0E 03 EE   ...%............
1817:ABC0  8A 46 08 BA 0D 03 EE 8B-C6 25 00 0F B1 08 D3 F8   .F.......%......
1817:ABD0  0C A0 BA 0E 03 EE 8B C6-25 00 0F B1 08 D3 F8 0C   ........%.......
1817:ABE0  E0 BA 0E 03 EE 8B C6 25-00 0F B1 08 D3 F8 0C A0   .......%........
1817:ABF0  BA 0E 03 EE 8B C6 25 00-0F B1 08 D3 F8 0C 80 BA   ......%.........
1817:AC00  0E 03 EE C7 06 97 00 00-00 C7 06 95 00 0F 00 EB   ................
1817:AC10  00 A1 95 00 0B 06 97 00-75 F7 B0 00 BA 0C 03 EE   ........u.......
1817:AC20  B0 B0 BA 0E 03 EE B0 83-BA 0F 03 EE 56 0E E8 FE   ............V...
1817:AC30  FE 59 EB F8 3B 7E 08 74-05 B8 1F 00 EB 04 33 C0   .Y..;~.t......3.
1817:AC40  EB 00 5F 5E 5D CB 39 26-98 0D 77 05 9A CF 09 17   .._^].9&..w.....
1817:AC50  18 B8 10 00 50 B8 C9 05-50 1E B8 34 0D 50 0E E8   ....P...P..4.P..
1817:AC60  73 FE 83 C4 08 0B C0 74-05 B8 27 00 EB 04 33 C0   s......t..'...3.
1817:AC70  EB 00 CB 55 8B EC 83 EC-02 56 57 39 26 98 0D 77   ...U.....VW9&..w
1817:AC80  05 9A CF 09 17 18 B8 FC-07 50 0E E8 A1 FE 59 3D   ..........P...Y=
1817:AC90  24 00 75 1C B8 FD 07 50-0E E8 93 FE 59 3D 49 00   $.u....P....Y=I.
1817:ACA0  75 0E B8 FE 07 50 0E E8-85 FE 59 3D 92 00 74 06   u....P....Y=..t.
1817:ACB0  B8 21 00 E9 AB 00 B8 10-00 50 B8 C9 05 50 1E B8   .!.......P...P..
1817:ACC0  34 0D 50 0E E8 CF FD 83-C4 08 33 F6 EB 31 8B C6   4.P.......3..1..
1817:ACD0  04 30 88 46 FF 83 FE 0A-75 04 C6 46 FF 08 83 FE   .0.F....u..F....
1817:ACE0  0B 75 04 C6 46 FF 0D 33-FF EB 0C 8A 9E 34 0D 3A   .u..F..3.....4.:
1817:ACF0  46 FF 75 02 EB 08 47 83-FF 0C 7C EF EB 0A 46 83   F.u...G...|...F.
1817:AD00  FE 0C 7C CA 33 C0 EB 59-C6 06 34 0D 37 C6 06 35   ..|.3..Y..4.7..5
1817:AD10  0D 34 C6 06 36 0D 31 C6-06 37 0D 30 C6 06 38 0D   .4..6.1..7.0..8.
1817:AD20  38 C6 06 39 0D 35 C6 06-3A 0D 32 C6 06 3B 0D 08   8..9.5..:.2..;..
1817:AD30  C6 06 3C 0D 39 C6 06 3D-0D 36 C6 06 3E 0D 33 C6   ..<.9..=.6..>.3.
1817:AD40  06 3F 0D 0D C6 06 40 0D-61 C6 06 41 0D 62 C6 06   .?....@.a..A.b..
1817:AD50  42 0D 63 C6 06 43 0D 64-0E E8 EA FE 59 28 00 EB   B.c..C.d....Y(..
1817:AD60  00 5F 5E 8B E5 5D CB 55-8B EC 83 EC 02 39 26 98   ._^..].U.....9&.
1817:AD70  0D 77 05 9A CF 09 17 18-9A A9 03 ED 22 9A 18 02   .w..........."...
1817:AD80  A2 1A B8 01 00 50 9A 39-04 A2 1A 59 1E B8 F0 18   .....P.9...Y....
1817:AD90  50 9A 8D 00 D7 19 59 59-9A 21 06 A2 1A 83 46 FF   P.....YY.!....F.
1817:ADA0  3C 08 75 02 EB 49 9A A9-03 ED 22 8A 46 FF 98 2D   <.u..I....".F..-
1817:ADB0  31 00 3D 04 00 77 36 8B-D8 D1 E3 2E FF A7 60 00   1.=..w6.......`.
1817:ADC0  6A 00 71 00 78 00 7F 00-86 00 9A 93 00 ED 22 EB   j.q.x.........".
1817:ADD0  A7 9A D0 00 ED 22 EB A0-9A 08 01 ED 22 EB 99 9A   ....."......"...
1817:ADE0  40 01 ED 22 EB 92 9A 79-01 ED 22 EB 8B EB 89 9A   @.."...y..".....
1817:ADF0  18 02 A2 1A EB E5 5D CB-39 26 98 0D 77 05 9A CF   ......].9&..w...
1817:AE00  09 17 18 9A 18 02 A2 1A-B8 01 00 50 9A 39 04 A2   ...........P.9..
1817:AE10  1A 59 1E B8 F7 18 50 9A-8D 00 D7 19 59 59 C7 06   .Y....P.....YY..
1817:AE20  D6 6F 07 00 9A B0 01 ED-22 0B C0 75 02 EB D4 CB   .o......"..u....
1817:AE30  39 26 98 0D 77 05 9A CF-09 17 18 9A 18 02 A2 1A   9&..w...........
1817:AE40  B8 01 00 50 9A 39 04 A2-1A 59 1E B8 FE 18 50 9A   ...P.9...Y....P.
1817:AE50  8D 00 D7 19 59 59 C7 06-D6 6F 09 00 9A B0 01 ED   ....YY...o......
1817:AE60  22 0B C0 75 02 EB D4 CB-39 26 98 0D 77 05 9A CF   "..u....9&..w...
1817:AE70  09 17 18 9A 18 02 A2 1A-B8 01 00 50 9A 39 04 A2   ...........P.9..
1817:AE80  1A 59 1E B8 07 1C 50 9A-8D 00 D7 19 59 59 C7 06   .Y....P.....YY..
1817:AE90  D6 6F 0B 00 9A B0 01 ED-22 0B C0 75 02 EB D4 CB   .o......"..u....
1817:AEA0  39 26 98 0D 77 05 9A CF-09 17 18 9A 18 02 A2 1A   9&..w...........
1817:AEB0  B8 01 00 50 9A 39 04 A2-1A 59 1E B8 0D 1C 50 9A   ...P.9...Y....P.
1817:AEC0  8D 00 D7 19 59 59 C7 06-D6 6F 04 00 9A B0 01 ED   ....YY...o......
1817:AED0  22 0B C0 75 02 EB D4 CB-39 26 98 0D 77 05 9A CF   "..u....9&..w...
1817:AEE0  09 17 18 9A 18 02 A2 1A-B8 01 00 50 9A 39 04 A2   ...........P.9..
1817:AEF0  1A 59 1E B8 13 1C 50 9A-8D 00 D7 19 59 59 C7 06   .Y....P.....YY..
1817:AF00  D6 6F 02 00 9A B0 01 ED-22 0B C0 75 02 EB D4 CB   .o......"..u....
1817:AF10  55 8B EC 83 EC 10 39 26-98 0D 77 05 9A CF 09 17   U.....9&..w.....
1817:AF20  18 9A 21 06 A2 1A A3 D4-6F 3D 30 00 7C 07 83 3E   ..!.....o=0.|..>
1817:AF30  D4 6F 39 7E 08 9A A1 06-A2 1A E9 C4 01 9A 21 06   .o9~..........!.
1817:AF40  A2 1A A3 D2 6F 3D 0D 00-75 0E A1 D4 6F A3 D2 6F   ....o=..u...o..o
1817:AF50  C7 06 D4 6F 30 00 EB 23-83 3E D2 6F 30 7C 07 83   ...o0..#.>.o0|..
1817:AF60  3E D2 6F 39 7E 08 9A A1-06 A2 1A E9 93 01 9A CE   >.o9~...........
1817:AF70  05 A2 1A 3D 0D 00 74 03-E9 86 01 83 3E D2 6F 30   ...=..t.....>.o0
1817:AF80  A1 D4 6F 05 D0 FF 81 04-D3 E0 01 06 D2 6F A1 D6   ..o..........o..
```

```
1817:AF90  6F 48 48 3D 09 00 76 03-E9 58 01 8B D8 D1 E3 2E   oHH=..v..X......
1817:AFA0  FF A7 44 02 58 02 93 03-95 02 93 03 93 03 57 03   ..D.X.........W.
1817:AFB0  93 03 1E 03 93 03 D2 02-C6 46 F1 02 16 8D 46 F0   ..........F....F.
1817:AFC0  50 16 8D 46 F0 50 B8 1A-00 50 9A 03 00 D5 2D 83   P..F.P...P....-.
1817:AFD0  C4 0A A0 D2 6F 88 46 F4-C6 46 F1 03 16 8D 46 F0   ....o.F..F....F.
1817:AFE0  50 16 8D 46 F0 50 B8 1A-00 50 9A 03 00 D5 2D 83   P..F.P...P....-.
1817:AFF0  C4 0A E9 02 01 C6 46 F1-02 16 8D 46 F0 50 16 8D   ......F....F.P..
1817:B000  46 F0 50 B8 1A 00 50 9A-03 00 D5 2D 83 C4 0A A0   F.P...P....-....
1817:B010  D2 6F 88 46 F5 C6 46 F1-03 16 8D 46 F0 50 16 8D   .o.F..F....F.P..
1817:B020  46 F0 50 B8 1A 00 50 9A-03 00 D5 2D 83 C4 0A E9   F.P...P....-....
1817:B030  C5 00 C6 46 F1 04 16 8D-46 F0 50 16 8D 46 F0 50   ...F....F.P..F.P
1817:B040  B8 1A 00 50 9A 03 00 D5-2D 83 C4 0A A0 D2 6F 88   ...P....-.....o.
1817:B050  46 F4 81 3E D2 6F 88 00-7D 04 C6 46 F5 20 C6 46   F..>.o..}..F. .F
1817:B060  F1 05 16 8D 46 F0 50 16-8D 46 F0 50 B8 1A 00 50   ....F.P..F.P...P
1817:B070  9A 03 00 D5 2D 83 C4 0A-EB 7C 90 C6 46 F1 04 16   ....-....|..F...
1817:B080  8D 46 F0 50 16 8D 46 F0-50 B8 1A 00 50 9A 03 00   .F.P..F.P...P...
1817:B090  D5 2D 83 C4 0A A0 D2 6F-88 46 F7 C6 46 F1 05 16   .-.....o.F..F...
1817:B0A0  8D 46 F0 50 16 8D 46 F0-50 B8 1A 00 50 9A 03 00   .F.P..F.P...P...
1817:B0B0  D5 2D 83 C4 0A B0 40 C6-46 F1 04 16 8D 46 F0 50   .-....@.F....F.P
1817:B0C0  16 8D 46 F0 50 B8 1A 00-50 9A 03 00 D5 2D 83 C4   ..F.P...P....-..
1817:B0D0  0A A0 D2 6F 88 46 F6 C6-46 F1 05 16 8D 46 F0 50   ...o.F..F....F.P
1817:B0E0  16 8D 46 F0 50 B8 1A 00-50 9A 03 00 D5 2D 83 C4   ..F.P...P....-..
1817:B0F0  0A EB 04 33 C0 EB 05 9A-A9 03 ED 22 B8 01 00 EB   ...3......."....
1817:B100  04 33 C0 EB 00 8B E5 5D-C3 55 8B EC 83 EC 10 39   .3.....].U.....9
1817:B110  26 98 0D 77 05 9A CF 09-17 18 C6 46 F1 02 16 8D   %..w.......F....
1817:B120  46 F0 50 16 8D 46 F0 50-B8 1A 00 50 9A 03 00 D5   F.P..F.P...P....
1817:B130  2D 83 C4 0A 80 7E FC 00-74 03 E9 C9 00 C6 46 F1   -....~..t.....F.
1817:B140  2D 8A 46 FE B4 00 50 9A-AA 04 ED 22 59 88 46 FE   -.F...P...."Y.F.
1817:B150  8A 46 F4 B4 00 50 9A AA-04 ED 22 59 88 46 F4 8A   .F...P...."Y.F..
1817:B160  46 F7 B4 00 50 9A AA 04-ED 22 59 88 46 F7 C6 46   F...P...."Y.F..F
1817:B170  F6 00 16 8D 46 F0 50 16-8D 46 F0 50 B8 21 00 50   ....F.P..F.P.!.P
1817:B180  9A 03 00 D5 2D 83 C4 0A-C6 46 F1 04 16 8D 46 F0   ....-...F....F.
1817:B190  50 16 8D 46 F0 50 B8 1A-00 50 9A 03 00 D5 2D 83   P..F.P...P....-.
1817:B1A0  C4 0A 83 7E FC 00 74 02-EB 5C C6 46 F1 2B 8A 46   ...~..t..\.F.+.F
1817:B1B0  FE B4 00 50 9A AA 04 ED-22 59 BA 64 00 F7 E2 50   ...P...."Y.d...P
1817:B1C0  8A 46 F4 B4 00 50 9A AA-04 ED 22 59 5A 03 D0 89   .F...P...."YZ...
1817:B1D0  56 F4 8A 46 F7 B4 00 50-9A AA 04 ED 22 59 88 46   V..F...P...."Y.F
1817:B1E0  F7 8A 46 F6 B4 00 50 9A-AA 04 ED 22 59 88 46 F6   ..F...P...."Y.F.
1817:B1F0  16 8D 46 F0 50 16 8D 46-F0 50 B8 21 00 50 9A 03   ..F.P.writing dev
e PRN
Abort, Retry, Ignore? r
.F.P.'.P..
1817:B200  00 D5 2D 83 C4 0A 8B E5-5D CB 55 8B EC 39 26 98   ..-.....].U..9%.
1817:B210  0D 77 05 9A CF 09 17 18-8B 46 06 81 04 D3 F5 8A   .w.......F......
1817:B220  0A 00 F7 E2 8B 56 06 81-E2 0F 00 03 C2 8B 00 5D   .....V.........]
1817:B230  CB 55 8B EC 83 EC 08 56-57 39 26 98 0D 77 05 9A   .U.....VW9%..w..
1817:B240  CF 09 17 18 C6 46 FA 61-33 FF C7 06 03 01 00 00   .....F.a3.......
1817:B250  EB 12 8B 1E 03 01 D1 E3-83 BF F5 6D 00 74 01 47   ...........m.t.G
1817:B260  FF 06 03 01 83 3E 03 01-0C 7C E7 9A 18 02 A2 1A   .....>...|......
1817:B270  57 1E B8 2D 1C 50 9A 05-00 A8 2C 83 C4 06 33 F6   W..-.P.....,...3.
1817:B280  C6 84 7C 4A 00 FF 76 08-FF 76 06 1E B8 4F 1C 50   ..|J..v..v...O.P
1817:B290  9A 05 00 A8 2C 83 C4 08-9A 6C 03 A2 1A 33 F6 EB   .........l...3..
1817:B2A0  13 80 7E FB 03 75 02 EB-DC 8A 46 FB C4 1E 1A 1C   ..~..u....F.....
1817:B2B0  26 88 00 46 9A 21 06 A2-1A 88 46 FB 3C 0D 74 05   %..F.!....F.<.t.
1817:B2C0  83 FE 0D 7C DC 83 FE 0D-7C 0E 1E B8 7C 1C 50 9A   ...|....|...|.P.
1817:B2D0  05 00 A8 2C 59 59 EB AD-0B F6 75 17 33 F6 EB 0E   ...,YY....u.3...
1817:B2E0  C4 5E 06 26 8A 00 C4 1E-1A 1C 26 88 00 46 83 FE   .^.&......&..F..
1817:B2F0  08 7C ED C4 1E 1A 1C 26-C6 00 00 FF 36 1C 1C FF   .|.....%....6...
1817:B300  36 1A 1C 1E B8 93 1C 50-9A 05 00 A8 2C 83 C4 08   6......P........
1817:B310  1E B8 A9 1C 50 9A 04 00-D7 2C 59 59 9A 21 06 A2   ....P.....YY.!..
1817:B320  1A 88 46 FA 80 7E FA 0D-75 04 C6 46 FA 79 80 7E   ..F..~..u..F.y.~
1817:B330  FA 08 75 04 C6 46 FA 6E-80 7E FA 4E 74 06 80 7E   ..u..F.n.~.Nt..~
1817:B340  FA 6E 75 03 E9 3E FF 80-7E FA 59 74 08 80 7E FA   .nu..>..~.Yt..~.
1817:B350  79 74 03 EB A6 B8 44 0B-50 1E B8 C1 1C 50 9A 05   yt....D.P....P..
1817:B360  00 A8 2C 83 C4 06 1E B8-DF 1C 50 FF 36 1C 1C FF   ..........P.6...
1817:B370  36 1A 1C 9A 1A 02 5C 2B-83 C4 08 89 56 FE 89 46   6.....\+....V..F
1817:B380  FC 0B D0 75 13 FF 36 1C-1C FF 36 1A 1C 1E B8 E2   ...u..6...6.....
1817:B390  1C 50 9A 05 00 A8 2C 83-C4 08 E9 E8 FE FF 76 FE   .P....,.......v.
1817:B3A0  FF 76 FC B8 01 00 50 E8-44 03 50 1E B8 F8 49 50   .v....P.D.P...IP
1817:B3B0  9A 0B 00 3A 2C 83 C4 0C-E9 46 F8 3D 01 00 7D 28   ...:.....F.=..}(
1817:B3C0  FF 76 F8 FF 36 1C 1C FF-36 1A 1C 1E B8 F9 1C 50   .v..6...6......P
1817:B3D0  9A 05 00 A8 2C 83 C4 0A-FF 76 FE FF 76 FC 9A 28   .........v..v..(
1817:B3E0  1E A2 1A 59 59 E9 9D FE-FF 76 FE FF 76 FC 9A 28   ...YY....v..v..(
```

```
1817:B3F0  16 A2 1A 59 59 FF 36 1C-1C FF 36 1A 1C 1E 58 1E   ...YY.6...6.....
1817:B400  1D 50 1E 88 6E 3F 50 9A-0A 00 65 2D 83 C4 0C 5F   .P..n?P...e-..._
1817:B410  5E 8B E5 5D CB 55 8B EC-81 EC A6 00 56 57 39 26   ^..].U......VW9&
1817:B420  99 0D 77 05 9A CF 09 17-18 C7 86 64 FF 00 00 8C   ..w........d....
1817:B430  5E C3 37 46 C6 2E 1D 1E-98 34 1D 50 9A 04 00 D7   ^..F.....4.P....
1817:B440  2C 59 59 8C 5E FE C7 46-FC 32 3F C7 86 68 FF 02   ,YY.^..F.2?..h..
1817:B450  00 1E 88 46 1D 50 9A 04-00 D7 2C 59 59 1E 58 6A   ...F.P.....YY..j
1817:B460  1D 50 9A 04 00 D7 2C 59-59 1E 88 9C 1D 50 9A 04   .P.....YY....P..
1817:B470  00 D7 2C 59 59 1E 88 81-1D 50 9A 04 00 D7 2C 59   ...YY....P....,Y
1817:B480  59 1E 88 C3 1D 50 9A 04-00 D7 2C 59 59 1E 88 E4   Y....P.....YY...
1817:B490  1D 50 9A 05 00 A8 2C 59-59 83 BE 68 FF 01 75 0E   .P.....YY..h..u.
1817:B4A0  1E 88 F8 1D 50 9A 05 00-A8 2C 59 59 E8 0C 1E 88   ....P.....YY....
1817:B4B0  01 1E 50 9A 05 00 A8 2C-59 59 1E 88 0A 1E 50 9A   ..P.....YY....P.
1817:B4C0  04 00 D7 2C 59 59 1E 88-12 1E 50 9A 05 00 A8 2C   ....YY....P.....
1817:B4D0  59 59 83 BE 68 FF 01 75-0E 1E 88 14 1E 50 9A 05   YY..h..u.....P..
1817:B4E0  00 A8 2C 59 59 E8 0C 1E-88 1C 1E 50 9A 05 00 A8   ...YY......P....
1817:B4F0  2C 59 59 1E 88 24 1E 50-9A 05 00 A8 2C 59 59 1E   ,YY..$.P.....YY.
1817:B500  88 3F 1E 50 9A 04 00 D7-2C 59 59 1E 88 57 1E 50   .?.P.....YY..W.P
1817:B510  9A 04 00 D7 2C 59 59 C7-86 5A FF 00 00 9A 6C 03   .....YY..Z....l.
1817:B520  A2 1A 58 23 83 BE 5A FF-04 7D 1C 80 BE 6C FF 09   ...#..Z..}...l..
1817:B530  75 03 E9 1C FF 8A 86 6C-FF C4 5E C6 03 9E 5A FF   u......l..^...Z.
1817:B540  26 88 07 FF 86 5A FF 9A-21 06 A2 1A 83 86 6C FF   &....Z..!.....l.
1817:B550  3C 0D 75 D0 C4 5E C6 03-9E 5A FF 26 C6 07 00 83   <.u..^...Z.&....
1817:B560  BE 5A FF 01 74 03 E9 E3-FE 1E 88 6A 1E 50 9A 05   .Z..t......j.P..
1817:B570  00 A8 2C 59 59 C7 86 5C-FF 00 00 C7 86 5E FF 01   ...YY..\......^..
1817:B580  00 C7 86 6A FF 01 00 C4-5E 26 26 8A 07 98 50 9A   ...j....^.&...P.
1817:B590  00 00 86 2B 59 3B 86 6D-FF 80 BE 6D FF 35 75 2B   ....Y..m...m.5u+
1817:B5A0  83 BE 68 FF 01 75 13 C7-86 68 FF 02 00 8C 5E FE   ..h..u...h....^.
1817:B5B0  C7 46 FC 32 3F E9 99 FE-E8 11 C7 86 68 FF 01 00   .F.2?.......h...
1817:B5C0  8C 5E FE C7 46 FC 6E 3F-E9 86 FE 80 BE 6D FF 36   .^..F.n?.....m.6
1817:B5D0  75 03 E9 6D 0C 80 BE 6D-FF 31 75 06 C7 86 5C FF   u..m...m.1u...\.
1817:B5E0  01 00 80 BE 6D FF 34 75-06 C7 86 6A FF 00 00 1E   ....m.4u...j....
1817:B5F0  B8 6C 1E 50 9A 04 00 D7-2C 59 59 1E 88 89 1E 50   .l.P.....YY....P
1817:B600  9A 04 00 D7 2C 59 59 1E-B8 9D 1E 50 9A 04 00 D7   ....,YY....P....
1817:B610  2C 59 59 16 8D 86 60 FF-50 9A A6 08 A2 1A 59 59   ,YY...`.P.....YY
1817:B620  3D 01 00 75 0E 83 BE 60-FF 01 7C 07 83 BE 60 FF   =..u...`..|...`.
1817:B630  0C 7E 02 EB D2 1E B8 AB-1E 50 9A 04 00 D7 2C 59   .~.......P....,Y
1817:B640  59 16 8D 86 62 FF 50 9A-A6 08 A2 1A 59 59 3D 01   Y...b.P.....YY=.
1817:B650  00 75 0E 83 BE 62 FF 01-7C 07 83 BE 62 FF 0C 7E   .u...b..|...b..~
1817:B660  02 EB D2 80 BE 6D FF 33-74 03 E9 11 03 33 F6 C4   .....m.3t....3..
1817:B670  1E 1A 1C 8C 46 F6 89 5E-F4 E8 08 FF 46 F4 8A 46   ....F..^....F..F
1817:B680  F3 36 88 42 DE 46 83 FE-11 7D 13 C4 5E F4 26 8A   .6.B.F...}..^.&.
1817:B690  07 88 46 F3 0A C0 74 06-80 7E F3 2E 75 DD 36 C6   ..F...t..~..u.6.
1817:B6A0  42 DE 2E 46 36 C6 42 DE-70 46 36 C6 42 DE 6C 46   B..F6.B.pF6.B.lF
1817:B6B0  8A 86 64 FF 04 41 36 88-42 DE 46 FF 86 64 FF 36   ..d..A6.B.F..d.6
1817:B6C0  C6 42 DE 00 46 1E B8 B8-1E 50 9A 04 00 D7 2C 59   .B..F....P....,Y
1817:B6D0  59 16 8D 46 DE 50 1E B8-D4 1E 50 9A 0E 00 A8 2C   Y..F.P...P......
1817:B6E0  83 C4 0C 1E B8 F5 1E 50-16 8D 46 DE 50 9A 1A 02   .......P..F.P...
1817:B6F0  5C 2B 83 C4 08 89 56 F4-89 46 F6 0B D0 75 1E 16   \+....V..F...u..
1817:B700  8D 46 DE 50 1E B8 F8 1E-50 9A 05 00 A8 2C 83 C4   .F.P....P.....,.
1817:B710  0E E9 3D FD C7 46 BC 1C-40 C7 46 BA 00 00 C7 46   ..=..F..@.F....F
1817:B720  B8 00 00 C7 46 B6 00 00-C7 46 C4 F0 EF C7 46 C2   ....F....F....F.
1817:B730  00 00 C7 46 C0 00 00 C7-46 BE 00 00 8B 86 62 FF   ...F....F.....b.
1817:B740  2B 86 60 FF 40 50 1E B8-0F 1F 50 FF 76 FA FF 76   +.`.@P....P.v..v
1817:B750  F8 9A 0A 00 65 2D 83 C4-0A 8B 86 60 FF 48 A3 03   ....e-.....`.H..
1817:B760  01 E9 81 01 A1 03 01 BA-E0 00 F7 E2 8B D8 81 C3   ................
1817:B770  BC 4A 1E 07 CD 3C DD 47-0C CD 39 5E CE CD 3D A1   .J..<.G..9^..=.
1817:B780  03 01 BA E0 00 F7 E2 8B-D8 81 C3 BC 4A 1E 07 CD   ............J...
1817:B790  3C DD 47 04 CD 39 5E D6-CD 3D CD 39 46 D6 CD 38   <.G..9^..=.9F..8
1817:B7A0  5E CE CD 39 3E DC 6F CD-3D 8A 26 DD 6F 9E 77 0F   ^..9>.o.=.&.o.w.
1817:B7B0  CD 39 46 CE CD 38 06 D7-21 CD 39 5E D6 CD 3D FF   .9F..8..!.9^..=.
1817:B7C0  36 F7 00 1E B8 13 1F 50-FF 76 FA FF 76 F8 9A 0A   6......P.v..v...
1817:B7D0  00 65 2D 83 C4 0A 33 FF-E9 FD 00 A1 03 01 BA E0   .e-...3.........
1817:B7E0  00 F7 E2 8B D8 81 C3 BC-4A 1E 07 8B C7 D1 E0 D1   ........J.......
1817:B7F0  E0 03 D8 26 8B 57 1A 26-8B 47 18 39 56 DC 99 46   ...&.W.&.G..V..F
1817:B800  CA A1 03 01 BA E0 00 F7-E2 8B D8 81 C3 BC 4A 1E   ..............J.
1817:B810  07 26 8B 57 16 26 8B 47-14 52 50 CD 37 56 52 FF   .&.W.&.G.5P.7.R.
1817:B820  CD 3D 83 C4 04 83 EC 08-CD 39 9E 4E FF CD 3D FF   .=.......9.N..=.
1817:B830  76 DC FF 76 DA FF 76 D8-FF 76 D6 FF 76 D4 FF 76   v..v..v..v..v..v
1817:B840  D2 FF 76 D0 FF 76 CE FF-76 CC FF 76 CA 9A 26 0C   ..v..v..v..v..&.
1817:B850  3B 24 83 C4 1C CD 39 5E-86 CD 3D CD 39 46 86 CD   ;$....9^..=.9F..
1817:B860  38 5E 8E CD 39 3E DC 6F-CD 3D 8A 26 DD 6F 9E 76   8^..9>.o.=.&.o.v
```

```
1817:B870  1E 8B 46 8C 89 46 C4 8B-46 8A 89 46 C2 8B 46 88   ..F..F..F..F..F.
1817:B880  89 46 C0 8B 46 86 89 46-BE CD 39 46 86 CD 3E 5E   .F..F..F..9F..>^
1817:B890  86 CD 39 3E DC 6F CD 3D-8A 26 DD 6F 9E 73 1E 8B   ..9>.o.=.&.o.s..
1817:B8A0  46 8C 89 46 EC 8B 46 8A-89 46 8A 8B 46 88 89 46   F..F..F..F..F..F
1817:B8B0  58 8B 46 B6 89 46 B6 FF-76 BC FF 76 BA FF 76 B8   ..F..F..v..v..v.
1817:B8C0  FF 76 B6 57 1E B8 17 1F-50 FF 76 FA FF 76 F8 9A   .v.W....P.v..v..
1817:B8D0  0A 00 65 2D 83 C4 12 47-3B 3E F7 00 7D 03 E9 FA   ..e-...G;>..}...
1817:B8E0  FE FF 06 03 01 A1 03 01-3B 86 62 FF 7D 03 E9 73   ........;.b.}..s
1817:B8F0  FE FF 36 F7 00 1E B8 23-1F 50 FF 76 FA FF 76 F8   ..6....#.P.v..v.
1817:B900  9A 0A 00 65 2D 83 C4 0A-CD 39 46 8E CD 38 66 86   ...e-....9F..8f.
1817:B910  CD 38 36 DF 21 83 EC 08-CD 39 9E 4E FF CD 3D FF   .86.!....9.N..=.
1817:B920  76 C4 FF 76 C2 FF 76 C0-FF 76 BE FF 76 BC FF 76   v..v..v..v..v..v
1817:B930  8A FF 76 88 FF 76 86 1E-B8 3E 1F 50 FF 76 FA FF   ..v..v.....P.v..
1817:B940  76 F8 9A 0A 00 65 2D 83-C4 20 1E B8 44 1F 50 FF   v....e-.. ..D.P.
1817:B950  76 FA FF 76 F8 9A 0A 00-65 2D 83 C4 08 FF 76 FA   v..v....e-....v.
1817:B960  FF 76 F8 9A 28 15 A2 1A-59 59 1E B8 47 1F 50 9A   .v..(...YY..G.P.
1817:B970  04 00 D7 2C 59 59 9A 21-06 A2 1A E9 D3 FA 83 BE   ....YY.!........
1817:B980  68 FF 01 75 24 1E B8 65-1F 50 9A 04 00 D7 2C 59   h..u$..e.P....,Y
1817:B990  59 1E B8 81 1F 50 9A 04-00 D7 2C 59 59 1E B8 9F   Y....P....,YY...
1817:B9A0  1F 50 9A 04 00 D7 2C 59-59 C6 86 6C FF 41 83 BE   .P....,YY..l.A..
1817:B9B0  5C FF 00 75 1B FF 36 1C-1C FF 36 1A 1C 1E B8 A8   \..u..6...6.....
1817:B9C0  1F 50 FF 76 FE FF 76 FC-9A 0A 00 65 2D 83 C4 0C   .P.v..v....e-...
1817:B9D0  C7 86 74 FF 00 00 C7 86-72 FF 00 00 C7 86 70 FF   ..t.....r.....p.
1817:B9E0  00 00 C7 86 6E FF 00 00-C7 86 7C FF 00 00 C7 86   ....n.....|.....
1817:B9F0  7A FF 00 00 C7 86 78 FF-00 00 C7 86 76 FF 00 00   z.....x.....v...
1817:BA00  C7 46 84 00 00 C7 46 82-00 00 C7 46 80 00 00 C7   .F....F....F....
1817:BA10  86 7E FF 00 00 8B 86 60-FF 48 A3 03 01 E9 AE 04   .~.....`.H......
1817:BA20  A1 03 01 BA E0 00 F7 E2-8B D8 81 C3 BC 4A 1E 07   .............J..
1817:BA30  26 83 3F 00 75 03 E9 91-04 83 BE 5C FF 01 75 39   &.?.u......\..u9
1817:BA40  8B 1E 03 01 D1 E3 8B 87-0D 6E BA 1C 00 F7 E2 05   .........n......
1817:BA50  0D 01 8B DA 05 0A 00 52-50 FF 36 1C 1C FF 36 1A   .......RP.6...6.
1817:BA60  1C A1 03 01 40 50 1E B8-B7 1F 50 FF 76 FE FF 76   ....@P....P.v..v
1817:BA70  FC 9A 0A 00 65 2D 83 C4-12 A1 03 01 BA E0 00 F7   ....e-..........
1817:BA80  E2 8B D8 81 C3 BC 4A 1E-07 CD 3C DD 47 0C CD 39   ......J...<.G..9
1817:BA90  5E CE CD 3D A1 03 01 BA-E0 00 F7 E2 8B D8 81 C3   ^..=............
1817:BAA0  BC 4A 1E 07 CD 3C DD 47-04 CD 39 5E D6 CD 3D 83   .J...<.G..9^..=.
1817:BAB0  BE 5C FF 01 75 3E FF 76-D4 FF 76 D2 FF 76 D0 FF   .\..u>.v..v..v..
1817:BAC0  76 CE 1E B8 CE 1F 50 FF-76 FE FF 76 FC 9A 0A 00   v.....P.v..v....
1817:BAD0  65 2D 83 C4 10 FF 76 DC-FF 76 DA FF 76 D8 FF 76   e-....v..v..v..v
1817:BAE0  D6 1E B8 E9 1F 50 FF 76-FE FF 76 FC 9A 0A 00 65   .....P.v..v....e
1817:BAF0  2D 83 C4 10 CD 39 46 D6-CD 38 5E CE CD 39 3E DC   -....9F..8^..9>.
1817:BB00  6F CD 3D 8A 26 DD 6F 9E-77 0F CD 39 46 CE CD 38   o.=.&.o.w..9F..8
1817:BB10  06 D7 21 CD 39 5E D6 CD-3D A1 03 01 BA E0 00 F7   ..!.9^..=.......
1817:BB20  E2 8B D8 81 C3 BC 4A 1E-07 26 8B 57 16 26 8B 47   ......J..&.W.&.G
1817:BB30  14 89 56 CC 89 46 CA A1-03 01 BA E0 00 F7 E2 8B   ..V..F..........
1817:BB40  D8 81 C3 BC 4A 1E 07 26-8B 57 16 26 8B 47 14 52   ....J..&.W.&.G.R
1817:BB50  50 CD 37 86 52 FF CD 3D-83 C4 04 83 EC 08 CD 39   P.7.R..=.......9
1817:BB60  9E 4E FF CD 3D FF 76 DC-FF 76 DA FF 76 D8 FF 76   .N..=.v..v..v..v
1817:BB70  D6 FF 76 D4 FF 76 D2 FF-76 D0 FF 76 CE FF 76 CC   ..v..v..v..v..v.
1817:BB80  FF 76 CA 9A 26 0C 3B 24-83 C4 1C CD 39 5E 86 CD   .v..&.;$....9^..
1817:BB90  3D 83 BE 5C FF 01 74 03-E9 FF 00 1E B8 04 20 50   =..\..t...... P
1817:BBA0  FF 76 FE FF 76 FC 9A 0A-00 65 2D 83 C4 08 1E B8   .v..v....e-.....
1817:BBB0  17 20 50 FF 76 FE FF 76-FC 9A 0A 00 65 2D 83 C4   . P.v..v....e-..
1817:BBC0  08 FF 76 8C FF 76 8A FF-76 88 FF 76 86 FF 76 CC   ..v..v..v..v..v.
1817:BBD0  FF 76 CA 1E B8 2A 20 50-FF 76 FE FF 76 FC 9A 0A   .v...* P.v..v...
1817:BBE0  00 65 2D 83 C4 14 33 FF-E9 46 00 A1 03 01 BA E0   .e-...3..F......
1817:BBF0  00 F7 E2 8B D8 81 C3 BC-4A 1E 07 8B C7 D1 E0 D1   ........J.......
1817:BC00  E0 03 D8 26 8B 57 1A 26-8B 47 18 89 56 CC 89 46   ...&.W.&.G..V..F
1817:BC10  CA A1 03 01 BA E0 00 F7-E2 8B D8 81 C3 BC 4A 1E   ..............J.
1817:BC20  07 26 8B 57 16 26 8B 47-14 52 50 CD 37 86 52 FF   .&.W.&.G.RP.7.R.
1817:BC30  CD 3D 83 C4 04 83 EC 08-CD 39 9E 4E FF CD 3D FF   .=.......9.N..=.
1817:BC40  76 DC FF 76 DA FF 76 D8-FF 76 D6 FF 76 D4 FF 76   v..v..v..v..v..v
1817:BC50  D2 FF 76 D0 FF 76 CE FF-76 CC FF 76 CA 9A 26 0C   ..v..v..v..v..&.
1817:BC60  3B 24 83 C4 1C CD 39 5E-86 CD 3D FF 76 8C FF 76   ;$....9^..=.v..v
1817:BC70  8A FF 76 88 FF 76 86 FF-76 CC FF 76 CA 1E B8 49   ..v..v..v..v...I
1817:BC80  20 50 FF 76 FE FF 76 FC-9A 0A 00 65 2D 83 C4 14    P.v..v....e-...
1817:BC90  47 3B 3E F7 00 7D 03 E9-51 FF 8B 1E 03 01 D1 E3   G;>..}..Q.......
1817:BCA0  8B 87 0D 6E BA 1C 00 F7-E2 8B D8 81 C3 0D 01 1E   ...n............
1817:BCB0  07 26 8B 77 04 8B 1E 03-01 D1 E3 8B 87 0D 6E BA   .&.w..........n.
1817:BCC0  1C 00 F7 E2 8B D8 81 C3-0D 01 1E 07 26 8B 47 02   ............&.G.
1817:BCD0  A3 D8 6F FF 76 FE FF 76-FC FF 36 6A FF 16 8D 46   ..o.v..v...j...F
1817:BCE0  8E 50 8B 1E 03 01 D1 E3-8B 87 0D 6E BA 1C 00 F7   .P.........n....
1817:BCF0  E2 8B D8 81 C3 0D 01 1E-07 26 FF 77 06 56 FF 36   .........&.w.V.6
```

```
1817:BD00  D3 6F FF 76 DC FF 76 DA-FF 76 D8 FF 76 D6 FF 76   .o.v..v..v..v..v
1817:BD10  D4 FF 76 D2 FF 76 D0 FF-76 CE FF 36 03 01 9A 08   ..v..v..v..6....
1817:BD20  00 3B 24 83 C4 22 89 86-66 FF 08 C0 75 19 A1 03   .;$.."..f...u...
1817:BD30  01 40 50 1E B8 5C 20 50-FF 76 FE FF 76 FC 9A 0A   .@P..\ P.v..v...
1817:BD40  00 65 2D 83 C4 0A A1 D8-6F 0B C0 74 10 3D 01 00   .e-.....o..t.=..
1817:BD50  74 4B 3D 02 00 75 03 E9-3D 00 E9 F9 00 FF 76 94   tK=..u........v.
1817:BD60  FF 76 92 FF 76 90 FF 76-8E 8B 1E 03 01 D1 E3 8B   .v..v..v........
1817:BD70  87 0D 6E 8A 1C 00 F7 E2-05 0D 01 8C DA 05 0A 00   ..n.............
1817:BD80  52 50 A1 03 01 40 50 1E-B8 80 20 50 FF 76 FE FF   RP...@P... P.v..
1817:BD90  76 FC 9A 0A 00 65 2D 83-C4 16 E9 F8 00 83 BE 66   v....e-........f
1817:BDA0  FF 02 74 3F FF 76 94 FF-76 92 FF 76 90 FF 76 8E   ..t?.v..v..v..v.
1817:BDB0  8B 1E 03 01 D1 E3 8B 87-0D 6E 8A 1C 00 F7 E2 05   .........n......
1817:BDC0  0D 01 8C DA 05 0A 00 52-50 A1 03 01 40 50 1E B8   .......RP...@P..
1817:BDD0  97 20 50 FF 76 FE FF 76-FC 9A 0A 00 65 2D 83 C4   . P.v..v....e-..
1817:BDE0  16 E8 31 8B 1E 03 01 D1-E3 8B 87 0D 6E 8A 1C 00   ..1.........n...
1817:BDF0  F7 E2 05 0D 01 8C DA 05-0A 00 52 50 A1 03 01 40   ..........RP...@
1817:BE00  50 1E B8 AE 20 50 FF 76-FE FF 76 FC 9A 0A 00 65   P... P.v..v....e
1817:BE10  2D 83 C4 0E E9 7E 00 FF-76 94 FF 76 92 FF 76 90   -....~..v..v..v.
1817:BE20  FF 76 8E 8B 1E 03 01 D1-E3 8B 87 0D 6E 8A 1C 00   .v..........n...
1817:BE30  F7 E2 05 0D 01 8C DA 05-0A 00 52 50 A1 03 01 40   ..........RP...@
1817:BE40  50 1E B8 C8 20 50 FF 76-FE FF 76 FC 9A 0A 00 65   P... P.v..v....e
1817:BE50  2D 83 C4 16 E8 3F FF 76-94 FF 76 92 FF 76 90 FF   -....?.v..v..v..
1817:BE60  76 8E 8B 1E 03 01 D1 E3-8B 87 0D 6E 8A 1C 00 F7   v..........n....
1817:BE70  E2 05 0D 01 8C DA 05 0A-00 52 50 A1 03 01 40 50   .........RP...@P
1817:BE80  1E B8 DF 20 50 FF 76 FE-FF 76 FC 9A 0A 00 65 2D   ... P.v..v....e-
1817:BE90  83 C4 16 E8 00 CD 39 46-8E CD 38 4E 8E CD 39 86   ......9F..8N..8.
1817:BEA0  76 FF CD 39 9E 76 FF CD-3D CD 39 86 6E FF CD 38   v..9.v..=.9.n..8
1817:BEB0  46 8E CD 39 9E 6E FF CD-3D CD 39 86 7E FF CD 38   F..9.n..=.9.~..8
1817:BEC0  06 D7 21 CD 39 9E 7E FF-CD 3D FF 06 03 01 A1 03   ..!.9.~..=......
1817:BED0  01 3B 86 62 FF 7D 03 E9-46 F8 83 BE 5E FF 01 74   .;.b.}..F...^..t
1817:BEE0  03 E9 5B 03 80 BE 6C FF-7A 75 03 E9 51 03 83 BE   ..[...l.zu..Q...
1817:BEF0  5C FF 01 75 18 FF 36 1C-1C FF 36 1A 1C 1E B8 F6   \..u..6...6.....
1817:BF00  20 50 FF 76 FE FF 76 FC-9A 0A 00 65 2D 83 C4 0C    P.v..v....e-...
1817:BF10  E8 86 60 FF 48 A3 03 01-E8 25 8B 1E 03 01 D1 E3   ..`.H....%......
1817:BF20  FF 87 F8 49 FF 36 03 01-1E B8 0B 21 50 FF 76 FE   ...I.6.....!P.v.
1817:BF30  FF 76 FC 9A 0A 00 65 2D-83 C4 0C FF 06 03 01 A1   .v....e-........
1817:BF40  03 01 3B 86 62 FF 7C D2-1E B8 1A 21 50 FF 76 FE   ..;.b.|....!P.v.
1817:BF50  FF 76 FC 9A 0A 00 65 2D-83 C4 08 89 16 1A 4A A1   .v....e-......J.
1817:BF60  18 4A 52 50 CD 37 86 52-FF CD 3D 83 C4 04 8B 16   .JRP.7.R..=.....
1817:BF70  22 4A A1 20 4A 52 50 CD-37 86 52 FF CD 3D 83 C4   "J. JRP.7.R..=..
1817:BF80  04 CD 3B 36 E7 21 CD 3A-E9 CD 39 5E 96 CD 3D A1   ..;6.!.:..9^..=.
1817:BF90  20 4A 0B 06 22 4A 74 1F-8B 16 22 4A A1 20 4A 52    J.."Jt..."J. JR
1817:BFA0  50 CD 37 86 52 FF CD 3D-83 C4 04 CD 38 7E 96 CD   P.7.R..=....8~..
1817:BFB0  39 5E 96 CD 3D EB 14 C7-46 9C 00 40 C7 46 9A 00   9^..=...F..@.F..
1817:BFC0  00 C7 46 98 00 00 C7 46-96 00 00 CD 39 46 96 CD   ..F....F....9F..
1817:BFD0  38 0E EF 21 CD 38 2E F7-21 CD 39 5E 96 CD 3D FF   8..!.8..!.9^..=.
1817:BFE0  36 2A 4A FF 36 28 4A FF-36 22 4A FF 36 20 4A FF   6*J.6(J.6"J.6 J.
1817:BFF0  36 1A 4A FF 36 18 4A FF-76 9C FF 76 9A FF 76 98   6.J.6.J.v..v..v.
1817:C000  FF 76 96 1E B8 42 21 50-FF 76 FE FF 76 FC 9A 0A   .v...B!P.v..v...
1817:C010  00 65 2D 83 C4 1C 8B 16-1E 4A A1 1C 4A 52 50 CD   .e-......J..JRP.
1817:C020  37 86 52 FF CD 3D 83 C4-04 8B 16 1E 4A A1 1C 4A   7.R..=......J..J
1817:C030  52 50 CD 37 86 52 FF CD-3D 83 C4 04 CD 3B 36 E7   RP.7.R..=....;6.
1817:C040  21 CD 3A E9 CD 39 5E 96-CD 3D A1 24 4A 0B 06 26   !.:..9^..=.$J..&
1817:C050  4A 74 1F 8B 16 26 4A A1-24 4A 52 50 CD 37 86 52   Jt...&J.$JRP.7.R
1817:C060  FF CD 3D 83 C4 04 CD 38-7E 96 CD 39 5E 96 CD 3D   ..=....8~..9^..=
1817:C070  EB 14 C7 46 9C 00 40 C7-46 9A 00 00 C7 46 98 00   ...F..@.F....F..
1817:C080  00 C7 46 96 00 00 CD 39-46 96 CD 38 0E EF 21 CD   ..F....9F..8..!.
1817:C090  38 2E F7 21 CD 39 5E 96-CD 3D FF 36 2E 4A FF 36   8..!.9^..=.6.J.6
1817:C0A0  2C 4A FF 36 26 4A FF 36-24 4A FF 36 1E 4A FF 36   ,J.6&J.6$J.6.J.6
1817:C0B0  1C 4A FF 76 9C FF 76 9A-FF 76 98 FF 76 96 1E B8   .J.v..v..v..v...
1817:C0C0  63 21 50 FF 76 FE FF 76-FC 9A 0A 00 65 2D 83 C4   c!P.v..v....e-..
1817:C0D0  1C FF B6 74 FF FF B6 72-FF FF B6 70 FF FF B6 6E   ...t...r...p...n
1817:C0E0  FF FF 76 84 FF 76 82 FF-76 80 FF B6 7E FF 1E B8   ..v..v..v...~...
1817:C0F0  84 21 50 FF 76 FE FF 76-FC 9A 0A 00 65 2D 83 C4   .!P.v..v....e-..
1817:C100  18 CD 39 86 6E FF CD 38-86 7E FF CD 39 5E 9E CD   ..9.n..8.~..9^..
1817:C110  3D FF 76 A4 FF 76 A2 FF-76 A0 FF 76 9E 1E B8 A8   =.v..v..v..v....
1817:C120  21 50 FF 76 FE FF 76 FC-9A 0A 00 65 2D 83 C4 10   !P.v..v....e-...
1817:C130  CD 39 06 37 21 CD 39 86-7E FF CD 3A 39 CD 39 3E   .9..!.9.~..:..9>
1817:C140  DC 6F CD 3D 8A 26 DD 6F-9E 77 03 E9 F1 00 FF B6   .o.=.&.o.w......
1817:C150  74 FF FF B6 72 FF FF B6-70 FF FF B6 6E FF 9A 07   t...r...p...n...
1817:C160  00 5C 2A 83 C4 08 83 EC-0A CD 37 BE 4C FF CD 3D   .\*.......7.L..=
1817:C170  FF B6 74 FF FF B6 72 FF-FF B6 70 FF FF B6 6E FF   ..t...r...p...n.
1817:C180  9A 07 00 5C 2A 83 C4 08-CD 37 AE 4C FF CD 3D 83   ...\*....7.L..=.
```

```
1817:C190  C4 0A CD 3A C9 CD 3B 86-7E FF CD 3B AE 76 FF CD   ...:..8.~..8.v..
1817:C1A0  39 86 7E FF CD 3B 26 D7-21 CD 3A F9 83 EC 08 CD   9.~..3&.!.:.....
1817:C1B0  39 9E 4E FF CD 3D 9A 08-00 DD 2A 83 C4 08 CD 39   9.N..=....*....9
1817:C1C0  5E A6 CD 3D FF 76 AC FF-76 AA FF 76 A8 FF 76 A6   ^..=.v..v..v..v.
1817:C1D0  1E 28 B7 21 50 FF 76 FE-FF 76 FC 9A 0A 00 65 2D   ...!P.v..v....e-
1817:C1E0  83 C4 10 CD 39 06 FF 21-CD 39 46 9E CD 3A D9 C1   ....9..!.9F..:..
1817:C1F0  39 3E DC 6F CD 3D 8A 26-DD 6F 9E 74 42 FF 76 A4   9>.o.=.&.o.tB.v.
1817:C200  FF 76 A2 FF 76 A0 FF 76-9E 9A 07 00 5C 2A 83 C4   .v..v..v....\*..
1817:C210  08 CD 38 7E A6 CD 3B 3E-07 22 CD 39 5E AE CD 3D   ..8~..8..".9^..=
1817:C220  FF 76 B4 FF 76 B2 FF 76-B0 FF 76 AE 1E 33 38 21   .v..v..v..v....!
1817:C230  50 FF 76 FE FF 76 FC 9A-0A 00 65 2D 83 C4 10 E9   P.v..v....e-....
1817:C240  0F F2 5F 5E 8B E5 5D CB-55 8B EC 81 EC 8E 02 56   .._^..].U......V
1817:C250  57 32 EC 72 06 39 26 95-0D 77 05 9A CF 09 17 18   W:.r.9&..w......
1817:C260  8B 76 06 33 FF E9 31 00-8B C6 BA E0 00 F7 E2 8B   .v.3............
1817:C270  D8 81 C3 8C 4A 1E 07 26-8B 57 16 26 8B 47 14 52   ....J..&.W.&.G.R
1817:C280  50 CD 37 86 3A FD CD 3D-83 C4 04 83 EC 08 CD 39   P.7.:..=.......9
1817:C290  9E 36 FD CD 3D FF 76 16-FF 76 14 FF 76 12 FF 76   .6..=.v..v..v..v
1817:C2A0  10 FF 76 0E FF 76 0C FF-76 0A FF 76 08 8B C6 BA   ..v..v..v..v....
1817:C2B0  E0 00 F7 E2 8B D8 81 C3-8C 4A 1E 07 8B C7 D1 E0   .........J......
1817:C2C0  D1 E0 03 D8 26 FF 77 1A-26 FF 77 18 9A 26 0C 35   ....&.w.&.w..&.:
1817:C2D0  24 83 C4 1C 8B DF D1 E3-D1 E3 D1 E3 8D 86 52 FD   $.............R.
1817:C2E0  03 D8 CD 3C 5D 1F CD 3D-47 3B 3E F7 00 7D 03 E9   ...<]..=G:>..}..
1817:C2F0  76 FF 8B C6 BA E0 00 F7-E2 8B D8 81 C3 8C 4A 1E   v.............J.
1817:C300  07 26 8B 57 16 26 8B 47-14 52 50 CD 37 86 3A FD   .&.W.&.G.RP.7.:.
1817:C310  CD 3D 83 C4 04 CD 39 96-EA FE CD 3D CD 39 9E E2   .=....9....=.9..
1817:C320  FE CD 3D 33 FF E9 E1 00-8B C6 BA E0 00 F7 E2 8B   ..=3............
1817:C330  D8 81 C3 8C 4A 1E 07 8B-C7 D1 E0 D1 E0 03 D8 26   ....J..........&
1817:C340  8B 57 1A 26 8B 47 18 52-50 CD 37 86 3A FD CD 3D   .W.&.G.RP.7.:..=
1817:C350  83 C4 04 CD 38 9E E2 FE-CD 39 3E DC 6F CD 3D 8A   ....8....9>.o.=.
1817:C360  26 DD 6F 9E 73 32 8B C6-BA E0 00 F7 E2 8B D8 81   &.o.s2..........
1817:C370  C3 8C 4A 1E 07 8B C7 D1-E0 D1 E0 03 D8 26 8B 57   ..J..........&.W
1817:C380  1A 26 8B 47 18 52 50 CD-37 86 3A FD CD 3D 83 C4   .&.G.RP.7.:..=..
1817:C390  04 CD 39 9E E2 FE CD 3D-8B C6 BA E0 00 F7 E2 8B   ..9....=........
1817:C3A0  D8 81 C3 8C 4A 1E 07 8B-C7 D1 E0 D1 E0 03 D8 26   ....J..........&
1817:C3B0  8B 57 1A 26 8B 47 18 52-50 CD 37 86 3A FD CD 3D   .W.&.G.RP.7.:..=
1817:C3C0  83 C4 04 CD 38 9E EA FE-CD 39 3E DC 6F CD 3D 8A   ....8....9>.o.=.
1817:C3D0  26 DD 6F 9E 76 32 8B C6-BA E0 00 F7 E2 8B D8 81   &.o.v2..........
1817:C3E0  C3 8C 4A 1E 07 8B C7 D1-E0 D1 E0 03 D8 26 8B 57   ..J..........&.W
1817:C3F0  1A 26 8B 47 18 52 50 CD-37 86 3A FD CD 3D 83 C4   .&.G.RP.7.:..=..
1817:C400  04 CD 39 9E EA FE CD 3D-47 3B 3E F7 00 7D 03 E9   ..9....=G:>..}..
1817:C410  16 FF CD 39 06 CD 22 CD-39 86 EA FE CD 38 A6 E2   ...9..".9....8..
1817:C420  FE CD 3A D9 CD 39 3E DC-6F CD 3D 8A 26 DD 6F 9E   ..:..9>.o.=.&.o.
1817:C430  73 16 8B DE D1 E3 C7 87-25 6E 00 00 83 3E D1 00   s.......%n...>..
1817:C440  01 74 05 33 C0 E9 01 04-E8 46 13 0B C0 74 13 3D   .t.3.....F...t.=
1817:C450  01 00 75 03 E9 E8 01 3D-02 00 75 03 E9 58 03 E9   ..u....=..u..X..
1817:C460  55 03 8B C6 BA E0 00 F7-E2 8B D8 81 C3 8C 4A 1E   U.............J.
1817:C470  07 8B 46 1C D1 E0 D1 E0-03 D8 26 8B 57 1A 26 8B   ..F.......&.W.&.
1817:C480  47 18 29 96 44 FD 89 86-42 FD 83 7E 1C 1E 74 75   G...D...B..~..tu
1817:C490  8B C6 BA E0 00 F7 E2 8B-D8 81 C3 8C 4A 1E 07 8B   .............J...
1817:C4A0  46 1C 40 D1 E0 D1 E0 03-D8 26 8B 57 1A 26 8B 47   F.@.......&.W.&.G
1817:C4B0  18 52 50 8B C6 BA E0 00-F7 E2 8B D8 81 C3 8C 4A   .RP............J
1817:C4C0  1E 07 8B 46 1C D1 E0 D1-E0 03 D8 58 5A 26 2B 47   ...F.......XZ&+G
1817:C4D0  18 26 1B 57 1A 52 50 CD-37 86 3A FD CD 3D 83 C4   .&.W.RP.7.:..=..
1817:C4E0  04 8B C6 99 52 50 CD 37-86 3A FD CD 3D 83 C4 04   ....RP.7.:..=...
1817:C4F0  CD 38 36 D5 22 CD 3A C9-9A C7 05 17 18 01 86 42   .86.".:........B
1817:C500  FD 11 96 44 FD 8B C6 BA-E0 00 F7 E2 8B D8 81 C3   ...D............
1817:C510  8C 4A 1E 07 26 8B 57 16-26 8B 47 14 52 50 CD 37   .J..&.W.&.G.RP.7
1817:C520  86 3A FD CD 3D 83 C4 04-83 EC 08 CD 39 9E 36 FD   .:..=.......9.6.
1817:C530  CD 3D FF 76 16 FF 76 14-FF 76 12 FF 76 10 FF 76   .=.v..v..v..v..v
1817:C540  0E FF 76 0C FF 76 0A FF-76 08 FF B6 44 FD FF B6   ..v..v..v...D...
1817:C550  42 FD 9A 26 0C 35 24 83-C4 1C CD 39 9E 46 FD CD   B..&.:$....9.F..
1817:C560  3D 8B DE D1 E3 83 BF 0D-6E 03 74 03 E9 BF 00 16   =.......n.t.....
1817:C570  8D 86 50 FD 50 8B DE D1-E3 FF B7 0A 48 8B DE D1   ..P.P.......H...
1817:C580  E3 FF B7 0D 6E 9A 1F 05-4B 21 83 C4 08 0B C0 75   ....n...K!.....u
1817:C590  05 33 C0 E9 B3 02 8B C6-BA E0 00 F7 E2 8B D8 81   .3..............
1817:C5A0  C3 8C 4A 1E 07 26 8B 57-16 26 8B 47 14 52 50 CD   ..J..&.W.&.G.RP.
1817:C5B0  37 86 3A FD CD 3D 83 C4-04 83 EC 08 CD 39 9E 36   7.:..=.......9.6
1817:C5C0  FD CD 3D FF 76 16 FF 76-14 FF 76 12 FF 76 10 FF   ..=.v..v..v..v..
1817:C5D0  76 0E FF 76 0C FF 76 0A-FF 76 08 8B C6 BA E0 00   v..v..v..v......
1817:C5E0  F7 E2 8B D8 81 C3 8C 4A-1E 07 26 FF 77 1A 26 FF   .......J..&.w.&.
1817:C5F0  77 18 9A 26 0C 35 24 83-C4 1C 8B 86 50 FD 5A F6   w..&.:$.....P...
1817:C600  00 F7 E2 C4 1E 74 49 03-D8 CD 3C DC 67 08 8B 86   .....tI...<.g...
1817:C610  50 FD 8A F6 00 F7 E2 C4-1E 74 49 03 D8 CD 3C DC   P........tI...<.
```

```
1817:C620  4F 10 CD 38 86 46 FD CD-39 9E 46 FD CD 3D CD 39  O..8.F..9.F..=.9
1817:C630  86 46 FD C4 5E 1E CD 3C-DD 1F CD 3D 8B 01 00 E9  .F..^..<...=....
1817:C640  07 02 83 7E 22 00 74 13-1E B8 10 22 50 FF 76 26  ...~".t...."P.v&
1817:C650  FF 76 24 9A 0A 00 65 2D-83 C4 08 16 8D 86 0A FF  .v$...e-........
1817:C660  50 9B DE D1 E3 FF 87 0A-48 83 DE D1 E3 FF 87 0D  P.......H.......
1817:C670  6E 9A 0F 06 3B 24 83 C4-08 0B C0 75 1E 83 7E 22  n...;$.....u..~"
1817:C680  00 74 13 1E B8 38 22 50-FF 76 26 FF 76 24 9A 0A  .t...8"P.v&.v$..
1817:C690  00 65 2D 83 C4 0E 33 C0-E9 AE 01 16 8D 86 02 FF  .e-...3.........
1817:C6A0  50 16 8D 86 FA FE 50 16-8D 86 F2 FE 50 FF 76 26  P.....P.....P.v&
1817:C6B0  FF 76 24 FF 76 22 1E 85-DE D1 E3 55 87 0D 6E 8A  .v$.v"........n.
1817:C6C0  1C 00 F7 E2 05 0D 01 50-16 8D 86 10 FF 50 FF 96  .......P.....P..
1817:C6D0  0A FF 16 8D 86 52 FD 50-A1 7A 4A 48 50 FA 3A 09  .....R.P.zJHP.:.
1817:C6E0  3B 24 83 C4 22 89 86 4E-FD 3D 01 00 74 03 E9 75  ;$.."..N.=..t..u
1817:C6F0  00 83 3E 5A 0D 01 75 07-CD 39 06 DD 22 EB 0E CD  ..>Z..u..9.."...
1817:C700  39 06 EE 22 CD 38 3E ED-22 CD 38 8E F2 FE C4 5E  9..".8>.".8....^
1817:C710  1E CD 3C 3D 1F CD 3D CD-39 06 F5 22 CD 39 86 FA  ..<...=.9..".9..
1817:C720  FE CD 3A D9 CD 39 3E DC-6F CD 3D 8A 26 3D 6F 9E  ..:..9>.o.=.&.o.
1817:C730  76 2E 83 7E 22 00 74 23-FF B6 00 FF FF B6 FE FE  v..~".t#........
1817:C740  FF B6 FC FE FF B6 FA FE-1E B8 5D 22 50 FF 76 26  ..........]"P.v&
1817:C750  FF 76 24 9A 0A 00 65 2D-83 C4 10 33 C0 E9 E9 00  .v$...e-...3....
1817:C760  B8 01 00 E9 E3 00 83 BE-4E FD 02 75 45 83 7E 22  ........N..uE.~"
1817:C770  00 74 13 1E B8 84 22 50-FF 76 26 FF 76 24 9A 0A  .t...."P.v&.v$..
1817:C780  00 65 2D 83 C4 08 83 3E-5A 0D 01 75 07 CD 39 06  .e-....>Z..u..9.
1817:C790  DD 22 EB 0E CD 39 06 EE-22 CD 38 3E ED 22 CD 38  ."...9..".8>.".8
1817:C7A0  8E F2 FE C4 5E 1E CD 3C-DD 1F CD 3D 8B 02 00 E9  ....^..<...=....
1817:C7B0  97 00 33 C0 E9 92 00 83-7E 22 00 74 13 1E B8 9F  ..3.....~".t....
1817:C7C0  22 50 FF 76 26 FF 76 24-9A 0A 00 65 2D 83 C4 08  "P.v&.v$...e-...
1817:C7D0  8B 5E 1C D1 E3 D1 E3 D1-E3 8D 86 52 FD 03 D8 CD  .^.........R....
1817:C7E0  3C 8D 07 8B 5E 1A D1 E3-D1 E3 D1 E3 8D 86 52 FD  <...^.........R.
1817:C7F0  03 D8 CD 3C 8D 27 8B 46-1C 2B 46 1A 99 52 50 CD  ...<\'.F.+F..RP.
1817:C800  37 86 3A FD CD 3D 83 C4-04 CD 3A F9 83 EC 0A CD  7.:..=....:.....
1817:C810  37 8E 34 FD CD 3D 83 3E-5A 0D 01 75 07 CD 39 06  7.4..=.>Z..u..9.
1817:C820  DD 22 EB D5 CD 39 06 EE-22 CD 38 3E ED 22 CD 37  ."...9..".8>.".7
1817:C830  AE 34 FD CD 3D 83 C4 0A-CD 3A C9 C4 5E 1E CD 3C  .4..=....:..^..<
1817:C840  DD 1F CD 3D 8B 01 00 E5-00 5F 5E 8B E5 5D C3 55  ...=....._^..].U
1817:C850  8B EC 83 EC 02 39 26 98-0D 77 05 9A CF 0F 17 18  .....9&..w......
1817:C860  16 8D 46 FE 50 FF 76 08-FF 76 06 9A 00 0E 3B 24  ..F.P.v..v....;$
1817:C870  83 C4 08 0B C0 74 42 98-F6 00 50 FF 76 0A 8B 46  .....tB...P.v..F
1817:C880  0C 50 8B 46 FE 8A F6 00-F7 E2 8B 0E 71 6E 8B 1E  .P.F........qn..
1817:C890  6F 6E 03 D8 43 43 53 8B-46 FE 8A F6 00 F7 E2 8B  on..CCS.F.......
1817:C8A0  0E 71 6E 8B 1E 6F 6E 03-D8 43 43 51 9A 0A 00 E2  .qn..on..CCQ....
1817:C8B0  2D 83 C4 0A 8B 01 00 EB-04 33 C0 EB 00 8B E5 5D  -........3.....]
1817:C8C0  CB 55 8B EC 83 EC 48 56-57 39 26 98 0D 77 05 9A  .U....HVW9&..w..
1817:C8D0  CF 09 17 18 C7 46 BE 00-00 C7 46 BC 00 00 C7 46  .....F....F....F
1817:C8E0  BA 00 00 C7 46 B8 00 00-C7 46 C6 00 00 C7 46 C4  ....F....F....F.
1817:C8F0  00 00 C7 46 C2 00 00 C7-46 C0 00 00 C7 46 CE 00  ...F....F....F..
1817:C900  00 C7 46 CC 00 00 C7 46-CA 00 00 C7 46 C8 00 00  ..F....F....F...
1817:C910  C7 46 D6 00 00 C7 46 D4-00 00 C7 46 D2 00 00 C7  .F....F....F....
1817:C920  46 D0 00 00 C7 46 DE 00-00 C7 46 DC 00 00 C7 46  F....F....F....F
1817:C930  DA 00 00 C7 46 D8 00 00-8B 46 08 3B 46 0E 7E 05  ....F....F.;F.~.
1817:C940  33 C0 E9 2F 02 8B 7E 08-2B 7E 06 47 8B C7 0B C0  3../..~.+~.G....
1817:C950  75 2D 1E B8 FD 22 50 9A-0A 00 D7 19 59 59 B8 19  u-..."P.....YY..
1817:C960  00 50 9A 30 0E A2 1A 59-9A 64 08 A2 1A 1E B8 05  .P.0...Y.d......
1817:C970  23 50 9A 0A 00 D7 19 59-59 33 C0 E9 F6 01 8B 76  #P.....YY3.....v
1817:C980  06 E9 A6 00 8B C6 99 52-50 CD 37 46 B0 CD 3D 83  .......RP.7F..=.
1817:C990  C4 04 CD 38 46 58 CD 39-5E 58 CD 3D 8B C6 D1 E0  ...8F..9^..=....
1817:C9A0  D1 E0 D1 E0 C4 5E 0A 03-D8 CD 3C DD 07 CD 38 46  .....^....<...8F
1817:C9B0  C0 CD 39 5E C0 CD 3D 8B-C6 F7 E6 99 52 50 CD 37  ..9^..=.....RP.7
1817:C9C0  46 B0 CD 3D 83 C4 04 CD-38 46 C8 CD 39 5E C8 CD  F..=....8F..9^..
1817:C9D0  3D 8B C6 D1 E0 D1 E0 D1-E0 C4 5E 0A 03 D8 CD 3C  =.........^....<
1817:C9E0  DD 07 8B C6 D1 E0 D1 E0-D1 E0 C4 5E 0A 03 D8 CD  ...........^....
1817:C9F0  3C DC 0F CD 38 46 D0 CD-39 5E D0 CD 3D 8B C6 D1  <...8F..9^..=...
1817:CA00  E0 D1 E0 D1 E0 C4 5E 0A-03 D8 CD 3C DD 07 8B C6  ......^....<....
1817:CA10  99 52 50 CD 37 46 B0 CD-3D 83 C4 04 CD 3A C9 CD  .RP.7F..=....:..
1817:CA20  38 46 D8 CD 39 5E D8 CD-3D 46 3B 76 08 7F 03 E9  8F..9^..=F;v....
1817:CA30  52 FF CD 39 46 B8 CD 38-4E B8 8B C7 99 52 50 CD  R..9F..8N....RP.
1817:CA40  37 46 B0 CD 3D 83 C4 04-CD 3A F9 CD 38 6E C8 CD  7F..=....:..8n..
1817:CA50  39 5E E0 CD 3D CD 39 46-C0 CD 38 4E C0 8B C7 99  9^..=.9F..8N....
1817:CA60  52 50 CD 37 46 B0 CD 3D-83 C4 04 CD 3A F9 CD 38  RP.7F..=....:..8
1817:CA70  6E D0 CD 39 5E E8 CD 3D-CD 39 46 58 CD 38 4E C0  n..9^..=.9F..8N.
1817:CA80  8B C7 99 52 50 CD 37 46-B0 CD 3D 83 C4 04 CD 3A  ...RP.7F..=....:
1817:CA90  F9 CD 38 6E D8 CD 39 5E-F0 CD 3D CD 39 06 3E 23  ..8n..9^..=.9.>#
1817:CAA0  CD 39 46 E0 CD 3A D9 CD-39 3E DC 6F CD 3D 8A 26  .9F..:..9>.o.=.&
```

```
1817:CAB0  DD 6F 9E 75 3F 1E B8 0E-23 50 9A 0A 00 D7 19 59   .o.u?...#P.....Y
1817:CAC0  59 FF 76 08 FF 76 06 1E-B8 17 23 50 9A 0E 00 A3   Y.v..v....#P....
1817:CAD0  2C 83 C4 0E 5B 1B 00 50-9A 30 0E A2 1A 59 9A 64   .......P.0...Y.d
1817:CAE0  08 A2 1A 1E B8 1D 23 50-9A 0A 00 D7 19 59 59 33   ......#P.....YY3
1817:CAF0  C0 E9 80 00 CD 39 46 F0-CD 38 76 E0 C4 5E 10 CD   .....9F..8v..^..
1817:CB00  3C DD 1F CD 3D 83 FF 02-75 2B 1E B8 26 23 50 9A   <...=...u+..&#P.
1817:CB10  0A 00 D7 19 59 59 E9 1E-00 50 9A 30 0E A2 1A 59   ....YY...P.0...Y
1817:CB20  9A 64 08 A2 1A 1E B8 2C-23 50 9A 0A 00 D7 19 59   .d.....,#P.....Y
1817:CB30  59 33 C0 EB 3F C4 5E 10-CD 3C DD 07 CD 38 4E F0   Y3..?.^..<...8N.
1817:CB40  CD 38 6E EB 8B C7 05 FE-FF 99 52 50 CD 37 46 E0   .8n.......RP.7F.
1817:CB50  CD 3D 83 C4 04 CD 3A F9-CD 39 5E F8 CD 3D CD 39   .=....:..9^..=.9
1817:CB60  46 F8 CD 38 76 E0 C4 5E-14 CD 3C DD 1F CD 3D 8B   F..8v..^..<...=.
1817:CB70  01 00 EB 00 5F 5E 8B E5-5D CB 55 8B EC 83 EC 24   ...._^..].U....$
1817:CB80  56 57 39 26 9B 0D 77 05-9A CF 09 17 18 83 7E 16   VW?%..w.......~.
1817:CB90  00 74 21 C4 5E 12 26 FF-77 06 C4 5E 12 26 FF 77   .t!.^.&.w..^.&.w
1817:CBA0  04 1E B8 3D 23 50 FF 76-1A FF 76 18 9A 0A 00 65   ...=#P.v..v....e
1817:CBB0  2D 83 C4 0C 16 8D 46 F8-50 FF 76 26 FF 76 24 FF   -.....F.P.v&.v$.
1817:CBC0  76 06 FF 76 0A FF 76 08-C4 5E 12 26 FF 77 06 C4   v..v..v..^.&.w..
1817:CBD0  5E 12 26 FF 77 04 0E E8-E7 FC 83 C4 12 0B C0 75   ^.&.w..........u
1817:CBE0  05 33 C0 E9 7A 02 83 7E-16 00 74 31 C4 5E 24 CD   .3..z..~..t1.^$.
1817:CBF0  3C DD 07 83 EC 08 CD 39-5E D0 CD 3D C4 5E 12 26   <......9^..=.^.&
1817:CC00  FF 77 06 C4 5E 12 26 FF-77 04 1E B8 62 23 50 FF   .w..^.&.w...b#P.
1817:CC10  76 1A FF 76 18 9A 0A 00-65 2D 83 C4 14 8D 46 DC   v..v....e-....F.
1817:CC20  89 46 F6 C7 46 F4 00 00-EB 48 C4 5E 0E CD 3C D9   .F..F....H.^..<.
1817:CC30  47 04 C4 5E 24 CD 3C DD-1F CD 39 3E DC 6F CD 3D   G..^$.<...9>.o.=
1817:CC40  8A 26 DD 6F 9E 76 0E 8E-01 00 EB 02 33 F6 C4 5E   .&.o.v......3..^
1817:CC50  12 26 8B 7F 08 0B F6 74-04 C5 FF 74 08 0B F6 75   .&.....t...t...u
1817:CC60  0A 0B FF 74 06 83 46 F4-E9 46 F6 FF 46 F4 83 46   ...t..F..F..F..F
1817:CC70  0E 0C 3B 46 F4 3E 46 0C-7D 08 3B 46 F6 3E 46 0C   ...F.:F.}..F.;F.
1817:CC80  74 4B 83 6E 0E 0C 83 46-F6 3B 46 0C 75 03 E9 8E   t..n...F.;F.u...
1817:CC90  01 C4 5E 0E 26 8B 07 89-46 DE C4 5E 0E 26 8B 47   ..^.&...F..^.&.G
1817:CCA0  02 89 46 E2 C4 5E 0E CD-3C D9 47 04 CD 39 5E EC   ..F..^..<.G..9^.
1817:CCB0  CD 3D 83 7E F6 00 7F 03-E9 E6 00 83 6E 0E 0C C4   .=.~........n...
1817:CCC0  5E 0E 26 8B 07 89 46 DC-C4 5E 0E 26 8B 47 02 89   ^.&...F..^.&.G..
1817:CCD0  46 E0 C4 5E 0E CD 3C D9-47 04 CD 39 5E E4 CD 3D   F..^..<.G..9^..=
1817:CCE0  83 46 0E 0C CD 39 06 34-23 CD 39 46 EC CD 38 66   .F...9.4#.9F..8f
1817:CCF0  E4 CD 3A D9 CD 39 3E DC-6F CD 3D 8A 26 DD 6F 9E   ..:..9>.o.=.&.o.
1817:CD00  75 03 E9 94 00 8B 46 DE-2B 46 DC 99 52 50 CD 37   u.....F.+F..RP.7
1817:CD10  46 D4 CD 3D 83 C4 04 C4-5E 24 CD 3C DD 07 CD 38   F..=....^$.<...8
1817:CD20  66 E4 CD 3A C9 CD 39 46-EC CD 38 66 E4 CD 3A F9   f..:..9F..8f..:.
1817:CD30  8B 46 DC 99 52 50 CD 37-46 D4 CD 3D 83 C4 04 CD   .F..RP.7F..=....
1817:CD40  3A C1 CD 38 06 D1 23 9A-C7 0E 17 18 85 F0 8B 46   :..8..#........F
1817:CD50  E2 2B 46 E0 99 52 50 CD-37 46 D4 CD 3D 83 C4 04   .+F..RP.7F..=...
1817:CD60  C4 5E 24 CD 3C DD 07 CD-38 66 E4 CD 3A C9 CD 39   .^$.<...8f..:..9
1817:CD70  46 EC CD 38 66 E4 CD 3A-F9 8B 46 E0 99 52 50 CD   F..8f..:..F..RP.
1817:CD80  37 46 D4 CD 3D 83 C4 04-CD 3A C1 CD 38 06 C1 23   7F..=....:..8..#
1817:CD90  9A C7 05 17 18 8B F5 8B-06 8B 76 DE 8B 7E E2 8B   ..........v..~..
1817:CDA0  06 83 76 DE 83 7E E2 3B-76 06 7E 05 8B 76 06 EB   ..v..~.:v.~..v..
1817:CDB0  06 0B F6 7D 02 33 F6 3B-7E 06 7E 05 8B 7E 06 EB   ...}.3.:~.~..~..
1817:CDC0  06 0B FF 7D 02 33 FF FF-76 22 FF 76 20 FF 76 1E   ...}.3..v".v .v.
1817:CDD0  FF 76 1C FF 76 06 FF 76-0A FF 76 08 57 56 0E E8   .v..v..v..v.WV..
1817:CDE0  DF FA 83 C4 12 0B C0 75-04 33 C0 EB 73 83 7E 16   .......u.3..s.~.
1817:CDF0  00 74 25 C4 5E 1C CD 3C-DD 07 83 EC 08 CD 39 5E   .t%.^..<......9^
1817:CE00  D0 CD 3D 57 56 1E B8 97-23 50 FF 76 1A FF 76 18   ..=WV...#P.v..v.
1817:CE10  9A 0A 00 65 2D 83 C4 14-E9 01 00 EB 43 E5 41 E3   ...e-.......C.A.
1817:CE20  7E 16 00 74 1C 1E B8 AD-23 50 FF 76 1A FF 76 18   ~..t....#P.v..v.
1817:CE30  9A 0A 00 65 2D 83 C4 08-C4 5E 24 CD 3C DD 07 CD   ...e-....^$.<...
1817:CE40  38 0E D9 23 C4 5E 1C CD-3C DD 1F CD 3D CD 39 06   8..#.^..<...=.9.
1817:CE50  34 23 C4 5E 20 CD 3C DD-1F CD 3D 9B 02 00 EB 00   4#.^ .<...=.....
1817:CE60  5F 5E 8B E5 5D CB 55 8B-EC 83 EC 18 39 26 9B 0D   _^..].U.....9%..
1817:CE70  77 05 9A CF 09 17 18 8B-56 08 2B 46 06 52 50 CD   w.......V..F.RP.
1817:CE80  37 46 E4 CD 3D 83 C4 04-CD 38 5E 0A CD 39 3E DC   7F..=....8^..9>.
1817:CE90  6F CD 3D 8A 26 DD 6F 9E-77 08 CD 39 46 0A CD 38   o.=.&.o.w..9F..8
1817:CEA0  06 D1 23 EB 3A 89 56 08-99 46 06 52 50 CD 37 46   ..#.:.V..F.RP.7F
1817:CEB0  E4 CD 3D 83 C4 04 CD 38-5E 12 CD 39 3E DC 6F CD   ..=....8^..9>.o.
1817:CEC0  3D 8A 26 DD 6F 9E 76 06-CD 39 46 12 EB 11 8B 56   =.&.o.v..9F....V
1817:CED0  08 8B 46 06 52 50 CD 37-46 E4 CD 3D 83 C4 04 CD   ..F.RP.7F..=....
1817:CEE0  39 5E E8 CD 3D CD 39 46-12 CD 38 66 0A CD 39 46   9^..=.9F..8f..9F
1817:CEF0  E8 CD 38 66 0A CD 3A F9-CD 39 5E F0 CD 3D FF 76   ..8f..:..9^..=.v
1817:CF00  F6 FF 76 F4 FF 76 F2 FF-76 F0 9A 0E 00 72 2A 83   ..v..v..v....r*.
1817:CF10  C4 08 CD 39 5E F0 CD 3D-83 3E 4E 0C 01 74 03 E9   ...9^..=.>N..t..
1817:CF20  95 00 CD 39 46 1A CD 38-5E 0A CD 39 3E DC 6F CD   ...9F..8^..9>.o.
```

```
1817:CF30  3D 9A 26 DD 6F 9E 77 05-CD 39 46 0A CD 38 06 D1   =.&.o.w..9F..8..
1817:CF40  23 EB 2D 93 56 05 8B 46-06 52 50 CD 37 46 E4 CD   #.-.V..F.RP.7F..
1817:CF50  3D 83 C4 04 CD 38 5E 12-CD 39 3E DC 6F CD 3D 8A   =....8^..9>.o.=.
1817:CF60  26 DD 6F 9E 76 06 CD 39-46 12 EB 04 CD 39 46 1A   &.o.v..9F....9F.
1817:CF70  CD 39 5E EB CD 3D CD 39-46 12 CD 38 66 0A CD 39   .9^..=.9F..8f..9
1817:CF80  46 E8 CD 38 66 0A CD 3A-FF CD 39 5E F8 CD 3D FF   F..8f..:..9^..=.
1817:CF90  76 FE FF 76 FC FF 76 FA-FF 76 F8 FA 0E 00 72 2A   v..v..v..v....r*
1817:CFA0  83 C4 0E CD 39 5E FE CD-3D CD 39 46 F0 CD 38 66   ....9^..=.9F..8f
1817:CFB0  F8 CD 39 5E F0 CD 3D CD-39 46 F0 E5 00 8B E5 5D   ..9^..=.9F.....]
1817:CFC0  C3 55 8B EC 83 EC 02 56-57 39 26 98 0D 77 05 9A   .U.....VW9&..w..
1817:CFD0  CF 09 17 18 33 D2 8B ED-07 52 50 9A 01 02 14 2B   ....3....RP....+
1817:CFE0  59 59 89 16 71 6E A3 6F-6E 0E D0 75 0A EB 31 C0   YY..qn.on..u..1.
1817:CFF0  50 9A 07 00 72 1D 59 33-FF C4 1E 6F 6E 26 C7 07   P...r.Y3...on&..
1817:D000  00 00 33 F6 EB 2D 1E 8B-46 FE 50 EB DE D1 E3 8B   ..3..-..F.P.....
1817:D010  9F 22 0D D1 E3 FF 83 FF-E6 8B DE D1 E3 FF 57 22   .".......V......"
1817:D020  0D 9A 00 0E 3B 24 83 C4-08 0B C0 75 03 BF 3D 00   ....;$.....u..O.
1817:D030  46 83 FE 08 7C 30 2B C7-EB 00 5F 5E 8B E5 5D CB   F...|0+..._^..].
1817:D040  55 8B EC 81 EC FA 00 56-57 8D 72 06 39 26 98 0D   U......VW.r.9&..
1817:D050  77 05 9A CF 09 17 18 BE-01 00 C4 5E 0A 26 C7 07   w..........^.&..
1817:D060  00 00 C4 1E 6F 6E 26 83-3F 00 74 5C C4 5E 0A 26   ....on&.?.t\.^.&
1817:D070  C7 07 00 00 E9 43 C4 5E-0A 26 8B 07 BA F6 00 F7   .....C.^.&......
1817:D080  E2 C4 1E 6F 6E 03 D8 26-8B 47 04 3B 46 06 75 23   ...on..&.G.;F.u#
1817:D090  C4 5E 0A 26 8B 07 BA F6-00 F7 E2 C4 1E 6F 6E 03   .^.&.........on.
1817:D0A0  D8 26 8B 47 06 3B 46 08-75 07 8B C6 E9 FF 00 EB   .&.G.;F.u.......
1817:D0B0  02 EB 15 C4 5E 0A 26 FF-07 C4 5E 0A 26 8B 07 C4   ....^.&...^.&...
1817:D0C0  1E 6F 6E 26 3B 07 7C AE-1E 58 E4 23 50 1E 58 D9   .on&;.|.....#P..
1817:D0D0  23 50 9A 1A 02 5C 2B 83-C4 08 89 96 08 FF 89 86   #P...\+.........
1817:D0E0  06 FF 0B D0 75 03 E9 82-00 E9 89 00 8B 46 06 3B   ....u........F.;
1817:D0F0  86 0C FF 74 03 E9 7D 00-8B 46 08 3B 86 0E FF 75   ...t..}..F.;...u
1817:D100  74 8B F6 00 50 C4 5E 0A-26 8B 07 BA F6 00 F7 E2   t...P.^.&.......
1817:D110  8B 0E 71 6E 8B 1E 6F 6E-03 D8 43 43 53 C4 5E 0A   ..qn..on..CCS.^.
1817:D120  26 8B 07 BA F6 00 F7 E2-8B 0E 71 6E 8B 1E 6F 6E   &.........qn..on
1817:D130  03 D8 43 43 51 8C D2 8D-86 0A FF 50 8C D2 8D 86   ..CCQ......P....
1817:D140  0A FF 52 9A 0A 00 E2 2D-83 C4 0A C4 5E 0A 26 8B   ..R....-....^.&.
1817:D150  07 C4 1E 6F 6E 26 3B 07-75 07 C4 1E 6F 6E 26 FF   ...on&;.u...on&.
1817:D160  07 FF 86 08 FF FF 86 06-FF 9A 28 15 A2 1A 59 59   ..........(...YY
1817:D170  83 01 00 E8 39 FF B6 08-FF FF B6 06 FF 59 01 00   ....9...........
1817:D180  50 8B F6 00 50 16 8D 86-0A FF 50 9A 12 01 13 2C   P...P.....P....,
1817:D190  83 C4 0C 3D 01 00 75 03-E9 51 FF FF 86 08 FF FF   ...=..u..Q......
1817:D1A0  B6 06 FF 9A 28 15 A2 1A-59 59 33 C0 E8 00 5E 8B   ....(...YY3...^.
1817:D1B0  E5 5D C8 56 57 39 26 98-0D 77 05 9A CF 09 17 18   .].VW9&..w......
1817:D1C0  1E 8B E8 23 50 9A 0A 00-D7 19 59 59 C7 06 3D 6E   ...#P.....YY..=n
1817:D1D0  00 00 1E 8B 3D 6E 50 9A-A6 08 A2 1A 59 59 85 F8   ....=nP.....YY..
1817:D1E0  89 07 03 C0 75 02 EB D8-83 FF 01 7E 02 EB 66 83   ....u......~..f.
1817:D1F0  3E 3D 6E 01 7C 07 83 3E-3D 6E 0C 7E 02 EB C1 9A   >=n.|..>=n.~....
1817:D200  0A 00 B2 1D 3D 01 00 74-02 E3 B5 1E 8B F1 23 50   ....=..t......#P
1817:D210  9A 0A 00 D7 19 59 59 33-F6 EB 2C EB 09 33 C0 50   ......YY3......3.P
1817:D220  9A 39 04 A2 1A 59 8A 12-03 E2 AB 80 75 EF 9A 6E   .9...Y......u..n
1817:D230  01 10 1D E8 09 33 C0 50-9A 39 04 A2 1A 59 8A 12   .....3.P.9...Y..
1817:D240  03 EC AB 80 74 EF 46 3B-36 3D 6E 7C DE 9A A1 06   ....t.F;6=n|....
1817:D250  A2 1A E9 6B FF 5F 5E C3-55 8B EC 83 EC 02 39 26   ...k._^.U.....9&
1817:D260  98 0D 77 05 9A CF 09 17-18 1E 8B FA 23 50 9A 0A   ..w.........#P..
1817:D270  00 D7 19 59 59 9A CE 05-A2 1A 8A 46 FF 3C 31 7C   ...YY......F.<1|
1817:D280  06 80 7E FF 39 7E 10 80-7E FF 08 75 03 E9 97 00   ..~.9~..~..u....
1817:D290  9A A1 06 A2 1A E8 DE FF-06 32 3F 7D 13 8A 46 FF   .........2?}..F.
1817:D2A0  FF 06 3E 3F C4 1E 3E 3F-49 26 88 07 B4 00 EB 10   ..>?..>?I&......
1817:D2B0  1E 8B 32 3F 50 FF 76 FF-9A 09 00 4A 2C 83 C4 06   ..2?P.v.........
1817:D2C0  8A 46 FF 98 2D 31 00 3D-18 00 77 5E 8B D8 D1 E3   .F..-1.=..w^....
1817:D2D0  2E FF A7 8E 00 97 00 9F-00 A7 00 AF 00 B7 00 BF   ................
1817:D2E0  00 C7 00 CF 00 CF 00 9A-03 00 32 25 E9 7A FF 9A   ..........2%.z..
1817:D2F0  9C 10 A2 1A E9 72 FF 9A-4C 11 A2 1A E9 6A FF 9A   .....r..L....j..
1817:D300  92 09 17 22 E9 62 FF 9A-18 03 D1 21 E9 5A FF 9A   ...".b.....!.Z..
1817:D310  0B 00 17 22 E9 52 FF 9A-6C 01 3C 25 E9 4A FF 9A   ...".R..l.<%.J..
1817:D320  A1 06 A2 1A E9 42 FF 8B-E5 5D C3 55 8B EC 83 EC   .....B...].U....
1817:D330  04 56 39 26 98 0D 77 05-9A CF 09 17 18 1E 8B 01   .V9&..w.........
1817:D340  24 50 9A 0A 00 D7 19 59-59 C7 06 03 01 00 90 EB   $P.....YY.......
1817:D350  1E 03 01 D1 E3 D1 E3 C7-87 41 6E 02 00 C7 87 3F   .........An....?
1817:D360  6E 48 65 9A F7 03 10 1D-8B F0 8B 1E 03 01 D1 E3   nHe.............
1817:D370  D1 E3 8B 87 41 6E 8B 87-3F 6E 89 56 FE 89 46 FC   ....An..?n.V..F.
1817:D380  8A 02 00 8B 48 6E 2B 46-FC 1B 56 FE 89 56 FE 89   ....Hn+F..V..V..
1817:D390  46 FC 56 FF 76 FE FF 76-FC 1E 8B 0A 24 50 9A 05   F.V.v..v....$P..
1817:D3A0  00 A8 2C 83 C4 0A 9A CE-05 A2 1A 3D 0D 00 74 02   ...........=..t.
```

```
1817:D3B0  E8 E8 9A 18 02 A2 1A 5E-5B E5 5D C3 56 39 26 9B   .......^..].V9%.
1817:D3C0  0D 77 05 9A CF 09 17 18-1E B8 13 24 50 9A 0A 00   .w.........$P...
1817:D3D0  D7 19 59 59 33 F6 EB 10-9A 21 06 A2 1A 8B 84 47   ..YY3....!.....G
1817:D3E0  0C 3C 09 75 02 EB E1 46-83 FE 05 7C E8 9A 23 06   .<.u...F...|..#.
1817:D3F0  17 22 96 6C 03 A2 1A 5E-C3 55 8B EC 83 EC 04 56   .".l...^.U.....V
1817:D400  39 26 9B 0D 77 05 9A CF-09 17 18 1E B8 24 24 50   9%..w........$$P
1817:D410  9A 0A 00 D7 19 59 59 9A-CE 05 A2 1A 8B 46 FD 3C   .....YY......F.<
1817:D420  31 7C 06 80 7E FD 39 7E-10 80 7E FD 08 75 03 E9   1|..~.9~..~..u..
1817:D430  94 01 9A A1 06 A2 1A EB-DE FF 06 32 3F 7D 13 8A   ...........2?}..
1817:D440  46 FD FF 06 3E 3F C4 1E-3E 3F 4B 26 8B 07 B4 00   F...>?..>?K%....
1817:D450  E8 10 1E 8B 32 3F 50 FF-76 FD 9A 09 00 AA 2C 83   ....2?P.v.....,.
1817:D460  C4 06 8A 46 FD 96 3D 31-00 3D 08 00 76 03 E9 4D   ...F..=1.=..v..M
1817:D470  01 8B D8 D1 E3 2E FF A7-8A 00 9C 00 A4 00 B2 00   ................
1817:D480  C0 00 C8 00 FA 00 2C 01-43 01 CE 01 9A D8 01 56   ......,.C......V
1817:D490  25 E9 77 FF C7 06 C9 00-01 00 9A 93 02 56 25 E9   %.w..........V%.
1817:D4A0  69 FF C7 06 C9 00 FF FF-9A 93 02 56 25 E9 53 FF   i..........V%.S.
1817:D4B0  9A E8 02 56 25 E9 53 FF-83 3E 52 0D 00 75 14 9A   ...V%.S..>R..u..
1817:D4C0  8A 02 6B 1C 8B F0 8B C6-0B C0 74 07 56 9A 07 00   ..k.......t.V...
1817:D4D0  72 1D 59 9A 95 00 A4 20-8B F0 8B C6 0B C0 74 07   r.Y.... ......t.
1817:D4E0  56 9A 07 00 72 1D 59 E9-21 FF 83 3E 52 0D 00 75   V...r.Y.!..>R..u
1817:D4F0  14 9A 8A 02 6B 1C 8B F0-8B C6 0B C0 74 07 56 9A   ....k.......t.V.
1817:D500  07 00 72 1D 59 9A FE 00-A4 20 8B F0 8B C6 0B C0   ..r.Y.... ......
1817:D510  74 07 56 9A 07 00 72 1D-59 E9 EF FE 9A E4 00 CF   t.V...r.Y.......
1817:D520  20 8B F0 8B C6 0B C0 74-07 56 9A 07 00 72 1D 59    ......t.V...r.Y
1817:D530  E9 D8 FE 1E B8 2B 24 50-9A 0A 00 D7 19 59 59 16   .....+$P.....YY.
1817:D540  8D 46 FE 50 9A A6 08 A2-1A 59 59 8B F0 8B C6 0B   .F.P.....YY.....
1817:D550  C0 75 02 EB DE 83 FE 01-7E 03 E9 AE FE C7 06 C9   .u......~.......
1817:D560  00 01 00 83 7E FE 01 7C-06 83 7E FE 02 7E 02 EB   ....~..|..~..~..
1817:D570  C2 83 7E FE 02 75 06 C7-06 C9 00 FF FF 1E B8 33   ..~..u.........3
1817:D580  24 50 9A 0A 00 D7 19 59-59 16 8D 46 FE 50 9A A6   $P.....YY..F.P..
1817:D590  08 A2 1A 59 59 3D 01 00-74 02 EB E1 83 7E FE 01   ...YY=..t....~..
1817:D5A0  7D 02 EB D9 FF 76 FE 9A-71 01 6B 1C 59 9A 63 02   }....v..q.k.Y.c.
1817:D5B0  A2 1A EB 00 83 3E 9D 00-00 75 F9 E9 4D FE 9A A1   .....>...u..M...
1817:D5C0  06 A2 1A E9 45 FE 5E 8B-E5 5D C3 39 26 9B 0D 77   ....E.^..].9%..w
1817:D5D0  05 9A CF 09 17 18 9A 8A-02 6B 1C 0B C0 74 03 E9   .........k...t..
1817:D5E0  8F 00 9A 52 06 17 22 0B-C0 74 0F 9A 52 06 17 22   ...R.."..t..R.."
1817:D5F0  0B C0 74 06 C7 06 19 0C-00 00 C7 06 03 01 00 00   ..t.............
1817:D600  B8 01 00 50 9A 21 00 6B-1C 59 1E B8 3C 24 50 9A   ...P.!.k.Y..<$P.
1817:D610  0A 00 D7 19 59 59 B8 01-00 50 9A 21 00 6B 1C 59   ....YY...P.!.k.Y
1817:D620  9A 6C 03 A2 1A 9A CE 05-A2 1A 3D 0D 00 74 2D 3D   .l........=..t-=
1817:D630  31 00 74 07 3D 32 00 74-15 EB 23 FF 06 19 0C A1   1.t.=2.t..#.....
1817:D640  19 0C B9 90 06 99 F7 F9-89 16 19 0C EB C8 FF 0E   ................
1817:D650  19 0C 7D 06 81 06 19 0C-90 06 EB 8A EB 07 9A A1   ..}.............
1817:D660  06 A2 1A EB 81 9A 63 02-A2 1A 9A D7 06 17 22 EB   ......c.......".
1817:D670  11 1E B8 45 24 50 9A 0A-00 D7 19 59 59 9A CE 05   ...E$P.....YY...
1817:D680  A2 1A C3 39 26 9B 0D 77-05 9A CF 09 17 18 1E B8   ...9%..w........
1817:D690  4E 24 50 9A 0A 00 D7 19-59 59 C7 06 48 0D 01 00   N$P.....YY..H...
1817:D6A0  B8 03 00 50 9A 71 01 6B-1C 59 EB 09 33 C0 50 9A   ...P.q.k.Y..3.P.
1817:D6B0  39 04 A2 1A 59 9A 70 06-A2 1A 0B C0 74 EE 9A 63   9...Y.p.....t..c
1817:D6C0  02 A2 1A 9A CE 05 A2 1A-C7 06 48 0D 00 00 EB 00   ..........H.....
1817:D6D0  83 3E 9D 00 00 75 F9 CB-56 57 39 26 9B 0D 77 05   .>...u..VW9%..w.
1817:D6E0  9A CF 09 17 18 9A 13 02-A2 1A B8 0A 00 50 1E B8   .............P..
1817:D6F0  57 24 50 9A 05 00 A8 2C-83 C4 06 33 F6 EB 3B 8B   W$P....,...3..;.
1817:D700  DE D1 E3 FF 97 55 00 8B-C6 40 50 1E B8 73 24 50   .........@P..s$P
1817:D710  9A 05 00 A8 2C 83 C4 06-1E 8B C6 D1 E0 05 25 00   ....,...........
1817:D720  50 9A A6 08 A2 1A 59 59-8B F8 8B C7 0B C0 75 02   P.....YY......u.
1817:D730  EB CD 83 FF 02 75 02 EB-C6 46 83 FE 0A 7C C0 9A   .....u...F...|..
1817:D740  18 02 A2 1A 1E B8 3D 24-50 9A 05 00 A8 2C 59 59   ......=$P....,YY
1817:D750  FF 36 44 0D 1E B8 AC 24-50 9A 05 00 A8 2C 83 C4   .6D....$P....,..
1817:D760  06 1E B8 44 0D 50 9A A6-08 A2 1A 59 59 8B F8 8B   ...D.P.....YY...
1817:D770  C7 0B C0 75 02 EB C8 83-FF 02 75 02 EB C1 1E B8   ...u......u.....
1817:D780  D5 24 50 9A 0A 00 D7 19-59 59 C7 06 03 01 00 00   .$P.....YY......
1817:D790  EB 6F FF 06 03 01 A1 03-01 B9 0C 00 99 F7 F9 89   .o..............
1817:D7A0  16 03 01 9A 12 00 F1 2D-B9 04 00 99 F7 F9 8B C2   .......-........
1817:D7B0  3D 03 00 77 29 8B D8 D1-E3 2E FF A7 CE 03 D6 03   =..w)...........
1817:D7C0  E2 03 EE 03 EE 03 B8 04-00 50 9A 21 00 6B 1C 59   .........P.!.k.Y
1817:D7D0  EB 13 B8 05 00 50 9A 21-00 6B 1C 59 EB 0C B8 06   .....P.!.k.Y....
1817:D7E0  00 50 9A 21 00 6B 1C 59-EB 00 B8 0E 00 50 9A 6D   .P.!.k.Y.....P.m
1817:D7F0  11 A2 1A 44 44 CD 39 D8-33 C0 50 9A 39 04 A2 1A   ...DD.9.3.P.9...
1817:D800  59 9A 70 06 A2 1A 0B C0-74 89 9A CE 05 A2 1A 5F   Y.p.....t......_
1817:D810  5E CB 55 8B EC 83 EC 08-56 39 26 9B 0D 77 05 9A   ^.U.....V9%..w..
1817:D820  CF 09 17 18 8C 5E FA C7-46 F8 DE 24 33 F6 EB 0B   .....^..F..$3...
1817:D830  8B DE D1 E3 C7 87 23 56-02 00 46 83 FE 0A 7C F0   ......#V..F...|.
```

```
1817:D840  1E B8 E8 24 50 FF 76 FA-FF 76 F8 9A 1A 02 5C 2B   ...$P.v..v....\+
1817:D850  83 C4 08 89 56 FE 89 46-FC 0B D0 75 05 B8 24 00   ....V..F...u..$.
1817:D860  EB 4F FF 76 FE FF 76 FC-E8 02 00 50 B8 20 03 50   .O.v..v....P. .P
1817:D870  1E B8 B5 67 50 9A 12 01-13 2C 83 C4 0C 3D 02 00   ...gP....,...=..
1817:D880  73 12 FF 76 FE FF 76 FC-9A 28 15 A2 1A 59 59 8B   s..v..v..(...YY.
1817:D890  24 00 EB 1D FF 76 FE FF-76 FC 9A 28 15 A2 1A 59   $....v..v..(...Y
1817:D8A0  59 C7 06 25 56 00 00 C7-06 27 56 01 00 33 C0 EB   Y..%V....'V..3..
1817:D8B0  00 5E 8B E5 5D CB 55 8B-EC 83 EC 14 56 57 39 26   .^..].U.....VW9&
1817:D8C0  98 0D 77 05 9A CF 09 17-18 C7 46 F0 00 00 C7 46   ..w.......F....F
1817:D8D0  F2 00 00 C7 46 FA 00 00-33 F6 8C 5E FE C7 46 FC   ....F...3..^..F.
1817:D8E0  E0 24 EB 1B 33 C0 C4 5E-FC 26 89 47 04 C4 5E FC   .$..3..^.&.G..^.
1817:D8F0  26 89 07 C4 5E FC 26 89-47 02 46 83 46 FC 58 83   &...^.&.G.F.F.X.
1817:D900  FE 3B 7D E0 C7 46 EC 00-00 E9 B8 01 33 F6 EB 2A   .;}..F......3..*
1817:D910  8B 5E EC D1 E3 8B 87 0D-6E 8B DE D1 E3 3B 87 0D   .^......n....;..
1817:D920  6E 75 16 8B 5E EC D1 E3-8B 87 80 49 8B DE D1 E3   nu..^......I....
1817:D930  3B 87 80 49 75 03 E9 8B-01 46 3B 76 EC 7C D1 8B   ;..Iu....F;v.|..
1817:D940  5E EC D1 E3 8B 87 80 49-0B C0 75 03 E9 73 01 3D   ^......I..u..s.=
1817:D950  01 00 75 03 E9 EA 00 3D-02 00 74 03 E9 63 01 33   ..u....=..t..c.3
1817:D960  F6 8C 5E FE C7 46 FC E0-24 E9 9A 00 C4 5E FC 83   ..^..F..$....^..
1817:D970  C3 44 8C 46 F8 89 5E F6-33 FF E9 72 00 C4 5E F6   .D.F..^.3..r..^.
1817:D980  26 8B 07 B9 64 00 99 F7-F9 8B 5E EC D1 E3 3B 97   &...d.....^...;.
1817:D990  0D 6E 75 56 C4 5E F6 26-8B 07 B9 64 00 99 F7 F9   .nuV.^.&...d....
1817:D9A0  89 46 EE 83 7E EE 01 75-1C C4 5E FC 26 FF 07 C4   .F..~..u..^.&...
1817:D9B0  5E FC 26 8B 07 3B 46 F0-7E 09 C4 5E FC 26 89 07   ^.&..;F.~..^.&..
1817:D9C0  89 46 F0 EB 3C 83 7E EE-02 75 1F C4 5E FC 26 FF   .F..<.~..u..^.&.
1817:D9D0  47 02 C4 5E FC 26 8B 47-02 3B 46 F2 7E 0A C4 5E   G..^.&.G.;F.~..^
1817:D9E0  FC 26 8B 47 02 89 46 F2-EB 17 47 83 46 F6 02 83   .&.G..F...G.F...
1817:D9F0  FF 0A 7D 0D C4 5E F6 26-81 3F 0F 27 74 03 E9 7C   ..}..^.&.?.'t..|
1817:DA00  FF 46 83 46 FC 58 83 FE-3B 7D 03 E9 5E FF E9 83   .F.F.X..;}..^...
1817:DA10  00 33 F6 8C 5E FE C7 46-FC E0 24 E9 9A 00 C4 5E   .3..^..F..$....^
1817:DA20  FC 83 C3 44 8C 46 F8 89-5E F6 33 FF E9 72 00 C4   ...D.F..^.3..r..
1817:DA30  5E F6 26 8B 07 B9 64 00-99 F7 F9 8B 5E EC D1 E3   ^.&...d.....^...
1817:DA40  3B 97 0D 6E 75 56 C4 5E-F6 26 8B 07 B9 64 00 99   ;..nuV.^.&...d..
1817:DA50  F7 F9 89 46 EE 83 7E EE-05 75 1C C4 5E FC 26 FF   ...F..~..u..^.&.
1817:DA60  07 C4 5E FC 26 8B 07 3B-46 F0 7E 09 C4 5E FC 26   ..^.&..;F.~..^.&
1817:DA70  89 07 89 46 F0 EB 3C 83-7E EE 04 75 1F C4 5E FC   ...F..<.~..u..^.
1817:DA80  26 FF 47 02 C4 5E FC 26-8B 47 02 3B 46 F2 7E 0A   &.G..^.&.G.;F.~.
1817:DA90  C4 5E FC 26 8B 47 02 89-46 F2 EB 17 47 83 46 F6   .^.&.G..F...G.F.
1817:DAA0  02 83 FF 0A 7D 0D C4 5E-F6 26 81 3F 0F 27 74 03   ....}..^.&.?.'t.
1817:DAB0  E9 7C FF 46 83 46 FC 58-83 FE 3B 7D 03 E9 5E FF   .|.F.F.X..;}..^.
1817:DAC0  EB 02 EB 00 FF 46 EC 83-7E EC 0C 7D 03 E9 3C FE   .....F..~..}..<.
1817:DAD0  C7 46 FA 00 00 C7 06 DA-6F 00 00 1E B8 34 39 50   .F......o....49P
1817:DAE0  9A 0A 00 D7 19 59 59 83-7E F0 E9 79 00 E8 0A 00   .....YY.~..y....
1817:DAF0  2B C7 3B 46 F2 7D 07 8B-0A 00 2B C7 EB 03 8B 46   +.;F.}....+....F
1817:DB00  F2 89 46 F4 EB 4F 33 F6-8C 5E FE C7 46 FC E0 24   ..F..O3..^..F..$
1817:DB10  EB 3B C4 5E FC 26 8B 07-3B C7 75 2C C4 5E FC 26   .;.^.&..;.u,.^.&
1817:DB20  83 47 02 3B 46 F4 75 20-FF 46 F4 8B 46 FA C4 5E   .G.;F.u .F..F..^
1817:DB30  FC 26 89 47 04 FF 76 FE-FF 76 FC 9A EA 02 A2 25   .&.G..v..v.....%
1817:DB40  59 59 0B C0 75 02 EB 4C-46 83 46 FC 58 83 FE 3B   YY..u..LF.F.X..;
1817:DB50  7C C0 FF 4E F4 83 7E F4-00 7F AB 0B FF 74 06 83   |..N..~......t..
1817:DB60  7E F4 00 74 A1 4F 03 FF-7C 03 E9 80 FF 83 7E FA   ~..t.O..|.....~.
1817:DB70  00 75 13 1E B8 3B 39 50-9A 87 00 D7 19 59 59 9A   .u...;9P.....YY.
1817:DB80  64 08 A2 1A EB 05 9A 46-03 A2 25 0B C0 75 02 EB   d......F..%..u..
1817:DB90  03 E9 3C FF 5F 5E 8B E5-5D CB 55 8B EC 39 26 98   ..<._^..].U..9&.
1817:DBA0  0D 77 05 9A CF 09 17 18-C4 5E 06 26 8B 47 06 01   .w.......^.&.G..
1817:DBB0  06 DA 6F 83 3E DA 6F 08-7E 17 9A 46 03 A2 25 0B   ..o.>.o.~..F..%.
1817:DBC0  C0 75 04 33 C0 EB 2D C4-5E 06 26 8B 47 06 A3 DA   .u.3..-.^.&.G...
1817:DBD0  6F 8B 56 08 8B 46 06 05-08 00 52 50 C4 5E 06 26   o.V..F....RP.^.&
1817:DBE0  FF 77 04 1E B8 43 39 50-9A 05 00 A8 2C 8B E5 B8   .w...C9P........
1817:DBF0  01 00 EB 00 5D CB 55 8B-EC 83 EC 02 56 39 26 98   ....].U.....V9&.
1817:DC00  0D 77 05 9A CF 09 17 18-1E B8 50 39 50 9A 8D 00   .w........P9P...
1817:DC10  D7 19 59 59 C6 46 FF 32-EB 08 9A CE 05 A2 1A 88   ..YY.F.2........
1817:DC20  46 FF 80 7E FF 0D 74 0C-80 7E FF 0A 74 06 80 7E   F..~..t..~..t..~
1817:DC30  FF 31 75 E6 80 7E FF 08-75 04 33 C0 EB 32 80 7E   .1u..~..u.3..2.~
1817:DC40  FF 31 75 13 B8 18 00 50-9A 30 0E A2 1A 59 8B F0   .1u....P.0...Y..
1817:DC50  8B C6 0B C0 74 07 56 9A-07 00 72 1D 59 EB 05 1E   ....t.V...r.Y...
1817:DC60  B8 57 39 50 9A 0A 00 D7-19 59 59 B8 01 00 EB 00   .W9P.....YY.....
1817:DC70  5E 8B E5 5D CB 55 8B EC-83 EC 02 56 39 26 98 0D   ^..].U.....V9&..
1817:DC80  77 05 9A CF 09 17 18 1E-B8 5E 39 50 9A 0A 00 D7   w........^9P....
1817:DC90  19 59 59 9A CE 05 A2 1A-8A 46 FF 3C 31 7C 06 80   .YY......F.<1|..
1817:DCA0  7E FF 39 7E 10 80 7E FF-08 75 03 E9 D5 00 9A A1   ~.9~..~..u......
1817:DCB0  06 A2 1A EB DE FF 06 32-3F 7D 13 8A 46 FF FF 06   .......2?}..F...
```

```
1817:DCC0  3E 3F C4 1E 3E 3F 4B 26-8B 07 54 00 E8 10 1E 8B   >?..>?K&........
1817:DCD0  3B 3F 50 FF 76 FF 9A 09-00 AA 2C 83 C4 06 8A 46   ;?P.v..........F
1817:DCE0  FF 93 2D 31 00 3D 08 00-76 03 E9 3E 00 83 D8 D1   ..-1.=..v.......
1817:DCF0  E3 2E FF A7 86 00 98 00-9B 00 A3 00 CA 00 E8 00   ................
1817:DD00  F3 00 F5 00 03 01 0B 01-E9 7C FF 9A 18 01 DE 25   ..........|....%
1817:DD10  E9 74 FF 2B 01 00 50 3D-00 50 50 9A 60 01 DE 25   .t....P=.PP.`..%
1817:DD20  83 C4 06 2B F0 8B C6 0B-C0 74 0C 83 FE 2B 74 07   .........t...+t.
1817:DD30  56 9A 07 00 72 1D 59 E9-4D FF 3B 01 00 50 3B 01   V...r.Y.M...P..
1817:DD40  00 50 9A 0C 00 CF 20 59-E9 83 F0 85 C6 05 C0 74   .P.... YY......t
1817:DD50  07 56 9A 07 00 72 1D 59-E9 2C FF 9A 4D 1E DE 25   .V...r.Y...,M..%
1817:DD60  E9 24 FF 9A CA 18 DE 25-E9 1C FF 9A FE 1A DE 25   .$....%.......%
1817:DD70  E9 14 FF 9A 8F 04 10 1D-E9 0C FF 9A A1 06 A3 1A   ................
1817:DD80  E9 04 FF 5E 3B E3 5D C8-56 39 26 99 0D 77 05 9A   ...^..].V9%..w..
1817:DD90  CF 09 17 18 9A FE 00 A4-20 85 F0 8B C6 05 C0 74   ........ ......t
1817:DDA0  07 56 9A 07 00 72 1D 59-C7 06 03 01 00 00 83 01   .V...r.Y........
1817:DDB0  00 50 9A 21 00 6B 1C 59-1E 3B 65 39 50 9A 0A 00   .P.!.k.Y..e9P...
1817:DDC0  D7 19 59 59 92 CC 00 50-9A E3 00 A2 1A 59 5E C2   ..YY...P.....Y^.
1817:DDD0  55 8B EC 81 EC A0 00 56-57 39 26 95 0D 77 05 9A   U......VW9%..w..
1817:DDE0  CF 09 17 18 8B 7E 0A 83-FF 01 75 58 1E 8B 6E 39   .....~....uX..n9
1817:DDF0  50 9A 0A 00 D7 19 59 59-9A CE 05 A2 1A 8B 86 61   P.....YY.......a
1817:DE00  FF 3C 31 72 0E 80 3E 61-FF 3C 7E 09 80 3E 61 FF   .<1r...a.<~...a.
1817:DE10  08 74 03 E8 D7 80 3E 61-FF 08 75 03 E9 64 13 80   .t.....a..u..d..
1817:DE20  BE 61 FF 31 75 05 E8 3C-3F EB 03 E8 6E 3F 1E 07   .a.1u..<?...n?..
1817:DE30  8C 86 64 FF 89 9E 62 FF-1E 58 77 39 50 9A 0A 00   ..d...b...w9P...
1817:DE40  D7 19 59 59 9A 9C 10 A2-1A 33 F0 8B C6 0B C0 74   ..YY...........t
1817:DE50  07 56 9A 07 00 72 1D 59-9A 06 07 17 22 8B F0 5B   .V...r.Y...."...
1817:DE60  C6 0B C0 74 07 56 9A 07-00 72 1D 59 3B 16 DE 47   ...t.V...r.Y...G
1817:DE70  A1 DC 47 52 50 CD 37 86-58 FF CD 3D 83 C4 04 CD   ..GRP.7.X..=....
1817:DE80  39 5E A0 CD 3D 8B 16 E6-47 A1 E4 47 52 50 CD 37   9^..=...G..GRP.7
1817:DE90  86 58 FF CD 3D 83 C4 04-CD 39 5E A8 CD 3D 8B 16   .X..=....9^..=..
1817:DEA0  EA 47 A1 E8 47 52 50 CD-37 86 58 FF CD 3D 83 C4   .G..GRP.7.X..=..
1817:DEB0  04 CD 39 5E B0 CD 3D 8B-16 E2 47 A1 E0 47 52 50   ..9^..=...G..GRP
1817:DEC0  CD 37 86 58 FF CD 3D 83-C4 04 CD 39 5E B8 CD 3D   .7.X..=....9^..=
1817:DED0  8B 16 EE 47 A1 EC 47 52-50 CD 37 86 58 FF CD 3D   ...G..GRP.7.X..=
1817:DEE0  83 C4 04 CD 39 5E C0 CD-3D 8B 16 F2 47 A1 F0 47   ....9^..=...G..G
1817:DEF0  52 50 CD 37 86 58 FF CD-3D 83 C4 04 CD 39 5E C8   RP.7.X..=....9^.
1817:DF00  CD 3D 8B 16 56 43 A1 54-43 52 50 CD 37 86 58 FF   .=..VC.TCRP.7.X.
1817:DF10  CD 3D 83 C4 04 CD 39 5E-90 CD 3D 8B 16 5A 43 A1   .=....9^..=..ZC.
1817:DF20  58 43 52 50 CD 37 86 58-FF CD 3D 83 C4 04 CD 39   XCRP.7.X..=....9
1817:DF30  5E 98 CD 3D 9A FE 00 A4-20 8B F0 8B C6 0B C0 74   ^..=.... ......t
1817:DF40  07 56 9A 07 00 72 1D 59-E3 FF 01 75 21 8B 96 64   .V...r.Y...u!..d
1817:DF50  FF 8B 86 62 FF 5B 3C 3F-EC D9 3B D1 75 10 3B C3   ...b..<?..;.u.;.
1817:DF60  75 0C 1E 8B 80 39 50 9A-05 00 A8 3C 59 59 C7 06   u....9P....,YY..
1817:DF70  03 01 00 00 33 C0 50 9A-D7 0D A2 1A 59 C7 86 66   ....3.P.....Y..f
1817:DF80  FF 00 00 8B 1E 03 01 D1-E3 D1 E3 C7 87 41 6E 02   .............An.
1817:DF90  00 C7 87 3F 6E 48 65 EB-00 8B 1E 03 01 D1 E3 D1   ...?nHe.........
1817:DFA0  E3 8B 97 41 6E 3B 87 3F-6E 3B 16 56 CD 7F EA 75   ...An.;?n;.V...u
1817:DFB0  06 3B 06 54 CD 77 E2 16-3D 56 68 FF 50 9A EE 0C   .;.T.w....h.P...
1817:DFC0  A2 1A 59 59 8B F0 3B C6-0B C0 75 03 E9 22 00 C7   ..YY......u.....
1817:DFD0  86 6A FF 00 00 C7 86 68-FF 00 00 FF 86 66 FF 8B   .j.....h.....f..
1817:DFE0  86 66 FF 3D 04 00 7D 02-EB 99 83 FF 01 75 5B 1E   .f.=..}......u[.
1817:DFF0  8B 9A 39 50 FF B6 64 FF-FF B6 62 FF 9A D9 00 D7   ..9P..d...b.....
1817:E000  19 83 C4 08 1E 89 9F 39-50 FF B6 64 FF FF B6 62   .......9P..d...b
1817:E010  FF 9A 0A 00 65 2D 83 C4-08 1E 58 A1 39 50 FF B6   ....e-......9P..
1817:E020  64 FF FF B6 62 FF 9A D9-00 D7 19 83 C4 08 1E 89   d...b...........
1817:E030  AA 39 50 FF B6 64 FF FF-B6 62 FF 9A 0A 00 65 2D   .9P..d...b....e-
1817:E040  83 C4 08 8B C6 E9 3B 16-EE 05 E8 C6 E9 94 16 E8   ................
1817:E050  37 83 FF 01 75 32 1E 8B-AC 39 50 FF B6 64 FF FF   7...u2...9P..d..
1817:E060  B6 62 FF 9A D9 00 D7 19-E3 C4 08 FF B6 6A FF FF   .b...........j..
1817:E070  B6 68 FF 1E 8B 82 39 50-FF B6 64 FF FF B6 62 FF   .h....9P..d...b.
1817:E080  9A 0A 00 65 2D 83 C4 0C-83 96 6A FF EB 36 68 FF   ...e-.....j...h.
1817:E090  89 16 3E 55 A3 3C 55 83-01 00 50 9A D7 0D A2 1A   ..>U.<U...P.....
1817:E0A0  59 C7 86 66 FF 00 00 8B-1E 03 01 D1 E3 D1 E3 C7   Y..f............
1817:E0B0  87 41 6E 02 00 C7 87 3F-6E 48 65 E8 00 8B 1E 03   .An....?nHe.....
1817:E0C0  01 D1 E3 D1 E3 8B 97 41-6E 3B 87 3F 6E 3B 16 56   .......An..?n;.V
1817:E0D0  0D 7F EA 75 06 3B 06 54-0D 77 E2 16 8D 96 78 FF   ...u.;.T.w....x.
1817:E0E0  50 9A EE 0C A2 1A 59 59-8B F0 8B C6 0B C0 75 03   P.....YY......u.
1817:E0F0  E9 7F 00 E3 FF 01 75 59-1E 8B 89 39 50 FF B6 64   ......uY...9P..d
1817:E100  FF FF B6 62 FF 9A D9 00-D7 19 83 C4 08 1E 8B C4   ...b............
1817:E110  39 50 FF B6 64 FF FF B6-62 FF 9A 0A 00 65 2D 83   9P..d...b....e-.
1817:E120  C4 08 1E 8B C6 39 50 FF-B6 64 FF FF B6 62 FF 9A   .....9P..d...b..
1817:E130  D9 00 D7 19 83 C4 08 1E-8B CF 39 50 FF B6 64 FF   ..........9P..d.
1817:E140  FF B6 62 FF 9A CA 00 65-2D 83 C4 08 9A DF 06 A2   ..b....e-.......
```

```
1817:E150  1A C7 86 7A FF 00 00 C7-86 78 FF 50 C3 FF 86 66   ...z.....x.P...f
1817:E160  FF 99 86 66 FF 3D C4 00-7D 03 E9 3A FF 95 C6 E9   ...f.=..}..:....
1817:E170  61 15 3B 16 3E 55 A1 3C-55 29 86 78 FF 19 86 7A   a...>U.<U).x...z
1817:E180  FF 8B 96 7A FF 8B 86 78-FF 52 50 CD 37 86 58 FF   ...z...x.RP.7.X.
1817:E190  CD 3D 83 C4 04 CD 39 5E-F8 3D 3D 83 FF 01 75 2D   .=...9^..=...u-
1817:E1A0  FF 86 7A FF FF 86 78 FF-FF 36 5A 43 FF 36 58 43   ..z...x..6ZC.6XC
1817:E1B0  FF 36 56 43 FF 36 54 43-1E 8B D1 39 50 FF 86 64   .6VC.6TC...9P..d
1817:E1C0  FF FF 86 62 FF 9A 0A 00-65 2D 83 C4 14 9A 7F 1C   ...b....e-......
1817:E1D0  A2 1A 8B F0 8B C6 0B C0-74 07 56 9A 07 00 72 1D   ........t.V...r.
1817:E1E0  59 C7 06 03 01 06 00 E8-04 00 50 9A 21 00 6B 1C   Y.........P.!.k.
1817:E1F0  59 C7 06 97 00 00 00 C7-06 95 00 64 00 E5 00 A1   Y..........d....
1817:E200  9E 00 0B 06 97 00 75 F7-9A 70 06 A2 1A 3D 01 00   .......u..p...=..
1817:E210  75 0C 9A CE 05 A2 1A 88-86 61 FF E9 65 14 33 C0   u........a..e.3.
1817:E220  50 9A 55 0C A2 1A 59 33-C0 50 9A FD 0B A2 1A 59   P.U...Y3.P.....Y
1817:E230  8B 1E 03 01 D1 E3 D1 E3-C7 87 41 6E 02 00 C7 87   ...........An....
1817:E240  3F 6E 48 65 E8 00 8B 1E-03 01 D1 E3 D1 E3 8B 97   ?nHe............
1817:E250  41 6E 8B 87 3F 6E 3B 16-56 0D 7F EA 75 06 3B 06   An..?n;.V...u.;.
1817:E260  54 0D 77 E2 16 8D 86 7C-FF 50 9A EE 0C A2 1A 59   T.w....!.P.....Y
1817:E270  59 8B F0 8B C6 0B C0 74-07 56 9A 07 00 72 1D 59   Y......t.V...r.Y
1817:E280  9A 54 0B A2 1A 8B 16 3E-55 A1 3C 55 29 86 7C FF   .......>U.<U).!.
1817:E290  19 96 7E FF 8B 96 7E FF-8B 86 7C FF 52 50 CD 37   ..~...~...!.RP.7
1817:E2A0  86 58 FF CD 3D 83 C4 04-CD 39 5E D0 CD 3D 83 FF   .X..=....9^..=..
1817:E2B0  01 75 42 FF 76 A6 FF 76-A4 FF 76 A2 FF 76 A0 1E   .uB.v..v..v..v..
1817:E2C0  8B EF 39 50 FF 86 64 FF-FF 86 62 FF 9A 0A 00 65   ..9P..d...b....e
1817:E2D0  2D 83 C4 10 FF 76 D6 FF-76 D4 FF 76 D2 FF 76 D0   -....v..v..v..v.
1817:E2E0  1E 8B FD 39 50 FF 86 64-FF FF 86 62 FF 9A 0A 00   ...9P..d...b....
1817:E2F0  65 2D 83 C4 10 9A 70 06-A2 1A 3D 01 00 75 0C 9A   e-....p...=..u..
1817:E300  CE 05 A2 1A 88 86 61 FF-E9 78 13 B8 01 00 50 9A   .......a..x....P.
1817:E310  55 0C A2 1A 59 B8 01 00-50 9A FD 0B A2 1A 59 8B   U...Y...P.....Y.
1817:E320  1E 03 01 D1 E3 D1 E3 C7-87 41 6E 02 00 C7 87 3F   ..........An....?
1817:E330  6E 48 65 E8 00 8B 1E 03-01 D1 E3 D1 E3 8B 97 41   nHe.............A
1817:E340  6E 8B 87 3F 6E 3B 16 56-0D 7F EA 75 06 3B 06 54   n..?n;.V...u.;.T
1817:E350  0D 77 E2 16 8D 86 7C FF-50 9A EE 0C A2 1A 59 59   .w....!.P.....YY
1817:E360  8B F0 8B C6 0B C0 74 07-56 9A 07 00 72 1D 59 9A   ......t.V...r.Y.
1817:E370  E4 0B A2 1A 8B 16 3E 55-A1 3C 55 29 86 7C FF 19   ......>U.<U).!..
1817:E380  96 7E FF 8B 96 7E FF 8B-86 7C FF 52 50 CD 37 86   .~...~...!.RP.7.
1817:E390  58 FF CD 3D 83 C4 04 CD-39 5E D8 CD 3D 83 FF 01   X..=....9^..=...
1817:E3A0  75 42 FF 76 B6 FF 76 B4-FF 76 B2 FF 76 B0 1E 8B   uB.v..v..v..v...
1817:E3B0  0A 3A 50 FF 86 64 FF FF-86 62 FF 9A 0A 00 65 2D   .:P..d...b....e-
1817:E3C0  83 C4 10 FF 76 DE FF 76-DC FF 76 DA FF 76 D8 1E   ....v..v..v..v..
1817:E3D0  8B 1E 3A 50 FF 86 64 FF-FF 86 62 FF 9A 0A 00 65   ..:P..d...b....e
1817:E3E0  2D 83 C4 10 9A 70 06 A2-1A 3D 01 00 75 0C 9A CE   -....p...=..u...
1817:E3F0  05 A2 1A 88 86 61 FF E9-89 12 B8 02 00 50 9A 55   .....a.......P.U
1817:E400  0C A2 1A 59 B8 02 00 50-9A FD 0B A2 1A 59 8B 1E   ...Y...P.....Y..
1817:E410  03 01 D1 E3 D1 E3 C7 87-41 6E 02 00 C7 87 3F 6E   ........An....?n
1817:E420  48 65 E8 00 8B 1E 03 01-D1 E3 D1 E3 8B 97 41 6E   He............An
1817:E430  8B 87 3F 6E 3B 16 56 0D-7F EA 75 06 3B 06 54 0D   ..?n;.V...u.;.T.
1817:E440  77 E2 16 8D 86 7C FF 50-9A EE 0C A2 1A 59 59 8B   w....!.P.....YY.
1817:E450  F0 8B C6 0B C0 74 07 56-9A 07 00 72 1D 59 9A E4   .....t.V...r.Y..
1817:E460  0B A2 1A 8B 16 3E 55 A1-3C 55 29 86 7C FF 19 96   .....>U.<U).!...
1817:E470  7E FF 8B 96 7E FF 8B 86-7C FF 52 50 CD 37 86 58   ~...~...!.RP.7.X
1817:E480  FF CD 3D 83 C4 04 CD 39-5E E0 CD 3D 83 FF 01 75   ..=....9^..=...u
1817:E490  42 FF 76 AE FF 76 AC FF-76 AA FF 76 A8 1E 8B 25   B.v..v..v..v...%
1817:E4A0  3A 50 FF 86 64 FF FF 86-62 FF 9A 0A 00 65 2D 83   :P..d...b....e-.
1817:E4B0  C4 10 FF 76 E6 FF 76 E4-FF 76 E2 FF 76 E0 1E 8B   ....v..v..v..v...
1817:E4C0  3B 3A 50 FF 86 64 FF FF-86 62 FF 9A 0A 00 65 2D   ;:P..d...b....e-
1817:E4D0  83 C4 10 9A 70 06 A2 1A-3D 01 00 75 0C 9A CE 05   ....p...=..u....
1817:E4E0  A2 1A 88 86 61 FF E9 9A-11 B8 05 00 50 9A 55 0C   ....a.......P.U.
1817:E4F0  A2 1A 59 B8 05 00 50 9A-FD 0B A2 1A 59 8B 1E 03   ..Y...P.....Y...
1817:E500  01 D1 E3 D1 E3 C7 87 41-6E 02 00 C7 87 3F 6E 48   .......An....?nH
1817:E510  65 E8 00 8B 1E 03 01 D1-E3 D1 E3 8B 97 41 6E 8B   e.............An.
1817:E520  87 3F 6E 3B 16 56 0D 7F-EA 75 06 3B 06 54 0D 77   .?n;.V...u.;.T.w
1817:E530  E2 16 8D 86 7C FF 50 9A-EE 0C A2 1A 59 59 8B F0   ....!.P.....YY..
1817:E540  8B C6 0B C0 74 07 56 9A-07 00 72 1D 59 9A E4 0B   ....t.V...r.Y...
1817:E550  A2 1A 8B 16 3E 55 A1 3C-55 29 86 7C FF 19 96 7E   ....>U.<U).!...~
1817:E560  FF 8B 96 7E FF 8B 86 7C-FF 52 50 CD 37 86 58 FF   ...~...!.RP.7.X.
1817:E570  CD 3D 83 C4 04 CD 39 5E-E8 CD 3D 83 FF 01 75 42   .=....9^..=...uB
1817:E580  FF 76 BE FF 76 BC FF 76-BA FF 76 B8 1E 8B 40 3A   .v..v..v..v...@:
1817:E590  50 FF 86 64 FF FF 86 62-FF 9A 0A 00 65 2D 83 C4   P..d...b....e-..
1817:E5A0  10 FF 76 EE FF 76 EC FF-76 EA FF 76 E8 1E 8B 4E   ..v..v..v..v...N
1817:E5B0  3A 50 FF 86 64 FF FF 86-62 FF 9A 0A 00 65 2D 83   :P..d...b....e-.
1817:E5C0  C4 10 9A 70 06 A2 1A 3D-01 00 75 0C 9A CE 05 A2   ...p...=..u.....
1817:E5D0  1A 88 86 61 FF E9 AB 10-B8 0B 00 50 9A 21 00 6B   ...a.......P.!.k
```

```
1817:E5E0  1C 59 C7 06 97 00 00 00-C7 06 95 00 64 00 E8 00   .Y..........d...
1817:E5F0  A1 95 00 05 06 97 00 75-F7 E8 03 00 50 9A 55 0C   ........u....P.U.
1817:E600  A3 1A 59 8B 1E 03 01 D1-E3 D1 E3 C7 87 41 6E 02   ..Y..........An.
1817:E610  00 C7 87 3F 6E 48 65 E8-00 8B 1E 03 01 D1 E3 D1   ...?nHe.........
1817:E620  E3 8B 97 41 6E 8B 87 3F-6E 3B 16 56 0D 7F EA 75   ...An..?n;.V...u
1817:E630  06 3B 06 54 0D 77 E2 16-E3 86 7C FF 50 9A EE 0C   .:.T.w....!.P...
1817:E640  A3 1A 59 59 8B F0 8B C6-05 C0 74 07 56 9A 07 00   ..YY......t.V...
1817:E650  72 1D 59 8B 16 3E 55 A1-3C 55 29 86 7C FF 19 96   r.Y..>U.<U).!...
1817:E660  7E FF 8B 96 7E FF 8B 86-7C FF 52 50 CD 37 86 58   ~...~...!.RP.7.X
1817:E670  FF CD 3D 83 C4 04 CD 39-5E F0 CD 3D 83 FF 01 75   ..=....9^..=...u
1817:E680  42 FF 76 36 FF 76 C4 FF-76 C2 FF 76 C0 1E 8B 5B   B.v..v..v..v...[
1817:E690  3A 50 FF 86 64 FF FF 86-62 FF 9A 0A 00 65 2D 83   :P..d...b....e-.
1817:E6A0  C4 10 FF 76 F6 FF 76 F4-FF 76 F2 FF 76 F0 1E 8B   ...v..v..v..v...
1817:E6B0  69 3A 50 FF 86 64 FF FF-86 62 FF 9A 0A 00 65 2D   i:P..d...b....e-
1817:E6C0  83 C4 10 9A 70 06 A3 1A-3D 01 00 75 0C 9A CE 05   ....p...=..u....
1817:E6D0  A3 1A 8B 86 61 FF E9 AA-0F 88 0C 00 50 9A 21 00   ....a.......P.!.
1817:E6E0  6B 1C 59 C7 06 97 00 00-00 C7 06 95 00 64 00 E8   k.Y..........d..
1817:E6F0  00 A1 95 00 05 06 97 00-75 F7 E8 04 00 50 9A 55   ........u....P.U
1817:E700  0C A3 1A 59 8B 1E 03 01-D1 E3 D1 E3 C7 87 41 6E   ...Y..........An
1817:E710  02 00 C7 87 3F 6E 48 65-E8 00 8B 1E 03 01 D1 E3   ....?nHe........
1817:E720  D1 E3 8B 97 41 6E 8B 87-3F 6E 3B 16 56 0D 7F EA   ....An..?n:.V...
1817:E730  75 06 3B 06 54 0D 77 E2-16 8D 86 7C FF 50 9A EE   u.:.T.w....!.P..
1817:E740  0C A3 1A 59 59 8B F0 8B-C6 0B C0 74 07 56 9A 07   ...YY......t.V..
1817:E750  00 72 1D 59 8B 16 3E 55-A1 3C 55 29 86 7C FF 19   .r.Y..>U.<U).!..
1817:E760  96 7E FF 8B 96 7E FF 8B-86 7C FF 52 50 CD 37 86   .~...~...!.RP.7.
1817:E770  58 FF CD 3D 83 C4 04 CD-39 5E F8 CD 3D 83 FF 01   X..=....9^..=...
1817:E780  75 6C FF 76 CE FF 76 CC-FF 76 CA FF 76 C8 1E 8B   ul.v..v..v..v...
1817:E790  76 3A 50 FF 86 64 FF FF-86 62 FF 9A 0A 00 65 2D   v:P..d...b....e-
1817:E7A0  83 C4 10 FF 76 FE FF 76-FC FF 76 FA FF 76 F8 1E   ....v..v..v..v..
1817:E7B0  8B 84 3A 50 FF 86 64 FF-FF 86 62 FF 9A 0A 00 65   ..:P..d...b....e
1817:E7C0  2D 83 C4 10 8B 86 64 FF-8B 96 62 FF 8B 6E 3F 8C   -.....d...b..n?.
1817:E7D0  D9 3B D1 75 19 3B C3 75-15 1E 8B 91 3A 50 FF 86   .:.u.:.u....:P..
1817:E7E0  64 FF FF 86 62 FF 9A 0A-00 65 2D 83 C4 08 83 FF   d...b....e-.....
1817:E7F0  01 75 15 1E 8B 93 3A 50-FF 86 64 FF FF 86 62 FF   .u....:P..d...b.
1817:E800  9A D9 00 D7 19 83 C4 08-C7 06 03 01 00 00 E9 3D   ...............=
1817:E810  02 33 C0 50 9A 9A 0C A3-1A 59 C7 06 97 00 00 00   .3.P.....Y......
1817:E820  C7 06 95 00 64 00 E8 00-A1 95 00 05 06 97 00 75   ....d..........u
1817:E830  F7 33 C0 50 9A 55 0C A3-1A 59 C7 06 41 6E 00 00   .3.P.U...Y..An..
1817:E840  C7 06 3F 6E 6C 01 33 C0-50 9A FD 05 A3 1A 59 C7   ..?nl.3.P.....Y.
1817:E850  86 76 FF 00 00 C7 86 74-FF 36 01 E8 00 33 D2 8B   .v.....t.6...3..
1817:E860  6C 01 52 50 FF 36 41 6E-FF 36 3F 6E 9A 23 09 17   l.RP.6An.6?n.#..
1817:E870  18 3B 96 76 FF 75 86 3B-86 74 FF 75 E0 16 8D 86   .;.v.u.;.t.u....
1817:E880  68 FF 50 9A EE 0C A3 1A-59 59 8B F0 8B C6 0B C0   h.P.....YY......
1817:E890  74 07 56 9A 07 00 72 1D-59 9A E4 05 A3 1A 8B 16   t.V...r.Y.......
1817:E8A0  3E 55 A1 3C 55 29 86 68-FF 19 96 6A FF 8B 96 6A   >U.<U).h...j...j
1817:E8B0  FF 8B 86 68 FF 52 50 CD-37 86 58 FF CD 3D 83 C4   ...h.RP.7.X..=..
1817:E8C0  04 CD 39 5E 80 CD 3D CD-39 46 90 CD 38 76 98 CD   ..9^..=.9F..8v..
1817:E8D0  38 4E 80 CD 39 5E 90 CD-3D CD 39 46 A0 CD 38 76   8N..9^..=.9F..8v
1817:E8E0  D0 CD 38 4E 80 CD 39 5E-90 CD 3D 8B 1E 03 01 D1   ..8N..9^..=.....
1817:E8F0  E3 D1 E3 D1 E3 CD 39 87-5C 43 9A C7 05 17 18 89   ......9.\C......
1817:E900  96 6E FF 89 86 6C FF 8B-1E 03 01 D1 E3 D1 E3 D1   .n...l..........
1817:E910  E3 CD 39 87 9C 45 9A C7-05 17 18 89 96 72 FF 89   ..9..E.......r..
1817:E920  86 70 FF 8B 96 6E FF 8B-96 6C FF 3B 96 72 FF 7F   .p...n...l.;.r..
1817:E930  1E 75 06 3B 86 70 FF 77-16 8B 96 72 FF 8B 86 70   .u.;.p.w...r...p
1817:E940  FF 05 01 00 83 D2 00 89-96 6E FF 89 86 6C FF 83   .........n...l..
1817:E950  FF 01 75 74 8B 96 6E FF-8B 86 6C FF 52 50 CD 37   ..ut..n...l.RP.7
1817:E960  86 58 FF CD 3D 83 C4 04-83 EC 08 CD 39 9E 54 FF   .X..=.......9.T.
1817:E970  CD 3D 8B 96 72 FF 8B 86-70 FF 52 50 CD 37 86 50   .=..r...p.RP.7.P
1817:E980  FF CD 3D 83 C4 04 83 EC-08 CD 39 9E 4C FF CD 3D   ..=.......9.L..=
1817:E990  FF 76 86 FF 76 84 FF 76-82 FF 76 80 9A 69 1A DE   .v..v..v..v..i..
1817:E9A0  25 83 C4 18 83 EC 08 CD-39 9E 54 FF CD 3D A1 03   %.......9.T..=..
1817:E9B0  01 40 50 1E 8B 9C 3A 50-FF 86 64 FF FF 86 62 FF   .@P...:P..d...b.
1817:E9C0  9A 0A 00 65 2D 83 C4 12-8B 46 06 0B 46 08 74 64   ....e-....F..F.td
1817:E9D0  8B 96 6E FF 8B 86 6C FF-52 50 CD 37 86 58 FF CD   ..n...l.RP.7.X..
1817:E9E0  3D 83 C4 04 83 EC 08 CD-39 9E 54 FF CD 3D 8B 96   =.......9.T..=..
1817:E9F0  72 FF 8B 86 70 FF 52 50-CD 37 86 50 FF CD 3D 83   r...p.RP.7.P..=.
1817:EA00  C4 04 83 EC 08 CD 39 9E-4C FF CD 3D FF 76 86 FF   ......9.L..=.v..
1817:EA10  76 84 FF 76 82 FF 76 80-9A 69 1A DE 25 83 C4 18   v..v..v..i..%...
1817:EA20  A1 03 01 D1 E0 D1 E0 D1-E0 C4 5E 06 03 D8 8D 3C   ..........^....<
1817:EA30  8D 1F CD 3D 9A 70 06 A3-1A 3D 01 00 75 0C 9A CE   ...=.p...=..u...
1817:EA40  05 A3 1A 8B 86 61 FF E9-39 0C FF 06 03 01 83 3E   .....a..9......>
1817:EA50  03 01 0C 7D 03 E9 89 FD-83 FF 01 75 15 1E 8B AA   ...}.......u....
1817:EA60  3A 50 FF 86 64 FF FF 86-62 FF 9A D9 00 D7 19 83   :P..d...b.......
```

```
1817:EA70  C4 08 C7 06 03 01 00 00-E9 42 02 E8 02 00 50 9A   .........B....P.
1817:EA80  9A 0C A2 1A 59 C7 06 97-00 00 00 C7 06 95 00 64   ....Y..........d
1817:EA90  00 E8 00 A1 95 00 0B 06-97 00 75 F7 E8 02 00 50   ..........u....P
1817:EAA0  9A 55 0C A2 1A 59 C7 06-41 6E 00 00 C7 06 3F 6E   .U...Y..An....?n
1817:EAB0  6C 01 E8 02 00 50 9A FD-0B A2 1A 59 C7 86 76 FF   l....P.....Y..v.
1817:EAC0  00 00 C7 86 74 FF 36 01-EB 00 33 D2 E8 6C 01 52   ....t.6...3..l.R
1817:EAD0  50 FF 36 41 6E FF 36 3F-6E 9A 23 09 17 18 3B 96   P.6An.6?n.#...;.
1817:EAE0  76 FF 75 E6 3B 86 74 FF-75 E0 16 8D 96 68 FF 50   v.u.;.t.u....h.P
1817:EAF0  9A EE 0C A2 1A 59 59 8B-F0 3B C6 0B C0 74 07 56   .....YY......t.V
1817:EB00  9A 07 00 72 1D 59 9A E4-0B A2 1A 8B 16 3E 55 A1   ...r.Y.......>U.
1817:EB10  3C 55 29 96 68 FF 19 96-6A FF 8B 96 6A FF 8B 86   <U).h...j...j...
1817:EB20  68 FF 52 50 CD 37 86 58-FF CD 3D 83 C4 04 CD 39   h.RP.7.X..=....9
1817:EB30  5E 80 CD 3D CD 39 46 90-CD 38 76 98 CD 38 4E 80   ^..=.9F..8v..8N.
1817:EB40  CD 39 5E 80 CD 3D CD 39-46 A8 CD 38 76 E0 CD 38   .9^..=.9F..8v..8
1817:EB50  4E 80 CD 39 5E 80 CD 3D-8B 1E 03 01 D1 E3 D1 E3   N..9^..=........
1817:EB60  D1 E3 CD 39 87 1C 44 9A-C7 05 17 18 89 96 6E FF   ...9..D.......n.
1817:EB70  89 86 6C FF 8B 1E 03 01-D1 E3 D1 E3 D1 E3 CD 39   ..l............9
1817:EB80  87 5C 46 9A C7 05 17 18-89 96 72 FF 89 86 70 FF   .\F.......r...p.
1817:EB90  8B 96 6E FF 8B 86 6C FF-3B 96 72 FF 7F 1E 75 06   ..n...l.;.r...u.
1817:EBA0  3B 86 70 FF 77 16 8B 96-72 FF 8B 86 70 FF 05 01   ;.p.w...r...p...
1817:EBB0  00 83 D2 00 89 96 6E FF-89 86 6C FF 83 FF 01 75   ......n...l....u
1817:EBC0  74 8B 96 6E FF 8B 86 6C-FF 52 50 CD 37 86 58 FF   t..n...l.RP.7.X.
1817:EBD0  CD 3D 83 C4 04 83 EC 08-CD 39 9E 54 FF CD 3D 8B   .=.......9.T..=.
1817:EBE0  96 72 FF 8B 86 70 FF 52-50 CD 37 86 50 FF CD 3D   .r...p.RP.7.P..=
1817:EBF0  83 C4 04 83 EC 08 CD 39-9E 4C FF CD 3D FF 76 86   .......9.L..=.v.
1817:EC00  FF 76 84 FF 76 82 FF 76-80 9A 69 1A DE 25 83 C4   .v..v..v..i..%..
1817:EC10  18 83 EC 08 CD 39 9E 54-FF CD 3D A1 03 01 40 50   .....9.T..=...@P
1817:EC20  1E B8 8D 3A 50 FF B6 64-FF FF B6 62 FF 9A 0A 00   ...:P..d...b....
1817:EC30  65 2D 83 C4 12 8B 46 06-0B 46 08 74 66 8B 96 6E   e-.....F..F.tf..n
1817:EC40  FF 8B 86 6C FF 52 50 CD-37 86 58 FF CD 3D 83 C4   ...l.RP.7.X..=..
1817:EC50  04 83 EC 08 CD 39 9E 54-FF CD 3D 8B 96 72 FF 8B   .....9.T..=..r..
1817:EC60  86 70 FF 52 50 CD 37 86-50 FF CD 3D 83 C4 04 83   .p.RP.7.P..=....
1817:EC70  EC 08 CD 39 9E 4C FF CD-3D FF 76 86 FF 76 84 FF   ...9.L..=.v..v..
1817:EC80  76 82 FF 76 80 9A 69 1A-DE 25 83 C4 18 A1 03 01   v..v..i..%......
1817:EC90  D1 E0 D1 E0 D1 E0 C4 5E-06 03 D8 CD 3C DD 9F C0   .......^....<...
1817:ECA0  00 CD 3D 9A 70 06 A2 1A-3D 01 00 75 0C 9A CE 05   ..=.p...=..u....
1817:ECB0  A2 1A 89 26 61 FF E9 CA-09 FF 06 03 01 83 3E 03   ....a.........>.
1817:ECC0  01 0C 7D 03 E9 B4 FD E3-FF 01 75 13 1E B8 C1 3A   ..}.......u....:
1817:ECD0  50 FF B6 64 FF FF B6 62-FF 9A D9 00 D7 19 83 C4   P..d...b........
1817:ECE0  08 C7 06 03 01 00 00 E9-41 02 E8 01 00 50 9A 9A   ........A....P..
1817:ECF0  0C A2 1A 59 C7 06 97 00-00 00 C7 06 95 00 64 00   ...Y..........d.
1817:ED00  E8 00 A1 95 00 03 06 97-00 75 F7 E8 01 00 50 9A   .........u....P.
1817:ED10  55 0C A2 1A 59 C7 06 41-6E 00 00 C7 06 3F 6E 6C   U...Y..An....?nl
1817:ED20  01 E8 01 00 50 9A FD 0B-A2 1A 59 C7 86 76 FF 00   ....P.....Y..v..
1817:ED30  00 C7 86 74 FF 36 01 EB-00 33 D2 E8 6C 01 52 50   ...t.6...3..l.RP
1817:ED40  FF 36 41 6E FF 36 3F 6E-9A 23 09 17 18 3B 96 76   .6An.6?n.#...;.v
1817:ED50  FF 75 E6 3B 86 74 FF 75-E0 16 8D 96 68 FF 50 9A   .u.;.t.u....h.P.
1817:ED60  EE 0C A2 1A 59 59 8B F0-3B C6 0B C0 74 07 56 9A   ....YY......t.V.
1817:ED70  07 00 72 1D 59 9A E4 0B-A2 1A 8B 16 3E 55 A1 3C   ..r.Y.......>U.<
1817:ED80  55 29 96 68 FF 19 96 6A-FF 8B 96 6A FF 8B 86 68   U).h...j...j...h
1817:ED90  FF 52 50 CD 37 86 58 FF-CD 3D 83 C4 04 CD 39 5E   .RP.7.X..=....9^
1817:EDA0  80 CD 3D CD 39 46 90 CD-38 76 98 CD 38 4E 80 CD   ..=.9F..8v..8N..
1817:EDB0  39 5E 80 CD 3D CD 39 46-A8 CD 38 76 D8 CD 38 4E   9^..=.9F..8v..8N
1817:EDC0  80 CD 39 5E 80 CD 3D 8B-1E 03 01 D1 E3 D1 E3 D1   ..9^..=.........
1817:EDD0  E3 CD 39 87 5C 43 9A C7-05 17 18 89 96 6E FF 89   ..9..C.......n..
1817:EDE0  86 6C FF 8B 1E 03 01 D1-E3 D1 E3 D1 E3 CD 39 87   .l............9.
1817:EDF0  5C 45 9A C7 05 17 18 89-96 72 FF 89 86 70 FF 8B   .E.......r...p..
1817:EE00  96 6E FF 8B 86 6C FF 3B-96 72 FF 7F 1E 75 06 3B   .n...l.;.r...u.;
1817:EE10  86 70 FF 77 16 8B 96 72-FF 8B 86 70 FF 05 01 00   .p.w...r...p....
1817:EE20  83 D2 00 89 96 6E FF 89-86 6C FF 83 FF 01 75 74   .....n...l....ut
1817:EE30  8B 96 6E FF 8B 86 6C FF-52 50 CD 37 86 58 FF CD   ..n...l.RP.7.X..
1817:EE40  3D 83 C4 04 83 EC 08 CD-39 9E 54 FF CD 3D 8B 96   =.......9.T..=..
1817:EE50  72 FF 8B 86 70 FF 52 50-CD 37 86 50 FF CD 3D 83   r...p.RP.7.P..=.
1817:EE60  C4 04 83 EC 08 CD 39 9E-4C FF CD 3D FF 76 86 FF   ......9.L..=.v..
1817:EE70  76 84 FF 76 82 FF 76 80-9A 69 1A DE 25 83 C4 18   v..v..v..i..%...
1817:EE80  83 EC 08 CD 39 9E 54 FF-CD 3D A1 03 01 40 50 1E   ....9.T..=...@P.
1817:EE90  B8 CA 3A 50 FF B6 64 FF-FF B6 62 FF 9A 0A 00 65   ..:P..d...b....e
1817:EEA0  2D 83 C4 12 8B 46 06 0B-46 08 74 65 8B 96 6E FF   -.....F..F.te..n.
1817:EEB0  8B 86 6C FF 52 50 CD 37-86 58 FF CD 3D 83 C4 04   ..l.RP.7.X..=...
1817:EEC0  83 EC 08 CD 39 9E 54 FF-CD 3D 8B 96 72 FF 8B 86   ....9.T..=..r...
1817:EED0  70 FF 52 50 CD 37 86 50-FF CD 3D 83 C4 04 83 EC   p.RP.7.P..=.....
1817:EEE0  08 CD 39 9E 4C FF CD 3D-FF 76 86 FF 76 84 FF 76   ..9.L..=.v..v..v
```

```
1817:EEF0  83 FF 76 80 9A 69 1A DE-25 83 C4 18 A1 03 01 D1   ..v..i..%.......
1817:EF00  E0 D1 E3 D1 E0 C4 5E 06-03 D8 CD 3C DD 5F 60 CD   ......^....<._`.
1817:EF10  3D 9A 70 06 A2 1A 3D 01-00 75 0C 9A CE 05 A2 1A   =.p...=..u......
1817:EF20  38 86 61 FF E9 5C 07 FF-06 03 01 83 3E 03 01 0C   ..a..\......>...
1817:EF30  7D 03 E9 85 FD 83 FF 01-75 15 1E 88 D8 3A 50 FF   }.......u....:P.
1817:EF40  86 64 FF FF 56 62 FF 9A-D9 00 D7 19 83 C4 08 C7   .d...b..........
1817:EF50  06 03 01 00 00 E9 42 02-86 05 00 50 9A 9A 0C A2   ......B....P....
1817:EF60  1A 59 C7 06 97 00 00 00-C7 06 95 00 64 00 E8 00   .Y..........d...
1817:EF70  A1 95 00 08 06 97 00 75-F7 89 05 00 50 9A 55 0C   .......u....P.U.
1817:EF80  A2 1A 59 C7 06 41 6E 00-00 C7 06 3F 6E 6C 01 B8   ..Y..An....?nl..
1817:EF90  05 00 50 9A FD 0B A2 1A-59 C7 86 76 FF 00 00 C7   ..P.....Y..v....
1817:EFA0  86 74 FF 36 01 EB 00 33-D2 8B 6C 01 52 50 FF 36   .t.6...3..l.RP.6
1817:EFB0  41 6E FF 36 3F 6E 9A 23-09 17 18 3B 96 76 FF 75   An.6?n.#...;.v.u
1817:EFC0  E6 3B 86 74 FF 75 E0 16-8D 86 68 FF 50 9A EE 0C   .;.t.u....h.P...
1817:EFD0  A2 1A 59 59 8B F0 8B C6-0B C0 74 07 56 9A 07 00   ..YY......t.V...
1817:EFE0  72 1D 59 9A E4 0B A2 1A-8B 16 3E 55 A1 3C 55 29   r.Y.......>U.<U)
1817:EFF0  86 68 FF 19 96 6A FF 8B-96 6A FF 8B 86 68 FF 52   .h...j...j...h.R
1817:F000  50 CD 37 86 58 FF CD 3D-83 C4 04 CD 39 5E 80 CD   P.7.X..=....9^..
1817:F010  3D CD 39 46 90 CD 38 76-98 CD 38 4E 80 CD 39 5E   =.9F..8v..8N..9^
1817:F020  80 CD 3D CD 39 46 88 CD-38 76 88 CD 38 4E 80 CD   ..=.9F..8v..8N..
1817:F030  39 5E 80 CD 3D 8B 1E 03-01 D1 E3 D1 E3 D1 E3 CD   9^..=...........
1817:F040  39 87 3C 45 9A C7 05 17-18 89 96 6E FF 89 86 6C   9.<E.......n...l
1817:F050  FF 8B 1E 03 01 D1 E3 D1-E3 D1 E3 CD 39 87 7C 47   ............9.|G
1817:F060  9A C7 05 17 18 89 96 72-FF 89 86 70 FF 8B 96 6E   .......r...p...n
1817:F070  FF 8B 86 6C FF 3B 96 72-FF 7F 1E 75 06 3B 86 70   ...l.;.r...u.;.p
1817:F080  FF 77 16 89 96 72 FF 89-86 70 FF 05 01 00 83 D2   .w...r...p......
1817:F090  00 89 96 6E FF 89 86 6C-FF 83 FF 01 75 74 8B 96   ...n...l....ut..
1817:F0A0  6E FF 8B 86 6C FF 52 50-CD 37 86 58 FF CD 3D 83   n...l.RP.7.X..=.
1817:F0B0  C4 04 83 EC 08 CD 39 9E-54 FF CD 3D 8B 96 72 FF   ......9.T..=..r.
1817:F0C0  8B 86 70 FF 52 50 CD 37-86 50 FF CD 3D 83 C4 04   ..p.RP.7.P..=...
1817:F0D0  83 EC 08 CD 39 9E 4C FF-CD 3D FF 76 86 FF 76 84   `....9.L..=.v..v.
1817:F0E0  FF 76 82 FF 76 80 9A 69-1A DE 25 83 C4 18 83 EC   .v..v..i..%.....
1817:F0F0  08 CD 39 9E 54 FF CD 3D-A1 03 01 40 50 1E 89 E1   ..9.T..=...@P...
1817:F100  3A 50 FF 86 64 FF FF 56-62 FF 9A 0A 00 65 3D 83   :P..d...b....e-.
1817:F110  C4 12 8B 46 06 0B 46 08-74 65 8B 96 6E FF 8B 86   ...F..F.tf..n...
1817:F120  6C FF 52 50 CD 37 86 58-FF CD 3D 83 C4 04 83 EC   l.RP.7.X..=.....
1817:F130  08 CD 39 9E 54 FF CD 3D-8B 96 72 FF 8B 86 70 FF   ..9.T..=..r...p.
1817:F140  52 50 CD 37 86 50 FF CD-3D 83 C4 04 83 EC 08 CD   RP.7.P..=.......
1817:F150  39 9E 4C FF CD 3D FF 76-86 FF 76 84 FF 76 82 FF   9.L..=.v..v..v..
1817:F160  76 80 9A 69 1A DE 25 83-C4 18 A1 03 01 D1 E0 D1   v..i..%.........
1817:F170  E0 D1 E0 C4 5E 06 03 D8-CD 3C 3D 9F 50 01 CD 3D   ....^....<.....=
1817:F180  9A 70 06 A2 1A 3D 01 00-75 0C 9A CE 05 A2 1A 8B   .p...=..u.......
1817:F190  86 61 FF E9 ED 04 FF 06-03 01 83 3E 03 01 0C 7D   .a.........>...}
1817:F1A0  03 E9 84 FD 83 FF 01 75-15 1E 8B EF 3A 50 FF 86   .......u....:P..
1817:F1B0  64 FF FF 56 62 FF 9A D9-00 D7 19 83 C4 08 C7 06   d...b...........
1817:F1C0  03 01 00 00 E9 42 02 89-03 00 50 9A 9A 0C A2 1A   .....B....P.....
1817:F1D0  59 C7 06 97 00 00 00 C7-06 95 00 64 00 E8 00 A1   Y...........d....
1817:F1E0  95 00 0B 06 97 00 75 F7-B8 03 00 50 9A 55 0C A2   .......u....P.U..
1817:F1F0  1A 59 C7 06 41 6E 00 00-C7 06 3F 6E 6C 01 B8 03   .Y..An....?nl...
1817:F200  00 50 9A FD 0B A2 1A 59-C7 86 76 FF 00 00 C7 86   .P.....Y..v.....
1817:F210  74 FF 36 01 EB 00 33 D2-8B 6C 01 52 50 FF 36 41   t.6...3..l.RP.6A
1817:F220  6E FF 36 3F 6E 9A 23 09-17 18 3B 96 76 FF 75 E6   n.6?n.#...;.v.u.
1817:F230  3B 86 74 FF 75 E0 16 8D-86 68 FF 50 9A EE 0C A2   ;.t.u....h.P....
1817:F240  1A 59 59 8B F0 8B C6 0B-C0 74 07 56 9A 07 00 72   .YY......t.V...r
1817:F250  1D 59 9A E4 0B A2 1A 8B-16 3E 55 A1 3C 55 29 86   .Y.......>U.<U).
1817:F260  68 FF 19 96 6A FF 8B 96-6A FF 8B 86 68 FF 52 50   h...j...j...h.RP
1817:F270  CD 37 86 58 FF CD 3D 83-C4 04 CD 39 5E 80 CD 3D   .7.X..=....9^..=
1817:F280  CD 39 46 88 CD 38 76 98-CD 38 4E 80 CD 39 5E 80   .9F..8v..8N..9^.
1817:F290  CD 3D CD 39 46 C0 CD 38-76 F0 CD 38 4E 80 CD 39   .=.9F..8v..8N..9
1817:F2A0  5E 80 CD 3D 8B 1E 03 01-D1 E3 D1 E3 D1 E3 CD 39   ^..=...........9
1817:F2B0  87 7C 44 9A C7 05 17 18-89 96 6E FF 89 86 6C FF   .|D.......n...l.
1817:F2C0  8B 1E 03 01 D1 E3 D1 E3-D1 E3 CD 39 87 BC 46 9A   ...........9..F.
1817:F2D0  C7 05 17 18 89 96 72 FF-89 86 70 FF 8B 96 6E FF   ......r...p...n.
1817:F2E0  8B 86 6C FF 3B 96 72 FF-7F 1E 75 06 3B 86 70 FF   ..l.;.r...u.;.p.
1817:F2F0  77 16 89 96 72 FF 89 86-70 FF 05 01 00 83 D2 00   w...r...p.......
1817:F300  89 96 6E FF 89 86 6C FF-83 FF 01 75 74 8B 96 6E   ..n...l....ut..n
1817:F310  FF 8B 86 6C FF 52 50 CD-37 86 58 FF CD 3D 83 C4   ...l.RP.7.X..=..
1817:F320  04 83 EC 08 CD 39 9E 54-FF CD 3D 8B 96 72 FF 8B   .....9.T..=..r..
1817:F330  86 70 FF 52 50 CD 37 86-50 FF CD 3D 83 C4 04 83   .p.RP.7.P..=....
1817:F340  EC 08 CD 39 9E 4C FF CD-3D FF 76 86 FF 76 84 FF   ...9.L..=.v..v..
1817:F350  76 82 FF 76 80 9A 69 1A-DE 25 83 C4 18 83 EC 08   v..v..i..%......
1817:F360  CD 39 9E 54 FF CD 3D A1-03 01 40 50 1E 89 F8 3A   .9.T..=...@P...:
```

```
1817:F370  50 FF B6 64 FF FF B6 62-FF 9A 0A 00 65 2D 83 C4   P..d...b....e-..
1817:F380  12 8B 46 06 0B 46 08 74-66 8B 96 6E FF 8B 96 6C   ..F..F.tf..n...l
1817:F390  FF 52 50 CD 37 86 58 FF-CD 3D 83 C4 04 83 EC 08   .RP.7.X..=......
1817:F3A0  CD 39 9E 54 FF CD 3D 8B-96 72 FF 8B 86 70 FF 52   .9.T..=..r...p.R
1817:F3B0  50 CD 37 86 50 FF CD 3D-83 C4 04 83 EC 08 CD 39   P.7.P..=.......9
1817:F3C0  9E 4C FF CD 3D FF 76 86-FF 76 84 FF 76 82 FF 76   .L..=.v..v..v..v
1817:F3D0  80 9A 69 1A DE 25 83 C4-18 A1 03 01 D1 E0 D1 E0   ..i..%..........
1817:F3E0  D1 E0 C4 5E 06 03 D8 CD-3C DD 9F 20 01 CD 3D 9A   ...^....<.. ..=.
1817:F3F0  70 06 A2 1A 3D 01 00 75-0C 9A CE 05 A2 1A 8B 86   p...=..u........
1817:F400  61 FF E9 7E 02 FF 06 03-01 83 3E 03 01 0C 7D 03   a..~......>...}.
1817:F410  E9 84 FD 83 FF 01 75 15-1E 8B 06 3B 50 FF B6 64   ......u....;P..d
1817:F420  FF FF B6 62 FF 9A D9 00-D7 19 83 C4 08 C7 06 03   ...b............
1817:F430  01 00 00 E9 41 02 B8 04-00 50 9A 9A 0C A2 1A 59   ....A....P.....Y
1817:F440  C7 06 97 C0 00 00 C7 06-95 00 64 00 EB 00 A1 95   ..........d.....
1817:F450  00 0B 06 97 00 75 F7 E8-04 00 50 9A 55 0C A2 1A   .....u....P.U...
1817:F460  59 C7 06 41 6E 00 00 C7-06 3F 6E 6C 01 38 04 00   Y..An....?nl....
1817:F470  50 9A FD 0B A2 1A 59 C7-86 76 FF 00 00 C7 86 74   P.....Y..v.....t
1817:F480  FF 36 01 EB 00 33 D2 B8-6C 01 52 50 FF 36 41 6E   .6...3..l.RP.6An
1817:F490  FF 36 3F 6E 9A 23 09 17-18 3B 96 76 FF 75 E6 3B   .6?n.#...;.v.u.;
1817:F4A0  86 74 FF 75 E0 16 8D 86-68 FF 50 9A EE 0C A2 1A   .t.u....h.P.....
1817:F4B0  59 59 8B F0 8B C6 0B C0-74 07 56 9A 07 00 72 1D   YY......t.V...r.
1817:F4C0  59 9A E4 09 A2 1A 8B 16-3E 55 A1 3C 55 29 86 68   Y.......>U.<U).h
1817:F4D0  FF 19 96 6A FF 3B 96 6A-FF 8B 86 68 FF 52 50 CD   ...j...j...h.RP.
1817:F4E0  37 86 58 FF CD 3D 83 C4-04 CD 39 5E 80 CD 3D CD   7.X..=....9^..=.
1817:F4F0  39 46 88 CD 38 76 98 CD-38 4E 80 CD 39 5E 80 CD   9F..8v..8N..9^..
1817:F500  3D CD 39 46 C8 CD 38 76-F8 CD 38 4E 80 CD 39 5E   =.9F..8v..8N..9^
1817:F510  80 CD 3D 8B 1E 03 01 D1-E3 D1 E3 D1 E3 CD 39 87   ..=...........9.
1817:F520  DC 44 9A C7 05 17 18 89-96 6E FF 89 86 6C FF 8B   .D.......n...l..
1817:F530  1E 03 01 D1 E3 D1 E3 D1-E3 CD 39 87 1C 47 9A C7   ..........9..G..
1817:F540  05 17 18 89 96 72 FF 89-86 70 FF 8B 96 6E FF 8B   .....r...p...n..
1817:F550  86 6C FF 3B 96 72 FF 7F-1E 75 06 3B 86 70 FF 77   .l.;.r...u.;.p.w
1817:F560  16 8B 96 72 FF 8B 86 70-FF 05 01 00 83 D2 00 89   ...r...p........
1817:F570  96 6E FF 89 86 6C FF 83-FF 01 75 74 8B 96 6E FF   .n...l....ut..n.
1817:F580  8B 86 6C FF 52 50 CD 37-86 58 FF CD 3D 83 C4 04   ..l.RP.7.X..=...
1817:F590  83 EC 08 CD 39 9E 54 FF-CD 3D 8B 96 72 FF 8B 86   ....9.T..=..r...
1817:F5A0  70 FF 52 50 CD 37 86 50-FF CD 3D 83 C4 04 83 EC   p.RP.7.P..=.....
1817:F5B0  08 CD 39 9E 4C FF CD 3D-FF 76 86 FF 76 84 FF 76   ..9.L..=.v..v..v
1817:F5C0  82 FF 76 80 9A 69 1A DE-25 83 C4 18 83 EC 08 CD   ..v..i..%.......
1817:F5D0  39 9E 54 FF CD 3D A1 03-01 40 50 1E 8B 0F 3B 50   9.T..=...@P...;P
1817:F5E0  FF B6 64 FF FF B6 62 FF-9A 0A 00 65 2D 83 C4 12   ..d...b....e-...
1817:F5F0  8B 46 06 0B 46 08 74 66-8B 96 6E FF 8B 86 6C FF   .F..F.tf..n...l.
1817:F600  52 50 CD 37 86 58 FF CD-3D 83 C4 04 83 EC 08 CD   RP.7.X..=.......
1817:F610  39 9E 54 FF CD 3D 8B 96-72 FF 8B 86 70 FF 52 50   9.T..=..r...p.RP
1817:F620  CD 37 86 50 FF CD 3D 83-C4 04 83 EC 08 CD 39 9E   .7.P..=.......9.
1817:F630  4C FF CD 3D FF 76 86 FF-76 84 FF 76 82 FF 76 80   L..=.v..v..v..v.
1817:F640  9A 69 1A DE 25 83 C4 18-A1 03 01 D1 E0 D1 E0 D1   .i..%...........
1817:F650  E0 C4 5E 06 03 D8 CD 3C-DD 9F 20 01 CD 3D 9A 70   ..^.....<.....=.p
1817:F660  06 A2 1A 3D 01 00 75 0B-9A CE 05 A2 1A 8B 86 61   ...=..u.........a
1817:F670  FF EB 10 FF 06 03 01 83-3E 03 01 0C 7D 03 E9 85   ........>...}...
1817:F680  FD EB 03 EE 2B 00 33 F6-9A 6C 03 A2 1A 83 FF 01   ....+.3..l......
1817:F690  75 3D 8B 96 64 FF 8B 86-62 FF 8B 32 3F 8C D9 3B   u=..d...b..2?..;
1817:F6A0  D1 75 17 3B C3 75 13 1E-B8 1D 3B 50 9A 37 00 D7   .u.;.u....;P....
1817:F6B0  19 59 59 9A 40 08 A2 1A-EB 15 1E B8 22 3B 50 FF   .YY.@......";P.
1817:F6C0  B6 64 FF FF B6 62 FF 9A-0A 00 65 2D 83 C4 08 8B   .d...b....e-....
1817:F6D0  C6 EB 00 5F 5E 8B E5 5D-CB 55 8B EC 83 EC 10 39   ..._^..].U.....9
1817:F6E0  26 98 0D 77 05 9A CF 09-17 18 CD 39 46 06 CD 38   &..w.......9F..8
1817:F6F0  5E 0E CD 39 3E DC 6F CD-3D 8A 26 DD 6F 9E 77 08   ^..9>.o.=.&.o.w.
1817:F700  CD 39 46 0E CD 38 06 24-3E EB 20 CD 39 46 06 CD   .9F..8.$:. .9F..
1817:F710  38 5E 16 CD 39 3E DC 6F-CD 3D 8A 26 DD 6F 9E 76   8^..9>.o.=.&.o.v
1817:F720  06 CD 39 46 16 EB 04 CD-39 46 06 CD 39 5E F0 CD   ..9F....9F..9^..
1817:F730  3D CD 39 46 16 CD 38 66-0E CD 39 46 F0 CD 38 66   =.9F..8f..9F..8f
1817:F740  0E CD 3A F9 CD 39 5E F8-CD 3D FF 76 FE FF 76 FC   ..:...9^..=.v..v.
1817:F750  FF 76 FA FF 76 F8 9A 0E-00 72 2A 83 C4 08 CD 39   .v..v....r*....9
1817:F760  5E F8 CD 3D CD 39 46 F8-EB 00 8B E5 5D CB 39 26   ^..=.9F.....].9&
1817:F770  98 0D 77 05 9A CF 09 17-18 1E B8 2C 3B 50 9A 0A   ..w.........;P..
1817:F780  00 D7 19 59 59 EB 26 33-C0 50 9A 36 03 A2 1A 59   ...YY.&3.P.6...Y
1817:F790  8A 0E 03 EC A6 02 75 04-33 C0 EB 03 B8 01 00 50   ......u.3......P
1817:F7A0  1E B8 34 3B 50 9A 05 00-A8 2C 83 C4 06 9A 70 06   ..4;P....,.....p.
1817:F7B0  A2 1A 3D 01 00 75 D0 9A-6C 03 A2 1A CB 56 39 26   ..=..u..l....V9&
1817:F7C0  98 0D 77 05 9A CF 09 17-18 9A 93 08 17 22 1E B8   ..w.........."..
1817:F7D0  37 3B 50 9A 0A 00 D7 19-59 59 5B 01 00 50 9A 36   7;P.....YY...P.6
1817:F7E0  03 A2 1A 59 FF 36 3B 0C-FF 36 39 0C FF 36 37 0C   ...Y.6;..69..67.
```

```
1817:F7F0  FF 36 35 0C 1E 58 40 3B-50 9A C5 00 A8 2C 93 C4   .65...@;P.......
1817:F800  0C 33 C0 50 9A 36 03 A2-1A 59 1E B8 35 0C 50 B8   .3.P.6...Y..5.P.
1817:F810  02 00 50 9A 72 09 A2 1A-83 C4 06 8B F0 8B C6 0B   ..P.r...........
1817:F820  C0 75 02 EB A4 83 FE 02-7C 07 9A 93 08 17 22 EB   .u......|.....".
1817:F830  07 9A 64 08 17 22 EB 91-5E C5 55 8B EC 83 EC 04   ..d.."..^.U.....
1817:F840  56 57 39 26 98 0D 77 05-9A CF 09 17 19 9A 73 0C   VW9%..w.......s.
1817:F850  17 22 1E 59 44 3B 50 9A-0A 00 D7 19 59 59 33 F6   ."..D;P.....YY3.
1817:F860  EB 66 93 C6 04 30 98 46-FE 83 FE 0A 75 04 C6 46   .f...0.F....u..F
1817:F870  FE 08 83 FE 0B 75 04 C6-46 FE 00 9A CE 05 A2 1A   .....u..F.......
1817:F880  88 46 FF 33 FF EB 0C 8A-8E 34 00 3A 46 FF 75 02   .F.3.....4.:F.u.
1817:F890  EB 06 47 83 FF 0C 7C EF-C7 46 FC 00 00 EB 11 8B   ..G...|..F......
1817:F8A0  5E FC 8A 87 34 0D 3A 46-FE 75 02 EB 09 FF 46 FC   ^...4.:F.u....F.
1817:F8B0  83 7E FC 0C 7C E9 8A 46-FE 88 85 34 0D 8A 46 FF   .~..|..F...4..F.
1817:F8C0  8B 5E FC 88 87 34 0D 46-83 FE 0C 7D 03 E9 92 FF   .^...4.F...}....
1817:F8D0  9A 46 0C 17 22 5F 5E 8B-E5 5D CB 55 8B EC 83 EC   .F.."_^..].U....
1817:F8E0  02 56 57 39 26 98 0D 77-05 9A CF 09 17 19 33 F6   .VW9%..w......3.
1817:F8F0  E5 47 3B C6 5B 06 00 99-F7 FB 3A 06 00 F7 E2 8B   .G..............
1817:F900  F3 83 C7 04 3B C6 BB 06-00 99 F7 FB 8B C2 5A 05   ................
1817:F910  00 F7 E2 40 89 46 FE 57-FF 76 FE 9A F7 02 A2 1A   ...@.F.W.v......
1817:F920  59 59 56 94 7E 08 A2 1A-59 52 50 1E E8 4E 3B 50   YYV.~...YRP..N;P
1817:F930  9A 05 00 A8 2C 83 C4 08-46 3B 36 09 01 7C B3 5F   ........F;6..|._
1817:F940  5E 8B E5 5D CB 56 39 26-98 0D 77 05 9A CF 09 17   ^..].V9%..w.....
1817:F950  18 EB 4B 9A CE 05 A2 1A-3D 08 00 75 41 1E E8 54   ..K.....=..uA..T
1817:F960  3B 50 9A 0A 00 D7 19 59-59 EB 01 00 50 B8 01 00   ;P.....YY...P...
1817:F970  50 9A 0C 00 CF 20 59 59-8B F0 8B C6 0B C0 74 07   P.... YY......t.
1817:F980  56 9A 07 00 72 1D 59 9A-6C 03 A2 1A C7 06 05 01   V...r.Y.l.......
1817:F990  00 00 C7 06 07 01 00 00-E8 2B 00 E9 92 00 9A 70   .........+.....p
1817:F9A0  06 A2 1A 0B C0 75 AC 80-3E 94 00 00 75 03 E9 7B   .....u..>...u..{
1817:F9B0  00 C7 06 05 01 00 00 C7-06 07 01 00 00 1E B8 5D   ...............]
1817:F9C0  3B 50 9A 0A 00 D7 19 59-59 EB 09 33 C0 50 9A 39   ;P.....YY..3.P.9
1817:F9D0  04 A2 1A 59 8A 12 03 EC-A8 08 74 EF 9A 8A 02 6B   ...Y......t....k
1817:F9E0  1C 8B F0 8B C6 0B C0 74-07 56 9A 07 00 72 1D 59   .......t.V...r.Y
1817:F9F0  9A 98 00 A4 20 85 F0 8B-C6 0B C0 74 07 56 9A 07   .... ......t.V..
1817:FA00  00 72 1D 59 B8 01 00 50-B8 01 00 50 9A 0C 00 CF   .r.Y...P...P....
1817:FA10  20 59 59 8B F0 8B C6 0B-C0 74 07 56 9A 07 00 72    YY......t.V...r
1817:FA20  1D 59 C6 06 94 00 00 B8-2B 00 EB 04 33 C0 E5 00   .Y......+...3...
1817:FA30  5E CB 00 00 00 00 00 00-00 00 00 00 00 00 00 00   ^...............
1817:FA40  87 E2 00 0C 18 24 30 3C-48 54 60 6C 78 84 90 9C   .....$0<HT`lx...
1817:FA50  A8 B4 00 00 00 00 00 00-00 80 01 00 00 00 B8 12   ................
1817:FA60  00 E8 64 FE 8A 18 CD 4B-78 9A D4 02 00 00 00 89   ..d....Kx.......
1817:FA70  23 00 EB 53 B6 F0 17 5C-29 3B AA B8 01 00 00 00   #..S...\);......
1817:FA80  B8 34 00 EB 42 35 C2 68-21 A2 DA 0F C9 02 00 00   .4..B5.h!.......
1817:FA90  00 E8 45 00 EB 31 99 F7-CF FB 84 9A 20 9A FF FF   ..E..1...... ...
1817:FAA0  00 00 B8 56 00 EB 20 AC-79 CF D1 F7 17 72 B1 00   ...V.. .y....r..
1817:FAB0  00 00 00 B8 67 00 EB CF-00 00 00 00 00 00 00 00   ....g...........
1817:FAC0  01 C0 00 00 B8 78 00 1E-8C C9 8E D9 96 FC B9 06   .....x..........
1817:FAD0  00 F3 A5 83 EF 0C 96 1F-C3 57 50 2B C0 FC AB AB   .........WP+....
1817:FAE0  AB AB 58 AB 8A C1 B4 00-AB 5F C3 B5 01 EB 14 1D   ..X......_......
1817:FAF0  57 2B C0 FC AB AB AB B4-C0 AB B8 01 40 AB EB 01   W+..........@...
1817:FB00  00 AB 5F C3 56 57 8B 3E-D8 00 83 EF 0C 89 3E D8   .._.VW.>......>.
1817:FB10  00 06 1E 07 FC B9 06 00-F3 A5 07 5F 5E C3 56 57   ..........._^.VW
1817:FB20  8B 3E D8 00 83 EF 0C 89-3E D8 00 1E 06 1E 07 8E   .>......>.......
1817:FB30  1F FC B9 06 00 F3 A5 07-1F 5F 5E C3 56 57 8B 36   ........._^.VW.6
1817:FB40  D8 00 FC B9 06 00 F3 A5-89 36 D8 00 5F 5E C3 56   .........6.._^.V
1817:FB50  57 8B 36 D8 00 8D 7C F4-89 3E D8 00 FC 06 1E 07   W.6...|..>......
1817:FB60  B9 06 00 F3 A5 07 5F 5E-C3 56 57 8B 36 D8 00 8B   ......_^.VW.6...
1817:FB70  FE FC 06 1E 07 B9 06 00-AD 87 45 0C AB E2 F9 C7   ..........E.....
1817:FB80  5F 5E C3 26 8B 04 2B C9-8A 00 00 0B C0 7C 07 7F   _^.&..+......|..
1817:FB90  09 EB 01 C3 EB 10 F7 D8-B2 01 2B DB 91 43 D1 E9   ..........+..C..
1817:FBA0  D1 D8 E3 02 EB F7 89 55-0A 89 5D 08 89 45 06 89   .......U..]..E..
1817:FBB0  4D 04 89 4D 02 89 0D C3-8B 4C 08 83 F9 0F 7F 0A   M..M.....L......
1817:FBC0  81 F9 01 C0 7F 0E 2B C0-EB 6E B5 01 E8 35 1C B8   ......+..n...5..
1817:FBD0  C0 80 EB 64 8B 5C 06 2B-C0 8B D0 83 F9 00 7D 04   ...d.\.+......}.
1817:FBE0  D1 E5 D1 DA 0B 14 0B 54-02 0B 54 04 83 F9 00 7E   .......T..T....~
1817:FBF0  06 D1 E3 D1 D0 E2 FA 0A-DE 0A DA B1 0C 22 0E D7   .............."..
1817:FC00  00 80 F9 0C 74 2A 30 F9-00 74 16 02 4C 0A 80 F9   ....t*...t..L...
1817:FC10  04 74 1D 80 F9 09 74 16-F7 D8 15 00 00 78 AB E8   .t....t......x..
1817:FC20  0F 82 01 22 D0 0A DA 81-C3 FF 7F 15 00 00 78 94   ..."..........x.
1817:FC30  80 7C 0A 01 75 02 F7 D8-26 89 05 C3 56 57 FC E9   .|..u...&...VW..
1817:FC40  06 00 F3 A5 5F 5E 87 F7-8D 74 08 81 3C 01 C0 7E   ...._^...t..<..~
1817:FC50  0F 81 3C 01 40 7D 0A FF-0C E8 27 FF C7 04 01 00   ..<.@}....'.....
1817:FC60  C3 C7 04 01 C0 C7 45 08-0D 00 C6 45 07 80 E3 F0   ......E....E....
```

```
1817:FC70  55 8B EC 56 57 8B 4C 08-8B F9 0F 7F 08 0B C9 7F   U..VW.L.........
1817:FC80  0E 2B C0 EB 1C B5 01 E3-7A 1B 8B FF 7F EB 0A 8B   .+......z.......
1817:FC90  44 06 F6 D9 80 C1 10 D3-E8 80 7C 0A 01 75 02 F7   D.........|..u..
1817:FCA0  D8 8B 4D 08 81 F9 01 C0-7E 15 81 F9 01 40 7D 0F   ..M.....~....@}.
1817:FCB0  03 C1 3D 01 C0 7E 16 3D-01 40 7D 07 89 45 08 5F   ..=..~.=.@}..E._
1817:FCC0  5E 5D C3 B5 08 EB 3C 13-B8 01 40 EB 08 B5 10 EB   ^]....<...@.....
1817:FCD0  32 1B E8 01 C0 EB 01 FE-EB E5 26 8B 1C 26 8B 54   2.........&..&.T
1817:FCE0  02 2B C0 B9 00 00 0B D2-79 09 F7 D2 F7 DB 83 DA   .+......y.......
1817:FCF0  FF B1 01 89 4D 0A B9 10-00 0B D2 75 04 87 DA B1   ....M......u....
1817:FD00  00 0B D2 74 0C 41 D1 EA-D1 DB D1 D8 EB F3 59 01   ...t.A..........
1817:FD10  C0 E3 FE 89 4D 0B 89 5D-C6 59 45 04 89 55 02 89   ....M..]..E..U..
1817:FD20  15 C3 E8 4C 08 83 F9 1F-7F 33 0B C9 7D 3C 81 F9   ...L.....3..}<..
1817:FD30  01 C0 7E 13 83 0C 22 15-D7 00 02 5C 0A 80 FB 05   ..~...."....\....
1817:FD40  74 05 80 FB 06 74 06 2B-D2 8B C2 EB 1A 2B D2 B8   t....t.+......+..
1817:FD50  01 00 80 FB 05 75 10 F7-D8 F7 D2 EB 0A B5 01 EB   .....u..........
1817:FD60  A2 1A BA 00 80 2B C0 E9-87 00 83 5C 02 0A 1C 0A   .....+.....\....
1817:FD70  5C 01 55 44 04 8B 54 06-80 E9 10 77 10 0A C3 0A   \..D..T....w....
1817:FD80  C7 93 92 2B D2 80 C1 10-7E F3 80 E1 0F E3 1D 56   ...+....~......V
1817:FD90  BE FF FF 33 C2 D3 C0 D3-E6 8B CE 23 C8 33 C1 23   ...........#.3.#
1817:FDA0  F2 33 D6 0B C6 0A DF 0A-D9 8A FD 5E 81 0C 22 0E   .3.........^..".
1817:FDB0  D7 00 80 F9 0C 74 2D 80-F9 00 74 13 02 4C 0A 80   .....t-...t..L..
1817:FDC0  F9 04 74 20 80 F9 09 74-15 F7 DB 72 0C EB 15 81   ..t ...t...r....
1817:FDD0  01 22 C8 0A D9 81 C3 FF-7F 15 00 00 83 D2 00 79   .".............y
1817:FDE0  03 E9 79 FF 80 7C 0A 01-75 07 F7 D2 F7 D8 83 DA   ..y..|..u.......
1817:FDF0  FF 26 89 05 26 89 55 02-C3 55 56 26 8B 04 26 8B   .&..&.U..UV&..&.
1817:FE00  5C 02 26 8B 4C 04 26 8B-54 06 8D 00 00 0B D2 7D   \.&.L.&.T......}
1817:FE10  13 7F 26 0B C9 75 22 0B-DB 75 1E 0B C0 75 1A 8E   ..&..u"..u...u..
1817:FE20  01 C0 E8 33 F7 D2 F7 D1-F7 D3 F7 D8 F5 83 D3 00   ...3............
1817:FE30  83 D1 00 83 D2 00 8D 01-10 8E 40 00 05 D2 75 0A   ...........3...u.
1817:FE40  87 D1 87 CB 93 E3 EE 10-EB F2 78 03 4E 03 C0 13   ..........x.N...
1817:FE50  DB 13 C9 13 D2 79 F5 E9-6D 0A 89 75 08 89 55 06   .....y..m..u..U.
1817:FE60  89 4D 04 89 5D 02 89 05-5E 5D C3 55 57 8B 4C 09   .M..]...^].UW.L.
1817:FE70  83 F9 3F 7F 39 0B C9 7D-46 81 F9 01 C0 7E 13 83   ..?.9..}F....~..
1817:FE80  0C 22 15 D7 00 02 5C 0A-80 FB 05 74 09 80 FB 0B   ."....\....t....
1817:FE90  74 04 2B ED EB 20 2B ED-EB D5 EB 01 00 80 FB 05   t.+.. +.........
1817:FEA0  8B DD 75 18 F7 DB F7 D3-F7 D2 F7 D5 EB 0E 55 01   ..u.............
1817:FEB0  E5 51 19 ED 00 80 2B D2-EB DA 85 33 E9 91 00 8B   .Q....+.........
1817:FEC0  6C 06 8B 54 04 8B 5C 02-8B 3C 2B C0 80 E9 3C 77   l..T..\..<+...Ow
1817:FED0  16 0A C4 B4 00 0B C7 EB-F3 E5 DA 85 D5 2B ED 80   ..............+..
1817:FEE0  C1 10 7E ED 80 E1 0F F6-D9 74 11 80 C1 10 0A C4   ..~......t......
1817:FEF0  D1 ED D1 DA D1 DB D1 DF-E0 3C E2 F2 81 0C 22 0E   ..............".
1817:FF00  D7 00 80 F9 0C 74 30 80-F9 00 74 15 02 4C 0A 80   .....t0...t..L..
1817:FF10  F9 04 74 23 80 F9 09 74-1E F7 DB 72 0D EB 18 EB   ..t#...t...r....
1817:FF20  8D 81 01 23 CF 0A C1 05-FF 7F 89 00 00 13 F9 13   ...#............
1817:FF30  D9 13 D1 13 E9 78 E8 97-90 7C 0A 01 75 12 F7 D5   .....x...|..u...
1817:FF40  F7 D2 F7 D3 F7 D8 F5 83-D3 00 83 D2 00 83 D5 00   ................
1817:FF50  5F A8 93 A8 92 A8 95 A8-E3 EF 08 ED C3 55 56 57   _...........].UVW
1817:FF60  87 EE 8B 4E 08 83 F9 40-7D 33 0B C9 7D 4E 81 F9   ...N...@}...}E..
1817:FF70  01 C0 7E 13 81 0C 22 0E-D7 00 02 4E 0A 80 F9 05   ..~...."....N....
1817:FF80  74 0C 80 F9 08 74 07 2B-D8 EE 01 C0 EB 11 BE 01   t....t.+........
1817:FF90  00 8B 00 80 EB 09 74 15-E5 20 EB 67 18 EB 11 2B   ......t.. .g...+
1817:FFA0  C0 89 46 00 89 46 02 89-46 04 89 5E 06 89 76 08   ..F..F..F..^..v.
1817:FFB0  E9 80 00 EE 33 00 23 F1-23 CE D1 EE D1 EE D1 EE   ....3.#.3.......
1817:FFC0  F7 DE 83 C6 07 83 FE 07-75 06 B4 00 8A 02 EB 02   ........u.......
1817:FFD0  8B 02 2B 2B 8B FE 4F 7D-16 0A 1E 8B 7B E2 F7 3A   ..+...O!.......:...
1817:FFE0  FF 00 80 E1 07 D3 EA 8B-FA 47 23 D3 75 04 0A 2B   ..........G#.u...
1817:FFF0  74 71 85 20 E8 0D 18 33-C2 51 0C 22 0E D7 00 80   tq. ...3..."....
-d 2817:0 1 cfe9
2817:0000  F9 0C 74 13 80 F9 00 74-1E 02 4E 0A 80 F9 04 74   ..t....t..N....t
2817:0010  08 80 F9 09 74 06 0A DA-75 23 EE 47 88 02 80 7E   ....t...u#.G...~
2817:0020  07 00 75 3F E9 60 FF 0A-D3 75 0C 85 C7 7E 08 03   ..u?.`...u...u..
2817:0030  D2 3B D7 76 E7 EB 06 03-D2 3B D7 72 DF 83 EE 07   .;.v.....;.r....
2817:0040  7C 09 03 C7 8B 42 07 F6-DC EB 0F 03 C7 89 42 07   |....B.........B.
2817:0050  46 46 7F 06 80 52 07 00-72 F7 73 07 F9 D1 5E 06   FF...R..r.s...^.
2817:0060  FF 46 08 5F 5E 5D C3 8B-44 04 8B 54 06 8B 5C 08   .F._^]..D..T..\.
2817:0070  8A 4C 0A 83 3C 00 75 0F-83 7C 02 00 75 09 A8 7F   .L..<.u..|..u...
2817:0080  75 05 F6 C4 01 74 0F 03-C0 80 D4 00 83 D2 00 73   u....t.........s
2817:0090  05 D1 DA D1 D8 43 83 C3-7E 7E 32 81 FB FF 00 7D   .....C..~~2....}
2817:00A0  17 D1 E2 D0 E9 D0 D8 D1-DA 8A C4 8A E2 8A D6 8A   ................
2817:00B0  F3 A8 92 48 83 EF 04 C3-81 7C 03 01 40 7D 09 85   ..........|..@}..
2817:00C0  02 E8 40 17 2B D2 2B C0-EB FF 00 EB D4 81 7C 08   ..@.+.+........|.
2817:00D0  01 C0 7E 05 B5 10 E9 2B-17 2B DB 8B D3 8B C3 EB   ..~.....+.+.......
2817:00E0  C0 56 57 06 FC 26 8B 04-26 8B 54 02 2B F6 D1 E2   .VW..&..&.T.+...
2817:00F0  D1 D6 2B DB 02 DE 74 30-80 FE FF 74 20 83 E5 7E   ..+...t0...t ..~
```

```
2817:0100  F9 D0 DA 8A F2 8A D4 8A-E8 B1 00 1E 07 23 C0 AB   .............+..
2817:0110  AB 91 AB 92 AB 93 AB 96-AB 07 5F 5E C3 8B D8 0A   .........._^....
2817:0120  DA F7 D9 8B 01 40 E8 D8-8B CA 0B C8 74 0E 83 EB   .....@......t...
2817:0130  7E D0 EA 03 D0 13 D2 78-DA 4B EB F7 2B 01 C0 EB   ~.......x.K.....
2817:0140  D2 57 8B 44 01 3B 7C 03-8B 4C 05 2A 54 07 83 5C   .W.D..;..L..T..\
2817:0150  08 E6 03 22 F0 0A 34 75-04 A3 08 74 11 05 04 00   ..."..4u...t....
2817:0160  83 D7 00 83 D1 00 80 D2-00 73 03 D0 DA 43 81 C3   ..........s...C..
2817:0170  FE 03 7E 42 81 FB FF 07-7D 4A 24 FB D0 E2 D1 E8   ..~B....}J$.....
2817:0180  D0 DA 0A C7 8A F3 88 DF-D1 EF D1 D8 D1 DA D1 D9   ................
2817:0190  D1 D8 D1 EF D1 D8 D1 DA-D1 D9 D1 D8 0A 44 0A D1   ..............D..
2817:01A0  EF D1 D8 D1 DA D1 D9 D1-D8 5F FC A5 93 AB 91 AB   ........._......
2817:01B0  92 AB 93 EF 08 C3 8A 00-00 81 7C 08 01 C0 7E 13   ..........|...~.
2817:01C0  E8 10 E8 0C 81 7D 08 01-40 7D 15 8A E0 FF E5 C5   .....|..@}......
2817:01D0  E8 D1 16 0A 54 0A D1 DA-D8 D9 88 D9 8B D1 E8 C9   .1..T...+.......
2817:01E0  B8 FF 07 E8 95 57 8C D8-8C 03 8E D8 8E C0 8B 54   .....W.........T
2817:01F0  06 2B C0 D1 E2 D1 D0 FD-E0 7D 0A 48 81 05 D3 EA   .+.......}......
2817:0200  74 60 81 FA FF 07 74 44-E3 10 81 EA FE 03 92 AB   t`....tD........
2817:0210  8B 54 05 90 E6 0F 0A FD-8B 4C 03 89 5C 01 8A 24   .T.......L..\..$
2817:0220  80 00 D1 E0 D1 D3 D1 D1-D1 D2 D1 E0 D1 D3 D1 D1   ................
2817:0230  D1 D2 D1 E0 D1 D3 D1 D1-D1 D2 92 AB 91 AB 93 AB   ................
2817:0240  92 AB 8C D8 8C C3 8E D8-8E C0 5F C3 8A 5C 06 83   .........._..\..
2817:0250  E3 0F 0B 5C 04 0B 5C 02-0B 1C BA 01 40 80 CB 10   ...\..\.....@...
2817:0260  E3 AC 8A 5C 06 83 E3 0F-0B 5C 04 0B 5C 02 0B 1C   ...\.....\..\...
2817:0270  75 05 EA 01 C0 E8 97 88-54 05 80 E6 0F E2 4C 03   u.......T.....L.
2817:0280  8B 5C 01 8A 24 80 04 FE-D8 D0 E4 D1 D3 D1 D1 13   .\..$...........
2817:0290  D2 79 F4 50 54 00 2D FE-03 AB 58 50 00 EB 98 56   .y.P..-...X....V
2817:02A0  57 FC A5 A5 A5 A5 AD 3E-3C 3D 01 40 7D 0F 05 FE   W........=.@}...
2817:02B0  3F 7C 3F D1 E0 D1 E9 D1-D3 AE 5F 5E C3 88 FF 7F   ?|........_^....
2817:02C0  E8 F1 2B 20 8E 8D 86 57-1E 06 8C 28 8C C3 9E D0   ..-...VW........
2817:02D0  8E D2 FD 8D 74 08 8D 7D-0A AD 93 22 D0 D1 E3 D1   ....t..}...+....
2817:02E0  D0 AB D1 EB 74 10 81 E3-FE 3F 93 AE A5 A5 A5 A5   ....t....?......
2817:02F0  FC 07 1F 5F 5E C3 8B 01-C0 A5 25 C0 A5 AB AB AB   ..._^....:+.....
2817:0300  E8 5E 52 56 83 54 06 81-E2 FF 7F 08 14 0B E4 02   ..RV.T........T.
2817:0310  0B 54 04 75 21 83 FB FF-74 19 81 7F 08 01 40 7C   .T.u!...t.....@|
2817:0320  11 8B 57 06 81 E2 FF 7F-0B 17 0B 57 02 0B 57 04   ..W........W..W.
2817:0330  75 45 F8 5E 5A C3 83 FE-FF 74 3E 81 7F 08 01 40   uE.^Z....t>....@
2817:0340  7C 37 8B 57 06 81 E2 FF-7F 0B 17 0B 57 02 0B 57   |7.W........W..W
2817:0350  04 74 26 8B 54 06 3B 57-06 77 1E 72 1A 8B 54 04   .t&.T.;W.w.r..T.
2817:0360  3B 57 04 77 14 72 10 8B-54 02 3B 57 02 77 0A 72   ;W.w.r..T.;W.w.r
2817:0370  06 8B 14 3B 17 77 02 EB-F3 57 E5 01 EB 85 14 59   ...;.w...W......
2817:0380  06 00 FC F3 A5 F9 5F E8-4A 21 01 E8 02 81 00 55   ......_........U
2817:0390  8B EC 83 66 FA 56 57 82-76 08 8B 7E 06 8A C1 32   ...f.VW.v..~...2
2817:03A0  45 0A 32 44 0A 88 46 F4-E8 44 08 8B 5D 08 3D 01   E.2D..F..D..].=.
2817:03B0  40 7D 39 81 FB 01 40 7D-59 3B C3 7D 05 32 4D 0A   @}9...@}Y;.}.2M.
2817:03C0  93 87 F7 8B 03 8A 4C 0A-E8 4E FB 8B 4C 02 89 4E   ......L..N..L..N
2817:03D0  FC 81 FB 01 C0 7E 07 2B-C3 3D 40 00 7E 5E 8B 04   .....~.+.=@.~^..
2817:03E0  89 5C 02 8B 4C 04 8B 54-06 E9 30 01 53 57 9B DF   .\..L..T..0.SW..
2817:03F0  8B 7E 04 E8 0C FF 5F 5B-72 3F 81 F5 01 40 7C 26   .~...._[r?...@|&
2817:0400  84 44 0A 32 46 FA 3A 45-0A 8A 46 FA 0A C0 75 23   .D.2F.:E..F...u#
2817:0410  E8 14 8B FF FF 8A 45 0A-32 C1 88 F7 5B 7E 04 E8   ......E.2...~..
2817:0420  E0 FE 72 15 E8 03 8A 44-0A 88 46 F8 C7 46 FC 01   ..r....D..F..F..
2817:0430  40 E8 AE 85 7E 04 E8 82-F6 E9 F3 00 89 46 FF E8   @...~.........F..
2817:0440  05 E8 ED 02 E8 4D 04 83-EE 06 C6 46 FE 00 80 6E   ..]..M..U..F...n
2817:0450  FF 08 7C 19 E8 46 FE 8A-C4 8A E3 8A CF 8A F7 8A   ..|..F..........
2817:0460  D2 8A EA 8A D6 86 00 80-6E FF 08 73 E3 80 66 FF   ........n..]..f.
2817:0470  07 74 10 D1 EA D1 D9 D1-D8 D1 D8 D0 EE FE FE 4E   .t............^..N
2817:0480  FF 75 F0 25 FF 80 7E FA-00 75 15 07 04 13 5C 02   .u.+..~..u....\.
2817:0490  13 4C 04 13 54 06 73 64-D1 DA D1 D9 D1 D8 D1 D8   .L..T.sd........
2817:04A0  D0 5E FE FF 46 FC E8 54-E0 76 FE 01 2B 04 1B 5C   .^..F..T.v..+..\
2817:04B0  02 1B 4C 04 1B 54 06 73-1B 80 76 FE 01 F7 D2 F7   ..L..T.s..v.....
2817:04C0  D1 F7 D3 F7 D0 F6 5E FE-FE 13 C7 13 DF 13 CF 13   ......^.........
2817:04D0  D7 8E 40 00 0A F6 78 24-4E 74 16 D0 66 FE D1 D0   ..@...x$Nt..f...
2817:04E0  D1 D3 D1 D1 13 D2 79 F0-83 EE 40 01 76 FC E8 0C   ......y...@.v...
2817:04F0  90 C7 46 FC 01 C0 C6 46-F8 00 EB 20 D0 66 FE 13   ..F....F... .f..
2817:0500  C7 13 DF 13 CF 13 D7 73-05 D1 DA FF 46 FC 81 7E   .......s....F..~
2817:0510  FC 01 40 7D 22 81 7E FC-01 C0 7E 24 FC 85 7E 04   ..@}".~...~$..~.
2817:0520  AB 93 AB 91 AB 92 AB 8B-46 FC AB 8A 46 FB AA 5F   ........F...F.._
2817:0530  5E 8B 5E 5D C2 06 00 85-08 C7 46 FC 01 40 EB 07   ^..]......F..@..
2817:0540  85 10 C7 46 FC 01 C0 E8-8A 12 C6 46 FB 00 2B C0   ...F.......F..+.
2817:0550  8B D8 8B C8 8B D0 EB C4-55 8B EC 8D 66 FE 56 57   ........U...f.VW
2817:0560  FC 8B 76 08 8B 7E 06 8A-4C 0A 32 4D 0A 88 4E FE   ..v..~..L.2M..N.
2817:0570  8B 5D 08 8B 44 08 3D 01-40 7D 28 81 FB 01 40 7D   .]..D.=.@}(...@}
2817:0580  37 3B C3 7C 01 93 3D 01-C0 7E 13 03 C3 48 3D 01   7;.|..=..~...H=.
```

```
2817:0590  40 7D 43 40 3D 01 C0 7F-50 3E 10 EB 66 12 8B 01   @}C@=...P>..f...
2817:05A0  C0 E8 3E 57 8B DF E8 7E-04 E8 E6 FE EF 72 3B 81   ..>W...~..V._r8.
2817:05B0  7D 08 01 C0 7E 18 E8 23-E6 8B FF FF 83 F7 8B 7E   }...~..#V......~
2817:05C0  04 E8 3E FD 8E 72 20 81-7D 08 01 C0 7F 0D 8B 7E   ..>.^r .}......~
2817:05D0  04 E8 17 F5 EB 5B 8B 02-EB 29 12 E8 01 40 8B 7E   .....[...)...@.~
2817:05E0  04 8A 4E FE E8 F3 F4 E8-48 50 E8 17 F5 87 F7 E8   ..N.....HP......
2817:05F0  12 F5 E8 44 00 83 06 D8-00 18 5F 05 C2 78 0B 4F   ...D......_..x.O
2817:0600  D1 E6 D1 D0 D1 D3 D1 D1-D1 D2 D1 E6 1E 00 00 83   ................
2817:0610  D3 00 83 D1 00 83 D2 00-73 03 D1 DA 47 8B F7 8B   ........s...G...
2817:0620  7E 04 AB 93 AB 91 AB 92-AB 96 AB 8A 46 FE 84 C0   ~...........F...
2817:0630  A5 5F 5E 5B 8B 5D C2 06-00 55 57 8B 3E 5B 00 2B   ._^[.]...UW.>[.+
2817:0640  FF 83 CF 8B F7 F6 46 0F-80 74 06 8B 4E 00 EB 76   ......F..t..N..v
2817:0650  02 F6 46 03 80 74 0F 03-4E 0C 13 76 0E 13 FF F6   ..F..t..N..v....
2817:0660  46 0F 80 74 01 4F 2B D8-8B 46 0C F7 66 04 03 C8   F..t.O+..F..f...
2817:0670  13 F2 83 D7 00 8B 46 10-05 D0 74 17 F7 66 00 03   ......F...t..f..
2817:0680  C8 13 F2 83 D7 00 8B 46-10 F7 66 02 03 F0 13 FA   .......F..f.....
2817:0690  83 D3 00 8B 46 0C F7 66-06 03 F0 13 FA 83 D3 00   ....F..f........
2817:06A0  8B 46 0E F7 66 04 03 F0-13 FA 83 D3 00 8B 46 12   .F..f.........F.
2817:06B0  0B C0 74 0A F7 66 00 03-F0 13 FA 83 D3 00 2B C9   ..t..f........+.
2817:06C0  56 8B F1 8B 46 0E F7 66-06 03 F8 13 DA 83 D1 00   V...F..f........
2817:06D0  8B 46 10 05 C0 74 17 F7-66 04 03 F8 13 DA 83 D1   .F...t..f.......
2817:06E0  C0 8B 46 10 F7 66 06 03-D8 13 CA 83 D6 00 8B 46   ..F..f.........F
2817:06F0  12 0B C0 74 24 F7 66 02-03 F8 13 DA 83 D1 00 83   ...t$.f.........
2817:0700  D6 00 8B 46 12 F7 66 04-03 D8 13 CA 83 D6 00 8B   ...F..f.........
2817:0710  46 12 F7 66 06 03 C8 13-F2 8B 26 F7 8E 5F 5D C3   F..f.........^_].
2817:0720  55 8B EC 83 6E FE 8B 8E-C8 FF 77 06 FF 77 04 FF   U...f.^..w..w..
2817:0730  77 02 FF 37 2B C0 50 56-57 FC 8B 7E 06 8A 47 0A   w..7+.PVW..~..G.
2817:0740  3C 45 0A 8B 46 FD 82 75-08 8B 47 08 81 FE 01 40   <E..F..u..G....@
2817:0750  7D 3E 3D 01 40 7D 4F 81-FE 01 C0 7E 1F 3D 01 C0   }>=.@}O....~.=..
2817:0760  7E 11 2B C6 3D 01 40 7D-0F 3D 01 C0 7F 47 8B 10   ~.+.=.@}.=...G..
2817:0770  E8 91 10 E9 01 C0 E8 02-E5 08 E8 02 8E 04 EB 83   ................
2817:0780  10 E9 01 40 8A 4E FD 83-7E 04 E8 4C F3 EF D5 01   ...@.N..~..L....
2817:0790  8B F7 8B 7E 04 E8 6A FE-72 F3 81 7F 08 01 40 7C   ...~..j.r.....@|
2817:07A0  D2 E8 47 F3 E8 E7 8B F3-E8 FF FF 8B 7E 04 E8 51   ..G.........~..Q
2817:07B0  F2 72 DA E8 CC 89 46 FE-2B C9 8B 56 F6 8B 75 06   .r....F.+..V..u.
2817:07C0  3B F2 77 03 2B D6 41 8B-46 F4 F7 F6 15 01 00 12   ;.w.+.A.F.......
2817:07D0  C3 8B 4E F3 89 46 FA 50-E8 05 8B 5D 02 E3 11 8B   ..N..F.P...]....
2817:07E0  55 04 29 46 F0 19 5E F2-19 56 F4 19 76 F6 E2 F2   U.)F..^..V..v...
2817:07F0  5E F7 E6 89 46 EE F2 93-F7 E6 03 D8 13 CA 8B 45   ^...F..........E
2817:0800  04 F7 E6 03 C8 83 D2 00-92 96 F7 65 06 03 C6 83   ...........e....
2817:0810  D2 00 2B 5E F0 15 4E F2-15 46 F4 15 56 F6 89 5E   ..+^..N..F..V..^
2817:0820  F0 89 4E F2 89 46 F4 8B-75 06 F7 F6 91 F7 F6 2B   ..N..F..u......+
2817:0830  D2 F9 13 C2 13 CA 2B D0-89 56 F8 19 4E FA 80 5E   ......+..V..N..^
2817:0840  FC 00 50 8B 05 89 5D 02-E3 11 8B 55 04 29 46 EE   ..P...]....U.)F.
2817:0850  19 5E F0 19 56 F2 19 76-F4 E2 F2 5E F7 E6 F2 93   .^..V..v...^....
2817:0860  F7 E6 03 D8 13 CA 8B 45-04 F7 E6 03 C8 83 D2 00   .......E........
2817:0870  92 96 F7 65 06 03 C6 83-D2 00 2B 5E EE 18 4E F0   ...e......+^..N.
2817:0880  1B 46 F2 1B 56 F4 89 5E-EE 89 4E F0 89 46 F2 8B   .F..V..^..N..F..
2817:0890  75 06 F7 F6 91 F7 F6 2B-D2 F9 13 C2 13 CA 89 46   u......+.......F
2817:08A0  F6 01 4E F8 11 56 FA 10-56 FC 96 8B 55 02 92 E3   ..N..V..V...U...
2817:08B0  5D 04 E3 08 29 46 EE 19-5E F0 19 56 F2 E2 F5 F7   ]...)F..^..V....
2817:08C0  E6 92 93 F7 E6 03 D8 13-CA 8B 45 06 F7 E6 03 C1   ...........E....
2817:08D0  83 D2 00 2B 5E EE 1B 46-F0 1B 56 F2 89 5E EE 89   ...+^..F..V..^..
2817:08E0  46 F0 8B 75 04 03 F6 8B-75 06 83 D6 00 73 04 87   F..u....u....s..
2817:08F0  DA E3 11 D1 E3 D1 D0 D1-D2 F7 F6 93 F7 F6 D1 E8   ................
2817:0900  D1 D3 D0 D3 39 FF FF 8B-F1 8A D1 F7 D3 F7 D0 F6   ................
2817:0910  DE F5 15 00 00 13 5E F6-13 4E F8 13 76 FA 12 56   ......^..N..v..V
2817:0920  FC D0 EA 73 0D D1 DE D1-D9 D1 DB D1 D8 D0 DE FF   ...s............
2817:0930  46 FE 2B FF 02 F6 13 C7-13 DF 13 CF 13 F7 80 D2   F.+.............
2817:0940  00 8B 56 FE 74 04 8E 00-80 42 81 FA 01 40 7C 03   ..V.t....B...@|.
2817:0950  E9 2E FE 8B 7E 04 FC AB-F3 AB 91 AB 96 AB 92 AB   ....~...........
2817:0960  8A 46 FD 98 A8 5F 5E 8B-E5 5D C2 06 00 55 8B EC   .F..._^..]...U..
2817:0970  56 57 8B 44 08 3D 01 C0-7E 29 3D 01 40 7D 28 80   VW.D.=..~)=.@}(.
2817:0980  7C 0A 00 75 2C E8 7C F1-E8 37 00 8B 3E D8 00 56   |..u.,.|..7..>..V
2817:0990  57 56 E8 8E FD 57 56 56-E8 F2 F9 FF 4C 08 83 06   WV...WVV....L...
2817:09A0  D8 00 0C 5F 5E 5D C3 8B-FF FF 8B FE E8 E3 F9 E2   ..._^]........S..
2817:09B0  F1 8B 01 E8 4E 0E 8B FE-E8 09 F1 C7 45 08 01 40   ....N.......E..@
2817:09C0  E8 E1 56 57 8B 3E D8 00-8B 5D 08 8E 55 06 83 45   ..VW.>...]..U..E
2817:09D0  04 8B 4D 02 D1 F8 73 07-43 D1 EA D1 D8 D1 D9 83   ..M...s.C.......
2817:09E0  FA FE 73 1D 53 51 83 CA-8B D8 8B F2 F9 D1 DE F7   ..s.SQ..........
2817:09F0  F6 4E 3B F0 76 12 46 03-F0 D1 DE 8B D1 83 C3 E8   .N;.v.F.........
2817:0A00  EE F9 D1 DA D1 D8 E3 17-46 3B F0 73 01 96 59 5B   ........F;.s..Y[
2817:0A10  91 F7 F6 2B 32 03 F1 D1-DE D1 D8 13 C2 13 D6 FC   ...+............
2817:0A20  2B C9 91 AB A5 91 AB 92-AB 93 AB 8B 00 00 43 5F   +.............._
2817:0A30  5E C3 00 02 40 42 01 03-41 43 55 8B EC FF 75 0A   ^...@B..ACU...u.
```

```
2817:0A40  8D 66 FA 56 57 E8 05 E8-ED 02 8B 4D 04 8B 55 06   .f.VW...]..M..U.
2817:0A50  C7 46 FC 00 00 EB 7D 0E-2B 7C 06 7D 1E EB 52 F0   .F....}.+|.}..R.
2817:0A60  47 E8 3D 4F 7C FA D1 66-FC D1 E0 D1 D3 D1 D1 13   G.=O|..f........
2817:0A70  D2 72 1B 79 EE 3B 54 06-77 14 72 E7 3B 4C 04 77   .r.y.;T.w.r.;L.w
2817:0A80  0D 72 E0 3B 5C 02 77 06-72 D9 3B 04 72 D5 FF 46   .r.;\.w.r.;.r..F
2817:0A90  FC 2B 04 1B 5C 02 1B 4C-04 1B 54 06 0B FF 7F 03   .+..\..L..T.....
2817:0AA0  0B D2 78 0D 74 44 4F D1-E0 D1 D3 D1 D1 13 D2 79   ..x.tDO........y
2817:0AB0  F5 03 7C 08 57 8B 7E F6-AB 93 AB 91 AB 92 AB 58   ..|.W.~........X
2817:0AC0  AB 8A 46 FE 98 A3 90 26-D5 00 BC 8F 07 00 8B 46   ..F....&.......F
2817:0AD0  FC 80 7E FE 01 75 02 F7-D8 23 F8 2E 8A 95 F2 0F   ..~..u...#......
2817:0AE0  08 16 D5 00 5F 5E 5B E8-ED C3 87 D1 87 C8 93 83   ...._^[.........
2817:0AF0  EF 10 03 D3 75 AA 87 D1-87 CB 83 EF 10 87 D1 83   ....u...........
2817:0B00  EF 10 03 D3 75 9A 8F 01-C0 2B D2 2B C9 2B 2B 2B   ....u.....+.+.+-
2817:0B10  C0 EB A1 93 54 06 81 E2-FF 7F 0B 14 0B 54 02 0B   ....T........T..
2817:0B20  54 04 74 34 E5 01 EB D3-0C 2B 00 45 E9 91 00 8B   T.t4.......E....
2817:0B30  55 06 81 E2 FF 7F 0B 15-0B 55 02 0B 55 04 75 E4   U........U..U.u.
2817:0B40  E8 10 55 89 EC 56 57 8B-76 06 8B 7E 04 8B 44 08   ..U..VW.v..~..D.
2817:0B50  5B 5D 0B 3D 01 40 7D E8-81 FB 01 40 7D D1 8B D0   .].=.@}....@}...
2817:0B60  3B C3 7F 02 8B D3 81 FA-01 C0 7E 3B 8A 4C 0A 3A   ;.........~;.L.:
2817:0B70  4D 0A 7C 49 7F 3D 3B C3-7C 34 7F 3C 8B 44 06 3B   M.|I.=;.|4.<.D.;
2817:0B80  45 06 75 28 8B 03 22 3E-D7 00 74 3E 8B 44 04 3B   E.u(.."...t>.D.;
2817:0B90  45 04 75 1B 8B 44 02 3B-45 02 75 10 80 FD 02 74   E.u..D.;E.u....t
2817:0BA0  4B 8B 04 3B 05 75 05 8B-00 40 EB 14 77 0A 80 F9   K..;.u...@..w...
2817:0BB0  00 75 0A 8B 00 01 EB 08-80 F9 00 75 F6 8B 00 00   .u.........u....
2817:0BC0  8B 26 D5 00 5F 5E 5D C2-04 00 8B 1C 2B 1D 8B 5C   .&.._^]....+..\
2817:0BD0  02 1B 5D 02 8B 5C 04 1B-5D 04 77 09 F7 D8 83 E3   ..]..\..].w.....
2817:0BE0  80 74 C4 E8 C9 5D E3 80-74 BD EB C3 EB 1C 2B 1D   .t.....t.....+.
2817:0BF0  77 09 F7 D8 80 E7 FC 74-4E E8 5D 80 E7 FD 74 A7   w......t......t.
2817:0C00  EB 86 EB 00 40 81 7C 03-01 C0 7E 13 81 7C 08 01   ....@.|...~..|..
2817:0C10  40 7D 11 B8 00 01 80 7C-0A 01 74 03 B9 00 00 89   @}.....|..t.....
2817:0C20  26 D5 00 C3 8B 54 06 81-E2 FF 7F 0B 14 0B 54 02   &....T........T.
2817:0C30  0B 54 04 74 DE 8B 01 E8-CA 0B E8 00 45 E5 E0 2B   .T.t........E...
2817:0C40  00 40 81 7C 08 01 C0 7E-13 81 7C 06 01 40 7D 11   .@.|...~..|..@}.
2817:0C50  B8 00 04 80 7C 0A 01 75-03 0D 00 02 58 26 D5 00   ....|..u.....&..
2817:0C60  C3 2B 00 05 E8 54 06 81-E2 FF 7F 0B 14 0B 54 02   .....T........T.
2817:0C70  0B 54 04 74 DE 5B 00 01-EB D9 55 56 57 8B 2E D8   .T.t......UVW...
2817:0C80  00 8B 46 00 8B 5E 02 8B-4E 04 8B 56 06 2B FF 8B   ..F..^..N..V.+..
2817:0C90  76 08 83 FE F0 7F 0D 8B-F8 8B C3 8B D9 8B CA 2B   v..............+
2817:0CA0  D2 83 C6 10 46 7F 0C D1-EA D1 D9 D1 DB D1 D8 D1   ....F...........
2817:0CB0  DF EB F1 D1 E7 8F 00 00-13 C7 13 DF 13 CF 13 D7   ................
2817:0CC0  89 46 00 89 5E 02 89 4E-04 89 56 06 8B DF 8B CF   .F..^..N..V.....
2817:0CD0  8B F7 F6 46 03 80 74 0A-8B 5E 00 8B 4E 02 D1 E3   ...F..t..^..N...
2817:0CE0  D1 D1 8B 46 00 F7 66 04-03 D8 13 CA 13 F7 03 D8   ...F..f.........
2817:0CF0  13 CA 13 F7 8B D9 8B CE-2B F6 8B 46 02 F7 66 04   .........+..F..f.
2817:0D00  03 D8 13 CA 13 F7 03 D8-13 CA 13 F7 8B 46 00 F7   .............F..
2817:0D10  66 06 03 D8 13 CA 13 F7-03 D8 13 CA 13 F7 D1 E3   f...............
2817:0D20  13 CF 13 F7 8B D9 8B CE-2B F6 8B 46 04 F7 E0 03   .........+..F....
2817:0D30  D8 13 CA 13 F7 8B 46 06-F7 66 02 03 D8 13 CA 13   .......F..f......
2817:0D40  F7 03 D8 13 CA 13 F7 8B-46 06 F7 66 04 03 C8 13   .........F..f....
2817:0D50  F2 13 FF 03 C8 13 F2 83-D7 00 8B 46 06 F7 E0 03   .............F...
2817:0D60  F0 13 FA 89 5E 00 89 4E-02 89 76 04 89 7E 06 C6   ....^..N..v..~..
2817:0D70  46 0A 00 C7 46 08 00 00-5F 5E 5D C3 55 8B EC 56   F...F..._^].U..V
2817:0D80  57 1E 06 1F 0C F6 66 06-2D 0C 00 96 0C 76 04 E8   W.....f.-....v..
2817:0D90  8C ED 8B FE FE 4E 06 7E-7E 57 8B 3E D8 00 8A 45   .....N.~~W.>...E
2817:0DA0  16 30 45 0A E8 92 F3 E9-05 8B 5D 02 89 4D 04 89   .0E.......]..M..
2817:0DB0  55 06 5F 83 EF 0C 55 8B-2E D8 00 2E 8B 1D 2E 82   U._...U.........
2817:0DC0  4D 02 2E 8B 55 04 2E 8B-75 06 2E 8A 45 0A 3A 46   M...U...u...E.:F
2817:0DD0  0A 74 34 2B 5E 00 1B 4E-02 1B 56 04 1B 76 06 73   .t4+^..N..V..v.s
2817:0DE0  14 F7 D6 F7 D2 F7 D1 F7-D3 F3 83 D1 00 83 D2 00   ................
2817:0DF0  83 D6 00 34 01 89 5E 00-89 4E 02 89 56 04 89 76   ...4..^..N..V..v
2817:0E00  06 88 46 0A 5D E8 8D 01-EB 00 11 4E 02 11 56 04   ..F.]...^..N..V.
2817:0E10  11 76 06 5D E9 7D FF 8B-D8 D8 00 FC AD 93 AD 91   .v.].}..........
2817:0E20  AD 92 AD 97 AD AD 89 36-D8 00 87 F7 2B FF 3C 01   .......6....+.<.
2817:0E30  75 11 F7 D6 F7 D2 F7 D1-F7 DB F5 13 CF 13 D7 13   u...............
2817:0E40  F7 EB 12 F9 D1 DE D1 DA-D1 D9 D1 DB 13 DF 13 CF   ................
2817:0E50  13 D7 13 F7 47 A1 D8 00-97 93 AB 91 AB 92 AB 96   ....G...........
2817:0E60  AB 93 A5 58 00 00 AB 07-1F 5F 5E 5D C2 04 00 08   ..........._^]....
2817:0E70  00 00 00 00 00 00 00 00-00 00 00 00 86 AA AA   ................
2817:0E80  AA AA AA AA 2A 00 00 01-00 03 24 22 22 22 22 22   ....*.....$"""""
2817:0E90  02 00 00 00 00 E3 E4 00-0D 30 00 0D 00 00 00 01   ................
2817:0EA0  00 6E 0B 4B C7 3B 3E 00-00 00 00 00 00 C6 40 16   .n.K.;........@.
2817:0EB0  99 6B 00 00 00 00 00 01-00 CC 45 F2 50 00 00 00   .k........E.....
2817:0EC0  00 00 00 00 00 D5 45 D6-00 00 00 00 00 00 00 01   ......E.........
```

```
2817:0ED0  00 03 00 00 00 00 00 00-00 00 00 00 00 00 00 E8   ................
2817:0EE0  FF FF FF FF FF FF 7F 00-00 01 00 46 9A AA AA AA   ................
2817:0EF0  AA AA 0A 00 00 00 00 7F-E6 04 5B 20 05 5B 00 00   ..........[..[..
2817:0F00  00 01 00 EF 26 9E 01 1A-A0 01 00 00 00 00 00 1D   ....&...........
2817:0F10  CE 3C 93 9F 04 00 00 00-00 01 00 0F B1 4B F7 03   .............K..
2817:0F20  00 00 00 00 00 00 00 03-28 7B 0C 00 00 00 00 00   .........{......
2817:0F30  00 01 00 E9 CE E2 E3 41-FD 3E FF 36 2F 14 B8 31   .......A...6/..1
2817:0F40  14 50 E8 37 FE FF 36 D2-00 56 56 E2 0A F6 83 06   .P.7..6..VV.....
2817:0F50  03 00 0C 23 E2 23 FD 2E-FF 36 91 14 E2 93 14 50   .....#...6.....P
2817:0F60  E8 19 FE 03 E2 9D E8 E3-10 FD E2 E2 E3 5B C9 FF   ................
2817:0F70  E8 E4 FF 33 35 C2 68 21-A2 DA 0F C9 01 00 00 00   ....5.h!........
2817:0F80  09 00 00 00 00 00 00 00-00 00 00 00 00 00 57 55   ..............WU
2817:0F90  55 55 55 55 55 01 00 00-01 00 EE 33 33 33 33 33   UUUUU......33333
2817:0FA0  03 00 00 00 00 00 7D 1E-49 92 24 09 00 00 00 00   ......}.I.$.....
2817:0FB0  01 00 8C FE C6 71 1C 00-00 00 00 00 00 00 5C FF   .....c........\.
2817:0FC0  16 5D 00 00 00 00 00 00-01 00 D6 E8 3A 01 00 00   .]..........:...
2817:0FD0  00 00 00 00 00 00 0A 0C-04 00 00 00 00 00 00 00   ................
2817:0FE0  01 00 00 00 00 00 00 00-00 E7 FD FF 00 00 BD A4   ................
2817:0FF0  D6 7B EE 64 5C B3 FF FF-00 00 95 85 47 FC 74 30   .{.d\.......G.t0
2817:1000  11 A1 00 00 00 00 00 00-00 00 00 00 00 80 01 00   ................
2817:1010  00 00 9C FA 64 50 82 1D-07 E6 FE FF 00 00 9C FA   ....d...........
2817:1020  64 B0 B2 1D 07 E6 FF FF-00 00 F5 85 4B 04 46 56   d...........K.FV
2817:1030  85 AC 00 00 00 00 E6 6E-D9 1F 5D 09 FA E9 FE FF   .......n........
2817:1040  00 00 8D 7B 35 8D 5B 84-DD F6 FF FF 00 00 7F D5   ...{5.[.........
2817:1050  35 02 D3 80 73 CC 00 00-00 00 E5 8B ED 8D 66 FE   5...s.....U...f.
2817:1060  56 57 56 57 56 E8 59 F6-C7 46 FE 00 00 8F A2 15   VWVWV....F......
2817:1070  83 7E FE 03 73 21 87 F7-E8 A3 EA 87 FE 56 FF 36   .~..s!.......V.6
2817:1080  D2 00 E8 5D FA 83 06 D8-00 0C 3D 00 00 75 08 FF   ..........=..u..
2817:1090  46 FE 83 C7 0C E8 D9 83-7E FE 00 75 05 E8 6D 00   F.......~..u..m.
2817:10A0  E8 63 88 5E FE 4B 2E 8A-9F 02 00 89 5E FE 81 C3   .e.^.K......^...
2817:10B0  F6 15 E8 F8 87 F7 E8 65-EA 87 FE 56 E8 3E D8 00   ........e...V.>..
2817:10C0  57 8D 45 F4 A3 D3 00 50-E8 8E F2 56 57 56 E8 87   W.E....P...VWV..
2817:10D0  F4 E8 8A E9 57 56 E6 E8-8C F2 FF 36 D8 00 56 56   ....WV.....6..VV
2817:10E0  E8 3D F6 83 06 D8 00 1E-E8 22 00 8B 7E FE 81 C7   .=.......".~....
2817:10F0  D2 15 87 F7 E8 27 EA 87-FE FF 36 D8 00 56 56 E8   .....'....6..VV.
2817:1100  8B F2 83 06 D8 00 0C 5F-5E 83 E8 5D C3 56 57 E8   ......._^..].VW.
2817:1110  F2 E9 83 7C 08 E0 7F 07-E8 FE E8 1F EA E8 22 E8   ...|..........".
2817:1120  3E D8 00 83 45 08 03 E8-E0 F8 2E FF 36 40 15 E8   >...E.......6@..
2817:1130  42 15 50 E8 46 FC 57 56-56 E8 1C F4 83 06 D8 00   B.P.F.WVV.......
2817:1140  0C 5F 5E C3 00 00 00 00-00 00 00 00 00 00 00 00   ._^.............
2817:1150  00 00 03 00 00 00 00 00-00 40 00 00 00 00 A9 AA   .........@......
2817:1160  AA AA AA AA AA 0A 00 00-00 00 78 55 55 55 55 55   ..........xUUUUU
2817:1170  55 01 00 00 00 00 26 23-22 22 22 22 22 00 00 00   U.....&#"""""...
2817:1180  00 00 1C 23 03 E2 2D D3-02 00 00 00 00 00 FC F9   ...#..-.........
2817:1190  33 40 03 34 00 00 00 00-00 00 14 52 03 34 40 03   3@.4.......R.4@.
2817:11A0  00 00 00 00 00 00 1E 6D-07 3B 23 00 00 00 00 00   .......m.;#.....
2817:11B0  00 00 4C 20 C9 4F 02 00-00 00 00 00 00 00 91 0E   ..L..O..........
2817:11C0  E6 1A 00 00 00 00 00 00-00 00 E1 76 1F 01 00 00   ...........v....
2817:11D0  00 00 00 00 00 00 0E 2C-0B 00 00 00 00 00 00 00   ................
2817:11E0  00 00 5E 56 57 93 2E D8-00 8D 7E F4 39 3E D8 00   ..^VW.....~.9>..
2817:11F0  58 C0 E8 57 56 56 E8 EF-F3 89 2E D8 00 EB 7C 0E   X..WVV.......|.
2817:1200  83 FF E0 7E 57 E8 04 8E-5C 02 EB 4C 04 EB 54 06   ...~W...\..L..T.
2817:1210  47 7D 17 D1 EA D1 D9 D1-D9 D1 D6 47 7C F5 15 00   G}.........G|...
2817:1220  00 83 D3 00 83 D1 00 83-D2 00 83 2E D2 00 0C FC   ................
2817:1230  8B 3E D8 00 A5 93 A8 91-A8 92 AB 2B C0 AB AB 83   .>.........+....
2817:1240  EF 0C 2E FF 36 04 17 88-06 17 50 E8 2E F2 A1 D3   ....6.....P.....
2817:1250  00 50 56 56 E8 01 F3 E3-06 D8 00 0C 5F 5E 5D C3   .PVV........_^].
2817:1260  5B F0 17 5C 29 3B AA 3B-01 00 00 00 09 00 00 00   [..\);..........
2817:1270  00 00 00 00 00 00 00 00-00 00 68 55 55 55 55 55   ..........hUUUUU
2817:1280  55 05 00 00 00 00 34 33-33 33 33 33 33 00 00 00   U.....4333333...
2817:1290  00 00 47 33 48 92 24 49-02 00 00 00 00 00 4D 5D   ..G3H.$I......M]
2817:12A0  22 07 71 1C 00 00 00 00-00 00 24 56 E8 5C 74 01   ".q.......$V.\t.
2817:12B0  00 00 00 00 00 00 39 A2-ED 81 13 00 00 00 00 00   ......9.........
2817:12C0  00 00 FD D6 80 0F 01 00-00 00 00 00 00 00 95 7A   ...............z
2817:12D0  E4 10 00 00 00 00 00 00-00 00 55 8B EC FF 75 08   ..........U...u.
2817:12E0  56 57 8B 0E 8B 5D 02 E3-4D 04 E8 55 06 81 FA 05   VW...]..M..U....
2817:12F0  8B 77 10 D1 E0 D1 D3 D1-D1 D1 D2 8E 00 00 FF 4E   .w.............N
2817:1300  FE E2 15 F7 D2 F7 D1 F7-D3 F7 D8 F3 83 D3 00 83   ................
2817:1310  D1 00 E3 E2 00 8E 31 00-2B FF 08 D2 75 19 93 91   ......1.+...u...
2817:1320  92 83 EF 10 83 FF C0 7F-F1 83 2E 38 00 0C 8B 3E   ...............>
2817:1330  D8 00 E8 EF E7 EB 2D 78-0B 4F D1 E0 D1 D3 D1 D1   ......-x.O......
2817:1340  13 D2 79 F3 E6 E7 E2 81-E3 50 8B F4 E8 79 00 8E   ..y......P...y..
2817:1350  20 15 E8 C9 E7 89 36 D9-00 8B C4 56 50 56 E8 F7    .....6....VPV..
```

```
2817:1360  F1 8B C4 0C 3D 76 FE 8B-2E D3 00 0C 3B 3E D3 00   .....v.......>..
2817:1370  EB 10 E9 8D 7E 0C 56 E7-57 E8 11 F0 57 FF 76 FC   ....u.VWW...W.v.
2817:1380  FF 76 FC E8 D2 F1 8B 06-D2 00 13 5F 5E 8B E5 5D   .v.........._^..]
2817:1390  C3 55 8B EC 56 57 8B F7-E8 69 E7 1B 76 D3 00 E8   .U..VW...i..6...
2817:13A0  28 00 8B 3D 13 EB 76 E7-5B 36 DE 00 56 8D 74 0C   (.. ..v..6..V.t.
2817:13B0  56 56 E8 AD F1 56 FF 76-FE FF 76 FE E8 99 F1 8B   VV...V.v..v.....
2817:13C0  06 D3 00 13 5F 5E 3B EE-5D C3 55 3E EC 56 57 8B   ...._^..].U..VW.
2817:13D0  7C 08 C0 7E 46 8B 2E D8-00 0C 3E 3E D8 00 EB 7D   |..~F.......>...}
2817:13E0  E6 FF 45 08 56 57 57 E3-AD EF 56 57 57 E8 30 F3   ..E.VWW...VWW.0.
2817:13F0  5B 5C E7 EB 1E D8 00 83-47 08 02 E5 7C F8 2E FF   .\......G...|...
2817:1400  36 2C 18 E8 2E 18 50 E8-72 F9 FF 36 D3 00 57 56   6.....P.r..6..WV
2817:1410  E8 45 F1 FF 44 08 83 06-D8 00 13 5F 5E 8B E5 5D   .E..D......_^..]
2817:1420  C3 81 00 EB 06 B1 02 EB-02 B1 04 8E C7 8B EC 3B   ................
2817:1430  3E D8 00 8A 6D 0A 51 50-E3 7D 08 50 7F 03 30 F9   >...m.QP.}......
2817:1440  02 75 03 E8 13 E6 E9 EA-00 83 7D 08 40 7E 0B E8   .u........}.@~..
2817:1450  F9 E6 C7 45 06 21 00 E9-A9 00 C6 45 0A 00 ED 75   ...E.!.....E...u
2817:1460  F4 69 36 D3 00 37 FE E8-27 E6 87 FE 8B 6C 08 02   ..6.....'....l..
2817:1470  E5 C7 FE 24 07 E8 46 FC-8A 5E FE 30 F8 04 74 3B   ...$..F..^....t;
2817:1480  C2 5E FC 30 E3 07 3E 5E-FD D1 EB 73 11 87 FE E9   .^.....^...s....
2817:1490  FF E3 87 FE 83 6C 08 02-E6 57 57 58 EB EE E9 3E   .....l..VWW....>
2817:14A0  D3 00 93 F7 F6 46 FD 03-7A 05 EE A7 FA E3 03 EB   .....F..z.......
2817:14B0  81 FA 8A 5E FC D0 E3 D0-E3 E8 3C F6 46 FC 01 74   ...^......<.F..t
2817:14C0  11 87 F7 E3 C9 E5 87 F7-8C 6C 08 02 E6 57 57 E8   .........l..VWW.
2817:14D0  87 EE 89 3E D8 00 8B F7-E6 99 F4 ED 7C F4 89 C6   ...>........|...
2817:14E0  F6 46 FC 03 7A 02 87 F7-97 56 50 57 E8 31 F2 8A   .F..z....VPW.1..
2817:14F0  5E FC D0 EB 80 E3 01 80-7E FE 02 74 03 32 5E FF   ^.......~..t.2^.
2817:1500  88 5D 0A 89 3E D8 00 8B-EE C3 8E C7 83 36 D8 00   .]..>........6..
2817:1510  8D 7C F4 89 3E D8 00 E8-44 E5 85 44 08 3D 01 40   .|..>...D..D.=.@
2817:1520  7D 38 3D 01 C0 7E 2E 81-00 8B DE 48 7C 07 E3 38   }8=..~.....H|..8
2817:1530  E6 EB DF 81 01 25 00 E6-6F 0A 51 E2 1C F8 59 80   ........o.Q...Y.
2817:1540  F9 01 75 0E 51 EB 49 EE-FF 4D 08 57 56 56 E8 38   ..u.Q.I..M.WVV.8
2817:1550  EE 59 88 6C 0A 59 36 D8-00 C3 E5 FE FF 74 0A EB   .Y.l..6......t..
2817:1560  2F EE 2F 44 0A FF 4C 09-E3 E9 2E C7 8B 76 D3 00   /../D..L......6..
2817:1570  E3 7C F4 E9 3E D8 00 E8-3F EE E5 22 9E 07 EB 36   .|..>....?.."...6
2817:1580  D6 00 8D 7C FA 89 3E D8-00 E8 D2 E4 EE 10 EE 07   ...|..>.........
2817:1590  8B 36 D3 00 8D 7C F4 E9-3E D8 00 EE 04 EE E8 C8   .6...|..>.......
2817:15A0  E5 30 7D 0A 00 75 19 E8-45 08 3D 01 C0 7E 03 3D   .0}..u..E.=..~.=
2817:15B0  01 40 7D 0C E8 23 FD E9-76 D3 00 C3 85 04 E5 02   .@}..#..6.......
2817:15C0  8E 01 E8 3F 02 E9 01 40-E8 FE 51 00 EE 04 EE E8   ...?...@..Q.....
2817:15D0  56 38 40 00 E5 0E EE C7-E8 36 D8 00 8D 7C F4 E8   .8@......6...|..
2817:15E0  1C 89 2F 00 6E C7 E5 36-D8 00 8D 7C F4 3F 3E D8   ../...6...|..>.
2817:15F0  00 FF 30 56 57 56 E8 5F-EF 59 36 D8 00 EB ED E8   ...VWV._..6.....
2817:1600  00 00 50 2E 44 C3 3D 03-00 7F 4E 3D C3 FF 7E 5A   ..P.D.=...N=..~Z
2817:1610  E5 3C E5 FF 45 06 FF 36-D6 00 80 26 D7 00 F3 80   .<..E..6...&....
2817:1620  0E D7 00 04 E3 F7 E3 34-E7 9F 06 D5 00 50 89 FC   .......4.....P..
2817:1630  EE E5 E5 FF 4C 08 ED 7C-00 57 E6 57 EE 4A EC 58   ....L..|.WVW.J.X
2817:1640  D1 F3 73 2D C7 04 83 64-C7 44 02 DE F9 C7 44 04   ..s-...d.D....D.
2817:1650  33 F3 C7 44 06 04 85 E3-2E E3 FE 2B 03 E8 44 01   3..D....+.....D.
2817:1660  B8 01 40 31 00 EE 71 E4-E3 40 E3 FE EE EF E3 EB   ..@...q..@......
2817:1670  39 C7 04 00 00 C7 44 02-00 00 C7 44 04 00 00 C7   9.....D....D....
2817:1680  44 06 00 80 40 89 44 05-C6 44 0A 00 E5 FE ED 75   D...@.D..D.....u
2817:1690  0C 58 4E FB 56 57 56 E8-EE EE 56 57 56 E8 ED EC   ..N.VWV...VWV...
2817:16A0  80 7E FE 01 75 04 E0 74-0A 01 E9 36 D8 00 E8 EE   .~..u..t...6....
2817:16B0  C3 8E C7 8D 7E 18 55 00-E5 E9 50 0A F6 E1 03 F8   ....~...........
2817:16C0  8E C0 00 83 EE 0C 83 EF-0A E3 D3 E2 4D 7F F4 83   .............M...
2817:16D0  CE 2B 0E D6 00 83 EE 02-5F EE 00 FD D1 E9 74 02   .+.............t.
2817:16E0  F3 AE 47 47 39 3E 13 00-C3 EE C7 E3 00 E9 E9 8A   ..GG9..........
2817:16F0  D9 E7 00 2E 8A FF C2 00-85 36 D8 00 E5 FE 2B F5   .........6....+.
2817:1700  89 3E D3 00 E9 C0 00 2B-CE 74 05 FC D1 E9 F3 A5   .>.....+.t......
2817:1710  8D 76 18 E5 E0 EB 83 C7-0C E3 C6 0A 4D 7F F4 C3   .v..........M...
2817:1720  83 1E D3 00 53 8D 77 0C-56 83 C6 0C EE 14 83 1E   ....S.w.V.......
2817:1730  3E 00 53 8D 77 0C 56 E8-09 8E 36 D3 00 56 8D 5C   ..S.w.V...6..V.\
2817:1740  0C 53 3E C7 EE F3 F3 E9-76 D3 00 E3 66 16 C3 30   .S.......6...f...
2817:1750  26 C7 00 FC EB 05 80 26-37 00 FE 9E C7 8B 1C D8   &......&........
2817:1760  00 53 8D 77 0C 56 E8 D9-F3 80 0E 37 00 03 83 C6   .S.w.V..........
2817:1770  0C 89 36 D3 00 28 66 16-C3 EE C7 E2 36 D8 00 E3   ..6...f.....6...
2817:1780  80 F4 89 66 16 C3 9E C7-93 36 D3 00 E2 80 F4 39   ...f.....6.......
2817:1790  46 0E C3 71 1C A9 1C 0F-1D 16 1D E0 1C EE 1C 39   F..q............9
2817:17A0  1D 46 1D E1 19 E5 19 E9-19 CA 1A 2A 1B 3C 1B 4E   .F.........*.<.N
2817:17B0  1B 91 1E 96 1B A1 1B FB-FC 52 50 53 55 56 57 06   .........RPSUVW.
2817:17C0  51 1E 8B EC 36 89 2E DE-00 C5 76 12 AD 89 76 12   Q...6.....v...v.
2817:17D0  8C D7 EE DF 8A CC 95 93-80 FB DC 72 1D 2E FF 97   ...........r....
2817:17E0  77 1D 36 81 3E D3 00 C0-00 77 16 36 E9 26 DE 00   w.6.>...w.6.&..
```

```
2817:17F0  1F 59 07 5F 5E 5D 5B 58-5A CF 55 01 EB 05 00 E8   .Y._^][XZ.......
2817:1800  EA CC 5E E7 50 51 1E 16-1F A0 D4 00 8A 0E D6 00   ....PQ..........
2817:1810  80 E1 3F 80 F1 3F 0A CE-8A E0 22 E1 32 E0 F6 C4   ..?..?...."2....
2817:1820  08 74 02 0C 20 84 C1 74-0F 0C 80 A2 D4 00 22 C1   .t.. ..t.......".
2817:1830  3C 20 75 0D 1F 59 58 CF-24 7F A2 D4 00 1F 59 58   < u..YX.$.....YX
2817:1840  CF 3B 02 33 C0 21 36 89-1E D0 00 36 8C 06 D2 00   ...3.!6....6....
2817:1850  36 8B 26 DE 00 1F 59 07-5F 5E 5D 5B 58 5A 36 FF   6.&...Y._^][XZ6.
2817:1860  2E D0 00 53 51 52 31 04-E5 0A 26 8B 1C 8A C7 D2   ...SQR....&.....
2817:1870  8E F6 E5 82 0F 22 D7 02-C2 F6 E5 8A F0 00 22 D3   ....."........".
2817:1880  D3 EA 03 C2 89 0A 00 F7-E1 83 E3 0F 03 C3 5A 59   ..............ZY
2817:1890  5B C3 55 8B EC 56 57 26-8A 44 09 25 80 00 D0 C0   [.U..VW&.D.%....
2817:18A0  89 45 0A 51 04 26 8A 44-08 D3 E0 D2 E8 D5 0A EF   .E...&.D........
2817:18B0  10 27 F7 E7 93 8D 74 06-8B A8 FF 03 C3 12 D6 8B   .'....t.........
2817:18C0  DA F7 E7 93 8B CA F7 E7-03 C3 12 D6 83 EE 02 E3   ................
2817:18D0  91 FF 03 C3 83 D1 00 12-D6 56 8B DA F7 E7 91 8B   .........V......
2817:18E0  F2 F7 E7 93 87 FA F7 E2-03 DE 13 F8 5E 83 EE 02   ............^...
2817:18F0  E2 70 FF 03 C1 13 DA 13-FA 8E 10 27 F7 E6 93 8B   .p.........'....
2817:1900  CA F7 E6 96 87 FA F7 E2-03 DE 13 F8 83 D2 00 8B   ................
2817:1910  76 FE E8 4E FF 03 C8 83-D1 00 93 D7 00 83 D2 00   v..N............
2817:1920  8B 40 00 03 D2 75 0D 2D-10 00 74 2D 87 E7 E7 F9   .@...u.-..t-....
2817:1930  87 C8 E5 EF 78 03 48 D1-E3 D1 D1 D1 D7 13 D2 79   ....x.H........y
2817:1940  F5 8B 76 FC 89 1C 89 4C-02 89 7C 04 89 54 06 89   ..v....L..|..T..
2817:1950  44 08 5F 5E 8B E5 5D C3-5B 01 C0 EB 54 E0 51 50   D._^..]......PQ.
2817:1960  64 81 04 F2 76 F2 8A D4-D4 0A D2 E4 0A E0 92 24   d...............
2817:1970  0A D2 E4 0A C4 8A E6 A8-59 58 C3 5E 8B EC 56 57   ........YX.^..VW
2817:1980  FC 8B 44 03 8B 1C 8B 4C-02 8B 54 06 8B 74 04 3D   ..D....L..T..t.=
2817:1990  00 00 7C 38 2D 3C 00 7C-1F 7F 33 81 FA C3 DE 72   ..|8-<.|..3....r
2817:19A0  17 77 2B 81 FE 3A 6B 72-0F 77 23 81 F9 3F 76 72   .w+..:kr.w#..?vr
2817:19B0  07 77 1B 83 F8 F0 77 16-B4 00 2C 04 04 10 7F 10   .w....w.........
2817:19C0  8A E7 8B D9 32 CE 8B F2-2B D2 EB F0 EB 67 E8 6E   ........+....g.n
2817:19D0  2C 10 7D 0E D1 EA D1 DE-D1 D9 D1 D8 E0 DC FE C0   ..}.............
2817:19E0  7C F2 02 E4 83 D3 00 83-D1 00 83 D6 00 83 D2 00   |...............
2817:19F0  F6 8E 10 27 F7 F6 91 F7-F6 93 F7 F6 E8 5E FF 2B   ...'.........^.+
2817:1A00  D2 91 F7 F6 93 F7 F6 91-F7 F6 E8 50 FF 8B D3 91   ...........P....
2817:1A10  F7 F6 91 F7 F6 E8 45 FF-8B D1 F7 F6 E8 3E FF D4   ......E......>..
2817:1A20  0A 81 04 D2 E4 0A C4 AA-8B 76 FE 8A 44 0A D0 C8   .........v..D...
2817:1A30  AA 5F 5E 5D C3 80 00 89-09 00 F3 AA 8B EA 8E 08   ._^]............
2817:1A40  E3 C1 FD 80 99 E3 F0 FE-20 08 21 12 21 10 21 26   ........ .!.!.!&
2817:1A50  21 2D 21 4B 21 34 21 D1-24 46 25 AC 25 AE 25 A1   !-!K!4!.$F%.%.%.
2817:1A60  06 9A 02 A5 07 43 01 DC-21 E3 21 ED 21 EA 21 F4   .....C..!.!.!.!.
2817:1A70  21 F3 21 F0 21 FB 21 A1-06 9A 02 A5 07 43 01 27   !.!.!.!......C.'
2817:1A80  06 E2 02 01 07 78 01 74-22 6E 22 05 23 F8 22 7D   .....x.t"n".#."}
2817:1A90  22 A3 22 6E 22 E8 22 E8-22 6E 22 D9 22 6F 23 41   "."n"."."n"."o#A
2817:1AA0  23 7C 23 46 23 62 23 85-01 58 58 FD E9 6D 05 77   #|#F#b#...X..m.w
2817:1AB0  24 F6 C4 20 75 F1 42 E9-C4 E8 CF C4 20 74 0E 3C   $.. u.B....$.t.<
2817:1AC0  80 8C D7 72 08 83 7E 04-77 03 E8 7E 14 26 AC 86   ...r..~.w..~.&..
2817:1AD0  E0 24 07 E8 32 3C 09 75-09 26 07 44 FD E9 E4 E9   .$..2<.u.&.D....
2817:1AE0  3A 05 E9 5C FD E3 00 F8-FC 52 50 53 55 56 57 06   :..\.....RPSUVW.
2817:1AF0  51 1E 8B 8C 36 E9 2E 2E-00 C4 76 12 4E 82 00 26   Q...6.....v.N..&
2817:1B00  AD 2C 34 3C 0E 77 A8 E8-07 00 22 DC 22 FC 91 80   ..4<.w....".."...
2817:1B10  FF 30 73 67 E0 FF 40 77-12 74 14 2B C0 80 FB 06   ..sg..@w.t.+....
2817:1B20  75 10 26 AD 89 7E 12 8C-D8 E8 65 26 AD E8 03 26   u.&..~....e&...&
2817:1B30  AC 98 89 76 12 B7 00 D1-E3 2E FF A7 07 20 03 46   ...v......... .F
2817:1B40  0C 03 46 03 8C DE E3 48-03 46 0C 03 46 06 3C DE   ..F....H.F..F...
2817:1B50  EB 3E 03 46 0A 03 46 08-8C D6 EB 34 03 46 0A 03   .>.F..F....4.F..
2817:1B60  46 06 8C D6 EB 2A 03 46-08 8C DE EB 23 03 46 06   F....*.F....#.F.
2817:1B70  8C DE EB 1C 03 46 0C 8C-DE EB 15 89 76 12 8C D0   .....F......v...
2817:1B80  8E D8 8E C0 F6 C1 01 74-33 EB 17 03 46 0A 8C D6   .......t3...F...
2817:1B90  96 50 FA 01 75 01 97 8E-C0 8C D0 8E D8 F6 C1 01   ....u...........
2817:1BA0  74 1A 80 FD C0 73 03 E9-99 00 F6 C5 20 75 03 E9   t....s...... u..
2817:1BB0  37 02 8B 06 00 22 D9 2E-FF A7 17 20 58 3E 00 22   7...."..... .X."
2817:1BC0  C5 D1 E8 D1 E3 95 80 FD-C0 73 2A E8 3E D9 00 83   ..........s*.>..
2817:1BD0  EF 0C 89 3E D8 00 53 06-00 22 D9 2E FF 97 1F 20   ...>.....".....
2817:1BE0  8C D1 8E C1 8E 0C 00 2B-DF 8D 00 89 20 E9 D7 25   ...............%
2817:1BF0  2E FF A6 27 20 87 00 2E-2A 9F 02 00 A1 D8 00 03   ...' ...........
2817:1C00  D8 F6 C1 04 83 D0 74 02-8B 33 2E F6 F6 C1 02 74   ......t...+....t
2817:1C10  03 E8 0C 00 89 27 25 2E-FF A6 27 20 50 53 52 51   .......%...' PSRQ
2817:1C20  E9 6A E7 5D 5B 52 51 E9-2E E9 93 C6 0C 50 53 51   .j.][RQ......PSQ
2817:1C30  E9 0F EF 93 50 53 52 51-E9 4E E7 93 50 53 52 51   ....PSRQ.N..PSRQ
2817:1C40  E9 DD EA 80 06 00 23 E9-F6 C5 20 75 42 F6 C5 10   .......#... uB...
2817:1C50  75 1A F6 C5 08 75 54 E9-3E D8 00 E8 F4 FF 03 F8   u....uT.>.......
2817:1C60  A3 D4 00 E8 D2 25 50 2E-FF A6 37 20 8B 3E D8 00   .....%P...7 .>..
2817:1C70  87 F7 F6 C5 08 75 09 E8-DC 25 50 2E FF A6 3F 20   .....u...%P...?
```

```
2817:1C80  C7 06 DA 00 0C 00 B8 D2-25 50 2E FF A6 3F 20 B8   ........%P...? .
2817:1C90  0B 00 22 C5 06 E8 B8 DC-25 50 F6 C5 10 75 05 2E   .."......%P...u..
2817:1CA0  FF A6 47 20 87 F7 2E FF-A6 57 20 E9 6E 03 B5 01   ..G .....W .n...
2817:1CB0  E8 51 FE C3 81 04 26 E8-44 02 A3 D4 00 26 8B 04   .Q....&.D....&..
2817:1CC0  A3 D6 00 8E 00 E8 3C F8-83 3E D8 00 83 EF 0C E8   ......<..>......
2817:1CD0  27 E1 83 3E D8 00 0C 03-E5 3E D8 00 83 EF 0C E8   '........>......
2817:1CE0  B0 F8 83 3E D8 00 0C 03-E8 3E D8 00 83 EF 0C E8   ..........>.....
2817:1CF0  C4 E8 83 3E D8 00 0C 03-E8 86 00 E8 88 00 EB 03   ................
2817:1D00  00 E8 06 D2 00 8E 1C F6-F2 8F FF FF 91 03 8F D3   .+..............
2817:1D10  E8 AB 2B 0C A5 AB AB AB-03 E8 DC FF E2 C6 E8 00   ..+..........6..
2817:1D20  26 8B 6D F6 81 03 55 55-E5 0F EB 72 E8 83 C6 00   &.m...UU...r....
2817:1D30  83 C7 0A D1 EE D1 EE 74-11 79 EF E8 C8 2B C0 E9   .......t.y...+..
2817:1D40  05 00 F7 A3 D1 EE D1 E8-75 F7 C3 EF C0 00 26 83   ........u.....&.
2817:1D50  6C 04 83 C6 54 81 CD 55-55 D1 ED D1 ED 73 03 83   l...T..UU....s..
2817:1D60  EE 0A 08 ED 75 F3 E8 0F-D1 ED 83 EF 0C E3 56 E8   ....u.........V.
2817:1D70  83 EE 0A D1 ED 72 F1 E9-3E D8 00 83 C6 FC E9 33   .....r..>.......
2817:1D80  FF A1 D6 00 A3 C3 A1 D8-00 2D C0 00 B1 0C F6 F7   .........-......
2817:1D90  24 07 B1 03 D2 E0 8B 0E-D4 00 80 E5 C7 0A E5 91   $...............
2817:1DA0  A3 C3 8B 36 D8 00 E8 D2-E0 83 06 D8 00 0C C3 85   ...6............
2817:1DB0  36 D8 00 E8 C5 F2 E8 06-E8 00 0C C3 8B 36 D8 00   6............6..
2817:1DC0  E8 DC E4 83 06 D8 00 0C-03 C3 23 15 24 DC 23 D6   ..........#.$.#.
2817:1DD0  23 22 24 1B 24 22 24 22-24 16 24 1B 24 33 24 3E   #"$.$"$"$.$.$3$>
2817:1DE0  24 3E 24 1B 24 3E 24 3E-24 B7 00 2E 8A FF C2 00   $>$.$>$>$.......
2817:1DF0  8B 36 D8 00 03 F3 83 18-22 8D 80 E1 06 0A D9 FC   .6......".......
2817:1E00  B9 06 00 2E FF A7 BF 23-83 2E D3 00 0C E8 3E D8   .......#......>.
2817:1E10  00 F3 A5 E9 06 02 8F DC-00 E5 04 90 8F 00 00 81   ................
2817:1E20  FE 84 00 74 10 87 FE EB-01 40 21 00 E8 AA DC 01   ...t.....@......
2817:1E30  36 D8 00 E8 55 83 C7 0D-E8 D7 E8 CE 2B 0E D8 00   6...U.......+...
2817:1E40  74 0E 16 07 83 EE 02 8F-8E 00 FD D1 E9 F3 A5 FC   t...............
2817:1E50  01 16 D8 00 E8 34 F6 C3-07 74 2F 8B 01 E8 A4 F9   .....4...t/.....
2817:1E60  E8 28 8B 3E D8 00 8B 0E-87 04 A2 83 C6 02 E2 F6   .(.>............
2817:1E70  E9 A9 01 E8 FE E8 36 D8-00 F3 A5 E9 FE 01 BE FE   ......6.........
2817:1E80  8B 36 D8 00 F3 A5 E9 36-D8 00 EF EF 01 04 04 04   .6.....6........
2817:1E90  04 04 04 04 04 00 00 00-00 00 00 00 04 04 03 06   ................
2817:1EA0  03 06 04 02 00 0A 02 04-04 04 0A 04 04 AD 24 B2   ..............$.
2817:1EB0  24 BF 24 EF 24 C2 11 FF-11 BF 24 BF 24 1E 00 2F   $.$.$.....$.$../
2817:1EC0  00 40 00 E1 00 62 00 77-00 84 00 8F 24 AD 17 9A   .@.C.b.$....$. .
2817:1ED0  18 24 15 1A 16 E7 24 BF-24 BF 24 EF 24 FA 0F 51   .$....$.$.$.$..Q
2817:1EE0  19 2D 0F BF 24 1D 0E 30-02 BF 24 EF 24 80 74 0A   .-..$..0..$.$.t.
2817:1EF0  01 C3 C6 44 0A 00 C3 56-57 E8 40 DD 5F 5E C3 B5   ...D...VW.@._^..
2817:1F00  01 E8 00 F9 C3 E4 24 1B-25 F7 24 06 25 23 25 36   ......$.%.$.%#%6
2817:1F10  25 8B 1F 00 22 DD 2E 8A-87 4D 24 98 97 D1 E3 2E   %..."....M$.....
2817:1F20  FF A5 C5 24 E8 3E D8 00-83 EF 0C 2E FF 97 6D 24   ...$.>........m$
2817:1F30  89 3E D8 00 E9 55 00 8B-36 D8 00 E8 FE B8 DC 25   .>......6......%
2817:1F40  50 2E FF A7 6D 24 8B 36-D8 00 8B FE 83 EF 0C 2E   P...m$.6........
2817:1F50  FF 97 6D 24 89 3E D8 00-E9 C1 00 83 06 D8 00 0C   ..m$.>..........
2817:1F60  E9 E9 00 8B 3E D8 00 ED-75 0C 2E FF 97 6D 24 89   ....>...u....m$.
2817:1F70  36 D8 00 E9 A6 00 E8 3E-D8 00 8D 75 0C 38 DC 25   6.......>...u...%
2817:1F80  50 2E FF A7 6D 24 90 E5-1F 80 FD 03 75 4A 8F C0   P...m$......uJ..
2817:1F90  00 89 3E D8 00 E8 01 40-E1 00 EE 3C DB 8D 75 0A   ..>....@...<..u.
2817:1FA0  83 EF 02 FD 83 EC 60 89-30 00 F3 A5 C7 06 D4 00   ......`.0.......
2817:1FB0  00 41 C7 06 D6 00 3F 03-C7 06 DA 00 00 00 C7 06   .A....?.........
2817:1FC0  D8 00 C0 00 C7 06 E0 00-65 6D C7 06 E2 00 75 87   ........em....u.
2817:1FD0  C7 06 E4 00 01 00 E8 11-80 FD 02 75 07 C6 06 D4   ...........u....
2817:1FE0  00 00 E8 03 85 01 E8 1B-F5 E8 31 90 E8 F6 F6 C5   ..........1.....
2817:1FF0  1F 75 F1 A1 D8 00 2D C0-00 B1 0C F6 F7 24 07 B1   .u....-......$..
2817:2000  03 D2 E0 8B 0E D4 00 80-E5 C7 0A E8 89 4E 0E E8   .............N..
2817:2010  0B 90 36 E8 36 DA 00 36-01 36 D8 00 36 81 3E D8   ..6.6..6.6..6.>.
2817:2020  00 D0 00 77 0F 36 8B 26-DE 00 1F 59 07 5F 5E 5D   ...w.6.&...Y._^]
2817:2030  5B 58 5A CF 0C E8 EE 00-00 00 00 00 00 00 00 00   [XZ.............
2817:2040  35 D2 68 21 A2 DA 0F C9-FE 3F 35 D2 68 21 A2 DA   5.h!.....?5.h!..
2817:2050  0F C9 FF 3F 00 42 C0 FF-00 48 C0 FF 00 4A C0 FF   ...?.B...H...J..
2817:2060  00 00 00 3F 8E 64 DE F9-33 F3 04 B5 FF 3F 00 00   ...?.d..3....?..
2817:2070  80 7F B1 00 E5 06 B1 02-E8 02 B1 04 9E D9 E8 55   ...............U
2817:2080  8B ED 8D 66 FE 9B DD 7E-FE 9B 8A 66 FF 9E 72 0F   ...f...~...f..r.
2817:2090  75 2E 80 F9 02 75 06 95-DD D8 9B D9 E8 EB 1E 74   u....u.........t
2817:20A0  0E 7B 0C 9B DD DE 9B 2E-D9 06 14 00 9B D9 E1 E8   .{..............
2817:20B0  0C 9B DE D9 9B DE D9 06-14 00 9B D9 E4 E9 47 00   ................
2817:20C0  9B D9 E1 9B 2E D8 2E 00-00 9B D9 C9 9B D9 FE E8   ................
2817:20D0  02 22 EC D0 ED 9B DD 7E-FE 9B 8A 66 FF 9E 7A D1   ."......~...f.z.
2817:20E0  B0 03 22 C4 D0 E4 D0 E4-D0 D0 04 FC D0 D0 80 F8   ..".............
2817:20F0  02 75 04 02 C1 EB 00 24-07 A8 01 74 05 9B DE E9   .u.....$...t....
```

```
2817:2100  E3 03 9B DD D9 9B D9 FD-80 F9 04 74 29 AB 03 7A   ...........t)..z
2817:2110  03 9B D9 C9 9B D9 C1 9B-D8 C8 9B D9 C9 9B D8 C8   ................
2817:2120  9B DE C1 9B D9 FA D0 E3-DC EB 32 C0 74 03 9B D9   ..........2.t...
2817:2130  E0 95 DE F9 EB 31 8A E0-D0 EC 80 E4 01 32 E3 74   .....1.......2.t
2817:2140  03 9B D9 E0 A8 03 7A 1C-9B D9 C9 9B D9 E4 9B DD   ......z.........
2817:2150  7E FE 9B F6 46 FF 40 74-03 9B DE C9 9B DE D9 06   ~...F.@t........
2817:2160  2E 00 EB 03 9B DE F9 83-EE 5D 03 9B D9 EE EE 55   .........]....U.
2817:2170  8C ED 66 FE 9B DD 7E FE-9B 8A 66 FF 9E 91 72 04   ..f...~...f...r.
2817:2180  75 1C EB 4C 74 4A 7B 48-9B DD D8 9B DE D8 DE 0A   u..LtJ{H........
2817:2190  00 EB 35 9B DE D9 9B DE-D5 DE 00 00 EB 2A 9B D9   ..5..........*..
2817:21A0  E1 9B D9 EE 9B DB D1 9B-DD 7E FE 9B 8A 66 FF 9E   ..........~...f..
2817:21B0  74 E1 73 03 9B D9 C9 9B-D9 F3 73 0C 9B DE D8 DE   t.s.......s.....
2817:21C0  0A 00 9B DE E9 80 FE 02-F6 D5 02 74 03 9B D9 E0   ...........t....
2817:21D0  8B EE ED 03 9B D9 EE EB-08 9B D9 ED EB 03 9B D9   ..].............
2817:21E0  ED 9B D9 D9 55 EB ED 9B-D9 EE 8D 66 F6 9B DD 7E   ....U......f...~
2817:21F0  F6 9B 8A 66 F7 9E 72 0C-74 05 F6 C4 02 74 17 9B   ...f..r.t....t..
2817:2200  DD D8 EB 04 74 08 7B 09-9B DD D8 9B DE D9 06 18   ....t.{.........
2817:2210  00 9B D9 E4 EB 24 9B D9-C0 95 D5 7E F6 9B 81 7E   .....$.....~...~
2817:2220  FE FF 3F 75 12 81 7E FC-00 80 75 0B 9B D9 E8 9B   ..?u..~...u.....
2817:2230  DE E9 9B D9 F9 EB 03 9B-D9 F1 8B EE 5D C3 95 D9   .............]...
2817:2240  EA 81 01 EB 08 23 D9 EB-07 9B D9 E9 81 01 EB 00   ......+.........
2817:2250  EB 07 9B D9 C9 9E D9 EE-E5 EB EC ED 66 FC 95 DD   ........U...f...
2817:2260  7E FD E3 03 9B D9 C9 92-E4 66 FD 9E 93 72 10 75   ~.........f...r.u
2817:2270  26 9B DD D8 EB 03 9B DD-D8 9B D9 E8 E9 AB 00 E3   &...............
2817:2280  0C 9B DD D8 74 05 7B 09-9B DD D8 9B DE D9 06 1C   ....t.{.........
2817:2290  00 9B D9 E4 E7 90 00 E3-03 95 DE C9 9B D9 E1 9B   ................
2817:22A0  2E 38 16 20 00 9B DD 7E-FC 9B F6 46 FD 41 74 08   ... ...~...F.At.
2817:22B0  9B D9 F0 9B D9 E8 9B DE-C1 EB 61 9B D9 E8 9B D9   ...........a.....
2817:22C0  C1 9B D9 7E FC 9B D9 FD-80 4E FD 0F 9B D9 6E FC   ...~.....N....n.
2817:22D0  9B D9 FC 80 66 FD F3 9B-D9 6E FC 9B DF 56 FE 9B   ....f....n...V..
2817:22E0  D9 C9 9B D9 E0 9B D9 C9-9B D9 FD 9B DD D9 9B DE   ................
2817:22F0  E9 81 7E FE FF CF 7F 90-9B D9 F0 9B D9 E8 9B DE   ..~.............
2817:2300  C1 D1 6E FE 73 09 9B 2E-D8 2E 24 00 9B DE D9 9B   ..n.s.....$.....
2817:2310  DF 46 FE 9B D9 C9 9B D9-FD 9B DD D9 F6 C7 02 74   .F.............t
2817:2320  06 9B D9 E8 9B DE F1 E8-E3 5D C3 55 8B EC 50 56   ..........].U..PV
2817:2330  1E F6 46 07 02 74 01 FB-C5 76 02 E8 44 FF 2C 34   ..F..t...v..D.,4
2817:2340  3C 09 73 0C 83 EE 02 81-04 CE AC 39 76 02 EB 23   <.s...........v..#
2817:2350  77 26 F6 C4 20 75 2E 83-EE 02 89 76 02 C6 04 9B   w&.. u.....v....
2817:2360  46 8A C4 25 C0 07 D0 E5-D0 E3 D0 EE 34 18 05 26   F..%.........4..&
2817:2370  D8 89 34 1F 5E 58 5D CF-3C 09 77 09 83 EE 02 07   ....^X].<.w.....
2817:2380  04 90 9B E8 C6 E8 EC 8C-03 A0 03 21 03 86 03 ED   ................
2817:2390  03 FF 03 39 04 0E 04 32-00 36 00 3A 00 2B 01 FE   .......2.6.:.+..
2817:23A0  01 94 01 97 01 FE 01 0E-02 09 02 F8 50 56 06 55   ............PV.U
2817:23B0  8B EC C4 76 08 26 AD 89-76 08 3C 8C 72 09 3E F0   ...v.&..v.<.r...
2817:23C0  9B 96 2E FF 94 68 03 5D-07 5E 58 CF FE 2C 7C 0E   .....h.].^X...|.
2817:23D0  B0 0A F6 E4 96 9B D8 7A-CE 83 EE 0A 7D F7 9B C3   .......z....}...
2817:23E0  2B F6 FE CC 7C 09 93 D8-6A 0E 83 C6 0A EB F2 9B   +...|...j.......
2817:23F0  C3 80 00 EB 03 90 50 01-55 50 8B EC 95 D9 7E 00   .........UP....~.
2817:2400  9B 8B 76 00 80 66 01 FC-08 46 01 9B D9 6E 00 9B   ..v..f...F...n..
2817:2410  D9 EE 9B DC EA 95 DE C1-89 76 00 9B D9 6E 00 9B   .........v...n..
2817:2420  DE D9 9B DD 7E 00 9B 58-5D 88 66 0C 03 9B DE D9   ....~..X].f.....
2817:2430  8A 66 0D 9B DD 7E 0C 9B-8A 46 0D 89 46 0C 03 9B   .f...~...F..F...
2817:2440  D8 C9 E3 ED 9B D3 D1 E8-E7 95 D9 E4 58 E2 9B D9   ................
2817:2450  E5 9B DD 7E 06 9B C3 55-8B EC 8D 3D 80 66 0D 7F   ...~...U...=.f..
2817:2460  CD 39 46 06 5D C3 5E 8B-ED 8C ED 04 A1 40 70 03   .9F.].U.......p.
2817:2470  06 A2 70 74 67 3D C0 50-50 E8 08 00 50 FF 1E 40   ..ptg].PP...P...
2817:2480  70 83 C4 06 89 56 FE 89-46 FC 52 50 85 03 00 50   p....V..F.RP...P
2817:2490  FF 1E A0 70 83 C4 06 83-7E FE 00 75 06 83 7E FC   ...p....~..u..~.
2817:24A0  01 74 76 2B 46 FC 05 46-FE 74 71 3C C0 50 50 E8   .tv.F..F.tI].PP.
2817:24B0  08 00 50 FF 1E A0 70 83-C4 06 C4 5E 06 26 8B 07   ..P...p....^.&..
2817:24C0  48 8A 06 00 F7 E3 3B D3-81 C3 E3 3B 1E 07 26 FF   H..........;..&.
2817:24D0  37 58 08 00 50 FF 5E FC-59 59 E8 3D C4 5E 06 26   7X..P.^.YY.=.^.&
2817:24E0  8B 07 48 BA 06 00 F7 E2-83 D3 81 C3 E3 3E 1E 07   ..H..........:..
2817:24F0  26 FF 77 04 26 FF 77 02-1E 55 55 3C 50 15 3B 46   &.w.&.w...U<P..F
2817:2500  3F 50 9A 0A 00 65 2D 83-C4 0C 9A 0D 00 68 2A 2B   ?P...e-......h*.
2817:2510  01 00 50 9A CD 01 17 19-59 5E 8B 5D 3B 9A ED 02   ..P.....Y..].....
2817:2520  17 13 C8 55 8B EC 83 EC-04 33 C9 8B FE 43 35 6A   ...U.....3...C.j
2817:2530  3F 8C 7E 13 00 75 06 58-7E 40 8B 6A 3F 8B 56 1C   ?.~...u..~@.j?.V.
2817:2540  D1 E2 D1 D1 D1 EA 81 FA-FF 7F 74 68 3B D0 74 09   ..........th;.t.
2817:2550  7E 3C CD 39 46 06 E8 4D-90 CD 35 7E FC 35 00 CC   ~<.9F..M..5~....
2817:2560  CD 3D 08 46 FC 39 46 FE-CD 35 6E FE CD 37 6E 0E   .=.F..F..5n..7n.
2817:2570  83 7E 18 00 75 0A CD 35-5E 06 CD 35 46 06 EB 08   .~..u..5^..5F...
2817:2580  CD 39 5E 06 CD 39 46 06-CD 35 6E FC EB 2A EB D2   .9^..9F..5n..*..
```

```
2817:2590  0B 46 14 03 46 12 0B 46-10 03 46 0E 74 16 3B D3   .F..F..F..F.t.;.
2817:25A0  7D 12 CD 35 EB 0B C9 74-0C 03 35 E0 07 06 7F 00   }..5...t..5.....
2817:25B0  22 00 EB 04 CD 37 6E 0E-EB EE ED CA 14 00 55 8B   "....7n.......U.
2817:25C0  EC 83 EC 08 56 57 3D 39-46 06 83 46 3C 31 E0 74   ....VW.9F..F...t
2817:25D0  0E 72 3D 3D E0 FF 74 1A-3D 3E F8 90 EE 74 70 EE   .r==..t.=>...t..
2817:25E0  02 00 CD 39 06 74 3C CD-3E E0 C3 39 EE FE C3 3D   ...9.t<.>..9^..=
2817:25F0  EB 38 EE 03 00 A1 7A 3C-39 46 FE A1 78 3C 39 46   .8....z<9F..x<9F
2817:2600  FC A1 76 3C 39 46 FA A1-74 3C 39 46 F8 EB 13 EE   ..v<9F..t<9F....
2817:2610  01 00 A1 7A 3C 39 46 FE-A1 78 3C 39 46 FC A1 76   ...z<9F..x<9F..v
2817:2620  3C 39 46 FA A1 94 3C 39-46 F8 CD 39 E3 FF 76 FE   <9F...<9F..9..v.
2817:2630  FF 76 FC FF 76 FA FF 76-F8 33 C0 50 50 16 8D 46   .v..v..v.3.PP..F
2817:2640  06 50 1E 33 9C 3C 50 3B-36 50 9A 06 00 FE 2A 83   .P...<P..P....*.
2817:2650  C4 16 5F 5E 8B E5 5D CB-55 8B EC 56 8B 46 06 3D   .._^..].U..V.F.=
2817:2660  BC E3 7D 05 CD 35 EE E9-83 00 3D 44 13 7E 03 CD   ..}..5....=D.~..
2817:2670  35 06 1E 3D E9 A6 00 0B-C0 75 06 CD 35 EB E9 9C   5..=......u..5..
2817:2680  00 0B C0 7D 02 F7 D8 BE-07 00 23 F0 D1 E6 D1 E6   ...}......#.....
2817:2690  CD 35 84 A2 3C D1 E8 D1-E8 D1 E8 D1 E8 73 05 CD   .5..<........s..
2817:26A0  34 0E C2 3C 75 03 E8 6A-90 D1 E8 73 05 CD 38 0E   4..<u..j...s..8.
2817:26B0  C6 3C D1 E8 73 08 CD 37-2E CE 3C CD 3A C9 D1 E8   .<..s..7..<.:...
2817:26C0  73 08 CD 37 2E D8 3C CD-3A C9 D1 E8 73 08 CD 37   s..7..<.:...s..7
2817:26D0  2E E2 3C CD 3A C9 D1 E8-73 08 CD 37 2E EC 3C CD   ..<.:...s..7..<.
2817:26E0  3A C9 D1 E8 73 08 CD 37-2E F6 3C CD 3A C9 D1 E8   :...s..7..<.:...
2817:26F0  73 08 CD 37 2E 00 3D CD-3A C9 D1 E8 73 08 CD 37   s..7..=.:...s..7
2817:2700  2E 0A 3D CD 3A C9 D1 E8-73 08 CD 37 2E 14 3D CD   ..=.:...s..7..=.
2817:2710  3A C9 F6 46 07 80 74 05-CD 34 3E A2 3C 5E 5D CB   :..F..t..4>.<^].
2817:2720  90 5F 22 C2 3C 47 75 0E-26 80 7F FF 30 75 07 4B   ._".<Gu.&...0u.K
2817:2730  3B D9 77 F4 EB 08 26 80-7F FF 2E 75 01 4B C3 55   ;.w...&....u.K.U
2817:2740  8B EC 83 EC 30 56 57 06-8B 46 10 3D 28 00 76 06   ....0VW..F.=(.v.
2817:2750  B8 28 00 89 46 10 8B 46-FE 8A 56 0A 80 E2 DF 80   .(..F..F..V.....
2817:2760  FA 46 75 02 F7 D8 7E 10-2B C0 89 46 10 EB 09 03   .Fu...~.+..F....
2817:2770  D0 7F 05 B8 01 00 EB 09-80 FA 46 74 04 40 FF 46   ..........Ft.@.F
2817:2780  10 FF 76 14 FF 76 12 3D-00 00 7E 03 B8 46 FE 50   ..v..v.=..~..F.P
2817:2790  16 8D 5E FC 53 16 8D 76-D0 56 8B 46 06 50 9A 0B   ..^.S..v.V.F.P..
2817:27A0  00  1 2A 83 C4 7E 0C FC-81 FB FF 7F 74 08 81 FB   ..*..~......t...
2817:27B0  FE 7F 74 15 EB 25 8B 2B-49 83 7E FC 00 74 02 40   ..t..%.+I.~..t.@
2817:27C0  40 AB 8B 4E 46 A3 E9 FA-00 EB 2B 4E 83 7E FC 00   @..NF.....+N.~..
2817:27D0  74 02 40 40 AB 80 41 AB-E9 EE 00 80 7E FC 00 74   t.@@..A......~..t
2817:27E0  03 B0 2D AA 8A 56 0A 80-E2 5F 80 FA 46 74 0F 80   ..-..V..._..Ft..
2817:27F0  FA 45 74 6D 83 F8 FD 7C-68 3B E8 10 7F 63 83 F8   .Etm...|h;...c..
2817:2800  28 7F 5E 0B DB 7F 0F 8B-3C 2B AB 39 01 00 74 09   (.^.....<.....t.
2817:2810  80 30 4A 43 75 FC 89 00-00 36 AC 0A C0 74 0A AA   .0.Cu....6...t..
2817:2820  4B 75 F6 80 3E 4A 41 EB-F0 8B 46 10 03 4E FE 3B   Ku....A...F..N.;
2817:2830  C1 76 0D 2B C1 8B C8 03-D8 B0 30 F3 AA 4B 74 16   .v.+......0..Kt.
2817:2840  4B 74 13 80 7E 09 00 75-0D 8A 56 0A 8B 4E 0C 87   Kt..~..u..V..N..
2817:2850  DF E8 C3 FE 57 F8 3B 7E-0C 7E 03 E0 30 AA EB 63   .......;~.u..0..c
2817:2860  90 36 AD A4 80 3E 0A E4-74 1D AA EA C4 AA 36 AC   .6......t.....6.
2817:2870  0A C0 75 F9 80 7E 08 00-75 0D 8A 56 0A 8B 4E 0C   ..u..~..u..V..N.
2817:2880  87 DF E8 93 FE 87 F3 80-20 22 46 0A 0C 45 AA 8B   ........ "F..E..
2817:2890  2B 2D 4B 7D 04 B6 C4 F7-D8 AA 93 89 30 30 3D 63   +-K}........00=c
2817:28A0  00 76 19 3D E7 03 76 0A-F9 B3 E3 03 F7 F3 32 C1   .v.=..v.........
2817:28B0  AA 92 B3 64 F6 F3 02 C1-AA 86 C4 98 53 0A F6 F3   ...d............
2817:28C0  03 C1 AB 32 C0 AA 07 5F-5E 8B E5 5D CA 10 00 C8   ...2..._^..]....
2817:28D0  55 8B EC 83 EC 18 56 57-C6 46 ED 00 C6 46 EE 01   U.....VW.F...F..
2817:28E0  C6 46 EF 00 C6 46 F0 00-C6 46 F1 00 C7 46 F2 00   .F...F...F...F..
2817:28F0  00 C7 46 F4 01 00 CD 37-2E 32 3D CD 37 7E F6 CD   ..F....7.2=.7~..
2817:2900  3D 06 8E 00 80 3F FE FF-FF 46 F2 FF 76 10 FF 76   =........F..v..v
2817:2910  0E FF 5E 06 59 59 0B C0-7D 03 E9 31 00 98 93 F6   ..^.YY..}.......
2817:2920  C3 80 75 07 F6 87 1D 3E-01 75 3D 93 FF 4E 12 7C   ..u....>.u...N.|
2817:2930  68 3C 2B 74 07 3C 2D 75-3E FE 46 ED FE 46 EF FF   h<+t.<-u>.F..F..
2817:2940  4E 12 7C 55 FF 46 F2 FF-76 10 FF 76 0E FF 5E 06   N.|U.F..v..v..^.
2817:2950  59 59 80 7E EE 01 75 16-80 7E EF 00 74 10 3C 49   YY.~..u..~..t.<I
2817:2960  74 06 3C 4E 74 05 EB 06-E9 E2 01 E9 21 02 C6 46   t.<Nt.......!..F
2817:2970  EE 00 3C 2E 74 32 3C 39-77 2E 3C 30 72 27 2C 30   ..<.t2<9w.<0r',0
2817:2980  93 47 7F 34 EB 46 F6 BF-01 00 0A C0 75 81 F7 DF   .G.4.F......u...
2817:2990  81 FE 00 80 74 A9 4E EB-A6 80 65 E9 90 00 C7 46   ....t.N...e....F
2817:29A0  F4 FF FF EB 6D E9 86 00-E1 FE 00 E0 75 ED 2B F6   ....m.......u.+.
2817:29B0  3E FF 7E 8B 8B F7 EB 87-E3 FF 05 77 14 93 EB 0A   ..~..........w....
2817:29C0  00 F7 66 F6 03 C3 13 D6-E9 46 F6 89 56 FE E9 6E   ..f......F..V..n
2817:29D0  FF 83 FF 12 77 34 93 8B-0A 00 F7 66 FC 89 46 FC   .....w4....f..F.
2817:29E0  93 0A 00 F7 66 FA 89 46-FA 83 8B CA 00 F7 66 F8   ....f..F.R....f.
2817:29F0  89 46 F8 52 8B 0A 00 F7-66 F6 03 C3 89 46 F6 11   .F.R....f....F..
2817:2A00  56 F8 5A 11 56 FA 5A 11-56 FC E9 32 FF C7 46 FA   V.Z.V.Z.V..2..F.
2817:2A10  00 00 83 7E 12 00 7C 10-FF 76 10 FF 76 0E 50 FF   ...~..|..v..v.P.
2817:2A20  5E 0A 83 C4 06 FF 4E F2-CD 35 EE E9 00 01 83 FF   ^.....N..5......
2817:2A30  FE 74 2A 81 FE 00 80 75-02 EB F7 89 7E EA 89 76   .t*....u....~..v
```

```
2817:2A40  EB 2B FF 3C 45 74 04 3C-65 75 52 FF 4E 12 7C 5D   .+.<Et.<euR.N.|]
2817:2A50  FF 46 F2 FF 76 10 FF 76-0E FF 5E 06 59 59 3C 2B   .F..v..v..^.YY<+
2817:2A60  74 07 3C 2D 75 16 FE 46-F0 FF 4E 12 7C 3F FF 46   t.<-u..F..N.|?.F
2817:2A70  F2 FF 76 10 FF 76 0E FF-5E 06 59 59 3C 39 77 1D   ..v..v..^.YY<9w.
2817:2A80  2C 30 72 17 98 97 8A 0A-00 F7 E2 03 F8 81 FF 44   .0r............D
2817:2A90  13 7E D6 33 FF C6 46 F1-01 E8 CE 04 3D FF 76 10   .~.3..F.....=.v.
2817:2AA0  FF 76 0E E8 FF 5E 0A 83-C4 06 FF 4E F2 F6 46 F0   .v...^.....N..F.
2817:2AB0  FF 74 05 F7 DF F6 5E F1-8B 5E EA 05 DB 7D 06 CD   .t....^..^...}..
2817:2AC0  35 EE E8 6A 90 9B 4E E8-8B C1 03 C7 80 7E F1 01   5..j..N......~..
2817:2AD0  74 0B 80 7E F1 FF 75 25-CD 35 EE EB 13 2B FF FF   t..~..u%.5......
2817:2AE0  89 46 F6 89 46 F8 89 46-FA 89 46 FC C7 46 FE FE   .F..F..F..F..F..
2817:2AF0  7F CD 37 6E F6 C7 46 F4-02 00 EB 32 90 9B CD 3D   ..7n..F....2....
2817:2B00  FE 12 76 03 E9 12 00 03-D1 23 C2 07 FF 2D 3B 6E   ..v......#...-;n
2817:2B10  F6 8B C7 0B C0 74 17 7B-02 F7 D8 E8 9A 09 00 7C   .....t.{.......|
2817:2B20  2A 58 0B FF 7D 0E CD 3A-F9 E2 03 CD 3A C9 80 7E   *X..}..:....:..~
2817:2B30  ED 00 74 03 CD 35 E0 C4-7E 14 8B 5E F2 26 01 1D   ..t..5..~..^.&..
2817:2B40  C4 7E 18 8B 5E F4 26 89-1D 07 5F 5D 00 FF 46 F2   .~..^.&.......F.
2817:2B50  FF 76 10 FF 76 0E FF 5E-06 59 59 FF 4E 12 7C 72   .v..v..^.YY.N.|r
2817:2B60  3C 4E 75 6E FF 46 F2 FF-76 10 FF 76 0E FF 5E 06   <Nun.F..v..v..^.
2817:2B70  59 59 FF 4E 12 7C 5B 3C-46 75 57 80 7E ED 00 74   YY.N.|[<FuW.~..t
2817:2B80  07 CD 35 06 26 3D E8 05-CD 35 06 22 3D E8 A3 FF   ..5.&=...5."=...
2817:2B90  46 F2 FF 76 10 FF 76 0E-FF 5E 06 59 59 FF 4E 12   F..v..v..^.YY.N.
2817:2BA0  7C 30 3C 41 75 2C FF 46-F2 FF 76 10 FF 76 0E FF   |0<Au..F..v..v..
2817:2BB0  5E 06 59 59 FF 4E 12 7C-17 3C 4E 75 15 80 7E ED   ^.YY.N.|.<Nu..~.
2817:2BC0  00 74 07 CD 35 06 2E 3D-EE 05 CD 35 36 2A CD 39   .t..5..=...5.*=.
2817:2BD0  65 FF C7 46 F4 00 00 E9-33 FE 5F 5E 8B E5 5D C3   e..F....3._^..].
2817:2BE0  CD 39 D8 C8 55 8B EC 83-EC 0A CD 37 7E F6 F7 46   .9..U......7~..F
2817:2BF0  0A 04 00 74 31 8B 01 00-50 CD 37 6E F6 83 EC 0A   ...t1...P.7n....
2817:2C00  CD 37 7E EA CD 3D FF 36-7A 3C FF 36 78 3C FF 36   .7~..=.6z<.6x<.6
2817:2C10  76 3C FF 36 74 3C 9A 03-10 69 2A C4 5E 06 CD 3C   v<.6t<...i*.^..<
2817:2C20  DD 1F CD 3D EB 3D F7 46-0A 08 00 74 0F CD 37 6E   ...=.=.F...t..7n
2817:2C30  F6 C4 5E 06 CD 3C D8 3F-CD 3D EB 27 33 C0 50 CD   ..^..<.?.=.'3.P.
2817:2C40  37 6E F6 83 ED 0A CD 37-7E EA CD 3D 8B F0 7F 50   7n.....7~..=...P
2817:2C50  33 C0 50 50 50 9A 03 00-69 2A C4 5E 06 CD 3C D9   3.PPP...i*.^..<.
2817:2C60  1F CD 3D 8B E5 5D C3 C8-55 8B EC CD 39 46 06 8B   ..=..]..U...9F..
2817:2C70  46 0C D1 E0 74 05 72 05-CD 35 FA EB 2C CD 39 D8   F...t.r..5..,.9.
2817:2C80  FF 36 42 3D FF 36 40 3D-FF 36 3E 3D FF 36 3C 3D   .6B=.6@=.6>=.6<=
2817:2C90  33 C0 50 50 16 8D 46 16-50 1E 8B 44 3D 50 8B 01   3.PP..F.P..D=P..
2817:2CA0  00 50 9A 06 00 FE 2A 8B-E5 5D C3 55 8B EC 83 EC   .P....*..].U....
2817:2CB0  0E 56 57 C7 46 F2 0A 00-06 C4 7E 12 8B FF 7F EB   .VW.F.....~.....
2817:2CC0  5E 06 26 8B 09 26 21 01-D1 E3 D1 E3 D1 E3 2E FF   ^.&..&!.........
2817:2CD0  A7 33 00 39 00 3F 00 45-00 CD 3C D9 05 EB 0E CD   .3.9.?.E..<.....
2817:2CE0  3C DD 05 EB 08 26 80 25-F0 CD 3C DE 2D 33 DB D1   <....&.%..<.-3..
2817:2CF0  E1 D1 E3 C4 7E 0C 26 89-1D CD 35 EE CD 39 7E F4   ....~.&...5..9~.
2817:2D00  CD 3D 8B 46 F4 80 E4 47-80 FC 40 74 16 80 FC 05   .=.F...G..@t....
2817:2D10  74 0C 80 FC 01 74 02 EB-30 8A FE 7F EB 25 8A FF   t....t..0....%..
2817:2D20  7F EB 20 9A 01 00 B0 30-EB 4E 10 08 C9 7F 03 F7   .. ....0.N......
2817:2D30  D9 41 83 F9 28 76 03 E9-28 00 FC C4 7E 08 F3 AA   .A..(v..(...~...
2817:2D40  32 C0 AA CD 39 D3 E9 21-C1 CD 35 D0 CD 37 7E F6   2...9..!..5..7~.
2817:2D50  CD 3D 8B 46 FE 2D FF 3F-EA 10 4D F7 EA F3 84 4D   .=.F.-.?..M....M
2817:2D60  8A 46 FD D0 E0 F6 E4 03-C2 83 D2 00 F7 D2 8B D2   .F..............
2817:2D70  00 EB 46 10 C6 C0 7F 06-F7 DB 13 D3 7C A5 3D 12   ..F.........|.=.
2817:2D80  00 7E 03 E9 12 00 9B D3-2B D2 E9 F0 74 17 7D 02   .~......+...t.}.
2817:2D90  F7 D8 E8 9A 09 00 7C 2A-58 05 F6 7F 0E CD 3A F9   ..F...|*X.....:.
2817:2DA0  E8 03 CD 3A C9 E3 9A 08-00 7C 2A 58 CD 34 D9 CD   ...:.E...|*X.4..
2817:2DB0  39 7E F4 CD 3D F6 46 F8-45 74 14 42 43 8C F5 12   9~..=.F.Et.BC...
2817:2DC0  77 06 83 7E 10 00 7E 2D-CD 3A 76 F2 4B 8B 26 89   w..~..~-.:v.K.&.
2817:2DD0  CD 48 50 9A 08 00 7C 2A-58 CD 34 D9 CD 39 7E F4   .HP...|*X.4..9~.
2817:2DE0  CD 3D F6 46 F5 41 75 0D-4A 4B 83 7E 10 00 7E 05   .=.F.Au.JK.~..~.
2817:2DF0  CD 3A 4E F2 43 CD 35 FC-CD 3A 76 F6 C4 7E 08 03   .:N.C.5..:v..~..
2817:2E00  F8 57 32 C0 FD AA 8D 76-F6 89 04 00 CD 3D 0B D8   .W2....v.....=..
2817:2E10  75 08 36 8A 2C 80 F5 01-E5 15 36 8A 04 46 2A E0   u.6.......6..F..
2817:2E20  D2 EC 24 0F 05 30 30 AA-0A E8 4B 74 08 8A C4 AA   ..$..00...Kt....
2817:2E30  0A E8 4B 75 E5 5B 80 E5-0F 75 07 42 43 26 C6 45   ..Ku.[...u.BC&.E
2817:2E40  01 31 8B 4E 10 0B C9 7F-04 F7 D9 03 CA 83 F9 28   .1.N...........(
2817:2E50  76 03 B9 28 00 26 C6 07-00 8B C3 2B 46 08 2B D2   v..(.&.....+F.+.
2817:2E60  76 08 26 C7 07 30 00 43-E2 F8 FC 07 8B C2 5F 5E   v.&..0.C......_^
2817:2E70  8B E5 5D CA 10 00 55 8B-EC 83 EC 1E 8B 46 06 89   ..]...U......F..
2817:2E80  46 E2 C4 5E 08 8C 46 E6-89 5E E4 89 46 0C 0B 46   F..^..F..^..F..F
2817:2E90  0E 75 07 CD 39 06 95 3D-EB 07 C4 5E 0C CD 3C DD   .u..9..=...^..<.
2817:2EA0  07 CD 39 5E E8 CD 3D 8B-46 0C 0B 46 0E 75 07 CD   ..9^..=.F..F.u..
2817:2EB0  39 06 9A 3D EB 07 C4 5E-10 CD 3C DD 07 CD 39 5E   9..=...^..<...9^
2817:2EC0  F0 CD 3D 8B 46 1A 89 46-FE 8B 46 18 89 46 FC 8B   ..=.F..F..F..F..
```

```
2817:2ED0  46 16 89 46 FA 8B 46 14-89 46 F8 16 8D 46 E2 50   F..F..F..F...F.P
2817:2EE0  9A 5D 14 AC 1A 59 59 0B-C0 75 3F 8B 5E 06 4B D1   .]...YY..u?.^.K.
2817:2EF0  E3 D1 E3 FF B7 4C 3D FF-B7 4A 3D FF 76 0A FF 76   .....L=..J=.v..v
2817:2F00  06 1E 8D 8D 3D 50 1E 8B-46 3F 50 9A 0A 00 65 2D   ....=P..F?P...e-
2817:2F10  83 C4 10 83 7E 06 03 74-06 83 7E 06 04 75 05 B8   ....~..t..~..u..
2817:2F20  22 00 EB 03 B8 21 00 A3-7F 00 CD 39 46 F8 8B E5   "....!.....9F...
2817:2F30  5D CB 55 8B EC 56 8B 76-06 0B F6 7C 14 83 FE 58   ].U..V.v...|...X
2817:2F40  76 0F 8E 57 00 89 36 A4-3D 8A 84 A6 3D 98 96 EB   v..W..6.=...=...
2817:2F50  CD F7 DE 83 FE 23 77 EA-C7 06 A4 3D FF FF 8B C6   .....#w....=....
2817:2F60  A3 7F 00 B8 FF FF EB 00-5E 5D CA 02 00 02 3E 55   ........^]....U.
2817:2F70  EC 83 EC 08 1E 00 3E D1-E3 D1 E3 FF 9F 3E 6F A1   ......>.......o.
2817:2F80  00 3E FF 0E 00 3E 08 00-75 E9 FF 1E 00 3E FF 1E   .>...>..u....>..
2817:2F90  04 3E FF 1E 08 3E FF 76-06 9A 0D 01 17 18 59 5D   .>...>.v......Y]
2817:2FA0  CB 55 8B EC 83 3E 00 3E-20 75 05 B8 01 00 EB 1E   .U...>.> u......
2817:2FB0  8B 56 06 8B 46 06 8B 1E-00 3E D1 E3 D1 E3 89 87   .V..F....>......
2817:2FC0  E0 6F 89 87 3E 6F FF 06-00 3E 33 C0 EB 00 5D CB   .o...o...>3...].
2817:2FD0  55 8B EC 8B 46 06 33 C0-50 50 9A 01 00 14 2B 8B   U...F.3.PP....+.
2817:2FE0  55 E8 00 5D CB 55 8B EC-83 EC 04 C4 5E 06 26 8B   ...].U......^.&.
2817:2FF0  57 0E 26 8B 47 0C 89 16-18 3E A3 16 3E 8B 4E 08   W.&.G....>..>.N.
2817:3000  8B 5E 06 9A 97 07 17 18-75 0C C7 06 18 3E 00 00   .^......u....>..
2817:3010  C7 06 16 3E 00 00 EB 31-C4 5E 06 26 C4 5F 18 8D   ...>...1.^.&._..
2817:3020  46 FE 89 5E FC 89 56 FE-8B 46 FC C4 1E 16 3E 26   F..^..V..F....>&
2817:3030  89 57 0A 26 89 47 08 8B-16 18 3E A1 16 3E C4 5E   .W.&.G....>..>.^
2817:3040  FC 26 89 57 0E 26 89 47-0C 8B E5 5D CB 55 8B EC   .&.W.&.G...].U..
2817:3050  83 EC 04 8B 56 0C 8B 46-0A C4 5E 06 26 29 07 26   ....V..F..^.&).&
2817:3060  19 57 02 C4 5E 06 26 8B-4F 02 26 8B 1F 8B 56 08   .W..^.&.O.&...V.
2817:3070  8B 46 06 9A 3C 07 17 18-89 56 FE 89 46 FC 8B 56   .F..<....V..F..V
2817:3080  0C 8B 46 0A 05 01 00 83-D2 00 C4 5E FC 26 89 57   ..F........^.&.W
2817:3090  02 26 89 07 8B 56 0A 8B-46 08 C4 5E FC 26 89 57   .&...V..F..^.&.W
2817:30A0  06 26 89 47 04 8B 4E 08-8B 5E 06 8B 16 14 3E A1   .&.G..N..^....>.
2817:30B0  12 3E 9A 97 07 17 18 75-0D C4 5E FC 8C 06 14 3E   .>.....u..^....>
2817:30C0  89 1E 12 3E 8B 28 8B 56-FE 8B 46 FC 8B 4E 0C 8B   ...>.(.V..F..N..
2817:30D0  5E 0A 9A 3C 07 17 18 89-56 08 89 46 06 8B 56 FE   ^..<....V..F..V.
2817:30E0  8B 46 FC C4 5E 06 26 89-57 06 26 89 47 04 8B 56   .F..^.&.W.&.G..V
2817:30F0  FE 8B 46 FC 0B C2 00 8B-00 8B E5 5D CB 55 8B EC   ..F........].U..
2817:3100  83 EC 04 FF 76 08 FF 76-06 9A 57 00 45 2B 59 59   ....v..v..W.E+YY
2817:3110  89 56 FE 89 46 FC 83 7E-FE FF 75 0C 83 7E FC FF   .V..F..~..u..~..
2817:3120  75 06 33 C0 33 C0 EB 3F-8B 16 14 3E A1 12 3E C4   u.3.3..?...>..>.
2817:3130  5E FC 26 89 57 06 26 89-47 04 8B 56 08 8B 46 06   ^.&.W.&.G..V..F.
2817:3140  05 01 00 83 D2 00 C4 5E-FC 26 89 57 02 26 89 07   .......^.&.W.&..
2817:3150  C4 5E FC 8C 06 14 3E 89-1E 12 3E 8B 16 14 3E A1   .^....>...>...>.
2817:3160  12 3E 05 08 00 EB 00 8B-E5 5D CB 55 8B EC 83 EC   .>.......].U....
2817:3170  04 FF 76 18 FF 76 06 9A-07 00 45 2B 59 59 89 56   ..v..v....E+YY.V
2817:3180  FE 89 46 FC 83 7E FE FF-75 0C 83 7E FC FF 75 06   ..F..~..u..~..u.
2817:3190  33 D2 33 C0 EB 37 C4 5E-FC 8C 06 10 3E 89 1E 0E   3.3..7.^....>...
2817:31A0  3E C4 5E FC 8C 06 14 3E-89 1E 12 3E 8B 56 08 8B   >.^....>...>.V..
2817:31B0  46 06 05 01 00 83 D2 00-C4 5E FC 26 89 57 02 26   F........^.&.W.&
2817:31C0  89 07 8B 56 FE 8B 46 FC-05 08 00 EB 00 8B E5 5D   ...V..F........]
2817:31D0  CB 55 8B EC 83 EC 04 8B-46 06 0B 46 08 75 07 33   .U......F..F.u.3
2817:31E0  D2 33 C0 E9 F6 00 8B 56-08 8B 46 06 05 17 00 83   .3.....V..F.....
2817:31F0  D2 00 25 F0 FF 81 E2 FF-FF 89 56 08 89 46 06 33   ..%......V..F.3
2817:3200  C9 33 DB 8B 16 10 3E A1-0E 3E 9A 97 07 17 18 75   .3....>..>.....u
2817:3210  0F FF 76 08 FF 76 06 0E-E8 50 FF 59 59 E9 8C 00   ..v..v...P.YY...
2817:3220  8B 16 12 3E A1 16 3E 89-56 FE 89 46 FC 33 C9 33   ...>..>.V..F.3.3
2817:3230  DB 9A 97 07 17 18 75 03-E9 93 00 C4 5E FC 26 8B   ......u.....^.&.
2817:3240  57 02 26 8B 07 8B 4E 08-8B 5E 06 83 33 30 83 D1   W.&...N..^...0..
2817:3250  00 3B D1 72 18 75 04 3B-C3 72 15 FF 76 08 FF 76   .;.r.u.;.r..v..v
2817:3260  06 FF 76 FE FF 76 FC 0E-E8 E2 FD 83 C4 08 EB 6C   ..v..v.........l
2817:3270  C4 5E FC 26 8B 57 02 26-8B 07 3B 56 08 72 2A 75   .^.&.W.&..;V.r*u
2817:3280  05 3B 46 06 72 23 FF 76-FE FF 76 FC 0E E8 55 FD   .;F.r#.v..v...U.
2817:3290  59 59 C4 5E FC 26 83 07-01 26 83 57 02 00 8B 56   YY.^.&...&.W...V
2817:32A0  FE 8B 46 FC 05 08 00 E9-33 C4 5E FC 26 C4 5F 0C   ..F.....3.^.&._.
2817:32B0  8C 46 FE 89 5E FC 8B 06-0E 3E 8B 1E 16 3E 8B 56   .F..^....>...>.V
2817:32C0  FE 8B 46 FC 9A 97 07 17-18 74 03 E9 6D FF FF 76   ..F......t..m..v
2817:32D0  08 FF 76 06 0E E8 25 FE-59 59 E8 00 8B E5 5D CB   ..v...%.YY....].
2817:32E0  55 8B EC 56 57 8B 76 06-46 2B 36 7B 00 8B C6 05   U..VW.v.F+6{....
2817:32F0  3F 00 81 06 D3 EE 8B F0-3B 36 1A 3E 75 10 C4 5E   ?.......;6.>u..^
2817:3300  04 8C 06 8D 00 89 1E 8B-00 8B 01 00 E8 5C 81 06   ............\..
2817:3310  D3 E6 8B 3E 91 00 8B C6-03 06 7B 00 3A C7 76 06   ...>......{.:.v.
2817:3320  8B F7 2B 36 7B 00 56 FF-36 7B 00 9A 0D 00 5A 2B   ..+6{.V.6{....Z+
2817:3330  59 59 8B F8 83 FF FF 75-15 8B C6 81 C6 D3 E3 A3   YY.....u........
2817:3340  1A 3E C4 5E 04 8C 06 8D-00 89 1E 8B 00 8B 01 00   .>.^............
2817:3350  EB 15 EB 16 A1 7B 00 03-C7 33 D2 8B D0 33 C0 89   .....{..3...3...
```

```
2817:3360  16 91 00 A3 BF 00 33 C0-EB 00 5F 5E 5D C2 04 00   ......3..._^]...
2817:3370  55 8B EC 8B 0E 89 00 8B-1E 87 00 8B 56 08 8B 46   U...........V..F
2817:3380  06 9A 97 07 17 18 72 22-8B 0E 91 00 8B 1E 8F 00   ......r"........
2817:3390  8B 56 08 8B 46 06 9A 97-17 17 18 77 0D FF 76 08   .V..F......w..v.
2817:33A0  FF 76 06 8B 3A FF 0E C0-75 07 8E FF FF 8B 06 8B   .v..:...u.......
2817:33B0  04 33 C0 EB 00 5D C3 55-8B EC 83 EC 08 89 16 8D   .3...].U........
2817:33C0  00 A1 8B 00 8B 4E 08 8B-5E 06 9A 3C 07 17 18 89   .....N..^..<....
2817:33D0  56 FA 89 46 F8 8B 0E 89-00 8B 1E 87 00 8B 56 FA   V..F..........V.
2817:33E0  8B 46 F8 9A 97 07 17 18-72 15 8B 0E 91 00 8B 1E   .F......r.......
2817:33F0  8F 00 8B 56 FA 8B 46 F8-9A 97 07 17 18 76 08 EA   ...V..F......v..
2817:3400  FF FF 2B FF FF EB 27 C4-1E 8B 00 8C 46 FE 89 5E   ......'.....F..^
2817:3410  FC FF 76 FA FF 76 F8 E8-C6 FE 0B C0 75 03 EA FF   ..v..v......u...
2817:3420  FF 2B FF FF EB 08 8B 56-FE 8B 46 FC 8B 00 8B E5   ........V..F....
2817:3430  5D C3 55 8B EC B4 4A 8B-5E 08 8E 46 06 CD 21 72   ].U...J.^..F..!r
2817:3440  05 B8 FF FF EB 0A 8C 8D-9A 02 00 0A 2B 58 EB 00   ......8P....+X..
2817:3450  5D C3 55 8B EC 83 EC 04-56 57 33 F6 C7 46 FC 00   ].U.....VW3..F..
2817:3460  00 33 FF C4 5E 0C FF 46-0C 26 8A 07 88 46 FF 3C   .3..^..F.&...F.<
2817:3470  72 75 03 E9 01 00 EB 01-00 EB 2B 80 7E FF 77 75   ru........+.~.wu
2817:3480  0D BE 02 00 C7 46 FC 80-00 BF 02 00 EB 18 80 7E   .....F.........~
2817:3490  FF 61 75 0D BE 02 09 C7-46 FC 80 00 BF 02 00 EB   .au.....F.......
2817:34A0  05 33 C0 E9 96 00 C4 5E-0C 26 8A 07 88 46 FF FF   .3.....^.&...F..
2817:34B0  46 0C 80 7E FF 2B 74 15-C4 5E 0C 26 80 3F 2B 75   F..~.+t..^.&.?+u
2817:34C0  2D 80 7E FF 74 74 06 80-7E FF 62 75 21 80 7E FF   -.~.tt..~.bu!.~.
2817:34D0  2D 75 09 C4 5E 0C 26 8A-07 88 46 FF 8B C6 25 FC   -u..^.&...F...%.
2817:34E0  FF 0D 04 00 8B F0 C7 46-FC 80 01 BF 03 00 80 7E   .......F.......~
2817:34F0  FF 74 75 06 81 CE 00 40-EB 13 80 7E FF 62 75 0A   .tu....3.#.~.bu.
2817:3500  81 CE 00 80 81 CF 40 00-EB 13 A1 D6 40 25 00 C0   ......@.....@%..
2817:3510  0B F0 8B C6 A9 00 80 74-04 81 CF 40 00 C7 06 06   .......t...@....
2817:3520  3E 0C 22 C7 06 04 3E 06-00 C4 5E 0C 26 89 37 8B   >.......>..^.&.7.
2817:3530  46 FC C4 5E 04 26 89 07-8B C7 EB 00 5F 5E 8B E5   F..^.&......_^..
2817:3540  5D C3 00 00 55 8B EC 83-EC 04 FF 76 06 FF 76 04   ]...U......v..v.
2817:3550  16 8D 46 FC 50 16 8D 46-FE 50 E8 F5 FE C4 5E 0C   ..F.P..F.P....^.
2817:3560  26 89 47 02 0B C0 74 29-C4 5E 0C 26 80 7F 04 00   &.G...t).^.&....
2817:3570  7D 36 FF 76 FE FF 76 FC-FF 76 0A FF 76 08 9A 40   }6.v..v..v..v..@
2817:3580  00 8B 2B 83 C4 08 C4 5E-0C 26 8A 47 04 0A C0 7D   ..+....^.&.G...}
2817:3590  17 C4 5E 0C 26 C6 47 04-FF C4 5E 0C 26 C7 47 02   ..^.&.G...^.&.G.
2817:35A0  00 00 33 D2 33 C0 EB 6F-C4 5E 0C 26 8A 47 04 98   ..3.3..o.^.&.G..
2817:35B0  50 9A 05 00 E4 2B 59 0B-C0 74 09 C4 5E 0C 26 81   P....+Y..t..^.&.
2817:35C0  4F 02 00 02 B8 00 02 50-C4 5E 0C 26 F7 47 02 00   O......P.^.&.G..
2817:35D0  02 74 05 B8 01 00 EB 02-33 C0 50 33 C0 50 50 FF   .t......3.P3.PP.
2817:35E0  76 0E FF 76 0C 9A CD 00-E5 2B 83 C4 0C 0B C0 74   v..v.....+.....t
2817:35F0  15 FF 76 0E FF 76 0C 9A-0F 00 F9 2B 59 59 33 D2   ..v..v.....+YY3.
2817:3600  33 C0 EB 13 EB 11 C4 5E-0C 26 C7 47 10 00 00 8B   3......^.&.G....
2817:3610  56 0E 8B 46 0C EB 00 8B-E5 5D C2 0C 00 55 8B EC   V..F.....]...U..
2817:3620  83 EC 04 8C 5E FE C7 46-FC 1E 3F EB 02 EB 00 C4   ....^..F..?.....
2817:3630  5E FC 26 80 7F 04 00 7C-13 8B 56 FE 8B 46 FC 83   ^.&....|..V..F..
2817:3640  46 FC 14 8B AE 40 8C D8-3B C3 72 E1 C4 5E FC 26   F....@..;.r..^.&
2817:3650  80 7F 04 00 7C 08 33 D2-33 C0 EB 0A EB C9 8B 56   ....|.3.3......V
2817:3660  FE 8B 46 FC EB 00 8B E5-5D C3 55 8B EC 83 EC 04   ..F.....].U.....
2817:3670  E8 AA FF 89 56 FE 89 46-FC 0B D0 75 05 33 D2 33   ....V..F...u.3.3
2817:3680  C0 EB 19 EB 17 FF 76 FE-FF 76 FC FF 76 08 FF 76   ......v..v..v..v
2817:3690  06 FF 76 0C FF 76 0A E8-AA FE EB 00 8B E5 5D CB   ..v..v........].
2817:36A0  55 8B EC C4 5E 0E 26 8B-47 12 3B 46 0E 74 06 33   U...^.&.G.;F.t.3
2817:36B0  D2 33 C0 EB 24 FF 76 10-FF 76 0E 9A 0F 00 F9 2B   .3..$.v..v.....+
2817:36C0  8B E5 FF 76 10 FF 76 0E-FF 76 08 FF 76 06 FF 76   ...v..v..v..v..v
2817:36D0  0C FF 76 0A E8 6D FE EB-00 5D CB 55 8B EC 83 EC   ..v..m...].U....
2817:36E0  04 83 7E 06 00 7C 0D E8-33 FF 89 56 FE 89 46 FC   ..~..|..3..V..F.
2817:36F0  0B D0 75 06 33 D2 33 C0-EB 1F 8B 46 06 C4 5E FC   ..u.3.3....F..^.
2817:3700  26 8B 47 04 FF 76 FE FF-76 FC 33 C0 50 50 FF 76   &.G..v..v.3.PP.v
2817:3710  0A FF 76 08 E8 2D FE EB-00 8B E5 5D CB 55 8B EC   ..v..-.....].U..
2817:3720  1E 8B 4E 0A B4 3C C5 56-06 CD 21 1F 72 02 EB 08   ..N..<.V..!.r...
2817:3730  50 9A 02 00 0A 2B EB 00-5D C2 06 00 55 8B EC 8B   P....+..]...U...
2817:3740  5E 04 2B C9 2B D2 B4 40-CD 21 EB 00 5D C2 02 00   ^.+.+..@.!..]...
2817:3750  55 8B EC 83 EC 04 56 57-8B 7E 0A F7 C7 00 C0 75   U.....VW.~.....u
2817:3760  08 A1 D6 40 25 00 C0 0B-F8 F7 C7 00 01 75 03 E9   ...@%........u..
2817:3770  9F 00 A1 D8 40 21 46 0C-8B 46 0C A9 80 01 75 09   ....@!F..F....u.
2817:3780  B8 01 00 50 9A 02 00 0A-2B 33 C0 50 FF 76 08 FF   ...P....+3.P.v..
2817:3790  76 06 9A 0C 00 90 2C 83-C4 06 89 46 FC 3D FF FF   v.....,....F.=..
2817:37A0  75 13 F7 46 0C 80 00 74-04 33 C0 EB 03 B8 01 00   u..F...t.3......
2817:37B0  89 46 FC EB 16 F7 C7 00-04 74 0E B8 50 00 50 9A   .F.......t..P.P.
2817:37C0  02 00 0A 2B E9 F0 00 EB-02 EB 46 F7 C7 F0 00 74   ...+......F....t
2817:37D0  24 FF 76 08 FF 76 06 33-C0 50 E8 40 FF 8B F0.8B   $.v..v.3.P.@....
```

```
2817:37E0  C6 05 E0 7D 05 E3 26 E9-3D 00 56 9A 00 00 0A 2C   ...}......V....,
2817:37F0  59 E8 23 EB 19 FF 76 19-FF 76 06 FF 76 FC E8 1C   Y.#...v..v..v...
2817:3800  FF 98 F0 85 D6 09 C0 7D-05 83 C6 E9 A9 00 E9 81   .......}........
2817:3810  00 C7 46 FC 00 00 57 FF-76 08 FF 76 06 9A 0D 00   ..F...W.v..v....
2817:3820  A2 2B 3D C4 06 EB F0 8B-D6 0B C0 7C 65 33 C0 50   .+.........|e3.P
2817:3830  56 9A 08 00 E1 2B 59 59-29 46 FE A9 80 00 74 26   V....+YY)F....t&
2817:3840  81 CF 00 20 F7 C7 00 80-74 1A 8B 46 FE 25 FF 00   ... ....t..F.%..
2817:3850  0D 20 00 33 D2 52 50 8B-01 00 50 56 9A 08 00 E1   . .3.RP...PV....
2817:3860  2B 83 C4 08 EB 0A F7 C7-00 02 74 04 56 E8 CC FE   +.........t.V...
2817:3870  83 7E FC 00 74 1C F7 C7-F0 00 74 16 29 01 00 50   .~..t.....t....P
2817:3880  E8 01 00 50 FF 76 08 FF-76 06 9A 0C 00 90 2C 83   ...P.v..v.....,.
2817:3890  C4 08 08 F6 7C 1D F7 C7-00 03 74 05 E8 00 10 EB   ....|.....t.....
2817:38A0  02 33 C0 8B D7 81 E2 FF-F8 0B C2 8B CE D1 E3 89   .3..............
2817:38B0  87 AE 40 8B C6 EB 00 5F-5E 8B E5 5D C3 55 8B EC   ..@...._^..].U..
2817:38C0  56 80 01 8B 4E 0A F7 C1-02 00 75 04 80 02 F7 C1   V...N.....u.....
2817:38D0  04 00 75 02 80 00 1E 05-56 08 E1 F0 22 4E 0A CA   ..u.....V..."N..
2817:38E0  C1 34 3D C0 21 1F 72 17-55 F0 8E 46 0A 25 FF F8   ..=.!.r...F.%..
2817:38F0  3D 00 90 E9 3E 31 53 89-87 AE 40 8E C6 E8 05 50   ..........@....P
2817:3900  9A 02 00 0A 2B E5 00 5E-5D C3 55 8B EC 83 EC 04   ....+..^].U.....
2817:3910  56 57 C4 5E 04 26 8B 37-E5 FE C4 5E 04 26 F7 47   VW.^.&.7...^.&.G
2817:3920  02 40 00 74 04 33 C6 E3-27 C4 5E 04 26 C4 5F 0C   .@.t....'.^.&._.
2817:3930  8C 46 FE 89 5E FC EB 0D-C4 5E FC FF 46 FC 26 80   .F..^....^..F.&.
2817:3940  3F 0A 75 01 47 83 C6 4E-0B 33 75 EC 8B C7 E8 00   ?.u.G..N..u.....
2817:3950  5F 5E 8B E5 5D C2 04 00-55 8B EC FF 76 08 FF 76   _^..]...U...v..v
2817:3960  06 9A 0D 00 99 2C 3B E3-0B C0 74 06 E3 FF FF 59   ..........t.....
2817:3970  72 00 83 7E 0E 01 75 19-C4 5E 06 26 83 3F 00 7E   r..~..u..^.&.?.~
2817:3980  10 FF 76 08 FF 76 06 E8-90 FF 99 29 46 0A 19 56   ..v..v.....)F..V
2817:3990  0C C4 5E 06 26 81 67 02-5F FE C4 5E 06 26 C7 07   ..^.&.g._..^.&..
2817:39A0  00 00 C4 5E 06 26 8B 57-0A 26 8B 47 08 C4 5E 06   ...^.&.W.&.G..^.
2817:39B0  26 89 57 0E 26 89 47 0C-FF 76 0E FF 76 0C FF 76   &.W.&.G..v..v..v
2817:39C0  0A C4 5E 06 26 8A 47 04-98 50 9A 06 00 62 2C 83   ..^.&.G..P...b,.
2817:39D0  55 83 FA FF 75 0A 3D FF-FF 75 05 B8 FF FF EB 02   ....u.=..u......
2817:39E0  33 C0 EB 00 5D C3 55 8B-EC 83 EC 04 FF 76 08 FF   3...].U......v..
2817:39F0  76 06 9A 0D 00 99 2C 59-59 0B C0 74 03 E9 FF FF   v......YY..t....
2817:3A00  58 FF FF E9 4E 8B 01 00-50 33 C0 50 50 C4 5E 06   ....N...P3.PP.^.
2817:3A10  26 8A 47 04 98 50 9A 06-00 62 2C 83 C4 08 89 56   &.G..P...b,....V
2817:3A20  FE 89 46 FC C4 5E 06 26-83 7F 00 7E 1E 8B 56 FE   ..F..^.&.?.~..V.
2817:3A30  8B 46 FC 52 50 FF 76 08-FF 76 06 E8 CC FE 99 8B   .F.RP.v..v......
2817:3A40  D8 85 CA 58 5A 2B C3 1B-D1 8B 06 83 56 FE 8B 46   ...XZ+......V..F
2817:3A50  FC EB 00 8B E5 5D C3 55-8B EC 83 EC 04 56 BE 14   .....].U....V..
2817:3A60  00 8C 5E FE C7 46 FC 1E-3F 8B 20 C4 5E FC 26 83   ..^..F..?. .^.&.
2817:3A70  47 02 25 00 0C 3D 00 0C-75 0D FF 76 FE FF 76 FC   G.%..=..u..v..v.
2817:3A80  9A 0D 00 99 2C 59 59 83-46 FC 14 8B C6 4E 03 C0   .....YY.F....N..
2817:3A90  75 D9 5E 8B E5 5D C3 55-8B EC C4 5E 04 26 F7 47   u.^..].U...^.&.G
2817:3AA0  02 00 02 74 03 E8 AF FF-C4 5E 04 26 FF 77 06 C4   ...t.....^.&.w..
2817:3AB0  5E 04 26 8B 57 0A 26 8B-47 08 C4 5E 04 26 89 57   ^.&.W.&.G..^.&.W
2817:3AC0  0E 26 89 47 0C 52 50 C4-5E 04 26 8A 47 04 98 50   .&.G.RP.^.&.G..P
2817:3AD0  9A 06 00 2C 2C 83 C4 04-5E 04 26 89 07 0B C0 7E   ........^.&....~
2817:3AE0  0F C4 5E 04 26 81 67 02-DF FF 33 C0 EB 37 EB 30   ..^.&.g...3..7.0
2817:3AF0  C4 5E 04 26 83 3F 00 75-16 C4 5E 04 26 8B 47 02   .^.&.?.u..^.&.G.
2817:3B00  25 7F FE 0D 20 00 C4 5E-04 26 89 47 02 EB 11 C4   %... ..^.&.G....
2817:3B10  5E 04 26 C7 07 00 00 C4-5E 04 26 81 4F 02 10 00   ^.&......^.&.O...
2817:3B20  83 FF FF EB 00 5D C2 04-00 55 8B EC C4 5E 06 26   .....]...U...^.&
2817:3B30  FF 07 FF 76 08 FF 76 06-9A F3 00 BC 2B 8B E5 5E   ...v..v.....+...
2817:3B40  00 5D C2 55 8B EC 83 EC-02 C4 5E 06 26 FF 0F 7C   .].U......^.&..|
2817:3B50  14 C4 5E 06 26 FF 47 0C-26 C4 5F 0C 4B 26 8A 07   ..^.&.G.&._.K&..
2817:3B60  B4 00 E9 31 01 C4 5E 06-26 FF 07 7C 0B C4 5E 06   ...1..^.&..|..^.
2817:3B70  26 F7 47 02 10 01 74 0F-C4 5E 06 26 81 4F 02 10   &.G...t..^.&.O..
2817:3B80  00 B8 FF FF E9 0F 01 C4-5E 06 26 81 4F 02 80 00   ........^.&.O...
2817:3B90  C4 5E 06 26 83 7F 06 00-74 1B FF 76 08 FF 76 06   .^.&.?..t..v..v.
2817:3BA0  E8 F4 FE 0B C0 74 06 B8-FF FF E9 E9 00 E9 9A E9   .....t..........
2817:3BB0  E4 00 83 3E DA 40 00 75-54 8B 46 06 8B 1E 3F 80   ...>.@.uT.F...?.
2817:3BC0  D9 3B C3 75 48 C4 5E 06-26 8A 47 04 98 50 9A 05   .;.uH.^.&.G..P..
2817:3BD0  00 E4 2B 59 0B C0 75 09-C4 5E 06 26 81 67 02 FF   ..+Y..u..^.&.g..
2817:3BE0  FD 83 00 02 50 C4 5E 06-26 F7 47 02 00 02 74 05   ....P.^.&.G...t.
2817:3BF0  B8 01 00 EB 02 33 C0 50-33 C0 50 50 FF 76 08 FF   .....3.P3.PP.v..
2817:3C00  76 06 9A 0D 00 EE 2B 83-C4 0C E9 7A FF C4 5E 06   v.....+....z..^.
2817:3C10  26 F7 47 02 00 02 74 03-E8 3C FE 8B 01 00 50 16   &.G...t..<....P.
2817:3C20  8D 46 FF 50 C4 5E 06 26-8A 47 04 98 50 9A 05 00   .F.P.^.&.G..P...
2817:3C30  38 2C 83 C4 08 3D 01 00-74 38 C4 5E 06 26 8A 47   8,...=..t8.^.&.G
2817:3C40  04 98 50 9A 0D 00 92 2D-59 3D 01 00 74 09 C4 5E   ..P....-Y=..t..^
2817:3C50  06 26 81 4F 02 10 00 EB-14 C4 5E 06 26 8B 47 02   .&.O.......^.&.G.
```

```
2817:3C60  25 7F FE 0D 20 00 C4 5E-06 26 89 47 02 EB FF FF   %... .. ^.&.G....
2817:3C70  E8 24 80 7E FF CD 75 0E-C4 5E 06 26 F7 47 02 40   .$.~..u..^.&.G.@
2817:3C80  00 75 03 E9 87 FF C4 5E-06 26 81 67 02 DF FF 8A   .u.....^.&.g....
2817:3C90  46 FF E4 00 EB 00 8B E5-5D CB 1E 89 1E 3F 80 0E   F.......]....?F.
2817:3CA0  E8 A0 FE 59 59 EB 00 C3-55 8B EC 1E B8 44 8A 46   ...YY...U....D.F
2817:3CB0  08 8B 5E 0E 8B 4E 0E 03-56 0A CD 21 1F 72 0C 83   ..^..N..V..!.r..
2817:3CC0  7E 08 00 75 04 33 C0 EB-0A 8B 08 50 9A 02 00 0A   ~..u.......P....
2817:3CD0  2B EB 00 5D CB 55 8B EC-B8 00 44 8B 5E 06 CD 21   +..].U....D.^..!
2817:3CE0  B8 00 00 72 04 D1 E0 D1-D0 EB 00 5D CB 55 8B EC   ...r.......].U..
2817:3CF0  56 57 8B 76 10 8B 7E 0E-C4 5E 06 26 8B 47 12 8B   VW.v..~..^.&.G..
2817:3D00  56 06 3B C2 75 08 83 FF-02 7F 06 81 FE FF 7F 76   V.;.u..........v
2817:3D10  06 B8 FF FF E9 14 01 83-3E DC 40 00 75 14 8B 46   ........>.@.u..F
2817:3D20  06 3B 32 3F 8C D9 3B C3-75 08 C7 06 DC 40 01 00   ..2?..;.u....@..
2817:3D30  EB 19 83 3E DA 40 00 75-12 8B 46 06 8B 1E 3F 8C   ...>.@.u..F...?.
2817:3D40  D9 3B C3 75 06 C7 06 DA-40 01 00 C4 5E 06 26 83   .;.u....@...^.&.
2817:3D50  3F 00 74 16 B8 01 00 50-33 C0 50 50 FF 76 08 FF   ?.t....P3.PP.v..
2817:3D60  76 06 9A 58 00 A7 2B 83-C4 0A C4 5E 06 26 F7 47   v..X..+....^.&.G
2817:3D70  02 04 00 74 12 C4 5E 06-26 FF 77 0A 26 FF 77 08   ...t..^.&.w.&.w.
2817:3D80  9A 36 00 33 2D 59 59 C4-5E 06 26 81 67 02 F3 FF   ...3-YY.^.&.g...
2817:3D90  C4 5E 06 26 C7 47 06 00-00 8B 56 08 8B 46 06 05   .^.&.G....V..F..
2817:3DA0  05 00 C4 5E 06 26 89 57-0A 26 89 47 08 C4 5E 06   ...^.&.W.&.G..^.
2817:3DB0  26 89 57 0E 26 89 47 0C-83 FF 0C 74 6A 0B F6 76   &.W.&.G....tj..v
2817:3DC0  66 87 06 02 3E 0F 22 07-06 00 3E 0E 30 8B 46 0A   f...>.....>...F.
2817:3DD0  0B 46 0C 75 21 56 9A 00-00 14 2B 59 89 56 0C 89   .F.u!V....+Y.V..
2817:3DE0  46 0A 0B D0 74 0B C4 5E-06 26 81 4F 02 04 00 EB   F...t..^.&.O....
2817:3DF0  05 E8 FF FF EB 35 89 56-0C 8B 46 0A C4 5E 06 26   .....5.V..F..^.&
2817:3E00  89 57 0E 26 89 47 0C C4-5E 06 26 89 57 0A 26 89   .W.&.G..^.&.W.&.
2817:3E10  47 08 C4 5E 06 26 89 77-06 83 FF 01 75 09 C4 5E   G..^.&.w....u..^
2817:3E20  06 26 81 4F 02 08 00 33-C0 EB 00 5F 5E 5D CB 55   .&.O...3..._^].U
2817:3E30  8B EC 56 BE FF FF C4 5E-06 26 8B 47 12 8B 56 06   ..V....^.&.G..V.
2817:3E40  3B C2 74 05 B8 D6 E9 8D-00 C4 5E 06 26 83 7F 06   ;.t........^.&..
2817:3E50  00 74 3C C4 5E 06 26 83-3F 00 7D 16 FF 76 08 FF   .t<.^.&.?.}..v..
2817:3E60  76 06 9A 0D 00 F9 2C 59-59 0B C0 74 05 B8 D6 E9   v......YY..t....
2817:3E70  8A 00 C4 5E 06 26 F7 47-02 04 00 74 12 C4 5E 06   ...^.&.G...t..^.
2817:3E80  26 FF 77 0A 26 FF 77 08-9A 06 00 33 2D 59 59 C4   &.w.&.w....3-YY.
2817:3E90  5E 06 26 80 7F 04 00 7C-11 C4 5E 06 26 8A 47 04   ^.&....|..^.&.G.
2817:3EA0  98 50 9A 0F 00 06 2D 59-EB F0 C4 5E 06 26 C7 47   .P.....Y...^.&.G
2817:3EB0  02 00 00 C4 5E 06 26 C7-47 06 00 00 C4 5E 06 26   ....^.&.G....^.&
2817:3EC0  C7 07 00 00 C4 5E 06 26-C6 47 04 FF C4 5E 06 26   .....^.&.G...^.&
2817:3ED0  83 7F 10 00 74 22 33 C0-50 50 C4 5E 06 26 FF 77   ....t"3.PP.^.&.w
2817:3EE0  10 9A 0F 00 74 2D 52 50-9A 0F 00 7F 2D 59 59 C4   ....t.RP.....YY.
2817:3EF0  5E 06 26 C7 47 10 00 00-EB 06 EB 00 5E 5D CB 55   ^.&.G.......^].U
2817:3F00  8B EC 56 8B 76 06 0B F6-7C 05 83 FE 14 7C 05 B8   ..V.v...|....|..
2817:3F10  06 00 50 9A 02 00 0A 2B-EB 1C 8B DE D1 E3 C7 87   ..P....+........
2817:3F20  AE 40 FF FF 56 9A 00 00-0A 2C 59 EB 00 5E 5D CB   .@..V.....Y..^].
2817:3F30  55 8B EC 56 8B 76 06 B4-3E 8B DE CD 21 72 0C D1   U..V.v..>...!r..
2817:3F40  E3 C7 87 AE 40 FF FF 33-C0 EB 08 50 9A 02 00 0A   ....@..3...P....
2817:3F50  2B EB 00 5E 5D CB 55 8B-EC 83 EC 04 56 BE 0F 00   +..^].U.....V...
2817:3F60  8C 5E FE C7 46 FC 8D 3F-EB 1C C4 5E FC 26 F7 47   .^..F..?...^.&.G
2817:3F70  02 03 00 74 0D FF 76 FE-FF 76 FC 9A 0F 00 F9 2B   ...t..v..v.....+
2817:3F80  59 59 83 46 FC 14 4E 75-E1 5E 8B E5 5D CB 55 8B   YY.F..Nu.^..].U.
2817:3F90  EC 83 EC 04 56 BE 04 00-8C 5E FE C7 46 FC 1E 3F   ....V....^..F..?
2817:3FA0  EB 1D C4 5E FC 26 F7 47-02 03 00 74 0D FF 76 FE   ...^.&.G...t..v.
2817:3FB0  FF 76 FC 9A 0D 00 F9 2C-59 59 4E 83 46 FC 14 0B   .v.......YYN.F..
2817:3FC0  F6 75 DF 5E 8B E5 5D CB-55 8B EC 56 57 E9 8E 00   .u.^..].U..VW...
2817:3FD0  FF 46 08 C4 5E 04 26 8B-47 06 3B 46 08 76 05 8B   .F..^.&.G.:F.v..
2817:3FE0  7E 08 EB 07 C4 5E 04 26-8B 7F 06 C4 5E 04 26 F7   ~....^.&.....^.&.
2817:3FF0  47 02 40 00 75 0C E9 71-00 C4 5E 04 26 83 7F 06   G.@.u..q.^.&....
2817:4000  00 74 67 C4 5E 04 26 8B-47 06 3B 46 08 73 5B C4   .tg.^.&.G.:F.s[.
2817:4010  5E 04 26 83 3F 00 75 52-FF 4E 08 33 FF EB 13 C4   ^.&.?.uR.N.3....
2817:4020  5E 04 26 8B 47 06 03 F8-C4 5E 04 26 89 47 06 29   ^.&.G....^.&.G.)
2817:4030  46 08 C4 5E 04 26 8B 47-06 3B 46 08 76 E1 57 FF   F..^.&.G.:F.v.W.
2817:4040  76 0C FF 76 0A C4 5E 04-26 8A 47 04 98 50 9A 0B   v..v..^.&.G..P..
2817:4050  00 38 2C 83 C4 08 8B F8-01 7E 0A 3B F7 74 09 EB   .8.......v.:.t..
2817:4060  C7 2B C6 01 46 08 EB 5F-EB 54 8B 3E 83 C6 C4 5E   .+..F.._T.....^
2817:4070  0A 26 8B 07 FF 46 0A FF-4E 08 8B 46 08 0B C0 74   .&...F..N..F...t
2817:4080  36 4F 74 3D C4 5E 04 26-FF 0F 7C 15 C4 5E 04 26   6Ot=.^.&..|..^.&
2817:4090  FF 47 0C 26 C4 5F 0C 4B-26 8A 07 34 00 8B F0 EB   .G.&._.K&.......
2817:40A0  0F FF 76 06 FF 76 04 9A-5F 00 8D 2B 59 59 8B F0   ..v..v.....+YY..
2817:40B0  3B C6 3D FF FF 75 85 83-FE FF 75 02 EB 09 83 7E   ..=..u....u....~
2817:40C0  08 00 74 03 E9 09 FF 8B-46 08 EB 00 5F 5E 5D CB   ..t.....F..._^].
2817:40D0  0A 00 55 8B EC 83 EC 04-56 57 8B 76 0A 0B F6 75   ..U.....VW.v...u
2817:40E0  04 33 C0 EB 6B 8B C6 33-D2 8B 5E 0C 33 C9 9A 33   .3..k..3..^.3...
2817:40F0  07 17 1B 89 56 FE 89 46-FC 83 FA 01 77 27 72 04   ....V..F....w'r.
```

```
2817:4100  05 C0 73 21 FF 76 08 FF-76 06 FF 76 FC FF 76 10   ..s!.v..v..v..v.
2817:4110  FF 76 0E E8 B2 FE 50 E8-46 FC 5A 2B C0 33 D2 F7   .v....P.F.Z+.3..
2817:4120  F6 E3 2D 5E 2B 8B 7E 0C-47 EB 03 01 76 06 4F 8B   ..-.+.~.G...v.O.
2817:4130  C7 05 C0 74 14 FF 76 08-FF 76 06 56 FF 76 10 FF   ...t..v..v.V.v..
2817:4140  76 0E E8 87 FE 0E 00 74-E2 8B 46 00 2B C7 EB 00   v.......t..F.+...
2817:4150  5F 5E 8B E5 5D C3 55 8B-EC 83 EC 04 56 57 8E 46   _^..].U.....VW.F
2817:4160  0C 40 3D 02 00 72 0D 8B-5E 06 D1 E3 F7 87 AE 40   .@=..r..^......@
2817:4170  00 02 74 05 33 C0 E9 9D-00 FF 76 0C FF 76 0A FF   ..t.3.....v..v..
2817:4180  76 08 FF 76 06 9A 0E 00-7B 20 83 C4 08 E9 46 FC   v..v....@.....F.
2817:4190  8B 46 FC 40 3D 02 00 72-0D 8B 5E 06 D1 E3 F7 87   .F.@=..r..^.....
2817:41A0  AE 40 00 80 74 05 8B 46-FC E8 6A 90 8B 4E FC 0A   .@..t..F..j..N..
2817:41B0  76 08 8B FE 8B 3E FC 26-AC 3C 1A 74 03 3C 0D 74   v......&.<.t.<.t
2817:41C0  05 AA E2 F3 EB 1F E2 EF-06 E3 89 01 00 50 8D 46   ...........S...P.F
2817:41D0  FF 16 50 FF 76 06 9A 08-00 3B 20 83 C4 08 5B 07   ..P.v....8....[.
2817:41E0  FC 3A 46 FF AA 3E F6 75-02 E3 8E E3 22 53 8B 02   ..F..:.u...."S..
2817:41F0  00 50 F7 D9 1B C0 50 51-FF 76 06 9A 06 00 62 20   .P....PQ.v....b.
2817:4200  83 C4 08 89 5E 06 D1 E3-81 8F AE 40 00 02 5B 83   ....^......@..[.
2817:4210  C7 2B C3 EB 00 5F 5E 8B-E5 5D C3 55 8B EC 1E 54   .+..._^..].U....
2817:4220  3F 8B 5E 06 8B 4E 0C C5-56 08 CD 21 1F 72 02 EB   ?.^..N..V..!.r..
2817:4230  09 50 9A 02 00 0A 2B EB-00 5D C3 55 8B EC 87 EC   .P....+..].U....
2817:4240  04 56 57 83 76 0A 05 F6-75 06 83 46 0C E9 6F 00   .VW.v...u..F..o.
2817:4250  8B C6 3D 22 EB 5E 0C 3D-C9 9A 8B 07 17 18 89 36   ..=..^.=........V
2817:4260  FE 89 46 FC 83 FA 01 77-29 72 04 09 C0 73 23 FF   ..F....w)r...s#.
2817:4270  76 08 FF 76 06 FF 76 FC-FF 76 10 FF 76 0E 9A E3   v..v..v..v..v...
2817:4280  01 A6 2C 50 8B 46 FC EA-2B C0 33 D2 F7 F6 E3 2F   ...P.F.Z+.3..../
2817:4290  EB 2D 8B 7E 0C 47 EB 03-01 76 06 4F E3 C7 0E C0   .-.~.G...v.O....
2817:42A0  74 16 FF 76 08 FF 76 06-56 FF 76 10 FF 76 0E 9A   t..v..v.V.v..v..
2817:42B0  E3 01 A6 22 08 C0 74 E0-8B 46 00 2B C7 EB 00 5F   ......t..F.+..._
2817:42C0  5E 8B E5 5D C3 55 8B EC-81 EC 9E 00 56 57 8B 46   ^..].U......VW.F
2817:42D0  0C 40 3D C2 00 73 05 33-C0 E9 49 01 8B 5E 06 D1   .@=..s.3..I..^..
2817:42E0  E3 F7 87 AE 40 00 80 74-17 FF 76 0C FF 76 0A FF   ....@..t..v..v..
2817:42F0  76 08 FF 76 06 9A 08 00-E9 2C 83 C4 08 E9 25 01   v..v....Y,....%.
2817:4300  EB 8E 06 D1 E3 81 A7 AE-40 FF FD C4 8E 08 8D 86   .^......@...^...
2817:4310  7C FF 89 9E 7A FF 8B 46-0C 89 86 76 FF 8C D3 8E   |...z..F...v....
2817:4320  C3 8D 9E 7E FF 8D 86 74-FF 89 9E 72 FF E9 A1 00   ...~...t...r....
2817:4330  FF 8E 76 FF C4 9E 7A FF-FF 86 7A FF 26 84 07 8B   ..v...z...z.&...
2817:4340  86 79 FF 3C 0A 75 0C C4-9E 72 FF 26 C6 07 0D FF   .y.<.u...r.&....
2817:4350  86 72 FF 84 86 79 FF C4-9E 72 FF 26 88 07 FF 86   .r...y...r.&....
2817:4360  72 FF 8B 86 72 FF 8D D1-8D 9E 7E FF 3D D2 2B C3   r...r.....~.=.+.
2817:4370  83 DA 00 3B D2 7C 5A 75-0E 3D 80 00 72 53 8B 86   .....|Zu.=..rS..
2817:4380  72 FF 8C D1 8D 9E 7E FF-3D D2 2B C3 83 DA 00 8B   r.....~.=.+.....
2817:4390  F0 56 16 8D 86 7E FF 50-FF 76 06 9A 02 00 E9 2C   .V...~.P.v....Y,
2817:43A0  83 C4 08 8B F3 3B C7 3B-C6 74 16 0B FF 73 05 E9   ........;.t...s..
2817:43B0  FF FF EB 08 E9 46 0C 2B-86 76 FF 03 C7 2B C6 EB   .....F.+.v...+..
2817:43C0  64 90 33 8E C3 8D 9E 7E-FF 3C 86 74 FF 89 9E 72   d......~...t...r
2817:43D0  FF 8E 8E 76 FF 00 74 03-E9 55 FF E8 86 72 FF 8C   ...v..t..U...r..
2817:43E0  D1 8D 9E 7E FF 3D D2 2B-C3 83 DA 00 8B F0 8B C6   ...~.=.+........
2817:43F0  05 C0 76 20 56 16 8D 86-7E FF 50 FF 76 06 9A 08   ..v.V...~.P.v...
2817:4400  00 E9 2C 83 C4 08 8B FB-E8 C7 3B C6 74 12 0B FF   .Y,.......;.t...
2817:4410  73 1E 8B FF FF EB 07 8B-46 0C 03 C7 2B C6 EB 05   s.......F...+...
2817:4420  8B 46 0C 8B 00 5F 5E 8B-E5 5D C3 55 8B EC 8B 5E   .F..._^..].U...^
2817:4430  06 D1 E3 F7 87 AE 40 00-08 74 12 B9 02 00 50 33   ......@..t....P3
2817:4440  C0 50 50 FF 76 06 9A 06-00 62 20 8B E5 1E B4 40   .PP.v....b.....@
2817:4450  8B 5E 06 8B 4E 0C C5 56-08 CD 21 1F 72 0F 50 8B   .^..N..V..!.r.P.
2817:4460  5E 06 D1 E3 81 8F AE 40-00 10 58 EB 08 50 9A 02   ^......@..X..P..
2817:4470  00 0A 2B EB 00 5D C3 55-8B EC 56 33 C0 50 FF 76   ..+..].U..V3.P.v
2817:4480  08 FF 76 06 9A 03 00 90-2C 83 C4 06 8B F0 83 FE   ..v.............
2817:4490  FF 75 04 8B C6 EB 1C F7-46 0A 02 00 74 06 F7 C6   .u......F...t...
2817:44A0  01 00 75 04 33 C0 EB 08-C7 06 7F 00 05 00 B9 FF   ..u.3...........
2817:44B0  FF EB 00 5E 5D CB 55 8B-EC 8B 8E 06 D1 E3 81 A7   ...^].U...^.....
2817:44C0  AE 40 FF FD 8A 42 8A 46-0C 85 5E 06 3B 4E 0A 8B   .@...B.F..^..N..
2817:44D0  56 08 CD 21 72 02 EB 09-50 9A 02 00 0A 2B 99 EB   V..!r...P....+..
2817:44E0  00 5D C3 55 8B EC 83 EC-22 56 57 06 C4 7E 0C 8B   .].U...."VW..~..
2817:44F0  5E 0A 8C FB 24 77 5C 80-FB 02 72 57 8B 46 10 2B   ^...$w\...rW.F..
2817:4500  4E 12 0B C9 7D 12 80 7E-0B 00 74 0C 26 C6 05 2D   N...}..~..t.&..-
2817:4510  47 F7 D9 F7 D8 83 D9 00-2D 76 DE E3 10 91 2B D2   G.......-v....+.
2817:4520  F7 F3 91 F7 F3 36 88 14-46 E3 0A E5 F0 2B D2 F7   .....6..F....+..
2817:4530  F3 36 88 14 46 0B C0 75-F4 8D 4E 3E F7 D9 03 CE   .6..F..u..N.....
2817:4540  FC 4E 36 8A 04 3C 0A 73-04 04 3A EB 03 02 46 36   .N6....s..:...F.
2817:4550  AA E2 EE 80 00 8A 07 8B-E5 0E 8B 46 0C EB 00 5F   .........V..F..._
2817:4560  5E 8B 5E 5D CA 0E 00 8B-8B 5D 83 7E 0C 0A 75 06   ^..]...U...~..u.
2817:4570  8E 46 06 99 EB 05 8B 46-06 33 D2 52 50 FF 76 0A   .F.....F.3.RP.v.
2817:4580  FF 76 08 FF 76 0C E0 01-50 50 61 50 0E E8 53 FF   .v..v...P.aP..S.
2817:4590  E8 00 5D C8 55 8B EC FF-76 08 FF 76 06 FF 76 0C   ..].U...v..v..v.
```

```
2817:45A0  FF 76 0A FF 76 0E E8 00-50 8D 61 50 0E E8 3D FF   .v..v...P.aF..3.
2817:45B0  E8 00 5D C3 55 8B EC FF-76 08 FF 76 06 FF 76 0C   ..].U...v..v..v.
2817:45C0  FF 76 0A FF 76 0E E8 7E-0E CA 75 05 B8 01 00 EB   .v..v..~..u.....
2817:45D0  02 33 C0 50 8D 61 50 0E-E8 06 FF E8 00 5D C3 55   .3.P.aP......].U
2817:45E0  8B EC 8B 46 08 0B 46 0A-75 08 8C 5E 0A C7 46 08   ...F..F.u..^..F.
2817:45F0  60 70 C4 5E 08 26 C6 07-00 1E E8 3E 40 50 FF 76   `p.^.&......@P.v
2817:4600  0A FF 76 08 9A 09 00 81-2C E8 EE E8 0A 00 50 E8   ..v...........P.
2817:4610  56 0A 8B 46 02 C5 03 00-52 50 8B 46 06 33 D2 52   V..F....RP.F.3.R
2817:4620  50 9A 34 00 65 22 8B E5-1E 8B EC 40 50 FF 76 0A   P...e......@P.v.
2817:4630  FF 76 08 9A C8 00 81 2C-E5 EE E8 56 0A E8 46 08   .v.......,...V..F.
2817:4640  E8 00 5D CA 06 00 55 8B-EC FF 76 06 FF 76 06 8D   ..]...U...v..v..
2817:4650  3E 5E 70 FF 75 05 E8 02-00 EB 03 E8 01 00 01 06   >^p.u...........
2817:4660  5E 70 A1 5E 70 E0 0E E8-75 FF E9 56 08 39 46 06   ^p.^pP..u..V..F.
2817:4670  33 C0 50 FF 76 08 FF 76-06 9A C7 00 EE 2C 83 E5   3.P.v..v....^...
2817:4680  3D FF FF 75 C4 8B 56 08-8B 46 06 E8 00 5D C3 55   =..u..V..F...].U
2817:4690  8B EC 1E 84 41 CE 56 06-CD 21 1F 72 04 33 C0 EB   ....A.V..!.r.3..
2817:46A0  08 50 9A 02 00 0A 2B E3-00 5D C3 55 8B EC 56 57   .P....+..].U..VW
2817:46B0  FC 1E C4 7E 06 8B D7 32-C0 B9 FF FF F2 AE 06 8D   ...~...2........
2817:46C0  75 FF C4 7E 0A 8B FF FF-F2 AE F7 D1 2B F9 06 1F   u..~........+...
2817:46D0  07 87 F7 F3 C6 01 00 74-02 A4 49 D1 E9 F3 A5 73   .......t..I....s
2817:46E0  01 A4 8B 32 8D 32 1F 8E-00 5F 5E 5D C3 55 8B EC   ........._^].U..
2817:46F0  56 57 FC C4 7E 06 32 C0-B9 FF FF F2 AE 8B C1 F7   VW..~.2.........
2817:4700  D0 48 EB 00 5F 5E 5D C3-55 8B EC 56 57 FC C4 7E   .H.._^].U..VW..~
2817:4710  0A 8B F7 32 C0 B9 FF FF-F2 AE F7 D1 1E 06 1F C4   ...2............
2817:4720  7E 06 F3 A4 1F 8B 56 08-8B 46 06 E8 00 5F 5E 5D   ~.....V..F..._^]
2817:4730  C3 55 8B EC 56 57 8C DA-C4 7E 06 C5 76 0A 8B 4E   .U..VW...~..v..N
2817:4740  0E D1 E9 FC F3 A5 73 01-A4 8E DA 8B 56 08 8B 46   ......s.....V..F
2817:4750  06 E8 00 5F 5E 5D C3 55-8B EC 56 57 C4 7E 06 8B   ..._^].U..VW.~..
2817:4760  4E 0A 8A 46 0C 8A E0 FC-F7 C7 01 00 74 04 E3 09   N..F........t...
2817:4770  AA 49 D1 E9 F3 AB 73 01-AA 5F 5E 5D C3 55 8B EC   .I....s.._^].U..
2817:4780  FF 76 0A FF 76 0C FF 76-08 FF 76 06 0E E8 C7 FF   .v..v..v..v.....
2817:4790  8B E5 8B 56 08 8B 46 06-E8 00 5D C3 55 8B EC 1E   ...V..F...].U...
2817:47A0  B4 43 8A 46 0A 8E 4E 0C-C5 56 06 CD 21 1F 72 03   .C.F..N..V..!.r.
2817:47B0  91 E8 08 50 9A 02 00 0A-2B EB 00 5D C3 55 8B EC   ...P....+..].U..
2817:47C0  8B ED 04 55 5E 06 D1 E7-F7 37 4E 40 00 02 74 06   ....^......3..t.
2817:47D0  E8 01 00 E8 54 90 8B 00-44 8B 5E 06 CD 21 72 41   ....T...D.^..!rA
2817:47E0  F6 C2 80 75 38 B8 01 42-33 C9 33 D2 CD 21 72 31   ...u8..B3.3..!r1
2817:47F0  52 50 8B 02 42 33 C9 33-D2 CD 21 59 46 FC 3B 56   RP..B3.3..'.F..V
2817:4800  FE 5A 59 72 10 B3 00 32-CD 21 72 1E 3B 56 FE 72   .ZYr...B.!r.:V.r
2817:4810  0C 77 05 3B 46 FC 72 05-B8 01 00 EB 0C 33 C0 EB   .w.:F.r......3..
2817:4820  08 50 9A 02 00 0A 2B EB-00 8B E5 5D C3 55 8B EC   .P....+....].U..
2817:4830  56 C4 5E 06 26 8B 47 12-8B 56 06 3B C2 74 06 B8   V.^.&.G..V.;.t..
2817:4840  FF FF E9 CD 00 C4 5E 06-26 80 3F 00 7C 65 C4 5E   ......^.&.?.|e.^
2817:4850  06 26 F7 47 02 08 00 75-1C C4 5E 06 26 8B 57 0E   .&.G...u..^.&.W.
2817:4860  26 8B 47 0C 8B 4E 08 8B-5E 06 8B 3D 05 3B D1 75   &.G..N..^....:.u
2817:4870  3E 3B C2 75 3A C4 5E 06-26 C7 07 00 00 C4 5E 06   >;.u:.^.&.....^.
2817:4880  26 89 57 0E 26 89 47 0C-8B 4E 08 8B 5E 06 83 C3   &.W.&.G..N..^...
2817:4890  05 3B D1 75 1A 3B C3 75-16 C4 5E 06 26 8B 57 0A   .;.u.;.u..^.&.W.
2817:48A0  26 8B 47 08 C4 5E 06 26-89 57 0E 26 89 47 0C 33   &.G..^.&.W.&.G.3
2817:48B0  C0 EB 5F C4 5E 06 26 8B-77 06 C4 5E 06 26 03 37   .._.^.&.w..^.&.7
2817:48C0  46 C4 5E 06 26 29 37 56-C4 5E 06 26 8B 57 0A 26   F.^.&)7V.^.&.W.&
2817:48D0  8B 47 08 C4 5E 06 26 89-57 0E 26 89 47 0C 52 50   .G..^.&.W.&.G.RP
2817:48E0  C4 5E 06 26 8A 47 04 98-50 9A 05 00 43 2C 83 C4   .^.&.G..P...C...
2817:48F0  08 3B C6 74 19 C4 5E 06-26 F7 47 02 00 02 75 0E   .;.t..^.&.G...u.
2817:4900  C4 5E 06 26 81 4F 02 10-00 B8 FF FF EB 04 33 C0   .^.&.O........3.
2817:4910  EB 00 5E 5D CB 55 8B EC-83 AA 2C 50 B8 E3 01 50   ..^].U.....?...F
2817:4920  1E 8B 32 3F 50 FF 76 08-FF 76 06 16 8D 46 0A 50   ..2?P.v..v...F.P
2817:4930  9A 3A 00 D8 2C EB 00 5D-C3 55 8B EC C4 5E 08 26   .:.....].U...^.&
2817:4940  FF 0F FF 76 0A FF 76 08-8A 46 06 98 50 9A 28 00   ...v..v..F..P.(.
2817:4950  9A 2C 8B E5 EB 00 5D C3-55 8B EC 83 EC 02 8A 46   ..:...].U......F
2817:4960  06 88 46 FF C4 5E 08 26-FF 07 7D 48 8A 46 FF C4   ..F..^.&..}H.F..
2817:4970  5E 08 26 FF 47 0C 26 C4-5F 0C 48 26 88 07 C4 5E   ^.&.G.&._.K&...^
2817:4980  08 26 F7 47 02 08 00 74-23 80 7E FF 0A 74 06 80   .&.G...t#.~..t..
2817:4990  7E FF 0D 75 17 FF 76 0A-FF 76 08 9A 0D 00 99 2C   ~..u..v..v.....,
2817:49A0  59 59 0B C0 74 06 B8 FF-FF E9 4A 01 8A 46 FF B4   YY..t.....J..F..
2817:49B0  00 E9 42 01 C4 5E 08 26-FF 0F C4 5E 08 26 F7 47   ..B..^.&...^.&.G
2817:49C0  02 90 00 75 0B C4 5E 08-26 F7 47 02 02 00 75 0F   ...u..^.&.G...u.
2817:49D0  C4 5E 08 26 81 4F 02 10-00 B8 FF FF E9 17 01 C4   .^.&.O..........
2817:49E0  5E 08 26 81 4F 02 00 01-C4 5E 08 26 83 7F 06 00   ^.&.O....^.&....
2817:49F0  74 3A C4 5E 08 26 83 3F-00 74 19 FF 76 0A FF 76   t:.^.&.?.t..v..v
2817:4A00  08 9A 0D 00 99 2C 59 59-0B C0 74 06 B8 FF FF E9   ......YY..t.....
2817:4A10  E4 00 EB 12 C4 5E 08 33-FF FF 26 8B 57 06 2B C2   .....^....&.W.+.
2817:4A20  C4 5E 08 26 89 07 E9 0B-FF E9 CA 00 83 7E 0C 40   .^.&.......~.>.@
```

```
2817:4A30  00 75 54 8B 46 08 3B 0D-7F 8D 09 7B C0 75 4B C4   .uT.F.;..{..uK.
2817:4A40  5E 08 26 8A 47 04 98 E0-9A 05 00 E1 2B 59 05 D0   ^.&.G.......+Y..
2817:4A50  75 09 C4 5E 08 26 81 67-02 FF FD 3B C0 02 50 C4   u..^.&.g......P.
2817:4A60  5E 08 26 F7 47 02 00 02-74 05 B8 02 00 EB 02 33   ^.&.G...t......3
2817:4A70  C0 50 0E C0 50 50 FF 76-0A FF 76 08 9A 0D 00 E5   .P..PP.v..v.....
2817:4A80  23 83 C4 0C E9 58 FF 80-7E FF 0A 75 2A C4 5E 08   #....X..~..u*.^.
2817:4A90  26 F7 47 02 40 00 75 1F-E8 01 00 50 1E E8 1A 41   &.G.@.u....P...A
2817:4AA0  50 C4 5E 08 26 8A 47 04-98 50 9A 0E 00 59 2D 83   P.^.&.G..P...Y-.
2817:4AB0  C4 08 3D 01 00 75 1F E8-01 00 50 16 8D 46 C6 50   ..=..u....P..F.P
2817:4AC0  C4 5E 08 26 8A 47 04 98-50 9A 05 00 59 2D 83 C4   .^.&.G..P...Y-..
2817:4AD0  08 3D 01 00 74 1F C4 5E-08 26 F7 47 02 00 02 75   .=..t..^.&.G...u
2817:4AE0  0E C4 5E 08 26 81 4F 02-10 00 B8 FF FF EB 07 8A   ..^.&.O.........
2817:4AF0  46 FF 84 C0 EB 00 8B E5-5D C3 55 8B EC 56 8B 76   F.......].U..V.v
2817:4B00  06 1E E8 32 3F 50 56 0E-E8 4D FE 83 C4 06 EB 00   ...2?PV..M......
2817:4B10  5E 5D C3 55 8B EC 56 57-8B 76 0A 46 C4 5E 06 26   ^].U..VW.v.F.^.&
2817:4B20  F7 47 02 08 00 74 2B E8-02 EB 00 4E EB C6 0B C0   .G...t+....N....
2817:4B30  74 1D FF 76 0C FF 76 08-C4 5E 0C FF 46 0C 26 8A   t..v..v..^..F.&.
2817:4B40  07 98 50 0E E8 11 FE 83-C4 06 3D FF FF 75 DA E9   ..P.......=..u..
2817:4B50  A8 00 C4 5E 06 26 F7 47-02 40 00 74 52 C4 5E 06   ...^.&.G.@.tR.^.
2817:4B60  26 83 7F 06 00 74 48 C4-5E 06 26 8B 47 06 3B C6   &....tH.^.&.G.;.
2817:4B70  73 3D C4 5E 06 26 8B 3F-00 74 15 FF 76 0B FF 76   s=.^.&.?.t..v..v
2817:4B80  06 9A 0D 00 59 59 E9 59-0B C0 74 04 33 C0 EB 6E   ......YY..t.3..n
2817:4B90  4E 56 FF 76 0E FF 76 0C-C4 5E 06 26 8A 47 04 98   NV.v..v..^.&.G..
2817:4BA0  50 9A 0B 00 5F 2D 83 C4-08 8B F8 3B F7 EB 4B EB   P...Y-....+..K..
2817:4BB0  0D EB 00 4E 3B C6 0B C0-74 40 C4 5E 06 26 FF 07   ...N...t@.^.&..
2817:4BC0  7D 1D C4 5E 0C FF 46 0C-26 8A 07 C4 5E 06 26 FF   }..^..F.&...^.&.
2817:4BD0  47 0C 26 C4 5F 0C 4B 26-88 07 54 00 EB 17 FF 76   G.&._.K&..T....v
2817:4BE0  0B FF 76 06 C4 5E 0C FF-46 0C 26 8A 07 50 0E E8   ..v..^..F.&..P..
2817:4BF0  47 FD 83 C4 06 3D FF FF-75 57 EB 06 5B 00 5F 5E   G....=..uW..[._^
2817:4C00  5D CA 0A 00 55 8B EC FF-76 0E FF 76 06 FF 76 0B   ]...U...v..v..v.
2817:4C10  FF 76 06 9A CD 00 8E 2C-E9 59 50 1E E8 32 3F 50   .v.....,.YP..2?P
2817:4C20  9A E3 01 AA 2C 05 C0 74-05 B8 FF FF EB 1F 1E E8   ....,..t........
2817:4C30  32 3F 50 28 0A 00 50 9A-28 00 AA 2C 8B EC 3D 0A   2?P...P.(.....=.
2817:4C40  00 74 05 B8 FF FF EB 03-B8 0A 00 EB 00 5D C8 55   .t...........].U
2817:4C50  8B EC 8B 56 04 B9 04 0F-E8 23 41 FC 8A C6 D2 E8   ...V.....#A.....
2817:4C60  D7 AA 8A C6 22 C5 D7 AA-8A C2 D2 E8 D7 AA 8A C2   ...."...........
2817:4C70  22 C5 D7 AA EB 00 5D C2-02 00 55 8B EC 81 EC 96   "......]...U.....
2817:4C80  00 56 57 C7 46 AA 00 00-C6 46 AD 50 EB 3D 57 99   .VW.F....F.P.=W.
2817:4C90  FF FF 32 C0 F2 AE F7 D1-49 5F 03 36 8B 05 47 FE   ..2.....I_.6..G.
2817:4CA0  4E AD 7E 25 53 51 52 06-8D 46 AE 2B F8 16 8D 46   N.~%SQR..F.+...F
2817:4CB0  AE 50 57 FF 76 10 FF 76-0E FF 8E 12 C6 46 AD 50   .PW.v..v..^..F.P
2817:4CC0  01 7E AA 8D 7E AE 07 5A-59 5B 03 06 FC 8D 7E AE   .~..~..ZY[....~.
2817:4CD0  E9 8E 6C FF E8 8E 6C FF-24 76 0A 26 AC 3A C0 74   ..l...l.$v.&.:.t
2817:4CE0  12 3C 25 74 11 36 E8 0E-47 FE 4E AD 7F ED EB 3D   .<%t.6..G.N.....
2817:4CF0  FF 8B EB E9 F4 04 E9 26-75 FF 26 AC 3C 25 74 EE   .........x.&.<%t.
2817:4D00  89 BE 6C FF 33 C9 89 8E-76 FF C7 86 6A FF 20 00   ..l.3...v...j. .
2817:4D10  8B EE 75 FF C7 86 70 FF-FF FF C7 86 72 FF FF FF   ..u...p.....r...
2817:4D20  EB 02 26 AC 32 E4 8B D0-8B DB 80 EB 20 80 FB 60   ..&.2....... ..`
2817:4D30  73 47 8A 9F 3D 41 95 2E-3D 17 00 76 03 E9 74 04   sG..=A..=..v..t.
2817:4D40  8B D8 D1 E3 2E FF A7 09-01 54 01 3C 01 95 01 48   .........T.<...H
2817:4D50  01 8D 01 C7 01 09 02 13-02 23 02 7B 01 59 02 3B   .........#.{.Y.;
2817:4D60  02 37 02 3A 02 E3 02 9C-03 39 03 5B 03 0E 0E 34   .7.:.....9.[...4
2817:4D70  05 34 05 34 05 67 01 71-01 E9 F8 03 80 FD 00 77   .4.4.g.q.......w
2817:4D80  F3 83 8E 6A FF 01 E8 9A-80 FD 00 77 E0 83 8E 6A   ...j.......w...j
2817:4D90  FF 02 EB 8E 80 FD 00 77-E0 80 8E 75 FF 2B 74 04   .......w...u.+t.
2817:4DA0  88 96 75 FF E9 7B FF 83-A6 6A FF DF EB 05 E9 71   ..u..{...j.....q
2817:4DB0  FF 83 8E 6A FF 20 EB C5-EB 67 FF 80 FD 00 77 47   ...j. ...g....wG
2817:4DC0  F7 86 6A FF 02 00 75 24-83 8E 6A FF 08 95 01 E9   ..j...u$..j.....
2817:4DD0  50 FF E9 FF 3C 06 C4 7E-06 26 8B 05 83 46 06 02   P.......~.&...F..
2817:4DE0  07 80 FD 02 73 09 89 86-70 FF 8E 07 E7 33 FF 30   ....s...p....3..
2817:4DF0  FD 04 75 DE 89 86 72 FF-FE 25 E9 2E FF 80 FD 04   ..u...r...%.....
2817:4E00  73 D0 8E 04 E7 1B FF 92-1C 30 98 80 FD 02 77 13   s........0....w.
2817:4E10  85 02 87 86 70 FF 05 C0-7C D2 D1 E0 8B D0 D1 E0   ....p...|.......
2817:4E20  D1 E0 03 C2 01 86 70 FF-E9 57 FE 80 FD 04 75 A2   ......p......u.
2817:4E30  87 86 72 FF 0B C0 7D 84-D1 E0 8B D0 D1 E0 D1 E0   ..r...|.........
2817:4E40  03 C2 01 86 72 FF E9 D9-FE 83 8E 6A FF 10 B5 05   ....r......j....
2817:4E50  E9 CF FE 81 8E 6A FF 00-01 83 A6 6A FF EF B5 0E   .....j.....j....
2817:4E60  E9 8F FE 83 A6 64 FF EF-E1 3E 6A FF 80 00 B5 0E   .....d......j....
2817:4E70  E9 AF FE 87 09 E8 0A 87-0A E9 05 87 10 E3 E9 02   ................
2817:4E80  DA 26 86 7E FF 00 C6 86-6F FF 00 E3 F6 6E FF 34   ...u.....o....n..
2817:4E90  7E 06 26 8B 05 33 D2 EB-12 87 0A C6 86 6F FF 01   ~.&..3.......o..
2817:4EA0  88 96 6E FF C4 7E 06 26-8B 05 99 47 47 89 76 0A   ..n..~.&...GG.v.
2817:4EB0  F7 86 6A FF 10 00 74 05-26 8B 15 47 47 89 7E 06   ..j...t.&..GG.~.
```

```
2817:4EC0  8D 5E 7B FF 0B C0 75 03-0B D2 75 2F 83 BE 72 FF   ..{...u...u/..r.
2817:4ED0  00 75 03 E9 EE 6C FF 8E-8E 70 FF E3 18 83 F9 FF   .u-..l...p......
2817:4EE0  74 16 8B 36 6A FF 2E 03-00 74 04 32 C0 EB 02 B2   t...j.%..t..0...
2817:4EF0  20 EA C2 E8 A5 F2 E2 F9-E9 DD FD 83 8E 6A FF 04   .............j..
2817:4F00  52 50 16 57 8A C7 98 50-9A 86 6F FF 50 53 9A 0C   RP.W...P..o.PS..
2817:4F10  00 65 C0 16 07 8B 96 72-FF 0B D2 7F 03 E9 1F 01   .e.....r........
2817:4F20  E9 20 01 83 7E 6E FF 39-76 0A 8D 3E 7A FF C4 5E   .....n..v...z..^
2817:4F30  06 26 FF 37 43 43 89 5E-06 F7 36 6A FF 20 00 74   .&.7CC.^...j. .t
2817:4F40  10 26 FF 37 43 43 89 5E-06 16 07 8E 01 FD 50 3A   .&.7CC.^.......:
2817:4F50  AA 16 07 E8 F9 FC 76 C6-05 00 C6 86 6F FF 00 8C   ......v.....o...
2817:4F60  A6 6A FF F9 3D 8E 7A FF-2B F9 97 CF 8E 96 72 FF   .j....z.+.....r.
2817:4F70  3E D1 7F 02 E8 D1 E9 36-00 E9 76 0A 89 96 6E FF   :..........v...n.
2817:4F80  C4 7E 06 26 8B 05 83 46-06 02 16 07 8D 8E 7B FF   .~.&...F......{.
2817:4F90  32 E4 26 89 05 89 01 00-E9 3E 00 E9 76 CA 8B 96   2.&.........v...
2817:4FA0  6E FF C4 7E 06 F7 86 6A-FF 20 00 75 0D 26 8B 3D   n..~...j. .u.&.=
2817:4FB0  8C 46 06 02 1E 07 C5 FF-E8 0B 26 C4 3D 83 46 06   .F.......&.=.F.
2817:4FC0  04 8C C0 05 C7 75 05 1E-07 BF 1C 41 E8 EF FC 3B   .....u.....A...;
2817:4FD0  8E 72 FF 76 04 E8 8E 72-FF E9 9D 00 89 76 0A 8B   .r.v...r.....v..
2817:4FE0  96 6E FF C4 7E 06 3B 8E-72 FF 0B C9 7D 03 89 06   .n..~..r...}...
2817:4FF0  00 06 57 51 16 E8 9E 72-FF 53 52 E8 01 00 23 86   ..WQ...{.SR...#.
2817:5000  6A FF 50 3B 86 6A FF A9-80 00 74 0A B8 02 00 C7   j.P..j....t.....
2817:5010  46 FE 04 00 EB 17 A9 00-01 74 0A B8 08 00 C7 46   F........t.....F
2817:5020  FE 0A 00 EB 08 C7 46 FE-08 00 B8 06 00 50 9A F4   ......F......P..
2817:5030  07 17 18 83 46 FE 01 46-06 16 07 8D 8E 7B FF F7   ....F..F.....{..
2817:5040  36 6A FF 0B 00 74 13 83-96 70 FF 0B D2 7E 09 E8   .j...t...p...~..
2817:5050  3C FC 2B D1 7E 04 89 96-76 FF 8A 86 75 FF 0A D0   <.+.~...v...u...
2817:5060  74 14 26 80 3D 2D 74 0E-83 AE 76 FF 01 83 96 76   t.&.=-t...v....v
2817:5070  FF 00 4F 26 88 05 E8 15-FD 8B F7 E8 8E 6C FF 8B   ..O&.........l..
2817:5080  9E 70 FF E8 05 00 23 36-6A FF 3D 05 00 75 16 8A   .p....#.j.=..u..
2817:5090  A6 6E FF 80 FC 6F 75 10-E3 8E 76 FF 00 7F 0E 27   .n...ou...v.....
2817:50A0  86 76 FF 01 00 E5 1F 90-90 FD 78 74 05 8C F2 E8   .v........xt...X
2817:50B0  75 14 E3 8E 6A FF 40 4B-4B 83 AE 76 FF 02 7D 06   u...j.@KK..v..}.
2817:50C0  C7 86 76 FF 00 00 03 8E-76 FF F7 86 6A FF 02 00   ..v.....v...j...
2817:50D0  75 0C EB 0E 80 20 E8 02-FE 4B 3B 29 7F F6 F7 86   u.... ...K:.....
2817:50E0  6A FF 40 00 74 0C 50 30-E8 80 F8 8A 86 6E FF E8   j.@.t..0.....n..
2817:50F0  A9 FB 8B 96 76 FF 0B D2-7E 27 2B CA 2B DA 26 8A   ....v...~'+.+.&.
2817:5100  04 3C 2D 74 03 3C 20 74-04 3C 2B 75 07 26 AC E8   .<-t.< t.<+u.&..
2817:5110  89 FE 49 4B E7 CA E3 07-B0 30 E8 7E F8 E2 F9 97   ..IK.....0.~....
2817:5120  CA E3 12 E8 E9 26 AC 36-8B 05 47 FE 4E 4D 7F 03   .....&.&..G.N...
2817:5130  E8 71 FB E2 F0 0E D8 7E-09 8B 0B 80 20 E8 E8 FB   .c......~..... .[.
2817:5140  E2 F9 E9 93 F8 89 76 0A-C4 7E 06 F7 86 6A FF 3D   ......v..~...j.
2817:5150  00 75 05 26 8B 3D 83 46-06 02 1E 07 8B 07 26 C4   .u.&.=.F.......&.
2817:5160  3D 83 46 06 04 8E 50 00-2A 46 FD 0C 46 AA 26 89   =.F...P.*F..F.&.
2817:5170  05 E9 60 F9 E8 56 75 FF-8E 46 0C 85 8E 6C FF 90   ..`....x..F...l..
2817:5180  25 E8 17 F9 26 AC 0A C0-75 F7 80 7E 4D 50 7D 03   %...&...u..~.P}.
2817:5190  E8 11 F5 07 E8 46 AA E2-00 5F 5E 8B E5 5D CA 10   .....F..._^..]..
2817:51A0  00 9A 09 00 31 2D E8 00-0E E5 16 91 00 A1 5F 00   ....1-..........
2817:51B0  8B 0E 8D 00 8B 1E E8 00-9A DF 09 17 18 C5 F2 FF   ................
2817:51C0  83 D2 FF E9 00 03 E8 23-E0 FF 76 08 FF 76 05 9A   ......U.../..v..
2817:51D0  E0 02 33 2D 28 55 5D 3E-55 33 E0 83 ED 04 33 C9   ..3-..].U.....3.
2817:51E0  33 D5 E3 16 18 3E A1 16-3E 9A 97 07 17 18 74 56   3.....>.......tV
2817:51F0  C4 1E 16 3E 26 C4 5F 0C-8D 46 FE 89 5E FC 8B 56   ...>&._..F..^..V
2817:5200  08 8B 46 06 C4 1E 16 3E-26 89 57 0E 26 89 47 0C   ..F....>&.W.&.G.
2817:5210  8E 56 08 8B 46 06 C4 5E-FC 26 89 57 0A 26 89 47   .V..F..^.&.W.&.G
2817:5220  08 8B 56 FE 8B 46 FC C4-5E 06 26 89 57 0E 26 89   ..V..F..^.&.W.&.
2817:5230  47 0C 8B 16 18 3E A1 16-3E C4 5E 06 26 89 57 0A   G....>..>.^.&.W.
2817:5240  26 89 47 09 E8 2D C4 5E-06 8C 06 12 3E 89 1E 16   &.G..-.^.....>...
2817:5250  3E E8 56 08 8E 46 06 C4-5E 06 26 89 57 0A 26 89   >.V..F..^.&.W.&.
2817:5260  47 08 8B 56 08 8B 46 06-C4 5E 06 26 89 57 0E 26   G..V..F..^.&.W.&
2817:5270  89 47 0D 8E 5E 5D C3 5E-EB EC 83 EC 04 C4 5E 0A   .G...].U......^.
2817:5280  26 8B 57 02 26 8B 07 C4-5E 06 26 01 07 26 11 57   &.W.&...^.&..&.W
2817:5290  02 8B 4E 0C EB 5E CA 8B-16 14 3E A1 12 3E 9A 97   ..N..^....>..>..
2817:52A0  07 17 18 75 0D C4 5E 06-8C 06 14 3E 89 1E 12 3E   ...u..^....>...>
2817:52B0  8E 2C C4 5E 0A 26 8B 4F-02 26 8E 1F 8B 56 0C 8B   ...^.&.O.&...V..
2817:52C0  46 0A 9A 3D 07 17 18 89-56 FE 89 46 FC 8B 56 08   F..{....V..F..V.
2817:52D0  8B 46 06 C4 5E FC 26 89-57 06 26 89 47 04 FF 76   .F..^.&.W.&.G..v
2817:52E0  0C FF 76 0A 9A 18 00 14-28 59 59 8B 8E 5D C3 55   ..v.....+YY..].U
2817:52F0  8B 3C 8B EC 04 8B 05 14-3E 8B 1E 12 3E 8B 16 10   .........>...>...
2817:5300  3E A1 08 3E 9A 97 07 17-18 75 30 FF 36 10 3E FF   >.........u.6.>.
2817:5310  36 0E 3E 9A 90 00 45 2B-E5 59 C7 06 14 3E 00 00   6.>...E+.Y...>..
2817:5320  C7 06 12 3E 00 00 33 D3-8E C7 33 33 EC 06 10 3E   ......3.....3....>
2817:5330  89 1E 0E 3E E9 9F 00 C3-1E 12 3E 26 C4 5F 04 8C   ..../........&._..
2817:5340  46 FE 89 5E FC C4 5E FC-26 8B 57 02 26 8B 07 25   F..^..^.&.W.&..%
```

```
2817:5350  01 00 81 ED 00 00 09 00-75 5C FF 76 FE FF 76 FC   ........u\.v..v.
2817:5360  9A 15 00 14 2B 59 59 8B-0E 10 3E 8B 1E 0E 3E 89   ....+YY...>...>.
2817:5370  56 FE 8B 46 FC 9A 97 07-17 18 75 1C C7 06 14 3E   V..F......u....>
2817:5380  00 00 C7 06 12 3E 00 00-33 D2 8E DA 33 DB 8C 06   .....>..3...3...
2817:5390  10 3E 89 1E 0E 3E 8B 0F-C4 5E FC 26 C4 5F 04 8C   .>...>...^.&._..
2817:53A0  06 14 3E 89 1E 12 3E FF-76 FE FF 76 FC 9A 90 00   ..>...>.v..v....
2817:53B0  45 2B 59 59 E2 1A FF 36-14 3E FF 36 12 3E 9A 90   E+YY...6.>.6.>..
2817:53C0  00 45 2B 59 59 C4 5E FC-8C 06 14 3E 89 1E 12 3E   .E+YY.^....>...>
2817:53D0  8B E5 5D CB 55 8B EC 83-EC 08 C4 5E 06 26 83 2F   ..].U......^.&./
2817:53E0  01 26 83 5F 02 00 C4 5E-06 26 8B 4F 02 26 8B 1F   .&._...^.&.O.&..
2817:53F0  8B 56 08 8B 46 06 9A 3C-07 17 18 89 56 FA 89 46   .V..F..<....V..F
2817:5400  F3 C4 5E 06 26 C4 5F 04-8C 46 FE 89 5E FC C4 5E   ..^.&._..F..^..^
2817:5410  FC 26 8B 57 02 26 8B 07-25 01 00 81 E2 00 00 0B   .&.W.&..%.......
2817:5420  D0 75 45 8B 0E 10 3E 8B-1E 0E 3E 8B 56 08 8B 46   .uE...>...>.V..F
2817:5430  06 9A 97 07 17 18 74 30-C4 5E 06 26 8B 57 02 26   ......t0.^.&.W.&
2817:5440  8B 07 C4 5E FC 26 01 07-26 11 57 02 8B 56 FE 8B   ...^.&..&.W..V..
2817:5450  46 FC C4 5E F8 26 89 57-06 26 89 47 04 C4 5E FC   F..^.&.W.&.G..^.
2817:5460  8C 46 06 89 5E 04 E9 00-FF 76 08 FF 76 06 0E E8   .F..^....v..v...
2817:5470  E8 FD 59 59 C4 5E F8 26-8B 57 02 26 8B 07 25 01   +.YY.^.&.W.&..%.
2817:5480  00 81 ED 00 00 09 00 75-12 FF 76 FA FF 76 F8 FF   .......u..v..v..
2817:5490  76 08 FF 76 06 0E E8 3E-FD 83 C4 08 8B E5 5D CB   v..v...>......].
2817:54A0  55 8B EC 8B 46 06 0B 46-08 75 02 EB 73 8B 56 08   U...F..F.u..s.V.
2817:54B0  8B 46 06 05 FF FF 83 D2-FF 9A 3C 07 17 18 89 56   .F........<....V
2817:54C0  08 89 46 06 89 56 08 8B-46 06 3B 16 14 3E 75 0C   ..F..V..F.;..>u.
2817:54D0  3B 06 12 3E 75 06 0E E8-15 FE EB 0C FF 76 08 FF   ;..>u........v..
2817:54E0  76 06 0E E8 E2 FE 8B E5-5D CB 55 8B EC 83 AA 2C   v.......].U....,
2817:54F0  50 B8 E3 01 50 FF 76 08-FF 76 06 FF 76 0C FF 76   P...P.v..v..v..v
2817:5500  0A 16 8D 46 D4 50 9A 3A-00 D8 2C EB 00 5D CB 55   ...F.P.:..,..].U
2817:5510  8B EC 83 EC 08 C6 46 FD-00 9A 01 00 8F 2E 84 00   ......F.........
2817:5520  89 46 FB 9A 01 00 8F 2E-81 08 D3 E8 84 00 89 46   .F.............F
2817:5530  FA E9 F9 00 C4 5E 0C FF-46 0C 26 8A 07 88 46 FD   .....^..F.&...F.
2817:5540  B4 00 2D 07 00 3D 06 00-77 46 8B D8 D1 E3 2E FF   ..-..=..wF......
2817:5550  A7 5C 00 61 00 72 00 90-00 9B 00 90 00 90 00 81   .\.a.r..........
2817:5560  00 B4 0E E8 07 9A 3C 08-17 18 8A 46 FD B4 00 E9   ......<....F....
2817:5570  3E 00 A0 94 41 B4 00 3B-46 F8 7D 03 FF 4E F8 EB   >...A..;F.}..N..
2817:5580  6F A0 94 41 B4 00 89 46-F8 EB 65 FF 46 FA EB 60   o..A...F..e.F..`
2817:5590  80 3E 9D 41 00 75 32 83-3E A3 41 00 74 2B 8A 26   .>.A.u2.>.A.t+.&
2817:55A0  98 41 8A 46 FD 89 46 FE-8B 46 FE 40 50 8B 46 FA   .A.F..F..F.@P.F.
2817:55B0  40 50 9A 00 00 E5 2E 52-50 16 8D 46 FE 50 E8 01   @P.....RP..F.P..
2817:55C0  00 50 9A 25 00 E5 2E EB-22 8A 56 FB 8A 76 FA B4   .P.%...."..V..v..
2817:55D0  02 B7 00 9A 3C 08 17 18-8A 1E 98 41 8A 46 FD B4   ....<......A.F..
2817:55E0  09 B7 00 B9 01 00 9A 3C-08 17 18 FF 46 FE EB 03   .......<....F...
2817:55F0  A0 96 41 B4 00 3B 46 FE-7E 05 A0 94 41 B4 00 3B   ..A..;F.~...A...
2817:5600  46 F8 FF 46 FA A0 97 41-B4 00 3B 46 FA 7D 1E 8D   F..F...A..;F.}..
2817:5610  06 50 FF 36 94 41 FF 36-95 41 FF 36 96 41 FF 36   .P.6.A.6.A.6.A.6
2817:5620  97 41 B0 01 50 9A 2E 00-F4 2D FF 4E F4 8B 46 0A   .A..P....-.N..F.
2817:5630  FF 4E 0A 0B C0 74 07 E9-FA FE 8A 56 F9 8A 76 FA   .N...t.....V..v.
2817:5640  B4 02 B7 00 9A 3C 08 17-18 8A 46 FD B4 00 EB 00   .....<....F.....
2817:5650  8B E5 5D CA 0A 00 55 8B-EC 0E E8 0F 00 50 33 C0   ..]...U......P3.
2817:5660  50 50 FF 76 08 FF 76 06-16 8D 46 0A 50 9A 3A 00   PP.v..v...F.P.:.
2817:5670  D8 2C EB 00 5D CB 80 3E-AC 41 00 74 0A C6 06 AC   ....]..>.A.t....
2817:5680  41 00 A0 AD 41 EB 05 B8-00 07 CD 21 B4 00 EB 00   A...A......!....
2817:5690  C3 56 80 3E AC 41 00 74-08 0E E8 D9 FF EB F0 EB   .V.>.A.t........
2817:56A0  0F 0E E8 D1 FF 8A F0 95-C6 50 9A 08 00 EF 2D 59   .........P....-Y
2817:56B0  8B 16 EB 00 5E C3 55 8B-EC 80 3E AC 41 00 74 05   ....^.U...>.A.t.
2817:56C0  B8 FF FF EB 0D C6 06 AC-41 01 8B 46 06 A2 AD 41   ........A..F...A
2817:56D0  B4 00 5D CB 55 8B EC 56-57 1E 55 C4 76 06 FC 2B   ..].U..VW.U.v..+
2817:56E0  C0 99 B9 0A 00 B7 00 BF-1D 3E 26 8A 1C 46 F6 C1   ..........&..F..
2817:56F0  01 75 F7 ED 00 00 80 FB-2B 74 06 80 FB 2D 75 05   .u......+t...-u.
2817:5700  45 26 8A 1C 46 83 FE 3F-77 2F 80 FB 30 72 2A F7   E&..F..?w/..0r*.
2817:5710  E1 03 C3 13 D6 74 5A EB-12 8B FA B9 0A 00 F7 E1   .....t..........
2817:5720  97 87 D1 F7 E1 92 97 03-C7 13 D1 26 8A 1C 46 80   ...........&..F.
2817:5730  FB 39 77 05 80 EB 30 73-E0 4D 7D 07 F7 DA F7 D8   .9w...0s.M}.....
2817:5740  83 DA 00 5D 07 EB 00 5F-5E 5D CB 55 8B EC FF 76   ...]..._^].U...v
2817:5750  08 FF 76 06 0E E8 7D FF-8B E5 E5 00 5D CB 55 8B   ..v...}.....].U.
2817:5760  EC 83 EC 02 56 57 33 D2-B8 3C 00 52 50 FF 76 08   ....VW3..<.RP.v.
2817:5770  FF 76 06 9A 23 09 17 18-A3 8A 70 33 D2 B8 3C 00   .v..#.....p3..<.
2817:5780  52 50 FF 76 08 FF 76 06-9A 1A 09 17 18 89 56 08   RP.v..v.......V.
2817:5790  89 46 06 33 D2 B8 3C 00-52 50 FF 76 08 FF 76 06   .F.3..<.RP.v..v.
2817:57A0  9A 23 09 17 18 A3 8C 70-33 D2 B8 3C 00 52 50 FF   .#.....p3..<.RP.
2817:57B0  76 08 FF 76 06 9A 1A 09-17 18 89 56 08 89 46 06   v..v.......V..F.
2817:57C0  33 D2 B8 18 00 52 50 FF-76 08 FF 76 06 9A 1A 09   3....RP.v..v....
```

```
2817:57D0  17 18 89 46 FE 8B 46 FE-D1 E0 D1 E0 05 46 00 A3   ...F..F......F..
2817:57E0  94 70 8B 46 FE 8A 8B 05-F7 E2 8B F8 33 D2 8B FE   .p.F........3...
2817:57F0  8B 52 50 FF 76 08 FF 76-06 9A 23 09 17 18 8B 56   .RP.v..v..#....V
2817:5800  08 89 46 06 8B 7E 22 F7-06 84 70 00 80 75 07 83   ..F..~"...p..u..
2817:5810  C6 1B 8B C6 99 3B 56 08-7C 05 7F 05 3B 46 06 76   .....;V.|...;F.v
2817:5820  02 E5 19 89 C6 8B 1E 00-FF F7 F3 03 F8 FF 06 94   ................
2817:5830  70 8B C6 99 29 46 06 19-56 08 83 C8 87 7E 0A 00   p...)F..V....~..
2817:5840  74 50 83 3E 84 42 00 74-49 33 D2 8B 18 00 52 50   tP.>.B.tI3....RP
2817:5850  FF 76 08 FF 76 06 9A 23-09 17 18 50 33 D2 8B 18   .v..v..#...P3...
2817:5860  00 52 50 FF 76 08 FF 76-06 9A 1A 09 17 18 50 33   .RP.v..v......P3
2817:5870  C0 50 A1 94 70 05 8A FF-50 9A E6 01 89 2E 0E C0   .P..p...P.......
2817:5880  74 10 83 46 06 01 83 56-08 00 C7 06 9A 70 01 00   t..F...V.....p..
2817:5890  EB 06 C7 06 9A 70 00 00-33 D2 8B 18 00 52 50 FF   .....p..3....RP.
2817:58A0  76 08 FF 76 06 9A 23 09-17 18 A3 8E 70 33 D2 8B   v..v..#.....p3..
2817:58B0  1E 00 52 50 FF 76 08 FF-76 06 9A 1A 09 17 18 89   ..RP.v..v.......
2817:58C0  56 08 89 46 06 8B 46 06-A3 92 70 8B 46 06 05 04   V..F..F...p.F...
2817:58D0  00 03 F8 8B C7 8B 07 00-FF F7 F3 89 16 96 70 83   ..............p.
2817:58E0  46 06 01 83 56 08 00 F7-06 94 70 03 00 75 37 83   F...V.....p..u7.
2817:58F0  7E 08 00 7C 12 7F 06 83-7E 06 3C 76 0A 83 6E 06   ~..|....~.<v..n.
2817:5900  01 83 5E 08 00 EB 1F 83-7E 08 00 75 19 83 7E 06   ..^.....~..u..~.
2817:5910  3C 75 13 C7 06 92 70 01-00 C7 06 90 70 1D 00 8B   <u....p.....p...
2817:5920  8A 70 8B D4 EB 3F C7 06-92 70 00 00 E8 14 8B 1E   .p...?..p.......
2817:5930  92 70 EA 87 AE 41 9B 99-29 46 06 19 56 08 FF 06   .p...A..)F..V...
2817:5940  92 70 8B 1E 92 70 8A 87-AE 41 98 99 3B 56 08 7C   .p...p...A..;V.|
2817:5950  DD 75 05 3B 46 06 72 D6-8B 46 06 A3 90 70 8B 8A   .u.;F.r..F...p..
2817:5960  70 8B DA EB 00 5F 5E 8B-E5 5D CB 55 8B EC 33 C0   p...._^..].U..3.
2817:5970  50 C4 5E 06 26 FF 77 02-26 FF 37 0E E8 DF FD 8B   P.^.&.w.&.7.....
2817:5980  E5 EB 00 5D CB 55 8B EC-83 EC 04 9A 01 00 89 2E   ...].U..........
2817:5990  C4 5E 06 26 8B 57 02 26-8B 07 2B 06 80 42 1E 16   .^.&.W.&..+..B..
2817:59A0  8B 42 97 56 FE 89 46 FC-8B 01 00 50 FF 76 FE FF   .B.V..F....P.v..
2817:59B0  76 FC 0E E8 A8 FD 83 C4-06 8B 00 8B E5 5D CB 55   v............].U
2817:59C0  8B EC C4 5E 06 26 8B 47-0A 05 6C 07 50 C4 5E 06   ...^.&.G..l.P.^.
2817:59D0  26 FF 37 C4 5E 06 26 FF-77 02 C4 5E 06 26 FF 77   &.7.^.&.w..^.&.w
2817:59E0  04 C4 5E 06 26 FF 77 06-C4 5E 06 26 9A 5F 08 D1   ..^.&.w..^.&._..
2817:59F0  E3 D1 E3 FF B7 D8 41 FF-B7 D6 41 C4 5E 06 26 8B   ......A...A.^.&.
2817:5A00  5F 0C D1 E3 D1 E3 FF B7-DC 41 FF B7 DA 41 1E B8   _........A...A..
2817:5A10  52 42 50 1E B8 70 70 50-9A 43 00 36 2E 8B EE 8B   RBP..ppP.C.6....
2817:5A20  70 70 8C DA 8B 00 5D CB-55 8B EC FF 76 08 FF 76   pp....].U...v..v
2817:5A30  06 0E E8 50 FF 8B 8B 52-50 0E E8 82 FF 8B E5 8B   ...P...RP.......
2817:5A40  00 5D CB 50 53 51 52 06-1E 56 57 55 8B EC 1E 8E   .].PSQR..VWU....
2817:5A50  DD FF 1E 9C 70 0E C0 75-09 33 C0 50 9A 0D 01 17   ....p..u.3.P....
2817:5A60  18 59 5D 5F 5E 1F 07 5A-59 5B 58 CF 55 8B EC C4   .Y]_^..ZY[X.U...
2817:5A70  5E 06 8C 06 9E 70 89 1E-9C 70 0E B8 03 00 50 8B   ^....p...p....P.
2817:5A80  23 00 50 9A 1D 00 09 2D-8B E5 5D CB 55 8B EC 84   #.P....-..].U...
2817:5A90  2A CD 21 C4 5E 06 26 89-07 C4 5E 06 26 89 57 02   *.!.^.&...^.&.W.
2817:5AA0  5D CB 55 8B EC B4 2C CD-21 C4 5E 06 26 89 0F C4   ].U...,.!.^.&...
2817:5AB0  5E 06 26 89 57 02 5D CB-55 8B EC 83 EC 04 56 57   ^.&.W.].U.....VW
2817:5AC0  C4 7E 06 83 3D 00 C7 74-20 80 00 26 8A 25 89 FF   .~.....t ..&.%..
2817:5AD0  FF FC F2 AE F7 D1 49 74-10 C4 3E 71 00 8C 46 FE   ......It..>q..F.
2817:5AE0  8C C3 03 DF 89 7E FC 75-0E 33 D2 33 C0 EB 36 90   .....~.u.3.3..6.
2817:5AF0  8C 46 FC C4 C4 7E FC 26-C4 3D 8C C3 08 DF 74 E9   .F...~.&.=....t.
2817:5B00  26 8A 05 0A C0 74 E2 3A-E0 75 E3 3B D9 26 80 39   &....t.:.u...&.9
2817:5B10  3D 75 DD 1E 8E 76 06 F3-A6 1F 87 CB 75 D2 47 8B   =u...v......u.G.
2817:5B20  C7 8C C2 EB 00 5F 5E 8B-E5 5D CB 55 8B EC B4 35   ....._^..].U...5
2817:5B30  8A 46 06 CD 21 8B C3 8C-C2 8B 00 5D CB 55 8B EC   .F..!......].U..
2817:5B40  B4 25 8A 46 06 1E C5 56-08 CD 21 1F 5D CB 55 8B   .%.F...V..!.].U.
2817:5B50  EC 56 57 FF 76 06 FF 76-08 FF 76 0A FF 76 0C 9A   .VW.v..v..v..v..
2817:5B60  91 01 0E 2E 0B C0 75 04-33 C0 EB 35 8B 7E 0A 2B   ......u.3..5.~.+
2817:5B70  7E 06 47 8B 76 08 8B 1F-FF 76 10 FF 76 0E FF 76   ~.G.v....v..v..v
2817:5B80  06 56 96 00 00 8B 2E 52-50 57 9A 54 01 0E 2E 8B   .V.....RPW.T....
2817:5B90  C7 D1 E0 01 46 0E 46 3B-76 0C 7E DC 2B 01 00 EB   ....F.F;v.~.....
2817:5BA0  00 5F 5E 5D CB 55 8B EC-56 57 8B 7E 0A 2B 7E 06   ._^].U..VW.~.+~.
2817:5BB0  47 8B 76 08 8B 1F FF 76-06 56 9A 00 00 8E 2E 52   G.v....v.V.....R
2817:5BC0  50 FF 76 10 FF 76 0E 57-9A 54 01 0E 2E 8B C7 D1   P.v..v.W.T......
2817:5BD0  E0 01 46 0E 46 3B 76 0C-7E DC 8B 01 00 EB 00 5F   ..F.F;v.~......_
2817:5BE0  5E 5D CB 55 8B EC 83 EC-16 8D 46 FE 50 9A 94 05   ^].U......F.P...
2817:5BF0  00 2B 2E 59 59 16 8D 46-FE 50 FF 76 0E FF 76 0C   .+.YY..F.P.v..v.
2817:5C00  FF 76 0A FF 76 08 FF 76-06 9A 37 00 D5 2D 83 C4   .v..v..v..7..-..
2817:5C10  0E 8B 00 8B E5 5D CB 55-8B EC 83 EC 0E 56 57 1E   .....].U.....VW.
2817:5C20  8D 4E F6 89 4E F2 8C 56-F4 C6 46 F6 55 C6 46 F7   .N..N..V..F.U.F.
2817:5C30  CD 8B 46 06 88 46 F8 C7-46 F9 5D CB 3C 25 72 15   ..F..F..F.].<%r.
2817:5C40  3C 26 77 11 C6 46 F9 36-C7 46 FA 8F 06 E9 4E FC   <&w..F.6.F....N.
2817:5C50  C7 46 FE 5D C5 CE 76 10-FF 34 FF 74 06 C5 76 08   .F.]..v..4.t..v.
```

```
2817:5C60  8B 04 83 5C 02 8B 4C 04-EB 54 06 8B 7C 0A 8B 74   ...\..L..T..|..t
2817:5C70  C9 1F 07 FF 5E FC 9C FC-56 1E 06 C8 76 10 8B 04   ....^...V...v...
2817:5C80  8F 44 06 C5 76 0C 8F 44-08 8F 44 0E 8F 44 0C 8C   .D..v..D..D..D..
2817:5C90  64 0C 01 8B 7C 0A 89 54-0E 89 4C 04 89 5C 0C 89   d...|..T..L..\..
2817:5CA0  04 1F 74 08 50 50 FA 02-00 0A 2B 58 EB 00 5F 5E   ..t.PP....+X.._^
2817:5CB0  8B E5 5D C3 84 08 CD 21-F8 C3 55 8B EC 56 57 FC   ..]....!..U..VW.
2817:5CC0  8B 4E 0E 8B 7E 0C 8B 46-0A 8E 76 08 1E 8E 5E 06   .N..~..F..v...^.
2817:5CD0  D1 E9 F3 A5 73 01 A4 1F-5F 5E 5D CB 55 8B EC 83   ....s..._^].U...
2817:5CE0  EC 06 56 57 8B 76 08 FF-76 06 56 FF 76 04 FF 76   ..VW.v..v.V.v..v
2817:5CF0  0C 9A 91 01 0E 2E 0E 00-74 22 FF 76 0E FF 76 10   ........t".v..v.
2817:5D00  83 46 0A 2B 46 06 03 46-0E 50 8B 46 0C 2B 06 03   .F.+F..F.P.F.+..
2817:5D10  46 10 50 9A 91 01 0E 2E-0B C0 75 04 33 C0 EB 62   F.P.......u.3..b
2817:5D20  89 76 FA 8B 46 0C 89 46-FC C7 46 FE 01 00 3B 76   .v..F..F..F...;v
2817:5D30  10 7D 0E 8B 46 0C 89 46-FA 89 76 FC C7 46 FE FF   .}..F..F..v..F..
2817:5D40  FF 8B 7E FA 8B 3D FF 76-0E 8B C7 2B C6 03 46 10   ..~..=.v...+..F.
2817:5D50  50 9A 00 00 8E 2E 50 50-FF 76 06 57 9A 00 00 3A   P.....PP.v.W...:
2817:5D60  2E 50 50 8B 46 0A 2B 46-06 40 50 9A 54 01 0E 2E   .PP.F.+F.@P.T...
2817:5D70  03 7E FE 8B 46 FC 03 46-FE 3B C7 75 C9 EB 01 00   .~..F..F.;.u....
2817:5D80  E3 00 5F 5E 8B E5 5D CB-55 8B EC 16 8D 46 06 50   .._^..].U....F.P
2817:5D90  E8 01 00 50 33 C0 50 50-9A 0F 00 67 2D EB 00 5D   ...P3.PP...g-..]
2817:5DA0  CB 55 8B EC 8B 46 06 3D-DD 89 16 74 42 A3 72 42   .U...F.=...tB.rB
2817:5DB0  5D CB 8B 16 74 42 A1 72-42 8B 5A 01 8B 35 4E 9A   ]...tB.rB.Z..5N.
2817:5DC0  3B 07 17 1B 05 01 00 8D-DE 00 8B 16 74 42 A3 72   ............tB.r
2817:5DD0  42 A1 74 42 25 FF 7F 8B-00 CB 55 8B EC 8A 2E 98   B.tB%.....U.....
2817:5DE0  41 81 2D E9 0D 04 5E 03-26 8F 0F 83 46 03 02 FF   A.-...^.&...F...
2817:5DF0  46 06 3B 46 06 7E 46 04-7E EB 5D C2 08 00 55 8B   F..F.:F.~.]...U.
2817:5E00  EC 81 EC A0 00 8D 3E 9D-41 00 74 03 E9 4A 01 8B   ......>.A.t..J..
2817:5E10  3E A3 41 00 75 03 E9 40-01 80 7E 06 01 74 03 E9   >.A.u..@..~..t..
2817:5E20  37 01 FE 46 0E FE 46 0C-FE 46 0A FE 46 08 80 7E   7..F..F..F..F..~
2817:5E30  10 06 74 03 E9 F1 00 8A-46 0C B4 00 50 8A 46 0E   ..t.....F...P.F.
2817:5E40  B4 00 50 8A 46 08 B4 00-50 8A 46 0A B4 00 50 9A   ..P.F...P.F...P.
2817:5E50  46 0D B4 00 40 50 9A 46-0E B4 00 50 9A 0C 00 B4   F...@P.F...P....
2817:5E60  2D 9D C4 0C 16 8D 86 60-FF 50 8A 46 08 B4 00 50   -......`.P.F...P
2817:5E70  8A 46 0E B4 00 50 8A 46-0C B4 00 50 8A 46 0E B4   .F...P.F...P.F..
2817:5E80  00 50 9A 0E 00 D3 2D 8D-C4 0C 16 8D 86 60 FF 50   .P....-......`.P
2817:5E90  8A 46 0E B4 00 50 8A 46-0A B4 00 50 8B 3B FF 16   .F...P.F...P.:..
2817:5EA0  8D 86 60 FF 50 8A 46 0B-B4 00 50 8A 46 0A B4 00   ..`.P.F...P.F...
2817:5EB0  50 8A 46 0E B4 00 50 8A-46 0E B4 00 50 9A 65 00   P.F...P.F...P.e.
2817:5EC0  03 2D 8D C4 0D E9 9F 00-8A 46 0C B4 00 40 50 8A   .-.......F...@P.
2817:5ED0  46 0E B4 00 50 8A 46 08-B4 00 48 50 8A 46 0A B4   F...P.F...HP.F..
2817:5EE0  00 50 8A 46 0C B4 00 50-8A 46 0E B4 00 50 9A 0D   .P.F...P.F...P..
2817:5EF0  00 E4 2D 83 C4 0C 16 8D-86 60 FF 50 8A 46 0C B4   ..-......`.P.F..
2817:5F00  00 50 8A 46 0E B4 00 50-8A 46 0C B4 00 50 8A 46   .P.F...P.F...P.F
2817:5F10  0E B4 00 50 9A 0E 00 C2-2D 83 C4 0C 16 8D 86 60   ...P....-......`
2817:5F20  FF 50 8A 46 0E B4 00 50-8A 46 0A B4 00 50 E8 A9   .P.F...P.F...P..
2817:5F30  FE 16 8D 86 60 FF 50 8A-46 0C B4 00 50 8A 46 0A   ....`.P.F...P.F.
2817:5F40  B4 00 50 8A 46 0C B4 00-50 8A 46 0E B4 00 50 9A   ..P.F...P.F...P.
2817:5F50  65 00 C3 2D 83 C4 0C EB-1B 8A 3E 95 41 8A 66 10   e..-......>.A.f.
2817:5F60  8A 46 06 8A 6E 0C 8A 4E-0E 8A 76 0B 8A 56 0A 9A   .F..n..N..v..V..
2817:5F70  3C 08 17 18 5E 8B 5D CA-0C 00 55 8B EC 83 EC 02   <.....]...U.....
2817:5F80  56 35 76 04 D1 EE 8B C6-8A 16 9C 41 B6 00 8B DA   V5v........A....
2817:5F90  33 D2 F7 F3 8B 46 FE 8A-46 FE B4 00 8A 16 9C 41   3....F..F......A
2817:5FA0  B6 00 F7 E2 8B D0 2A D0-88 56 FF 8A 66 FE 8A 46   ......*..V..f..F
2817:5FB0  FF 5E 00 5E 8B E5 5D C2-04 00 55 8B EC C4 5E 08   ...^..]...U...^.
2817:5FC0  26 8B 17 C4 5E 04 26 3B-17 74 0F 8B 00 B4 02 9A   &...^.&;.t......
2817:5FD0  3C 08 17 18 C4 5E 04 26-8B 17 FE C2 8A C2 3A C6   <....^.&......:.
2817:5FE0  9C 41 72 04 FE C6 B2 00-C4 5E 08 26 89 17 5D CA   .Ar......^.&..].
2817:5FF0  08 00 55 8B EC 83 EC 0A-56 57 9A 01 00 8F 2E 8B   ..U.....VW......
2817:6000  FE 8B C7 89 46 FA 8B 46-02 3B 06 A1 41 75 05 8B   ....F..F.;..Au..
2817:6010  01 00 EB 02 33 C0 89 46-FC 0B C0 74 0C FF 76 0C   ....3..F...t..v.
2817:6020  FF 76 0A E8 54 FF 89 46-F6 8B 46 08 3B 06 A1 41   .v..T..F..F.;..A
2817:6030  75 05 B8 01 00 EB 02 33-C0 89 46 FE 0B C0 74 0C   u......3..F...t.
2817:6040  FF 76 08 FF 76 06 E8 31-FF 89 46 F8 EB 59 8B 7E   .v..v..1..F..Y.~
2817:6050  FE 00 74 1A 16 8D 46 F8-50 16 8D 46 FA 50 E8 59   ..t...F.P..F.P.Y
2817:6060  FF 57 00 34 0B 9A 3C 08-17 18 8B FC 8B 0A C4 5E   ......<........^
2817:6070  06 26 8B 37 8B 46 06 02-8B 7E FD 00 74 1F 16 8D   .&.7.F...~..t...
2817:6080  46 F6 50 16 8D 46 FA 50-E8 2F FF 8B 26 8A 2C 8B   F.P..F.P./......
2817:6090  01 00 87 00 34 09 9A 3C-08 17 18 8B 0A C4 5E 0A   .......<......^.
2817:60A0  26 89 37 8B 46 0A 02 8B-46 04 FF 4E 04 0B C0 75   &.7.F...F..N...u
2817:60B0  9D 8B 37 87 00 84 12 9A-3C 08 17 18 5F 5E 8B E5   ........<..._^..
2817:60C0  5D C2 0A 00 55 8B EC 80-3E 9D 41 00 75 1D 80 3E   ]...U...>.A.u..>
2817:60D0  A3 41 00 74 16 FF 76 0E-FF 76 0C FF 76 0A FF 76   .A.t..v..v..v..v
2817:60E0  08 FF 76 06 9A 25 00 8B-0E E8 12 FF 76 0E FF 76   ..v..%......v..v
```

```
2817:60F0  0C FF 76 0A FF 76 08 FF-76 06 E8 F5 FE 5D CA 0A   ..v..v..v....]..
2817:6100  00 55 8B EC A0 9C 41 B4-00 8B C8 A0 9B 41 B4 00   .U....A......A..
2817:6110  8B D0 3B 46 0C 7E C1 77-0A 85 46 08 7E C1 77 23   ...F.:.w*.F.;.w#
2817:6120  8B 46 0C 3B 46 08 7F 1B-3B 46 0A 7E 02 77 14 8B   .F.;F....F.;.w..
2817:6130  46 06 3B C2 77 0D 8B 46-0A 3B 46 06 7F 05 B8 01   F.;.w..F.;F.....
2817:6140  00 EB 02 33 C0 EB 00 5D-CA 0E 00 55 8B EC 56 8D   ...3...]...U..V.
2817:6150  0C C4 76 06 26 8B 04 26-3B 4C 02 26 3B 54 04 26   ..v.&..&.L.&.T.&
2817:6160  8C 5C 06 8E D0 5E 5D CB-55 8B EC 56 84 2B C4 76   .\...^].U..V.+.v
2817:6170  06 26 8B 0C 26 8B 54 02-2B 21 5E 5D CB 55 8B EC   .&..&.T..!^].U..
2817:6180  56 2B 2D C4 76 06 26 8B-0C 26 8B 54 02 CD 21 5E   V.-.v.&..&.T..!^
2817:6190  5D CB 55 8B EC 56 57 8D-3E 85 CF C4 7E 06 FC 8D   ].U..VW.....~...
2817:61A0  46 06 A5 8D D0 A5 9C 58-A5 8E 46 04 A3 83 46 02   F......X..F...F.
2817:61B0  A5 8B 46 00 AB 8B C1 A5-8B C2 AB 8B C6 A5 8D D8   ..F.............
2817:61C0  AB 8E 33 33 C0 EB 00 5F-5E 5D CB 55 8B EC 56 57   ...3..._^].U..VW
2817:61D0  8B 5E 0A 83 FE 01 83 D3-00 0E 76 06 FC AD 8E 14   .^.........v.....
2817:61E0  8B 50 AD AD 50 AD 50 AD-50 AD 8B 8B AD 8B FB AD   ....P.P.P.......
2817:61F0  8E C0 AD 8E 1D 8B F0 8B-C3 CF 5F 5E 5D CB 55 8B   .........._^].U.
2817:6200  EC FF 76 0A FF 76 0E FF-76 0C C4 5E 06 26 FF 77   ..v..v..v..^.&.w
2817:6210  02 26 FF 37 9A 01 00 8A-2C 8B E5 8B 46 0A C4 5E   .&.7........F..^
2817:6220  06 26 21 07 26 C4 1F 26-C6 07 00 33 C0 EB 00 5D   .&..&..&...3...]
2817:6230  CA 0A 00 55 8B 8D C4 5E-06 26 C6 07 00 0E 8B 0E   ...U...^.&......
2817:6240  00 50 16 8D 46 06 50 FF-76 0C FF 76 0A 16 8D 46   .P..F.P.v..v...F
2817:6250  0E 50 9A 3A 00 2B 2C 8B-00 5D CB 8B 8B EC 34 5E   .P.:.....].U...^
2817:6260  06 26 C6 07 00 0E 8B 0E-00 ED 16 8D 46 0E 50 FF   .&.......P..F.P.
2817:6270  76 0C FF 76 0A FF 76 10-FF 76 0E 9A 3A 00 2B 2C   v..v..v..v..:..,
2817:6280  8B 00 5D CB 55 8B EC 83-EC 08 16 8D 46 FC 50 16   ..].U.......F.P.
2817:6290  8D 46 F8 50 C4 5E 06 26-FF 77 02 26 FF 37 9A 3C   .F.P.^.&.w.&.7.<
2817:62A0  01 50 2E 83 C4 0C 16 8D-46 FE 50 9A C8 00 2D 2E   .P......F.P...-.
2817:62B0  59 59 16 8D 46 FC 50 9A-1D 00 2D 2E 59 59 3B C0   YY..F.P...-.YY;.
2817:62C0  EB 00 8B E5 5D CB 55 8B-EC 83 EC 0C 16 8D 46 F4   ....].U.......F.
2817:62D0  50 9A CC 00 8F 2D 59 59-16 8D 46 F8 50 9A 22 00   P....-YY..F.P.".
2817:62E0  8F 2D 59 59 16 8D 46 F8-50 16 8D 46 F4 50 9A 09   .-YY..F.P..F.P..
2817:62F0  00 50 2E 83 C4 08 89 56-FE 89 46 FC 8B 46 06 0B   .P.....V..F..F..
2817:6300  46 08 74 10 83 56 FE 8B-46 FC C4 5E 06 26 89 57   F.t..V..F..^.&.W
2817:6310  02 26 89 07 8B 56 FE 8B-46 FC EB 00 8B E5 5D CB   .&...V..F.....].
2817:6320  55 8B EC 56 57 FC C4 7E-0A 8B F7 32 C0 8B 5E 0E   U..VW..~...2..^.
2817:6330  8B C8 F2 AE 2B C9 1E 8D-37 8E DF C4 7E 06 87 CB   ....+.......~...
2817:6340  F3 A4 8B C2 F3 AA 1F 8B-56 0E 8B 46 06 5E 00 5F   ........V..F..._
2817:6350  5E 5D CB 55 8B EC 56 57-1E FC C5 76 06 C4 7E 0A   ^].U..VW...v..~.
2817:6360  8B 4E 0E 33 C0 8B D8 E4-7A 61 E3 24 AC 26 8A 1D   .N.3....za.$.&..
2817:6370  0A C0 74 1C 3E E1 F3 3A-C6 72 06 3A C2 77 02 2C   ..t.....:.r.:.w..
2817:6380  20 3A DE 72 07 3A DA 77-03 80 EB 20 3A C3 74 DA    :.r.:.w... :.t.
2817:6390  2B C3 1F EB 00 5F 5E 5D-CB 55 8B EC 83 EC 06 56   +...._^].U.....V
2817:63A0  57 9A 01 00 9F 2E 8B 16-52 42 A1 50 42 05 00 A6   W........B..B...
2817:63B0  81 D2 CE 12 89 56 FC 89-46 FA C4 5E 06 26 8B 37   .....V..F..^.&.7
2817:63C0  81 C6 44 F8 8B C6 D1 F8-D1 F8 99 29 86 07 83 80   ..D.............
2817:63D0  1F 9A E8 07 17 19 01 46-FA 11 56 FC 8B C6 2E 03   .......F..V...%.
2817:63E0  00 99 39 E1 01 8B 50 33-9A 5B 07 17 19 01 46 FA   .......3......F.
2817:63F0  11 56 FC F7 C6 03 00 74-09 81 46 FA 80 51 83 56   .V.....t..F..Q.V
2817:6400  FC 01 33 FF C4 5E 06 26-8A 47 03 FB E5 F0 4E EB   ..3..^.&.G....N.
2817:6410  08 4E 8A 84 76 42 98 03-F8 0B F6 7F F4 C4 5E 06   .N..vB........^.
2817:6420  26 8A 47 02 98 48 03 F8-C4 5E 06 26 80 7F 03 02   &.G..H...^.&....
2817:6430  7E 05 C4 5E 06 26 F7 07-03 00 75 01 47 8B C7 BA   ~..^.&....u.G...
2817:6440  18 00 F7 E2 C4 5E CA 26-8A 57 01 26 00 03 C2 39   .....^.&.W......
2817:6450  46 FE 8B 7E 54 42 00 74-24 C4 5E CA 26 8A 47 01   F..>.B.t$.^.&.G.
2817:6460  34 00 50 57 33 D0 50 C4-5E 06 26 8B 07 05 4E F8   ..PW3.P.^.&...N.
2817:6470  50 9A E6 01 8F 2E 0B 30-74 03 FF 4E FE 8B 46 FE   P.......t..N..F.
2817:6480  99 33 C9 E5 10 CE 9A 8B-07 17 19 01 46 FA 11 56   .3...........F..V
2817:6490  FC C4 5E 0A 26 8A 07 B4-00 99 33 C9 8B 3C 00 9A   ..^.&.....3..<..
2817:64A0  8B 07 17 19 01 5E 0A 26-8A 5F 03 97 00 52 50 8B   .....^.&._...RP.
2817:64B0  33 99 5B 59 03 D8 13 CA-01 5E FA 11 4E FC 8B 56   ..[Y.....^..N..V
2817:64C0  FC 8B 46 FA EB 00 5F 5E-8B E5 5D CB 55 8B EC 9A   ..F..._^..].U...
2817:64D0  01 00 89 2E 8B 16 52 42-A1 50 42 05 00 A6 81 D2   .......B..B.....
2817:64E0  CE 12 29 46 06 17 56 08-C4 5E 0E 26 C6 47 02 00   ..)F..V..^.&.G..
2817:64F0  33 D2 5B 3C 00 52 50 FF-76 08 FF 76 06 9A 23 09   3..<.RP.v..v..#.
2817:6500  17 19 C4 5E 0E 26 85 47-03 33 D2 5B 3C 00 52 50   ...^.&.G.3..<.RP
2817:6510  FF 76 08 FF 76 06 9A 1A-09 17 19 89 56 08 89 46   .v..v.......V..F
2817:6520  06 33 D2 B3 3C 00 52 50-FF 76 08 FF 76 06 9A 23   .3..<.RP.v..v..#
2817:6530  09 17 19 C4 5E 0E 26 88-07 33 D2 5B 3C 00 52 50   ....^.&..3..<.RP
2817:6540  FF 76 08 FF 76 06 9A 1A-09 17 19 89 56 08 89 46   .v..v.......V..F
2817:6550  06 33 D2 5B F8 89 52 50-FF 76 08 FF 76 06 9A 1A   .3....RP.v..v...
2817:6560  09 17 19 D1 E0 D1 E0 05-3C 07 C4 5E 0A 26 89 07   ...........^.&..
```

```
2817:6570  33 D2 E8 F8 8B 52 50 FF-76 08 FF 76 06 9A 23 09   3....RP.v..v..#.
2817:6580  17 18 89 56 08 89 46 06-83 7E 08 00 7C 48 7F 07   ...V..F..~..|H..
2817:6590  81 7E 06 50 22 76 3F 81-6E 06 50 22 83 5E 08 00   .~.P"v?.n.P".^..
2817:65A0  C4 5E 0A 26 FF 07 33 D2-B8 22 22 52 50 FF 76 08   .^.&..3..""RP.v.
2817:65B0  FF 76 06 9A 1A 09 17 18-C4 5E 0A 26 01 07 33 D2   .v.......^.&..3.
2817:65C0  B8 22 22 52 50 FF 76 08-FF 76 06 9A 23 09 17 18   .""RP.v..v..#...
2817:65D0  89 56 08 89 46 06 83 3E-84 42 00 74 44 33 D2 B8   .V..F....B.tD3..
2817:65E0  18 00 52 50 FF 76 08 FF-76 06 9A 23 09 17 18 50   ..RP.v..v..#...P
2817:65F0  33 D2 B8 18 00 52 50 FF-76 08 FF 76 06 9A 1A 09   3....RP.v..v....
2817:6600  17 18 50 33 C0 50 C4 5E-0A 26 8B 07 05 4E FE 50   ..P3.P.^.&...N.P
2817:6610  9A E6 01 8F 2E 18 C0 74-09 83 46 06 01 83 56 08   .......t..F...V.
2817:6620  00 33 D2 B8 18 00 52 50-FF 76 08 FF 76 06 9A 23   .3....RP.v..v..#
2817:6630  09 17 18 C4 5E 0E 26 8B-47 01 33 D2 B8 18 00 52   ....^.&.G.3....R
2817:6640  50 FF 76 08 FF 76 06 9A-1A 09 17 18 89 56 08 89   P.v..v.......V..
2817:6650  46 06 83 46 06 01 83 56-08 00 C4 5E 0A 26 F7 07   F..F...V...^.&..
2817:6660  03 00 75 36 83 7E 08 00-7C 12 7F 06 83 7E 06 3C   ..u6.~..|....~.<
2817:6670  76 0A 83 6E 06 01 83 5E-08 00 EB 1E 83 7E 08 00   v..n...^.....~..
2817:6680  75 12 83 7E 06 3C 75 12-C4 5E 0A 26 C6 47 03 02   u..~.<u..^.&.G..
2817:6690  C4 5E 0A 26 C6 47 02 1D-EB 54 C4 5E 0A 26 C6 47   .^.&.G...T.^.&.G
2817:66A0  03 00 EB 1D C4 5E 0A 26-8A 47 03 98 8B D8 8A 87   .....^.&.G......
2817:66B0  76 42 98 99 39 46 06 19-56 08 C4 5E 0A 26 FE 47   vB..9F..V..^.&.G
2817:66C0  03 C4 5E 0A 26 8A 47 03-98 8B D8 8A 87 76 42 98   ..^.&.G......vB.
2817:66D0  99 3B 56 08 7C 0E 75 05-3B 46 06 72 07 C4 5E 0A   .;V.|.u.;F.r..^.
2817:66E0  26 FE 47 03 8A 46 06 C4-5E 0A 26 88 47 02 5D CB   &.G..F..^.&.G.].
2817:66F0  55 8B EC 83 7E 06 FF 75-0E E8 FF FF EB 21 8A 46   U...~..u......!.F
2817:6700  06 B4 00 8B D8 F6 87 1D-7E 09 74 0D 8A 46 06 B4   ........~.t..F..
2817:6710  00 05 E0 FF EB 09 8B 07-8A 46 06 B4 00 EB 00 5D   .........F.....]
2817:6720  CB 55 8B EC 83 EC 04 56-1E B8 56 42 50 9A 03 00   .U.....V..VBP...
2817:6730  C2 2D 59 59 89 56 FE 89-46 FC 0B D0 75 03 E9 8E   .-YY.V..F...u...
2817:6740  00 FF 76 FE FF 76 FC 9A-0D 00 8E 2D 59 59 3D 04   ..v..v......YY=.
2817:6750  00 73 03 E9 7A 90 C4 5E-FC 26 8A 07 98 8B D8 F6   .s..z..^.&......
2817:6760  87 1D 3E 02 74 69 C4 5E-FC 26 8A 47 01 98 8B D8   ..>.ti.^.&.G....
2817:6770  F6 87 1D 3E 02 74 58 C4-5E FC 26 8A 47 02 98 8B   ...>.tX.^.&.G...
2817:6780  D8 F6 87 1D 3E 02 74 47-C4 5E FC 26 80 7F 03 2D   ....>.tG.^.&...-
2817:6790  74 1E C4 5E FC 26 80 7F-03 2B 74 11 C4 5E FC 26   t..^.&...+t..^.&
2817:67A0  8A 47 03 98 8B D8 F6 87-1D 3E 02 74 22 C4 5E FC   .G......>.t".^.
2817:67B0  26 8A 47 03 98 8B D8 F6-87 1D 3E 02 75 50 C4 5E   &.G.......>.uP.^
2817:67C0  FC 26 8A 47 04 98 8B D8-F6 87 1D 3E 02 75 3F C7   .&.G.......>.u?.
2817:67D0  06 B4 42 01 00 C7 06 B2-42 00 00 C7 06 B0 42 50   ..B.....B.....BP
2817:67E0  46 1E B8 89 42 50 FF 36-AA 42 FF 36 A8 42 9A 0B   F...BP.6.B.6.B..
2817:67F0  00 E7 2D 83 C4 08 1E B8-BD 42 50 FF 36 AE 42 FF   .........BP.6.B.
2817:6800  36 AC 42 9A 0B 00 87 2D-83 C4 08 EB F3 00 2B 04   6.B.............
2817:6810  00 50 33 C0 50 FF 36 AE-42 FF 36 AC 42 9A 2D 00   .P3.P.6.B.6.B.-.
2817:6820  8C 2D 83 C4 08 EB 07 00-50 FF 76 FE FF 76 FC FF   .,......P.v..v..
2817:6830  36 AA 42 FF 36 A8 42 9A-00 00 49 2E 83 C4 0A C4   6.B.6.B...I.....
2817:6840  1E A8 42 26 C6 47 03 00-8B 56 FE 8B 46 FC 05 03   ..B&.G...V..F...
2817:6850  00 52 50 9A 04 00 84 2D-59 59 33 C9 EB 10 0E 9A   .RP....-YY3.....
2817:6860  88 07 17 18 89 16 B2 42-A3 B0 42 C7 06 B4 42 00   .......B..B...B.
2817:6870  00 8B 03 00 EB 7F 90 C4-5E FC 26 8A 07 98 8B D8   .........^.&....
2817:6880  F6 87 1D 3E 02 74 6D 83-56 FE 8B 46 FC 03 C6 52   ...>.tm.V..F...R
2817:6890  50 9A 0C 00 8E 2D 59 59-3D 07 00 72 26 C4 5E FC   P.....YY=..r&.^.
2817:68A0  03 DE 26 8A 47 01 98 8B-D8 F6 87 1D 3E 02 74 17   ..&.G.......>.t.
2817:68B0  C4 5E FC 03 DE 26 8A 47-02 98 8B D8 F6 87 1D 3E   .^...&.G.......>
2817:68C0  02 75 02 EB 3C 8B 03 00-50 8B 56 FE 8B 46 FC 03   .u..<...P.V..F..
2817:68D0  C6 52 50 FF 36 AE 42 FF-36 AC 42 9A 00 00 49 2E   .RP.6.B.6.B...I.
2817:68E0  83 C4 0A C4 1E AC 42 26-C6 47 03 00 C7 06 B4 42   ......B&.G.....B
2817:68F0  01 00 EB 0D 46 C4 5E FC-26 80 38 00 74 03 E9 76   ....F.^.&.8.t..v
2817:6900  FF 5E 8B E5 5D CB 55 8B-EC 56 57 8B 76 08 0B F6   .^..].U..VW.v...
2817:6910  75 28 8B 7E 0A 83 7E 0A-3B 72 0C EB 46 06 05 46   u(.~..~.;r..F..F
2817:6920  00 A9 03 00 75 01 4F 33-F6 EB 01 46 8B DE D1 E3   ....u.O3...F....
2817:6930  8B 87 8E 42 3B C7 76 F3-EB 1F 83 FE 03 72 08 8B   ...B;.v......r..
2817:6940  46 06 05 46 00 A9 03 00-74 03 FF 4E 0A 8B DE 4B   F..F....t..N...K
2817:6950  D1 E3 8B 87 8E 42 01 46-0A 83 FE 04 72 78 74 07   .....B.F....rxt.
2817:6960  83 7E 0A 77 71 75 6A 8B-DE D1 E3 83 7E 06 10 7E   ...wquj.....~..~
2817:6970  0F 83 FE 04 75 0A 8B 5F-83 42 83 C1 07 EB 05 90   ....u....B......
2817:6980  8B 8F 8E 42 2B 5E 06 81-C3 E2 07 F6 C3 03 74 01   ...B+^........t.
2817:6990  49 8B 5E 06 43 D1 FB D1-FB 03 D9 B8 6D 01 F7 66   I.^.C.......m..f
2817:69A0  06 03 C3 05 04 00 33 D2-B9 07 00 F7 F1 2B CA 8B   ......3......+..
2817:69B0  46 CA 83 FE 04 75 0E 3B-C1 77 16 75 1F 80 7E 0C   F....u.;.w.u..~.
2817:69C0  02 72 10 EB 0C 3B C1 72-09 75 0B 80 7E 0C 01 77   .r...;.r.u..~..w
2817:69D0  05 EB 01 C0 EB 04 33 C0-EB 00 5F 5E 5D CA 08 00   ......3..._^]...
2817:69E0  55 8B EC 8B 46 06 48 8A-16 9C 41 B6 00 F7 E2 03   U...F.H...A.....
2817:69F0  06 9F 41 8B 56 08 4A 03-C2 D1 E0 8B 16 A1 41 EB   ..A.V.J.......A.
```

```
2817:6A00  00 ED C4 04 00 55 8B EC-83 EC 02 56 57 A0 9E 41   .]...U.....VW..A
2817:6A10  E4 00 89 46 FE 1E 8B 4E-06 E3 5A C4 7E 0C 05 76   ...F...N..Z.~..v
2817:6A20  0E FD 3A 87 73 0A 8B C1-48 D1 E3 03 F0 03 F3 FD   ..:.s...H.......
2817:6A30  83 7E FE 00 75 04 F3 A5-EB 7B 8A DA 03 8C C0 8C   .~..u....{......
2817:6A40  D3 73 03 74 11 FA ED D0-CB 72 FB EC D0 C8 73 F5   .:.t.....r....s.
2817:6A50  A5 F8 E2 F1 EB 1F F4 EC-D0 C8 72 FB EC D0 C8 73   ...........r....s
2817:6A60  F8 AD F8 8B D8 ED D0 C8-72 FB EC D0 C8 73 F8 8B   ........r....s..
2817:6A70  C3 AB F8 E2 E1 FC 1F EB-00 5F 5E 8B E5 5D CA 0A   ........._^..]..
2817:6A80  00 B4 03 87 30 9A 3C 08-17 1E 8B C3 E5 00 CB 0E   ......<.........
2817:6A90  E8 EE FF 84 00 8A 16 94-41 B6 00 2B C2 40 EB 00   ........A..+.@..
2817:6AA0  C3 CE E8 3C FF 81 C8 D3-EB 84 00 8A 16 9E 41 B6   ..............A.
2817:6AB0  00 2B C2 40 EB 00 CB 00-00 00 00 00 00 00 00 00   .+.@............
2817:6AC0  00 00 00 00 54 75 72 62-6F 2D 43 20 2D 20 43 6F   ....Turbo-C - Co
2817:6AD0  70 79 72 69 67 68 74 20-28 63 29 20 31 39 38 38   pyright (c) 1988
2817:6AE0  20 42 6F 72 6C 61 6E 64-20 49 6E 74 6C 2E 00 44    Borland Intl..D
2817:6AF0  69 76 69 64 65 20 65 72-72 6F 72 0D 0A 41 62 6E   ivide error..Abn
2817:6B00  6F 72 6D 61 6C 20 70 72-6F 67 72 61 6D 20 74 65   ormal program te
2817:6B10  72 6D 69 6E 61 74 69 6F-6E 0D 0A 00 00 00 00 00   rmination.......
2817:6B20  00 00 00 00 00 00 00 00-00 00 00 00 00 00 00 00   ................
2817:6B30  00 00 00 00 00 00 00 00-00 00 00 00 00 00 00 00   ................
2817:6B40  00 00 00 00 00 00 00 00-00 00 00 00 00 00 00 00   ................
2817:6B50  00 00 00 00 00 00 00 00-00 00 00 00 00 00 00 0A   ................
2817:6B60  00 09 00 09 00 01 00 05-00 04 00 06 00 02 00 02   ................
2817:6B70  00 02 00 00 00 0A 00 09-00 08 00 07 00 06 00 05   ................
2817:6B80  00 04 00 03 00 02 00 02-00 01 00 00 00 00 00 00   ................
2817:6B90  00 00 00 00 00 01 00 00-00 00 00 00 00 A0 00 30   ................
2817:6BA0  00 70 00 10 00 50 00 40-00 60 00 30 00 01 00 02   .....F.G.`. ....
2817:6BB0  00 00 00 00 00 00 00 00-00 01 00 FF FF FF FF 00   ................
2817:6BC0  00 00 00 00 00 00 00 00-00 00 00 24 00 02 00 00   ...........$....
2817:6BD0  00 00 00 1E 00 00 00 47-4C 55 20 05 00 01 00 6D   .......GLU ....m
2817:6BE0  67 2F 64 6C 20 60 00 00-00 00 00 00 00 00 00 1E   g/dl ...........
2817:6BF0  00 00 00 42 55 4E 20 05-00 01 00 6D 67 2F 64 6C   ...BUN ....mg/dl
2817:6C00  20 00 00 00 00 00 00 00-00 00 00 00 00 00 00 4E    ...............N
2817:6C10  42 49 4C 1E 00 00 00 6D-67 2F 64 6C 20 01 00 00   BIL....mg/dl ...
2817:6C20  00 05 00 00 00 00 00 1E-00 00 00 43 61 20 20 05   ...........Ca  .
2817:6C30  00 02 00 6D 67 2F 64 6C-20 00 00 00 00 01 00 00   ...mg/dl .......
2817:6C40  00 00 00 1E 00 00 00 43-52 45 41 05 00 02 00 6D   .......CREA....m
2817:6C50  67 2F 64 6C 20 01 00 00-00 00 00 00 00 00 00 1E   g/dl ...........
2817:6C60  00 00 00 55 52 49 43 05-00 00 00 6D 67 2F 64 6C   ...URIC....mg/dl
2817:6C70  20 01 00 00 00 02 00 00-00 00 00 1E 00 00 00 54    ..............T
2817:6C80  50 20 20 05 00 02 00 20-67 2F 64 6C 20 00 00 00   P  .... g/dl ...
2817:6C90  00 02 00 00 00 00 00 1E-00 00 00 54 52 49 47 05   ...........TRIG.
2817:6CA0  00 01 00 6D 67 2F 64 6C-20 00 00 00 00 02 00 00   ...mg/dl .......
2817:6CB0  00 00 00 1E 00 00 00 43-48 4F 4C 05 00 01 00 6D   .......CHOL....m
2817:6CC0  67 2F 64 6C 20 00 00 00-00 00 00 00 00 00 00 06   g/dl ...........
2817:6CD0  00 00 00 41 4C 42 20 05-00 02 00 20 67 2F 64 6C   ...ALB .... g/dl
2817:6CE0  20 00 00 00 00 01 00 00-00 00 00 1E 00 00 00 4E    ...............N
2817:6CF0  48 33 20 05 00 01 00 75-6D 6F 6C 2F 6C 00 00 00   H3 ....umol/l...
2817:6D00  00 00 00 00 00 00 00 1E-00 00 00 47 4C 4F 4C 05   ...........GLOL.
2817:6D10  00 00 00 6D 67 2F 64 6C-20 01 00 00 00 00 00 00   ...mg/dl .......
2817:6D20  00 00 00 1E 00 00 00 50-48 4F 53 05 00 02 00 6D   .......PHOS....m
2817:6D30  67 2F 64 6C 20 00 00 00-00 02 00 03 00 00 00 00   g/dl ...........
2817:6D40  00 00 00 4C 41 43 20 05-00 00 00 6D 67 2F 64 6C   ...LAC ....mg/dl
2817:6D50  20 01 00 00 00 02 00 00-00 00 00 1E 00 00 00 54    ..............T
2817:6D60  42 49 4C 05 00 02 00 6D-67 2F 64 6C 20 00 00 00   BIL....mg/dl ...
2817:6D70  00 00 00 02 00 02 00 10-00 00 00 43 52 45 41 05   ...........CREA.
2817:6D80  00 02 00 6D 67 2F 64 6C-20 00 00 00 00 00 00 00   ...mg/dl .......
2817:6D90  00 00 00 1E 00 00 00 2A-2A 2A 2A 05 00 00 00 6D   .......****....m
2817:6DA0  67 2F 64 6C 20 01 00 00-00 00 00 00 00 00 00 1E   g/dl ...........
2817:6DB0  00 00 00 2A 2A 2A 2A 05-00 00 00 6D 67 2F 64 6C   ...****....mg/dl
2817:6DC0  20 01 00 00 00 00 00 02-00 0D 00 10 00 00 00 43    ..............C
2817:6DD0  52 53 43 05 00 02 00 6D-67 2F 64 6C 20 00 00 00   RSC....mg/dl ...
2817:6DE0  00 00 00 00 00 00 00 1E-00 00 00 2A 2A 2A 2A 05   ...........****.
2817:6DF0  00 00 00 6D 67 2F 64 6C-20 01 00 00 00 00 00 00   ...mg/dl .......
2817:6E00  00 00 00 1E 00 00 00 4D-47 32 30 05 00 00 00 6D   .......MG20....m
2817:6E10  67 2F 64 6C 20 01 00 00-00 02 00 00 00 00 00 1E   g/dl ...........
2817:6E20  00 00 00 48 42 2A 2A 05-00 00 00 6D 67 2F 64 6C   ...HB**....mg/dl
2817:6E30  20 01 00 00 00 00 00 00-00 00 00 1E 00 00 00 48    ..............H
2817:6E40  44 4C 43 1E 00 00 00 6D-67 2F 64 6C 20 01 00 00   DLC....mg/dl ...
2817:6E50  00 04 00 00 00 00 00 1E-00 00 00 42 55 42 43 05   ...........BUBC.
2817:6E60  00 00 00 6D 67 2F 64 6C-20 01 00 00 00 00 00 00   ...mg/dl .......
2817:6E70  00 00 00 1E 00 00 00 2A-2A 2A 2A 05 00 00 00 6D   .......****....m
```

```
2817:6E80  67 2F 64 6C 20 01 00 00-00 00 00 00 00 00 00 1E   g/dl ...........
2817:6E90  00 00 00 2A 2A 2A 2A 05-00 00 00 6D 67 2F 64 6C   ...****....mg/dl
2817:6EA0  20 01 00 00 00 00 00 00-00 00 00 1E 00 00 00 2A    ..............*
2817:6EB0  2A 2A 2A 05 00 00 00 6D-67 2F 64 6C 20 01 00 00   ***....mg/dl ...
2817:6EC0  00 00 00 00 00 00 00 1E-00 00 00 2A 2A 2A 2A 05   ............****.
2817:6ED0  00 00 00 6D 67 2F 64 6C-20 01 00 00 00 00 00 00   ...mg/dl .......
2817:6EE0  00 00 00 1E 00 00 00 2A-2A 2A 2A 05 00 00 00 6D   .......****....m
2817:6EF0  67 2F 64 6C 20 01 00 00-00 00 00 00 00 00 00 1E   g/dl ...........
2817:6F00  00 00 00 2A 2A 2A 2A 05-00 00 00 6D 67 2F 64 6C   ...****....mg/dl
2817:6F10  20 01 00 00 00 00 00 00-00 00 00 1E 00 00 00 2A    ..............*
2817:6F20  2A 2A 2A 05 00 00 00 6D-67 2F 64 6C 20 01 00 00   ***....mg/dl ...
2817:6F30  00 00 00 01 00 00 00 1E-00 00 00 2A 2A 2A 2A 05   ............****.
2817:6F40  00 00 00 6D 67 2F 64 6C-20 01 00 00 00 00 00 00   ...mg/dl .......
2817:6F50  00 00 00 1E 00 00 00 4D-67 20 20 05 00 02 00 6D   .......Mg  ....m
2817:6F60  67 2F 64 6C 20 00 00 00-00 00 00 00 00 00 00 1E   g/dl ...........
2817:6F70  00 00 00 2A 2A 2A 2A 05-00 00 00 6D 67 2F 64 6C   ...****....mg/dl
2817:6F80  20 01 00 00 00 00 00 00-00 00 00 1E 00 00 00 2A    ..............*
2817:6F90  2A 2A 2A 05 00 00 00 6D-67 2F 64 6C 20 01 00 00   ***....mg/dl ...
2817:6FA0  00 00 00 00 00 00 00 1E-00 00 00 2A 2A 2A 2A 05   ............****.
2817:6FB0  00 00 00 6D 67 2F 64 6C-20 01 00 00 00 00 00 00   ...mg/dl .......
2817:6FC0  00 00 00 1E 00 00 00 2A-2A 2A 2A 05 00 00 00 6D   .......****....m
2817:6FD0  67 2F 64 6C 20 01 00 00-00 00 00 00 00 00 00 1E   g/dl ...........
2817:6FE0  00 00 00 2A 2A 2A 2A 05-00 00 00 6D 67 2F 64 6C   ...****....mg/dl
2817:6FF0  20 01 00 00 00 00 00 00-00 00 00 1E 00 00 00 2A    ..............*
2817:7000  2A 2A 2A 05 00 00 00 6D-67 2F 64 6C 20 01 00 00   ***....mg/dl ...
2817:7010  00 00 00 00 00 00 00 1E-00 00 00 2A 2A 2A 2A 05   ............****.
2817:7020  00 00 00 6D 67 2F 64 6C-20 01 00 00 00 00 00 03   ...mg/dl .......
2817:7030  00 00 00 00 00 00 00 43-4C 2D 20 05 00 00 00 6D   .......CL- ....m
2817:7040  67 2F 64 6C 20 01 00 00-00 00 00 03 00 00 00 00   g/dl ...........
2817:7050  00 00 00 4B 2B 20 20 05-00 00 00 6D 67 2F 64 6C   ...K+  ....mg/dl
2817:7060  20 01 00 00 00 00 00 03-00 00 00 00 00 00 00 4E    ..............N
2817:7070  41 2B 20 05 00 00 00 6D-67 2F 64 6C 20 01 00 00   A+ ....mg/dl ...
2817:7080  00 00 00 03 00 00 00 00-00 00 00 43 4F 32 20 05   ...........CO2 .
2817:7090  00 00 00 6D 67 2F 64 6C-20 01 00 00 00 00 00 00   ...mg/dl .......
2817:70A0  00 00 00 1E 00 00 00 2A-2A 2A 2A 05 00 00 00 6D   .......****....m
2817:70B0  67 2F 64 6C 20 01 00 00-00 00 00 00 00 00 00 1E   g/dl ...........
2817:70C0  00 00 00 2A 2A 2A 2A 05-00 00 00 6D 67 2F 64 6C   ...****....mg/dl
2817:70D0  20 01 00 00 00 00 00 00-00 00 00 1E 00 00 00 2A    ..............*
2817:70E0  2A 2A 2A 05 00 00 00 6D-67 2F 64 6C 20 01 00 00   ***....mg/dl ...
2817:70F0  00 02 00 01 00 03 00 05-00 00 00 41 4D 59 4C 05   ...........AMYL.
2817:7100  00 00 00 49 55 20 20 20-20 00 00 E7 03 03 00 01   ...IU    .......
2817:7110  00 04 00 1E 00 01 00 41-53 54 20 05 00 00 00 49   .......AST ....I
2817:7120  55 20 20 20 20 00 00 1E-04 00 00 00 00 00 00 1E   U    ...........
2817:7130  00 00 00 2A 2A 2A 2A 05-00 00 00 6D 67 2F 64 6C   ...****....mg/dl
2817:7140  20 01 00 00 00 00 00 00-00 00 00 1E 00 00 00 2A    ..............*
2817:7150  2A 2A 2A 05 00 00 00 6D-67 2F 64 6C 20 01 00 00   ***....mg/dl ...
2817:7160  00 00 00 00 00 00 00 1E-00 00 00 2A 2A 2A 2A 05   ............****.
2817:7170  00 00 00 6D 67 2F 64 6C-20 01 00 00 00 00 00 00   ...mg/dl .......
2817:7180  00 00 00 1E 00 00 00 2A-2A 2A 2A 05 00 00 00 6D   .......****....m
2817:7190  67 2F 64 6C 20 01 00 00-00 00 00 00 00 00 00 1E   g/dl ...........
2817:71A0  00 00 00 2A 2A 2A 2A 05-00 00 00 6D 67 2F 64 6C   ...****....mg/dl
2817:71B0  20 01 00 00 00 00 00 00-00 00 00 1E 00 00 00 2A    ..............*
2817:71C0  2A 2A 2A 05 00 00 00 6D-67 2F 64 6C 20 01 00 00   ***....mg/dl ...
2817:71D0  00 00 00 00 00 00 00 1E-00 00 00 2A 2A 2A 2A 05   ............****.
2817:71E0  00 00 00 6D 67 2F 64 6C-20 01 00 00 00 00 00 00   ...mg/dl .......
2817:71F0  00 00 00 1E 00 00 00 2A-2A 2A 2A 05 00 00 00 6D   .......****....m
2817:7200  67 2F 64 6C 20 01 00 00-00 00 00 00 00 00 00 1E   g/dl ...........
2817:7210  00 00 00 2A 2A 2A 2A 05-00 00 00 6D 67 2F 64 6C   ...****....mg/dl
2817:7220  20 01 00 00 00 00 00 00-00 00 00 1E 00 00 00 2A    ..............*
2817:7230  2A 2A 2A 05 00 00 00 6D-67 2F 64 6C 20 01 00 00   ***....mg/dl ...
2817:7240  00 00 00 01 00 02 00 10-00 00 00 4C 49 50 41 05   ...........LIPA.
2817:7250  00 00 00 49 55 20 20 20-20 00 00 9D 03 02 00 00   ...IU    .......
2817:7260  00 00 00 1E 00 00 00 2A-2A 2A 2A 05 00 00 00 49   .......****....I
2817:7270  55 20 20 20 20 01 00 00-00 00 00 00 00 00 00 1E   U    ...........
2817:7280  00 00 00 2A 2A 2A 2A 05-00 00 00 6D 67 2F 64 6C   ...****....mg/dl
2817:7290  20 01 00 00 00 03 00 01-00 03 00 CD 00 01 00 41    ..............A
2817:72A0  4C 54 20 05 00 00 00 49-55 20 20 20 20 00 00 5D   LT ....IU    ..]
2817:72B0  03 03 00 01 00 00 00 CA-00 01 00 4C 44 48 20 05   ...........LDH .
2817:72C0  00 00 00 49 55 20 20 20-20 00 00 8D 04 05 00 01   ...IU    .......
2817:72D0  00 03 00 0F 00 00 00 43-4B 20 20 05 00 00 00 49   .......CK  ....I
2817:72E0  55 20 20 20 20 00 00 84-00 04 00 01 00 00 00 0A   U    ...........
2817:72F0  00 00 00 41 4C 4B 50 05-00 00 00 49 55 20 20 20   ...ALKP....IU
```

```
2817:7300  20 00 00 72 3E 02 00 01-00 0E 00 06 00 00 00 2A   ..r............*
2817:7310  2A 2A 2A 05 00 00 00 49-55 20 20 20 20 01 00 FD   ***....IU    ...
2817:7320  03 04 00 01 00 02 00 07-00 00 00 47 47 54 20 05   ...........GGT .
2817:7330  00 00 00 49 55 20 20 20-20 00 00 C7 3C 00 00 00   ...IU    .......
2817:7340  00 00 00 1E 00 00 00 2A-2A 2A 2A 05 00 00 00 6D   .......****....m
2817:7350  67 2F 64 6C 20 01 00 00-00 00 00 00 00 00 00 1E   g/dl ...........
2817:7360  00 00 00 2A 2A 2A 2A 05-00 00 00 6D 67 2F 64 6C   ...****....mg/dl
2817:7370  20 01 00 00 00 00 00 00-00 00 00 1E 00 00 00 2A    ...............*
2817:7380  2A 2A 2A 05 00 00 00 6D-67 2F 64 6C 20 01 00 00   ***....mg/dl ...
2817:7390  00 00 00 00 00 00 00 1E-00 00 00 2A 2A 2A 2A 05   ...........****.
2817:73A0  00 00 00 6D 67 2F 64 6C-20 01 00 00 00 00 00 00   ...mg/dl .......
2817:73B0  00 00 00 1E 00 00 00 2A-2A 2A 2A 05 00 00 00 6D   .......****....m
2817:73C0  67 2F 64 6C 20 01 00 00-00 00 00 00 00 00 00 1E   g/dl ...........
2817:73D0  00 00 00 2A 2A 2A 2A 05-00 00 00 6D 67 2F 64 6C   ...****....mg/dl
2817:73E0  20 01 00 00 00 00 00 00-00 00 00 1E 00 00 00 2A    ...............*
2817:73F0  2A 2A 2A 05 00 00 00 6D-67 2F 64 6C 20 01 00 00   ***....mg/dl ...
2817:7400  00 00 00 00 00 00 00 1E-00 00 00 2A 2A 2A 2A 05   ...........****.
2817:7410  00 00 00 6D 67 2F 64 6C-20 01 00 00 00 00 00 00   ...mg/dl .......
2817:7420  00 00 00 1E 00 00 00 2A-2A 2A 2A 05 00 00 00 6D   .......****....m
2817:7430  67 2F 64 6C 20 01 00 00-00 00 00 00 00 00 00 1E   g/dl ...........
2817:7440  00 00 00 2A 2A 2A 2A 05-00 00 00 6D 67 2F 64 6C   ...****....mg/dl
2817:7450  20 01 00 00 00 00 00 00-00 00 00 1E 00 00 00 2A    ...............*
2817:7460  2A 2A 2A 05 00 00 00 6D-67 2F 64 6C 20 01 00 00   ***....mg/dl ...
2817:7470  00 00 00 00 00 00 00 1E-00 00 00 2A 2A 2A 2A 05   ...........****.
2817:7480  00 00 00 6D 67 2F 64 6C-20 01 00 00 00 00 00 00   ...mg/dl .......
2817:7490  00 00 00 1E 00 00 00 2A-2A 2A 2A 05 00 00 00 6D   .......****....m
2817:74A0  67 2F 64 6C 20 01 00 00-00 00 00 00 00 00 00 1E   g/dl ...........
2817:74B0  00 00 00 2A 2A 2A 2A 05-00 00 00 6D 67 2F 64 6C   ...****....mg/dl
2817:74C0  20 01 00 00 00 00 00 00-00 00 00 1E 00 00 00 2A    ...............*
2817:74D0  2A 2A 2A 05 00 00 00 6D-67 2F 64 6C 20 01 00 00   ***....mg/dl ...
2817:74E0  00 00 00 00 00 00 00 1E-00 00 00 2A 2A 2A 2A 05   ...........****.
2817:74F0  00 00 00 6D 67 2F 64 6C-20 01 00 00 00 00 00 00   ...mg/dl .......
2817:7500  00 00 00 1E 00 00 00 2A-2A 2A 2A 05 00 00 00 6D   .......****....m
2817:7510  67 2F 64 6C 20 01 00 00-00 00 00 00 00 00 00 1E   g/dl ...........
2817:7520  00 00 00 2A 2A 2A 2A 05-00 00 00 6D 67 2F 64 6C   ...****....mg/dl
2817:7530  20 01 00 00 00 00 00 00-00 00 00 1E 00 00 00 2A    ...............*
2817:7540  2A 2A 2A 05 00 00 00 6D-67 2F 64 6C 20 01 00 00   ***....mg/dl ...
2817:7550  00 00 00 00 00 00 00 1E-00 00 00 2A 2A 2A 2A 05   ...........****.
2817:7560  00 00 00 6D 67 2F 64 6C-20 01 00 00 00 00 00 00   ...mg/dl .......
2817:7570  00 00 00 1E 00 00 00 2A-2A 2A 2A 05 00 00 00 6D   .......****....m
2817:7580  67 2F 64 6C 20 01 00 00-00 00 00 00 00 00 00 1E   g/dl ...........
2817:7590  00 00 00 2A 2A 2A 2A 05-00 00 00 6D 67 2F 64 6C   ...****....mg/dl
2817:75A0  20 01 00 00 00 00 00 00-00 00 00 1E 00 00 00 2A    ...............*
2817:75B0  2A 2A 2A 05 00 00 00 6D-67 2F 64 6C 20 01 00 00   ***....mg/dl ...
2817:75C0  00 00 00 00 00 00 00 1E-00 00 00 2A 2A 2A 2A 05   ...........****.
2817:75D0  00 00 00 6D 67 2F 64 6C-20 01 00 00 00 00 00 00   ...mg/dl .......
2817:75E0  00 00 00 1E 00 00 00 2A-2A 2A 2A 05 00 00 00 6D   .......****....m
2817:75F0  67 2F 64 6C 20 01 00 00-00 00 00 00 00 00 00 1E   g/dl ...........
2817:7600  00 00 00 2A 2A 2A 2A 05-00 00 00 6D 67 2F 64 6C   ...****....mg/dl
2817:7610  20 01 00 00 00 00 00 00-00 00 00 1E 00 00 00 2A    ...............*
2817:7620  2A 2A 2A 05 00 00 00 6D-67 2F 64 6C 20 01 00 00   ***....mg/dl ...
2817:7630  00 00 00 00 00 00 00 1E-00 00 00 2A 2A 2A 2A 05   ...........****.
2817:7640  00 00 00 6D 67 2F 64 6C-20 01 00 00 00 00 00 00   ...mg/dl .......
2817:7650  00 00 00 1E 00 00 00 2A-2A 2A 2A 05 00 00 00 6D   .......****....m
2817:7660  67 2F 64 6C 20 01 00 00-00 00 00 00 00 00 00 1E   g/dl ...........
2817:7670  00 00 00 2A 2A 2A 2A 05-00 00 00 6D 67 2F 64 6C   ...****....mg/dl
2817:7680  20 01 00 00 00 00 00 00-00 00 00 1E 00 00 00 2A    ...............*
2817:7690  2A 2A 2A 05 00 00 00 6D-67 2F 64 6C 20 01 00 00   ***....mg/dl ...
2817:76A0  00 00 00 00 00 00 00 1E-00 00 00 2A 2A 2A 2A 05   ...........****.
2817:76B0  00 00 00 6D 67 2F 64 6C-20 01 00 00 00 00 00 00   ...mg/dl .......
2817:76C0  00 00 00 1E 00 00 00 4F-50 45 4E 05 00 00 00 6D   .......OPEN....m
2817:76D0  67 2F 64 6C 20 01 00 00-00 00 00 00 00 00 00 00   g/dl ...........
2817:76E0  00 01 00 01 00 01 00 01-00 01 00 01 00 01 00 01   ................
2817:76F0  00 01 00 01 00 00 00 00-00 00 00 00 00 06 02 AD   ................
2817:7700  00 34 00 00 00 00 00 20-20 20 20 00 00 00 00 00   .4.....    .....
2817:7710  09 00 41 00 3E 00 2F 00-30 00 01 00 03 00 08 00   ..A.>./.0.......
2817:7720  40 00 0F 00 12 00 43 00-00 00 3F 00 3B 00 20 00   @.....C...?.;. .
2817:7730  0A 00 0C 00 0E 00 06 00-07 00 B4 1C 00 00 30 75   ..............0u
2817:7740  00 00 54 3D 00 00 99 3A-00 00 E0 2E 00 00 C0 5D   ..T=...:.......]
2817:7750  00 00 F8 2A 00 00 38 4A-00 00 04 5B 00 00 90 65   ...*..8J...[...e
2817:7760  00 00 90 65 00 00 D0 39-00 00 A8 61 00 00 78 1E   ...e...9...a..x.
2817:7770  00 00 8C 3C 00 00 F8 2A-00 00 B0 3E 00 00 60 54   ...<...*...>..`T
```

```
2817:7780  00 00 2E 59 00 00 0D 17-00 00 90 3E 00 00 64 02   ...?.......e....
2817:7790  00 00 30 0C 00 00 64 19-00 00 94 11 00 00 9E 13   ......d.........
2817:77A0  00 00 D4 FE FF FF F4 01-00 00 F4 01 00 00 DA FE   ................
2817:77B0  FF FF 78 05 00 00 78 05-00 00 54 0D 00 00 AC 0D   ..x...x.........
2817:77C0  00 00 F0 0A 00 00 70 FE-FF FF 9C FF FF FF F8 2A   ......p........*
2817:77D0  00 00 90 18 00 00 E0 2E-00 00 A4 06 00 00 00 00   ................
2817:77E0  00 00 41 00 3E 00 2F 00-30 00 40 00 43 00 3F 00   ..A.>./.0.@.C.?.
2817:77F0  3B 00 00 00 30 31 34 37-2E 32 35 38 2E 33 36 39   ;...0147.258.369
2817:7800  61 62 63 64 00 00 01 00-00 00 00 00 00 00 05 00   abcd............
2817:7810  00 00 00 00 12 65 02 00-01 00 00 00 73 6B 75 63   .....e......skuc
2817:7820  6F 75 6E 74 2E 6C 6F 67-00 72 62 00 77 62 00 64   ount.log.rb.wb.d
2817:7830  61 74 61 6C 6F 67 2E 6C-6F 67 00 61 62 00 65 72   atalog.log.ab.er
2817:7840  72 63 6F 75 6E 74 2E 6C-6F 67 00 72 62 00 77 62   rcount.log.rb.wb
2817:7850  00 00 42 01 68 01 E8 01-E4 E8 2D 2D 2D 2D 2D 2D   ..B.h.....------
2817:7860  00 2D 2D 2D 2D 2D 2D 2D-2D 2D 2D 00 70 6C 65 61   .----------.plea
2817:7870  73 65 77 74 00 6D 61 69-6E 64 69 73 70 00 64 6F   sewt.maindisp.do
2817:7880  6E 74 69 6E 73 72 00 6D-61 69 6E 6D 65 6E 75 00   ntinsr.mainmenu.
2817:7890  73 65 74 74 69 6E 67 73-00 00 00 00 10 00 00 00   settings........
2817:78A0  2D 2D 2D 2D 2D 2D 00 2D-2D 2D 2D 2D 2D 2D 2D 2D   ------.---------
2817:78B0  2D 00 63 6F 70 79 72 69-74 65 00 4F 63 74 20 31   -.copyrite.Oct 1
2817:78C0  37 20 31 39 38 39 00 20-00 31 31 3A 32 32 3A 32   7 1989. .11:22:2
2817:78D0  32 00 77 61 72 6D 69 6E-67 00 70 6C 65 61 73 65   2.warming.please
2817:78E0  77 74 00 70 6C 65 61 73-65 77 32 00 70 6C 65 61   wt.pleasew2.plea
2817:78F0  73 65 77 74 00 66 66 66-66 66 66 42 40 44 4F 53   sewt.ffffffB@DOS
2817:7900  2E 4F 4B 00 61 00 25 73-20 61 74 20 25 75 0A 00   .OK.a.%s at %u..
2817:7910  00 00 00 00 74 65 6D 70-6E 61 6D 65 00 74 65 6D   ....tempname.tem
2817:7920  70 6E 61 6D 65 00 74 65-6D 70 6C 61 74 73 2E 64   pname.templats.d
2817:7930  61 74 00 25 38 73 3A 25-31 30 73 00 2D 2D 2D 2D   at.%8s:%10s.----
2817:7940  2D 2D 2D 2D 2D 2D 2D 2D-2D 2D 2D 2D 2D 2D 2D 2D   ----------------
2817:7950  2D 2D 2D 2D 2D 2D 2D 2D-2D 2D 2D 2D 00 74 65 78   ------------.tex
2817:7960  74 20 65 72 72 6F 72 3A-0A 20 20 20 63 61 6E 6E   t error:.   cann
2817:7970  6F 74 20 6C 6F 63 61 74-65 20 25 73 00 74 65 78   ot locate %s.tex
2817:7980  74 20 65 72 72 6F 72 3A-0A 20 20 20 63 61 6E 6E   t error:.   cann
2817:7990  6F 74 20 6C 6F 63 61 74-65 20 25 73 00 72 00 0A   ot locate %s.r..
2817:79A0  0A 0A 0A 41 4E 41 4C 59-5A 45 52 20 46 41 49 4C   ...ANALYZER FAIL
2817:79B0  55 52 45 0A 00 0A 20 44-49 53 4B 45 54 54 45 20   URE... DISKETTE
2817:79C0  54 45 58 54 20 44 41 54-41 0A 20 20 4E 4F 54 20   TEXT DATA.  NOT
2817:79D0  52 45 41 44 41 42 4C 45-0A 00 20 20 20 20 43 41   READABLE..    CA
2817:79E0  4C 4C 20 53 45 52 56 49-43 45 0A 00 0A 0A 0A 0A   LL SERVICE......
2817:79F0  41 4E 41 4C 59 5A 45 52-20 46 41 49 4C 55 52 45   ANALYZER FAILURE
2817:7A00  2E 0A 00 0A 20 54 45 58-54 20 4D 45 4D 4F 52 59   .... TEXT MEMORY
2817:7A10  20 49 53 0A 20 20 4E 4F-54 20 41 56 41 49 4C 41    IS.  NOT AVAILA
2817:7A20  42 4C 45 2E 0A 00 20 20-20 20 43 41 4C 4C 20 53   BLE...    CALL S
2817:7A30  45 52 56 49 43 45 0A 00-20 20 20 20 20 20 20 20   ERVICE..
2817:7A40  00 0A 0A 0A 0A 41 4E 41-4C 59 5A 45 52 20 46 41   .....ANALYZER FA
2817:7A50  49 4C 55 52 45 2E 0A 00-0A 20 54 45 58 54 20 44   ILURE.... TEXT D
2817:7A60  41 54 41 20 49 53 20 43-4F 52 52 55 50 54 2E 0A   ATA IS CORRUPT..
2817:7A70  00 20 20 20 20 43 41 4C-4C 20 53 45 52 56 49 43   .    CALL SERVIC
2817:7A80  45 2E 0A 00 0A 0A 0A 0A-41 4E 41 4C 59 5A 45 52   E.......ANALYZER
2817:7A90  20 46 41 49 4C 55 52 45-2E 0A 00 0A 20 4D 45 4D    FAILURE.... MEM
2817:7AA0  4F 52 59 20 46 55 4C 4C-2E 0A 00 20 20 20 20 43   ORY FULL...    C
2817:7AB0  41 4C 4C 20 53 45 52 56-49 43 45 2E 0A 00 0A 0A   ALL SERVICE.....
2817:7AC0  0A 0A 41 4E 41 4C 59 5A-45 52 20 46 41 49 4C 55   ..ANALYZER FAILU
2817:7AD0  52 45 2E 0A 00 0A 20 54-45 58 54 20 54 45 4D 50   RE.... TEXT TEMP
2817:7AE0  4C 41 54 45 20 4F 52 44-45 52 20 49 53 0A 20 43   LATE ORDER IS. C
2817:7AF0  4F 52 52 55 50 54 2E 0A-00 74 65 6D 70 6C 61 74   ORRUPT...templat
2817:7B00  65 20 3E 25 38 2E 38 73-3C 20 66 6F 6C 6C 6F 77   e >%8.8s< follow
2817:7B10  73 0A 20 3E 25 38 2E 38-73 3C 0A 00 20 20 20 20   s. >%8.8s<..
2817:7B20  43 41 4C 4C 20 53 45 52-56 49 43 45 2E 0A 00 0A   CALL SERVICE....
2817:7B30  0A 0A 0A 41 4E 41 4C 59-5A 45 52 20 46 41 49 4C   ...ANALYZER FAIL
2817:7B40  55 52 45 2E 0A 00 20 54-4F 4F 20 4D 41 4E 59 20   URE... TOO MANY
2817:7B50  54 45 4D 50 4C 41 54 45-53 0A 20 49 4E 20 54 45   TEMPLATES. IN TE
2817:7B60  4D 50 4C 41 54 45 20 46-49 4C 45 2E 0A 00 28 25   MPLATE FILE...(%
2817:7B70  64 20 3E 20 25 64 29 0A-0A 0A 00 20 20 20 20 43   d > %d)....    C
2817:7B80  41 4C 4C 20 53 45 52 56-49 43 45 2E 0A 00 2D 2D   ALL SERVICE...--
2817:7B90  2D 2D 2D 2D 00 2D 2D 2D-2D 2D 2D 2D 2D 2D 2D 00   ----.----------.
2817:7BA0  73 70 65 63 73 6C 63 74-00 64 6F 6E 74 69 6E 73   specslct.dontins
2817:7BB0  72 00 44 4F 47 00 43 41-54 00 4F 54 48 45 52 00   r.DOG.CAT.OTHER.
2817:7BC0  2D 2D 2D 2D 2D 2D 2D 2D-2D 2D 00 70 61 74 6E 75   ----------.patnu
2817:7BD0  6D 00 64 6F 6E 74 69 6E-73 72 00 2D 2D 2D 2D 2D   m.dontinsr.-----
2817:7BE0  2D 2D 2D 2D 2D 00 53 75-6E 4D 6F 6E 54 75 65 57   -----.SunMonTueW
2817:7BF0  65 64 54 68 75 46 72 69-53 61 74 4A 61 6E 46 65   edThuFriSatJanFe
```

```
2817:7C00  62 4D 61 72 41 70 72 4D-61 79 4A 75 6E 4A 75 6C   bMarAprMayJunJul
2817:7C10  41 75 67 53 65 70 4F 63-74 4E 6F 76 44 65 63 53   AugSepOctNovDecS
2817:7C20  2F 4E 20 00 00 00 00 00-00 F0 0F 25 32 2E 32 64   /N ........%2.2d
2817:7C30  00 25 32 2E 32 64 00 41-4D 00 50 4D 00 25 33 2E   .%2.2d.AM.PM.%3.
2817:7C40  33 73 20 25 32 64 20 25-33 2E 33 73 20 25 30 34   3s %2d %3.3s %04
2817:7C50  64 20 25 32 64 3A 25 30-32 64 25 32 73 00 25 31   d %2d:%02d%2s.%1
2817:7C60  64 3A 25 30 32 64 00 00-00 00 00 00 00 24 40 54   d:%02d.......$@T
2817:7C70  4D 50 41 2F 44 46 41 49-4C 20 00 74 6D 70 3A 25   MPA/DFAIL .tmp:%
2817:7C80  2B 37 2E 37 6C 64 20 00-52 45 46 41 2F 44 46 41   +7.7ld .REFA/DFA
2817:7C90  49 4C 20 00 72 65 66 3A-25 2B 37 2E 37 6C 64 20   IL .ref:%+7.7ld
2817:7CA0  00 52 45 46 41 44 3D 30-20 21 20 00 0A 00 25 2B   .REFAD=0 ! ...%+
2817:7CB0  35 2E 35 6C 66 20 43 20-00 00 00 00 00 00 00 69   5.5lf C .......i
2817:7CC0  40 00 00 00 00 00 80 42-40 0A 0A 0A 4D 41 54 48   @......B@...MATH
2817:7CD0  20 46 41 49 4C 55 52 45-2E 0A 00 20 54 55 52 4E    FAILURE... TURN
2817:7CE0  20 41 4E 41 4C 59 5A 45-52 20 4F 46 46 20 41 4E    ANALYZER OFF AN
2817:7CF0  44 20 4F 4E 0A 00 64 6F-6D 61 69 6E 20 65 72 72   D ON..domain err
2817:7D00  6F 72 0A 00 73 69 6E 67-75 6C 61 72 69 74 79 20   or..singularity
2817:7D10  65 72 72 6F 72 0A 00 6F-76 65 72 66 6C 6F 77 20   error..overflow
2817:7D20  65 72 72 6F 72 0A 00 75-6E 64 65 72 66 6C 6F 77   error..underflow
2817:7D30  20 65 72 72 6F 72 0A 00-74 6F 74 61 6C 20 6C 6F    error..total lo
2817:7D40  73 73 20 6F 66 20 73 69-67 2E 20 64 69 67 69 74   ss of sig. digit
2817:7D50  73 20 65 72 72 6F 72 0A-00 65 72 72 6F 72 20 25   s error..error %
2817:7D60  64 0A 00 69 6E 20 72 6F-75 74 69 6E 65 3A 20 25   d..in routine: %
2817:7D70  73 21 0A 00 70 61 73 73-65 64 20 76 61 6C 75 65   s!..passed value
2817:7D80  73 3D 25 6C 66 61 6E 64-25 6C 66 21 21 21 0A 00   s=%lfand%lf!!!..
2817:7D90  64 6F 6E 74 69 6E 73 72-00 6C 6F 64 73 6C 69 64   dontinsr.lodslid
2817:7DA0  73 00 63 6F 6E 74 69 6E-67 00 6E 6F 74 63 61 6C   s.conting.notcal
2817:7DB0  64 00 65 6E 74 72 63 6F-64 65 00 75 70 73 64 6F   d.entrcode.upsdo
2817:7DC0  77 6E 00 63 6F 6E 74 69-6E 67 00 6E 6F 74 73 70   wn.conting.notsp
2817:7DD0  72 74 64 00 62 61 72 66-61 69 6C 00 25 34 2E 34   rtd.barfail.%4.4
2817:7DE0  73 00 63 6F 6E 74 69 6E-67 00 63 6F 6E 74 69 6E   s.conting.contin
2817:7DF0  67 00 63 00 63 00 63 00-07 00 63 00 04 00 00 00   g.c.c.c...c.....
2817:7E00  63 00 63 00 02 00 09 00-63 00 06 00 63 00 63 00   c.c.....c...c.c.
2817:7E10  63 00 63 00 01 00 0E 00-63 00 05 00 63 00 63 00   c.c.....c...c.c.
2817:7E20  63 00 03 00 63 00 63 00-63 00 63 00 63 00 63 00   c...c.c.c.c.c.c.
2817:7E30  63 00 73 74 61 6E 64 2D-62 79 20 77 68 69 6C 65   c.stand-by while
2817:7E40  20 72 65 61 64 69 6E 67-20 62 61 72 63 6F 64 65    reading barcode
2817:7E50  2E 2E 00 20 20 20 20 20-20 00 73 6C 6F 74 25 32   ...      .slot%2
2817:7E60  64 20 63 6F 64 65 28 45-4E 54 45 52 20 66 6F 72   d code(ENTER for
2817:7E70  20 25 32 64 29 3A 00 20-20 20 20 20 00 73 6C 6F    %2d):.     .slo
2817:7E80  74 25 32 64 20 6C 6F 74-28 45 4E 54 45 52 20 66   t%2d lot(ENTER f
2817:7E90  6F 72 20 25 34 64 29 3A-00 20 20 20 20 20 20 20   or %4d):.
2817:7EA0  20 20 20 20 20 20 20 20-20 20 20 20 20 20 20 20
2817:7EB0  20 20 20 20 20 20 20 20-20 00 01 00 70 69 70 6C            ...pipl
2817:7EC0  69 66 65 31 00 70 69 70-6C 69 66 65 32 00 70 6C   ife1.piplife2.pl
2817:7ED0  65 61 73 65 77 74 00 62-61 63 6B 6C 61 73 68 00   easewt.backlash.
2817:7EE0  70 6C 65 61 73 65 77 74-00 70 69 70 63 61 6C 74   pleasewt.pipcalt
2817:7EF0  31 00 70 69 70 63 61 6C-74 32 00 00 66 64 73 6B   1.pipcalt2..fdsk
2817:7F00  68 6F 6D 65 00 66 68 6F-66 73 6C 6F 64 00 66 70   home.fhofslod.fp
2817:7F10  69 70 68 6F 6D 65 00 66-68 6F 66 73 61 76 65 00   iphome.fhofsave.
2817:7F20  66 64 73 6B 75 6A 61 6D-00 66 63 6F 76 69 6E 69   fdskujam.fcovini
2817:7F30  74 00 66 63 6F 76 6D 6F-76 65 00 66 65 6A 65 75   t.fcovmove.fejeu
2817:7F40  6A 61 6D 00 66 70 72 69-6E 74 00 66 69 63 6C 72   jam.fprint.ficlr
2817:7F50  65 61 64 00 66 69 63 6C-77 72 69 74 00 66 65 6A   ead.ficlwrit.fej
2817:7F60  6C 65 61 76 65 00 66 65-6A 72 65 74 72 6E 00 66   leave.fejretrn.f
2817:7F70  65 6A 73 74 61 79 00 66-61 64 6E 74 64 75 6E 00   ejstay.fadntdun.
2817:7F80  66 61 64 6F 76 65 72 00-66 70 69 70 73 65 6E 73   fadover.fpipsens
2817:7F90  00 66 63 61 6C 6F 70 65-6E 00 66 63 61 6C 72 65   .fcalopen.fcalre
2817:7FA0  61 64 00 66 6D 6F 74 74-69 6D 65 00 66 73 70 74   ad.fmottime.fspt
2817:7FB0  74 69 6D 65 00 66 61 70-6C 65 61 76 65 00 66 61   time.fapleave.fa
2817:7FC0  70 72 65 74 72 6E 00 66-61 70 73 74 61 79 00 66   pretrn.fapstay.f
2817:7FD0  61 70 69 6E 69 74 00 66-6C 6F 74 73 61 76 65 00   apinit.flotsave.
2817:7FE0  66 6C 6F 74 6C 6F 61 64-00 66 65 6A 61 6D 75 70   flotload.fejamup
2817:7FF0  00 66 75 76 6F 6E 33 00-66 64 6C 6F 67 00 66 65   .fuvon3.fdlog.fe
2817:8000  65 70 00 66 63 6C 6F 67-00 66 65 65 70 72 6F 6D   ep.fclog.feeprom
2817:8010  00 66 75 76 6F 6E 34 00-66 72 61 6E 67 65 72 64   .fuvon4.frangerd
2817:8020  00 66 68 73 6E 73 77 74-00 66 68 73 6E 73 72 64   .fhsnswt.fhsnsrd
2817:8030  00 66 6B 70 61 64 77 74-00 66 6B 70 61 64 72 64   .fkpadwt.fkpadrd
2817:8040  00 66 63 73 6E 73 77 74-00 66 63 73 6E 73 72 64   .fcsnswt.fcsnsrd
2817:8050  00 66 73 6E 73 61 76 65-00 66 73 6E 6C 6F 61 64   .fsnsave.fsnload
2817:8060  00 66 70 62 6C 73 61 76-65 00 66 70 62 6C 6C 6F   .fpblsave.fpbllo
2817:8070  61 64 00 66 70 72 6D 72-65 61 64 00 66 70 72 6D   ad.fprmread.fprm
```

```
2817:8080  61 6C 6C 6F 00 66 63 61-6F 66 73 61 76 00 66 72  allo.fcaofsav.fr
2817:8090  65 66 61 6C 6F 63 00 66-65 65 70 77 72 69 74 00  efaloc.feepwrit.
2817:80A0  25 64 00 66 75 6E 64 65-66 00 25 64 00 70 6C 65  %d.fundef.%d.ple
2817:80B0  61 73 65 77 74 00 6E 65-77 74 69 70 00 69 6E 69  asewt.newtip.ini
2817:80C0  74 73 79 72 67 00 6C 6F-61 64 70 69 70 74 00 74  tsyrg.loadpipt.t
2817:80D0  6F 6F 6C 6F 6E 67 00 00-20 54 45 4D 50 20 41 2F  oolong.. TEMP A/
2817:80E0  44 20 46 41 49 4C 55 52-45 20 00 5A 45 52 4F 20  D FAILURE .ZERO 
2817:80F0  41 2F 44 20 46 41 49 4C-55 52 45 20 00 20 52 45  A/D FAILURE . RE
2817:8100  46 20 41 2F 44 20 46 41-49 4C 55 52 45 20 00 70  F A/D FAILURE .p
2817:8110  6C 65 61 73 65 77 74 00-61 6E 61 6C 79 73 69 73  leasewt.analysis
2817:8120  00 70 69 70 69 6E 76 61-6C 00 70 6C 65 61 73 65  .pipinval.please
2817:8130  77 74 00 0A 62 75 67 20-69 6E 20 61 6E 61 6C 79  wt..bug in analy
2817:8140  7A 65 2E 63 2E 20 69 6E-76 61 6C 69 64 20 63 6F  ze.c. invalid co
2817:8150  6C 6F 72 00 20 54 45 4D-50 20 41 2F 44 20 46 41  lor. TEMP A/D FA
2817:8160  49 4C 55 52 45 20 00 20-52 45 46 20 41 2F 44 20  ILURE . REF A/D 
2817:8170  46 41 49 4C 55 52 45 20-00 5A 45 52 4F 20 41 2F  FAILURE .ZERO A/
2817:8180  44 20 46 41 49 4C 55 52-45 20 00 63 6F 6D 70 6C  D FAILURE .compl
2817:8190  65 74 65 00 70 6C 65 61-73 65 77 74 00 72 65 6D  ete.pleasewt.rem
2817:81A0  6F 76 74 69 70 00 00 00-00 00 00 00 40 40 72 65  ovtip.......@@re
2817:81B0  73 75 6C 74 73 00 0D 00-53 2F 4E 20 25 2A 2E 2A  sults...S/N %*.*
2817:81C0  73 0D 0A 00 0D 0A 25 38-73 3A 25 31 30 73 0D 0A  s.....%8s:%10s..
2817:81D0  00 73 70 6F 74 66 61 69-6C 00 25 34 2E 34 73 20  .spotfail.%4.4s 
2817:81E0  00 25 34 2E 34 73 20 00-6E 6F 73 70 6F 74 00 6E  .%4.4s .nospot.n
2817:81F0  6F 73 70 6F 74 00 6E 6F-63 61 6C 64 00 6E 6F 63  ospot.nocald.noc
2817:8200  61 6C 64 00 28 25 38 2E-35 6C 66 29 0A 00 28 25  ald.(%8.5lf)..(%
2817:8210  38 2E 35 6C 66 29 0D 0A-00 25 63 00 25 63 00 25  8.5lf)...%c.%c.%
2817:8220  2A 2E 2A 6C 66 20 25 36-2E 36 73 20 00 25 2A 2E  *.*lf %6.6s .%*.
2817:8230  2A 6C 66 20 25 36 2E 36-73 20 00 25 2A 6C 64 20  *lf %6.6s .%*ld 
2817:8240  25 36 2E 36 73 20 00 25-2A 6C 64 20 25 36 2E 36  %6.6s .%*ld %6.6
2817:8250  73 20 00 6C 6F 77 00 6C-6F 77 00 68 69 67 68 00  s .low.low.high.
2817:8260  68 69 67 68 00 6E 6F 72-6D 61 6C 00 6E 6F 72 6D  high.normal.norm
2817:8270  61 6C 00 6E 6F 72 6D 61-6C 00 6E 6F 72 6D 61 6C  al.normal.normal
2817:8280  00 0D 0A 00 28 25 38 2E-35 6C 66 29 0A 00 20 20  ....(%8.5lf)..  
2817:8290  20 20 20 20 20 20 20 28-25 38 2E 35 6C 66 29 0D         (%8.5lf).
2817:82A0  0A 00 0A 00 72 65 73 6C-74 69 6E 76 00 72 65 73  ....resltinv.res
2817:82B0  6C 74 69 6E 76 00 0A 00-0D 0A 00 20 20 20 20 20  ltinv......     
2817:82C0  20 20 20 28 25 36 2E 31-66 2D 25 36 2E 31 66 29     (%6.1f-%6.1f)
2817:82D0  0D 0A 00 74 6D 70 77 61-72 6E 31 00 25 36 2E 32  ...tmpwarn1.%6.2
2817:82E0  6C 66 0D 0A 00 74 6D 70-77 61 72 6E 32 00 25 36  lf...tmpwarn2.%6
2817:82F0  2E 32 6C 66 0D 0A 00 0D-0A 00 57 41 4E 54 50 52  .2lf......WANTPR
2817:8300  4F 46 00 77 72 69 74 66-69 6C 65 00 0A 0A 66 69  OF.writfile...fi
2817:8310  6C 65 6E 61 6D 65 20 69-73 20 25 73 0A 00 0A 20  lename is %s... 
2817:8320  49 73 20 74 68 69 73 20-63 6F 72 72 65 63 74 20  Is this correct 
2817:8330  28 79 2E 6E 29 00 77 74-00 65 72 72 6F 72 3A 20  (y.n).wt.error: 
2817:8340  63 61 6E 6E 6F 74 20 6F-70 65 6E 20 25 73 0A 00  cannot open %s..
2817:8350  25 34 2E 34 73 20 00 6E-6F 20 73 70 6F 74 00 6E  %4.4s .no spot.n
2817:8360  6F 20 63 61 6C 20 64 61-74 61 20 28 25 37 2E 37  o cal data (%7.7
2817:8370  6C 66 29 0A 00 25 63 00-20 20 25 2A 2E 2A 6C 66  lf)..%c.  %*.*lf
2817:8380  20 20 25 36 2E 36 73 00-20 20 25 2A 6C 64 20 20    %6.6s.  %*ld  
2817:8390  25 36 2E 36 73 00 20 20-20 25 38 2E 35 6C 66 0A  %6.6s.   %8.5lf.
2817:83A0  00 72 65 73 6C 74 69 6E-76 00 0A 00 0D 0A 74 65  .resltinv.....te
2817:83B0  78 74 20 66 69 6C 65 3A-25 73 0D 0A 0D 0D 0D 00  xt file:%s......
2817:83C0  57 41 4E 54 50 52 4F 46-00 00 00 00 00 00 00 69  WANTPROF.......i
2817:83D0  40 00 00 00 00 00 00 24-40 00 00 00 00 00 80 42  @......$@......B
2817:83E0  40 9A 99 99 99 99 59 42-40 66 66 66 66 66 A6 42  @.....YB@fffff.B
2817:83F0  40 00 65 6D 70 74 79 62-6F 78 00 63 6C 65 61 72  @.emptybox.clear
2817:8400  65 6A 65 00 70 6C 65 61-73 65 77 74 00 00 61 3A  eje.pleasewt..a:
2817:8410  66 69 6C 65 6E 61 6D 65-2E 65 78 74 00 63 75 72  filename.ext.cur
2817:8420  76 6D 65 6E 75 00 25 32-2E 32 63 25 34 2E 34 73  vmenu.%2.2c%4.4s
2817:8430  20 25 34 2E 34 64 00 63-68 61 6E 67 6C 6F 74 00   %4.4d.changlot.
2817:8440  25 34 2E 34 73 00 25 34-2E 34 64 00 70 6C 65 61  %4.4s.%4.4d.plea
2817:8450  73 65 77 74 00 6E 6F 74-61 76 61 69 6C 00 6C 6F  sewt.notavail.lo
2817:8460  74 66 69 6C 65 6E 00 72-62 00 6C 6F 74 66 69 6C  tfilen.rb.lotfil
2817:8470  65 6E 00 77 62 00 0A 0A-0A 46 41 54 41 4C 20 41  en.wb....FATAL A
2817:8480  4E 41 4C 59 5A 45 52 20-46 41 49 4C 55 52 45 2E  NALYZER FAILURE.
2817:8490  0A 00 0A 0A 55 6E 61 62-6C 65 20 74 6F 20 61 6C  ....Unable to al
2817:84A0  6C 6F 63 61 74 65 20 6D-65 6D 6F 72 79 20 66 6F  locate memory fo
2817:84B0  72 0A 00 20 20 20 20 20-63 68 65 6D 69 73 74 72  r..     chemistr
2817:84C0  79 20 63 61 6C 69 62 72-61 74 69 6F 6E 20 64 61  y calibration da
2817:84D0  74 61 2E 0A 00 0A 0A 0A-20 63 6F 72 65 6C 65 66  ta...... corelef
2817:84E0  74 3D 25 6C 75 20 62 79-74 65 73 0A 00 20 66 61  t=%lu bytes.. fa
2817:84F0  72 63 6F 72 65 6C 65 66-74 3D 25 6C 75 20 62 79  rcoreleft=%lu by
```

```
2817:8500  74 65 73 0A 00 20 61 6C-6C 6F 63 61 74 69 6E 67   tes.. allocating
2817:8510  20 66 61 72 20 66 6F 72-20 63 6E 6D 5F 63 61 6C    far for cnm_cal
2817:8520  0A 00 20 61 6C 6C 6F 63-61 74 69 6E 67 20 25 6C   .. allocating %l
2817:8530  75 20 62 79 74 65 73 0A-00 00 00 00 00 00 00 59   u bytes........Y
2817:8540  D0 00 00 00 00 00 00 00-00 00 00 00 00 00 00 00   ................
2817:8550  40 00 00 00 00 00 00 E0-3F 63 68 61 6D 78 78 2E   @.......?chamxx.
2817:8560  64 61 74 00 72 62 00 00-73 65 72 76 69 63 65 00   dat.rb..service.
2817:8570  6E 6F 74 69 6D 70 00 6E-6F 74 69 6D 70 00 70 6C   notimp.notimp.pl
2817:8580  65 61 73 65 77 74 00 74-75 72 6E 6C 61 6D 70 00   easewt.turnlamp.
2817:8590  20 25 63 20 00 61 64 66-61 69 6C 75 72 00 20 28    %c .adfailur. (
2817:85A0  25 64 29 0A 00 20 25 63-3A 20 25 2B 37 2E 37 6C   %d).. %c: %+7.7l
2817:85B0  64 0A 00 0A 0A 0A 0A 0A-0A 0A 0A 0A 0A 0A 0A 0A   d...............
2817:85C0  0A 0A 0A 0A 0A 0A 0A 0A-0A 0A 0A 0A 0A 0A 00 0A   ................
2817:85D0  76 69 73 72 65 66 3D 25-6C 64 0A 75 76 72 65 66   visref=%ld.uvref
2817:85E0  3D 25 6C 66 0A 00 73 6C-6F 74 20 25 32 2E 32 64   =%lf..slot %2.2d
2817:85F0  20 63 6F 6C 6F 72 20 25-31 2E 31 64 3A 0A 20 20    color %1.1d:.
2817:8600  63 61 6C 63 64 20 62 72-3D 25 37 2E 37 6C 66 0A   calcd br=%7.7lf.
2817:8610  0A 20 20 20 77 72 65 66-3D 25 37 2E 37 6C 66 0A   .   wref=%7.7lf.
2817:8620  00 77 68 69 74 65 20 72-65 66 20 63 6F 72 72 65   .white ref corre
2817:8630  63 74 69 6F 6E 20 64 69-73 6B 20 72 65 61 64 69   ction disk readi
2817:8640  6E 67 73 3A 00 33 35 30-3A 20 25 6C 64 20 34 30   ngs:.350: %ld 40
2817:8650  30 3A 25 6C 64 0A 00 36-36 30 3A 20 25 6C 64 20   0:%ld..660: %ld
2817:8660  35 39 35 3A 25 6C 64 0A-00 35 35 35 3A 20 25 6C   595:%ld..555: %l
2817:8670  64 20 36 38 30 3A 25 6C-64 0A 00 65 6E 64 2E 0A   d 680:%ld..end..
2817:8680  00 00 69 6E 69 74 65 65-70 72 00 65 65 70 6D 6F   ..initeepr.eepmo
2817:8690  64 31 00 65 65 70 6D 6F-64 32 00 25 34 2E 34 64   d1.eepmod2.%4.4d
2817:86A0  3A 25 33 2E 33 64 3A 20-20 20 20 20 20 20 00 00   :%3.3d:       ..
2817:86B0  73 65 74 63 6C 6B 00 73-65 74 64 61 79 00 73 65   setclk.setday.se
2817:86C0  74 6D 6F 6E 74 68 00 73-65 74 79 72 00 73 65 74   tmonth.setyr.set
2817:86D0  68 72 00 73 65 74 6D 69-6E 00 1E 1C 03 2E 61 3A   hr.setmin.....a:
2817:86E0  66 69 6C 65 6E 61 6D 65-2E 65 78 74 00 25 32 2E   filename.ext.%2.
2817:86F0  32 64 20 76 61 6C 69 64-20 63 75 72 76 65 73 20   2d valid curves
2817:8700  74 6F 20 62 65 20 73 74-6F 72 65 64 2E 0A 00 0A   to be stored....
2817:8710  66 69 6C 65 6E 61 6D 65-20 74 6F 20 77 72 69 74   filename to writ
2817:8720  65 20 74 6F 3A 0A 28 65-6E 74 65 72 20 66 6F 72   e to:.(enter for
2817:8730  20 25 31 30 2E 31 30 73-29 0A 3F 00 45 52 52 4F    %10.10s).?.ERRO
2817:8740  52 3A 74 6F 6F 20 6D 61-6E 79 20 63 68 61 72 61   R:too many chara
2817:8750  63 74 65 72 73 21 0A 00-0A 66 69 6C 65 6E 61 6D   cters!...filenam
2817:8760  65 20 69 73 20 25 73 0A-00 0A 20 49 73 20 74 68   e is %s... Is th
2817:8770  69 73 20 63 6F 72 72 65-63 74 20 28 79 2C 6E 29   is correct (y,n)
2817:8780  00 57 72 69 74 69 6E 67-20 74 6F 20 64 69 73 6B   .Writing to disk
2817:8790  20 25 64 20 62 79 74 65-73 20 2E 2E 2E 0A 00 77    %d bytes .....w
2817:87A0  62 00 65 72 72 6F 72 3A-20 63 61 6E 6E 6F 74 20   b.error: cannot
2817:87B0  6F 70 65 6E 20 25 73 0A-00 65 72 72 6F 72 3A 20   open %s..error:
2817:87C0  63 61 6E 6E 6F 74 20 77-72 69 74 65 20 25 73 2C   cannot write %s,
2817:87D0  20 73 74 61 74 75 73 20-3D 20 25 64 0A 00 0D 0A    status = %d....
2817:87E0  72 61 77 20 66 69 6C 65-3A 25 73 0D 0A 00 31 32   raw file:%s...12
2817:87F0  33 34 35 00 0A 0A 0A 0A-0A 0A 0A 0A 0A 0A 0A 0A   345.............

2817:8800  0A 0A 0A 0A 0A 00 2A 2A-2A 2A 2A 2A 2A 2A 2A 2A   ......**********
2817:8810  2A 2A 2A 2A 2A 2A 2A 2A-2A 2A 2A 2A 2A 2A 2A 2A   ****************
2817:8820  2A 2A 2A 2A 2A 2A 2A 2A-2A 00 31 3D 72 61 77 20   *********.1=raw
2817:8830  64 61 74 61 2C 70 61 72-61 6D 65 74 65 72 73 2C   data,parameters,
2817:8840  72 65 73 75 6C 74 73 20-61 6E 64 20 73 74 61 74   results and stat
2817:8850  73 00 32 3D 72 65 73 75-6C 74 73 2C 70 61 72 61   s.2=results,para
2817:8860  6D 65 74 65 72 73 20 61-6E 64 20 73 74 61 74 73   meters and stats
2817:8870  00 33 3D 77 72 69 74 65-20 74 6F 20 27 70 6C 6F   .3=write to 'plo
2817:8880  74 74 65 72 27 20 66 69-6C 65 00 34 3D 72 65 73   tter' file.4=res
2817:8890  75 6C 74 73 20 61 6E 64-20 73 74 61 74 73 20 6F   ults and stats o
2817:88A0  6E 6C 79 00 35 3D 73 77-69 74 63 68 20 6F 75 74   nly.5=switch out
2817:88B0  70 75 74 20 74 6F 20 00-63 6F 6E 73 6F 6C 65 0A   put to .console.
2817:88C0  00 70 72 69 6E 74 65 72-0A 00 36 3D 20 45 6E 64   .printer..6= End
2817:88D0  0A 00 28 10 70 72 69 6E-74 65 72 00 63 6F 6E 73   ..(.printer.cons
2817:88E0  6F 6C 65 00 20 77 69 6C-6C 20 62 65 20 75 73 65   ole. will be use
2817:88F0  64 20 66 6F 72 20 6F 75-74 70 75 74 29 0A 00 70   d for output)..p
2817:8900  72 65 73 73 20 6B 65 79-20 66 6F 72 20 73 65 6C   ress key for sel
2817:8910  65 63 74 69 6F 6E 00 20-20 74 68 65 6E 20 70 72   ection.  then pr
2817:8920  65 73 73 20 45 4E 54 45-52 00 0A 00 6E 6F 77 20   ess ENTER...now
2817:8930  65 6E 74 65 72 20 74 68-65 20 66 69 72 73 74 20   enter the first
2817:8940  61 6E 64 20 6C 61 73 74-00 20 73 6C 6F 74 73 20   and last. slots
2817:8950  74 6F 20 70 72 6F 63 65-73 73 2E 0A 00 0A 73 74   to process....st
2817:8960  61 72 74 20 73 6C 6F 74-20 3D 00 0A 6C 61 73 74   art slot =..last
2817:8970  20 73 6C 6F 74 20 3D 00-0A 0A 0A 0A 0A 0A 0A 0A    slot =.........
```

```
2317:8980  0A 0A 0A 0A 0A 0A 0A 0A-0A 0A 0A 0A 0A 0A 0A 0A  ................
2317:8990  0A 0A 0A 0A 0A 77 72 69-74 69 6E 67 20 74 6F 20  .....writing to 
2317:89A0  66 69 6C 65 20 25 73 0A-0A 0A 0A 0A 0A 0A 0A 0A  file %s.........
2317:89B0  0A 0A 0A 0A 00 77 74 00-65 72 72 6F 72 3A 20 63  .....wt.error: c
2317:89C0  61 6E 6E 6F 74 20 6F 70-65 6E 20 25 73 0A 00 25  annot open %s..%
2317:89D0  64 0A 00 25 64 0A 00 25-64 00 25 2B 35 2E 35 6C  d..%d..%d.%+5.5l
2317:89E0  66 0A 00 2D 31 00 25 64-00 31 00 30 0A 00 25 6C  f..-1.%d.1.0..%l
2317:89F0  66 00 25 6C 66 00 25 6C-66 00 30 0A 31 0A 31 0A  f.%lf.%lf.0.1.1.
2317:8A00  30 0A 0A 00 30 0A 00 0A-0A 64 6F 6E 65 20 77 72  0...0....done wr
2317:8A10  69 74 69 6E 67 2E 20 70-72 65 73 73 20 61 6E 79  iting. press any
2317:8A20  20 6B 65 79 00 0A 0A 0A-0A 0A 0A 0A 0A 0A 0A 0A   key............
2317:8A30  0A 0A 0A 0A 0A 0A 0A 0A-0A 0A 0A 0A 0A 0A 0A 0A  ................
2317:8A40  00 50 6C 65 61 73 65 20-77 61 69 74 20 77 68 69  .Please wait whi
2317:8A50  6C 65 20 70 72 69 6E 74-69 6E 67 2E 2E 2E 00 0A  le printing.....
2317:8A60  0A 0A 0A 0A 0A 0A 0A 00-0A 66 69 6C 65 6E 61 6D  .........filenam
2317:8A70  65 3A 20 25 73 0A 00 0A-73 6C 6F 74 20 25 32 2E  e: %s...slot %2.
2317:8A80  32 64 28 25 73 29 3D 25-34 2E 34 73 0A 00 62 6C  2d(%s)=%4.4s..bl
2317:8A90  61 63 6B 20 72 65 66 65-72 65 6E 63 65 20 72 61  ack reference ra
2317:8AA0  77 20 3D 20 25 6C 66 0A-00 77 68 69 74 65 20 72  w = %lf..white r
2317:8AB0  65 66 65 72 65 6E 63 65-20 72 61 77 20 3D 20 25  eference raw = %
2317:8AC0  6C 66 0A 00 20 20 20 20-20 20 20 20 7C 20 20 20  lf..        |   
2317:8AD0  20 20 20 20 20 0A 00 20-72 61 77 20 20 20 20 7C       .. raw    |
2317:8AE0  20 64 65 6E 73 69 74 79-0A 00 25 2B 37 2E 37 6C   density..%+7.7l
2317:8AF0  64 20 7C 20 25 2B 35 2E-35 6C 66 2E 2E 2E 20 70  d | %+5.5lf... p
2317:8B00  72 65 2D 73 70 6F 74 0A-00 25 2B 37 2E 37 6C 64  re-spot..%+7.7ld
2317:8B10  20 7C 20 25 2B 35 2E 35-6C 66 0A 00 2A 2A 2A 20   | %+5.5lf..*** 
2317:8B20  73 6C 6F 74 20 25 64 20-72 65 73 75 6C 74 73 20  slot %d results 
2317:8B30  69 6E 76 61 6C 69 64 61-74 65 64 2A 2A 2A 0A 00  invalidated***..
2317:8B40  73 6C 6F 74 25 64 20 25-34 2E 34 73 20 63 6F 6E  slot%d %4.4s con
2317:8B50  74 3D 25 6C 66 0A 00 73-6C 6F 74 25 64 20 25 34  t=%lf..slot%d %4
2317:8B60  2E 34 73 20 72 61 74 65-3D 25 6C 66 0A 00 73 6C  .4s rate=%lf..sl
2317:8B70  6F 74 25 64 20 25 34 2E-34 73 20 61 62 6F 76 65  ot%d %4.4s above
2317:8B80  20 72 61 6E 67 65 0A 00-73 6C 6F 74 25 64 20 25   range..slot%d %
2317:8B90  34 2E 34 73 20 74 77 6F-70 3D 25 6C 66 0A 00 73  4.4s twop=%lf..s
2317:8BA0  6C 6F 74 25 64 20 25 34-2E 34 73 20 20 20 20 20  lot%d %4.4s     
2317:8BB0  3D 25 6C 66 0A 00 73 74-61 74 69 73 74 69 63 73  =%lf..statistics
2317:8BC0  20 66 6F 72 20 25 73 3A-0A 0A 00 73 6C 6F 74 25   for %s:...slot%
2317:8BD0  64 2E 6C 6F 74 3D 25 64-0A 00 20 20 74 65 6D 70  d.lot=%d..  temp
2317:8BE0  20 43 20 20 72 61 77 20-74 65 6D 70 20 20 61 2F   C  raw temp  a/
2317:8BF0  64 20 72 65 66 2E 20 20-61 2F 64 20 7A 65 72 6F  d ref.  a/d zero
2317:8C00  0A 00 25 2B 37 2E 37 6C-66 20 25 2B 37 2E 37 6C  ..%+7.7lf %+7.7l
2317:8C10  64 20 25 2B 37 2E 37 6C-64 20 25 2B 37 2E 37 6C  d %+7.7ld %+7.7l
2317:8C20  64 0A 00 25 2B 37 2E 37-6C 66 20 25 2B 37 2E 37  d..%+7.7lf %+7.7
2317:8C30  6C 64 20 25 2B 37 2E 37-6C 64 20 25 2B 37 2E 37  ld %+7.7ld %+7.7
2317:8C40  6C 64 0A 00 6E 75 6D 62-65 72 20 6F 66 20 73 6C  ld..number of sl
2317:8C50  6F 74 73 3D 25 37 2E 37-6C 66 0A 20 73 75 6D 3D  ots=%7.7lf. sum=
2317:8C60  25 37 2E 37 6C 66 0A 00-6D 65 61 6E 3D 25 2B 37  %7.7lf..mean=%+7
2317:8C70  2E 37 6C 66 20 0A 00 53-2E 44 28 6E 2D 31 29 20  .7lf ..S.D(n-1) 
2317:8C80  3D 20 25 37 2E 37 6C 66-20 0A 00 63 76 3D 20 25  = %7.7lf ..cv= %
2317:8C90  37 2E 37 6C 66 0A 00 00-00 00 00 00 00 F0 3F 00  7.7lf.........?.
2317:8CA0  00 00 00 00 00 00 34 40-00 00 00 00 00 00 69 40  ......4@......i@
2317:8CB0  00 00 00 00 00 24 40 00-00 00 00 00 80 42 40 00  .....$@......B@.
2317:8CC0  00 00 00 00 00 00 00 00-00 00 00 00 00 59 40 00  .............Y@.
2317:8CD0  31 39 44 65 63 38 38 20-63 6F 6E 63 20 64 65 70  19Dec88 conc dep
2317:8CE0  65 6E 64 65 6E 74 20 6D-65 74 68 6F 64 3D 3D 3D  endent method===
2317:8CF0  3D 3D 3D 3D 3D 3D 0A 00-63 61 6E 27 74 20 66 69  ======..can't fi
2317:8D00  6E 64 20 70 61 72 61 6D-65 74 65 72 73 20 69 6E  nd parameters in
2317:8D10  20 70 61 72 61 6D 73 2E-64 61 74 0A 00 76 61 72   params.dat..var
2317:8D20  69 61 6E 63 65 20 74 6F-6F 20 68 69 67 68 28 25  iance too high(%
2317:8D30  6C 65 29 2E 72 65 73 6C-74 73 20 69 6E 76 61 6C  le).reslts inval
2317:8D40  69 64 0A 00 63 6F 6E 63-65 6E 74 72 61 74 69 6F  id..concentratio
2317:8D50  6E 20 61 62 6F 76 65 20-72 61 6E 67 65 0A 00 32  n above range..2
2317:8D60  39 53 65 70 74 38 38 20-73 6C 6F 74 2D 69 6E 64  9Sept88 slot-ind
2317:8D70  65 70 65 6E 64 65 6E 74-20 74 77 6F 20 70 6F 69  ependent two poi
2317:8D80  6E 74 20 72 61 74 65 3D-3D 3D 3D 0A 00 00 00 00  nt rate====.....
2317:8D90  00 00 40 7F 40 00 00 00-00 00 00 28 40 00 00 00  ..@.@......(@...
2317:8DA0  00 00 00 2E 40 E1 7A 14-AE 47 E1 7A 40 00 00 00  ....@.z..G.z@...
2317:8DB0  00 00 00 4E 40 ED ED 8E-40 F7 C6 B0 3E 7A 65 72  ...N@.......>zer
2317:8DC0  6F 70 74 73 00 70 6C 65-61 73 65 77 74 00 6E 6F  opts.pleasewt.no
2317:8DD0  77 69 6E 64 6F 77 00 25-64 00 25 64 00 70 6C 65  window.%d.%d.ple
2317:8DE0  61 73 65 77 74 00 6F 6E-6C 79 32 00 70 6C 65 61  asewt.only2.plea
2317:8DF0  73 65 77 74 00 00 00 00-00 00 00 00 00 74 61 6B  sewt.........tak
```

```
2817:8E00  69 6E 67 20 69 6E 69 74-20 73 6C 6F 70 65 20 66   ing init slope f
2817:8E10  72 6F 6D 0A 20 70 74 3A-25 64 20 74 6F 20 25 64   rom. pt:%d to %d
2817:8E20  0A 00 6F 76 65 72 61 6C-6C 20 73 6C 6F 70 65 20   ..overall slope 
2817:8E30  66 72 6F 6D 0A 20 70 74-3A 25 64 20 74 6F 20 25   from. pt:%d to %
2817:8E40  64 3D 25 6C 66 0A 00 73-6C 6F 70 65 20 63 6F 6D   d=%lf..slope com
2817:8E50  70 75 74 65 64 20 66 72-6F 6D 0A 20 70 74 3A 25   puted from. pt:%
2817:8E60  64 20 74 6F 20 25 64 3D-25 6C 66 0A 00 73 6C 6F   d to %d=%lf..slo
2817:8E70  70 65 20 6F 75 74 20 6F-66 20 72 61 6E 67 65 0A   pe out of range.
2817:8E80  00 00 00 00 00 00 00 E0-3F 00 00 00 00 00 8B C0   ........?.......
2817:8E90  40 00 00 00 00 00 00 F0-3F 70 61 72 61 6D 73 2E   @.......?params.
2817:8EA0  64 61 74 00 72 62 00 00-6F 6E 6C 79 70 69 70 31   dat.rb..onlypip1
2817:8EB0  00 6F 6E 6C 79 70 69 70-32 00 73 64 69 61 67 73   .onlypip2.sdiags
2817:8EC0  00 63 79 61 72 74 70 69-70 00 25 37 2E 37 6C 64   .cyartpip.%7.7ld
2817:8ED0  20 28 73 74 61 74 3D 25-64 29 00 65 6E 74 65 72    (stat=%d).enter
2817:8EE0  73 6E 00 00 6D 64 69 61-67 73 00 64 69 73 6B 64   sn..mdiags.diskd
2817:8EF0  69 72 00 64 69 73 6B 6D-6F 76 65 00 73 65 74 64   ir.diskmove.setd
2817:8F00  68 6F 6D 65 00 64 6E 6F-6D 66 61 69 6C 00 64 69   home.dnomfail.di
2817:8F10  73 6B 74 75 72 6E 00 0A-0A 45 6E 74 65 72 20 72   skturn...Enter r
2817:8F20  61 6D 70 20 6E 75 6D 62-65 72 73 20 31 2D 25 64   amp numbers 1-%d
2817:8F30  3A 0A 00 0A 72 61 6D 70-20 23 25 64 20 28 45 4E   :...ramp #%d (EN
2817:8F40  54 45 52 20 66 6F 72 20-25 64 29 3A 00 0A 0A 0A   TER for %d):....
2817:8F50  64 6F 20 79 6F 75 20 77-61 6E 74 20 68 61 6C 66   do you want half
2817:8F60  20 73 74 65 70 70 69 6E-67 3F 0A 00 20 28 30 3D    stepping?.. (0=
2817:8F70  6E 6F 2C 31 3D 79 65 73-2E 45 4E 54 45 52 3D 63   no,1=yes.ENTER=c
2817:8F80  75 72 72 65 6E 74 20 76-61 6C 75 65 20 6F 66 20   urrent value of 
2817:8F90  25 64 29 0A 00 64 69 73-6B 6C 69 66 65 00 72 61   %d)..disklife.ra
2817:8FA0  6E 67 65 73 2E 64 61 74-00 72 62 00 00 00 00 00   nges.dat.rb.....
2817:8FB0  00 00 02 00 45 78 74 72-61 2D 68 65 70 61 74 69   ....Extra-hepati
2817:8FC0  63 20 62 69 6C 69 61 72-79 0A 20 20 4F 62 73 74   c biliary.  Obst
2817:8FD0  72 75 63 74 69 6F 6E 00-00 00 00 00 00 00 00 00   ruction.........
2817:8FE0  00 00 00 00 00 00 00 00-00 00 00 00 00 00 00 00   ................
2817:8FF0  FD 01 02 02 32 02 37 02-35 02 0F 27 0F 27 0F 27   ....2.7.5..'.'.'
2817:9000  0F 27 0F 27 00 00 00 00-00 00 02 00 41 63 75 74   .'.'........Acut
2817:9010  65 20 68 65 70 61 74 69-63 0A 20 20 64 69 73 65   e hepatic.  dise
2817:9020  61 73 65 00 00 00 00 00-00 00 00 00 00 00 00 00   ase.............
2817:9030  00 00 00 00 00 00 00 00-00 00 00 00 00 00 00 00   ................
2817:9040  00 00 00 00 00 00 00 00-FE 01 9B 01 CF 00 FE 01   ................
2817:9050  32 02 24 02 CF 01 33 01-31 01 0F 27 00 00 00 00   2.$........'....
2817:9060  00 00 01 00 43 69 72 72-68 6F 73 69 73 00 00 00   ....Cirrhosis...
2817:9070  00 00 00 00 00 00 00 00-00 00 00 00 00 00 00 00   ................
2817:9080  00 00 00 00 00 00 00 00-00 00 00 00 00 00 00 00   ................
2817:9090  00 00 00 00 00 00 00 00-00 00 00 00 00 00 00 00   ................
2817:90A0  9E 01 CE 00 D1 00 9E 01-9A 01 32 02 24 02 CF 01   ..........2.$...
2817:90B0  D3 01 31 01 00 00 00 00-00 00 01 00 4C 69 76 65   ............Live
2817:90C0  72 20 54 75 6D 6F 75 72-73 00 00 00 00 00 00 00   r Tumours.......
2817:90D0  00 00 00 00 00 00 00 00-00 00 00 00 00 00 00 00   ................
2817:90E0  00 00 00 00 00 00 00 00-00 00 00 00 00 00 00 00   ................
2817:90F0  00 00 00 00 00 00 00 00-D1 00 FC 01 9E 01 CE 01   ................
2817:9100  C0 01 37 02 35 02 0F 27-0F 27 0F 27 00 00 00 00   ..7.5..'.'.'....
2817:9110  00 00 01 00 42 69 6C 69-61 72 79 20 53 74 61 73   ....Biliary Stas
2817:9120  69 73 00 00 00 00 00 00-00 00 00 00 00 00 00 00   is..............
2817:9130  00 00 00 00 00 00 00 00-00 00 00 00 00 00 00 00   ................
2817:9140  00 00 00 00 00 00 00 00-00 00 00 00 00 00 00 00   ................
2817:9150  FC 01 9E 01 CE 01 C0 01-CF 01 37 02 35 02 0F 27   ..........7.5..'
2817:9160  0F 27 0F 27 00 00 00 00-00 00 02 00 50 6F 72 74   .'.'........Port
2817:9170  6F 2D 53 79 73 74 65 6D-69 63 0A 20 20 53 68 75   o-Systemic.  Shu
2817:9180  6E 74 28 73 29 00 00 00-00 00 00 00 00 00 00 00   nt(s)...........
2817:9190  00 00 00 00 00 00 00 00-00 00 00 00 00 00 00 00   ................
2817:91A0  00 00 00 00 00 00 00 00-C8 00 90 01 69 00 6A 00   ............i.j.
2817:91B0  6D 00 D3 00 6B 00 FE 01-CE 01 0F 27 00 00 00 00   m...k......'....
2817:91C0  00 00 01 00 4C 69 70 69-64 6F 73 69 73 0A 20 28   ....Lipidosis. (
2817:91D0  65 2E 67 2E 29 20 44 69-61 62 65 74 65 73 20 4D   e.g.) Diabetes M
2817:91E0  65 6C 6C 69 74 75 73 00-00 00 00 00 00 00 00 00   ellitus.........
2817:91F0  00 00 00 00 00 00 00 00-00 00 00 00 00 00 00 00   ................
2817:9200  9E 01 CE 01 C0 01 35 02-0F 27 0F 27 0F 27 0F 27   ......5..'.'.'.'
2817:9210  0F 27 0F 27 00 00 00 00-00 00 01 00 43 68 6F 6C   .'.'........Chol
2817:9220  61 6E 67 69 6F 68 65 70-61 74 69 74 69 73 00 00   angiohepatitis..
2817:9230  00 00 00 00 00 00 00 00-00 00 00 00 00 00 00 00   ................
2817:9240  00 00 00 00 00 00 00 00-00 00 00 00 00 00 00 00   ................
2817:9250  00 00 00 00 00 00 00 00-9E 01 CE 01 C0 01 0F 27   ...............'
2817:9260  0F 27 0F 27 0F 27 0F 27-0F 27 0F 27 00 00 00 00   .'.'.'.'.'.'....
2817:9270  00 00 01 00 4C 79 6D 70-68 6F 63 79 74 69 63 20   ....Lymphocytic 
```

```
2817:9280  43 68 6F 6C 61 6E 67 69-74 69 73 00 00 00 00 00   Cholangitis.....
2817:9290  00 00 00 00 00 00 00 00-00 00 00 00 00 00 00 00   ................
2817:92A0  00 00 00 00 00 00 00 00-00 00 00 00 00 00 00 00   ................
2817:92B0  0D 00 32 00 B1 00 37 00-0F 27 0F 27 0F 27 0F 27   ..2.±.7..'.'.'.'
2817:92C0  0F 27 0F 27 00 00 00 00-00 00 01 00 48 69 67 68   .'.'........High
2817:92D0  20 70 72 6F 74 65 69 6E-20 64 69 65 74 00 00 00    protein diet...
2817:92E0  00 00 00 00 00 00 00 00-00 00 00 00 00 00 00 00   ................
2817:92F0  00 00 00 00 00 00 00 00-00 00 00 00 00 00 00 00   ................
2817:9300  00 00 00 00 00 00 00 00-FB 01 FC 01 0F 27 0F 27   .............'.'
2817:9310  0F 27 0F 27 0F 27 0F 27-0F 27 0F 27 00 00 00 00   .'.'.'.'.'.'....
2817:9320  00 00 01 00 4C 6F 77 20-70 72 6F 74 65 69 6E 20   ....Low protein 
2817:9330  64 69 65 74 00 00 00 00-00 00 00 00 00 00 00 00   diet............
2817:9340  00 00 00 00 00 00 00 00-00 00 00 00 00 00 00 00   ................
2817:9350  00 00 00 00 00 00 00 00-00 00 00 00 00 00 00 00   ................
2817:9360  69 00 0F 27 0F 27 0F 27-0F 27 0F 27 0F 27 0F 27   i..'.'.'.'.'.'.'
2817:9370  0F 27 0F 27 00 00 00 00-00 00 01 00 48 69 67 68   .'.'........High
2817:9380  20 66 61 74 20 64 69 65-74 00 00 00 00 00 00 00    fat diet.......
2817:9390  00 00 00 00 00 00 00 00-00 00 00 00 00 00 00 00   ................
2817:93A0  00 00 00 00 00 00 00 00-00 00 00 00 00 00 00 00   ................
2817:93B0  00 00 00 00 00 00 00 00-FD 01 FE 01 0F 27 0F 27   .............'.'
2817:93C0  0F 27 0F 27 0F 27 0F 27-0F 27 0F 27 00 00 00 00   .'.'.'.'.'.'....
2817:93D0  00 00 01 00 53 74 61 72-76 61 74 69 6F 6E 00 00   ....Starvation..
2817:93E0  00 00 00 00 00 00 00 00-00 00 00 00 00 00 00 00   ................
2817:93F0  00 00 00 00 00 00 00 00-00 00 00 00 00 00 00 00   ................
2817:9400  00 00 00 00 00 00 00 00-00 00 00 00 00 00 00 00   ................
2817:9410  64 00 FE 01 6A 00 6D 00-6C 00 FE 01 0F 27 0F 27   d...j.m.l....'.'
2817:9420  0F 27 0F 27 00 00 00 00-00 00 01 00 4D 61 6C 61   .'.'........Mala
2817:9430  62 73 6F 72 70 74 69 6F-6E 00 00 00 00 00 00 00   bsorption.......
2817:9440  00 00 00 00 00 00 00 00-00 00 00 00 00 00 00 00   ................
2817:9450  00 00 00 00 00 00 00 00-00 00 00 00 00 00 00 00   ................
2817:9460  00 00 00 00 00 00 00 00-70 00 0F 27 0F 27 0F 27   ........p..'.'.'
2817:9470  0F 27 0F 27 0F 27 0F 27-0F 27 0F 27 00 00 00 00   .'.'.'.'.'.'....
2817:9480  00 00 01 00 52 65 63 65-6E 74 20 46 6F 6F 64 20   ....Recent Food 
2817:9490  49 6E 67 65 73 74 69 6F-6E 00 00 00 00 00 00 00   Ingestion.......
2817:94A0  00 00 00 00 00 00 00 00-00 00 00 00 00 00 00 00   ................
2817:94B0  00 00 00 00 00 00 00 00-00 00 00 00 00 00 00 00   ................
2817:94C0  F4 01 F9 01 F4 01 00 00-FC 01 FE 01 0F 27 0F 27   .............'.'
2817:94D0  0F 27 0F 27 00 00 00 00-00 00 01 00 44 69 65 74   .'.'........Diet
2817:94E0  61 72 79 20 44 65 66 69-63 69 65 6E 63 79 0A 20   ary Deficiency. 
2817:94F0  28 76 65 72 79 20 76 61-72 69 61 62 6C 65 29 00   (very variable).
2817:9500  00 00 00 00 00 00 00 00-00 00 00 00 00 00 00 00   ................
2817:9510  00 00 00 00 00 00 00 00-FC 01 D4 00 C8 00 0F 27   ...............'
2817:9520  0F 27 0F 27 0F 27 0F 27-0F 27 0F 27 00 00 00 00   .'.'.'.'.'.'....
2817:9530  00 00 01 00 59 6F 75 74-68 00 00 00 00 00 00 00   ....Youth.......
2817:9540  00 00 00 00 00 00 00 00-00 00 00 00 00 00 00 00   ................
2817:9550  00 00 00 00 00 00 00 00-00 00 00 00 00 00 00 00   ................
2817:9560  00 00 00 00 00 00 00 00-00 00 00 00 00 00 00 00   ................
2817:9570  00 02 F7 01 33 02 35 02-0F 27 0F 27 0F 27 0F 27   ....3.5..'.'.'.'
2817:9580  0F 27 0F 27 00 00 00 00-00 00 01 00 41 67 65 00   .'.'........Age.
2817:9590  00 00 00 00 00 00 00 00-00 00 00 00 00 00 00 00   ................
2817:95A0  00 00 00 00 00 00 00 00-00 00 00 00 00 00 00 00   ................
2817:95B0  00 00 00 00 00 00 00 00-00 00 00 00 00 00 00 00   ................
2817:95C0  00 00 00 00 00 00 00 00-D3 00 0F 27 0F 27 0F 27   ...........'.'.'
2817:95D0  0F 27 0F 27 0F 27 0F 27-0F 27 0F 27 00 00 00 00   .'.'.'.'.'.'....
2817:95E0  00 00 01 00 50 72 65 67-6E 61 6E 63 79 00 00 00   ....Pregnancy...
2817:95F0  00 00 00 00 00 00 00 00-00 00 00 00 00 00 00 00   ................
2817:9600  00 00 00 00 00 00 00 00-00 00 00 00 00 00 00 00   ................
2817:9610  00 00 00 00 00 00 00 00-00 00 00 00 00 00 00 00   ................
2817:9620  64 00 0F 27 0F 27 0F 27-0F 27 0F 27 0F 27 0F 27   d..'.'.'.'.'.'.'
2817:9630  0F 27 0F 27 00 00 00 00-00 00 01 00 4C 61 63 74   .'.'........Lact
2817:9640  61 74 69 6F 6E 00 00 00-00 00 00 00 00 00 00 00   ation...........
2817:9650  00 00 00 00 00 00 00 00-00 00 00 00 00 00 00 00   ................
2817:9660  00 00 00 00 00 00 00 00-00 00 00 00 00 00 00 00   ................
2817:9670  00 00 00 00 00 00 00 00-64 00 D2 00 0F 27 0F 27   ........d....'.'
2817:9680  0F 27 0F 27 0F 27 0F 27-0F 27 0F 27 00 00 00 00   .'.'.'.'.'.'....
2817:9690  00 00 02 00 28 52 65 63-65 6E 74 20 70 72 6F 6C   ....(Recent prol
2817:96A0  6F 6E 67 65 64 29 0A 20-45 78 65 72 63 69 73 65   onged). Exercise
2817:96B0  00 00 00 00 00 00 00 00-00 00 00 00 00 00 00 00   ................
2817:96C0  00 00 00 00 00 00 00 00-00 00 00 00 00 00 00 00   ................
2817:96D0  64 00 34 02 0F 27 0F 27-0F 27 0F 27 0F 27 0F 27   d.4..'.'.'.'.'.'
2817:96E0  0F 27 0F 27 00 00 00 00-00 00 01 00 48 65 61 6C   .'.'........Heal
2817:96F0  69 6E 67 00 00 00 00 00-00 00 00 00 00 00 00 00   ing.............
```

```
2817:9700  00 00 00 00 00 00 00 00-00 00 00 00 00 00 00 00   ................
2817:9710  00 00 00 00 00 00 00 00-00 00 00 00 00 00 00 00   ................
2817:9720  00 00 00 00 00 00 00 00-00 02 0F 27 0F 27 0F 27   ...........'.'.'
2817:9730  0F 27 0F 27 0F 27 0F 27-0F 27 0F 27 00 00 00 00   .'.'.'.'.'.'....
2817:9740  00 00 01 00 53 74 72 65-73 73 20 2F 20 46 65 61   ....Stress / Fea
2817:9750  72 00 00 00 00 00 00 00-00 00 00 00 00 00 00 00   r...............
2817:9760  00 00 00 00 00 00 00 00-00 00 00 00 00 00 00 00   ................
2817:9770  00 00 00 00 00 00 00 00-00 00 00 00 00 00 00 00   ................
2817:9780  F4 01 FC 01 0F 27 0F 27-0F 27 0F 27 0F 27 0F 27   .....'.'.'.'.'.'
2817:9790  0F 27 0F 27 00 00 00 00-00 00 01 00 52 65 63 65   .'.'........Rece
2817:97A0  6E 74 20 4D 65 61 6C 00-00 00 00 00 00 00 00 00   nt Meal.........
2817:97B0  00 00 00 00 00 00 00 00-00 00 00 00 00 00 00 00   ................
2817:97C0  00 00 00 00 00 00 00 00-00 00 00 00 00 00 00 00   ................
2817:97D0  00 00 00 00 00 00 00 00-F4 01 F9 01 94 01 00 02   ................
2817:97E0  FC 01 F8 01 0F 27 0F 27-0F 27 0F 27 00 00 00 00   .....'.'.'.'....
2817:97F0  00 00 01 00 4E 65 6F 6E-61 74 65 00 00 00 00 00   ....Neonate.....
2817:9800  00 00 00 00 00 00 00 00-00 00 00 00 00 00 00 00   ................
2817:9810  00 00 00 00 00 00 00 00-00 00 00 00 00 00 00 00   ................
2817:9820  00 00 00 00 00 00 00 00-00 00 00 00 00 00 00 00   ................
2817:9830  69 00 DD 01 0F 27 0F 27-0F 27 0F 27 0F 27 0F 27   i....'.'.'.'.'.'
2817:9840  0F 27 0F 27 00 00 00 00-00 00 01 00 48 61 65 6D   .'.'........Haem
2817:9850  6F 72 72 68 61 67 65 00-00 00 00 00 00 00 00 00   orrhage.........
2817:9860  00 00 00 00 00 00 00 00-00 00 00 00 00 00 00 00   ................
2817:9870  00 00 00 00 00 00 00 00-00 00 00 00 00 00 00 00   ................
2817:9880  00 00 00 00 00 00 00 00-6A 00 6F 00 9E 01 0F 27   ........j.o....'
2817:9890  0F 27 0F 27 0F 27 0F 27-0F 27 0F 27 00 00 00 00   .'.'.'.'.'.'....
2817:98A0  00 00 01 00 42 75 72 6E-73 00 00 00 00 00 00 00   ....Burns.......
2817:98B0  00 00 00 00 00 00 00 00-00 00 00 00 00 00 00 00   ................
2817:98C0  00 00 00 00 00 00 00 00-00 00 00 00 00 00 00 00   ................
2817:98D0  00 00 00 00 00 00 00 00-00 00 00 00 00 00 00 00   ................
2817:98E0  6A 00 6D 00 0F 27 0F 27-0F 27 0F 27 0F 27 0F 27   j.m..'.'.'.'.'.'
2817:98F0  0F 27 0F 27 00 00 00 00-00 00 01 00 49 6E 74 65   .'.'........Inte
2817:9900  73 74 69 6E 61 6C 20 48-61 65 6D 6F 72 72 68 61   stinal Haemorrha
2817:9910  67 65 00 00 00 00 00 00-00 00 00 00 00 00 00 00   ge..............
2817:9920  00 00 00 00 00 00 00 00-00 00 00 00 00 00 00 00   ................
2817:9930  00 00 00 00 00 00 00 00-FF 01 94 01 0F 27 0F 27   .............'.'
2817:9940  0F 27 0F 27 0F 27 0F 27-0F 27 0F 27 00 00 00 00   .'.'.'.'.'.'....
2817:9950  00 00 02 00 4D 75 73 63-6C 65 20 49 6E 6A 75 72   ....Muscle Injur
2817:9960  79 20 6F 72 0A 20 20 4E-65 63 72 6F 73 69 73 00   y or.  Necrosis.
2817:9970  00 00 00 00 00 00 00 00-00 00 00 00 00 00 00 00   ................
2817:9980  00 00 00 00 00 00 00 00-00 00 00 00 00 00 00 00   ................
2817:9990  00 12 96 01 24 02 33 02-34 02 0F 27 0F 27 0F 27   ....$.3.4..'.'.'
2817:99A0  0F 27 0F 27 00 00 00 00-00 00 02 00 49 6E 74 72   .'.'........Intr
2817:99B0  61 2D 4D 75 73 63 75 6C-61 72 0A 20 20 20 49 6E   a-Muscular.   In
2817:99C0  6A 65 63 74 69 6F 6E 00-00 00 00 00 00 00 00 00   jection.........
2817:99D0  00 00 00 00 00 00 00 00-00 00 00 00 00 00 00 00   ................
2817:99E0  00 00 00 00 00 00 00 00-24 02 33 02 34 02 0F 27   ........$.3.4..'
2817:99F0  0F 27 0F 27 0F 27 0F 27-0F 27 0F 27 00 00 00 00   .'.'.'.'.'.'....
2817:9A00  00 00 02 00 49 6E 74 72-61 2D 76 61 73 63 75 6C   ....Intra-vascul
2817:9A10  61 72 0A 20 20 20 48 61-65 6D 6F 6C 79 73 69 73   ar.   Haemolysis
2817:9A20  00 00 00 00 00 00 00 00-00 00 00 00 00 00 00 00   ................
2817:9A30  00 00 00 00 00 00 00 00-00 00 00 00 00 00 00 00   ................
2817:9A40  9C 01 D2 02 D2 01 D0 01-DF 01 0F 27 0F 27 0F 27   ...........'.'.'
2817:9A50  0F 27 0F 27 00 00 00 00-00 00 02 00 48 79 70 6F   .'.'........Hypo
2817:9A60  61 64 72 65 6E 6F 63 6F-72 74 69 63 69 73 6D 0A   adrenocorticism.
2817:9A70  20 20 20 20 28 41 64 64-69 73 6F 6E 73 29 00 00       (Addisons)..
2817:9A80  00 00 00 00 00 00 00 00-00 00 00 00 00 00 00 00   ................
2817:9A90  00 00 00 00 00 00 00 00-D8 00 F5 01 F4 01 9C 01   ................
2817:9AA0  96 01 FD 01 0F 27 0F 27-0F 27 0F 27 00 00 00 00   .....'.'.'.'....
2817:9AB0  00 00 02 00 48 79 70 65-72 61 64 72 65 6E 6F 63   ....Hyperadrenoc
2817:9AC0  6F 72 74 69 63 69 73 6D-0A 20 20 28 43 75 73 68   orticism.  (Cush
2817:9AD0  69 6E 67 73 29 00 00 00-00 00 00 00 00 00 00 00   ings)...........
2817:9AE0  00 00 00 00 00 00 00 00-00 00 00 00 00 00 00 00   ................
2817:9AF0  90 01 FC 01 32 02 C0 01-35 02 0F 27 0F 27 0F 27   ....2...5..'.'.'
2817:9B00  0F 27 0F 27 00 00 00 00-00 00 01 00 48 79 70 65   .'.'........Hype
2817:9B10  72 70 61 72 61 74 68 79-72 6F 69 64 69 73 6D 00   rparathyroidism.
2817:9B20  00 00 00 00 00 00 00 00-00 00 00 00 00 00 00 00   ................
2817:9B30  00 00 00 00 00 00 00 00-00 00 00 00 00 00 00 00   ................
2817:9B40  00 00 01 00 00 00 00 00-F9 01 FB 01 70 00 F7 01   ............p...
2817:9B50  D1 01 0F 27 0F 27 0F 27-0F 27 0F 27 00 00 00 00   ...'.'.'.'.'....
2817:9B60  00 00 02 00 52 65 6E 61-6C 20 6F 72 20 4E 75 74   ....Renal or Nut
2817:9B70  72 69 74 69 6F 6E 61 6C-0A 20 73 65 63 6F 6E 64   ritional. second
```

```
2817:9B80  61 72 79 20 48 79 70 65-72 70 61 72 61 74 68 79   ary Hyperparathy
2817:9B90  72 6F 69 64 69 73 6D 00-00 00 00 00 00 00 00 00   roidism.........
2817:9BA0  F9 01 FB 01 00 02 D3 00-D1 01 0F 27 0F 27 0F 27   ............'.'.'
2817:9BB0  0F 27 0F 27 00 00 00 00-00 00 01 00 48 79 70 6F   .'.'........Hypo
2817:9BC0  70 61 72 61 74 68 79 72-6F 69 64 69 73 6D 00 00   parathyroidism..
2817:9BD0  00 00 00 00 00 00 00 00-00 00 00 00 00 00 00 00   ................
2817:9BE0  00 00 00 00 00 00 00 00-00 00 00 00 00 00 00 00   ................
2817:9BF0  00 00 00 00 00 00 00 00-00 02 67 00 0F 27 0F 27   ..........g..'.'
2817:9C00  0F 27 0F 27 0F 27 0F 27-0F 27 0F 27 00 00 00 00   .'.'.'.'.'.'....
2817:9C10  00 00 01 00 48 79 70 6F-74 68 79 72 6F 69 64 69   ....Hypothyroidi
2817:9C20  73 6D 00 00 00 00 00 00-00 00 00 00 00 00 00 00   sm..............
2817:9C30  00 00 00 00 00 00 00 00-00 00 00 00 00 00 00 00   ................
2817:9C40  00 00 00 00 00 00 00 00-00 00 00 00 00 00 00 00   ................
2817:9C50  FD 01 FB 01 DE 01 D1 01-0F 27 0F 27 0F 27 0F 27   .........'.'.'.'
2817:9C60  0F 27 0F 27 00 00 00 00-00 00 01 00 44 69 61 62   .'.'........Diab
2817:9C70  65 74 65 73 20 4D 65 6C-6C 69 74 75 73 00 00 00   etes Mellitus...
2817:9C80  00 00 00 00 00 00 00 00-00 00 00 00 00 00 00 00   ................
2817:9C90  00 00 00 00 00 00 00 00-00 00 00 00 00 00 00 00   ................
2817:9CA0  00 00 00 00 00 00 00 00-F4 01 FE 01 94 01 D4 00   ................
2817:9CB0  C8 00 FD 01 FB 01 CE 01-D0 01 D5 02 00 00 00 00   ..........E.....
2817:9CC0  00 00 01 00 48 79 70 65-72 74 68 79 72 6F 69 64   ....Hyperthyroid
2817:9CD0  69 73 6D 00 00 00 00 00-00 00 00 00 00 00 00 00   ism.............
2817:9CE0  00 00 00 00 00 00 00 00-00 00 00 00 00 00 00 00   ................
2817:9CF0  00 00 00 00 00 00 00 00-00 00 00 00 00 00 00 00   ................
2817:9D00  D2 02 D4 02 D3 02 D5 02-0F 27 0F 27 0F 27 0F 27   D.a.D.E..'.'.'.'
2817:9D10  0F 27 0F 27 00 00 00 00-00 00 01 00 50 61 6E 63   .'.'........Panc
2817:9D20  72 65 61 74 69 74 69 73-00 00 00 00 00 00 00 00   reatitis........
2817:9D30  00 00 00 00 00 00 00 00-00 00 00 00 00 00 00 00   ................
2817:9D40  00 00 00 00 00 00 00 00-00 00 00 00 00 00 00 00   ................
2817:9D50  00 00 00 00 00 00 00 00-90 01 CE 00 97 01 9E 01   ................
2817:9D60  CE 01 C1 01 D1 01 D2 02-2F 02 0F 27 00 00 00 00   ......*./..'....
2817:9D70  00 00 01 00 53 68 6F 63-6B 20 2F 20 44 65 68 79   ....Shock / Dehy
2817:9D80  64 72 61 74 69 6F 6E 00-00 00 00 00 00 00 00 00   dration.........
2817:9D90  00 00 00 00 00 00 00 00-00 00 00 00 00 00 00 00   ................
2817:9DA0  00 00 00 00 00 00 00 00-00 00 00 00 00 00 00 00   ................
2817:9DB0  F9 01 FB 01 FA 01 FD 01-24 02 D3 02 0F 27 0F 27   ........a.D..'.'
2817:9DC0  0F 27 0F 27 00 00 00 00-00 00 01 00 4D 79 6F 63   .'.'........Myoc
2817:9DD0  61 72 64 69 61 6C 20 49-6E 66 61 72 63 74 69 6F   ardial Infarctio
2817:9DE0  6E 0A 20 20 6F 72 20 6F-74 68 65 72 20 41 63 75   n.  or other Acu
2817:9DF0  74 65 0A 20 20 43 61 72-64 69 61 63 20 49 6E 73   te.  Cardiac Ins
2817:9E00  75 6C 74 00 00 00 00 00-F5 01 24 02 D3 02 D4 02   ult.......a.D.4.
2817:9E10  0F 27 0F 27 0F 27 0F 27-0F 27 0F 27 00 00 00 00   .'.'.'.'.'.'....
2817:9E20  00 00 02 00 44 65 63 72-65 61 73 65 64 20 43 61   ....Decreased Ca
2817:9E30  72 64 69 61 63 0A 20 20-4F 75 74 70 75 74 00 00   rdiac.  Output..
2817:9E40  00 00 00 00 00 00 00 00-00 00 00 00 00 00 00 00   ................
2817:9E50  00 00 00 00 00 00 00 00-00 00 00 00 00 00 00 00   ................
2817:9E60  F9 01 FB 01 CE 00 D1 00-0F 27 0F 27 0F 27 0F 27   .........'.'.'.'
2817:9E70  0F 27 0F 27 00 00 00 00-00 00 02 00 43 6F 6E 67   .'.'........Cong
2817:9E80  65 73 74 69 76 65 20 48-65 61 72 74 0A 20 20 46   estive Heart.  F
2817:9E90  61 69 6C 75 72 65 00 00-00 00 00 00 00 00 00 00   ailure..........
2817:9EA0  00 00 00 00 00 00 00 00-00 00 00 00 00 00 00 00   ................
2817:9EB0  00 00 00 00 00 00 00 00-F9 01 F8 01 CE 00 D1 00   ................
2817:9EC0  CE 01 C0 01 CF 01 D1 01-0F 27 0F 27 00 00 00 00   .........'.'....
2817:9ED0  00 00 02 00 55 72 69 6E-61 72 79 20 54 72 61 63   ....Urinary Trac
2817:9EE0  74 0A 20 20 4F 62 73 74-72 75 63 74 69 6F 6E 00   t.  Obstruction.
2817:9EF0  00 00 00 00 00 00 00 00-00 00 00 00 00 00 00 00   ................
2817:9F00  00 00 00 00 00 00 00 00-00 00 00 00 00 00 00 00   ................
2817:9F10  F9 01 FB 01 FD 01 C5 00-BF 01 CB 01 0F 27 0F 27   .............'.'
2817:9F20  0F 27 0F 27 00 00 00 00-00 00 01 00 41 63 75 74   .'.'........Acut
2817:9F30  65 20 52 65 6E 61 6C 20-46 61 69 6C 75 72 65 00   e Renal Failure.
2817:9F40  00 00 00 00 00 00 00 00-00 00 00 00 00 00 00 00   ................
2817:9F50  00 00 00 00 00 00 00 00-00 00 00 00 00 00 00 00   ................
2817:9F60  00 00 00 00 00 00 00 00-F9 01 F8 01 9D 01 BF 01   ................
2817:9F70  C8 01 0F 27 0F 27 0F 27-0F 27 0F 27 00 00 00 00   ...'.'.'.'.'....
2817:9F80  00 00 01 00 43 68 72 6F-6E 69 63 20 52 65 6E 61   ....Chronic Rena
2817:9F90  6C 20 46 61 69 6C 75 72-65 00 00 00 00 00 00 00   l Failure.......
2817:9FA0  00 00 00 00 00 00 00 00-00 00 00 00 00 00 00 00   ................
2817:9FB0  00 00 00 00 00 00 00 00-00 00 00 00 00 00 00 00   ................
2817:9FC0  F9 01 F8 01 9D 01 CE 00-D1 00 D1 01 BF 01 C8 01   ................
2817:9FD0  0F 27 0F 27 00 00 00 00-00 00 02 00 50 72 6F 74   .'.'........Prot
2817:9FE0  65 69 6E 20 4C 6F 73 69-6E 67 0A 20 20 4E 65 70   ein Losing.  Nep
2817:9FF0  68 72 6F 70 61 74 68 69-65 73 00 00 00 00 00 00   hropathies......
```

```
2817:A000  00 00 00 00 00 00 00 00-00 00 00 00 00 00 00 00  ................
2817:A010  00 00 00 00 00 00 00 00-F5 01 F4 01 F3 01 6A 00  ..............j.
2817:A020  6D 00 F2 01 F3 01 0F 27-0F 27 0F 27 00 00 00 00  m.....'.'.'....
2817:A030  00 00 01 00 43 6F 72 74-69 63 6F 73 74 65 72 6F  ....Corticostero
2817:A040  69 64 73 00 00 00 00 00-00 00 00 00 00 00 00 00  ids.............
2817:A050  00 00 00 00 00 00 00 00-00 00 00 00 00 00 00 00  ................
2817:A060  00 00 00 00 00 00 00 00-00 00 00 00 00 00 00 00  ................
2817:A070  F4 01 F3 01 F2 01 32 02-24 02 37 02 35 02 23 02  ......2.$.7.5.#.
2817:A080  2F 02 0F 27 00 00 00 00-00 00 01 00 43 68 65 6C  /..'........Chel
2817:A090  61 74 69 6E 67 20 41 67-65 6E 74 73 20 28 45 44  ating Agents (ED
2817:A0A0  54 41 29 00 00 00 00 00-00 00 00 00 00 00 00 00  TA).............
2817:A0B0  00 00 00 00 00 00 00 00-00 00 00 00 00 00 00 00  ................
2817:A0C0  00 00 00 00 00 00 00 00-E7 00 0F 27 0F 27 0F 27  ........ç..'.'.'
2817:A0D0  0F 27 0F 27 0F 27 0F 27-0F 27 0F 27 00 00 00 00  .'.'.'.'.'.'....
2817:A0E0  00 00 01 00 49 6E 73 75-6C 69 6E 20 4F 76 65 72  ....Insulin Over
2817:A0F0  64 6F 73 65 00 00 00 00-00 00 00 00 00 00 00 00  dose............
2817:A100  00 00 00 00 00 00 00 00-00 00 00 00 00 00 00 00  ................
2817:A110  00 00 00 00 00 00 00 00-00 00 00 00 00 00 00 00  ................
2817:A120  64 00 54 00 0F 27 0F 27-0F 27 0F 27 0F 27 0F 27  d....'.'.'.'.'.'
2817:A130  0F 27 0F 27 00 00 00 00-00 00 02 00 42 61 72 62  .'.'........Barb
2817:A140  69 74 75 72 61 74 65 73-20 2F 0A 20 20 41 6E 74  iturates /.  Ant
2817:A150  69 63 6F 6E 76 75 6C 73-61 6E 74 73 00 00 00 00  iconvulsants....
2817:A160  00 00 00 00 00 00 00 00-00 00 00 00 00 00 00 00  ................
2817:A170  00 00 00 00 00 00 00 00-93 01 32 02 24 02 37 02  ..........2.$.7.
2817:A180  35 02 0F 27 0F 27 0F 27-0F 27 0F 27 00 00 00 00  5..'.'.'.'.'....
2817:A190  00 00 01 00 50 68 65 6E-6F 74 68 69 61 7A 69 64  ....Phenothiazid
2817:A1A0  65 73 00 00 00 00 00 00-00 00 00 00 00 00 00 00  es..............
2817:A1B0  00 00 00 00 00 00 00 00-00 00 00 00 00 00 00 00  ................
2817:A1C0  00 00 00 00 00 00 00 00-00 00 00 00 00 00 00 00  ................
2817:A1D0  32 02 24 02 37 02 35 02-0F 27 0F 27 0F 27 0F 27  2.$.7.5..'.'.'.'
2817:A1E0  0F 27 0F 27 00 00 00 00-00 00 02 00 50 72 6F 74  .'.'........Prot
2817:A1F0  65 69 6E 2D 4C 6F 73 69-6E 67 0A 20 20 45 6E 74  ein-Losing.  Ent
2817:A200  65 72 6F 70 61 74 68 79-00 00 00 00 00 00 00 00  eropathy........
2817:A210  00 00 00 00 00 00 00 00-00 00 00 00 00 00 00 00  ................
2817:A220  00 00 00 00 00 00 00 00-6A 00 6D 00 D3 00 0F 27  ........j.m....'
2817:A230  0F 27 0F 27 0F 27 0F 27-0F 27 0F 27 00 00 00 00  .'.'.'.'.'.'....
2817:A240  00 00 01 00 4D 61 6C 61-62 73 6F 72 70 74 69 6F  ....Malabsorptio
2817:A250  6E 00 00 00 00 00 00 00-00 00 00 00 00 00 00 00  n...............
2817:A260  00 00 00 00 00 00 00 00-00 00 00 00 00 00 00 00  ................
2817:A270  00 00 00 00 00 00 00 00-00 00 00 00 00 00 00 00  ................
2817:A280  CB 00 D4 00 CB 00 0F 27-0F 27 0F 27 0F 27 0F 27  .......'.'.'.'.'
2817:A290  0F 27 0F 27 00 00 00 00-00 00 01 00 4C 79 6D 70  .'.'........Lymp
2817:A2A0  68 6F 73 61 72 63 6F 6D-61 00 00 00 00 00 00 00  hosarcoma.......
2817:A2B0  00 00 00 00 00 00 00 00-00 00 00 00 00 00 00 00  ................
2817:A2C0  00 00 00 00 00 00 00 00-00 00 00 00 00 00 00 00  ................
2817:A2D0  00 00 00 00 00 00 00 00-F7 01 0F 27 0F 27 0F 27  ...........'.'.'
2817:A2E0  0F 27 0F 27 0F 27 0F 27-0F 27 0F 27 00 00 00 00  .'.'.'.'.'.'....
2817:A2F0  00 00 02 00 50 65 72 69-2D 61 6E 61 6C 20 61 70  ....Peri-anal ap
2817:A300  6F 63 72 69 6E 65 0A 20-67 6C 61 6E 64 20 41 64  ocrine. gland Ad
2817:A310  72 65 6E 6F 63 61 72 63-69 6E 6F 6D 61 00 00 00  renocarcinoma...
2817:A320  00 00 00 00 00 00 00 00-00 00 00 00 00 00 00 00  ................
2817:A330  F7 01 0F 27 0F 27 0F 27-0F 27 0F 27 0F 27 0F 27  ...'.'.'.'.'.'.'
2817:A340  0F 27 0F 27 00 00 00 00-00 00 01 00 49 6E 73 75  .'.'........Insu
2817:A350  6C 69 6E 6F 6D 61 00 00-00 00 00 00 00 00 00 00  linoma..........
2817:A360  00 00 00 00 00 00 00 00-00 00 00 00 00 00 00 00  ................
2817:A370  00 00 00 00 00 00 00 00-00 00 00 00 00 00 00 00  ................
2817:A380  00 00 00 00 00 00 00 00-64 00 0F 27 0F 27 0F 27  ........d..'.'.'
2817:A390  0F 27 0F 27 0F 27 0F 27-0F 27 0F 27 00 00 00 00  .'.'.'.'.'.'....
2817:A3A0  00 00 01 00 4D 75 6C 74-69 70 6C 65 20 4D 79 65  ....Multiple Mye
2817:A3B0  6C 6F 6D 61 00 00 00 00-00 00 00 00 00 00 00 00  loma............
2817:A3C0  00 00 00 00 00 00 00 00-00 00 00 00 00 00 00 00  ................
2817:A3D0  00 00 00 00 00 00 00 00-00 00 00 00 00 00 00 00  ................
2817:A3E0  FA 01 FF 01 F7 01 0F 27-0F 27 0F 27 0F 27 0F 27  .......'.'.'.'.'
2817:A3F0  0F 27 0F 27 63 6F 6E 64-69 74 00 4E 4F 49 4E 44  .'.'condit.NOIND
2817:A400  49 43 00 25 32 2E 32 64-20 25 2E 36 30 73 0A 00  IC.%2.2d %.60s..
2817:A410  74 6F 63 6F 6E 74 00 63-6F 6E 64 69 74 00 70 64  tocont.condit.pd
2817:A420  69 61 67 73 00 6C 6F 64-73 6C 69 64 73 00 64 69  iags.lodslids.di
2817:A430  73 6F 72 70 72 74 00 70-6C 65 61 73 65 77 74 00  sorprt.pleasewt.
2817:A440  0A 0A 0A 0A 0A 0A 0A 0A-0A 0A 0A 0A 0A 0A 0A 0A  ................
2817:A450  0A 0A 0A 0A 0A 0A 0A 0A-0A 00 7A 65 72 6F 00 20  ..........zero.
2817:A460  00 61 64 66 61 69 6C 75-72 00 0A 00 61 64 74 65  .adfailur...adte
2817:A470  72 00 25 2B 37 2E 37 6C-64 0A 00 72 65 66 65 72  r.%+7.7ld..refer
```

```
2817:A480  65 6E 64 00 20 00 61 64-66 61 69 6C 75 72 0D 0A   end. .adfailur..
2817:A490  00 76 72 25 35 2E 35 6C-64 2C 75 72 3D 25 35 2E   .vr%5.5ld,ur=%5.
2817:A4A0  35 6C 64 2C 74 72 3D 25-35 2E 35 6C 64 0A 00 69   5ld.tr=%5.5ld..i
2817:A4B0  63 61 6C 5F 72 65 64 3D-25 6C 66 0A 00 77 68 74   cal_red=%lf..wht
2817:A4C0  5F 72 65 64 3D 25 6C 66-0A 00 69 63 61 6C 5F 76   _red=%lf..ical_v
2817:A4D0  65 6C 3D 25 6C 66 0A 00-77 68 74 5F 76 65 6C 3D   el=%lf..wht_vel=
2817:A4E0  25 6C 66 0A 00 69 63 61-6C 5F 67 72 6E 3D 25 6C   %lf..ical_grn=%l
2817:A4F0  66 0A 00 77 68 74 5F 67-72 6E 3D 25 6C 66 0A 00   f..wht_grn=%lf..
2817:A500  69 63 61 6C 5F 64 72 64-3D 25 6C 66 0A 00 77 68   ical_drd=%lf..wh
2817:A510  74 5F 64 72 64 3D 25 6C-66 0A 00 69 63 61 6C 5F   t_drd=%lf..ical_
2817:A520  33 35 30 3D 25 6C 66 0A-00 77 68 74 5F 33 35 30   350=%lf..wht_350
2817:A530  3D 25 6C 66 0A 00 69 63-61 6C 5F 34 30 30 3D 25   =%lf..ical_400=%
2817:A540  6C 66 0A 00 77 68 74 5F-34 30 30 3D 25 6C 66 0A   lf..wht_400=%lf.
2817:A550  00 0D 00 64 69 73 72 65-64 72 64 00 20 25 32 64   ...disredrd. %2d
2817:A560  20 20 25 35 2E 35 6C 66-0A 00 64 69 73 67 72 6E     %5.5lf..disgrn
2817:A570  72 64 00 20 25 32 64 20-20 25 35 2E 35 6C 66 0A   rd. %2d  %5.5lf.
2817:A580  00 64 69 73 76 65 6C 72-64 00 20 25 32 64 20 20   .disvelrd. %2d
2817:A590  25 35 2E 35 6C 66 0A 00-64 69 73 64 72 64 72 64   %5.5lf..disdrdrd
2817:A5A0  00 20 25 32 64 20 20 25-35 2E 35 6C 66 0A 00 64   . %2d  %5.5lf..d
2817:A5B0  69 73 33 35 30 72 64 00-20 25 32 64 20 20 25 35   is350rd. %2d  %5
2817:A5C0  2E 35 6C 66 0A 00 64 69-73 34 30 30 72 64 00 20   .5lf..dis400rd.
2817:A5D0  25 32 64 20 20 25 35 2E-35 6C 66 0A 00 64 6F 6E   %2d  %5.5lf..don
2817:A5E0  65 00 0D 00 00 00 00 00-00 00 F0 3F 74 69 70 73   e..........?tips
2817:A5F0  74 61 74 00 25 64 00 63-61 6F 66 66 73 65 74 00   tat.%d.caoffset.
2817:A600  25 6C 66 00 70 72 65 73-6B 65 79 73 00 00 25 34   %lf.preskeys..%4
2817:A610  2E 34 73 00 70 6C 65 61-73 65 77 74 00 64 6F 6E   .4s.pleasewt.don
2817:A620  74 69 6E 73 72 00 00 00-00 00 00 00 00 00 00 00   tinsr...........
2817:A630  00 00 00 00 00 00 00 00-00 00 00 00 00 00 00 00   ................
2817:A640  00 00 00 00 00 00 00 00-00 00 00 00 00 00 00 00   ................
2817:A650  00 00 90 1E 50 56 58 00-F0 8E D8 80 3E FE FF FD   ....PV......>...
2817:A660  75 06 E4 62 24 01 75 2E-8B 0E 3E 8E D8 A0 D6 00   u..b$.u...5.....
2817:A670  8A 26 D4 00 0E 1F 87 3E-81 00 00 8E 6A 3B 74 08   .&.....>....j;t.
2817:A680  D9 34 9B 84 04 54 64 02-F6 C4 80 74 09 F6 D0 22   .4....d....t..."
2817:A690  C4 EA 67 C3 00 00 8E 5E-1F 0E 3B 0E 00 2E FF 2E   ..g...^X........
2817:A6A0  66 3B 3F 8B 00 00 2E 00-E1 00 0D 3D C3 2E 82 00   f:.........<....
2817:A6B0  13 3C C3 2E 83 00 10 3D-C3 2E 84 00 28 3C C3 2E   .<.....<....(<..
2817:A6C0  8E 00 31 3C C3 2E 86 00-3B 3C C3 2E 44 6F 6D 61   ..1<....;<..Doma
2817:A6D0  69 6E 00 44 65 6E 6F 72-6D 61 6C 00 44 69 76 69   in.Denormal.Divi
2817:A6E0  64 65 20 62 79 20 30 00-4F 76 65 72 66 6C 6F 77   de by 0.Overflow
2817:A6F0  00 55 6E 64 65 72 66 6C-6F 77 00 50 61 72 74 69   .Underflow.Parti
2817:A700  61 6C 20 6C 6F 73 73 20-6F 66 20 70 72 65 63 69   al loss of preci
2817:A710  73 69 6F 6E 00 46 6C 6F-61 74 69 6E 67 20 70 6F   sion.Floating po
2817:A720  69 6E 74 20 65 72 72 6F-72 3A 20 25 73 2E 0A 00   int error: %s...
2817:A730  FF FF 7F 7F FF FF FF FF-FF FF EF 7F FF FF FF FF   ................
2817:A740  FF FF FF FF FE 7F 00 00-00 7F 00 00 00 00 00 00   ................
2817:A750  00 80 01 00 00 00 00 00-80 04 F0 FF 6C 6F 67 31   ............log1
2817:A760  30 00 00 00 80 3F 00 00-20 41 00 00 C8 42 00 00   0....?.. A...B..
2817:A770  7A 44 00 40 1C 46 00 50-C3 47 00 24 74 49 80 96   zD.@.F.P.G.$tI..
2817:A780  18 4B 20 BC BE 4C 00 80-E3 37 79 C3 41 43 9E B5   .K ..L...7y.AC..
2817:A790  70 2B 48 AD C5 9D 69 40-D5 A6 CF FF 49 1F 78 C2   p+....i@....I.x.
2817:A7A0  D3 40 DF 8D E9 81 C9 47-BA 93 A8 41 8D DE F9 9D   .@.....G...A....
2817:A7B0  F8 EB 7E AA 81 43 E7 91-CE A6 4E 40 19 E3 A3 46   ..~.CC.........F
2817:A7C0  17 0C 7E 81 E5 7E 75 D9-4B 4D 8B 8D 7D 3D 8D 3A   ..u..uv.KM.}=.:
2817:A7D0  88 9E F2 8A F8 87 20 8A-02 E2 60 04 25 7E 00 00   ...Z.. ..R`.%u..
2817:A7E0  80 7F 00 00 80 7F 00 00-80 FF 00 00 C0 7F 00 00   ................
2817:A7F0  C0 FF 00 00 00 00 00 00-00 00 00 00 00 00 00 00   ................
2817:A800  20 00 F0 7F 73 71 72 74-00 00 62 3D C3 2E 69 3D    ...sqrt..b=..i=
2817:A810  C3 2E 6E 3D C3 2E 77 3D-C3 2E 81 3D C3 2E 87 3D   ..n=..w=...=...=
2817:A820  C3 2E 44 4F 4D 41 49 4E-00 53 49 4E 47 00 4F 56   ..DOMAIN.SING.OV
2817:A830  45 52 46 4C 4F 57 00 55-4E 44 45 52 46 4C 4F 57   ERFLOW.UNDERFLOW
2817:A840  00 54 4C 4F 53 53 00 50-4C 4F 53 53 00 25 73 3A   .TLOSS.PLOSS.%s:
2817:A850  20 25 73 20 65 72 72 6F-72 0A 00 00 00 00 00 00    %s error.......
2817:A860  00 00 00 00 00 00 00 13-02 02 04 05 06 08 08 08   ................
2817:A870  14 15 05 13 FF 16 05 11-02 FF FF FF FF FF FF FF   ................
2817:A880  FF FF FF FF FF FF 05 05-FF FF FF FF FF FF FF FF   ................
2817:A890  FF FF FF FF FF FF FF FF-0F FF 23 02 FF 0F FF FF   ..........#.....
2817:A8A0  FF FF 13 FF FF 02 02 05-0F 02 FF FF FF 13 FF FF   ................
2817:A8B0  FF FF FF FF FF FF 23 FF-FF FF FF 23 FF 13 FF 00   ......#....#....
2817:A8C0  0D 00 00 2B 0D 00 0D 2B-0D 00 0D 2B 00 00 00 00   ...+...+...+....
2817:A8D0  00 00 00 00 00 00 00 00-00 00 00 00 00 20 20 20   .............
2817:A8E0  20 20 20 20 20 20 21 21-21 21 21 20 20 20 20 20         !!!!!
2817:A8F0  20 20 20 20 20 20 20 20-20 20 20 20 20 01 40 40                .@@
2817:A900  40 40 40 40 40 40 40 40-40 40 40 40 40 02 02 02   @@@@@@@@@@@@@...
```

```
2817:A910  02 02 02 02 02 02 02 40-40 40 40 40 40 40 14 14   .......@@@@@@@..
2817:A920  14 14 14 14 04 04 04 04-04 04 04 04 04 04 04 04   ................
2817:A930  04 04 04 04 04 04 04 04-40 40 40 40 40 40 18 18   ........@@@@@@..
2817:A940  18 18 18 18 08 08 08 08-08 08 08 08 08 08 08 08   ................
2817:A950  08 08 08 08 08 08 08 08-40 40 40 40 20 00 00 00   ........@@@@ ...
2817:A960  00 00 00 00 00 00 00 00-00 00 00 00 00 00 00 00   ................
2817:A970  00 00 00 00 00 00 00 00-00 00 00 00 00 00 00 00   ................
2817:A980  00 00 00 00 00 00 00 00-00 00 00 00 00 00 00 00   ................
2817:A990  00 00 00 00 00 00 00 00-00 00 00 00 00 00 00 00   ................
2817:A9A0  00 00 00 00 00 00 00 00-00 00 00 00 00 00 00 00   ................
2817:A9B0  00 00 00 00 00 00 00 00-00 00 00 00 00 00 00 00   ................
2817:A9C0  00 00 00 00 00 00 00 00-00 00 00 00 00 00 00 00   ................
2817:A9D0  00 00 00 00 00 00 00 00-00 00 00 00 00 00 00 00   ................
2817:A9E0  09 02 00 00 00 00 00 00-00 00 00 00 00 00 00 00   ................
2817:A9F0  1E 3F 00 00 0A 02 01 00-00 00 00 00 00 00 00 00   .?..............
2817:AA00  00 00 00 00 32 3F 00 00-02 02 00 00 00 00 00 00   ....2?..........
2817:AA10  00 00 00 00 00 00 00 00-46 3F 00 00 43 02 03 00   ........F?..C...
2817:AA20  00 00 00 00 00 00 00 00-00 00 00 00 5A 3F 00 00   ............Z?..
2817:AA30  42 02 04 00 00 06 00 00-00 00 00 00 00 00 00 00   B...............
2817:AA40  6E 3F 00 00 00 00 FF 00-00 00 00 00 00 00 00 00   n?..............
2817:AA50  00 00 00 00 82 3F 00 00-00 00 FF 00 00 00 00 00   .....?..........
2817:AA60  00 00 00 00 00 00 00 00-96 3F 00 00 00 00 FF 00   .........?......
2817:AA70  00 00 00 00 00 00 00 00-00 00 00 00 AA 3F 00 00   .............?..
2817:AA80  00 00 FF 00 00 00 00 00-00 00 00 00 00 00 00 00   ................
2817:AA90  BE 3F 00 00 00 00 FF 00-00 00 00 00 00 00 00 00   .?..............
2817:AAA0  00 00 00 00 D2 3F 00 00-00 00 FF 00 00 00 00 00   .....?..........
2817:AAB0  00 00 00 00 00 00 00 00-E6 3F 00 00 00 00 FF 00   .........?......
2817:AAC0  00 00 00 00 00 00 00 00-00 00 00 00 FA 3F 00 00   .............?..
2817:AAD0  00 00 FF 00 00 00 00 00-00 00 00 00 00 00 00 00   ................
2817:AAE0  0E 40 00 00 00 00 FF 00-00 00 00 00 00 00 00 00   .@..............
2817:AAF0  00 00 00 00 22 40 00 00-00 00 FF 00 00 00 00 00   ...."@..........
2817:AB00  00 00 00 00 00 00 00 00-36 40 00 00 00 00 FF 00   ........6@......
2817:AB10  00 00 00 00 00 00 00 00-00 00 00 00 4A 40 00 00   ............J@..
2817:AB20  00 00 FF 00 00 00 00 00-00 00 00 00 00 00 00 00   ................
2817:AB30  5E 40 00 00 00 00 FF 00-00 00 00 00 00 00 00 00   ^@..............
2817:AB40  00 00 00 00 72 40 00 00-00 00 FF 00 00 00 00 00   ....r@..........
2817:AB50  00 00 00 00 00 00 00 00-86 40 00 00 00 00 FF 00   .........@......
2817:AB60  00 00 00 00 00 00 00 00-00 00 00 00 9A 40 01 20   .............@. 
2817:AB70  02 20 02 20 04 40 02 40-FF FF FF FF FF FF FF FF   . . ............
2817:AB80  FF FF FF FF FF FF FF FF-FF FF FF FF FF FF FF FF   ................
2817:AB90  FF FF FF FF FF FF 00 40-FF FF 00 00 00 00 54 4D   .......@......TM
2817:ABA0  50 00 2E 24 24 24 00 00-70 72 69 6E 74 20 73 63   P..$$$..print sc
2817:ABB0  61 6E 66 20 3A 20 66 6C-6F 61 74 69 6E 67 20 70   anf : floating p
2817:ABC0  6F 69 6E 74 20 66 6F 72-6D 61 74 73 20 6E 6F 74   oint formats not
2817:ABD0  20 6C 69 6E 6B 65 64 0D-0A 00 0D 00 28 6E 75 6C    linked.....(nul
2817:ABE0  6C 29 00 30 31 32 33 34-35 36 37 38 39 41 42 43   l).0123456789ABC
2817:ABF0  44 45 46 00 14 14 01 14-15 14 14 14 14 02 00 14   DEF.............
2817:AC00  03 04 14 09 05 05 15 05-05 15 05 05 05 11 04 14   ................
2817:AC10  14 14 14 14 14 14 14 14-0F 17 0F 08 14 14 14 07   ................
2817:AC20  14 16 14 14 14 14 14 14-14 14 14 0D 14 14 14 14   ................
2817:AC30  14 14 14 14 14 14 10 0A-0F 0F 0F 08 1A 14 14 06   ................
2817:AC40  14 12 08 0E 14 14 11 14-0C 14 14 0D 14 14 14 14   ................
2817:AC50  14 14 14 00 00 00 00 00-00 00 00 00 00 00 00 00   ................
2817:AC60  00 00 00 01 00 43 4F 4D-50 41 51 00 00 00 1F 1C   .....COMPAQ.....
2817:AC70  1F 1E 1F 1E 1F 1F 1E 1F-1E 1F 06 42 C3 2E 0A 42   ...........B...B
2817:AC80  C3 2E 0E 42 C3 2E 12 42-C3 2E 16 42 C3 2E 1A 42   ...B...B...B...B
2817:AC90  C3 2E 1E 42 C3 2E 22 42-C3 2E 26 42 C3 2E 2A 42   ...B.."B..&B..*B
2817:ACA0  C3 2E 2E 42 C3 2E 32 42-C3 2E 36 42 C3 2E 3A 42   ...B..2B..6B..:B
2817:ACB0  C3 2E 3E 42 C3 2E 42 42-C3 2E 46 42 C3 2E 4A 42   ..>B..BB..FB..JB
2817:ACC0  C3 2E 4E 42 C3 2E 53 75-6E 00 4D 6F 6E 00 54 75   ..NB..Sun.Mon.Tu
2817:ACD0  65 00 57 65 64 00 54 68-75 00 46 72 69 00 53 61   e.Wed.Thu.Fri.Sa
2817:ACE0  74 00 4A 61 6E 00 46 65-62 00 4D 61 72 00 41 70   t.Jan.Feb.Mar.Ap
2817:ACF0  72 00 4D 61 79 00 4A 75-6E 00 4A 75 6C 00 41 75   r.May.Jun.Jul.Au
2817:AD00  67 00 53 65 70 00 4F 63-74 00 4E 6F 76 00 44 65   g.Sep.Oct.Nov.De
2817:AD10  63 00 25 73 20 25 73 20-25 30 32 64 20 25 30 32   c.%s %s %02d %02
2817:AD20  64 3A 25 30 32 64 3A 25-30 32 64 20 25 34 64 0A   d:%02d:%02d %4d.
2817:AD30  00 00 01 00 00 00 1F 1C-1F 1E 1F 1E 1F 1F 1E 1F   ................
2817:AD40  1E 1F 1F 1D 1F 1E 1F 1E-1F 1F 1E 1F 1E 1F 00 00   ................
2817:AD50  1F 00 3B 00 5A 00 78 00-97 00 B5 00 D4 00 F3 00   ..;.Z.x.........
2817:AD60  11 01 30 01 4E 01 6D 01-C4 70 C3 2E A8 70 C3 2E   ..0.N.m..p...p..
2817:AD70  50 46 00 00 01 00 54 5A-00 45 53 54 00 45 44 54   FF....TZ.EST.EDT
```

```
2817:AD80  00 00 83 02 43 03 4B 02-1F 00 8B 2A D1 07 17 18   ....C.K....*....
2817:AD90  00 00 A4 2A 14 03 A4 2A-10 03 A4 2A D6 07 17 18   ...*...*...*....
2817:ADA0  D6 07 17 18 D6 07 17 18-00 00 00 00 00 00 00 00   ................
2817:ADB0  00 00 00 00 00 00 00 00-00 00 00 00 00 00 00 00   ................
2817:ADC0  00 00 00 00 00 00 00 00-00 00 00 00 00 00 00 00   ................
2817:ADD0  00 00 00 00 00 00 00 00-00 00 00 00 00 00 00 00   ................
2817:ADE0  00 00 00 00 00 00 00 00-00 00 00 00 00 00 00 00   ................
2817:ADF0  00 00 00 00 00 00 00 00-00 00 00 00 00 00 00 00   ................
2817:AE00  00 00 00 00 00 00 00 00-00 00 00 00 00 00 00 00   ................
2817:AE10  00 00 00 00 00 00 00 00-00 00 00 00 00 00 00 00   ................
2817:AE20  00 00 00 00 00 00 00 00-00 00 00 00 00 00 00 00   ................
2817:AE30  00 00 00 00 00 00 00 00-00 00 00 00 00 00 00 00   ................
2817:AE40  00 00 00 00 00 00 00 00-00 00 00 00 00 00 00 00   ................
2817:AE50  00 00 00 00 00 00 00 00-00 00 00 00 00 00 00 00   ................
2817:AE60  00 00 00 00 00 00 00 00-00 00 00 00 00 00 00 00   ................
2817:AE70  00 00 00 00 00 00 00 00-00 00 00 00 00 00 00 00   ................
2817:AE80  00 00 00 00 00 00 00 00-00 00 00 00 00 00 00 00   ................
2817:AE90  00 00 00 00 00 00 00 00-00 00 00 00 00 00 00 00   ................
2817:AEA0  00 00 00 00 00 00 00 00-00 00 00 00 00 00 00 00   ................
2817:AEB0  00 00 00 00 00 00 00 00-00 00 00 00 00 00 00 00   ................
2817:AEC0  00 00 00 00 00 00 00 00-00 00 00 00 00 00 00 00   ................
2817:AED0  00 00 00 00 00 00 00 00-00 00 00 00 00 00 00 00   ................
2817:AEE0  00 00 00 00 00 00 00 00-00 00 00 00 00 00 00 00   ................
2817:AEF0  00 00 00 00 00 00 00 00-00 00 00 00 00 00 00 00   ................
2817:AF00  00 00 00 00 00 00 00 00-00 00 00 00 00 00 00 00   ................
2817:AF10  00 00 00 00 00 00 00 00-00 00 00 00 00 00 00 00   ................
2817:AF20  00 00 00 00 00 00 00 00-00 00 00 00 00 00 00 00   ................
2817:AF30  00 00 00 00 00 00 00 00-00 00 00 00 00 00 00 00   ................
2817:AF40  00 00 00 00 00 00 00 00-00 00 00 00 00 00 00 00   ................
2817:AF50  00 00 00 00 00 00 00 00-00 00 00 00 00 00 00 00   ................
2817:AF60  00 00 00 00 00 00 00 00-00 00 00 00 00 00 00 00   ................
2817:AF70  00 00 00 00 00 00 00 00-00 00 00 00 00 00 00 00   ................
2817:AF80  00 00 00 00 00 00 00 00-00 00 00 00 00 00 00 00   ................
2817:AF90  00 00 00 00 00 00 00 00-00 00 00 00 00 00 00 00   ................
2817:AFA0  00 00 00 00 00 00 00 00-00 00 00 00 00 00 00 00   ................
2817:AFB0  00 00 00 00 00 00 00 00-00 00 00 00 00 00 00 00   ................
2817:AFC0  00 00 00 00 00 00 00 00-00 00 00 00 00 00 00 00   ................
2817:AFD0  00 00 00 00 00 00 00 00-00 00 00 00 00 00 00 00   ................
2817:AFE0  00 00 00 00 00 00 00 00-00 00 00 00 00 00 00 00   ................
2817:AFF0  00 00 00 00 00 00 00 00-00 00 00 00 00 00 00 00   ................
2817:B000  00 00 00 00 00 00 00 00-00 00 00 00 00 00 00 00   ................
2817:B010  00 00 00 00 00 00 00 00-00 00 00 00 00 00 00 00   ................
2817:B020  00 00 00 00 00 00 00 00-00 00 00 00 00 00 00 00   ................
2817:B030  00 00 00 00 00 00 00 00-00 00 00 00 00 00 00 00   ................
2817:B040  00 00 00 00 00 00 00 00-00 00 00 00 00 00 00 00   ................
2817:B050  00 00 00 00 00 00 00 00-00 00 00 00 00 00 00 00   ................
2817:B060  00 00 00 00 00 00 00 00-00 00 00 00 00 00 00 00   ................
2817:B070  00 00 00 00 00 00 00 00-00 00 00 00 00 00 00 00   ................
2817:B080  00 00 00 00 00 00 00 00-00 00 00 00 00 00 00 00   ................
2817:B090  00 00 00 00 00 00 00 00-00 00 00 00 00 00 00 00   ................
2817:B0A0  00 00 00 00 00 00 00 00-00 00 00 00 00 00 00 00   ................
2817:B0B0  00 00 00 00 00 00 00 00-00 00 00 00 00 00 00 00   ................
2817:B0C0  00 00 00 00 00 00 00 00-00 00 00 00 00 00 00 00   ................
2817:B0D0  00 00 00 00 00 00 00 00-00 00 00 00 00 00 00 00   ................
2817:B0E0  00 00 00 00 00 00 00 00-00 00 00 00 00 00 00 00   ................
2817:B0F0  00 00 00 00 00 00 00 00-00 00 00 00 00 00 00 00   ................
2817:B100  00 00 00 00 00 00 00 00-00 00 00 00 00 00 00 00   ................
2817:B110  00 00 00 00 00 00 00 00-00 00 00 00 00 00 00 00   ................
2817:B120  00 00 00 00 00 00 00 00-00 00 00 00 00 00 00 00   ................
2817:B130  00 00 00 00 00 00 00 00-00 00 00 00 00 00 00 00   ................
2817:B140  00 00 00 00 00 00 00 00-00 00 00 00 00 00 00 00   ................
2817:B150  00 00 00 00 00 00 00 00-00 00 00 00 00 00 00 00   ................
2817:B160  00 00 00 00 00 00 00 00-00 00 00 00 00 00 00 00   ................
2817:B170  00 00 00 00 00 00 00 00-00 00 00 00 00 00 00 00   ................
2817:B180  00 00 00 00 00 00 00 00-00 00 00 00 00 00 00 00   ................
2817:B190  00 00 00 00 00 00 00 00-00 00 00 00 00 00 00 00   ................
2817:B1A0  00 00 00 00 00 00 00 00-00 00 00 00 00 00 00 00   ................
2817:B1B0  00 00 00 00 00 00 00 00-00 00 00 00 00 00 00 00   ................
2817:B1C0  00 00 00 00 00 00 00 00-00 00 00 00 00 00 00 00   ................
2817:B1D0  00 00 00 00 00 00 00 00-00 00 00 00 00 00 00 00   ................
2817:B1E0  00 00 00 00 00 00 00 00-00 00 00 00 00 00 00 00   ................
2817:B1F0  00 00 00 00 00 00 00 00-00 00 00 00 00 00 00 00   ................
```

```
2817:B200  00 00 00 00 00 00 00 00-00 00 00 00 00 00 00 00   ................
2817:B210  00 00 00 00 00 00 00 00-00 00 00 00 00 00 00 00   ................
2817:B220  00 00 00 00 00 00 00 00-00 00 00 00 00 00 00 00   ................
2817:B230  00 00 00 00 00 00 00 00-00 00 00 00 00 00 00 00   ................
2817:B240  00 00 00 00 00 00 00 00-00 00 00 00 00 00 00 00   ................
2817:B250  00 00 00 00 00 00 00 00-00 00 00 00 00 00 00 00   ................
2817:B260  00 00 00 00 00 00 00 00-00 00 00 00 00 00 00 00   ................
2817:B270  00 00 00 00 00 00 00 00-00 00 00 00 00 00 00 00   ................
2817:B280  00 00 00 00 00 00 00 00-00 00 00 00 00 00 00 00   ................
2817:B290  00 00 00 00 00 00 00 00-00 00 00 00 00 00 00 00   ................
2817:B2A0  00 00 00 00 00 00 00 00-00 00 00 00 00 00 00 00   ................
2817:B2B0  00 00 00 00 00 00 00 00-00 00 00 00 00 00 00 00   ................
2817:B2C0  00 00 00 00 00 00 00 00-00 00 00 00 00 00 00 00   ................
2817:B2D0  00 00 00 00 00 00 00 00-00 00 00 00 00 00 00 00   ................
2817:B2E0  00 00 00 00 00 00 00 00-00 00 00 00 00 00 00 00   ................
2817:B2F0  00 00 00 00 00 00 00 00-00 00 00 00 00 00 00 00   ................
2817:B300  00 00 00 00 00 00 00 00-00 00 00 00 00 00 00 00   ................
2817:B310  00 00 00 00 00 00 00 00-00 00 00 00 00 00 00 00   ................
2817:B320  00 00 00 00 00 00 00 00-00 00 00 00 00 00 00 00   ................
2817:B330  00 00 00 00 00 00 00 00-00 00 00 00 00 00 00 00   ................
2817:B340  00 00 00 00 00 00 00 00-00 00 00 00 00 00 00 00   ................
2817:B350  00 00 00 00 00 00 00 00-00 00 00 00 00 00 00 00   ................
2817:B360  00 00 00 00 00 00 00 00-00 00 00 00 00 00 00 00   ................
2817:B370  00 00 00 00 00 00 00 00-00 00 00 00 00 00 00 00   ................
2817:B380  00 00 00 00 00 00 00 00-00 00 00 00 00 00 00 00   ................
2817:B390  00 00 00 00 00 00 00 00-00 00 00 00 00 00 00 00   ................
2817:B3A0  00 00 00 00 00 00 00 00-00 00 00 00 00 00 00 00   ................
2817:B3B0  00 00 00 00 00 00 00 00-00 00 00 00 00 00 00 00   ................
2817:B3C0  00 00 00 00 00 00 00 00-00 00 00 00 00 00 00 00   ................
2817:B3D0  00 00 00 00 00 00 00 00-00 00 00 00 00 00 00 00   ................
2817:B3E0  00 00 00 00 00 00 00 00-00 00 00 00 00 00 00 00   ................
2817:B3F0  00 00 00 00 00 00 00 00-00 00 00 00 00 00 00 00   ................
2817:B400  00 00 00 00 00 00 00 00-00 00 00 00 00 00 00 00   ................
2817:B410  00 00 00 00 00 00 00 00-00 00 00 00 00 00 00 00   ................
2817:B420  00 00 00 00 00 00 00 00-00 00 00 00 00 00 00 00   ................
2817:B430  00 00 00 00 00 00 00 00-00 00 00 00 00 00 00 00   ................
2817:B440  00 00 00 00 00 00 00 00-00 00 00 00 00 00 00 00   ................
2817:B450  00 00 00 00 00 00 00 00-00 00 00 00 00 00 00 00   ................
2817:B460  00 00 00 00 00 00 00 00-00 00 00 00 00 00 00 00   ................
2817:B470  00 00 00 00 00 00 00 00-00 00 00 00 00 00 00 00   ................
2817:B480  00 00 00 00 00 00 00 00-00 00 00 00 00 00 00 00   ................
2817:B490  00 00 00 00 00 00 00 00-00 00 00 00 00 00 00 00   ................
2817:B4A0  00 00 00 00 00 00 00 00-00 00 00 00 00 00 00 00   ................
2817:B4B0  00 00 00 00 00 00 00 00-00 00 00 00 00 00 00 00   ................
2817:B4C0  00 00 00 00 00 00 00 00-00 00 00 00 00 00 00 00   ................
2817:B4D0  00 00 00 00 00 00 00 00-00 00 00 00 00 00 00 00   ................
2817:B500  00 00 00 00 00 00 00 00-00 00 00 00 00 00 00 00   ................
2817:B510  00 00 00 00 00 00 00 00-00 00 00 00 00 00 00 00   ................
2817:B520  00 00 00 00 00 00 00 00-00 00 00 00 00 00 00 00   ................
2817:B530  00 00 00 00 00 00 00 00-00 00 00 00 00 00 00 00   ................
2817:B540  00 00 00 00 00 00 00 00-00 00 00 00 00 00 00 00   ................
2817:B550  00 00 00 00 00 00 00 00-00 00 00 00 00 00 00 00   ................
2817:B560  00 00 00 00 00 00 00 00-00 00 00 00 00 00 00 00   ................
2817:B570  00 00 00 00 00 00 00 00-00 00 00 00 00 00 00 00   ................
2817:B580  00 00 00 00 00 00 00 00-00 00 00 00 00 00 00 00   ................
2817:B590  00 00 00 00 00 00 00 00-00 00 00 00 00 00 00 00   ................
2817:B5A0  00 00 00 00 00 00 00 00-00 00 00 00 00 00 00 00   ................
2817:B5B0  00 00 00 00 00 00 00 00-00 00 00 00 00 00 00 00   ................
2817:B5C0  00 00 00 00 00 00 00 00-00 00 00 00 00 00 00 00   ................
2817:B5D0  00 00 00 00 00 00 00 00-00 00 00 00 00 00 00 00   ................
2817:B5E0  00 00 00 00 00 00 00 00-00 00 00 00 00 00 00 00   ................
2817:B5F0  00 00 00 00 00 00 00 00-00 00 00 00 00 00 00 00   ................
2817:B600  00 00 00 00 00 00 00 00-00 00 00 00 00 00 00 00   ................
2817:B610  00 00 00 00 00 00 00 00-00 00 00 00 00 00 00 00   ................
2817:B620  00 00 00 00 00 00 00 00-00 00 00 00 00 00 00 00   ................
2817:B630  00 00 00 00 00 00 00 00-00 00 00 00 00 00 00 00   ................
2817:B640  00 00 00 00 00 00 00 00-00 00 00 00 00 00 00 00   ................
2817:B650  00 00 00 00 00 00 00 00-00 00 00 00 00 00 00 00   ................
2817:B660  00 00 00 00 00 00 00 00-00 00 00 00 00 00 00 00   ................
2817:B670  00 00 00 00 00 00 00 00-00 00 00 00 00 00 00 00   ................
2817:B680  00 00 00 00 00 00 00 00-00 00 00 00 00 00 00 00   ................
2817:B690  00 00 00 00 00 00 00 00-00 00 00 00 00 00 00 00   ................
2817:B6A0  00 00 00 00 00 00 00 00-00 00 00 00 00 00 00 00   ................
```

```
2817:B6B0  00 00 00 00 00 00 00 00-00 00 00 00 00 00 00 00   ................
2817:B6C0  00 00 00 00 00 00 00 00-00 00 00 00 00 00 00 00   ................
2817:B6D0  00 00 00 00 00 00 00 00-00 00 00 00 00 00 00 00   ................
2817:B6E0  00 00 00 00 00 00 00 00-00 00 00 00 00 00 00 00   ................
2817:B6F0  00 00 00 00 00 00 00 00-00 00 00 00 00 00 00 00   ................
2817:B700  00 00 00 00 00 00 00 00-00 00 00 00 00 00 00 00   ................
2817:B710  00 00 00 00 00 00 00 00-00 00 00 00 00 00 00 00   ................
2817:B720  00 00 00 00 00 00 00 00-00 00 00 00 00 00 00 00   ................
2817:B730  00 00 00 00 00 00 00 00-00 00 00 00 00 00 00 00   ................
2817:B740  00 00 00 00 00 00 00 00-00 00 00 00 00 00 00 00   ................
2817:B750  00 00 00 00 00 00 00 00-00 00 00 00 00 00 00 00   ................
2817:B760  00 00 00 00 00 00 00 00-00 00 00 00 00 00 00 00   ................
2817:B770  00 00 00 00 00 00 00 00-00 00 00 00 00 00 00 00   ................
2817:B780  00 00 00 00 00 00 00 00-00 00 00 00 00 00 00 00   ................
2817:B790  00 00 00 00 00 00 00 00-00 00 00 00 00 00 00 00   ................
2817:B7A0  00 00 00 00 00 00 00 00-00 00 00 00 00 00 00 00   ................
2817:B7B0  00 00 00 00 00 00 00 00-00 00 00 00 00 00 00 00   ................
2817:B7C0  00 00 00 00 00 00 00 00-00 00 00 00 00 00 00 00   ................
2817:B7D0  00 00 00 00 00 00 00 00-00 00 00 00 00 00 00 00   ................
2817:B7E0  00 00 00 00 00 00 00 00-00 00 00 00 00 00 00 00   ................
2817:B7F0  00 00 00 00 00 00 00 00-00 00 00 00 00 00 00 00   ................
2817:B800  00 00 00 00 00 00 00 00-00 00 00 00 00 00 00 00   ................
2817:B810  00 00 00 00 00 00 00 00-00 00 00 00 00 00 00 00   ................
2817:B820  00 00 00 00 00 00 00 00-00 00 00 00 00 00 00 00   ................
2817:B830  00 00 00 00 00 00 00 00-00 00 00 00 00 00 00 00   ................
2817:B840  00 00 00 00 00 00 00 00-00 00 00 00 00 00 00 00   ................
2817:B850  00 00 00 00 00 00 00 00-00 00 00 00 00 00 00 00   ................
2817:B860  00 00 00 00 00 00 00 00-00 00 00 00 00 00 00 00   ................
2817:B870  00 00 00 00 00 00 00 00-00 00 00 00 00 00 00 00   ................
2817:B880  00 00 00 00 00 00 00 00-00 00 00 00 00 00 00 00   ................
2817:B890  00 00 00 00 00 00 00 00-00 00 00 00 00 00 00 00   ................
2817:B8A0  00 00 00 00 00 00 00 00-00 00 00 00 00 00 00 00   ................
2817:B8B0  00 00 00 00 00 00 00 00-00 00 00 00 00 00 00 00   ................
2817:B8C0  00 00 00 00 00 00 00 00-00 00 00 00 00 00 00 00   ................
2817:B8D0  00 00 00 00 00 00 00 00-00 00 00 00 00 00 00 00   ................
2817:B8E0  00 00 00 00 00 00 00 00-00 00 00 00 00 00 00 00   ................
2817:B8F0  00 00 00 00 00 00 00 00-00 00 00 00 00 00 00 00   ................
2817:B900  00 00 00 00 00 00 00 00-00 00 00 00 00 00 00 00   ................
2817:B910  00 00 00 00 00 00 00 00-00 00 00 00 00 00 00 00   ................
2817:B920  00 00 00 00 00 00 00 00-00 00 00 00 00 00 00 00   ................
2817:B930  00 00 00 00 00 00 00 00-00 00 00 00 00 00 00 00   ................
2817:B940  00 00 00 00 00 00 00 00-00 00 00 00 00 00 00 00   ................
2817:B950  00 00 00 00 00 00 00 00-00 00 00 00 00 00 00 00   ................
2817:B960  00 00 00 00 00 00 00 00-00 00 00 00 00 00 00 00   ................
2817:B970  00 00 00 00 00 00 00 00-00 00 00 00 00 00 00 00   ................
2817:B980  00 00 00 00 00 00 00 00-00 00 00 00 00 00 00 00   ................
2817:B990  00 00 00 00 00 00 00 00-00 00 00 00 00 00 00 00   ................
2817:B9A0  00 00 00 00 00 00 00 00-00 00 00 00 00 00 00 00   ................
2817:B9B0  00 00 00 00 00 00 00 00-00 00 00 00 00 00 00 00   ................
2817:B9C0  00 00 00 00 00 00 00 00-00 00 00 00 00 00 00 00   ................
2817:B9D0  00 00 00 00 00 00 00 00-00 00 00 00 00 00 00 00   ................
2817:B9E0  00 00 00 00 00 00 00 00-00 00 00 00 00 00 00 00   ................
2817:B9F0  00 00 00 00 00 00 00 00-00 00 00 00 00 00 00 00   ................
2817:BA00  00 00 00 00 00 00 00 00-00 00 00 00 00 00 00 00   ................
2817:BA10  00 00 00 00 00 00 00 00-00 00 00 00 00 00 00 00   ................
2817:BA20  00 00 00 00 00 00 00 00-00 00 00 00 00 00 00 00   ................
2817:BA30  00 00 00 00 00 00 00 00-00 00 00 00 00 00 00 00   ................
2817:BA40  00 00 00 00 00 00 00 00-00 00 00 00 00 00 00 00   ................
2817:BA50  00 00 00 00 00 00 00 00-00 00 00 00 00 00 00 00   ................
2817:BA60  00 00 00 00 00 00 00 00-00 00 00 00 00 00 00 00   ................
2817:BA70  00 00 00 00 00 00 00 00-00 00 00 00 00 00 00 00   ................
2817:BA80  00 00 00 00 00 00 00 00-00 00 00 00 00 00 00 00   ................
2817:BA90  00 00 00 00 00 00 00 00-00 00 00 00 00 00 00 00   ................
2817:BAA0  00 00 00 00 00 00 00 00-00 00 00 00 00 00 00 00   ................
2817:BAB0  00 00 00 00 00 00 00 00-00 00 00 00 00 00 00 00   ................
2817:BAC0  00 00 00 00 00 00 00 00-00 00 00 00 00 00 00 00   ................
2817:BAD0  00 00 00 00 00 00 00 00-00 00 00 00 00 00 00 00   ................
2817:BAE0  00 00 00 00 00 00 00 00-00 00 00 00 00 00 00 00   ................
2817:BAF0  00 00 00 00 00 00 00 00-00 00 00 00 00 00 00 00   ................
2817:BB00  00 00 00 00 00 00 00 00-00 00 00 00 00 00 00 00   ................
2817:BB10  00 00 00 00 00 00 00 00-00 00 00 00 00 00 00 00   ................
2817:BB20  00 00 00 00 00 00 00 00-00 00 00 00 00 00 00 00   ................
2817:BB30  00 00 00 00 00 00 00 00-00 00 00 00 00 00 00 00   ................
```

```
2817:BB40  00 00 00 00 00 00 00 00-00 00 00 00 00 00 00 00   ................
2817:BB50  00 00 00 00 00 00 00 00-00 00 00 00 00 00 00 00   ................
2817:BB60  00 00 00 00 00 00 00 00-00 00 00 00 00 00 00 00   ................
2817:BB70  00 00 00 00 00 00 00 00-00 00 00 00 00 00 00 00   ................
2817:BB80  00 00 00 00 00 00 00 00-00 00 00 00 00 00 00 00   ................
2817:BB90  00 00 00 00 00 00 00 00-00 00 00 00 00 00 00 00   ................
2817:BBA0  00 00 00 00 00 00 00 00-00 00 00 00 00 00 00 00   ................
2817:BBB0  00 00 00 00 00 00 00 00-00 00 00 00 00 00 00 00   ................
2817:BBC0  00 00 00 00 00 00 00 00-00 00 00 00 00 00 00 00   ................
2817:BBD0  00 00 00 00 00 00 00 00-00 00 00 00 00 00 00 00   ................
2817:BBE0  00 00 00 00 00 00 00 00-00 00 00 00 00 00 00 00   ................
2817:BBF0  00 00 00 00 00 00 00 00-00 00 00 00 00 00 00 00   ................
2817:BC00  00 00 00 00 00 00 00 00-00 00 00 00 00 00 00 00   ................
2817:BC10  00 00 00 00 00 00 00 00-00 00 00 00 00 00 00 00   ................
2817:BC20  00 00 00 00 00 00 00 00-00 00 00 00 00 00 00 00   ................
2817:BC30  00 00 00 00 00 00 00 00-00 00 00 00 00 00 00 00   ................
2817:BC40  00 00 00 00 00 00 00 00-00 00 00 00 00 00 00 00   ................
2817:BC50  00 00 00 00 00 00 00 00-00 00 00 00 00 00 00 00   ................
2817:BC60  00 00 00 00 00 00 00 00-00 00 00 00 00 00 00 00   ................
2817:BC70  00 00 00 00 00 00 00 00-00 00 00 00 00 00 00 00   ................
2817:BC80  00 00 00 00 00 00 00 00-00 00 00 00 00 00 00 00   ................
2817:BC90  00 00 00 00 00 00 00 00-00 00 00 00 00 00 00 00   ................
2817:BCA0  00 00 00 00 00 00 00 00-00 00 00 00 00 00 00 00   ................
2817:BCB0  00 00 00 00 00 00 00 00-00 00 00 00 00 00 00 00   ................
2817:BCC0  00 00 00 00 00 00 00 00-00 00 00 00 00 00 00 00   ................
2817:BCD0  00 00 00 00 00 00 00 00-00 00 00 00 00 00 00 00   ................
2817:BCE0  00 00 00 00 00 00 00 00-00 00 00 00 00 00 00 00   ................
2817:BCF0  00 00 00 00 00 00 00 00-00 00 00 00 00 00 00 00   ................
2817:BD00  00 00 00 00 00 00 00 00-00 00 00 00 00 00 00 00   ................
2817:BD10  00 00 00 00 00 00 00 00-00 00 00 00 00 00 00 00   ................
2817:BD20  00 00 00 00 00 00 00 00-00 00 00 00 00 00 00 00   ................
2817:BD30  00 00 00 00 00 00 00 00-00 00 00 00 00 00 00 00   ................
2817:BD40  00 00 00 00 00 00 00 00-00 00 00 00 00 00 00 00   ................
2817:BD50  00 00 00 00 00 00 00 00-00 00 00 00 00 00 00 00   ................
2817:BD60  00 00 00 00 00 00 00 00-00 00 00 00 00 00 00 00   ................
2817:BD70  00 00 00 00 00 00 00 00-00 00 00 00 00 00 00 00   ................
2817:BD80  00 00 00 00 00 00 00 00-00 00 00 00 00 00 00 00   ................
2817:BD90  00 00 00 00 00 00 00 00-00 00 00 00 00 00 00 00   ................
2817:BDA0  00 00 00 00 00 00 00 00-00 00 00 00 00 00 00 00   ................
2817:BDB0  00 00 00 00 00 00 00 00-00 00 00 00 00 00 00 00   ................
2817:BDC0  00 00 00 00 00 00 00 00-00 00 00 00 00 00 00 00   ................
2817:BDD0  00 00 00 00 00 00 00 00-00 00 00 00 00 00 00 00   ................
2817:BDE0  00 00 00 00 00 00 00 00-00 00 00 00 00 00 00 00   ................
2817:BDF0  00 00 00 00 00 00 00 00-00 00 00 00 00 00 00 00   ................
2817:BE00  00 00 00 00 00 00 00 00-00 00 00 00 00 00 00 00   ................
2817:BE10  00 00 00 00 00 00 00 00-00 00 00 00 00 00 00 00   ................
2817:BE20  00 00 00 00 00 00 00 00-00 00 00 00 00 00 00 00   ................
2817:BE30  00 00 00 00 00 00 00 00-00 00 00 00 00 00 00 00   ................
2817:BE40  00 00 00 00 00 00 00 00-00 00 00 00 00 00 00 00   ................
2817:BE50  00 00 00 00 00 00 00 00-00 00 00 00 00 00 00 00   ................
2817:BE60  00 00 00 00 00 00 00 00-00 00 00 00 00 00 00 00   ................
2817:BE70  00 00 00 00 00 00 00 00-00 00 00 00 00 00 00 00   ................
2817:BE80  00 00 00 00 00 00 00 00-00 00 00 00 00 00 00 00   ................
2817:BE90  00 00 00 00 00 00 00 00-00 00 00 00 00 00 00 00   ................
2817:BEA0  00 00 00 00 00 00 00 00-00 00 00 00 00 00 00 00   ................
2817:BEB0  00 00 00 00 00 00 00 00-00 00 00 00 00 00 00 00   ................
2817:BEC0  00 00 00 00 00 00 00 00-00 00 00 00 00 00 00 00   ................
2817:BED0  00 00 00 00 00 00 00 00-00 00 00 00 00 00 00 00   ................
2817:BEE0  00 00 00 00 00 00 00 00-00 00 00 00 00 00 00 00   ................
2817:BEF0  00 00 00 00 00 00 00 00-00 00 00 00 00 00 00 00   ................
2817:BF00  00 00 00 00 00 00 00 00-00 00 00 00 00 00 00 00   ................
2817:BF10  00 00 00 00 00 00 00 00-00 00 00 00 00 00 00 00   ................
2817:BF20  00 00 00 00 00 00 00 00-00 00 00 00 00 00 00 00   ................
2817:BF30  00 00 00 00 00 00 00 00-00 00 00 00 00 00 00 00   ................
2817:BF40  00 00 00 00 00 00 00 00-00 00 00 00 00 00 00 00   ................
2817:BF50  00 00 00 00 00 00 00 00-00 00 00 00 00 00 00 00   ................
2817:BF60  00 00 00 00 00 00 00 00-00 00 00 00 00 00 00 00   ................
2817:BF70  00 00 00 00 00 00 00 00-00 00 00 00 00 00 00 00   ................
2817:BF80  00 00 00 00 00 00 00 00-00 00 00 00 00 00 00 00   ................
2817:BF90  00 00 00 00 00 00 00 00-00 00 00 00 00 00 00 00   ................
2817:BFA0  00 00 00 00 00 00 00 00-00 00 00 00 00 00 00 00   ................
2817:BFB0  00 00 00 00 00 00 00 00-00 00 00 00 00 00 00 00   ................
2817:BFC0  00 00 00 00 00 00 00 00-00 00 00 00 00 00 00 00   ................
```

```
2B17:BFD0  00 00 00 00 00 00 00 00-00 00 00 00 00 00 00 00   ................
2B17:BFE0  00 00 00 00 00 00 00 00-00 00 00 00 00 00 00 00   ................
2B17:BFF0  00 00 00 00 00 00 00 00-00 00 00 00 00 00 00 00   ................
2B17:C000  00 00 00 00 00 00 00 00-00 00 00 00 00 00 00 00   ................
2B17:C010  00 00 00 00 00 00 00 00-00 00 00 00 00 00 00 00   ................
2B17:C020  00 00 00 00 00 00 00 00-00 00 00 00 00 00 00 00   ................
2B17:C030  00 00 00 00 00 00 00 00-00 00 00 00 00 00 00 00   ................
2B17:C040  00 00 00 00 00 00 00 00-00 00 00 00 00 00 00 00   ................
2B17:C050  00 00 00 00 00 00 00 00-00 00 00 00 00 00 00 00   ................
2B17:C060  00 00 00 00 00 00 00 00-00 00 00 00 00 00 00 00   ................
2B17:C070  00 00 00 00 00 00 00 00-00 00 00 00 00 00 00 00   ................
2B17:C080  00 00 00 00 00 00 00 00-00 00 00 00 00 00 00 00   ................
2B17:C090  00 00 00 00 00 00 00 00-00 00 00 00 00 00 00 00   ................
2B17:C0A0  00 00 00 00 00 00 00 00-00 00 00 00 00 00 00 00   ................
2B17:C0B0  00 00 00 00 00 00 00 00-00 00 00 00 00 00 00 00   ................
2B17:C0C0  00 00 00 00 00 00 00 00-00 00 00 00 00 00 00 00   ................
2B17:C0D0  00 00 00 00 00 00 00 00-00 00 00 00 00 00 00 00   ................
2B17:C0E0  00 00 00 00 00 00 00 00-00 00 00 00 00 00 00 00   ................
2B17:C0F0  00 00 00 00 00 00 00 00-00 00 00 00 00 00 00 00   ................
2B17:C100  00 00 00 00 00 00 00 00-00 00 00 00 00 00 00 00   ................
2B17:C110  00 00 00 00 00 00 00 00-00 00 00 00 00 00 00 00   ................
2B17:C120  00 00 00 00 00 00 00 00-00 00 00 00 00 00 00 00   ................
2B17:C130  00 00 00 00 00 00 00 00-00 00 00 00 00 00 00 00   ................
2B17:C140  00 00 00 00 00 00 00 00-00 00 00 00 00 00 00 00   ................
2B17:C150  00 00 00 00 00 00 00 00-00 00 00 00 00 00 00 00   ................
2B17:C160  00 00 00 00 00 00 00 00-00 00 00 00 00 00 00 00   ................
2B17:C170  00 00 00 00 00 00 00 00-00 00 00 00 00 00 00 00   ................
2B17:C180  00 00 00 00 00 00 00 00-00 00 00 00 00 00 00 00   ................
2B17:C190  00 00 00 00 00 00 00 00-00 00 00 00 00 00 00 00   ................
2B17:C1A0  00 00 00 00 00 00 00 00-00 00 00 00 00 00 00 00   ................
2B17:C1B0  00 00 00 00 00 00 00 00-00 00 00 00 00 00 00 00   ................
2B17:C1C0  00 00 00 00 00 00 00 00-00 00 00 00 00 00 00 00   ................
2B17:C1D0  00 00 00 00 00 00 00 00-00 00 00 00 00 00 00 00   ................
2B17:C1E0  00 00 00 00 00 00 00 00-00 00 00 00 00 00 00 00   ................
2B17:C1F0  00 00 00 00 00 00 00 00-00 00 00 00 00 00 00 00   ................
2B17:C200  00 00 00 00 00 00 00 00-00 00 00 00 00 00 00 00   ................
2B17:C210  00 00 00 00 00 00 00 00-00 00 00 00 00 00 00 00   ................
2B17:C220  00 00 00 00 00 00 00 00-00 00 00 00 00 00 00 00   ................
2B17:C230  00 00 00 00 00 00 00 00-00 00 00 00 00 00 00 00   ................
2B17:C240  00 00 00 00 00 00 00 00-00 00 00 00 00 00 00 00   ................
2B17:C250  00 00 00 00 00 00 00 00-00 00 00 00 00 00 00 00   ................
2B17:C260  00 00 00 00 00 00 00 00-00 00 00 00 00 00 00 00   ................
2B17:C270  00 00 00 00 00 00 00 00-00 00 00 00 00 00 00 00   ................
2B17:C280  00 00 00 00 00 00 00 00-00 00 00 00 00 00 00 00   ................
2B17:C290  00 00 00 00 00 00 00 00-00 00 00 00 00 00 00 00   ................
2B17:C2A0  00 00 00 00 00 00 00 00-00 00 00 00 00 00 00 00   ................
2B17:C2B0  00 00 00 00 00 00 00 00-00 00 00 00 00 00 00 00   ................
2B17:C2C0  00 00 00 00 00 00 00 00-00 00 00 00 00 00 00 00   ................
2B17:C2D0  00 00 00 00 00 00 00 00-00 00 00 00 00 00 00 00   ................
2B17:C2E0  00 00 00 00 00 00 00 00-00 00 00 00 00 00 00 00   ................
2B17:C2F0  00 00 00 00 00 00 00 00-00 00 00 00 00 00 00 00   ................
2B17:C300  00 00 00 00 00 00 00 00-00 00 00 00 00 00 00 00   ................
2B17:C310  00 00 00 00 00 00 00 00-00 00 00 00 00 00 00 00   ................
2B17:C320  00 00 00 00 00 00 00 00-00 00 00 00 00 00 00 00   ................
2B17:C330  00 00 00 00 00 00 00 00-00 00 00 00 00 00 00 00   ................
2B17:C340  00 00 00 00 00 00 00 00-00 00 00 00 00 00 00 00   ................
2B17:C350  00 00 00 00 00 00 00 00-00 00 00 00 00 00 00 00   ................
2B17:C360  00 00 00 00 00 00 00 00-00 00 00 00 00 00 00 00   ................
2B17:C370  00 00 00 00 00 00 00 00-00 00 00 00 00 00 00 00   ................
2B17:C380  00 00 00 00 00 00 00 00-00 00 00 00 00 00 00 00   ................
2B17:C390  00 00 00 00 00 00 00 00-00 00 00 00 00 00 00 00   ................
2B17:C3A0  00 00 00 00 00 00 00 00-00 00 00 00 00 00 00 00   ................
2B17:C3B0  00 00 00 00 00 00 00 00-00 00 00 00 00 00 00 00   ................
2B17:C3C0  00 00 00 00 00 00 00 00-00 00 00 00 00 00 00 00   ................
2B17:C3D0  00 00 00 00 00 00 00 00-00 00 00 00 00 00 00 00   ................
2B17:C3E0  00 00 00 00 00 00 00 00-00 00 00 00 00 00 00 00   ................
2B17:C3F0  00 00 00 00 00 00 00 00-00 00 00 00 00 00 00 00   ................
```

```
2817:C400  00 00 00 00 00 00 00 00-00 00 00 00 00 00 00 00   ................
2817:C410  00 00 00 00 00 00 00 00-00 00 00 00 00 00 00 00   ................
2817:C420  00 00 00 00 00 00 00 00-00 00 00 00 00 00 00 00   ................
2817:C430  00 00 00 00 00 00 00 00-00 00 00 00 00 00 00 00   ................
2817:C440  00 00 00 00 00 00 00 00-00 00 00 00 00 00 00 00   ................
2817:C450  00 00 00 00 00 00 00 00-00 00 00 00 00 00 00 00   ................
2817:C460  00 00 00 00 00 00 00 00-00 00 00 00 00 00 00 00   ................
2817:C470  00 00 00 00 00 00 00 00-00 00 00 00 00 00 00 00   ................
2817:C480  00 00 00 00 00 00 00 00-00 00 00 00 00 00 00 00   ................
2817:C490  00 00 00 00 00 00 00 00-00 00 00 00 00 00 00 00   ................
2817:C4A0  00 00 00 00 00 00 00 00-00 00 00 00 00 00 00 00   ................
2817:C4B0  00 00 00 00 00 00 00 00-00 00 00 00 00 00 00 00   ................
2817:C4C0  00 00 00 00 00 00 00 00-00 00 00 00 00 00 00 00   ................
2817:C4D0  00 00 00 00 00 00 00 00-00 00 00 00 00 00 00 00   ................
2817:C4E0  00 00 00 00 00 00 00 00-00 00 00 00 00 00 00 00   ................
2817:C4F0  00 00 00 00 00 00 00 00-00 00 00 00 00 00 00 00   ................
2817:C500  00 00 00 00 00 00 00 00-00 00 00 00 00 00 00 00   ................
2817:C510  00 00 00 00 00 00 00 00-00 00 00 00 00 00 00 00   ................
2817:C520  00 00 00 00 00 00 00 00-00 00 00 00 00 00 00 00   ................
2817:C530  00 00 00 00 00 00 00 00-00 00 00 00 00 00 00 00   ................
2817:C540  00 00 00 00 00 00 00 00-00 00 00 00 00 00 00 00   ................
2817:C550  00 00 00 00 00 00 00 00-00 00 00 00 00 00 00 00   ................
2817:C560  00 00 00 00 00 00 00 00-00 00 00 00 00 00 00 00   ................
2817:C570  00 00 00 00 00 00 00 00-00 00 00 00 00 00 00 00   ................
2817:C580  00 00 00 00 00 00 00 00-00 00 00 00 00 00 00 00   ................
2817:C590  00 00 00 00 00 00 00 00-00 00 00 00 00 00 00 00   ................
2817:C5A0  00 00 00 00 00 00 00 00-00 00 00 00 00 00 00 00   ................
2817:C5B0  00 00 00 00 00 00 00 00-00 00 00 00 00 00 00 00   ................
2817:C5C0  00 00 00 00 00 00 00 00-00 00 00 00 00 00 00 00   ................
2817:C5D0  00 00 00 00 00 00 00 00-00 00 00 00 00 00 00 00   ................
2817:C5E0  00 00 00 00 00 00 00 00-00 00 00 00 00 00 00 00   ................
2817:C5F0  00 00 00 00 00 00 00 00-00 00 00 00 00 00 00 00   ................
2817:C600  00 00 00 00 00 00 00 00-00 00 00 00 00 00 00 00   ................
2817:C610  00 00 00 00 00 00 00 00-00 00 00 00 00 00 00 00   ................
2817:C620  00 00 00 00 00 00 00 00-00 00 00 00 00 00 00 00   ................
2817:C630  00 00 00 00 00 00 00 00-00 00 00 00 00 00 00 00   ................
2817:C640  00 00 00 00 00 00 00 00-00 00 00 00 00 00 00 00   ................
2817:C650  00 00 00 00 00 00 00 00-00 00 00 00 00 00 00 00   ................
2817:C660  00 00 00 00 00 00 00 00-00 00 00 00 00 00 00 00   ................
2817:C670  00 00 00 00 00 00 00 00-00 00 00 00 00 00 00 00   ................
2817:C680  00 00 00 00 00 00 00 00-00 00 00 00 00 00 00 00   ................
2817:C690  00 00 00 00 00 00 00 00-00 00 00 00 00 00 00 00   ................
2817:C6A0  00 00 00 00 00 00 00 00-00 00 00 00 00 00 00 00   ................
2817:C6B0  00 00 00 00 00 00 00 00-00 00 00 00 00 00 00 00   ................
2817:C6C0  00 00 00 00 00 00 00 00-00 00 00 00 00 00 00 00   ................
2817:C6D0  00 00 00 00 00 00 00 00-00 00 00 00 00 00 00 00   ................
2817:C6E0  00 00 00 00 00 00 00 00-00 00 00 00 00 00 00 00   ................
2817:C6F0  00 00 00 00 00 00 00 00-00 00 00 00 00 00 00 00   ................
2817:C700  00 00 00 00 00 00 00 00-00 00 00 00 00 00 00 00   ................
2817:C710  00 00 00 00 00 00 00 00-00 00 00 00 00 00 00 00   ................
2817:C720  00 00 00 00 00 00 00 00-00 00 00 00 00 00 00 00   ................
2817:C730  00 00 00 00 00 00 00 00-00 00 00 00 00 00 00 00   ................
2817:C740  00 00 00 00 00 00 00 00-00 00 00 00 00 00 00 00   ................
2817:C750  00 00 00 00 00 00 00 00-00 00 00 00 00 00 00 00   ................
2817:C760  00 00 00 00 00 00 00 00-00 00 00 00 00 00 00 00   ................
2817:C770  00 00 00 00 00 00 00 00-00 00 00 00 00 00 00 00   ................
2817:C780  00 00 00 00 00 00 00 00-00 00 00 00 00 00 00 00   ................
2817:C790  00 00 00 00 00 00 00 00-00 00 00 00 00 00 00 00   ................
2817:C7A0  00 00 00 00 00 00 00 00-00 00 00 00 00 00 00 00   ................
2817:C7B0  00 00 00 00 00 00 00 00-00 00 00 00 00 00 00 00   ................
2817:C7C0  00 00 00 00 00 00 00 00-00 00 00 00 00 00 00 00   ................
2817:C7D0  00 00 00 00 00 00 00 00-00 00 00 00 00 00 00 00   ................
2817:C7E0  00 00 00 00 00 00 00 00-00 00 00 00 00 00 00 00   ................
2817:C7F0  00 00 00 00 00 00 00 00-00 00 00 00 00 00 00 00   ................
2817:C800  00 00 00 00 00 00 00 00-00 00 00 00 00 00 00 00   ................
2817:C810  00 00 00 00 00 00 00 00-00 00 00 00 00 00 00 00   ................
2817:C820  00 00 00 00 00 00 00 00-00 00 00 00 00 00 00 00   ................
2817:C830  00 00 00 00 00 00 00 00-00 00 00 00 00 00 00 00   ................
2817:C840  00 00 00 00 00 00 00 00-00 00 00 00 00 00 00 00   ................
2817:C850  00 00 00 00 00 00 00 00-00 00 00 00 00 00 00 00   ................
2817:C860  00 00 00 00 00 00 00 00-00 00 00 00 00 00 00 00   ................
2817:C870  00 00 00 00 00 00 00 00-00 00 00 00 00 00 00 00   ................
2817:C880  00 00 00 00 00 00 00 00-00 00 00 00 00 00 00 00   ................
```

```
2B17:C890  00 00 00 00 00 00 00 00-00 00 00 00 00 00 00 00   ................
2B17:C8A0  00 00 00 00 00 00 00 00-00 00 00 00 00 00 00 00   ................
2B17:C8B0  00 00 00 00 00 00 00 00-00 00 00 00 00 00 00 00   ................
2B17:C8C0  00 00 00 00 00 00 00 00-00 00 00 00 00 00 00 00   ................
2B17:C8D0  00 00 00 00 00 00 00 00-00 00 00 00 00 00 00 00   ................
2B17:C8E0  00 00 00 00 00 00 00 00-00 00 00 00 00 00 00 00   ................
2B17:C8F0  00 00 00 00 00 00 00 00-00 00 00 00 00 00 00 00   ................
2B17:C900  00 00 00 00 00 00 00 00-00 00 00 00 00 00 00 00   ................
2B17:C910  00 00 00 00 00 00 00 00-00 00 00 00 00 00 00 00   ................
2B17:C920  00 00 00 00 00 00 00 00-00 00 00 00 00 00 00 00   ................
2B17:C930  00 00 00 00 00 00 00 00-00 00 00 00 00 00 00 00   ................
2B17:C940  00 00 00 00 00 00 00 00-00 00 00 00 00 00 00 00   ................
2B17:C950  00 00 00 00 00 00 00 00-00 00 00 00 00 00 00 00   ................
2B17:C960  00 00 00 00 00 00 00 00-00 00 00 00 00 00 00 00   ................
2B17:C970  00 00 00 00 00 00 00 00-00 00 00 00 00 00 00 00   ................
2B17:C980  00 00 00 00 00 00 00 00-00 00 00 00 00 00 00 00   ................
2B17:C990  00 00 00 00 00 00 00 00-00 00 00 00 00 00 00 00   ................
2B17:C9A0  00 00 00 00 00 00 00 00-00 00 00 00 00 00 00 00   ................
2B17:C9B0  00 00 00 00 00 00 00 00-00 00 00 00 00 00 00 00   ................
2B17:C9C0  00 00 00 00 00 00 00 00-00 00 00 00 00 00 00 00   ................
2B17:C9D0  00 00 00 00 00 00 00 00-00 00 00 00 00 00 00 00   ................
2B17:C9E0  00 00 00 00 00 00 00 00-00 00 00 00 00 00 00 00   ................
2B17:C9F0  00 00 00 00 00 00 00 00-00 00 00 00 00 00 00 00   ................
2B17:CA00  00 00 00 00 00 00 00 00-00 00 00 00 00 00 00 00   ................
2B17:CA10  00 00 00 00 00 00 00 00-00 00 00 00 00 00 00 00   ................
2B17:CA20  00 00 00 00 00 00 00 00-00 00 00 00 00 00 00 00   ................
2B17:CA30  00 00 00 00 00 00 00 00-00 00 00 00 00 00 00 00   ................
2B17:CA40  00 00 00 00 00 00 00 00-00 00 00 00 00 00 00 00   ................
2B17:CA50  00 00 00 00 00 00 00 00-00 00 00 00 00 00 00 00   ................
2B17:CA60  00 00 00 00 00 00 00 00-00 00 00 00 00 00 00 00   ................
2B17:CA70  00 00 00 00 00 00 00 00-00 00 00 00 00 00 00 00   ................
2B17:CA80  00 00 00 00 00 00 00 00-00 00 00 00 00 00 00 00   ................
2B17:CA90  00 00 00 00 00 00 00 00-00 00 00 00 00 00 00 00   ................
2B17:CAA0  00 00 00 00 00 00 00 00-00 00 00 00 00 00 00 00   ................
2B17:CAB0  00 00 00 00 00 00 00 00-00 00 00 00 00 00 00 00   ................
2B17:CAC0  00 00 00 00 00 00 00 00-00 00 00 00 00 00 00 00   ................
2B17:CAD0  00 00 00 00 00 00 00 00-00 00 00 00 00 00 00 00   ................
2B17:CAE0  00 00 00 00 00 00 00 00-00 00 00 00 00 00 00 00   ................
2B17:CAF0  00 00 00 00 00 00 00 00-00 00 00 00 00 00 00 00   ................
2B17:CB00  00 00 00 00 00 00 00 00-00 00 00 00 00 00 00 00   ................
2B17:CB10  00 00 00 00 00 00 00 00-00 00 00 00 00 00 00 00   ................
2B17:CB20  00 00 00 00 00 00 00 00-00 00 00 00 00 00 00 00   ................
2B17:CB30  00 00 00 00 00 00 00 00-00 00 00 00 00 00 00 00   ................
2B17:CB40  00 00 00 00 00 00 00 00-00 00 00 00 00 00 00 00   ................
2B17:CB50  00 00 00 00 00 00 00 00-00 00 00 00 00 00 00 00   ................
2B17:CB60  00 00 00 00 00 00 00 00-00 00 00 00 00 00 00 00   ................
2B17:CB70  00 00 00 00 00 00 00 00-00 00 00 00 00 00 00 00   ................
2B17:CB80  00 00 00 00 00 00 00 00-00 00 00 00 00 00 00 00   ................
2B17:CB90  00 00 00 00 00 00 00 00-00 00 00 00 00 00 00 00   ................
2B17:CBA0  00 00 00 00 00 00 00 00-00 00 00 00 00 00 00 00   ................
2B17:CBB0  00 00 00 00 00 00 00 00-00 00 00 00 00 00 00 00   ................
2B17:CBC0  00 00 00 00 00 00 00 00-00 00 00 00 00 00 00 00   ................
2B17:CBD0  00 00 00 00 00 00 00 00-00 00 00 00 00 00 00 00   ................
2B17:CBE0  00 00 00 00 00 00 00 00-00 00 00 00 00 00 00 00   ................
2B17:CBF0  00 00 00 00 00 00 00 00-00 00 00 00 00 00 00 00   ................
2B17:CC00  00 00 00 00 00 00 00 00-00 00 00 00 00 00 00 00   ................
2B17:CC10  00 00 00 00 00 00 00 00-00 00 00 00 00 00 00 00   ................
2B17:CC20  00 00 00 00 00 00 00 00-00 00 00 00 00 00 00 00   ................
2B17:CC30  00 00 00 00 00 00 00 00-00 00 00 00 00 00 00 00   ................
2B17:CC40  00 00 00 00 00 00 00 00-00 00 00 00 00 00 00 00   ................
2B17:CC50  00 00 00 00 00 00 00 00-00 00 00 00 00 00 00 00   ................
2B17:CC60  00 00 00 00 00 00 00 00-00 00 00 00 00 00 00 00   ................
2B17:CC70  00 00 00 00 00 00 00 00-00 00 00 00 00 00 00 00   ................
2B17:CC80  00 00 00 00 00 00 00 00-00 00 00 00 00 00 00 00   ................
2B17:CC90  00 00 00 00 00 00 00 00-00 00 00 00 00 00 00 00   ................
2B17:CCA0  00 00 00 00 00 00 00 00-00 00 00 00 00 00 00 00   ................
2B17:CCB0  00 00 00 00 00 00 00 00-00 00 00 00 00 00 00 00   ................
2B17:CCC0  00 00 00 00 00 00 00 00-00 00 00 00 00 00 00 00   ................
2B17:CCD0  00 00 00 00 00 00 00 00-00 00 00 00 00 00 00 00   ................
2B17:CCE0  00 00 00 00 00 00 00 00-00 00 00 00 00 00 00 00   ................
2B17:CCF0  00 00 00 00 00 00 00 00-00 00 00 00 00 00 00 00   ................
2B17:CD00  00 00 00 00 00 00 00 00-00 00 00 00 00 00 00 00   ................
2B17:CD10  00 00 00 00 00 00 00 00-00 00 00 00 00 00 00 00   ................
```

```
2B17:CD20  00 00 00 00 00 00 00 00-00 00 00 00 00 00 00 00   ................
2B17:CD30  00 00 00 00 00 00 00 00-00 00 00 00 00 00 00 00   ................
2B17:CD40  00 00 00 00 00 00 00 00-00 00 00 00 00 00 00 00   ................
2B17:CD50  00 00 00 00 00 00 00 00-00 00 00 00 00 00 00 00   ................
2B17:CD60  00 00 00 00 00 00 00 00-00 00 00 00 00 00 00 00   ................
2B17:CD70  00 00 00 00 00 00 00 00-00 00 00 00 00 00 00 00   ................
2B17:CD80  00 00 00 00 00 00 00 00-00 00 00 00 00 00 00 00   ................
2B17:CD90  00 00 00 00 00 00 00 00-00 00 00 00 00 00 00 00   ................
2B17:CDA0  00 00 00 00 00 00 00 00-00 00 00 00 00 00 00 00   ................
2B17:CDB0  00 00 00 00 00 00 00 00-00 00 00 00 00 00 00 00   ................
2B17:CDC0  00 00 00 00 00 00 00 00-00 00 00 00 00 00 00 00   ................
2B17:CDD0  00 00 00 00 00 00 00 00-00 00 00 00 00 00 00 00   ................
2B17:CDE0  00 00 00 00 00 00 00 00-00 00 00 00 00 00 00 00   ................
2B17:CDF0  00 00 00 00 00 00 00 00-00 00 00 00 00 00 00 00   ................
2B17:CE00  00 00 00 00 00 00 00 00-00 00 00 00 00 00 00 00   ................
2B17:CE10  00 00 00 00 00 00 00 00-00 00 00 00 00 00 00 00   ................
2B17:CE20  00 00 00 00 00 00 00 00-00 00 00 00 00 00 00 00   ................
2B17:CE30  00 00 00 00 00 00 00 00-00 00 00 00 00 00 00 00   ................
2B17:CE40  00 00 00 00 00 00 00 00-00 00 00 00 00 00 00 00   ................
2B17:CE50  00 00 00 00 00 00 00 00-00 00 00 00 00 00 00 00   ................
2B17:CE60  00 00 00 00 00 00 00 00-00 00 00 00 00 00 00 00   ................
2B17:CE70  00 00 00 00 00 00 00 00-00 00 00 00 00 00 00 00   ................
2B17:CE80  00 00 00 00 00 00 00 00-00 00 00 00 00 00 00 00   ................
2B17:CE90  00 00 00 00 00 00 00 00-00 00 00 00 00 00 00 00   ................
2B17:CEA0  00 00 00 00 00 00 00 00-00 00 00 00 00 00 00 00   ................
2B17:CEB0  00 00 00 00 00 00 00 00-00 00 00 00 00 00 00 00   ................
2B17:CEC0  00 00 00 00 00 00 00 00-00 00 00 00 00 00 00 00   ................
2B17:CED0  00 00 00 00 00 00 00 00-00 00 00 00 00 00 00 00   ................
2B17:CEE0  00 00 00 00 00 00 00 00-00 00 00 00 00 00 00 00   ................
2B17:CEF0  00 00 00 00 00 00 00 00-00 00 00 00 00 00 00 00   ................
2B17:CF00  00 00 00 00 00 00 00 00-00 00 00 00 00 00 00 00   ................
2B17:CF10  00 00 00 00 00 00 00 00-00 00 00 00 00 00 00 00   ................
2B17:CF20  00 00 00 00 00 00 00 00-00 00 00 00 00 00 00 00   ................
2B17:CF30  00 00 00 00 00 00 00 00-00 00 00 00 00 00 00 00   ................
2B17:CF40  00 00 00 00 00 00 00 00-00 00 00 00 00 00 00 00   ................
2B17:CF50  00 00 00 00 00 00 00 00-00 00 00 00 00 00 00 00   ................
2B17:CF60  00 00 00 00 00 00 00 00-00 00 00 00 00 00 00 00   ................
2B17:CF70  00 00 00 00 00 00 00 00-00 00 00 00 00 00 00 00   ................
2B17:CF80  00 00 00 00 00 00 00 00-00 00 00 00 00 00 00 00   ................
2B17:CF90  00 00 00 00 00 00 00 00-00 00 00 00 00 00 00 00   ................
2B17:CFA0  00 00 00 00 00 00 00 00-00                        .........
-
```

© VETTEST, S.A. 1989
ALL RIGHT S RESERVED

```
C>debug
-r
AX=0000  BX=0000  CX=0000  DX=0000  SP=FFEE  BP=0000  SI=0000  DI=0000
DS=17ED  ES=17ED  SS=17ED  CS=17ED  IP=0100   NV UP EI PL NZ NA PO NC
17ED:0100 4D            DEC     BP
-n lcd.com
-l
-r
AX=0000  BX=0000  CX=11CF  DX=0000  SP=FFFE  BP=0000  SI=0000  DI=0000
DS=1807  ES=1807  SS=1807  CS=1807  IP=0100   NV UP EI PL NZ NA PO NC
1807:0100 E9F110        JMP     11F4
-d cs:100 l 11cf
1807:0100  E9 F1 10 00 00 00 00 00-00 00 00 01 01 00 00 20   ................
1807:0110  20 20 20 20 20 20 20 20-20 20 20 20 20 20 20 20
1807:0120  20 20 20 20 20 20 20 20-20 20 20 20 20 20 20 20
1807:0130  20 20 20 20 20 20 20 20-20 20 20 20 20 20 20 20
1807:0140  20 20 20 20 20 20 20 20-20 20 20 20 20 20 20 20
1807:0150  20 20 20 20 20 20 20 20-20 20 20 20 20 20 20 20
1807:0160  20 20 20 20 20 20 20 20-20 20 20 20 20 20 20 20
1807:0170  20 20 20 20 20 20 20 20-20 20 20 20 20 20 20 20
1807:0180  20 20 20 20 20 20 20 20-20 20 20 20 20 20 20 20
1807:0190  20 20 20 20 20 20 20 20-20 20 20 20 20 20 20 20
1807:01A0  20 20 20 20 20 20 20 20-20 20 20 20 20 20 20 20
1807:01B0  20 20 20 20 20 20 20 20-20 20 20 20 20 20 20 20
1807:01C0  20 20 20 20 20 20 20 20-20 20 20 20 20 20 20 20
1807:01D0  20 20 20 20 20 20 20 20-20 20 20 20 20 20 20 20
1807:01E0  20 20 20 20 20 20 20 20-20 20 20 20 20 20 20 20
1807:01F0  20 20 20 20 20 20 20 20-20 20 20 20 20 20 20 20
1807:0200  20 20 20 20 20 20 20 20-20 20 20 20 20 20 20 20
1807:0210  20 20 20 20 20 20 20 20-20 20 20 20 20 20 20 20
1807:0220  20 20 20 20 20 20 20 20-20 20 20 20 20 20 20 20
1807:0230  20 20 20 20 20 20 20 20-20 20 20 20 20 20 20 20
1807:0240  20 20 20 20 20 20 20 20-20 20 20 20 20 20 20 20
1807:0250  20 20 20 20 20 20 20 20-20 20 20 20 20 20 20 20
1807:0260  20 20 20 20 20 20 20 20-20 20 20 20 20 20 20 20
1807:0270  20 20 20 20 20 20 20 20-20 20 20 20 20 20 20 20
1807:0280  20 20 20 20 20 20 20 20-20 20 20 20 20 20 20 20
1807:0290  20 20 20 20 20 20 20 20-20 20 20 20 20 20 20 20
1807:02A0  20 20 20 20 20 20 20 20-20 20 20 20 20 20 20 20
1807:02B0  20 20 20 20 20 20 20 20-20 20 20 20 20 20 20 20
1807:02C0  20 20 20 20 20 20 20 20-20 20 20 20 20 20 20 20
1807:02D0  20 20 20 20 20 20 20 20-20 20 20 20 20 20 20 20
1807:02E0  20 20 20 20 20 20 20 20-20 20 20 20 20 20 20 20
1807:02F0  20 20 20 20 20 20 20 20-20 20 20 20 20 20 20 20
1807:0300  20 20 20 20 20 20 20 20-20 20 20 20 20 20 20 20
1807:0310  20 20 20 20 20 20 20 20-20 20 20 20 20 20 20 20
1807:0320  20 20 20 20 20 20 20 20-20 20 20 20 20 20 20 20
1807:0330  20 20 20 20 20 20 20 20-20 20 20 20 20 20 20 20
1807:0340  20 20 20 20 20 20 20 20-20 20 20 20 20 20 20 20
1807:0350  20 20 20 20 20 20 20 20-20 20 20 20 20 20 20 20
1807:0360  20 20 20 20 20 20 20 20-20 20 20 20 20 20 20 20
1807:0370  20 20 20 20 20 20 20 20-20 20 20 20 20 20 20 20
1807:0380  20 20 20 20 20 20 20 20-20 20 20 20 20 20 20 20
1807:0390  20 20 20 20 20 20 20 20-20 20 20 20 20 20 20 20
1807:03A0  20 20 20 20 20 20 20 20-20 20 20 20 20 20 20 20
1807:03B0  20 20 20 20 20 20 20 20-20 20 20 20 20 20 20 20
1807:03C0  20 20 20 20 20 20 20 20-20 20 20 20 20 20 20 20
1807:03D0  20 20 20 20 20 20 20 20-20 20 20 20 20 20 20 20
```

```
1907:03E0  20 20 20 20 20 20 20 20-20 20 20 20 20 20 20 20
1907:03F0  20 20 20 20 20 20 20 20-20 20 20 20 20 20 20 20
1907:0400  20 20 20 20 20 20 20 20-20 20 20 20 20 20 20 20
1907:0410  20 20 20 20 20 20 20 20-20 20 20 20 20 20 20 20
1907:0420  20 20 20 20 20 20 20 20-20 20 20 20 20 20 20 20
1907:0430  20 20 20 20 20 20 20 20-20 20 20 20 20 20 20 20
1907:0440  20 20 20 20 20 20 20 20-20 20 20 20 20 20 20 20
1907:0450  20 20 20 20 20 20 20 20-20 20 20 20 20 20 20 20
1907:0460  20 20 20 20 20 20 20 20-20 20 20 20 20 20 20 20
1907:0470  20 20 20 20 20 20 20 20-20 20 20 20 20 20 20 20
1907:0480  20 20 20 20 20 20 20 20-20 20 20 20 20 20 20 20
1907:0490  20 20 20 20 20 20 20 20-20 20 20 20 20 20 20 20
1907:04A0  20 20 20 20 20 20 20 20-20 20 20 20 20 20 20 20
1907:04B0  20 20 20 20 20 20 20 20-20 20 20 20 20 20 20 20
1907:04C0  20 20 20 20 20 20 20 20-20 20 20 20 20 20 20 20
1907:04D0  20 20 20 20 20 20 20 20-20 20 20 20 20 20 20 20
1907:04E0  20 20 20 20 20 20 20 20-20 20 20 20 20 20 20 20
1907:04F0  20 20 20 20 20 20 20 20-20 20 20 20 20 20 20 20
1907:0500  20 20 20 20 20 20 20 20-20 20 20 20 20 20 20 20
1907:0510  20 20 20 20 20 20 20 20-20 20 20 20 20 20 20 20
1907:0520  20 20 20 20 20 20 20 20-20 20 20 20 20 20 20 20
1907:0530  20 20 20 20 20 20 20 20-20 20 20 20 20 20 20 20
1907:0540  20 20 20 20 20 20 20 20-20 20 20 20 20 20 20 20
1907:0550  20 20 20 20 20 20 20 20-20 20 20 20 20 20 20 20
1907:0560  20 20 20 20 20 20 20 20-20 20 20 20 20 20 20 20
1907:0570  20 20 20 20 20 20 20 20-20 20 20 20 20 20 20 20
1907:0580  20 20 20 20 20 20 20 20-20 20 20 20 20 20 20 20
1907:0590  20 20 20 20 20 20 20 20-20 20 20 20 20 20 20 20
1907:05A0  20 20 20 20 20 20 20 20-20 20 20 20 20 20 20 20
1907:05B0  20 20 20 20 20 20 20 20-20 20 20 20 20 20 20 20
1907:05C0  20 20 20 20 20 20 20 20-20 20 20 20 20 20 20 20
1907:05D0  20 20 20 20 20 20 20 20-20 20 20 20 20 20 20 20
1907:05E0  20 20 20 20 20 20 20 20-20 20 20 20 20 20 20 20
1907:05F0  20 20 20 20 20 20 20 20-20 20 20 20 20 20 20 20
1907:0600  20 20 20 20 20 20 20 20-20 20 20 20 20 20 20 20
1907:0610  20 20 20 20 20 20 20 20-20 20 20 20 20 20 20 20
1907:0620  20 20 20 20 20 20 20 20-20 20 20 20 20 20 20 20
1907:0630  20 20 20 20 20 20 20 20-20 20 20 20 20 20 20 20
1907:0640  20 20 20 20 20 20 20 20-20 20 20 20 20 20 20 20
1907:0650  20 20 20 20 20 20 20 20-20 20 20 20 20 20 20 20
1907:0660  20 20 20 20 20 20 20 20-20 20 20 20 20 20 20 20
1907:0670  20 20 20 20 20 20 20 20-20 20 20 20 20 20 20 20
1907:0680  20 20 20 20 20 20 20 20-20 20 20 20 20 20 20 20
1907:0690  20 20 20 20 20 20 20 20-20 20 20 20 20 20 20 20
1907:06A0  20 20 20 20 20 20 20 20-20 20 20 20 20 20 20 20
1907:06B0  20 20 20 20 20 20 20 20-20 20 20 20 20 20 20 20
1907:06C0  20 20 20 20 20 20 20 20-20 20 20 20 20 20 20 20
1907:06D0  20 20 20 20 20 20 20 20-20 20 20 20 20 20 20 20
1907:06E0  20 20 20 20 20 20 20 20-20 20 20 20 20 20 20 20
1907:06F0  20 20 20 20 20 20 20 20-20 20 20 20 20 20 20 20
1907:0700  20 20 20 20 20 20 20 20-20 20 20 20 20 20 20 20
1907:0710  20 20 20 20 20 20 20 20-20 20 20 20 20 20 20 20
1907:0720  20 20 20 20 20 20 20 20-20 20 20 20 20 20 20 20
1907:0730  20 20 20 20 20 20 20 20-20 20 20 20 20 20 20 20
1907:0740  20 20 20 20 20 20 20 20-20 20 20 20 20 20 20 20
1907:0750  20 20 20 20 20 20 20 20-20 20 20 20 20 20 20 20
1907:0760  20 20 20 20 20 20 20 20-20 20 20 20 20 20 20 20
1907:0770  20 20 20 20 20 20 20 20-20 20 20 20 20 20 20 20
1907:0780  20 20 20 20 20 20 20 20-20 20 20 20 20 20 20 20
1907:0790  20 20 20 20 20 20 20 20-20 20 20 20 20 20 20 20
1907:07A0  20 20 20 20 20 20 20 20-20 20 20 20 20 20 20 20
1907:07B0  20 20 20 20 20 20 20 20-20 20 20 20 20 20 20 20
1907:07C0  20 20 20 20 20 20 20 20-20 20 20 20 20 20 20 20
1907:07D0  20 20 20 20 20 20 20 20-20 20 20 20 20 20 20 20
1907:07E0  20 20 20 20 20 20 20 20-20 20 20 20 20 20 20 20
1907:07F0  20 20 20 20 20 20 20 20-20 20 20 20 20 20 20 20
1907:0800  20 20 20 20 20 20 20 20-20 20 20 20 20 20 20 20
1907:0810  20 20 20 20 20 20 20 20-20 20 20 20 20 20 20 20
1907:0820  20 20 20 20 20 20 20 20-20 20 20 20 20 20 20 20
1907:0830  20 20 20 20 20 20 20 20-20 20 20 20 20 20 20 20
1907:0840  20 20 20 20 20 20 20 20-20 20 20 20 20 20 20 20
1907:0850  20 20 20 20 20 20 20 20-20 20 20 20 20 20 20 20
1907:0860  20 20 20 20 20 20 20 20-20 20 20 20 20 20 20 20
1907:0870  20 20 20 20 20 20 20 20-20 20 20 20 20 20 20 20
```

```
1907:0880  20 20 20 20 20 20 20 20-20 20 20 20 20 20 20 20
1907:0890  20 20 20 20 20 20 20 20-20 20 20 20 20 20 20 20
1907:08A0  20 20 20 20 20 20 20 20-20 20 20 20 20 20 20 20
1907:08B0  20 20 20 20 20 20 20 20-20 20 20 20 20 20 20 20
1907:08C0  20 20 20 20 20 20 20 20-20 20 20 20 20 20 20 20
1907:08D0  20 20 20 20 20 20 20 20-20 20 20 20 20 20 20 00               .
1907:08E0  00 00 00 00 00 00 01 02-04 08 10 20 40 80 00 FE   ............ @...
1907:08F0  50 53 51 52 57 56 B0 FC-0A 74 05 B0 FD 1? 75 ??   PSQRWV...t.....u.
1907:0900  E8 3A 01 B0 FC 3C 74 6E-B0 FD 02 74 25 B0 FD 26   .:....tn...t%...
1907:0910  74 3A B0 FC 07 74 4E B0-FD 0B 75 0D E8 3A 01 B0   t:...tN...u..:..
1907:0920  FD 0D 75 03 E8 30 01 B0-FD 0D 75 03 E8 73 01 E8   ..u........u..s..
1907:0930  1D 01 0E E8 16 05 01 B0-FA 1F 76 02 B2 1F B0 FE   ..........v.....
1907:0940  0F 76 02 B6 0F 3C 3C 15-07 01 E8 0D 11 7D 3C 74   .v..........<.t
1907:0950  0E 3A 03 3D 3D 51 3D 15-07 E9 3D 7F EF F0 10 EB   ....=.=.Y.......
1907:0960  3E 3C 3C 3C 00 3C 00 74-F6 BA 3C 35 3C 51 3E 3D   .....<.t.....=..
1907:0970  3C 59 3C 3C 3C 3C 3C 3C-74 3C 3C 3C 3C 3C 3C 3C   .Y....<.t.<.u(..
1907:0980  B7 00 CD 10 B0 F4 3C 74-1A FE 3A B4 02 B7 10 CD   ........t........
1907:0990  10 B4 0E B7 00 CD 10 BA-3D 3B 3D 3F B7 00 E8 01   ..........  .....
1907:09A0  00 CD 10 3C 17 3C 3C 3C-75 15 B4 03 B7 00 CD 10   .......<.u.......
1907:09B0  3D 10 B4 02 B7 00 CD 10-5E 5F 5A 59 5B 58 CF 3C   ........^_ZYEX.<
1907:09C0  0A 75 3D B4 0E B7 00 CD-10 B0 FE 1E 74 0A FE C6   .u=.........t...
1907:09D0  B4 02 B7 00 CD 10 EB E0-B4 0F CD 10 50 B4 08 B7   .............P...
1907:09E0  00 CD 10 3A FD 3E 01 06-5A FE C2 BA 26 3B 1E 3?   ........:........
1907:09F0  00 00 CD 10 EB 3C 3C 1E-72 16 3C 1? 77 12 2E C6   ......<.r.<.w...
1907:0A00  06 3E 0E 00 3C 1E 75 06-3E 36 06 3E 0E FF 3E A3   ....<.u..........
1907:0A10  50 B4 1B B7 00 CD 10 EA-3D 58 B4 0F B7 10 E8 01   P........X.......
1907:0A20  00 CD 10 B4 0F 3C 10 B0-B4 0? B7 00 CD 10 59 3A   ........F......Y:
1907:0A30  3E 74 3B FE 3C 3C 00 B4-13 CD 10 E8 74 FF 3E 3B   .t..............=...
1907:0A40  16 07 01 EC EB 6E 11 E0-F3 5A 3E 3? 16 07 01 5E   ...P.n...Z......^
1907:0A50  5F 5A 59 5B 5? 3E FF 2E-07 01 5E 5F 5A 59 5B 58   _ZYEX.....^_ZYEX
1907:0A60  FC 2E FF 1E 0? ?? 5? 5?-51 E? 5? 56 ?? 2E 3? 16   ......SQRWVP....
1907:0A70  01 B4 06 B4 00 B1 04 3?-E0 3B 1B B1 1? ?? E0 03   ................
1907:0A80  C7 36 00 03 C2 2E 13 06-3F 1B 3D 3? 07 72 0? 2D   ...........= .r.-
1907:0A90  3? 17 3? 3E 3E FA 57 0F-01 5A 5A 56 5E 5F 5A 59   ..........Z..^_ZY
1907:0AA0  5B 0F EB A3 E9 11 FF 50-51 BB 02 B1 05 2? E0 59   [......PQ.......Y
1907:0AB0  51 50 8B D1 B1 07 D3 EB-E9 ?? C1 2E 0? 06 09 01   QP.......Y.......
1907:0AC0  25 FF 0F 2E A3 E1 0B 8B-15 07 00 8B E9 2E 8A 8?   %........XX......
1907:0AD0  E? 0B 2E A0 E4 0B 04 FF-2E A2 E5 0B 2E A1 E0 0B   ........4........
1907:0AE0  8A E0 B0 0A EB 78 0? 2E-A1 E? 0B B0 0B E8 6F 02   .....x........=
1907:0AF0  E3 0D 00 E8 69 02 52 E1-5A 0B 03 B0 91 EE EA 0A   ....i.PZ.........
1907:0B00  0? B0 0? EE B0 50 EE 3A-13 03 B9 00 00 E0 2? B0   ...............$
1907:0B10  74 12 E2 F? 5A 0A 03 B0-00 EE 8A 0A 0? B0 40 EE   t..............@
1907:0B20  B0 60 EE F0 90 F0 B0 40-EE F0 90 90 B0 00 EE B0   .`.....@........
1907:0B30  B0 EE E? 14 00 E2 FE B0-00 EE B0 40 EE B0 60 EE   ..........@..`
1907:0B40  5A 0B 3? E? 2E A? E1 08-5A 0A 0? B0 40 EE 5A 0B   ..........@..
1907:0B50  0? B0 91 EE E? 5A 5B 3C-20 72 14 2A 3? 7? 0? 2E   ....YZX<.r.*.t.
1907:0B60  A0 E1 0B 2E 2? 06 E4 0B-2E A? E1 0? EB 2? F? 8A   .....=........*.
1907:0B70  2E 2E 2? E1 0B 2E 2? 06-EE 0B 2E A? E1 0B 8A C1   ......."........
1907:0B80  24 07 74 0? 2E A0 E1 0?-2E 0? 06 E4 0? 2E A? E1   $.t.............
1907:0B90  1B 2E A1 E? 1B 8A E0 B0-0A EE ?? 01 2E 41 E? 1B   ................
1907:0BA0  3? 0? EB 8A 0? B? 0C 0?-EB B4 01 2E 40 E1 0B EB   ................
1907:0BB0  ?B 01 E8 FA FE 50 E? E?-51 E? 50 B4 0? B1 0? ?0   .....PEQRP......
1907:0BC0  3D 10 0A 72 7? 0? E?-1E-B2 00 00 8E E? B? 1E 7C   =..ru.P.........
1907:0BD0  0? A1 7E 00 EE C0 1F E?-?? 00 04 ?? ?? ?? ?B 2?   ..~....X-.......
1907:0BE0  8A 07 EB ?? 0? 2E A? E?-11 26 8A 47 01 5B EC 01   .........&.G...
1907:0BF0  2E A? E? 11 26 8A 47 0?-2E E? E1 01 2E A? EE 11   ....&.G.........
1907:0C00  26 8A 47 0? E? 26 01 2E-A? E? 11 26 8A 47 0A 5B   .G......&.G..
1907:0C10  01 2E A? F0 11 26 8A 47-05 EB C0 01 2E A? F1 11   ...&.G..........
1907:0C20  26 8A 47 06 E? B? 01 2E-A? F? 11 26 8A 47 07 EB   &.G........&.G.
1907:0C30  AA 01 2E A? F? 11 07 ??-?? ?4 0? E? ?? E? F? 2E   ................
1907:0C40  A1 ?? 01 2E ?? 06 0? 01-2E FF 0? 2E A? 0? 01 F?   ..........%.....
1907:0C50  3? 0? 00 2E A1 0? 01 5A-E0 B0 0A EB 01 01 2E A1   ................
1907:0C60  0? 01 2E ?? ?F E? 0? E?-?? 0? ?E ?? ?? EB EF ??   ..%.............
1907:0C70  2E A? 2E ?? ?? ?? ?? E?-?? 01 2E A1 ?? ?? ?? ??   ...=............
1907:0C80  0? 2E A? ?? 0? E? ?? ??-A1 0B 01 E4 0? 84 0? E1   ................
1907:0C90  04 0? E0 EB ?? E1 ?? ??-E0 ?? ?? ?? EB ?? ?? 01   ................
1907:0CA0  B6 00 0? ?? ?? ?? ?? ??-?? ?? ?? ?? ?? ?? ?? ??   ..........*..r.-
1907:0CB0  07 EB ?? ?? ?? ?? ?? 1?-01 5A 5? 5? 5? ?? ?? E4   ...X.....ZYEX..
1907:0CC0  C0 2E A1 0? 01 0? 0?-01-2E A? 0? 01 EA E1 E0 0B   ................
1907:0CD0  EB 8C ?? 2E A1 0? 01 2E-?? 0F B0 0? EB ?? ?? 2E   .........%......
1907:0CE0  A1 0F 1B 0E E0 ?? ?? 2?-?? ?? ?? ?? ?? ?? 2E A?   ....P.=..r.-....
1907:0CF0  0F 0B ?? 2E A1 0? 01 ??-?? 01 2E A? 0? 01 EA E0   .......-.......
```

```
1907:0D00  80 06 EB EA 00 2E A1 0F-01 2E 00 0F 80 0F EB 4E   ...Z......ú....Ò
1907:0D10  00 EB 11 00 2E A1 0F 0E-0E 80 00 77 00 7E 01 17   .........-F.s....
1907:0D20  2E A0 0F 0E 00 2E A1 0F-01 84 E0 E1 0A EB 0F 00   ............../.
1907:0D30  2E A1 0F 11 2E 00 1F E1-1E EB 2F 00 2E 10 10 EB   ....%......#.....
1907:0D40  1D 00 8F 00 01 80 00 EB-7F 00 E0 FF 2E BF 1E 0F   .........3.......
1907:0D50  06 EF E0 00 80 00 0E EB-87 0F 01 43 E0 F3 0F E0   ..P.. ......C...F
1907:0D60  E0 EA 0E 07 EB EA 0A 00-E0 E0 EB E0 40 EB E0 E0   F...............
1907:0D70  EE E8 EA 3C 0C 74 1E 3C-0D 74 1A EA C4 E0 EA 0E   .XZ<.t.<.t...R..
1907:0D80  00 EB EA 0A 00 E0 00 EB-E0 50 EB E0 00 EB EA 0F   ..........  ....Z.
1907:0D90  E8 06 00 EB 0F FF EB 0F-00 EB 0D FF E8 0A 00 EB   .................
1907:0DA0  E0 FF EB 03 00 EB E7 FF-EB 0D 00 EB E1 FF 8E 00   .................
1907:0DB0  00 2E A7 1F 01 E7 00 10-E0 00 EB 0C FF E0 FF E4   .................
1907:0DC0  0F 87 00 0D 10 E4 02 87-00 0D 10 EB 00 00 E7 D0   .................
1907:0DD0  07 E0 20 2E E8 E7 0F 01-47 E0 F8 0D E7 E1 3A D8   .. ......C...8D..
1907:0DE0  E9 08 00 00 0D 10 D8 E0-FA F9 E8 0D 00 00 00 00   ..........YE.....
1907:0DF0  00 00 00 00 7E E1 4E E1-FD FF E1 7E 7E FF 13 FF   ....~.......~~...
1907:0E00  0D E7 FF 7E 76 7F 7F 7F-7E 1D 38 10 08 1D 3E 7F   ...~e.........>.
1907:0E10  3E 1D 1E 1D 1D 7E 1D 7F-7F 3E 1D 7E 1B 3B 1D 7E   >..............>
1907:0E20  7F 3E 1D 7E 00 00 1E 3D-7D 1E 00 00 FF FF E7 0D   .........<.......
1907:0E30  0D E7 FF FF 1D 0D 66 40-40 66 7D 10 FF 0D FF ED   ..... f3Bf<.....,
1907:0E40  3D 99 0D FF F1 E0 F1 EE-7D 7D 0D 1E 7D 66 66 66   ........DDD.<fff
1907:0E50  3D 1E 7E 1E FD 0D FD 0D-0D 0E 1F 07 FE 06 FE 06   <.~..............
1907:0E60  06 E6 67 00 F8 E4 3C 7E-7E 3C 3A F9 01 07 1F 7F   ..g..Z<~~<Z......
1907:0E70  1F 07 01 00 40 73 70 7F-70 70 40 00 18 3C 7E 18   ....@p!.!p@..<~.
1907:0E80  18 7E 3C 18 66 66 66 66-66 00 66 00 FE DB DB 7E   .~<.fffff.f......
1907:0E90  1B 1B 1B 00 7C C6 1C 36-36 1C 3C 1E 00 00 00 00   ....|..66.3......
1907:0EA0  7E 7E 7E 00 18 3C 7E 18-7E 3C 18 FF 18 3C 7E 18   ~~~..<~.~<...<~.
1907:0EB0  18 18 18 00 18 18 18 18-7E 3C 18 00 00 18 30 7F   .........~<....0.
1907:0EC0  30 18 00 00 00 0C 06 7F-06 0C 00 00 00 00 0C 0C   0................
1907:0ED0  0C 7F 00 00 00 24 66 FF-66 24 00 00 00 18 3C 7E   .....$f.f$....<~
1907:0EE0  FF FF 00 00 00 FF FF 7E-3C 18 00 00 00 00 00 00   ........~<.......
1907:0EF0  00 00 00 00 0C 1E 1E 0C-0C 00 0C 00 36 36 36 00   ..............666.
1907:0F00  00 00 00 00 36 36 7F 36-7F 36 36 00 0C 3E 03 1E   ....66.6.66...>..
1907:0F10  30 1F 0C 00 00 63 33 18-0C 66 63 00 1C 36 1C 6E   0....c3..fc..6.n
1907:0F20  3B 33 6E 00 06 06 03 00-00 00 00 00 18 0C 06 06   ;3n..............
1907:0F30  06 0C 18 00 06 0C 18 18-18 0C 06 00 00 66 3C FF   ..............f<.
1907:0F40  3C 66 00 00 00 0C 0C 3F-0C 0C 00 00 00 00 00 00   <f......?........
1907:0F50  00 0C 0C 06 00 00 00 3F-00 00 00 00 00 00 00 00   .......?.........
1907:0F60  00 0C 0C 00 60 30 18 0C-06 03 01 00 3E 63 73 7B   ....`0......>cs{
1907:0F70  6F 67 3E 00 0C 0E 0C 0C-0C 0C 3F 00 1E 33 30 1C   og>.......?..30.
1907:0F80  06 33 3F 00 1E 33 30 1C-30 33 1E 00 38 3C 36 33   .3?..30.03..8<63
1907:0F90  7F 30 78 00 3F 03 1F 30-30 33 1E 00 1C 06 03 1F   .0x.?..003......
1907:0FA0  33 33 1E 00 3F 33 30 18-0C 0C 0C 00 1E 33 33 1E   33..?30......33.
1907:0FB0  33 33 1E 00 1E 33 33 3E-30 18 0E 00 00 0C 0C 00   33...33>0.......
1907:0FC0  00 0C 0C 00 00 0C 0C 00-00 0C 0C 06 18 0C 06 03   .................
1907:0FD0  06 0C 18 00 00 00 3F 00-00 3F 00 00 06 0C 18 30   ......?..?.....0
1907:0FE0  18 0C 06 00 1E 33 30 18-0C 00 0C 00 3E 63 7B 7B   .....30.....>c{{
1907:0FF0  7B 03 1E 00 0C 1E 33 33-3F 33 33 00 3F 66 66 3E   {.....33?33.?ff>
1907:1000  66 66 3F 00 3C 66 03 03-03 66 3C 00 1F 36 66 66   ff?.<f...f<..6ff
1907:1010  66 36 1F 00 7F 46 16 1E-16 46 7F 00 7F 46 16 1E   f6...F...F...F..
1907:1020  16 06 0F 00 3C 66 03 03-73 66 7C 00 33 33 33 3F   ....<f..sf|.333?
1907:1030  33 33 33 00 1E 0C 0C 0C-0C 0C 1E 00 78 30 30 30   333.........x000
1907:1040  33 33 1E 00 67 66 36 1E-36 66 67 00 0F 06 06 06   33..gf6.6fg.....
1907:1050  46 66 7F 00 63 77 7F 7F-6B 63 63 00 63 67 6F 7B   Ff..cw..kcc.cgo{
1907:1060  73 63 63 00 1C 36 63 63-63 36 1C 00 3F 66 66 3E   scc..6ccc6..?ff>
1907:1070  06 06 0F 00 1E 33 33 33-3B 1E 38 00 3F 66 66 3E   .....333;.8.?ff>
1907:1080  36 66 67 00 1E 33 07 0E-38 33 1E 00 3F 2D 0C 0C   6fg..3..83..?-..
1907:1090  0C 0C 1E 00 33 33 33 33-33 33 3F 00 33 33 33 33   ....333333?.3333
1907:10A0  33 1E 0C 00 63 63 63 6B-7F 77 63 00 63 63 36 1C   3...ccck.wc.cc6.
1907:10B0  1C 36 63 00 33 33 33 1E-0C 0C 1E 00 7F 63 31 18   .6c.333......c1.
1907:10C0  4C 66 7F 00 1E 06 06 06-06 06 1E 00 03 06 0C 18   Lf..............
1907:10D0  30 60 40 00 1E 18 18 18-18 18 1E 00 08 1C 36 63   0`@...........6c
1907:10E0  00 00 00 00 00 00 00 00-00 00 00 FF 0C 0C 18 00   ................
1907:10F0  00 00 00 00 00 00 1E 30-3E 33 6E 00 07 06 3E 66   .......0>3n....>f
1907:1100  66 66 3B 00 00 00 1E 33-03 33 1E 00 38 30 30 3E   ff;....3.3..800>
1907:1110  33 33 6E 00 00 00 1E 33-3F 03 1E 00 1C 36 06 0F   33n....3?....6..
1907:1120  06 06 0F 00 00 00 6E 33-33 3E 30 1F 07 06 36 6E   ......n33>0...6n
1907:1130  66 66 67 00 0C 00 0E 0C-0C 0C 1E 00 30 00 30 30   ffg.........0.00
1907:1140  30 33 33 1E 07 06 66 36-1E 36 67 00 0E 0C 0C 0C   033...f6.6g.....
1907:1150  0C 0C 1E 00 00 00 33 7F-7F 6B 63 00 00 00 1F 33   ......3..kc....3
1907:1160  33 33 33 00 00 00 1E 33-33 33 1E 00 00 00 3B 66   333....333....;f
1907:1170  66 3E 06 0F 00 00 6E 33-33 3E 30 78 00 00 3B 6E   f>....n33>0x..;n
1907:1180  66 06 0F 00 00 00 3E 03-1E 30 1F 00 08 0C 3E 0C   f.....>..0....>.
```

```
1807:1190  0D DC 13 00 00 00 DD DD-DD DD 6E 00 C0 00 DD DD   ......DDDDn...DD
1807:11A0  DD 1E CD 00 00 00 8D 6B-77 7F 76 00 00 00 6D 76   D.....cK..&...c&
1807:11B0  1C 76 8D 00 00 00 DD DD-DD DE D0 1F 00 00 DF 1F   .cE...DDD0C...?.
1807:11C0  00 26 7F 00 D3 0D 0D 17-0D 0D DE 00 1E 1B 1E 00   .&?.B.....B.....
1807:11D0  1B 1B 1E 00 17 0D 00 DE-0D 0D 07 00 6E 7E 00 00   .......B....n:..
1807:11E0  00 00 00 00 00 0B 1C D6-6D 6D 7F 00 00 00 00 00   ........&cc......
1807:11F0  00 00 00 00 8D DD 8E DE-8E 0D DE DD D1 EF 1E CD   ..........E.!...
1807:1200  D1 ED D6 1F 01 EA 0E 0D-B0 E1 EE EA 04 0D E1 D0   ................
1807:1210  EE E9 00 DD EB 48 F8 BE-01 77 EB 4C F5 E8 CD 1F   ...D.H....w.B....
1807:1220  EB DC 7B 8B 0D 7F DE D6-FB EA EF 0B 3B 1D DE CD   .<...?.&......%.
1807:1230  C1 DE D6 06 EE 1B 00 EB-E6 F5 BA F4 11 CD 27      !.......V.....'
```

PART C                                   PRINTER OPERATION

© VETTEST, S.A. 1989
ALL RIGHT S RESERVED

```
C>debug
-r
AX=0000  BX=0000  CX=0000  DX=0000  SP=FFEE  BP=0000  SI=0000  DI=0000
DS=17ED  ES=17ED  SS=17ED  CS=17ED  IP=0100   NV UP EI PL NZ NA PO NC
17ED:0100 4D            DEC     BP
-n prtr.com
-l
-r
AX=0000  BX=0000  CX=10DA  DX=0000  SP=FFFE  BP=0000  SI=0000  DI=0000
DS=1807  ES=1807  SS=1807  CS=1807  IP=0100   NV UP EI PL NZ NA PO NC
1807:0100 E9EF00        JMP     01F2
-d cs:100 l da
1807:0100  E9 EF 00 00 00 00 00 E0-FE B0 FA 00 74 0D EB 7D   ........P....t...
1807:0110  90 E3 E1 EE E0 BA 79 0D-ED DA D0 7E 07 5D EA E9   .BIRP.y..e u.XZ
1807:0120  E8 EB 6A 90 B0 FD D0 75-DF E8 E0 0C ED BA 0E 0D   [.j....uOXP.....
1807:0130  EE D4 7F F4 EE E9 DE 00-E0 FE 0C E0 EE F3 EB C1   .e....(.........
1807:0140  00 E9 00 00 EA 0E 0D ED-D4 E0 74 0C ED F6 4B DA   .........a.t...K.
1807:0150  DF 75 EE E4 D9 EE 0D 90-DA D0 DE EB D6 0D 01 BA   .u...........&...
1807:0160  05 0D E1 ED EE EB 1F 90-90 FD 01 75 07 B4 E0 DE   .............u..P.
1807:0170  EE D6 07 01 DE EA D6 07-01 E0 E4 7F BA CE 0D ED   .&.....&.........
1807:0180  D4 B0 D4 E0 0A E0 E9 BA-C1 E6 E9 EB DF DE FF DE   4.e...Y..IYI....
1807:0190  CD 01 E0 DB EE DE BE 17-D5 CD D1 E9 1E 0D 01 ED   .........E.!.....
1807:01A0  06 0E 01 EA 0B 01 BB 17-DE DE D1 EA 07 0D B0 E9   .........%.!.....
1807:01B0  EE EA 04 CD E0 17 EE BA-0E 0D E0 90 EE BA 0F 0D   .................
1807:01C0  B0 90 EE D4 0C 0D B0 FF-EE BA 0E 0D E0 FF EE BA   .................
1807:01D0  0F CD B0 EE EE BA 92 01-CD 27                     ..........'
-q

C>
```

What is claimed is:

1. A chemical analyzer for analyzing reagent test slides onto which a fluid sample is metered, which comprises:

a rotatable turntable, the rotatable turntable being adapted to hold a plurality of test slides in a circular arrangement, the rotatable turntable including a top surface and a peripheral edge, and having formed in the top surface a plurality of recesses, the recesses being spaced apart from each other circumferentially about the turntable, each recess defining a receiving slot for receiving a test slide;

means for inserting slides onto the rotatable turntable, the slide insertion means being situated adjacent to the circumferential periphery of the rotatable turntable;

means for metering out a predetermined volume of fluid sample and for depositing the predetermined sample volume onto each test slide carried by the rotatable turntable, at least a portion of the same metering and depositing means being positioned in alignment with the test slides carried by the rotatable turntable;

a slide cover, the slide cover being positioned above the rotatable turntable and being at least partially rotatable relative to the turntable to cover and uncover test slides carried by the turntable, the slide cover being mounted on the top surface of the rotatable turntable and concentric therewith, the cover including a plurality of radially extending plate finger members, adjacent plate finger members defining a slot therebetween, each plate finger member including an opening formed through the thickness of said finger member, the slide cover further including a plurality of button members, each button member being at least partially received by a corresponding opening formed in the plate finger members, the slide cover further including means for biasing the button members, the biasing means extending a force on the button members to force the button members into the openings of the plate finger members;

a reflectometer, the reflectometer having a portion which is situated below the rotatable turntable and positioned in alignment with the test slides carried by the turntable, the reflectometer including at least one source of light of a predetermined wavelength, the light source being positioned with respect to the test slides carried by the turntable so as to direct light onto the test slides, and further including at least one light sensor, the light sensor receiving light reflected by the test slides carried by the turntable; and means for removing test slides carried by the rotatable turntable, the slide removing means being situated in proximity to the rotatable turntable to engage the slides carried by the turntable and remove the slides.

2. A chemical analyzer as defined by claim 1, wherein the slide cover further includes internal sidewalls defining the openings of the plate finger members, each internal sidewall defining a respective opening being stepped inwardly of the opening to define a shoulder;

and wherein each button member includes a peripheral lip, the lips of the button members being adapted to rest on the cover opening shoulders.

3. A chemical analyzer as define by claim 1, wherein each of the button members extends through the thickness of the slide cover and includes a lower surface, the lower surface being adapted to engage a test slide carried by the rotatable turntable.

4. A chemical analyzer as defined in claim 3, wherein at least the lower surface of each button member is coated with an anti-fraction material.

5. A chemical analyer as defined by claim 3, wherein at least the lower surface of each button member is coated with an essentially inert and non-absorbing material.

* * * * *

UNITED STATES PATENT AND TRADEMARK OFFICE

CERTIFICATE OF CORRECTION

PATENT NO. : 5,089,229

DATED : February 18, 1992

INVENTOR(S) : Thomas Heidt, et al.

It is certified that error appears in the above-identified patent and that said Letters Patent is hereby corrected as shown below:

On title page, item [75], "Placensia" should read --Plasensia-- and "Hopatoong" should read --Hopatcong-- and add 5th inventor --Roger Clampitt, Herts, U.K.--.

Column 4, line 47, after "12" add period --.--

Column 4, line 54, after "13A" add period --.--

Column 11, line 52, change "cf" to --of--

Column 12, line 65, change TM to --(TM)--

Column 13, line 39, remove comma after "one detent"

Column 15, line 2, after "FIG. 11" add period --.--

Column 18, line 17, after "216" add period --.--

Column 24, line 33, after "will" change "and" to --add--

Column 24, line 41, change "tot he" to --to the--

Column 29, line 47, after "vertical" add period --.--

Column 30, line 62, add --1-- before "(white)"

Column 30, line 64, after "density)" add equal sign -- = --

Column 33, line 53, after "elements" change "39" to -- 395 --

Column 34, line 24, change "cove 54" to -- cover 54 --

UNITED STATES PATENT AND TRADEMARK OFFICE

CERTIFICATE OF CORRECTION

PATENT NO. : 5,089,229

DATED : February 18, 1992

INVENTOR(S) : Thomas Heidt, et al.

It is certified that error appears in the above-identified patent and that said Letters Patent is hereby corrected as shown below:

Column 36, line 43, change "BLOCK" to initial cap --Block--

Column 36, line 50, change "ten" to --then--

Column 36, line 54, change "block" to initial cap --Block--

Column 39, line 52, change "cf" to --of--

Column 40, line 18, delete "&" before "to the LED"

Column 43, line 59, delete minus sign before "5" to read -- +5 --

Column 45, line 33, correct comma placement to read -- 426), --

Column 49, line 56, insert period after "1116" to read --1116. --

Column 50, line 6, after "device" insert --1112. --

Column 50, line 43, after "flip" add --flop--

Column 50, line 44, after "connected" change "of" to --to--

Column 52, line 65, after "turntable" change "0" to --50--

Column 56, line 37, after "which" change "is" to --in--

UNITED STATES PATENT AND TRADEMARK OFFICE

CERTIFICATE OF CORRECTION

PATENT NO. : 5,089,229

DATED : February 18, 1992

INVENTOR(S) : Thomas Heidt, et al

It is certified that error appears in the above-indentified patent and that said Letters Patent is hereby corrected as shown below:

Col. 278, claim 4, line 1, after "defined" change "in" to --by--.

Signed and Sealed this

Fifth Day of October, 1993

Attest:

BRUCE LEHMAN

Attesting Officer

Commissioner of Patents and Trademarks